(12) United States Patent
Wu et al.

(10) Patent No.: US 11,760,764 B2
(45) Date of Patent: Sep. 19, 2023

(54) METHODS AND COMPOSITIONS FOR TARGETING PD-L1

(71) Applicant: Aligos Therapeutics, Inc., South San Francisco, CA (US)

(72) Inventors: Tongfei Wu, Boortmeerbeek (BE); Pierre Jean-Marie Bernard Raboisson, Wavre (FR); Antitsa Dimitrova Stoycheva, Half Moon Bay, CA (US); Francois Gonzalvez, Antwerp (BE); Jerome Deval, Pacifica, CA (US); Cheng Liu, Burlingame, CA (US)

(73) Assignee: Aligos Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 17/303,089

(22) Filed: May 19, 2021

(65) Prior Publication Data

US 2023/0002413 A1 Jan. 5, 2023

Related U.S. Application Data

(60) Provisional application No. 63/159,075, filed on Mar. 10, 2021, provisional application No. 63/028,882, filed on May 22, 2020.

(51) Int. Cl.

| | | |
|---|---|---|
| C07D 519/00 | (2006.01) |
| C07C 229/16 | (2006.01) |
| C07C 215/14 | (2006.01) |
| C07D 233/36 | (2006.01) |
| C07D 207/267 | (2006.01) |
| C07D 295/135 | (2006.01) |
| C07D 217/02 | (2006.01) |
| C07D 209/44 | (2006.01) |
| C07C 211/42 | (2006.01) |
| C07D 205/12 | (2006.01) |
| C07D 491/107 | (2006.01) |
| C07D 217/04 | (2006.01) |
| C07D 401/14 | (2006.01) |
| C07D 471/04 | (2006.01) |
| C07C 233/36 | (2006.01) |

(52) U.S. Cl.
CPC .......... *C07D 519/00* (2013.01); *C07C 211/42* (2013.01); *C07C 215/14* (2013.01); *C07C 229/16* (2013.01); *C07C 233/36* (2013.01); *C07D 205/12* (2013.01); *C07D 207/267* (2013.01); *C07D 209/44* (2013.01); *C07D 217/02* (2013.01); *C07D 217/04* (2013.01); *C07D 295/135* (2013.01); *C07D 401/14* (2013.01); *C07D 471/04* (2013.01); *C07D 491/107* (2013.01); *C07C 2602/08* (2017.05)

(58) Field of Classification Search
CPC ............... C07D 519/00; C07D 205/12; C07D 207/267; C07D 209/44; C07D 217/02; C07D 217/04; C07D 295/135; C07D 401/14; C07D 471/04; C07D 491/107; C07C 211/42; C07C 215/14; C07C 229/16; C07C 233/36; C07C 2602/08
USPC ..................................................... 514/210.16
See application file for complete search history.

(56) References Cited

U.S. PATENT DOCUMENTS

| | | |
|---|---|---|
| 2009/0098397 A1 | 4/2009 | Kim et al. |
| 2012/0097932 A1 | 4/2012 | Kim et al. |
| 2017/0331043 A1 | 11/2017 | Kuhn et al. |

FOREIGN PATENT DOCUMENTS

| | | |
|---|---|---|
| CN | 104478900 | 4/2015 |
| CN | 107721805 | 2/2018 |
| CN | 110746344 | 2/2020 |
| CN | 111039942 | 4/2020 |
| CN | 111574504 | 8/2020 |
| DE | 10104279 | 8/2002 |
| DE | 102019200805 | 7/2020 |
| EP | 0611764 | 8/1994 |
| EP | 3381906 | 10/2018 |
| JP | 2012-123292 | 6/2012 |
| KR | 10-2016-0001537 | 1/2016 |
| KR | 10-2018-0063710 | 6/2018 |
| WO | WO 2002/012224 | 2/2002 |
| WO | WO 2007/043835 | 4/2007 |
| WO | WO 2008/097428 | 8/2008 |
| WO | WO 2010/065681 | 6/2010 |
| WO | WO 2010/096777 | 8/2010 |
| WO | WO 2010/131764 | 11/2010 |
| WO | WO 2011/043254 | 4/2011 |
| WO | WO 2011/082400 | 7/2011 |
| WO | WO 2012/129562 | 9/2012 |

(Continued)

OTHER PUBLICATIONS

Zarganes-Tzitzikas, et al., "Inhibitors of programmed cell death 1 (PD-1): a patent review (2010-2015)", Expert Opinion on Therapeutic Patents (2016) 26(9):973-77.

(Continued)

*Primary Examiner* — Kristin A Vajda
(74) *Attorney, Agent, or Firm* — Knobbe Martens Olson & Bear LLP

(57) ABSTRACT

The present disclosure related to compounds that can be useful as inhibitors of PD-1, PD-L1 or the PD-1/PD-L1 interaction. Also disclosed herein are pharmaceutical compositions of that can include a compound of Formula (I), or a pharmaceutically acceptable salt thereof, and uses of or methods of using a compound of Formula (I), or a pharmaceutically acceptable salt thereof, for the treatment of PD-L1 related diseases including but not limited to liver diseases, cancer, hepatocellular carcinoma, viral diseases, or hepatitis B.

24 Claims, 1 Drawing Sheet

(56) References Cited

FOREIGN PATENT DOCUMENTS

| WO | WO 2012/156948 | 11/2012 |
| WO | WO 2015/124272 | 8/2015 |
| WO | WO 2016/046300 | 3/2016 |
| WO | WO 2018/026971 | 2/2018 |
| WO | WO 2018/119263 | 6/2018 |
| WO | WO 2018/195321 | 10/2018 |
| WO | WO 2019/069835 | 4/2019 |
| WO | WO 2019/069960 | 4/2019 |
| WO | WO 2019/204609 | 10/2019 |
| WO | WO 2019/216266 | 11/2019 |
| WO | WO 2020/011246 | 1/2020 |
| WO | WO 2020/126970 | 6/2020 |
| WO | WO 2020/210831 | 10/2020 |
| WO | WO 2020/211822 | 10/2020 |
| WO | WO 2020/257549 | 12/2020 |
| WO | WO 2022/040002 | 2/2022 |
| WO | WO 2022/266236 | 12/2022 |

OTHER PUBLICATIONS

International Search Report and Written Opinion dated Sep. 9, 2021 for PCT Application No. PCT/US2021/033159, filed May 19, 2021.
"IUPAC-IUB Commission on Biochemical Nomenclature Abbreviated Nomenclature of Synthetic Polypeptides (Polymerized Amino Acids)* Revised Recommendations (1971)" Biochemistry. (1972) 11(5):942-944.

Absolute configuration structure

ORTEP structure

Formate

METHODS AND COMPOSITIONS FOR TARGETING PD-L1

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. Provisional Applications Nos. 63/028,882, filed May 22, 2020 and 63/159,075, filed Mar. 10, 2021.

FIELD

The present application relates to the fields of chemistry, biochemistry, molecular biology and medicine. The present disclosure related to compounds that can be useful as inhibitors of PD-1, PD-L1 or the PD-1/PD-L1 interaction. Also disclosed herein are pharmaceutical compositions of compounds described herein and uses of or methods of using the compounds for the treatment of PD-L1 related diseases including but not limited to liver diseases, cancer, hepatocellular carcinoma, viral diseases, or hepatitis B.

BACKGROUND

The programmed cell death 1 (PD-1) immune checkpoint expressed on the surface of activated $CD4^+$ and $CD8^+$ T cells controls an inhibitory mechanism to prevent autoimmunity. Engagement of PD-1 by programmed death-ligand 1 (PD-L1) expressed on the multitude of cell types, including macrophages, dendritic cells, mast cells as well as cancer cells induces T cell exhaustion resulting in reduction or loss of effector cytokine production (e.g. IL-2, TNF-$\alpha$, IFN-$\gamma$) and upregulation of other inhibitory receptors and immune checkpoints (e.g. CTLA-4, LAG-3, and BTLA), or T cell apoptosis. High expression of PD-L1 is exhibited by many types of cancers to escape tumor immune surveillance and has been associated with poorer prognosis. PD-1-mediated immunosuppression is also linked to some viral infections, such as hepatitis B. There is an ongoing need for PD-1/PD-L1 therapies and improvements thereof for the treatment of disease.

DRAWINGS

SUMMARY

Figure 1A:
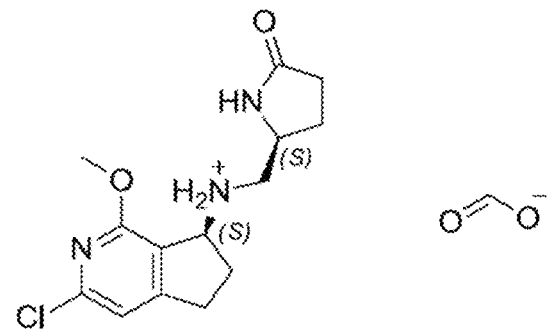
FIG. 1A shows the absolute configuration of the formate salt of intermediate 1-4b.

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below.

DETAILED DESCRIPTION

Hepatocellular carcinoma (HCC) is the most common form of liver cancer. HCC can be caused by a variety of conditions, such as alcohol consumption, cirrhosis, and viral infections that cause hepatitis, such as hepatitis B virus, hepatitis C virus, and hepatitis D virus. The inflammation, fibrosis, and cirrhosis linked with these conditions can induce malignancies in affected liver cells. HCC has relatively poor prognosis, with a five-year survival rate of about 30%, depending on if full surgical resection of the tumor is possible.

For early disease, surgical resection is used. However, most HCC are identified at later stages because of difficulties in diagnosing. Upon late stage diagnosis, the tumors are unresectable and most patients are given systemic therapies. The current standard of care in front line are multi-kinase inhibitors (including, for example, sorafenib and/or lenvatinib). Most patients are refractory or relapse from these treatments, and undergo second line therapies that have anti-angiogenic agents (including, for example, Regorafinib, Cabozantinib, and/or Ramicirumab) or immune checkpoint inhibitors (including, for example, nivolumab and/or pembrolizumab). However, most patients do not respond to first and second therapies, and the clinical benefit is poor, with overall survival not exceeding one year. In addition, biomarker driven therapies are lacking. Thus, there is a need to develop more tolerable and efficacious therapies for the treatment of HCC and related liver disorders.

HBV is a partially double-stranded circular DNA of about 3.2 kilobase (kb) pairs, and is classified into eight genotypes, A to H. The HBV replication pathway has been studied in great detail. One part of replication includes the formation of the covalently closed circular DNA (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of an HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Programmed cell death 1, or programmed death 1 (PD-1) is a 268 amino acid long type I transmembrane protein found as a surface marker on T cells and other immune cells. As an immune checkpoint, PD-1 serves to negatively regulate immune responses to prevent autoimmune disorder. PD-1 protein (NCBI accession number NP_005009.2) is expressed from the cluster of differentiation 279 (CD279) gene (NCBI accession number NG_012110.1) or mRNA transcript (NCBI accession number NM_005018.3). In some preferred embodiments, PD-1 is the human PD-1 protein, and CD279 is the human CD279 transcript or gene on chromosome 2. It should be understood that a person with ordinary skill in the art would view the terms PD-1 and CD279 as often nominally interchangeable when considering the nucleic acid (DNA or RNA) or corresponding translated protein, or the sequences thereof.

Programmed cell death-ligand 1, or programmed death-ligand 1 (PD-L1), also known as B7 homolog 1 (B7-H1) is 272 amino acid long type I transmembrane protein found as a surface marker on many different cell types. PD-L1 is a major ligand of PD-1 and results in inhibition of T cell cytotoxicity and cytokine production. Cancer cells such as HCC cells take advantage of this immune checkpoint by upregulating PD-L1 expression, resulting in dysfunctional anti-tumor immunity by proximal T cells. Viruses also have been observed to modulate the PD-1/PD-L1 pathway to inhibit immune host response. Hepatitis B virus has been shown to upregulate PD-L1 in infected hepatocytes, and PD-1 in associated T cells. PD-L1 protein (NCBI accession number NP_054862.1) is expressed from the cluster of differentiation 274 (CD274) transcript (NCBI accession number NM_014143.4). In some preferred embodiments, PD-L1 is the human PD-L1 protein, and CD274 is the human CD274 transcript or gene on chromosome 9. It should be understood that a person with ordinary skill in the art would view the terms PD-L1 and CD274 as often nominally interchangeable when considering the nucleic acid (DNA or RNA) or corresponding translated protein, or the sequences thereof.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. To the extent publications and patents or patent applications incorporated by reference contradict the disclosure contained in the specification, the specification is intended to supersede and/or take precedence over any such contradictory material. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) (such as 1, 2 or 3 groups) individually and independently selected from deuterium, alkyl, alkenyl, alkynyl, cycloalkyl, cycloalkenyl, aryl, heteroaryl, heterocyclyl, aryl(alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{1-4}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl) and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained —$CH_2$— tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. In some instances, an alkoxy can be —OR wherein R is an unsubstituted $C_{1-4}$ alkyl. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(=O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonyl" group refers to an "$X_3CSO_2$—" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(=S)—N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(=S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(=O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(=O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present.

For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt (for example, ammonium or triethylammonium salt), an alkali metal salt, such as a lithium, a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Examples of embodiments of the present application include the following:

Embodiment 1

A compound of Formula (I), or a pharmaceutically acceptable salt thereof, having the structure:

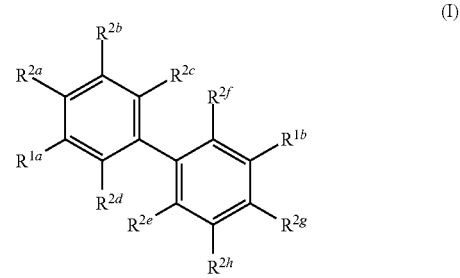

wherein:
$R^{1a}$ is selected from the group consisting of:

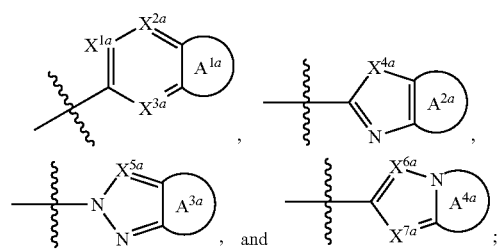

Ring A$^{1a}$, Ring A$^{2a}$, Ring A$^{3a}$ and Ring A$^{4a}$ are independently selected from the group consisting of:
  a monocyclic C$_{5-7}$ cycloalkyl substituted with R$^{3a1}$;
  a bicyclic C$_{6-12}$ cycloalkyl substituted with R$^{3a2}$;
  a 5-7 membered nitrogen-containing monocyclic heterocyclyl, wherein a nitrogen of the 5-7 membered nitrogen-containing monocyclic heterocyclyl is optionally substituted with R$^{3a3}$, wherein a carbon of the 5-7 membered nitrogen-containing monocyclic heterocyclyl is optionally substituted with R$^{3a4}$ or R$^{3a5}$, and wherein when R$^{3a5}$ is present, R$^{3a5}$ is attached at a carbon atom adjacent to a nitrogen of the 5-7 membered nitrogen-containing monocyclic heterocyclyl;
  a 6-12 membered nitrogen-containing bicyclic heterocyclyl, wherein a nitrogen of the 6-12 membered nitrogen-containing bicyclic heterocyclyl is optionally substituted with R$^{3a6}$; wherein a carbon of the 6-12 membered nitrogen-containing bicyclic heterocyclyl is optionally substituted with R$^{3a7}$ or R$^{3a8}$, and wherein R$^{3a8}$ is present, R$^{3a8}$ is attached at the carbon atom adjacent to a nitrogen of the 6-12 membered nitrogen-containing bicyclic heterocyclyl; and
  a 5-7 membered oxygen-containing monocyclic heterocyclyl substituted with R$^{3a9}$ or R$^{3a10}$; wherein R$^{3a10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens;
wherein Ring A$^{1a}$, Ring A$^{2a}$, Ring A$^{3a}$ and Ring A$^{4a}$ is optionally further substituted;
wherein when R$^{1a}$ is

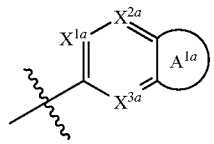

and Ring A$^{1a}$ is a 5-7 membered nitrogen-containing monocyclic heterocyclyl, then R$^{3a3}$ is present;
  wherein when R$^{1a}$ is

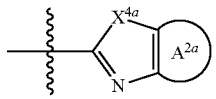

and Ring A$^{2a}$ is a 5-7 membered nitrogen-containing monocyclic heterocyclyl, then R$^{3a3}$ is present;
  wherein when R$^{1a}$ is

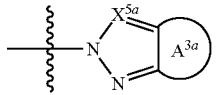

and Ring A$^{3a}$ is a 5-7 membered nitrogen-containing monocyclic heterocyclyl, then R$^{3a3}$ is present;

wherein when R$^{1a}$ is

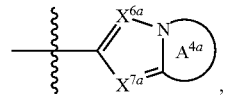

then Ring A$^{4a}$ cannot be a monocyclic C$_{5-7}$ cycloalkyl substituted with R$^{3a1}$ or a bicyclic C$_{6-12}$ cycloalkyl substituted with R$^{3a2}$; and
  wherein when R$^{1a}$ is

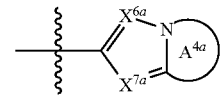

and Ring A$^{4a}$ is a 5-7 membered nitrogen-containing monocyclic heterocyclyl, then R$^{3a3}$ is optional;
  X$^{1a}$, X$^{2a}$ and X$^{3a}$ are independently N or CR$^{4a1}$;
  X$^{4a}$ is NR$^{4a2}$, O or S;
  X$^{5a}$, X$^{6a}$ and X$^{7a}$ are independently N or CR$^{4a3}$;
  R$^{1b}$ is selected from the group consisting of:

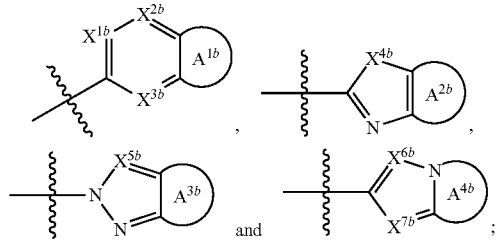

Ring A$^{1b}$, Ring A$^{2b}$, Ring A$^{3b}$ and Ring A$^{4b}$ are independently selected from the group consisting of:
  a monocyclic C$_{5-7}$ cycloalkyl substituted with R$^{3b1}$;
  a bicyclic C$_{6-12}$ cycloalkyl substituted with R$^{3b2}$;
  a 5-7 membered nitrogen-containing monocyclic heterocyclyl, wherein a nitrogen of the 5-7 membered nitrogen-containing monocyclic heterocyclyl is optionally substituted with R$^{3b3}$, wherein a carbon of the 5-7 membered nitrogen-containing monocyclic heterocyclyl is optionally substituted with R$^{3b4}$ or R$^{3b5}$, and wherein when R$^{3b5}$ is present, R$^{3b5}$ is attached at a carbon atom adjacent to a nitrogen of the 5-7 membered nitrogen-containing monocyclic heterocyclyl;
  a 6-12 membered nitrogen-containing bicyclic heterocyclyl, wherein a nitrogen of the 6-12 membered nitrogen-containing bicyclic heterocyclyl is optionally substituted with R$^{3b6}$; wherein a carbon of the 6-12 membered nitrogen-containing bicyclic heterocyclyl is optionally substituted with R$^{3b7}$ or R$^{3b8}$, and wherein R$^{3b8}$ is present, R$^{3b8}$ is attached at the carbon atom adjacent to a nitrogen of the 6-12 membered nitrogen-containing bicyclic heterocyclyl; and
  a 5-7 membered oxygen-containing monocyclic heterocyclyl substituted with R$^{3b9}$ or R$^{3b10}$; wherein R$^{3b10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens;
wherein Ring A$^{1b}$, Ring A$^{2b}$, Ring A$^{3b}$ and Ring A$^{4b}$ is optionally further substituted;

wherein when $R^{1b}$ is

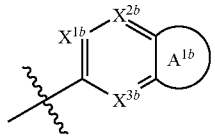

and Ring $A^{1b}$ is a 5-7 membered nitrogen-containing monocyclic heterocyclyl, then $R^{3b3}$ is present;
wherein when $R^{1b}$ is

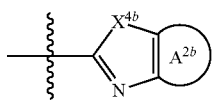

and Ring $A^{2b}$ is a 5-7 membered nitrogen-containing monocyclic heterocyclyl, then $R^{3b3}$ is present;
wherein when $R^{1b}$ is

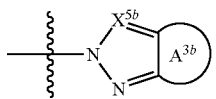

and Ring $A^{3b}$ is a 5-7 membered nitrogen-containing monocyclic heterocyclyl, then $R^{3b3}$ is present;
wherein when $R^{1b}$ is

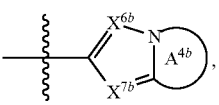

then Ring $A^{4b}$ cannot be a monocyclic $C_{5-7}$ cycloalkyl substituted with $R^{3b1}$ or a bicyclic $C_{6-12}$ cycloalkyl substituted with $R^{3b2}$; and
wherein when $R^{1b}$ is

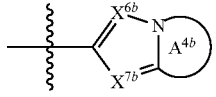

and Ring $A^{4b}$ is a 5-7 membered nitrogen-containing monocyclic heterocyclyl, then $R^{3b3}$ is optional;
$X^{1b}$, $X^{2b}$ and $X^{3b}$ are independently N or $CR^{4b1}$;
$X^{4b}$ is $NR^{4b2}$, O or S;
$X^{5b}$, $X^{6b}$ and $X^{7b}$ are independently N or $CR^{4b3}$;
$R^{3a1}$, $R^{3a2}$, $R^{3a9}$, $R^{3b1}$, $R^{3b2}$ and $R^{3b9}$ are independently selected from the group consisting of —OH, —N(R''')R'', —$C_{1-4}$ alkyl-N(R''')R'', —$OC_{2-4}$ alkyl-N(R''')R'',

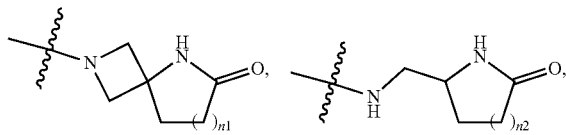

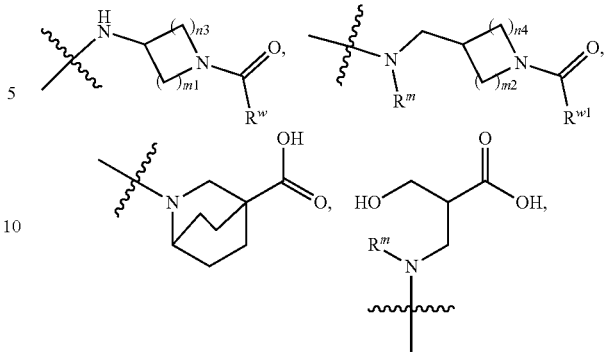

$R^{3a3}$, $R^{3b3}$, $R^{3a6}$ and $R^{3b6}$ are independently selected from the group consisting of —$R^{x1}$, —$C_{1-4}$ alkyl, —$C_{3-7}$ cycloalkyl, —C(=O)$C_{1-4}$ alkyl and -$Het^{a1}$, wherein the —$C_{3-7}$ cycloalkyl, the —C(=O)$C_{1-4}$alkyl and the -$Het^{a1}$ is optionally substituted with one or two or three substituents selected from the group consisting of -halogen, —$C_{1-4}$ alkyl, —OH, —N(R''')R'', —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R'', wherein the —$C_{1-4}$ alkyl is optionally substituted with one or two or three substituents selected from the group consisting of -halogen, —OH, —N(R''')R'', —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R'';
$R^{3a4}$, $R^{3a7}$, $R^{3b4}$ and $R^{3b7}$ are independently selected from the group consisting of -halogen, —$C_{1-4}$ alkyl, —$C_{3-7}$ cycloalkyl, —OH, —$OC_{1-4}$ alkyl, —N(R''')R'', —$C_{1-4}$ alkyl(R''')R'', —C(=O)OH, —$C_{1-4}$ alkyl-C(=O)OH, —C(=O)O$C_{1-4}$ alkyl and —$C_{1-4}$ alkyl-C(=O)O$C_{1-4}$ alkyl; wherein the —$C_{1-4}$ alkyl, is optionally substituted with one or two substituents selected from the group consisting of -halogen, —OH, —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R'', and wherein the —$C_{3-7}$ cycloalkyl and the —$OC_{1-4}$ alkyl is optionally substituted with one or two substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R'',
$R^{3a5}$, $R^{3a8}$, $R^{3b5}$ and $R^{3b8}$ are independently selected from the group consisting of —C(=O)OH, —$C_{1-4}$ alkyl and —$C_{3-7}$ cycloalkyl; wherein the —$C_{1-4}$ alkyl is optionally substituted with one or two or three substituents selected from the group consisting of -halogen, —OH, —$C_{1-4}$ alkoxy, —C(=O)OH, —C(=O)O$C_{1-4}$ alkyl, —C(=O)NHS(=O)$_2$ $C_{1-4}$ alkyl, —N(R''')C(=O)$C_{1-4}$ alkyl, —C(=O) N(R''')R'' and —N(R''')R'', and wherein the —$C_{3-7}$ cycloalkyl is optionally substituted with one or two or three substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2$C$_{1-4}$ alkyl, —N(R''')C(=O)C$_{1-4}$ alkyl, —C(=O) N(R''')R'' and —N(R''')R'';

R$^{3a10}$ and R$^{3b10}$ are independently selected from the group consisting of —C$_{1-4}$ alkyl, —C$_{3-7}$ cycloalkyl and —(C$_{1-4}$ alkyl)N(R''')R'', wherein the —C$_{1-4}$ alkyl is optionally substituted with one or two or three substituents selected from the group consisting of -halogen, —OH, —C$_{1-4}$ alkoxy, —C(=O)OH, —(C=O)NHS(=O)$_2$(C$_{1-4}$ alkyl) and —NHC(=O)C$_{1-4}$ alkyl, and wherein the —C$_{3-7}$ cycloalkyl and the —(C$_{1-4}$ alkyl)N(R''')R'' is optionally substituted with one or two or three substituents selected from the group consisting of -halogen, —OH, —C$_{1-4}$ alkyl, —C$_{1-4}$ alkoxy, —C(=O)OH, —C(=O)OC$_{1-4}$ alkyl, —(C=O)NHS(=O)$_2$ (C$_{1-4}$ alkyl) and —NHC(=O)C$_{1-4}$ alkyl;

each R''' and each R'' are independently selected from the group consisting of hydrogen, —R$^{x2}$, —C$_{1-4}$ alkyl, —C$_{3-7}$ cycloalkyl, —C(=O)C$_{1-4}$alkyl and -Het$^{a1}$, wherein the —C$_{1-4}$ alkyl, the —C$_{3-7}$ cycloalkyl and the —C(=O)C$_{1-4}$ alkyl is optionally substituted with one or two or three substituents selected from the group consisting of -halogen, —OH, —NH$_2$—C$_{1-4}$ alkyl, —OC$_{1-4}$ alkyl, —C(=O)OH, —C(=O)OC$_{1-4}$ alkyl, —C(=O)NHS(=O)$_2$C$_{1-4}$ alkyl and —NHC(=O)C$_{1-4}$ alkyl; or R''' and R'' are taken together along with the atom to which R''' and R'' are attached to form an optionally substituted 4-7 monocyclic heterocyclic ring or an optionally substituted 7-10 bicyclic heterocyclic ring;

R$^{x1}$ and R$^{x2}$ are independently selected from the group consisting of:

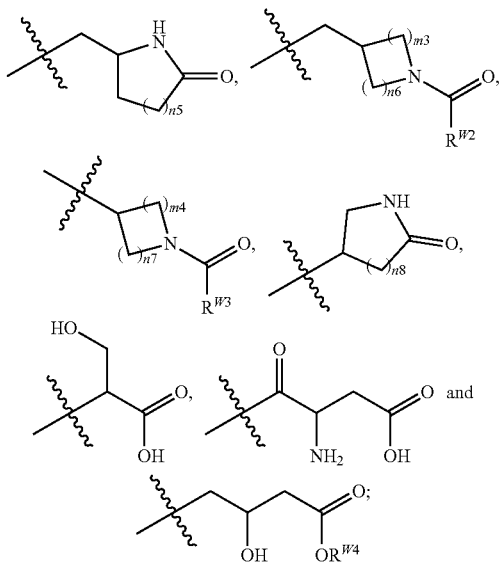

R$^W$, R$^{W1}$, R$^{W2}$, R$^{W3}$ and R$^{W4}$ are independently selected from the group consisting of an unsubstituted —C$_{1-4}$ alkyl and a substituted —C$_{1-4}$ alkyl substituted with one or two or three substituents selected from the group consisting of -halogen, —OH, —OC$_{1-4}$ alkyl, —C(=O)OH and —C(=O)OC$_{1-4}$ alkyl;

Het$^{a1}$ is an optionally substituted 5-, 6- or 7-membered monocyclic heteroaryl, an optionally substituted 4-, 5-, 6- or 7-membered monocyclic heterocyclyl, an optionally substituted fused 8-, 9-, 10- or 11-membered bicyclic heteroaryl or an optionally substituted fused 8-, 9-, 10- or 11-membered heterocyclyl, wherein each heteroaryl and each heterocyclyl contains at least one heteroatom independently selected from the group consisting of O, S, S(=O), S(=O)$_2$ and N;

n1, n2, n3, n4, n5, n6, n7 and n8 are independently 1 or 2;

m1, m2, m3 and m4 are independently 1 or 2;

R$^{2d}$ and R$^{2f}$ are independently selected from the group consisting of hydrogen, halogen, cyano, —CH$_3$, —CH$_2$CH$_3$, —CH$_2$OH, —OCH$_3$ and —SCH$_3$;

R$^{2a}$, R$^{2b}$, R$^{2c}$, R$^{2e}$, R$^{2g}$, R$^{2h}$ are independently selected from the group consisting of hydrogen and halogen;

R$^{4a1}$, R$^{4a3}$, R$^{4b1}$ and R$^{4b3}$ are selected from the group consisting of hydrogen, halogen, cyano, an unsubstituted C$_{1-4}$ alkyl, an unsubstituted C$_{1-4}$haloalkyl, an unsubstituted C$_{1-4}$ alkoxy and an unsubstituted C$_{1-4}$ haloalkoxy; and R$^{4a2}$ and R$^{4b2}$ are selected from the group consisting of hydrogen, an unsubstituted C$_{1-4}$ alkyl and an unsubstituted C$_{1-4}$ haloalkyl.

Embodiment 2

The compound of Embodiment 1, wherein R$^{1a}$ is

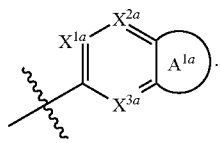

Embodiment 3

The compound of Embodiment 2, wherein Ring A$^{1a}$ is a monocyclic C$_{5-7}$ cycloalkyl substituted with R$^{3a1}$.

Embodiment 4

The compound of Embodiment 2, wherein Ring A$^{1a}$ is a bicyclic C$_{6-12}$ cycloalkyl substituted with R$^{3a2}$.

Embodiment 5

The compound of Embodiment 2, wherein Ring A$^{1a}$ is a 5-7 membered nitrogen-containing monocyclic heterocyclyl, wherein a nitrogen of the 5-7 membered nitrogen-containing monocyclic heterocyclyl is substituted with R$^{3a3}$, wherein a carbon of the 5-7 membered nitrogen-containing monocyclic heterocyclyl is optionally substituted with R$^{3a4}$ or R$^{3a5}$, and wherein when R$^{3a5}$ is present, R$^{3a5}$ is attached at a carbon atom adjacent to a nitrogen of the 5-7 membered nitrogen-containing monocyclic heterocyclyl.

Embodiment 6

The compound of Embodiment 2, wherein Ring A$^{1a}$ is a 6-12 membered nitrogen-containing bicyclic heterocyclyl, wherein a nitrogen of the 6-12 membered nitrogen-containing bicyclic heterocyclyl is optionally substituted with R$^{3a6}$; wherein a carbon of the 6-12 membered nitrogen-containing bicyclic heterocyclyl is optionally substituted with R$^{3a7}$ or R$^{3a8}$, and wherein R$^{3a8}$ is present, R$^{3a8}$ is attached at the carbon atom adjacent to a nitrogen of the 6-12 membered nitrogen-containing bicyclic heterocyclyl.

Embodiment 7

The compound of Embodiment 2, wherein Ring A$^{1a}$ is a 5-7 membered oxygen-containing monocyclic heterocyclyl substituted with $R^{3a9}$ or $R^{3a10}$; wherein $R^{3a10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 8

The compound of any one of Embodiments 2-7, wherein $X^{1a}$ is N.

Embodiment 9

The compound of any one of Embodiments 2-7, wherein $X^{1a}$ is $CR^{4a1}$.

Embodiment 10

The compound of any one of Embodiments 2-9, wherein $X^{2a}$ is N.

Embodiment 11

The compound of any one of Embodiments 2-9, wherein $X^{2a}$ is $CR^{4a1}$.

Embodiment 12

The compound of any one of Embodiments 2-11, wherein $X^{3a}$ is N.

Embodiment 13

The compound of any one of Embodiments 2-11, wherein $X^{3a}$ is $CR^{4a1}$.

Embodiment 14

The compound of Embodiment 9, 11 or 13, wherein $R^{4a1}$ is hydrogen.

Embodiment 15

The compound of Embodiment 9, 11 or 13, wherein $R^{4a1}$ is halogen.

Embodiment 16

The compound of Embodiment 9, 11 or 13, wherein $R^{4a1}$ is cyano.

Embodiment 17

The compound of Embodiment 9, 11 or 13, wherein $R^{4a1}$ is an unsubstituted $C_{1-4}$ alkyl.

Embodiment 18

The compound of Embodiment 9, 11 or 13, wherein $R^{4a1}$ is an unsubstituted $C_{1-4}$ haloalkyl.

Embodiment 19

The compound of Embodiment 9, 11 or 13, wherein $R^{4a1}$ is an unsubstituted $C_{1-4}$ alkoxy, such as methoxy.

Embodiment 20

The compound of Embodiment 9, 11 or 13, wherein $R^{4a1}$ is an unsubstituted $C_{1-4}$ haloalkoxy.

Examples of

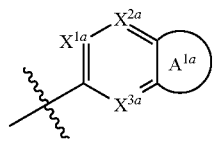

include, but are not limited to, the following:

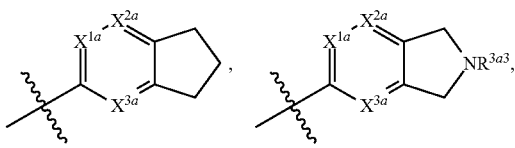

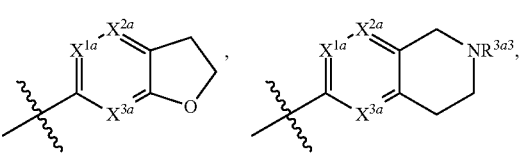

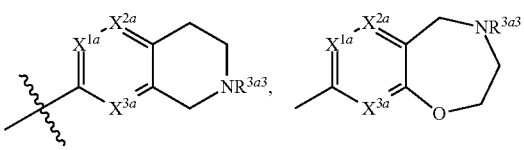

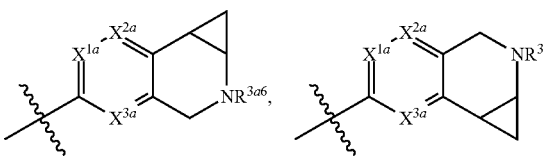

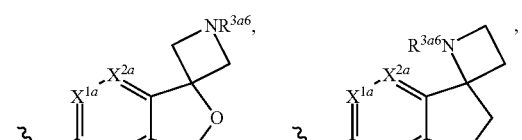

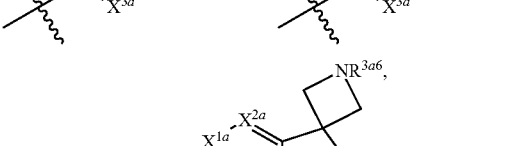

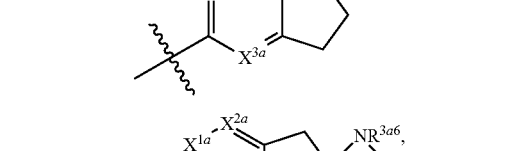

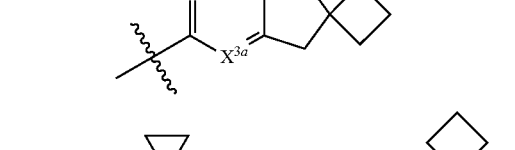

-continued

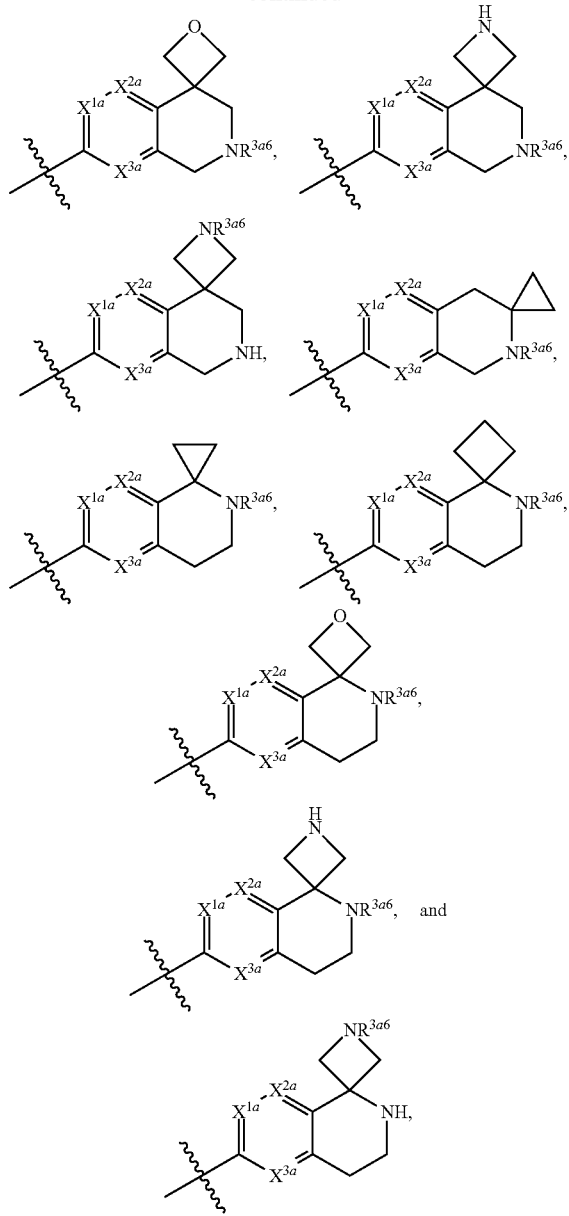

wherein each of shown rings can be further substituted, including replacing the hydrogen of the shown NH moiety.

Embodiment 21

The compound of Embodiment 1, wherein $R^{1a}$ is

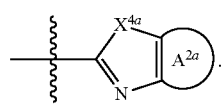

Embodiment 22

The compound of Embodiment 21, wherein Ring $A^{2a}$ is a monocyclic $C_{5-7}$ cycloalkyl substituted with $R^{3a1}$.

Embodiment 23

The compound of Embodiment 21, wherein Ring $A^{2a}$ is a bicyclic $C_{6-12}$ cycloalkyl substituted with $R^{3a2}$.

Embodiment 24

The compound of Embodiment 21, wherein Ring $A^{2a}$ is a 5-7 membered nitrogen-containing monocyclic heterocyclyl, wherein a nitrogen of the 5-7 membered nitrogen-containing monocyclic heterocyclyl is substituted with $R^{3a3}$, wherein a carbon of the 5-7 membered nitrogen-containing monocyclic heterocyclyl is optionally substituted with $R^{3a4}$ or $R^{3a5}$, and wherein when $R^{3a5}$ is present, $R^{3a5}$ is attached at a carbon atom adjacent to a nitrogen of the 5-7 membered nitrogen-containing monocyclic heterocyclyl.

Embodiment 25

The compound of Embodiment 21, wherein Ring $A^{2a}$ is a 6-12 membered nitrogen-containing bicyclic heterocyclyl, wherein a nitrogen of the 6-12 membered nitrogen-containing bicyclic heterocyclyl is optionally substituted with $R^{3a6}$; wherein a carbon of the 6-12 membered nitrogen-containing bicyclic heterocyclyl is optionally substituted with $R^{3a7}$ or $R^{3a8}$, and wherein $R^{3a8}$ is present, $R^{3a8}$ is attached at the carbon atom adjacent to a nitrogen of the 6-12 membered nitrogen-containing bicyclic heterocyclyl.

Embodiment 26

The compound of Embodiment 21, wherein Ring $A^{2a}$ is a 5-7 membered oxygen-containing monocyclic heterocyclyl substituted with $R^{3a9}$ or $R^{3a10}$; wherein $R^{3a10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 27

The compound of any one of Embodiments 21-26, wherein $X^{4a}$ is $NR^{4a2}$.

Embodiment 28

The compound of Embodiment 27, wherein $R^{4a2}$ is hydrogen.

Embodiment 29

The compound of Embodiment 27, wherein $R^{4a2}$ is an unsubstituted $C_{1-4}$ alkyl.

Embodiment 30

The compound of Embodiment 27, wherein $R^{4a2}$ is an unsubstituted $C_{1-4}$ haloalkyl.

Embodiment 31

The compound of any one of Embodiments 21-26, wherein $X^{4a}$ is O.

Embodiment 32

The compound of any one of Embodiments 21-26, wherein $X^{4a}$ is S.

Non-limiting examples of

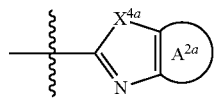

include the following:

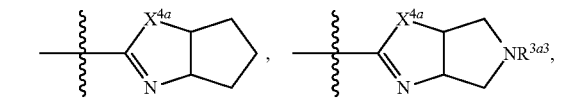

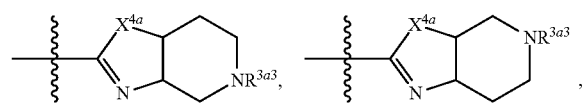

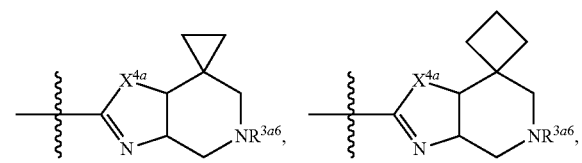

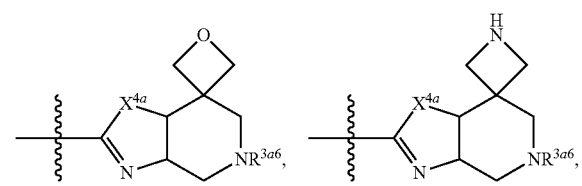

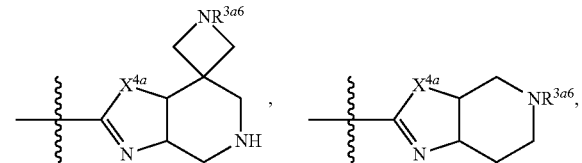

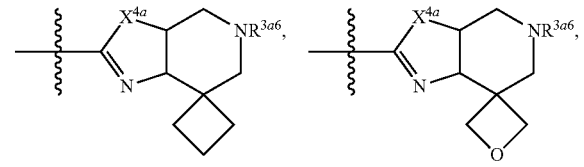

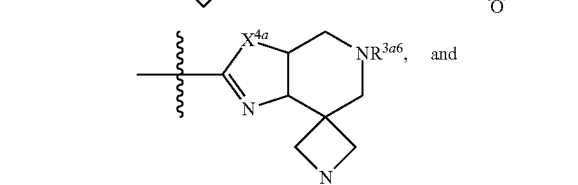

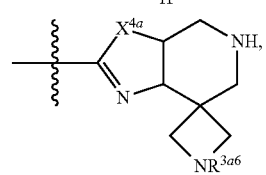

wherein each of shown rings can be further substituted, including replacing the hydrogen of the shown NH moiety.

Embodiment 33

The compound of Embodiment 1, wherein $R^{1a}$ is

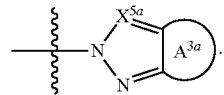

Embodiment 34

The compound of Embodiment 33, wherein Ring $A^{3a}$ is a monocyclic $C_{5-7}$ cycloalkyl substituted with $R^{3a1}$.

Embodiment 35

The compound of Embodiment 33, wherein Ring $A^{3a}$ is a bicyclic $C_{6-12}$ cycloalkyl substituted with $R^{3a2}$.

Embodiment 36

The compound of Embodiment 33, wherein Ring $A^{3a}$ is a 5-7 membered nitrogen-containing monocyclic heterocyclyl, wherein a nitrogen of the 5-7 membered nitrogen-containing monocyclic heterocyclyl is substituted with $R^{3a3}$, wherein a carbon of the 5-7 membered nitrogen-containing monocyclic heterocyclyl is optionally substituted with $R^{3a4}$ or $R^{3a5}$, and wherein when $R^{3a5}$ is present, $R^{3a5}$ is attached at a carbon atom adjacent to a nitrogen of the 5-7 membered nitrogen-containing monocyclic heterocyclyl.

Embodiment 37

The compound of Embodiment 33, wherein Ring $A^{3a}$ is a 6-12 membered nitrogen-containing bicyclic heterocyclyl, wherein a nitrogen of the 6-12 membered nitrogen-containing bicyclic heterocyclyl is optionally substituted with $R^{3a6}$; wherein a carbon of the 6-12 membered nitrogen-containing bicyclic heterocyclyl is optionally substituted with $R^{3a7}$ or $R^{3a5}$, and wherein $R^{3a8}$ is present, $R^{3a8}$ is attached at the carbon atom adjacent to a nitrogen of the 6-12 membered nitrogen-containing bicyclic heterocyclyl.

Embodiment 38

The compound of Embodiment 33, wherein Ring $A^{3a}$ is a 5-7 membered oxygen-containing monocyclic heterocyclyl substituted with $R^{3a9}$ or $R^{3a10}$; wherein $R^{3a10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 39

The compound of any one of Embodiments 33-38, wherein $X^{5a}$ is N.

Embodiment 40

The compound of any one of Embodiments 33-38, wherein $X^{5a}$ is $CR^{4a3}$.

Embodiment 41

The compound of Embodiment 40, wherein $R^{4a3}$ is halogen.

Embodiment 42

The compound of Embodiment 40, wherein $R^{4a3}$ is cyano.

Embodiment 43

The compound of Embodiment 40, wherein $R^{4a3}$ is an unsubstituted $C_{1-4}$ alkyl.

Embodiment 44

The compound of Embodiment 40, wherein $R^{4a3}$ is an unsubstituted $C_{1-4}$ haloalkyl.

Embodiment 45

The compound of Embodiment 40, wherein $R^{4a3}$ is an unsubstituted $C_{1-4}$ alkoxy, such as methoxy.

Embodiment 46

The compound of Embodiment 40, wherein $R^{4a3}$ is an unsubstituted $C_{1-4}$ haloalkoxy.

Exemplary

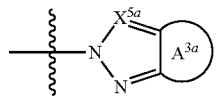

groups include, but are not limited to, the following:

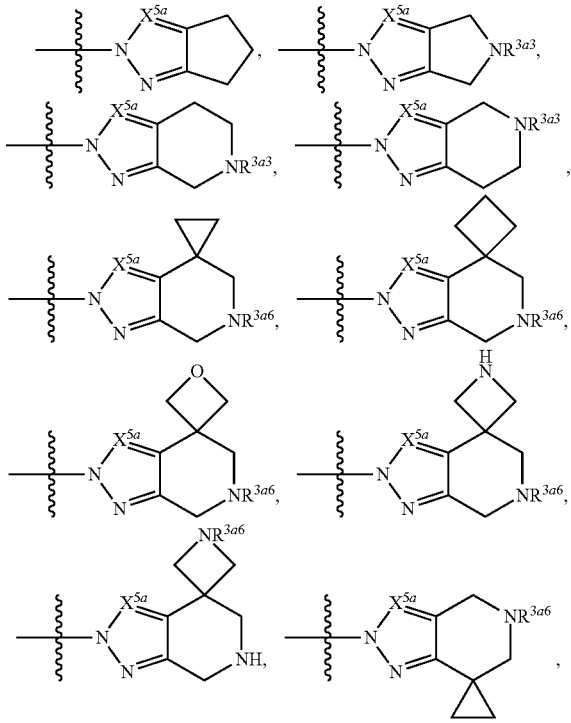

wherein each of shown rings can be further substituted, including replacing the hydrogen of the shown NH moiety.

Embodiment 47

The compound of Embodiment 1, wherein $R^{1a}$ is

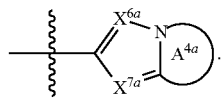

Embodiment 48

The compound of Embodiment 47, wherein Ring $A^{4a}$ is a 5-7 membered nitrogen-containing monocyclic heterocyclyl, wherein a nitrogen of the 5-7 membered nitrogen-containing monocyclic heterocyclyl is optionally substituted with $R^{3a3}$, wherein a carbon of the 5-7 membered nitrogen-containing monocyclic heterocyclyl is optionally substituted with $R^{3a4}$ or $R^{3a5}$, and wherein when $R^{3a5}$ is present, $R^{3a5}$ is attached at a carbon atom adjacent to a nitrogen of the 5-7 membered nitrogen-containing monocyclic heterocyclyl.

Embodiment 49

The compound of Embodiment 47, wherein Ring $A^{4a}$ is a 6-12 membered nitrogen-containing bicyclic heterocyclyl, wherein a nitrogen of the 6-12 membered nitrogen-containing bicyclic heterocyclyl is optionally substituted with $R^{3a6}$; wherein a carbon of the 6-12 membered nitrogen-containing bicyclic heterocyclyl is optionally substituted with $R^{3a7}$ or $R^{3a5}$, and wherein $R^{3a8}$ is present, $R^{3a8}$ is attached at the carbon atom adjacent to a nitrogen of the 6-12 membered nitrogen-containing bicyclic heterocyclyl.

Embodiment 50

The compound of Embodiment 47, wherein Ring $A^{4a}$ is a 5-7 membered oxygen-containing monocyclic heterocyclyl substituted with $R^{3a9}$ or $R^{3a10}$; wherein $R^{3a10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 51

The compound of any one of Embodiments 47-50, wherein $X^{6a}$ is N.

Embodiment 52

The compound of any one of Embodiments 47-50, wherein $X^{6a}$ is $CR^{4a3}$.

Embodiment 53

The compound of any one of Embodiments 47-52, wherein $X^{7a}$ is N.

Embodiment 54

The compound of any one of Embodiments 47-52, wherein $X^{7a}$ is $CR^{4a3}$.

Examples of include, but are not limited to, the following:

wherein each of shown rings can be further substituted, including replacing the hydrogen of the shown NH moiety.

Embodiment 55

The compound of Embodiment 3, 22 or 34, wherein $R^{3a1}$ is —OH.

Embodiment 56

The compound of Embodiment 3, 22 or 34, wherein $R^{3a1}$ is —N(R$^m$)R$^n$.

Embodiment 57

The compound of Embodiment 3, 22 or 34, wherein $R^{3a1}$ is —C$_{1-4}$ alkyl-N(R$^m$)R$^n$.

Embodiment 58

The compound of Embodiment 3, 22 or 34, wherein $R^{3a1}$ is —OC$_{2-4}$ alkyl-N(R$^m$)R$^n$.

Embodiment 59

The compound of Embodiment 3, 22 or 34, wherein $R^{3a1}$ is

Embodiment 60

The compound of Embodiment 59, wherein n1 is 1.

Embodiment 61

The compound of Embodiment 59, wherein n1 is 2.

Embodiment 62

The compound of Embodiment 3, 22 or 34, wherein $R^{3a1}$ is

Embodiment 63

The compound of Embodiment 62, wherein n2 is 1.

Embodiment 64

The compound of Embodiment 62, wherein n2 is 2.

Embodiment 65

The compound of Embodiment 3, 22 or 34, wherein $R^{3a1}$ is

Embodiment 66

The compound of Embodiment 65, wherein n3 is 1.

Embodiment 67

The compound of Embodiment 65, wherein n3 is 2.

Embodiment 68

The compound of any one of Embodiments 65-67, wherein m1 is 1.

Embodiment 69

The compound of any one of Embodiments 65-67, wherein m1 is 2.

Embodiment 70

The compound of any one of Embodiments 65-69, wherein $R^W$ is an unsubstituted —$C_{1-4}$ alkyl.

Embodiment 71

The compound of any one of Embodiments 65-69, wherein $R^W$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 72

The compound of Embodiment 3, 22 or 34, wherein $R^{3a1}$ is

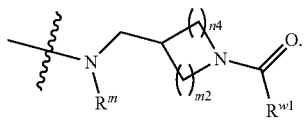

Embodiment 73

The compound of Embodiment 72, wherein n4 is 1.

Embodiment 74

The compound of Embodiment 72, wherein n4 is 2.

Embodiment 75

The compound of any one of Embodiments 72-74, wherein m2 is 1.

Embodiment 76

The compound of any one of Embodiments 72-74, wherein m2 is 2.

Embodiment 77

The compound of any one of Embodiments 72-76, wherein $R^{W1}$ is an unsubstituted —$C_{1-4}$ alkyl.

Embodiment 78

The compound of any one of Embodiments 72-76, wherein $R^{W1}$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 79

The compound of Embodiment 3, 22 or 34, wherein $R^{3a1}$ is

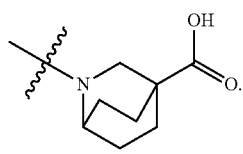 [SMILES: *N1CC2(C(=O)O)CCC1CC2]

Embodiment 80

The compound of Embodiment 3, 22 or 34, wherein $R^{3a1}$ is

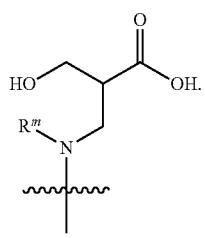

Embodiment 81

The compound of Embodiment 3, 22 or 34, wherein $R^{3a1}$ is

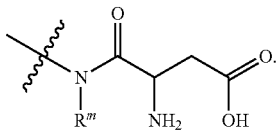

Embodiment 82

The compound of Embodiment 3, 22 or 34, wherein $R^{3a1}$ is

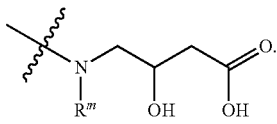

Embodiment 83

The compound of Embodiment 4, 23 or 35, wherein $R^{3a2}$ is —OH.

Embodiment 84

The compound of Embodiment 4, 23 or 35, wherein $R^{3a2}$ is —N(R$^m$)R$^n$.

Embodiment 85

The compound of Embodiment 4, 23 or 35, wherein $R^{3a2}$ is —C$_{1-4}$ alkyl-N(R$^m$)R$^n$.

Embodiment 86

The compound of Embodiment 4, 23 or 35, wherein $R^{3a2}$ is —OC$_{2-4}$ alkyl-N(R$^m$)R$^n$.

Embodiment 87

The compound of Embodiment 4, 23 or 35, wherein $R^{3a2}$ is

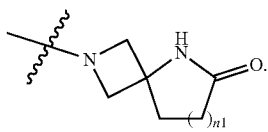

Embodiment 88

The compound of Embodiment 87, wherein n1 is 1.

Embodiment 89

The compound of Embodiment 87, wherein n1 is 2.

Embodiment 90

The compound of Embodiment 4, 23 or 35, wherein $R^{3a2}$ is

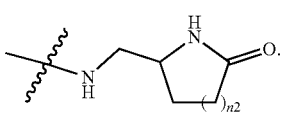

Embodiment 91

The compound of Embodiment 90, wherein n2 is 1.

Embodiment 92

The compound of Embodiment 90, wherein n2 is 2.

Embodiment 93

The compound of Embodiment 4, 23 or 35, wherein $R^{3a2}$ is

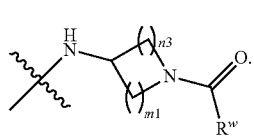

Embodiment 94

The compound of Embodiment 93, wherein n3 is 1.

Embodiment 95

The compound of Embodiment 93, wherein n3 is 2.

Embodiment 96

The compound of any one of Embodiments 93-95, wherein m1 is 1.

Embodiment 97

The compound of any one of Embodiments 93-95, wherein m1 is 2.

Embodiment 98

The compound of any one of Embodiments 93-97, wherein $R^W$ is an unsubstituted —C$_{1-4}$ alkyl.

Embodiment 99

The compound of any one of Embodiments 93-97, wherein $R^W$ is a substituted —C$_{1-4}$ alkyl substituted with one or two or three substituents selected from the group consisting of -halogen, —OH, —OC$_{1-4}$ alkyl, —C(=O)OH and —C(=O)OC$_{1-4}$ alkyl.

Embodiment 100

The compound of Embodiment 4, 23 or 35, wherein $R^{3a2}$ is

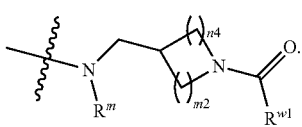

Embodiment 101

The compound of Embodiment 100, wherein n4 is 1.

Embodiment 102

The compound of Embodiment 100, wherein n4 is 2.

Embodiment 103

The compound of any one of Embodiments 100-102, wherein m2 is 1.

Embodiment 104

The compound of any one of Embodiments 100-102, wherein m2 is 2.

Embodiment 105

The compound of any one of Embodiments 100-104, wherein $R^{W1}$ is an unsubstituted —C$_{1-4}$ alkyl.

Embodiment 106

The compound of any one of Embodiments 100-104, wherein $R^{w1}$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 107

The compound of Embodiment 4, 23 or 35, wherein $R^{3a2}$ is

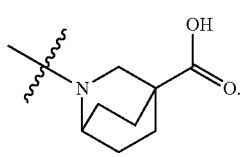 [SMILES: *N1CC2(C(=O)O)CCC1CC2]

Embodiment 108

The compound of Embodiment 4, 23 or 35, wherein $R^{3a2}$ is

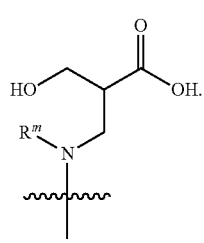

Embodiment 109

The compound of Embodiment 4, 23 or 35, wherein $R^{3a2}$ is

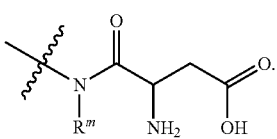

Embodiment 110

The compound of Embodiment 4, 23 or 35, wherein $R^{3a2}$ is

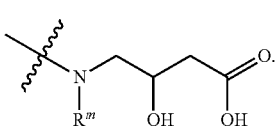

Embodiment 111

The compound of Embodiment 5, 24, 36 or 48, wherein $R^{3a3}$ is —$R^{x1}$.

Embodiment 112

The compound of Embodiment 109, wherein —$R^{x1}$ is

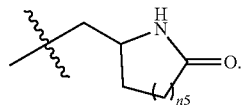

Embodiment 113

The compound of Embodiment 112, wherein n5 is 1.

Embodiment 114

The compound of Embodiment 112, wherein n5 is 2.

Embodiment 115

The compound of Embodiment 112, wherein —$R^{x1}$ is

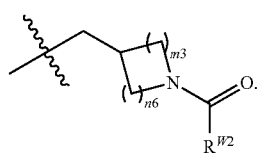

Embodiment 116

The compound of Embodiment 115, wherein n6 is 1.

Embodiment 117

The compound of Embodiment 115, wherein n6 is 2.

Embodiment 118

The compound of any one of Embodiments 115-117, wherein m3 is 1.

Embodiment 119

The compound of any one of Embodiments 115-117, wherein m3 is 2.

Embodiment 120

The compound of Embodiment 112, wherein —$R^{x1}$ is

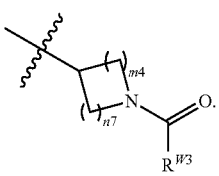

Embodiment 121

The compound of Embodiment 120, wherein n7 is 1.

Embodiment 122

The compound of Embodiment 120, wherein n7 is 2.

Embodiment 123

The compound of any one of Embodiments 120-122, wherein m4 is 1.

Embodiment 124

The compound of any one of Embodiments 120-122, wherein m4 is 2.

Embodiment 125

The compound of Embodiment 112, wherein —$R^{x1}$ is

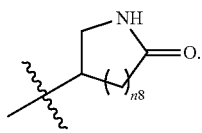

Embodiment 126

The compound of Embodiment 125, wherein n8 is 1.

Embodiment 127

The compound of Embodiment 125, wherein n8 is 2.

Embodiment 128

The compound of Embodiment 112, wherein —$R^{x1}$ is

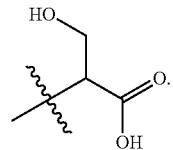

Embodiment 129

The compound of Embodiment 112, wherein —$R^{x1}$ is

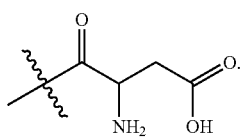

Embodiment 130

The compound of Embodiment 112, wherein —$R^{x1}$ is

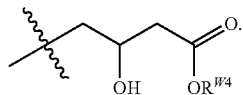

Embodiment 131

The compound of Embodiment 5, 24, 36 or 48, wherein $R^{3a3}$ is —$C_{1-4}$ alkyl, wherein the —$C_{1-4}$ alkyl is optionally substituted with one or two or three substituents selected from the group consisting of -halogen, —OH, —N(R''')R'', —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$alkyl and —C(=O)N(R''')R''.

Embodiment 132

The compound of Embodiment 5, 24, 36 or 48, wherein $R^{3a3}$ is —$C_{3-7}$ cycloalkyl, wherein the —$C_{3-7}$ cycloalkyl is optionally substituted with one or two or three substituents selected from the group consisting of -halogen, —$C_{1-4}$ alkyl, —OH, —N(R''')R'', —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$alkyl and —C(=O)N(R''')R''.

Embodiment 133

The compound of Embodiment 5, 24, 36 or 48, wherein $R^{3a3}$ is —C(=O)$C_{1-4}$alkyl, wherein the —C(=O)$C_{1-4}$alkyl is optionally substituted with one or two or three substituents selected from the group consisting of -halogen, —OH, —N(R''')R'', —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R''.

Embodiment 134

The compound of Embodiment 5, 24, 36 or 48, wherein $R^{3a3}$ is -Het$^{a1}$, wherein the -Het$^{a1}$ is optionally substituted with one or two or three substituents selected from the group consisting of -halogen, —OH, —N(R''')R'', —$C_{1-4}$ alkoxy, —C(=O)OH, —C(=O)O$C_{1-4}$ alkyl, —C(=O)NHS(=O)$_2$ $C_{1-4}$ alkyl, —NHC(=O)$C_{1-4}$ alkyl and —C(=O)N(R''')R''.

Embodiment 135

The compound of Embodiment 6, 25, 37 or 49, wherein $R^{3a6}$ is —$R^{x1}$.

Embodiment 136

The compound of Embodiment 135, wherein —$R^{x1}$ is

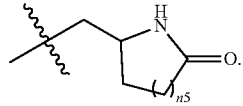

Embodiment 137

The compound of Embodiment 136, wherein n5 is 1.

Embodiment 138

The compound of Embodiment 136, wherein n5 is 2.

Embodiment 139

The compound of Embodiment 135, wherein —$R^{x1}$ is

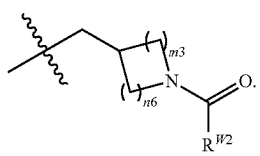

Embodiment 140

The compound of Embodiment 139, wherein n6 is 1.

Embodiment 141

The compound of Embodiment 139, wherein n6 is 2.

Embodiment 142

The compound of any one of Embodiments 139-141, wherein m3 is 1.

Embodiment 143

The compound of any one of Embodiments 139-141, wherein m3 is 2.

Embodiment 144

The compound of Embodiment 135, wherein —$R^{x1}$ is

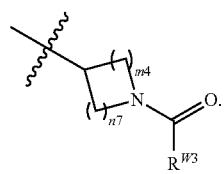

Embodiment 145

The compound of Embodiment 144, wherein n7 is 1.

Embodiment 146

The compound of Embodiment 144, wherein n7 is 2.

Embodiment 147

The compound of any one of Embodiments 144-146, wherein m4 is 1.

Embodiment 148

The compound of any one of Embodiments 144-146, wherein m4 is 2.

Embodiment 149

The compound of Embodiment 135, wherein —$R^{x1}$ is

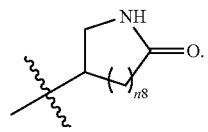

Embodiment 150

The compound of Embodiment 149, wherein n8 is 1.

Embodiment 151

The compound of Embodiment 149, wherein n8 is 2.

Embodiment 152

The compound of Embodiment 135, wherein —$R^{x1}$ is

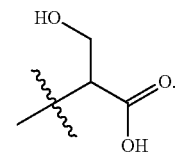 [SMILES: *C(CO)C(=O)O]

Embodiment 153

The compound of Embodiment 135, wherein —$R^{x1}$ is

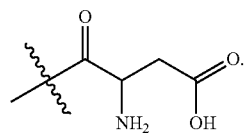 [SMILES: *C(=O)C(N)CC(=O)O]

Embodiment 154

The compound of Embodiment 135, wherein —$R^{x1}$ is

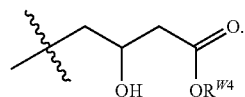

Embodiment 155

The compound of Embodiment 6, 25, 37 or 49, wherein $R^{3a6}$ is —$C_{1-4}$ alkyl, wherein the —$C_{1-4}$ alkyl is optionally substituted with one or two or three substituents selected from the group consisting of -halogen, —OH, —N(R''')R'', —$C_{1-4}$ alkoxy, —$C(=O)OH$, —$C(=O)OC_{1-4}$ alkyl, —$C(=O)NHS(=O)_2C_{1-4}$ alkyl, —$NHC(=O)C_{1-4}$alkyl and —$C(=O)N(R^m)R^n$.

Embodiment 156

The compound of Embodiment 6, 25, 37 or 49, wherein $R^{3a6}$ is —$C_{3-7}$ cycloalkyl, wherein the —$C_{3-7}$ cycloalkyl is optionally substituted with one or two or three substituents selected from the group consisting of -halogen, —$C_{1-4}$ alkyl, —OH, —$N(R^m)R^n$, —$C_{1-4}$ alkoxy, —$C(=O)OH$, —$C(=O)OC_{1-4}$ alkyl, —$C(=O)NHS(=O)_2C_{1-4}$ alkyl, —$NHC(=O)C_{1-4}$alkyl and —$C(=O)N(R^m)R^n$.

Embodiment 157

The compound of Embodiment 6, 25, 37 or 49, wherein $R^{3a6}$ is —$C(=O)C_{1-4}$alkyl, wherein the —$C(=O)C_{1-4}$alkyl is optionally substituted with one or two or three substituents selected from the group consisting of -halogen, —OH, —$N(R^m)R^n$, —$C_{1-4}$ alkoxy, —$C(=O)OH$, —$C(=O)OC_{1-4}$ alkyl, —$C(=O)NHS(=O)_2C_{1-4}$ alkyl, —$NHC(=O)C_{1-4}$ alkyl and —$C(=O)N(R^m)R^n$.

Embodiment 158

The compound of Embodiment 6, 25, 37 or 49, wherein $R^{3a6}$ is -Het$^{a1}$, wherein the -Het$^{a1}$ is optionally substituted with one or two or three substituents selected from the group consisting of -halogen, —OH, —$N(R^m)R^n$, —$C_{1-4}$ alkoxy, —$C(=O)OH$, —$C(=O)OC_{1-4}$ alkyl, —$C(=O)NHS(=O)_2C_{1-4}$ alkyl, —$NHC(=O)C_{1-4}$ alkyl and —$C(=O)N(R^m)R^n$.

Embodiment 159

The compound of Embodiment 7, 26, 38 or 50, wherein $R^{3a9}$ is —OH.

Embodiment 160

The compound of Embodiment 7, 26, 38 or 50, wherein $R^{3a9}$ is —$N(R^m)R^n$.

Embodiment 161

The compound of Embodiment 7, 26, 38 or 50, wherein $R^{3a9}$ is —$C_{1-4}$ alkyl-$N(R^m)R^n$.

Embodiment 162

The compound of Embodiment 7, 26, 38 or 50, wherein $R^{3a9}$ is —$OC_{2-4}$ alkyl-$N(R^m)R^n$.

Embodiment 163

The compound of Embodiment 7, 26, 38 or 50, wherein $R^{3a9}$ is

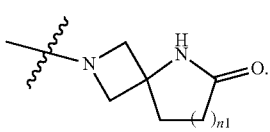

Embodiment 164

The compound of Embodiment 163, wherein n1 is 1.

Embodiment 165

The compound of Embodiment 163, wherein n1 is 2.

Embodiment 166

The compound of Embodiment 7, 26, 38 or 50, wherein $R^{3a9}$ is

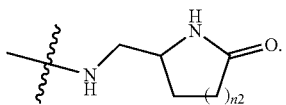

Embodiment 167

The compound of Embodiment 166, wherein n2 is 1.

Embodiment 168

The compound of Embodiment 166, wherein n2 is 2.

Embodiment 169

The compound of Embodiment 7, 26, 38 or 50, wherein $R^{3a9}$ is

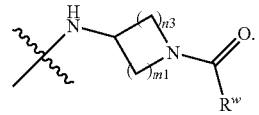

Embodiment 170

The compound of Embodiment 169, wherein n3 is 1.

Embodiment 171

The compound of Embodiment 169, wherein n3 is 2.

Embodiment 172

The compound of any one of Embodiments 169-171, wherein m1 is 1.

Embodiment 173

The compound of any one of Embodiments 169-171, wherein m1 is 2.

Embodiment 174

The compound of any one of Embodiments 169-173, wherein $R^W$ is an unsubstituted —$C_{1-4}$ alkyl.

Embodiment 175

The compound of any one of Embodiments 169-173, wherein $R^W$ is a substituted —$C_{1-4}$ alkyl substituted with one or two or three substituents selected from the group consisting of -halogen, —OH, —OC$_{1-4}$ alkyl, —C(=O)OH and —C(=O)OC$_{1-4}$ alkyl.

Embodiment 176

The compound of Embodiment 7, 26, 38 or 50, wherein R$^{3a9}$ is

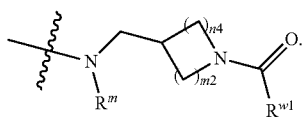

Embodiment 177

The compound of Embodiment 176, wherein n4 is 1.

Embodiment 178

The compound of Embodiment 176, wherein n4 is 2.

Embodiment 179

The compound of any one of Embodiments 176-178, wherein m2 is 1.

Embodiment 180

The compound of any one of Embodiments 176-178, wherein m2 is 2.

Embodiment 181

The compound of any one of Embodiments 176-180, wherein R$^{W1}$ is an unsubstituted —C$_{1-4}$ alkyl.

Embodiment 182

The compound of any one of Embodiments 176-180, wherein R$^{W1}$ is a substituted —C$_{1-4}$ alkyl substituted with one or two or three substituents selected from the group consisting of -halogen, —OH, —OC$_{1-4}$ alkyl, —C(=O)OH and —C(=O)OC$_{1-4}$ alkyl.

Embodiment 183

The compound of Embodiment 7, 26, 38 or 50, wherein R$^{3a9}$ is

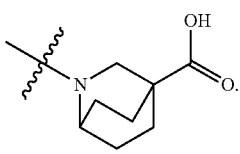 [SMILES: *N1CC2(C(=O)O)CCC1CC2]

Embodiment 184

The compound of Embodiment 7, 26, 38 or 50, wherein R$^{3a9}$ is

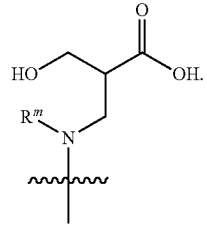

Embodiment 185

The compound of Embodiment 7, 26, 38 or 50, wherein R$^{3a9}$ is

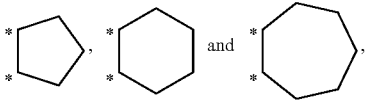

Embodiment 186

The compound of Embodiment 7, 26, 38 or 50, wherein R$^{3a9}$ is

Embodiment 187

The compound of Embodiment 3, 22 or 34, wherein the monocyclic C$_{5-7}$ cycloalkyl substituted with R$^{3a1}$ is selected from the group consisting of:

wherein asterisks indicate the position of the fused bond.

Embodiment 188

The compound of Embodiment 4, 23 or 35, wherein the bicyclic C$_{6-12}$ cycloalkyl substituted with R$^{3a2}$ is

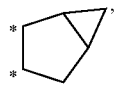

Embodiment 189

The compound of Embodiment 5, 24, 36 or 48, wherein the 5-7 membered nitrogen-containing monocyclic heterocyclyl, wherein a nitrogen of the 5-7 membered nitrogen-containing monocyclic heterocyclyl is optionally substituted with $R^{3a3}$, wherein a carbon of the 5-7 membered nitrogen-containing monocyclic heterocyclyl is optionally substituted with $R^{3a4}$ or $R^{3a5}$, and wherein when $R^{3a5}$ is present, $R^{3a5}$ is attached at a carbon atom adjacent to a nitrogen of the 5-7 membered nitrogen-containing monocyclic heterocyclyl is selected from the group consisting of:

wherein asterisks indicate the position of the fused bond, and $R^{3a4}$ and $R^{3a5}$ are each optionally present.

Embodiment 190

The compound of Embodiment 6, 25, 37 or 49, wherein the 6-12 membered nitrogen-containing bicyclic heterocyclyl, wherein a nitrogen of the 6-12 membered nitrogen-containing bicyclic heterocyclyl is optionally substituted with $R^{3a6}$; wherein a carbon of the 6-12 membered nitrogen-containing bicyclic heterocyclyl is optionally substituted with $R^{3a7}$ or $R^{3a8}$, and wherein $R^{3a8}$ is present, $R^{3a8}$ is attached at the carbon atom adjacent to a nitrogen of the 6-12 membered nitrogen-containing bicyclic heterocyclyl is selected from the group consisting of:

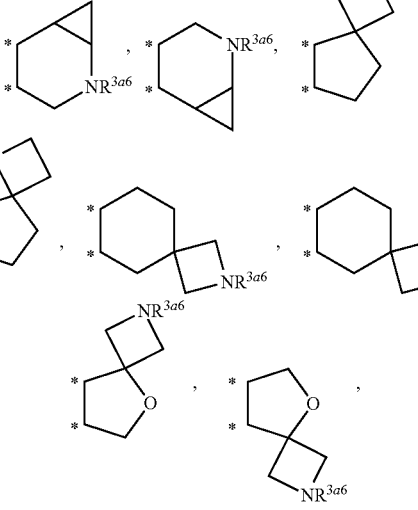
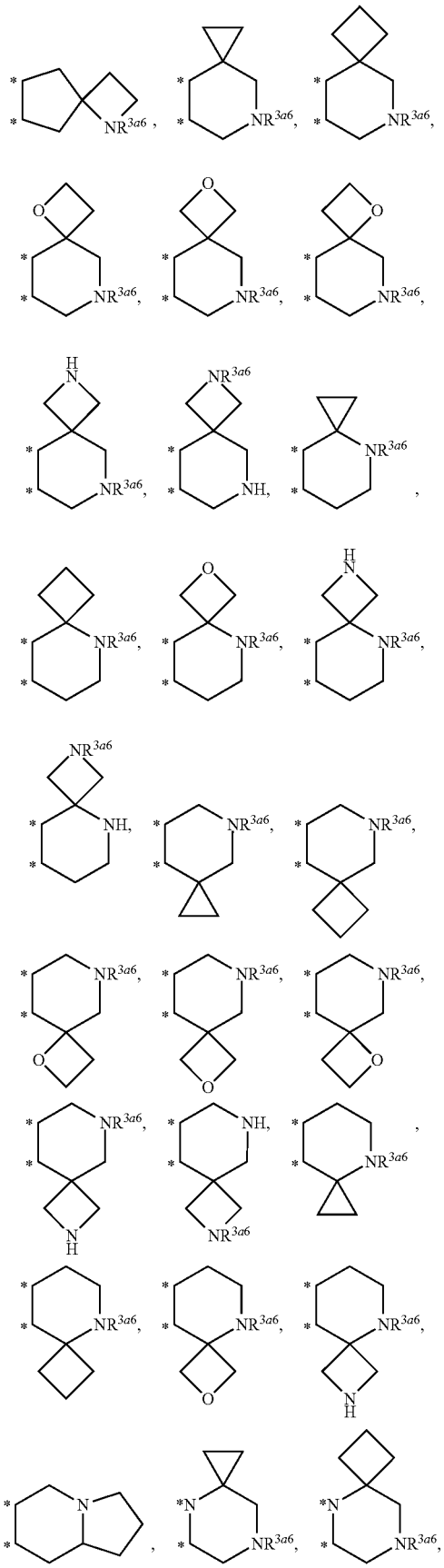

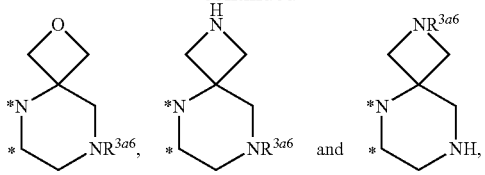

wherein asterisks indicate the position of the fused bond, $R^{3a7}$ and $R^{3a8}$ are each optionally present, and each of shown rings can be further substituted, including replacing the hydrogen of the shown NH moiety.

Embodiment 191

The compound of Embodiment 7, 26, 38 or 50, wherein the 5-7 membered oxygen-containing monocyclic heterocyclyl substituted with $R^{3a9}$ or $R^{3a10}$; wherein $R^{3a10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens is selected from the group consisting of:

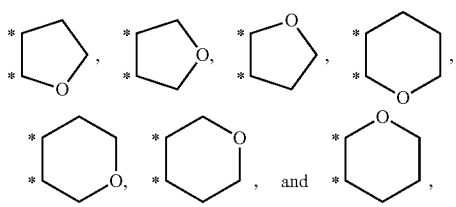

wherein asterisks indicate the position of the fused bond, and $R^{3a9}$ or $R^{3a10}$ is present.

Embodiment 192

The compound of Embodiment 5, 24, 36 or 48, wherein $R^{3a4}$ is -halogen.

Embodiment 193

The compound of Embodiment 5, 24, 36 or 48, wherein $R^{3a4}$ is —$C_{1-4}$ alkyl, wherein —$C_{1-4}$ alkyl, is optionally substituted with one or two substituents selected from the group consisting of -halogen, —OH, —$C_{1-4}$ alkoxy, —C(=O)OH, —C(=O)O$C_{1-4}$ alkyl, —C(=O)NHS(=O)$_2$$C_{1-4}$ alkyl, —NHC(=O)$C_{1-4}$ alkyl and —C(=O)N(R''')R''.

Embodiment 194

The compound of Embodiment 5, 24, 36 or 48, wherein $R^{3a4}$ is —$C_{3-7}$ cycloalkyl, wherein the —$C_{3-7}$ cycloalkyl is optionally substituted with one or two substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2$$C_{1-4}$ alkyl, —NHC(=O)$C_{1-4}$ alkyl and —C(=O)N(R''')R''.

Embodiment 195

The compound of Embodiment 5, 24, 36 or 48, wherein $R^{3a4}$ is —OH.

Embodiment 196

The compound of Embodiment 5, 24, 36 or 48, wherein $R^{3a4}$ is —O$C_{1-4}$ alkyl, wherein the —O$C_{1-4}$ alkyl is optionally substituted with one or two substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2$$C_{1-4}$ alkyl, —NHC(=O)$C_{1-4}$ alkyl and —C(=O)N(R''')R''.

Embodiment 197

The compound of Embodiment 5, 24, 36 or 48, wherein $R^{3a4}$ is —N(R''')R''.

Embodiment 198

The compound of Embodiment 5, 24, 36 or 48, wherein $R^{3a4}$ is —$C_{1-4}$ alkyl(R''')R''.

Embodiment 199

The compound of Embodiment 5, 24, 36 or 48, wherein $R^{3a4}$ is —C(=O)OH.

Embodiment 200

The compound of Embodiment 5, 24, 36 or 48, wherein $R^{3a4}$ is —$C_{1-4}$ alkyl-C(=O)OH.

Embodiment 201

The compound of Embodiment 5, 24, 36 or 48, wherein $R^{3a4}$ is —C(=O)O$C_{1-4}$ alkyl.

Embodiment 202

The compound of Embodiment 5, 24, 36 or 48, wherein $R^{3a4}$ is —$C_{1-4}$ alkyl-C(=O)O$C_{1-4}$ alkyl.

Embodiment 203

The compound of Embodiment 5, 24, 36 or 48, wherein $R^{3a5}$ is —C(=O)OH.

Embodiment 204

The compound of Embodiment 5, 24, 36 or 48, wherein $R^{3a5}$ is —$C_{1-4}$ alkyl, wherein the —$C_{1-4}$ alkyl is optionally substituted with one or two or three substituents selected from the group consisting of -halogen, —OH, —$C_{1-4}$ alkoxy, —C(=O)OH, —C(=O)O$C_{1-4}$ alkyl, —C(=O)NHS(=O)$_2$$C_{1-4}$ alkyl, —N(R''')C(=O)$C_{1-4}$ alkyl, —C(=O) N(R''')R'' and —N(R''')R''.

Embodiment 205

The compound of Embodiment 5, 24, 36 or 48, wherein $R^{3a5}$ is —$C_{3-7}$ cycloalkyl, wherein the —$C_{3-7}$ cycloalkyl is optionally substituted with one or two or three substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2$C$_{1-4}$ alkyl, —N(R$'''$)C(=O)C$_{1-4}$ alkyl, —C(=O) N(R$'''$)R$''$ and —N(R$'''$)R$''$.

Embodiment 206

The compound of Embodiment 6, 25, 37 or 49, wherein R$^{3a7}$ is -halogen.

Embodiment 207

The compound of Embodiment 6, 25, 37 or 49, wherein R$^{3a7}$ is —C$_{1-4}$ alkyl, wherein —C$_{1-4}$ alkyl, is optionally substituted with one or two substituents selected from the group consisting of -halogen, —OH, —C$_{1-4}$ alkoxy, —C(=O)OH, —C(=O)OC$_{1-4}$ alkyl, —C(=O)NHS(=O)$_2$ C$_{1-4}$ alkyl, —NHC(=O)C$_{1-4}$ alkyl and —C(=O)N(R$'''$)R$''$.

Embodiment 208

The compound of Embodiment 6, 25, 37 or 49, wherein R$^{3a7}$ is —C$_{3-7}$ cycloalkyl, wherein the —C$_{3-7}$ cycloalkyl is optionally substituted with one or two substituents selected from the group consisting of -halogen, —OH, —C$_{1-4}$ alkyl, —C$_{1-4}$ alkoxy, —C(=O)OH, —C(=O)OC$_{1-4}$ alkyl, —C(=O)NHS(=O)$_2$C$_{1-4}$ alkyl, —NHC(=O)C$_{1-4}$ alkyl and —C(=O)N(R$'''$)R$''$.

Embodiment 209

The compound of Embodiment 6, 25, 37 or 49, wherein R$^{3a7}$ is —OH.

Embodiment 210

The compound of Embodiment 6, 25, 37 or 49, wherein R$^{3a7}$ is —OC$_{1-4}$ alkyl, wherein the —OC$_{1-4}$ alkyl is optionally substituted with one or two substituents selected from the group consisting of -halogen, —OH, —C$_{1-4}$ alkyl, —C$_{1-4}$ alkoxy, —C(=O)OH, —C(=O)OC$_{1-4}$ alkyl, —C(=O)NHS(=O)$_2$C$_{1-4}$ alkyl, —NHC(=O)C$_{1-4}$ alkyl and —C(=O)N(R$'''$)R$''$.

Embodiment 211

The compound of Embodiment 6, 25, 37 or 49, wherein R$^{3a7}$ is —N(R$'''$)R$''$.

Embodiment 212

The compound of Embodiment 6, 25, 37 or 49, wherein R$^{3a7}$ is —C$_{1-4}$ alkyl(R$'''$)R$''$.

Embodiment 213

The compound of Embodiment 6, 25, 37 or 49, wherein R$^{3a7}$ is —C(=O)OH.

Embodiment 214

The compound of Embodiment 6, 25, 37 or 49, wherein R$^{3a7}$ is —C$_{1-4}$ alkyl-C(=O)OH.

Embodiment 215

The compound of Embodiment 6, 25, 37 or 49, wherein R$^{3a7}$ is —C(=O)OC$_{1-4}$ alkyl.

Embodiment 216

The compound of Embodiment 6, 25, 37 or 49, wherein R$^{3a7}$ is —C$_{1-4}$ alkyl-C(=O)OC$_{1-4}$ alkyl.

Embodiment 217

The compound of Embodiment 6, 25, 37 or 49, wherein R$^{3a8}$ is —C$_{1-4}$ alkyl, wherein the —C$_{1-4}$ alkyl is optionally substituted with one or two or three substituents selected from the group consisting of -halogen, —OH, —C$_{1-4}$ alkoxy, —C(=O)OH, —C(=O)OC$_{1-4}$ alkyl, —C(=O)NHS(=O)$_2$ C$_{1-4}$ alkyl, —N(R$'''$)C(=O)C$_{1-4}$ alkyl, —C(=O) N(R$'''$)R$''$ and —N(R$'''$)R$''$.

Embodiment 218

The compound of Embodiment 6, 25, 37 or 49, wherein R$^{3a8}$ is —C$_{3-7}$ cycloalkyl, wherein the —C$_{3-7}$ cycloalkyl is optionally substituted with one or two or three substituents selected from the group consisting of -halogen, —OH, —C$_{1-4}$ alkyl, —C$_{1-4}$ alkoxy, —C(=O)OH, —C(=O)OC$_{1-4}$ alkyl, —C(=O)NHS(=O)$_2$C$_{1-4}$ alkyl, —N(R$'''$)C(=O)C$_{1-4}$ alkyl, —C(=O) N(R$'''$)R$''$ and —N(R$'''$)R$''$.

Embodiment 219

The compound of Embodiment 7, 26, 38 or 50, wherein R$^{3a10}$ is —C$_{1-4}$ alkyl, wherein the —C$_{1-4}$ alkyl is optionally substituted with one or two or three substituents selected from the group consisting of -halogen, —OH, —C$_{1-4}$ alkoxy, —C(=O)OH, —C(=O)OC$_{1-4}$ alkyl, —(C=O)NHS(=O)$_2$ (C$_{1-4}$ alkyl) and —NHC(=O)C$_{1-4}$ alkyl.

Embodiment 220

The compound of Embodiment 7, 26, 38 or 50, wherein R$^{3a10}$ is —C$_{3-7}$ cycloalkyl, wherein the —C$_{3-7}$ cycloalkyl is optionally substituted with one or two or three substituents selected from the group consisting of -halogen, —OH, —C$_{1-4}$ alkyl, —C$_{1-4}$ alkoxy, —C(=O)OH, —C(=O)OC$_{1-4}$ alkyl, —(C=O)NHS(=O)$_2$(C$_{1-4}$ alkyl) and —NHC(=O) C$_{1-4}$ alkyl.

Embodiment 221

The compound of Embodiment 7, 26, 38 or 50, wherein R$^{3a10}$ is —(C$_{1-4}$ alkyl)N(R$'''$)R$''$, wherein the —(C$_{1-4}$ alkyl)N(R$'''$)R$''$ is optionally substituted with one or two or three substituents selected from the group consisting of -halogen, —OH, —C$_{1-4}$ alkyl, —C$_{1-4}$ alkoxy, —C(=O)OH, —C(=O)OC$_{1-4}$ alkyl, —(C=O)NHS(=O)$_2$(C$_{1-4}$ alkyl) and —NHC(=O)C$_{1-4}$ alkyl.

Embodiment 222

The compound of any one of Embodiments 1-221, wherein R$^{1b}$ is

Embodiment 223

The compound of Embodiment 222, wherein Ring $A^{1b}$ is a monocyclic $C_{5-7}$ cycloalkyl substituted with $R^{3b1}$.

Embodiment 224

The compound of Embodiment 222, wherein Ring $A^{1b}$ is a bicyclic $C_{6-12}$ cycloalkyl substituted with $R^{3b2}$.

Embodiment 225

The compound of Embodiment 222, wherein Ring $A^{1b}$ is a 5-7 membered nitrogen-containing monocyclic heterocyclyl, wherein a nitrogen of the 5-7 membered nitrogen-containing monocyclic heterocyclyl is substituted with $R^{3b3}$, wherein a carbon of the 5-7 membered nitrogen-containing monocyclic heterocyclyl is optionally substituted with $R^{3b4}$ or $R^{3b5}$, and wherein when $R^{3b5}$ is present, $R^{3b5}$ is attached at a carbon atom adjacent to a nitrogen of the 5-7 membered nitrogen-containing monocyclic heterocyclyl.

Embodiment 226

The compound of Embodiment 222, wherein Ring $A^{1b}$ is a 6-12 membered nitrogen-containing bicyclic heterocyclyl, wherein a nitrogen of the 6-12 membered nitrogen-containing bicyclic heterocyclyl is optionally substituted with $R^{3b6}$; wherein a carbon of the 6-12 membered nitrogen-containing bicyclic heterocyclyl is optionally substituted with $R^{3b7}$ or $R^{3b8}$, and wherein $R^{3b8}$ is present, $R^{3b8}$ is attached at the carbon atom adjacent to a nitrogen of the 6-12 membered nitrogen-containing bicyclic heterocyclyl.

Embodiment 227

The compound of Embodiment 222, wherein Ring $A^{1b}$ is a 5-7 membered oxygen-containing monocyclic heterocyclyl substituted with $R^{3b9}$ or $R^{3b10}$; wherein $R^{3b10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 228

The compound of any one of Embodiments 222-227, wherein $X^{1b}$ is N.

Embodiment 229

The compound of any one of Embodiments 222-227, wherein $X^{1b}$ is $CR^{4b1}$.

Embodiment 230

The compound of any one of Embodiments 222-229, wherein $X^{2b}$ is N.

Embodiment 231

The compound of any one of Embodiments 222-229, wherein $X^{2b}$ is $CR^{4b1}$.

Embodiment 232

The compound of any one of Embodiments 222-231, wherein $X^{3b}$ is N.

Embodiment 233

The compound of any one of Embodiments 222-231, wherein $X^{3b}$ is $CR^{4b1}$.

Embodiment 234

The compound of Embodiment 229, 231 or 233, wherein $R^{4b1}$ is hydrogen.

Embodiment 235

The compound of Embodiment 229, 231 or 233, wherein $R^{4b1}$ is halogen.

Embodiment 236

The compound of Embodiment 229, 231 or 233, wherein $R^{4b1}$ is cyano.

Embodiment 237

The compound of Embodiment 229, 231 or 233, wherein $R^{4b1}$ is an unsubstituted $C_{1-4}$ alkyl.

Embodiment 238

The compound of Embodiment 229, 231 or 233, wherein $R^{4b1}$ is an unsubstituted $C_{1-4}$ haloalkyl.

Embodiment 239

The compound of Embodiment 229, 231 or 233, wherein $R^{4b1}$ is an unsubstituted $C_{1-4}$ alkoxy, such as methoxy.

Embodiment 240

The compound of Embodiment 229, 231 or 233, wherein $R^{4b1}$ is an unsubstituted $C_{1-4}$ haloalkoxy.

Examples of

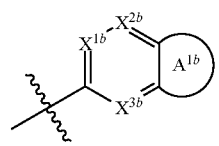

include, but are not limited to, the following:

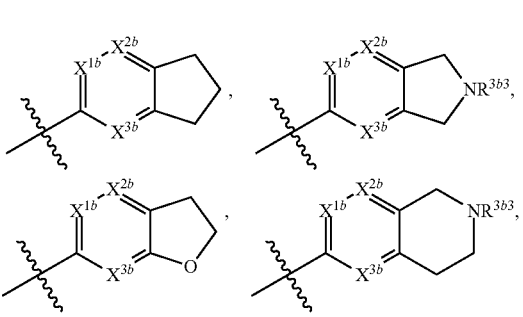

-continued

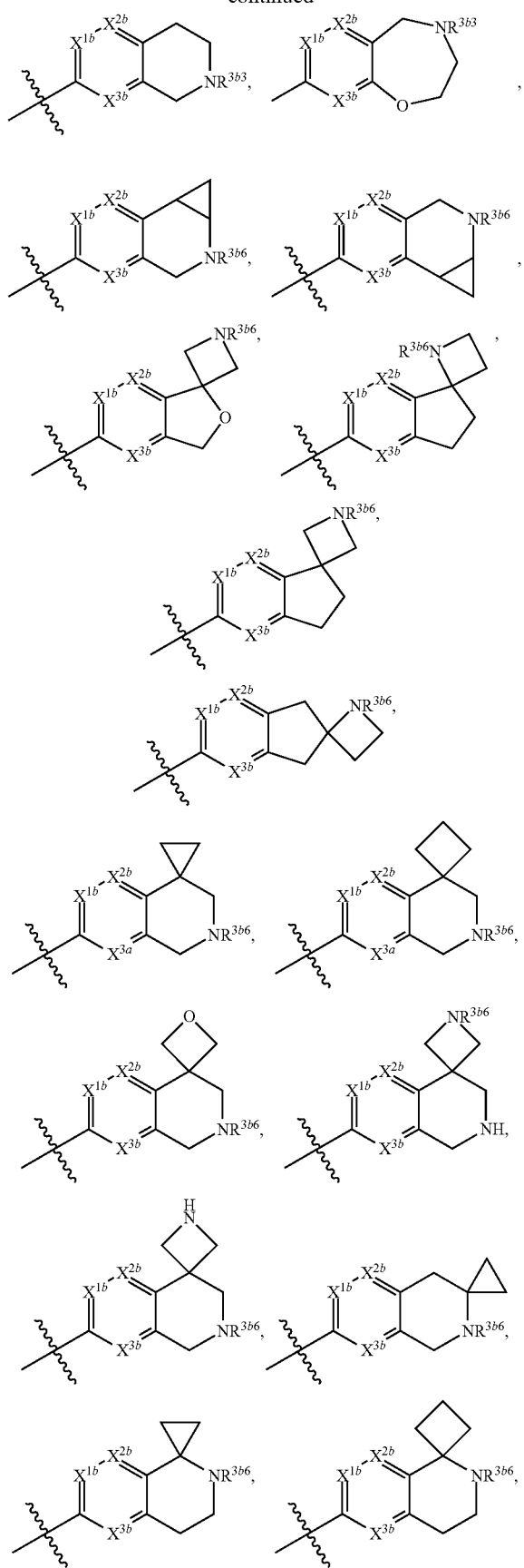

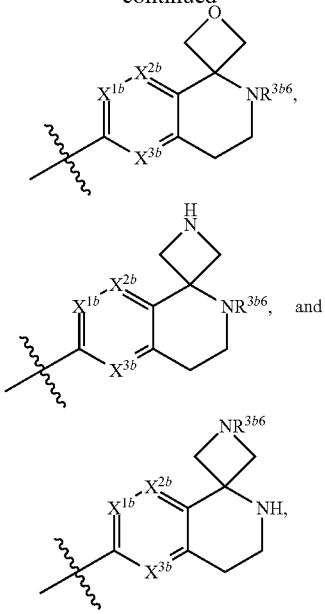

wherein each of shown rings can be further substituted, including replacing the hydrogen of the shown NH moiety.

Embodiment 241

The compound of any one of Embodiments 1-221, wherein $R^{1b}$ is

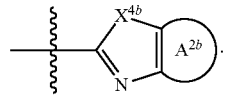

Embodiment 242

The compound of Embodiment 241, wherein Ring $A^{2b}$ is a monocyclic $C_{5-7}$ cycloalkyl substituted with $R^{3b1}$.

Embodiment 243

The compound of Embodiment 241, wherein Ring $A^{2b}$ is a bicyclic $C_{6-12}$ cycloalkyl substituted with $R^{3b2}$.

Embodiment 244

The compound of Embodiment 241, wherein Ring $A^{2b}$ is a 5-7 membered nitrogen-containing monocyclic heterocyclyl, wherein a nitrogen of the 5-7 membered nitrogen-containing monocyclic heterocyclyl is substituted with $R^{3b3}$, wherein a carbon of the 5-7 membered nitrogen-containing monocyclic heterocyclyl is optionally substituted with $R^{3b4}$ or $R^{3b5}$, and wherein when $R^{3b5}$ is present, $R^{3b5}$ is attached at a carbon atom adjacent to a nitrogen of the 5-7 membered nitrogen-containing monocyclic heterocyclyl.

Embodiment 245

The compound of Embodiment 241, wherein Ring $A^{2b}$ is a 6-12 membered nitrogen-containing bicyclic heterocyclyl, wherein a nitrogen of the 6-12 membered nitrogen-containing bicyclic heterocyclyl is optionally substituted with $R^{3b6}$; wherein a carbon of the 6-12 membered nitrogen-containing bicyclic heterocyclyl is optionally substituted with $R^{3b7}$ or $R^{3b8}$, and wherein $R^{3b8}$ is present, $R^{ba8}$ is attached at the carbon atom adjacent to a nitrogen of the 6-12 membered nitrogen-containing bicyclic heterocyclyl.

Embodiment 246

The compound of Embodiment 241, wherein Ring $A^{2b}$ is a 5-7 membered oxygen-containing monocyclic heterocyclyl substituted with $R^{3b9}$ or $R^{3b10}$; wherein $R^{3b10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 247

The compound of any one of Embodiments 241-246, wherein $X^{4b}$ is $NR^{4b2}$.

Embodiment 248

The compound of Embodiment 247, wherein $R^{4b2}$ is hydrogen.

Embodiment 249

The compound of Embodiment 247, wherein $R^{4b2}$ is an unsubstituted $C_{1-4}$ alkyl.

Embodiment 250

The compound of Embodiment 247, wherein $R^{4b2}$ is an unsubstituted $C_{1-4}$ haloalkyl.

Embodiment 251

The compound of any one of Embodiments 241-250, wherein $X^{4b}$ is O.

Embodiment 252

The compound of any one of Embodiments 241-250, wherein $X^{4b}$ is S.
Examples of

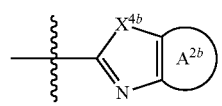

include, but are not limited to, the following:

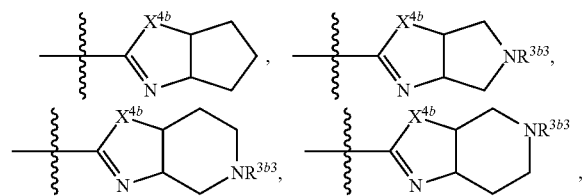

-continued

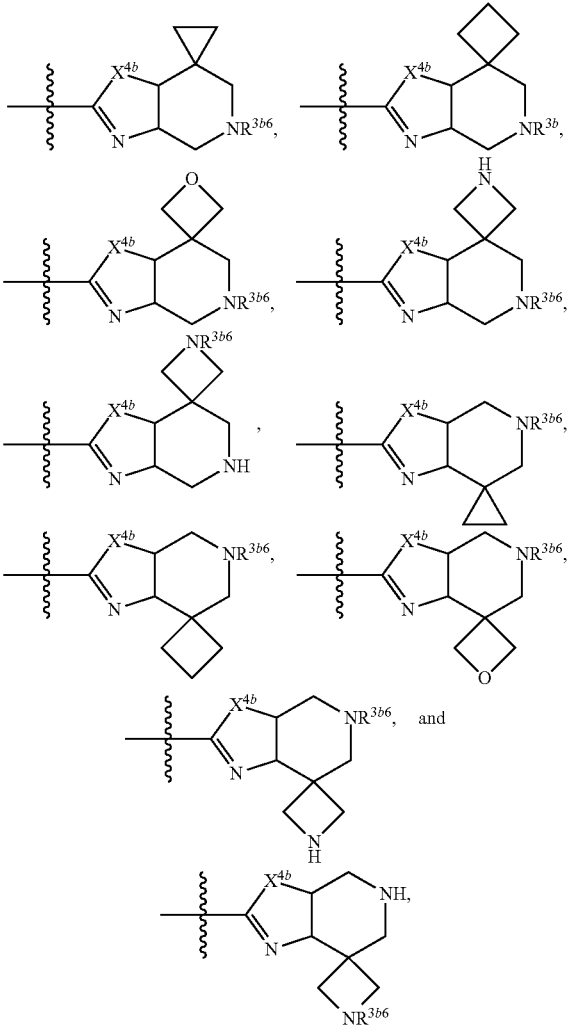

wherein each of shown rings can be further substituted, including replacing the hydrogen of the shown NH moiety.

Embodiment 253

The compound of any one of Embodiments 1-221, wherein $R^{1b}$ is

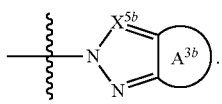

Embodiment 254

The compound of Embodiment 253, wherein Ring $A^{3b}$ is a monocyclic $C_{5-7}$ cycloalkyl substituted with $R^{3b1}$.

Embodiment 255

The compound of Embodiment 253, wherein Ring $A^{3b}$ is a bicyclic $C_{6-12}$ cycloalkyl substituted with $R^{3b2}$.

Embodiment 256

The compound of Embodiment 253, wherein Ring $A^{3b}$ is a 5-7 membered nitrogen-containing monocyclic heterocyclyl, wherein a nitrogen of the 5-7 membered nitrogen-containing monocyclic heterocyclyl is substituted with $R^{3b3}$, wherein a carbon of the 5-7 membered nitrogen-containing monocyclic heterocyclyl is optionally substituted with $R^{3b4}$ or $R^{3b5}$, and wherein when $R^{3b5}$ is present, $R^{3b5}$ is attached at a carbon atom adjacent to a nitrogen of the 5-7 membered nitrogen-containing monocyclic heterocyclyl.

Embodiment 257

The compound of Embodiment 253, wherein Ring $A^{3b}$ is a 6-12 membered nitrogen-containing bicyclic heterocyclyl, wherein a nitrogen of the 6-12 membered nitrogen-containing bicyclic heterocyclyl is optionally substituted with $R^{3b6}$; wherein a carbon of the 6-12 membered nitrogen-containing bicyclic heterocyclyl is optionally substituted with $R^{3b7}$ or $R^{3b8}$, and wherein $R^{3b8}$ is present, $R^{3b8}$ is attached at the carbon atom adjacent to a nitrogen of the 6-12 membered nitrogen-containing bicyclic heterocyclyl.

Embodiment 258

The compound of Embodiment 253, wherein Ring $A^{3b}$ is a 5-7 membered oxygen-containing monocyclic heterocyclyl substituted with $R^{3b9}$ or $R^{3b10}$; wherein $R^{3b10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 259

The compound of any one of Embodiments 253-258, wherein $X^{5b}$ is N.

Embodiment 260

The compound of any one of Embodiments 253-258, wherein $X^{5b}$ is $CR^{4b3}$.

Embodiment 261

The compound of Embodiment 260, wherein $R^{4b3}$ is halogen.

Embodiment 262

The compound of Embodiment 260, wherein $R^{4b3}$ is cyano.

Embodiment 263

The compound of Embodiment 260, wherein $R^{4b3}$ is an unsubstituted $C_{1-4}$ alkyl.

Embodiment 264

The compound of Embodiment 260, wherein $R^{4b3}$ is an unsubstituted $C_{1-4}$ haloalkyl.

Embodiment 265

The compound of Embodiment 260, wherein $R^{4b3}$ is an unsubstituted $C_{1-4}$ alkoxy, such as methoxy.

Embodiment 266

The compound of Embodiment 260, wherein $R^{4b3}$ is an unsubstituted $C_{1-4}$ haloalkoxy.

Exemplary

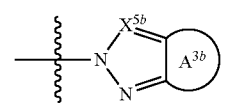

groups include, but are not limited to, the following:

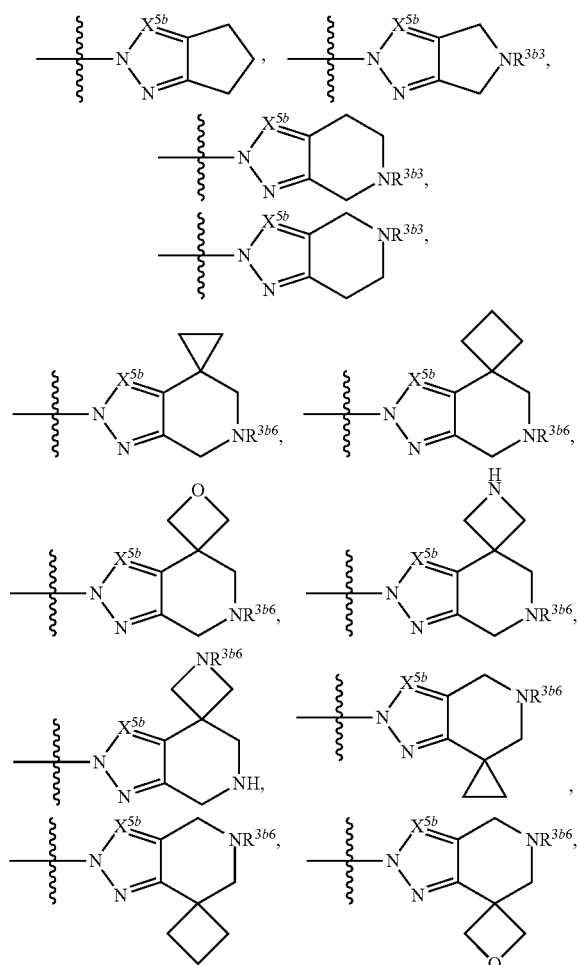

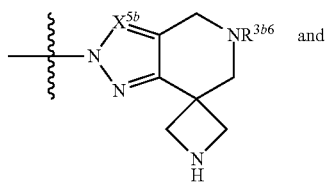

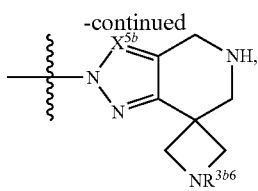

wherein each of shown rings can be further substituted, including replacing the hydrogen of the shown NH moiety.

Embodiment 267

The compound of any one of Embodiments 1-221, wherein $R^{1b}$ is

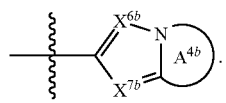

Embodiment 268

The compound of Embodiment 267, wherein Ring $A^{4b}$ is a 5-7 membered nitrogen-containing monocyclic heterocyclyl, wherein a nitrogen of the 5-7 membered nitrogen-containing monocyclic heterocyclyl is optionally substituted with $R^{3b3}$, wherein a carbon of the 5-7 membered nitrogen-containing monocyclic heterocyclyl is optionally substituted with $R^{3b4}$ or $R^{3b5}$ and wherein when $R^{3b5}$ is present, $R^{3b5}$ is attached at a carbon atom adjacent to a nitrogen of the 5-7 membered nitrogen-containing monocyclic heterocyclyl.

Embodiment 269

The compound of Embodiment 267, wherein Ring $A^{4b}$ is a 6-12 membered nitrogen-containing bicyclic heterocyclyl, wherein a nitrogen of the 6-12 membered nitrogen-containing bicyclic heterocyclyl is optionally substituted with $R^{3b6}$; wherein a carbon of the 6-12 membered nitrogen-containing bicyclic heterocyclyl is optionally substituted with $R^{3b7}$ or $R^{3b8}$, and wherein $R^{3b8}$ is present, $R^{3b8}$ is attached at the carbon atom adjacent to a nitrogen of the 6-12 membered nitrogen-containing bicyclic heterocyclyl.

Embodiment 270

The compound of Embodiment 267, wherein Ring $A^{4b}$ is a 5-7 membered oxygen-containing monocyclic heterocyclyl substituted with $R^{3b9}$ or $R^{3b10}$; wherein $R^{3b10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens.

Embodiment 271

The compound of any one of Embodiments 267-270, wherein $X^{6b}$ is N.

Embodiment 272

The compound of any one of Embodiments 267-270, wherein $X^{6b}$ is $CR^{4b3}$.

Embodiment 273

The compound of any one of Embodiments 267-272, wherein $X^{7b}$ is N.

Embodiment 274

The compound of any one of Embodiments 267-272, wherein $X^{7b}$ is $CR^{4b3}$.

Examples of

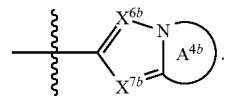

include, but are not limited to, the following:

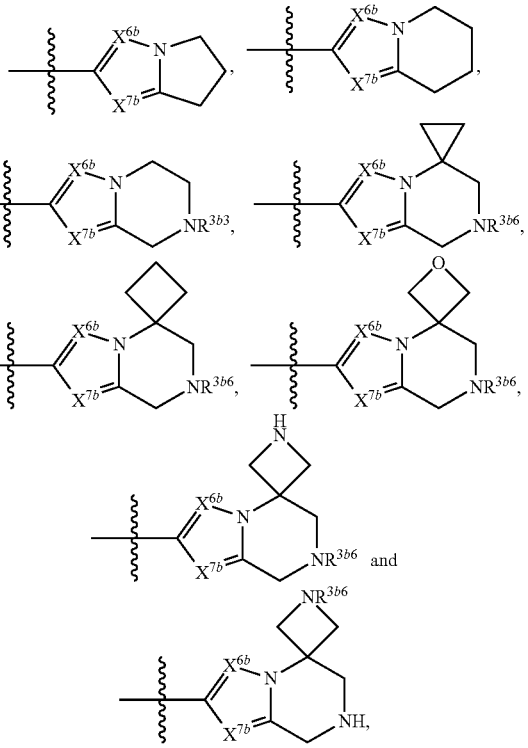

wherein each of shown rings can be further substituted, including replacing the hydrogen of the shown NH moiety.

Embodiment 275

The compound of Embodiment 223, 242 or 254, wherein $R^{3b1}$ is —OH.

Embodiment 276

The compound of Embodiment 223, 242 or 254, wherein $R^{3b1}$ is —N(R$^m$)R$^n$.

Embodiment 277

The compound of Embodiment 223, 242 or 254, wherein $R^{3b1}$ is —C$_{1-4}$ alkyl-N(R$^m$)R$^n$.

Embodiment 278

The compound of Embodiment 223, 242 or 254, wherein $R^{3b1}$ is —$OC_{2-4}$ alkyl-$N(R^m)R^n$.

Embodiment 279

The compound of Embodiment 223, 242 or 254, wherein $R^{3b1}$ is

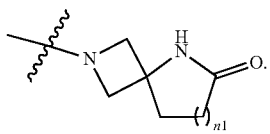

Embodiment 280

The compound of Embodiment 279, wherein n1 is 1.

Embodiment 281

The compound of Embodiment 279, wherein n1 is 2.

Embodiment 282

The compound of Embodiment 223, 242 or 254, wherein $R^{3b1}$ is

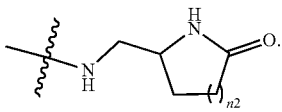

Embodiment 283

The compound of Embodiment 282, wherein n2 is 1.

Embodiment 284

The compound of Embodiment 282, wherein n2 is 2.

Embodiment 285

The compound of Embodiment 223, 242 or 254, wherein $R^{3b1}$ is

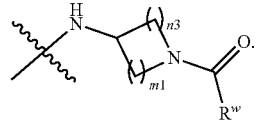

Embodiment 286

The compound of Embodiment 285, wherein n3 is 1.

Embodiment 287

The compound of Embodiment 285, wherein n3 is 2.

Embodiment 288

The compound of any one of Embodiments 285-287, wherein m1 is 1.

Embodiment 289

The compound of any one of Embodiments 285-287, wherein m1 is 2.

Embodiment 290

The compound of any one of Embodiments 285-289, wherein $R^W$ is an unsubstituted —$C_{1-4}$ alkyl.

Embodiment 291

The compound of any one of Embodiments 285-289, wherein $R^W$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 292

The compound of Embodiment 223, 242 or 254, wherein $R^{3b1}$ is

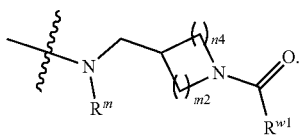

Embodiment 293

The compound of Embodiment 292, wherein n4 is 1.

Embodiment 294

The compound of Embodiment 292, wherein n4 is 2.

Embodiment 295

The compound of any one of Embodiments 292-294, wherein m2 is 1.

Embodiment 296

The compound of any one of Embodiments 292-294, wherein m2 is 2.

Embodiment 297

The compound of any one of Embodiments 292-296, wherein $R^{W1}$ is an unsubstituted —$C_{1-4}$ alkyl.

Embodiment 298

The compound of any one of Embodiments 292-296, wherein $R^{W1}$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 299

The compound of Embodiment 223, 242 or 254, wherein $R^{3b1}$ is

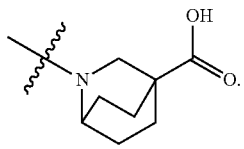 [SMILES: *N1CC2(C(=O)O)CCC1CC2]

Embodiment 300

The compound of Embodiment 223, 242 or 254, wherein $R^{3b1}$ is

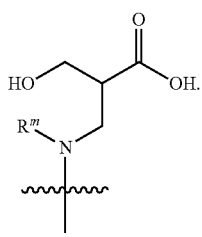

Embodiment 301

The compound of Embodiment 223, 242 or 254, wherein $R^{3b1}$ is

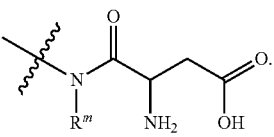

Embodiment 302

The compound of Embodiment 223, 242 or 254, wherein $R^{3b1}$ is

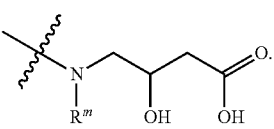

Embodiment 303

The compound of Embodiment 224, 243 or 255, wherein $R^{3b2}$ is —OH.

Embodiment 304

The compound of Embodiment 224, 243 or 255, wherein $R^{3b2}$ is —N(R''')R''.

Embodiment 305

The compound of Embodiment 224, 243 or 255, wherein $R^{3b2}$ is —$C_{1-4}$ alkyl-N(R''')R''.

Embodiment 306

The compound of Embodiment 224, 243 or 255, wherein $R^{3b2}$ is —O$C_{2-4}$ alkyl-N(R''')R''.

Embodiment 307

The compound of Embodiment 224, 243 or 255, wherein $R^{3b2}$ is

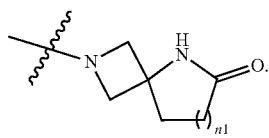

Embodiment 308

The compound of Embodiment 307, wherein n1 is 1.

Embodiment 309

The compound of Embodiment 307, wherein n1 is 2.

Embodiment 310

The compound of Embodiment 224, 243 or 255, wherein $R^{3b2}$ is

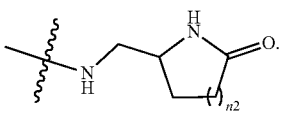

Embodiment 311

The compound of Embodiment 310, wherein n2 is 1.

Embodiment 312

The compound of Embodiment 310, wherein n2 is 2.

Embodiment 313

The compound of Embodiment 224, 243 or 255, wherein $R^{3b2}$ is

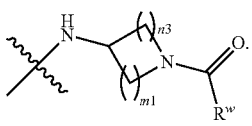

Embodiment 314

The compound of Embodiment 313, wherein n3 is 1.

Embodiment 315

The compound of Embodiment 313, wherein n3 is 2.

Embodiment 316

The compound of any one of Embodiments 313-315, wherein m1 is 1.

Embodiment 317

The compound of any one of Embodiments 313-315, wherein m1 is 2.

Embodiment 318

The compound of any one of Embodiments 313-317, wherein $R^{w}$ is an unsubstituted —$C_{1-4}$ alkyl.

Embodiment 319

The compound of any one of Embodiments 313-317, wherein $R^{w}$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 320

The compound of Embodiment 224, 243 or 255, wherein $R^{3b2}$ is

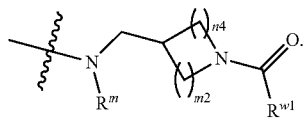

Embodiment 321

The compound of Embodiment 320, wherein n4 is 1.

Embodiment 322

The compound of Embodiment 320, wherein n4 is 2.

Embodiment 323

The compound of any one of Embodiments 320-322, wherein m2 is 1.

Embodiment 324

The compound of any one of Embodiments 320-322, wherein m2 is 2.

Embodiment 325

The compound of any one of Embodiments 320-324, wherein $R^{w1}$ is an unsubstituted —$C_{1-4}$ alkyl.

Embodiment 326

The compound of any one of Embodiments 320-324, wherein $R^{w1}$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 327

The compound of Embodiment 224, 243 or 255, wherein $R^{3b2}$ is

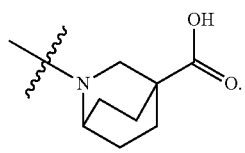 [SMILES: *N1CC2(C(=O)O)CCC1CC2]

Embodiment 328

The compound of Embodiment 224, 243 or 255, wherein $R^{3b2}$ is

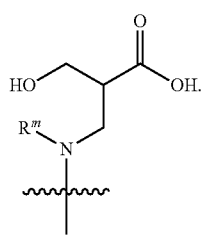

Embodiment 329

The compound of Embodiment 224, 243 or 255, wherein $R^{3b2}$ is

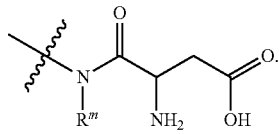

Embodiment 330

The compound of Embodiment 224, 243 or 255, wherein $R^{3b2}$ is

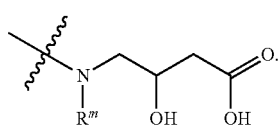

Embodiment 331

The compound of Embodiment 225, 244, 256 or 268, wherein $R^{3b3}$ is —$R^{x1}$.

Embodiment 332

The compound of Embodiment 331, wherein —R$^{x1}$ is

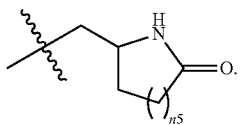

Embodiment 333

The compound of Embodiment 332, wherein n5 is 1.

Embodiment 334

The compound of Embodiment 332, wherein n5 is 2.

Embodiment 335

The compound of Embodiment 331, wherein —R$^{x1}$ is

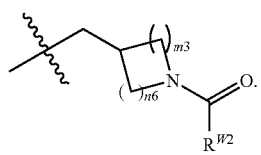

Embodiment 336

The compound of Embodiment 335, wherein n6 is 1.

Embodiment 337

The compound of Embodiment 335, wherein n6 is 2.

Embodiment 338

The compound of any one of Embodiments 335-337, wherein m3 is 1.

Embodiment 339

The compound of any one of Embodiments 335-337, wherein m3 is 2.

Embodiment 340

The compound of Embodiment 331, wherein —R$^{x1}$ is

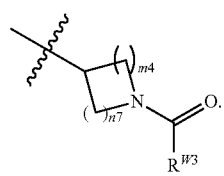

Embodiment 341

The compound of Embodiment 340, wherein n7 is 1.

Embodiment 342

The compound of Embodiment 340, wherein n7 is 2.

Embodiment 343

The compound of any one of Embodiments 340-342, wherein m4 is 1.

Embodiment 344

The compound of any one of Embodiments 340-342, wherein m4 is 2.

Embodiment 345

The compound of Embodiment 331, wherein —R$^{x1}$ is

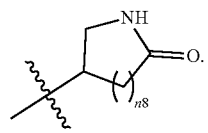

Embodiment 346

The compound of Embodiment 345, wherein n8 is 1.

Embodiment 347

The compound of Embodiment 345, wherein n8 is 2.

Embodiment 348

The compound of Embodiment 331, wherein —R$^{x1}$ is

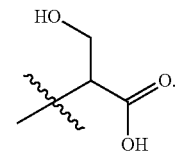 [SMILES: *C(CO)C(=O)O]

Embodiment 349

The compound of Embodiment 331, wherein —R$^{x1}$ is

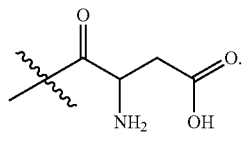 [SMILES: *C(=O)C(N)CC(=O)O]

Embodiment 350

The compound of Embodiment 331, wherein —R$^{x1}$ is

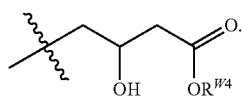

Embodiment 351

The compound of Embodiment 225, 244, 256 or 268, wherein $R^{3b3}$ is —$C_{1-4}$ alkyl, wherein the —$C_{1-4}$ alkyl is optionally substituted with one or two or three substituents selected from the group consisting of -halogen, —OH, —N(R''')R'', —$C_{1-4}$ alkoxy, —C(=O)OH, —C(=O)O$C_{1-4}$ alkyl, —C(=O)NHS(=O)$_2$$C_{1-4}$ alkyl, —NHC(=O)$C_{1-4}$alkyl and —C(=O)N(R''')R''.

Embodiment 352

The compound of Embodiment 225, 244, 256 or 268, wherein $R^{3b3}$ is —$C_{3-7}$ cycloalkyl, wherein the —$C_{3-7}$ cycloalkyl is optionally substituted with one or two or three substituents selected from the group consisting of -halogen, —$C_{1-4}$ alkyl, —OH, —N(R''')R'', —$C_{1-4}$ alkoxy, —C(=O)OH, —C(=O)O$C_{1-4}$ alkyl, —C(=O)NHS(=O)$_2$$C_{1-4}$ alkyl, —NHC(=O)$C_{1-4}$alkyl and —C(=O)N(R''')R''.

Embodiment 353

The compound of Embodiment 225, 244, 256 or 268, wherein $R^{3b3}$ is —C(=O)$C_{1-4}$ alkyl, wherein the —C(=O)$C_{1-4}$ alkyl is optionally substituted with one or two or three substituents selected from the group consisting of -halogen, —OH, —N(R''')R'', —$C_{1-4}$ alkoxy, —C(=O)OH, —C(=O)O$C_{1-4}$ alkyl, —C(=O)NHS(=O)$_2$$C_{1-4}$ alkyl, —NHC(=O)$C_{1-4}$ alkyl and —C(=O)N(R''')R''.

Embodiment 354

The compound of Embodiment 225, 244, 256 or 268, wherein $R^{3b3}$ is -Het$^{a1}$, wherein the -Het$^{a1}$ is optionally substituted with one or two or three substituents selected from the group consisting of -halogen, —OH, —N(R''')R'', —$C_{1-4}$ alkoxy, —C(=O)OH, —C(=O)O$C_{1-4}$ alkyl, —C(=O)NHS(=O)$_2$$C_{1-4}$ alkyl, —NHC(=O)$C_{1-4}$ alkyl and —C(=O)N(R''')R''.

Embodiment 355

The compound of Embodiment 226, 245, 257 or 269, wherein $R^{3b6}$ is —$R^{x1}$.

Embodiment 356

The compound of Embodiment 355, wherein —$R^{x1}$ is

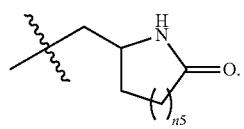

Embodiment 357

The compound of Embodiment 356, wherein n5 is 1.

Embodiment 358

The compound of Embodiment 356, wherein n5 is 2.

Embodiment 359

The compound of Embodiment 355, wherein —$R^{x1}$ is

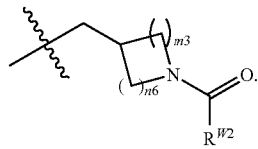

Embodiment 360

The compound of Embodiment 359, wherein n6 is 1.

Embodiment 361

The compound of Embodiment 359, wherein n6 is 2.

Embodiment 362

The compound of any one of Embodiments 359-361, wherein m3 is 1.

Embodiment 363

The compound of any one of Embodiments 359-361, wherein m3 is 2.

Embodiment 364

The compound of Embodiment 355, wherein —$R^{x1}$ is

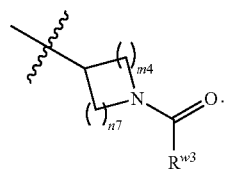

Embodiment 365

The compound of Embodiment 364, wherein n7 is 1.

Embodiment 366

The compound of Embodiment 364, wherein n7 is 2.

Embodiment 367

The compound of any one of Embodiments 364-366, wherein m4 is 1.

Embodiment 368

The compound of any one of Embodiments 364-366, wherein m4 is 2.

Embodiment 369

The compound of Embodiment 355, wherein —R$^{x1}$ is

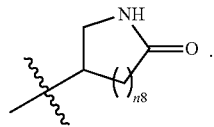

Embodiment 370

The compound of Embodiment 369, wherein n8 is 1.

Embodiment 371

The compound of Embodiment 369, wherein n8 is 2.

Embodiment 372

The compound of Embodiment 355, wherein —R$^{x1}$ is

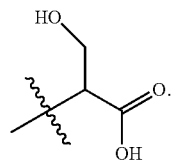 [SMILES: *C(CO)C(=O)O]

Embodiment 373

The compound of Embodiment 355, wherein —R$^{x1}$ is

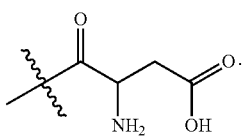

Embodiment 374

The compound of Embodiment 355, wherein —R$^{x1}$ is

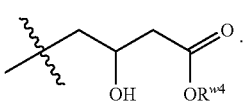

Embodiment 375

The compound of Embodiment 226, 245, 257 or 269, wherein R$^{3b6}$ is —C$_{1-4}$ alkyl, wherein the —C$_{1-4}$ alkyl is optionally substituted with one or two or three substituents selected from the group consisting of -halogen, —OH, —N(R$^m$)R$^n$, —C$_{1-4}$ alkoxy, —C(=O)OH, —C(=O)OC$_{1-4}$ alkyl, —C(=O)NHS(=O)$_2$C$_{1-4}$ alkyl, —NHC(=O)C$_{1-4}$alkyl and —C(=O)N(R$^m$)R$^n$.

Embodiment 376

The compound of Embodiment 226, 245, 257 or 269, wherein R$^{3b6}$ is —C$_{3-7}$ cycloalkyl, wherein the —C$_{3-7}$ cycloalkyl is optionally substituted with one or two or three substituents selected from the group consisting of -halogen, —C$_{1-4}$ alkyl, —OH, —N(R$^m$)R$^n$, —C$_{1-4}$ alkoxy, —C(=O)OH, —C(=O)OC$_{1-4}$ alkyl, —C(=O)NHS(=O)$_2$C$_{1-4}$ alkyl, —NHC(=O)C$_{1-4}$alkyl and —C(=O)N(R$^m$)R$^n$.

Embodiment 377

The compound of Embodiment 226, 245, 257 or 269, wherein R$^{3b6}$ is —C(=O)C$_{1-4}$ alkyl, wherein the —C(=O)C$_{1-4}$ alkyl is optionally substituted with one or two or three substituents selected from the group consisting of -halogen, —OH, —N(R$^m$)R$^n$, —C$_{1-4}$ alkoxy, —C(=O)OH, —C(=O)OC$_{1-4}$ alkyl, —C(=O)NHS(=O)$_2$C$_{1-4}$ alkyl, —NHC(=O)C$_{1-4}$ alkyl and —C(=O)N(R$^m$)R$^n$.

Embodiment 378

The compound of Embodiment 226, 245, 257 or 269, wherein R$^{3b6}$ is -Het$^{a1}$, wherein the -Het$^{a1}$ is optionally substituted with one or two or three substituents selected from the group consisting of -halogen, —OH, —N(R$^m$)R$^n$, —C$_{1-4}$ alkoxy, —C(=O)OH, —C(=O)OC$_{1-4}$ alkyl, —C(=O)NHS(=O)$_2$C$_{1-4}$ alkyl, —NHC(=O)C$_{1-4}$ alkyl and —C(=O)N(R$^m$)R$^n$.

Embodiment 379

The compound of Embodiment 227, 246, 258 or 270, wherein R$^{3b9}$ is —OH.

Embodiment 380

The compound of Embodiment 227, 246, 258 or 270, wherein R$^{3b9}$ is —N(R$^m$)R$^n$.

Embodiment 381

The compound of Embodiment 227, 246, 258 or 270, wherein R$^{3b9}$ is —C$_{1-4}$ alkyl-N(R$^m$)R$^n$.

Embodiment 382

The compound of Embodiment 227, 246, 258 or 270, wherein R$^{3b9}$ is —OC$_{2-4}$ alkyl-N(R$^m$)R$^n$.

Embodiment 383

The compound of Embodiment 227, 246, 258 or 270, wherein R$^{3b9}$ is

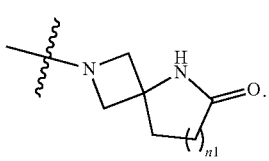

Embodiment 384

The compound of Embodiment 383, wherein n1 is 1.

Embodiment 385

The compound of Embodiment 383, wherein n1 is 2.

Embodiment 386

The compound of Embodiment 227, 246, 258 or 270, wherein $R^{369}$ is

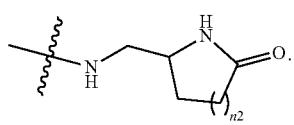

Embodiment 387

The compound of Embodiment 386, wherein n2 is 1.

Embodiment 388

The compound of Embodiment 386, wherein n2 is 2.

Embodiment 389

The compound of Embodiment 227, 246, 258 or 270, wherein $R^{369}$ is

Embodiment 390

The compound of Embodiment 389, wherein n3 is 1.

Embodiment 391

The compound of Embodiment 389, wherein n3 is 2.

Embodiment 392

The compound of any one of Embodiments 389-391, wherein m1 is 1.

Embodiment 393

The compound of any one of Embodiments 389-391, wherein m1 is 2.

Embodiment 394

The compound of any one of Embodiments 389-393, wherein $R^w$ is an unsubstituted —$C_{1-4}$ alkyl.

Embodiment 395

The compound of any one of Embodiments 389-393, wherein $R^w$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 396

The compound of Embodiment 227, 246, 258 or 270, wherein $R^{369}$ is

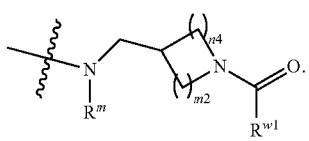

Embodiment 397

The compound of Embodiment 396, wherein n4 is 1.

Embodiment 398

The compound of Embodiment 396, wherein n4 is 2.

Embodiment 399

The compound of any one of Embodiments 396-398, wherein m2 is 1.

Embodiment 400

The compound of any one of Embodiments 396-398, wherein m2 is 2.

Embodiment 401

The compound of any one of Embodiments 396-400, wherein $R^{w1}$ is an unsubstituted —$C_{1-4}$ alkyl.

Embodiment 402

The compound of any one of Embodiments 396-401, wherein $R^{w1}$ is a substituted —$C_{1-4}$ alkyl substituted with one or two or three substituents selected from the group consisting of -halogen, —OH, —$OC_{1-4}$ alkyl, —C(=O)OH and —C(=O)$OC_{1-4}$ alkyl.

Embodiment 403

The compound of Embodiment 227, 246, 258 or 270, wherein $R^{369}$ is

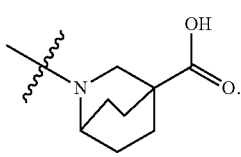 [SMILES: *N1CC2(C(=O)O)CCC1CC2]

Embodiment 404

The compound of Embodiment 227, 246, 258 or 270, wherein $R^{3b9}$ is

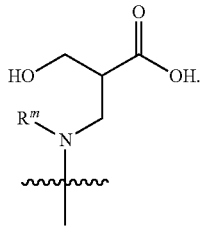

Embodiment 405

The compound of Embodiment 227, 246, 258 or 270, wherein $R^{3b9}$ is

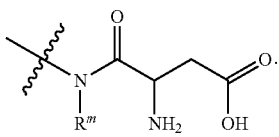

Embodiment 406

The compound of Embodiment 227, 246, 258 or 270, wherein $R^{3b9}$ is

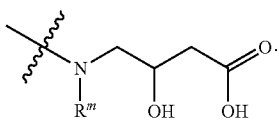

Embodiment 407

The compound of Embodiment 223, 242 or 254, wherein the monocyclic $C_{5-7}$ cycloalkyl substituted with $R^{3b1}$ is selected from the group consisting of:

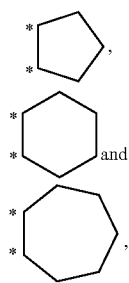

wherein asterisks indicate the position of the fused bond.

Embodiment 408

The compound of Embodiment 224, 243 or 255, wherein the bicyclic $C_{6-12}$ cycloalkyl substituted with $R^{3b2}$ is

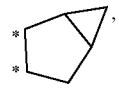

wherein asterisks indicate the position of the fused bond.

Embodiment 409

The compound of Embodiment 225, 244, 255 or 268, wherein the 5-7 membered nitrogen-containing monocyclic heterocyclyl, wherein a nitrogen of the 5-7 membered nitrogen-containing monocyclic heterocyclyl is optionally substituted with $R^{3b3}$, wherein a carbon of the 5-7 membered nitrogen-containing monocyclic heterocyclyl is optionally substituted with $R^{3b4}$ or $R^{3b5}$, and wherein when $R^{3b5}$ is present, $R^{3b5}$ is attached at a carbon atom adjacent to a nitrogen of the 5-7 membered nitrogen-containing monocyclic heterocyclyl is selected from the group consisting of:

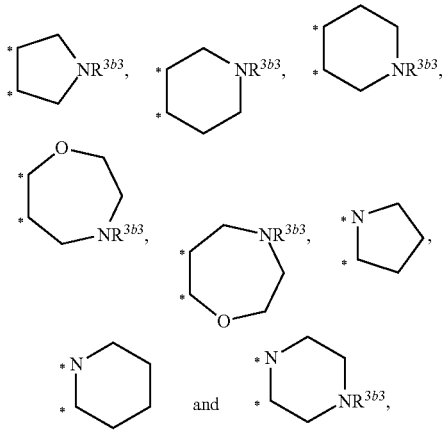

wherein asterisks indicate the position of the fused bond, and $R^{3b4}$ and $R^{3b5}$ are each optionally present.

Embodiment 410

The compound of Embodiment 226, 245, 257 or 269, wherein the 6-12 membered nitrogen-containing bicyclic heterocyclyl, wherein a nitrogen of the 6-12 membered nitrogen-containing bicyclic heterocyclyl is optionally substituted with $R^{3b6}$; wherein a carbon of the 6-12 membered nitrogen-containing bicyclic heterocyclyl is optionally substituted with $R^{3b7}$ or $R^{3b8}$, and wherein $R^{3b8}$ is present, $R^{3b8}$ is attached at the carbon atom adjacent to a nitrogen of the 6-12 membered nitrogen-containing bicyclic heterocyclyl is selected from the group consisting of:

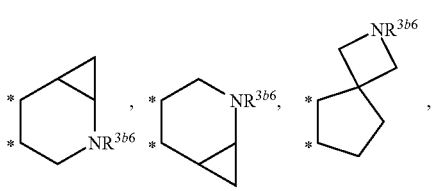

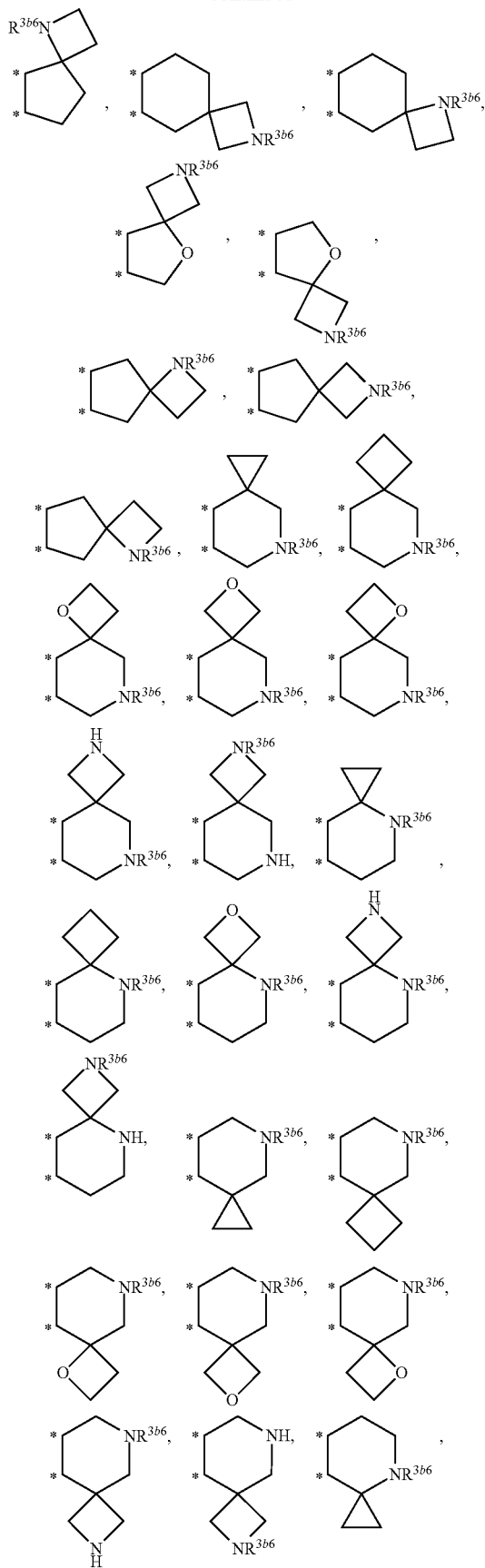

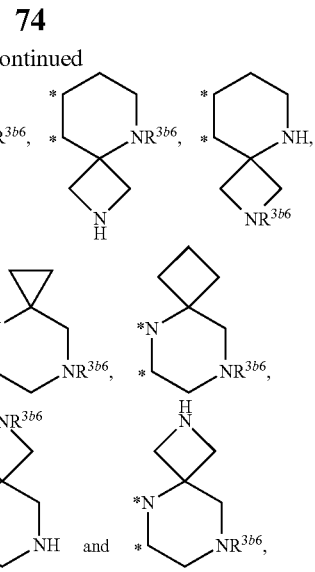

wherein asterisks indicate the position of the fused bond, $R^{3b7}$ and $R^{3b8}$ are each optionally present, and each of shown rings can be further substituted, including replacing the hydrogen of the shown NH moiety.

Embodiment 411

The compound of Embodiment 227, 246, 258 or 270, wherein the 5-7 membered oxygen-containing monocyclic heterocyclyl substituted with $R^{3b9}$ or $R^{3b10}$; wherein $R^{3b10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens is selected from the group consisting of:

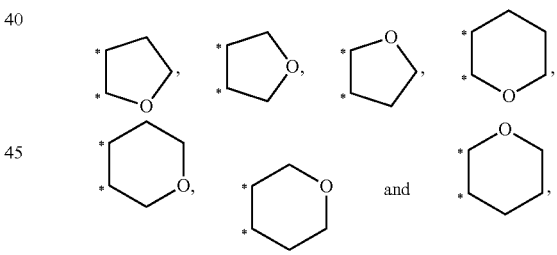

wherein asterisks indicate the position of the fused bond, and $R^{3b9}$ or $R^{3b10}$ is present.

Embodiment 412

The compound of Embodiment 225, 244, 256 or 268, wherein $R^{3b4}$ is -halogen.

Embodiment 413

The compound of Embodiment 225, 244, 256 or 268, wherein $R^{3b4}$ is —$C_{1-4}$ alkyl, wherein —$C_{1-4}$ alkyl, is optionally substituted with one or two substituents selected from the group consisting of -halogen, —OH, —$C_{1-4}$ alkoxy, —C(═O)OH, —C(═O)O$C_{1-4}$ alkyl, —C(═O)NHS(═O)$_2$ $C_{1-4}$ alkyl, —NHC(═O)$C_{1-4}$ alkyl and —C(═O)N(R$^m$)R$^n$.

Embodiment 414

The compound of Embodiment 225, 244, 256 or 268, wherein $R^{364}$ is —$C_{3-7}$ cycloalkyl, wherein the —$C_{3-7}$ cycloalkyl is optionally substituted with one or two substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R''.

Embodiment 415

The compound of Embodiment 225, 244, 256 or 268, wherein $R^{364}$ is —OH.

Embodiment 416

The compound of Embodiment 225, 244, 256 or 268, wherein $R^{364}$ is —O$C_{1-4}$ alkyl, wherein the —O$C_{1-4}$ alkyl is optionally substituted with one or two substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R''.

Embodiment 417

The compound of Embodiment 225, 244, 256 or 268, wherein $R^{364}$ is —N(R''')R''.

Embodiment 418

The compound of Embodiment 225, 244, 256 or 268, wherein $R^{364}$ is —$C_{1-4}$ alkyl(R''')R''.

Embodiment 419

The compound of Embodiment 225, 244, 256 or 268, wherein $R^{364}$ is —C(=O)OH.

Embodiment 420

The compound of Embodiment 225, 244, 256 or 268, wherein $R^{364}$ is —$C_{1-4}$ alkyl-C(=O)OH.

Embodiment 421

The compound of Embodiment 225, 244, 256 or 268, wherein $R^{364}$—C(=O)O$C_{1-4}$ alkyl.

Embodiment 422

The compound of Embodiment 225, 244, 256 or 268, wherein $R^{364}$—$C_{1-4}$ alkyl-C(=O)O$C_{1-4}$ alkyl.

Embodiment 423

The compound of Embodiment 225, 244, 256 or 268, wherein $R^{365}$ is —C(=O)OH.

Embodiment 424

The compound of Embodiment 225, 244, 256 or 268, wherein $R^{365}$ is —$C_{1-4}$ alkyl, wherein the —$C_{1-4}$ alkyl is optionally substituted with one or two or three substituents selected from the group consisting of -halogen, —OH, —$C_{1-4}$ alkoxy, —C(=O)OH, —C(=O)O$C_{1-4}$ alkyl, —C(=O)NHS(=O)$_2C_{1-4}$ alkyl, —N(R''')C(=O)$C_{1-4}$ alkyl, —C(=O) N(R''')R'' and —N(R''')R''.

Embodiment 425

The compound of Embodiment 225, 244, 256 or 268, wherein $R^{365}$ is —$C_{3-7}$ cycloalkyl, wherein the —$C_{3-7}$ cycloalkyl is optionally substituted with one or two or three substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2C_{1-4}$ alkyl, —N(R''')C(=O)$C_{1-4}$ alkyl, —C(=O) N(R''')R'' and —N(R''')R''.

Embodiment 426

The compound of Embodiment 226, 245, 257 or 269, wherein $R^{367}$ is -halogen.

Embodiment 427

The compound of Embodiment 226, 245, 257 or 269, wherein $R^{367}$ is —$C_{1-4}$ alkyl, wherein —$C_{1-4}$ alkyl, is optionally substituted with one or two substituents selected from the group consisting of -halogen, —OH, —$C_{1-4}$ alkoxy, —C(=O)OH, —C(=O)O$C_{1-4}$ alkyl, —C(=O)NHS(=O)$_2 C_{1-4}$ alkyl, —NHC(=O)$C_{1-4}$ alkyl and —C(=O)N(R''')R''.

Embodiment 428

The compound of Embodiment 226, 245, 257 or 269, wherein $R^{367}$ is —$C_{3-7}$ cycloalkyl, wherein the —$C_{3-7}$ cycloalkyl is optionally substituted with one or two substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R''.

Embodiment 429

The compound of Embodiment 226, 245, 257 or 269, wherein $R^{367}$ is —OH.

Embodiment 430

The compound of Embodiment 226, 245, 257 or 269, wherein $R^{367}$ is —O$C_{1-4}$ alkyl, wherein the —O$C_{1-4}$ alkyl is optionally substituted with one or two substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N(R''')R''.

Embodiment 431

The compound of Embodiment 226, 245, 257 or 269, wherein $R^{367}$ is —N(R''')R''.

Embodiment 432

The compound of Embodiment 226, 245, 257 or 269, wherein $R^{367}$ is —$C_{1-4}$ alkyl(R''')R''.

Embodiment 433

The compound of Embodiment 226, 245, 257 or 269, wherein $R^{367}$ is —C(=O)OH.

Embodiment 434

The compound of Embodiment 226, 245, 257 or 269, wherein $R^{3b7}$ is —$C_{1-4}$ alkyl-C(=O)OH.

Embodiment 435

The compound of Embodiment 226, 245, 257 or 269, wherein $R^{3b7}$ is —C(=O)O$C_{1-4}$ alkyl.

Embodiment 436

The compound of Embodiment 226, 245, 257 or 269, wherein $R^{3b7}$ is —$C_{1-4}$ alkyl-C(=O)O$C_{1-4}$ alkyl.

Embodiment 437

The compound of Embodiment 226, 245, 257 or 269, wherein $R^{3b8}$ is —$C_{1-4}$ alkyl, wherein the —$C_{1-4}$ alkyl is optionally substituted with one or two or three substituents selected from the group consisting of -halogen, —OH, —$C_{1-4}$ alkoxy, —C(=O)OH, —C(=O)O$C_{1-4}$ alkyl, —C(=O)NHS(=O)$_2$$C_{1-4}$ alkyl, —N(R''')C(=O)$C_{1-4}$ alkyl, —C(=O) N(R''')R'' and —N(R''')R''.

Embodiment 438

The compound of Embodiment 226, 245, 257 or 269, wherein $R^{3b}$s is —$C_{3-7}$ cycloalkyl, wherein the —$C_{3-7}$ cycloalkyl is optionally substituted with one or two or three substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2$$C_{1-4}$ alkyl, —N(R''')C(=O)$C_{1-4}$ alkyl, —C(=O) N(R''')R'' and —N(R''')R''.

Embodiment 439

The compound of Embodiment 227, 246, 268 or 270, wherein $R^{3b10}$ is —$C_{1-4}$ alkyl, wherein the —$C_{1-4}$ alkyl is optionally substituted with one or two or three substituents selected from the group consisting of -halogen, —OH, —$C_{1-4}$ alkoxy, —C(=O)OH, —C(=O)O$C_{1-4}$ alkyl, —(C=O)NHS(=O)$_2$($C_{1-4}$ alkyl) and —NHC(=O)$C_{1-4}$ alkyl.

Embodiment 440

The compound of Embodiment 227, 246, 268 or 270, wherein $R^{3b10}$ is —$C_{3-7}$ cycloalkyl, wherein the —$C_{3-7}$ cycloalkyl is optionally substituted with one or two or three substituents selected from the group consisting of -halogen, —OH, —$C_{1-4}$ alkyl, —$C_{1-4}$ alkoxy, —C(=O)OH, —C(=O)O$C_{1-4}$ alkyl, —(C=O)NHS(=O)$_2$($C_{1-4}$ alkyl) and —NHC(=O)$C_{1-4}$ alkyl.

Embodiment 441

The compound of Embodiment 227, 246, 268 or 270, wherein $R^{3b10}$ is —($C_{1-4}$ alkyl)N(R''')R'', wherein the —($C_{1-4}$ alkyl)N(R''')R'' is optionally substituted with one or two or three substituents selected from the group consisting of -halogen, —OH, —$C_{1-4}$ alkyl, —$C_{1-4}$ alkoxy, —C(=O)OH, —C(=O)O$C_{1-4}$ alkyl, —(C=O)NHS(=O)$_2$($C_{1-4}$ alkyl) and —NHC(=O)$C_{1-4}$ alkyl.

Embodiment 442

The compound of any one of Embodiments 56-58, 72, 80-82, 84-86, 100, 108-110, 131-134, 155-158, 160-162, 176, 184-186, 193, 194, 196-198, 204, 205, 207, 208, 210-212, 217, 218, 292, 300-302, 304-306, 320, 328-330, 351-354, 375-378, 380-328, 396, 404-406, 413, 414, 416-418, 424, 425, 427, 427, 430-432, 437 and 438, wherein R''' is hydrogen.

Embodiment 443

The compound of any one of Embodiments 56-58, 72, 80-82, 84-86, 100, 108-110, 131-134, 155-158, 160-162, 176, 184-186, 193, 194, 196-198, 204, 205, 207, 208, 210-212, 217, 218, 292, 300-302, 304-306, 320, 328-330, 351-354, 375-378, 380-328, 396, 404-406, 413, 414, 416-418, 424, 425, 427, 427, 430-432, 437 and 438, wherein R''' is —$R^{x2}$.

Embodiment 444

The compound of Embodiment 443, wherein —$R^{x2}$ is

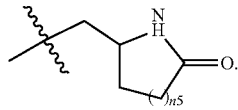

Embodiment 445

The compound of Embodiment 444, wherein n5 is 1.

Embodiment 446

The compound of Embodiment 444, wherein n5 is 2.

Embodiment 447

The compound of Embodiment 443, wherein —$R^{x2}$ is

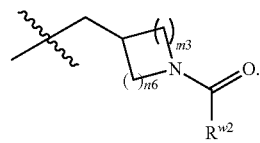

Embodiment 448

The compound of Embodiment 447, wherein n6 is 1.

Embodiment 449

The compound of Embodiment 447, wherein n6 is 2.

Embodiment 450

The compound of any one of Embodiments 447-449, wherein m3 is 1.

Embodiment 451

The compound of any one of Embodiments 447-449, wherein m3 is 2.

Embodiment 452

The compound of Embodiment 443, wherein —$R^{x2}$ is

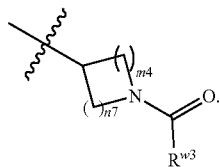

Embodiment 453

The compound of Embodiment 452, wherein n7 is 1.

Embodiment 454

The compound of Embodiment 452, wherein n7 is 2.

Embodiment 455

The compound of any one of Embodiments 452-454, wherein m4 is 1.

Embodiment 456

The compound of any one of Embodiments 452-454, wherein m4 is 2.

Embodiment 457

The compound of Embodiment 443, wherein —$R^{x2}$

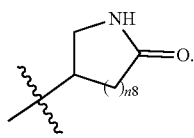

Embodiment 458

The compound of Embodiment 457, wherein n7 is 1.

Embodiment 459

The compound of Embodiment 457, wherein n7 is 2.

Embodiment 460

The compound of Embodiment 443, wherein —$R^{x2}$ is

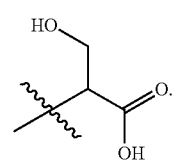

Embodiment 461

The compound of Embodiment 443, wherein —$R^{x2}$ is

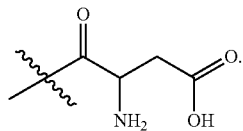 [SMILES: *C(=O)C(N)CC(=O)O]

Embodiment 462

The compound of Embodiment 443, wherein —$R^{x2}$ is

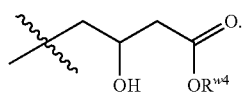

Embodiment 463

The compound of any one of Embodiments 56-58, 72, 80-82, 84-86, 100, 108-110, 131-134, 155-158, 160-162, 176, 184-186, 193, 194, 196-198, 204, 205, 207, 208, 210-212, 217, 218, 292, 300-302, 304-306, 320, 328-330, 351-354, 375-378, 380-328, 396, 404-406, 413, 414, 416-418, 424, 425, 427, 427, 430-432, 437 and 438, wherein $R'''$ is —$C_{1-4}$ alkyl, wherein the —$C_{1-4}$ alkyl, is optionally substituted with one or two or three substituents selected from the group consisting of -halogen, —OH, —$NH_2$—$C_{1-4}$ alkyl, —$OC_{1-4}$ alkyl, —C(=O)OH, —C(=O)$OC_{1-4}$ alkyl, —C(=O)NHS(=O)$_2C$—$_4$ alkyl and —NHC(=O)$C_{1-4}$alkyl.

Embodiment 464

The compound of any one of Embodiments 56-58, 72, 80-82, 84-86, 100, 108-110, 131-134, 155-158, 160-162, 176, 184-186, 193, 194, 196-198, 204, 205, 207, 208, 210-212, 217, 218, 292, 300-302, 304-306, 320, 328-330, 351-354, 375-378, 380-328, 396, 404-406, 413, 414, 416-418, 424, 425, 427, 427, 430-432, 437 and 438, wherein $R'''$ is —$C_{3-7}$ cycloalkyl, wherein the —$C_{3-7}$ cycloalkyl is optionally substituted with one or two or three substituents selected from the group consisting of -halogen, —OH, —$NH_2$—$C_{1-4}$ alkyl, —$OC_{1-4}$ alkyl, —C(=O)OH, —C(=O)$OC_{1-4}$ alkyl, —C(=O)NHS(=O)$_2C_{1-4}$ alkyl and —NHC(=O)$C_{1-4}$alkyl.

Embodiment 465

The compound of any one of Embodiments 56-58, 72, 80-82, 84-86, 100, 108-110, 131-134, 155-158, 160-162, 176, 184-186, 193, 194, 196-198, 204, 205, 207, 208, 210-212, 217, 218, 292, 300-302, 304-306, 320, 328-330, 351-354, 375-378, 380-328, 396, 404-406, 413, 414, 416-418, 424, 425, 427, 427, 430-432, 437 and 438, wherein $R'''$ is —C(=O)$C_{1-4}$ alkyl, wherein the —C(=O)$C_{1-4}$ alkyl is optionally substituted with one or two or three substituents selected from the group consisting of -halogen, —OH, —$NH_2$—$C_{1-4}$ alkyl, —$OC_{1-4}$ alkyl, —C(=O)OH, —C(=O)$OC_{1-4}$ alkyl, —C(=O)NHS(=O)$_2C_{1-4}$ alkyl and —NHC(=O)$C_{1-4}$alkyl.

Embodiment 466

The compound of any one of Embodiments 56-58, 72, 80-82, 84-86, 100, 108-110, 131-134, 155-158, 160-162, 176, 184-186, 193, 194, 196-198, 204, 205, 207, 208, 210-212, 217, 218, 292, 300-302, 304-306, 320, 328-330, 351-354, 375-378, 380-328, 396, 404-406, 413, 414, 416-418, 424, 425, 427, 427, 430-432, 437 and 438, wherein $R'''$ is -Het$^{a1}$.

Embodiment 467

The compound of any one of Embodiments 56-58, 84-86, 131-134, 155-158, 160-162, 193, 194, 196-198, 204, 205, 207, 208, 210-212, 217, 218, 304-306, 351-354, 375-378, 380-382, 413, 414, 416-418, 424, 425, 427, 428, 430-432, 437 and 438, wherein $R''$ is —$C_{1-4}$ alkyl, wherein the —$C_{1-4}$ alkyl, is optionally substituted with one or two or three substituents selected from the group consisting of -halogen, —OH, —NH$_2$—$C_{1-4}$ alkyl, —O$C_{1-4}$ alkyl, —C(=O)OH, —C(=O)O$C_{1-4}$ alkyl, —C(=O)NHS(=O)$_2$$C_{1-4}$ alkyl and —NHC(=O)$C_{1-4}$alkyl.

Embodiment 468

The compound of any one of Embodiments 56-58, 84-86, 131-134, 155-158, 160-162, 193, 194, 196-198, 204, 205, 207, 208, 210-212, 217, 218, 304-306, 351-354, 375-378, 380-382, 413, 414, 416-418, 424, 425, 427, 428, 430-432, 437 and 438, wherein $R''$ is —$C_{3-7}$ cycloalkyl, wherein the —$C_{3-7}$ cycloalkyl is optionally substituted with one or two or three substituents selected from the group consisting of -halogen, —OH, —NH$_2$—$C_{1-4}$ alkyl, —O$C_{1-4}$ alkyl, —C(=O)OH, —C(=O)O$C_{1-4}$ alkyl, —C(=O)NHS(=O)$_2$ $C_{1-4}$ alkyl and —NHC(=O)$C_{1-4}$alkyl.

Embodiment 469

The compound of any one of Embodiments 56-58, 84-86, 131-134, 155-158, 160-162, 193, 194, 196-198, 204, 205, 207, 208, 210-212, 217, 218, 304-306, 351-354, 375-378, 380-382, 413, 414, 416-418, 424, 425, 427, 428, 430-432, 437 and 438, wherein $R''$ is —C(=O)$C_{1-4}$ alkyl, wherein the —C(=O)$C_{1-4}$alkyl is optionally substituted with one or two or three substituents selected from the group consisting of -halogen, —OH, —NH$_2$—$C_{1-4}$ alkyl, —O$C_{1-4}$ alkyl, —C(=O)OH, —C(=O)O$C_{1-4}$ alkyl, —C(=O)NHS(=O)$_2$ $C_{1-4}$ alkyl and —NHC(=O)$C_{1-4}$alkyl.

Embodiment 470

The compound of any one of Embodiments 56-58, 84-86, 131-134, 155-158, 160-162, 193, 194, 196-198, 204, 205, 207, 208, 210-212, 217, 218, 304-306, 351-354, 375-378, 380-382, 413, 414, 416-418, 424, 425, 427, 428, 430-432, 437 and 438, wherein $R''$ is -Het$^{a1}$.

Embodiment 471

The compound of any one of Embodiments 56-58, 84-86, 131-134, 155-158, 160-162, 193, 194, 196-198, 204, 205, 207, 208, 210-212, 217, 218, 304-306, 351-354, 375-378, 380-382, 413, 414, 416-418, 424, 425, 427, 428, 430-432, 437 and 438, wherein $R'''$ and $R''$ are taken together along with the atom to which $R'''$ and $R''$ are attached to form an optionally substituted 4-7 monocyclic heterocyclic ring. In some embodiments, the optionally substituted 4-7 monocyclic heterocyclic ring contains an additional nitrogen, such that the optionally substituted 4-7 monocyclic heterocyclic ring contains 2 or 3 total ring nitrogens.

Embodiment 472

The compound of any one of Embodiments 56-58, 84-86, 131-134, 155-158, 160-162, 193, 194, 196-198, 204, 205, 207, 208, 210-212, 217, 218, 304-306, 351-354, 375-378, 380-382, 413, 414, 416-418, 424, 425, 427, 428, 430-432, 437 and 438, wherein $R'''$ and $R''$ are taken together along with the atom to which $R'''$ and $R''$ are attached to form an optionally substituted 7-10 bicyclic heterocyclic ring. In some embodiments, the optionally substituted 7-10 bicyclic heterocyclic ring contains 1, 2 or 3 heteroatoms selected from O (oxygen) and S (sulfur) along with a further nitrogen, such that the optionally substituted 7-10 bicyclic heterocyclic ring contains 2 or 3 total ring nitrogens.

Embodiment 473

The compound of Embodiment 471 or 472, wherein the heterocyclic ring is unsubstituted.

Embodiment 474

The compound of Embodiment 471 or 472, wherein heterocyclic ring is substituted.

Embodiment 475

The compound of Embodiment 474, wherein the 4-7 monocyclic heterocyclic ring is substituted with —$C_{1-4}$ alkyl, —$C_{3-7}$ cycloalkyl, —OH, —$C_{1-4}$ alkoxy, —C(=O) $C_{1-4}$ alkyl, —C(=O)OH or —C(=O)O$C_{1-4}$alkyl.

Embodiment 476

The compound of any one of Embodiments 471-474, wherein the heterocyclic ring is selected from the group consisting of

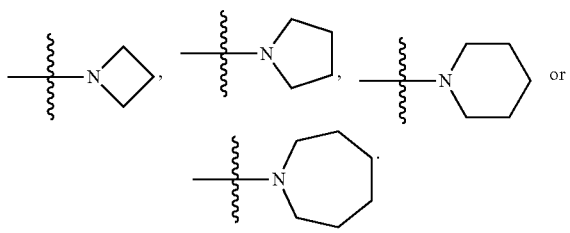

Embodiment 477

The compound of any one of Embodiments 471-474, wherein the heterocyclic ring is selected from the group consisting of

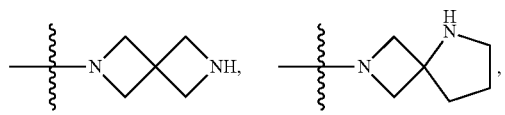

-continued

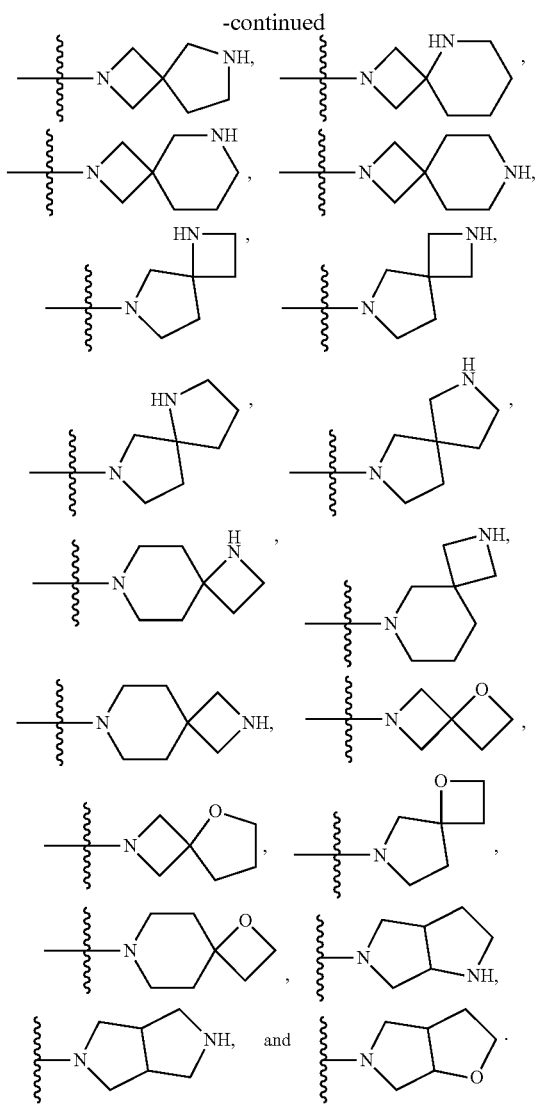

When the bicyclic heterocyclic ring is substituted, one or more hydrogens attached to a carbon and/or nitrogen of the bicyclic heterocyclic ring can be replaced with a non-hydrogen moiety, such as those described herein, including —$C_{1-4}$ alkyl, —$C_{3-7}$ cycloalkyl, —OH, —$C_{1-4}$ alkoxy, —C(=O)$C_{1-4}$ alkyl, —C(=O)OH or —C(=O)O$C_{1-4}$alkyl.

Embodiment 478

The compound of Embodiment 134 466 or 470, wherein -Het$^{a1}$ is an optionally substituted 5-, 6- or 7-membered monocyclic heteroaryl.

Embodiment 479

The compound of Embodiment 134 466 or 470, wherein -Het$^{a1}$ is an optionally substituted 4-, 5-, 6- or 7-membered monocyclic heterocyclyl.

Embodiment 480

The compound of Embodiment 134 466 or 470, wherein -Het$^{a1}$ is an optionally substituted fused 8-, 9-, 10- or 11-membered bicyclic heteroaryl.

Embodiment 481

The compound of Embodiment 134 466 or 470, wherein -Het$^{a1}$ is an optionally substituted fused 8-, 9-, 10- or 11-membered heterocyclyl.

Embodiment 482

The compound of any one of Embodiments 1-481, wherein $R^{2a}$ is hydrogen.

Embodiment 483

The compound of any one of Embodiments 1-481, wherein $R^{2a}$ is halogen.

Embodiment 484

The compound of any one of Embodiments 1-483, wherein $R^{2b}$ is hydrogen.

Embodiment 485

The compound of any one of Embodiments 1-483, wherein $R^{2b}$ is halogen.

Embodiment 486

The compound of any one of Embodiments 1-485, wherein $R^{2c}$ is hydrogen.

Embodiment 487

The compound of any one of Embodiments 1-485, wherein $R^{2c}$ is halogen.

Embodiment 488

The compound of any one of Embodiments 1-487, wherein $R^{2d}$ is hydrogen.

Embodiment 489

The compound of any one of Embodiments 1-487, wherein $R^{2d}$ is halogen.

Embodiment 490

The compound of any one of Embodiments 1-487, wherein $R^{2d}$ is cyano.

Embodiment 491

The compound of any one of Embodiments 1-487, wherein $R^{2d}$ is —$CH_3$.

Embodiment 492

The compound of any one of Embodiments 1-487, wherein $R^{2d}$ is —$CH_2CH_3$.

Embodiment 493

The compound of any one of Embodiments 1-487, wherein $R^{2d}$ is —$CH_2OH$.

Embodiment 494

The compound of any one of Embodiments 1-487, wherein $R^{2d}$ is —OCH$_3$.

Embodiment 495

The compound of any one of Embodiments 1-487, wherein $R^{2d}$ is —SCH$_3$.

Embodiment 496

The compound of any one of Embodiments 1-495, wherein $R^{2e}$ is hydrogen.

Embodiment 497

The compound of any one of Embodiments 1-495, wherein $R^{2e}$ is halogen.

Embodiment 498

The compound of any one of Embodiments 1-497, wherein $R^{2f}$ is hydrogen.

Embodiment 499

The compound of any one of Embodiments 1-497, wherein $R^{2f}$ is halogen.

Embodiment 500

The compound of any one of Embodiments 1-497, wherein $R^{2f}$ is cyano.

Embodiment 501

The compound of any one of Embodiments 1-497, wherein $R^{2f}$ is —CH$_3$.

Embodiment 502

The compound of any one of Embodiments 1-497, wherein $R^{2f}$ is —CH$_2$CH$_3$.

Embodiment 503

The compound of any one of Embodiments 1-497, wherein $R^{2f}$ is —CH$_2$OH.

Embodiment 504

The compound of any one of Embodiments 1-497, wherein $R^{2f}$ is —OCH$_3$.

Embodiment 505

The compound of any one of Embodiments 1-497, wherein $R^{2f}$ is —SCH$_3$.

Embodiment 506

The compound of any one of Embodiments 1-505, wherein $R^{2g}$ is hydrogen.

Embodiment 507

The compound of any one of Embodiments 1-505, wherein $R^{2g}$ is halogen.

Embodiment 508

The compound of any one of Embodiments 1-507, wherein $R^{2h}$ is hydrogen.

Embodiment 509

The compound of any one of Embodiments 1-507, wherein $R^{2h}$ is halogen.

Embodiment 510

A compound of Formula (I), or a pharmaceutically acceptable salt thereof, having the structure:

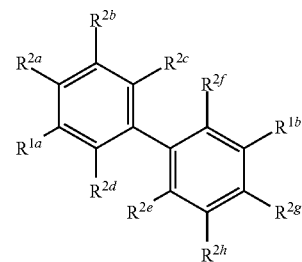

wherein:

$R^{1a}$ is selected from the group consisting of:

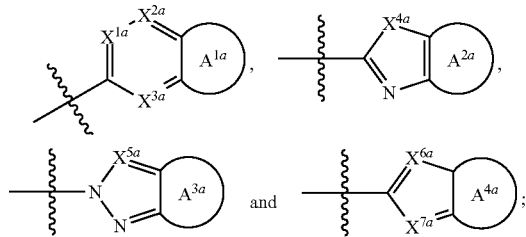

Ring $A^{1a}$, Ring $A^{2a}$, Ring $A^{3a}$ and Ring $A^{4a}$ are independently selected from the group consisting of:
  a monocyclic C$_{5-7}$ cycloalkyl substituted with $R^{3a1}$;
  a bicyclic C$_{6-12}$ cycloalkyl substituted with $R^{3a2}$;
  a 5-7 membered nitrogen-containing monocyclic heterocyclyl, wherein a nitrogen of the 5-7 membered nitrogen-containing monocyclic heterocyclyl is optionally substituted with $R^{3a3}$, wherein a carbon of the 5-7 membered nitrogen-containing monocyclic heterocyclyl is optionally substituted with $R^{3a4}$ or $R^{3a5}$, and wherein when $R^{3a5}$ is present, $R^{3a5}$ is attached at a carbon atom adjacent to a nitrogen of the 5-7 membered nitrogen-containing monocyclic heterocyclyl;
  a 6-12 membered nitrogen-containing bicyclic heterocyclyl, wherein a nitrogen of the 6-12 membered nitrogen-containing bicyclic heterocyclyl is optionally substituted with $R^{3a6}$; wherein a carbon of the 6-12 membered nitrogen-containing bicyclic heterocyclyl is optionally substituted with $R^{3a7}$ or $R^{3a8}$, and wherein R$^{3a8}$ is present, R$^{3a8}$ is attached at the carbon atom adjacent to a nitrogen of the 6-12 membered nitrogen-containing bicyclic heterocyclyl; and a 5-7 membered oxygen-containing monocyclic heterocyclyl substituted with R$^{3a9}$ or R$^{3a10}$; wherein R$^{3a10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens;

wherein Ring A$^{1a}$, Ring A$^{2a}$, Ring A$^{3a}$ and Ring A$^{4a}$ is optionally further substituted;

wherein when R$^{1a}$ is

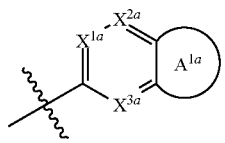

and Ring A$^{1a}$ is a 5-7 membered nitrogen-containing monocyclic heterocyclyl, then R$^{3a3}$ is present;

wherein when R$^{1a}$ is

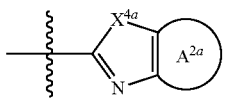

and Ring A$^{2a}$ is a 5-7 membered nitrogen-containing monocyclic heterocyclyl, then R$^{3a3}$ is present;

wherein when R$^{1a}$ is

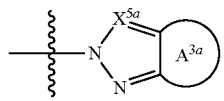

and Ring A$^{3a}$ is a 5-7 membered nitrogen-containing monocyclic heterocyclyl, then R$^{3a3}$ is present;

wherein when R$^{1a}$ is

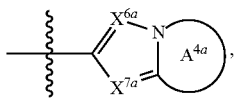

then Ring A$^{4a}$ cannot be a monocyclic C$_{5-7}$ cycloalkyl substituted with R$^{3a1}$ or a bicyclic C$_{6-12}$ cycloalkyl substituted with R$^{3a2}$; and wherein when R$^{1a}$ is

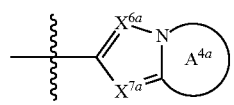

and Ring A$^{4a}$ is a 5-7 membered nitrogen-containing monocyclic heterocyclyl, then R$^{3a3}$ is optional;

X$^{1a}$, X$^{2a}$ and X$^{3a}$ are independently N or CR$^{4a1}$;
X$^{4a}$ is NR$^{4a2}$ O or S;
X$^{5a}$, X$^{6a}$ and X$^{7a}$ are independently N or CR$^{4a3}$;

R$^{1b}$ is selected from the group consisting of:

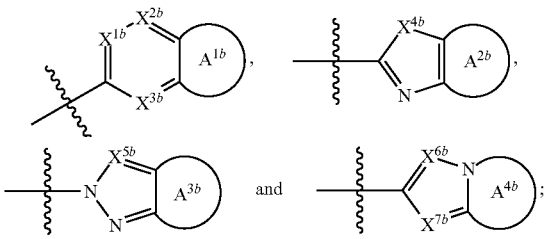

Ring A$^{1b}$, Ring A$^{2b}$, Ring A$^{3b}$ and Ring A$^{4b}$ are independently selected from the group consisting of:

a monocyclic C$_{5-7}$ cycloalkyl substituted with R$^{3b1}$;
a bicyclic C$_{6-12}$ cycloalkyl substituted with R$^{3b2}$;
a 5-7 membered nitrogen-containing monocyclic heterocyclyl, wherein a nitrogen of the 5-7 membered nitrogen-containing monocyclic heterocyclyl is optionally substituted with R$^{3b3}$, wherein a carbon of the 5-7 membered nitrogen-containing monocyclic heterocyclyl is optionally substituted with R$^{3b4}$ or R$^{3b5}$, and wherein when R$^{3b5}$ is present, R$^{3b5}$ is attached at a carbon atom adjacent to a nitrogen of the 5-7 membered nitrogen-containing monocyclic heterocyclyl;

a 6-12 membered nitrogen-containing bicyclic heterocyclyl, wherein a nitrogen of the 6-12 membered nitrogen-containing bicyclic heterocyclyl is optionally substituted with R$^{3b6}$; wherein a carbon of the 6-12 membered nitrogen-containing bicyclic heterocyclyl is optionally substituted with R$^{3b7}$ or R$^{3b8}$, and wherein R$^{3b8}$ is present, R$^{3b8}$ is attached at the carbon atom adjacent to a nitrogen of the 6-12 membered nitrogen-containing bicyclic heterocyclyl; and a 5-7 membered oxygen-containing monocyclic heterocyclyl substituted with R$^{3b9}$ or R$^{3b10}$; wherein R$^{3b10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens;

wherein Ring A$^{1b}$, Ring A$^{2b}$, Ring A$^{3b}$ and Ring A$^{4b}$ is optionally further substituted;

wherein when R$^{1b}$ is

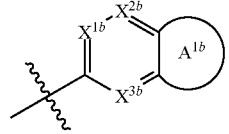

and Ring A$^{1b}$ is a 5-7 membered nitrogen-containing monocyclic heterocyclyl, then R$^{3b3}$ is present;

wherein when R$^{1b}$ is

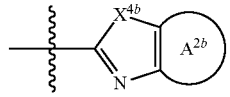

and Ring A$^{2b}$ is a 5-7 membered nitrogen-containing monocyclic heterocyclyl, then R$^{3b3}$ is present;

wherein when $R^{1b}$ is

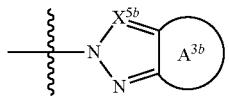

and Ring $A^{3b}$ is a 5-7 membered nitrogen-containing monocyclic heterocyclyl, then $R^{3b3}$ is present;

wherein when $R^{1b}$ is

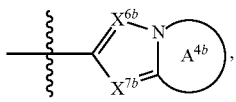

then Ring $A^{4b}$ cannot be a monocyclic $C_{5-7}$ cycloalkyl substituted with $R^{3b1}$ or a bicyclic $C_{6-12}$ cycloalkyl substituted with $R^{3b2}$; and wherein when $R^{1b}$ is

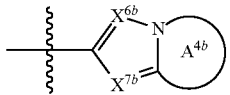

and Ring $A^{4b}$ is a 5-7 membered nitrogen-containing monocyclic heterocyclyl, then $R^{3b3}$ is optional;

$X^{1b}$, $X^{2b}$ and $X^{3b}$ are independently N or $CR^{4b1}$;

$X^{4b}$ is $NR^{4b2}$ O or S;

$X^{5b}$, $X^{6b}$ and $X^{7b}$ are independently N or $CR^{4b3}$;

$R^{3a1}$, $R^{3a2}$, $R^{3a9}$, $R^{3b1}$, $R^{3b2}$ and $R^{3b9}$ are independently selected from the group consisting of —OH, —N(R''')R'', —C$_{1-4}$ alkyl-N(R''')R'', —OC$_{2-4}$ alkyl-N(R''')R'',

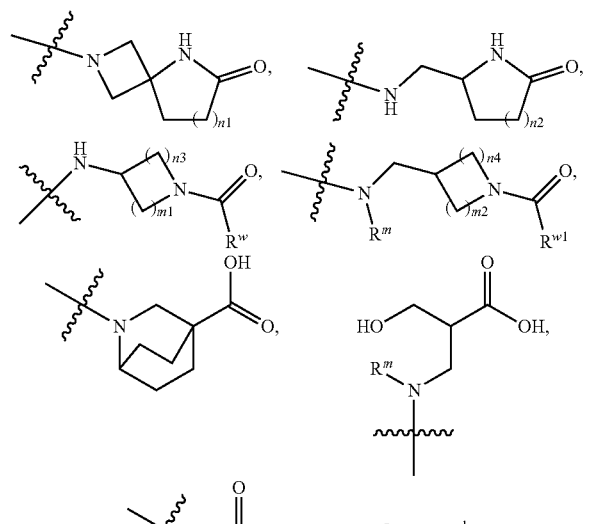

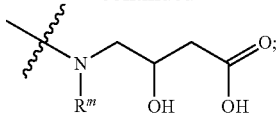

$R^{3a3}$, $R^{3b3}$, $R^{3a6}$ and $R^{3b6}$ are independently selected from the group consisting of —$R^{x1}$, —C$_{1-4}$ alkyl, —C$_{3-7}$ cycloalkyl, —C(=O)C$_{1-4}$ alkyl and -Het$^{a1}$, wherein the —C$_{3-7}$ cycloalkyl, the —C(=O)C$_{1-4}$ alkyl and the -Het$^{a1}$ is optionally substituted with one or two or three substituents selected from the group consisting of -halogen, —C$_{1-4}$ alkyl, —OH, —N(R''')R'', —C$_{1-4}$ alkoxy, —C(=O)OH, —C(=O)OC$_{1-4}$ alkyl, —C(=O)NHS(=O)$_2$C—$_4$ alkyl, —NHC(=O)C$_{1-4}$ alkyl and —C(=O)N(R''')R'', wherein the —C$_{1-4}$ alkyl is optionally substituted with one or two or three substituents selected from the group consisting of -halogen, —OH, —N(R''')R'', —C$_{1-4}$ alkoxy, —C(=O)OH, —C(=O)OC$_{1-4}$ alkyl, —C(=O)NHS(=O)$_2$C—$_4$ alkyl, —NHC(=O)C$_{1-4}$ alkyl and —C(=O)N(R''')R'';

$R^{3a4}$, $R^{3a7}$, $R^{3b4}$ and $R^{3b7}$ are independently selected from the group consisting of -halogen, —C$_{1-4}$ alkyl, —C$_{3-7}$ cycloalkyl, —OH, —OC$_{1-4}$ alkyl, —N(R$_m$)R'', —C$_{1-4}$ alkyl (R''')R'', —C(=O)OH, —C$_{1-4}$ alkyl-C(=O)OH, —C(=O)OC$_{1-4}$ alkyl and —C$_{1-4}$ alkyl-C(=O)OC$_{1-4}$ alkyl; wherein the —C$_{1-4}$ alkyl, is optionally substituted with one or two substituents selected from the group consisting of -halogen, —OH, —C$_{1-4}$ alkoxy, —C(=O)OH, —C(=O)OC$_{1-4}$ alkyl, —C(=O)NHS(=O)$_2$C$_{1-4}$ alkyl, —NHC(=O)C$_{1-4}$ alkyl and —C(=O)N(R''')R'', and wherein the —C$_{3-7}$ cycloalkyl and the —OC$_{1-4}$ alkyl is optionally substituted with one or two substituents selected from the group consisting of -halogen, —OH, —C$_{1-4}$ alkyl, —C$_{1-4}$ alkoxy, —C(=O)OH, —C(=O)OC$_{1-4}$ alkyl, —C(=O)NHS(=O)$_2$C$_{1-4}$ alkyl, —NHC(=O)C$_{1-4}$ alkyl and —C(=O)N(R''')R'', $R^{3a5}$, $R^{3a8}$, $R^{3b5}$ and $R^{3b8}$ are independently selected from the group consisting of —C(=O)OH, —C$_{1-4}$ alkyl and —C$_{3-7}$ cycloalkyl; wherein the —C$_{1-4}$ alkyl is optionally substituted with one or two or three substituents selected from the group consisting of -halogen, —OH, —C$_{1-4}$ alkoxy, —C(=O)OH, —C(=O)OC$_{1-4}$ alkyl, —C(=O)NHS(=O)$_2$ C$_{1-4}$ alkyl, —N(R''')C(=O)C$_{1-4}$ alkyl, —C(=O) N(R''')R'' and —N(R''')R'', and wherein the —C$_{3-7}$ cycloalkyl is optionally substituted with one or two or three substituents selected from the group consisting of -halogen, —OH, —C$_{1-4}$ alkyl, —C$_{1-4}$ alkoxy, —C(=O)OH, —C(=O)OC$_{1-4}$ alkyl, —C(=O)NHS(=O)$_2$C$_{1-4}$ alkyl, —N(R''')C(=O)C$_{1-4}$ alkyl, —C(=O) N(R''')R'' and —N(R''')R'';

$R^{3a10}$ and $R^{3b10}$ are independently selected from the group consisting of —C$_{1-4}$ alkyl, —C$_{3-7}$ cycloalkyl and —(C$_{1-4}$ alkyl)N(R''')R'', wherein the —C$_{1-4}$ alkyl is optionally substituted with one or two or three substituents selected from the group consisting of -halogen, —OH, —C$_{1-4}$ alkoxy, —C(=O)OH, —(C=O)NHS(=O)$_2$(C$_{1-4}$ alkyl) and —NHC(=O)C$_{1-4}$ alkyl, and wherein the —C$_{3-7}$ cycloalkyl and the —(C$_{1-4}$ alkyl)N(R''')R'' is optionally substituted with one or two or three substituents selected from the group consisting of -halogen, —OH, —C$_{1-4}$ alkyl, —C$_{1-4}$ alkoxy, —C(=O)OH, —C(=O)OC$_{1-4}$ alkyl, —(C=O)NHS(=O)$_2$ (C$_{1-4}$ alkyl) and —NHC(=O)C$_{1-4}$ alkyl;

each R''' and each R'' are independently selected from the group consisting of hydrogen, —$R^{x2}$, —C$_{1-4}$ alkyl, —C$_{3-7}$ cycloalkyl, —C(=O)C$_{1-4}$alkyl and -Het$^{a1}$, wherein the —C$_{1-4}$ alkyl, the —C$_{3-7}$ cycloalkyl and the —C(=O)C$_{1-4}$ alkyl is optionally substituted with one or two or three substituents selected from the group consisting of -halogen, —OH, —NH$_2$—C$_{1-4}$ alkyl, —OC$_{1-4}$ alkyl, —C(=O)OH, —C(=O)OC$_{1-4}$ alkyl, —C(=O)NHS(=O)$_2$C$_{1-4}$ alkyl and —NHC(=O)C$_{1-4}$ alkyl; or R$^m$ and R$^n$ are taken together along with the atom to which R$^m$ and R$^n$ are attached to form 4-7 monocyclic heterocyclic ring;

R$^{x1}$ and R$^{x2}$ are independently selected from the group consisting of:

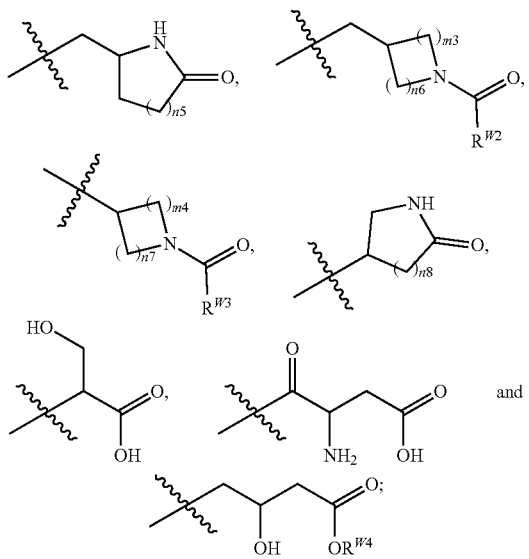

R$^W$, R$^{W1}$, R$^{W2}$, R$^{W3}$ and R$^{W4}$ are independently selected from the group consisting of an unsubstituted —C$_{1-4}$ alkyl and a substituted —C$_{1-4}$ alkyl substituted with one or two or three substituents selected from the group consisting of -halogen, —OH, —OC$_{1-4}$ alkyl, —C(=O)OH and —C(=O)OC$_{1-4}$ alkyl;

Het$^{a1}$ is an optionally substituted 5-, 6- or 7-membered monocyclic heteroaryl, an optionally substituted 4-, 5-, 6- or 7-membered monocyclic heterocyclyl, an optionally substituted fused 8-, 9-, 10- or 11-membered bicyclic heteroaryl or an optionally substituted fused 8-, 9-, 10- or 11-membered heterocyclyl, wherein each heteroaryl and each heterocyclyl contains at least one heteroatom independently selected from the group consisting of O, S, S(=O), S(=O)$_2$ and N;

n1, n2, n3, n4, n5, n6, n7 and n8 are independently 1 or 2;

m1, m2, m3 and m4 are independently 1 or 2;

R$^{2d}$ and R$^{2f}$ are independently selected from the group consisting of hydrogen, halogen, cyano, —CH$_3$, —CH$_2$CH$_3$, —CH$_2$OH, —OCH$_3$ and —SCH$_3$;

R$^{2a}$, R$^{2b}$, R$^{2c}$, R$^{2e}$, R$^{2g}$, R$^{2h}$ are independently selected from the group consisting of hydrogen and halogen;

R$^{4a1}$, R$^{4a3}$, R$^{4b1}$ and R$^{4b3}$ are selected from the group consisting of hydrogen, halogen, cyano, an unsubstituted C$_{1-4}$ alkyl, an unsubstituted C$_{1-4}$haloalkyl, an unsubstituted C$_{1-4}$ alkoxy and an unsubstituted C$_{1-4}$ haloalkoxy; and R$^{4a2}$ and R$^{4b2}$ are selected from the group consisting of hydrogen, an unsubstituted C$_{1-4}$ alkyl and an unsubstituted C$_{1-4}$ haloalkyl.

Examples of compounds of Formula (I) include the following:

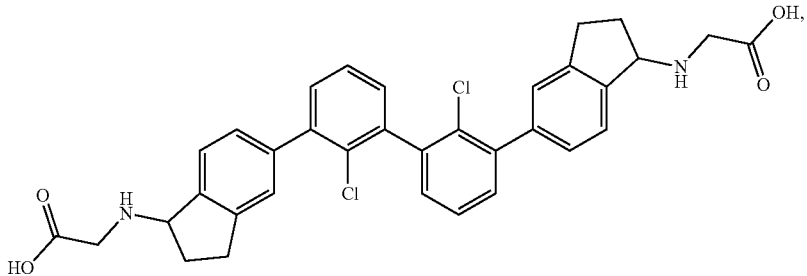

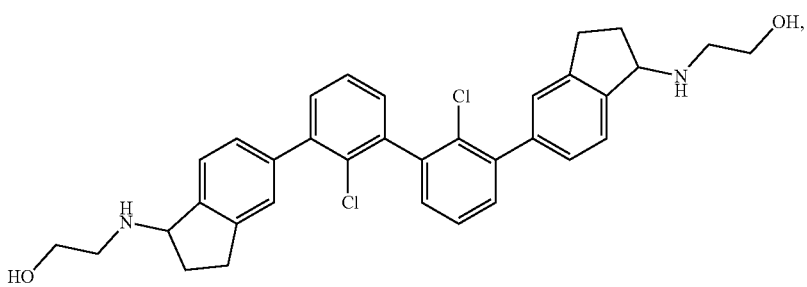

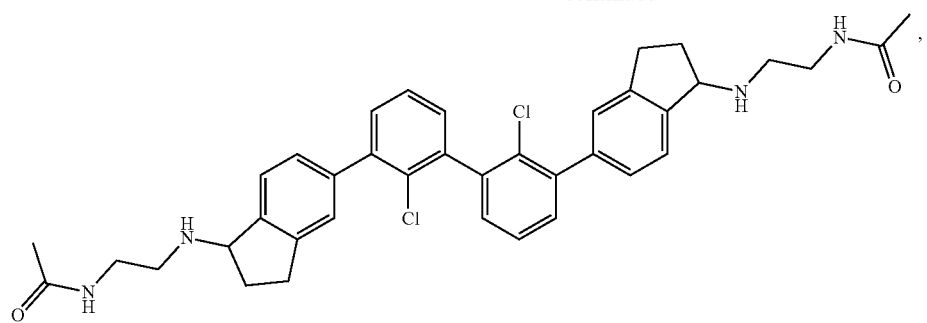
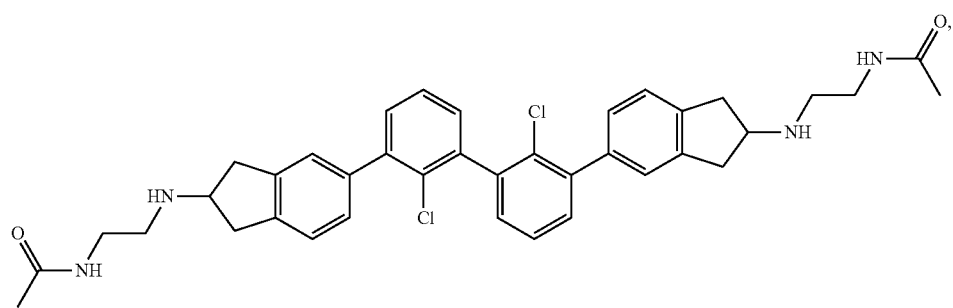
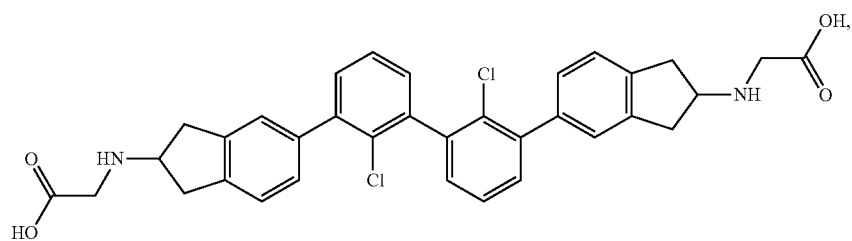
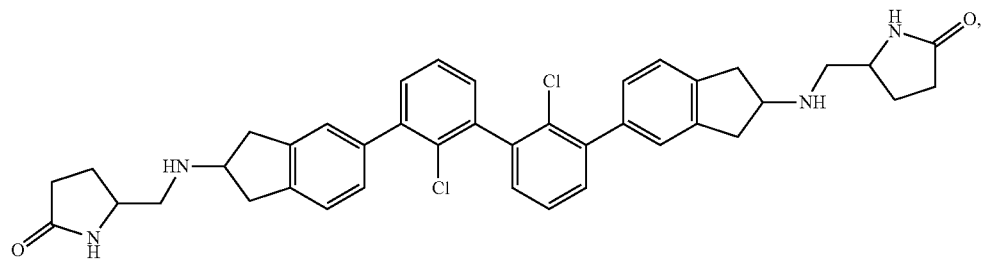
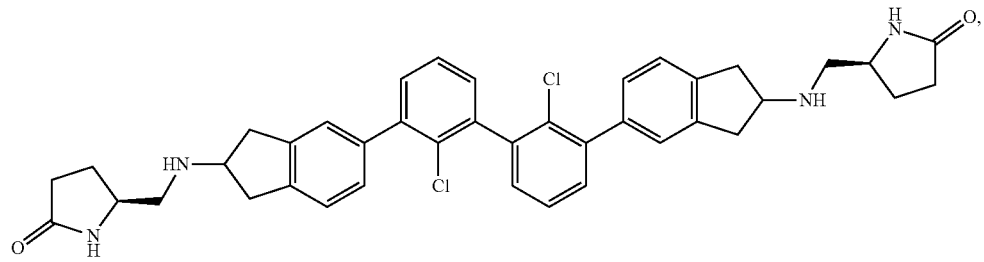

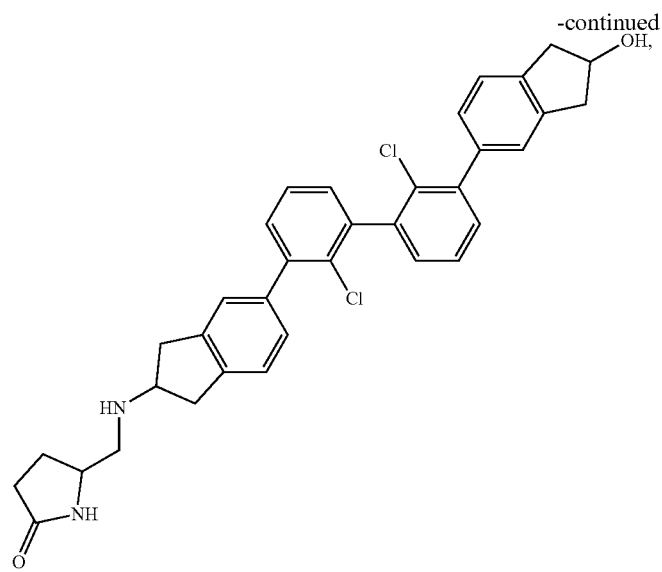
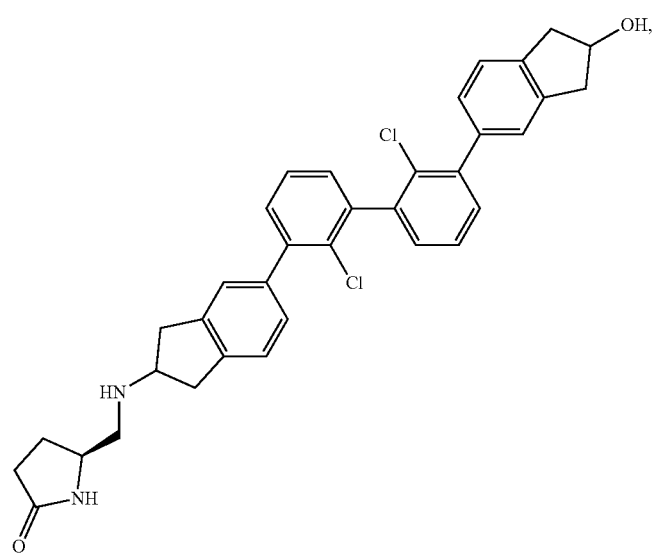
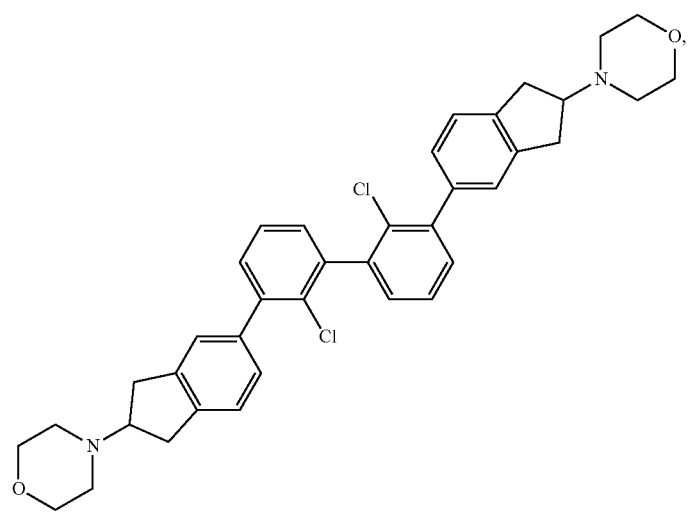

-continued
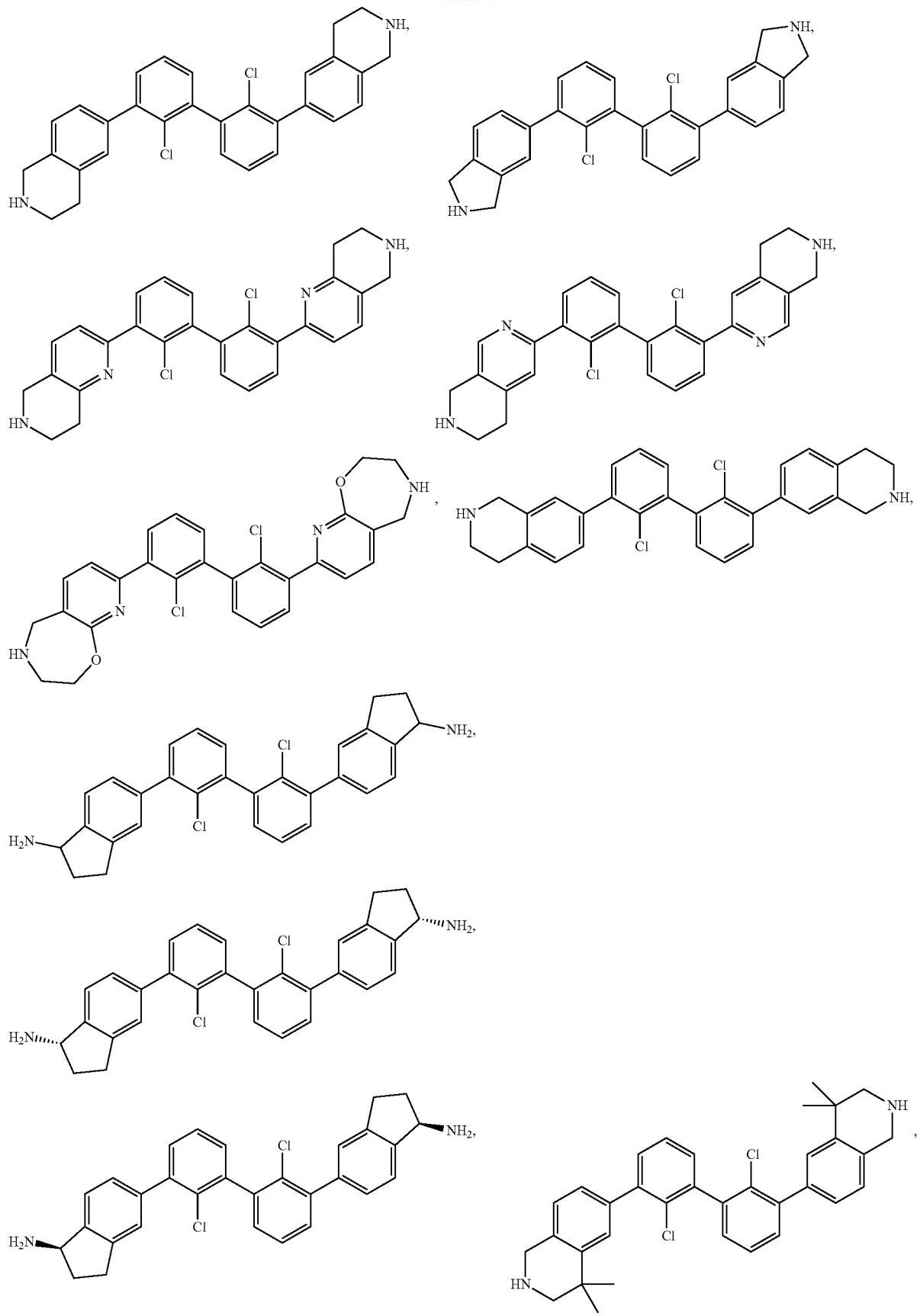

-continued
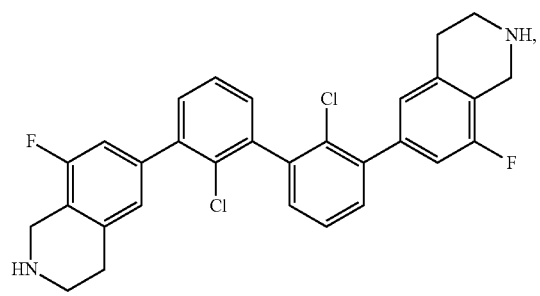
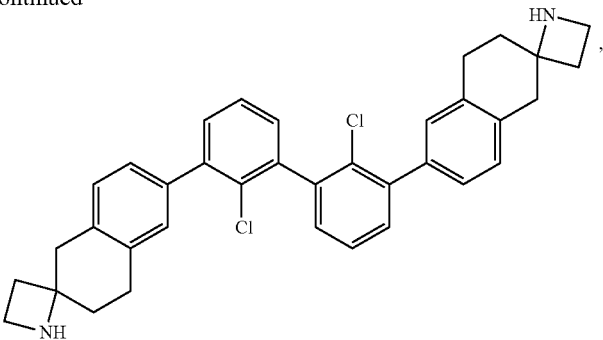
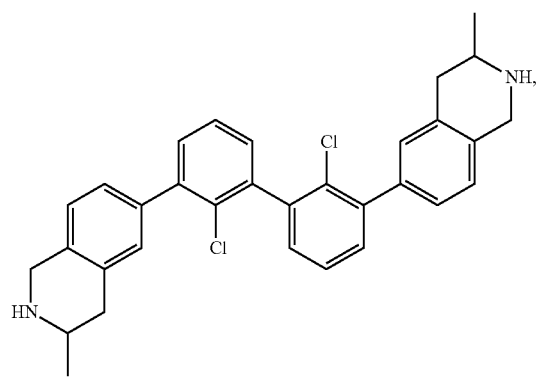
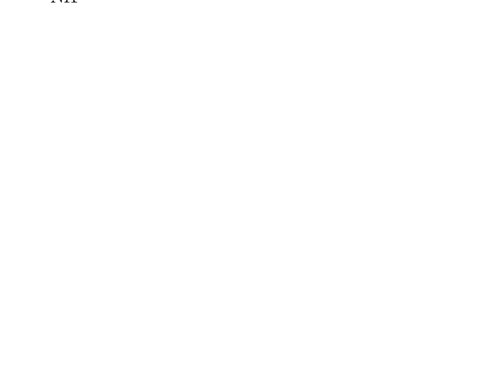
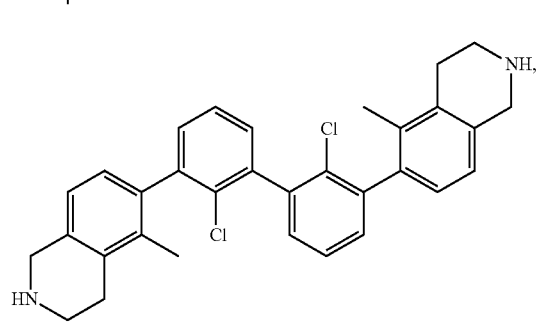
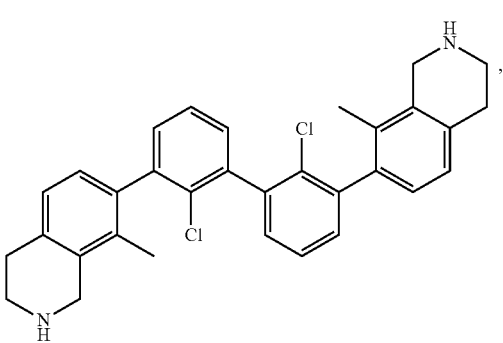
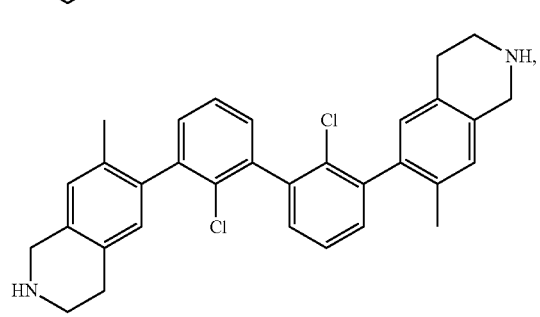
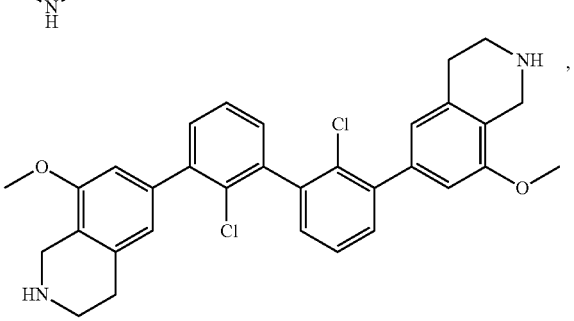
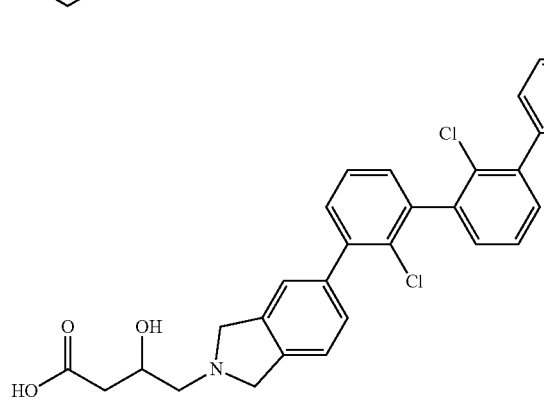

-continued
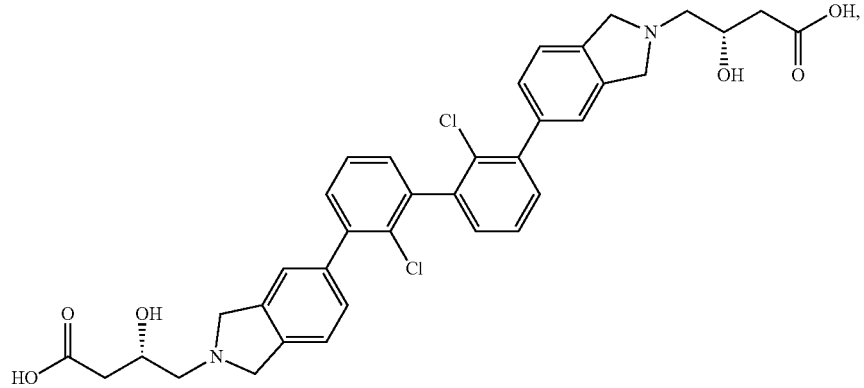
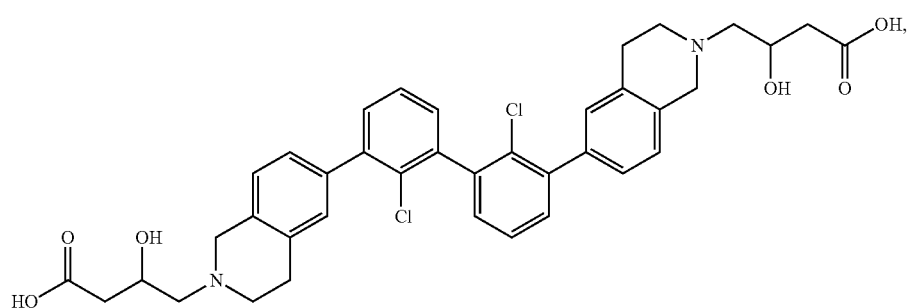
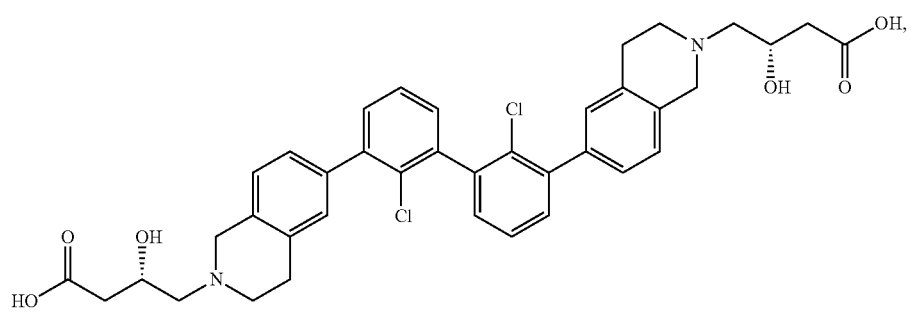
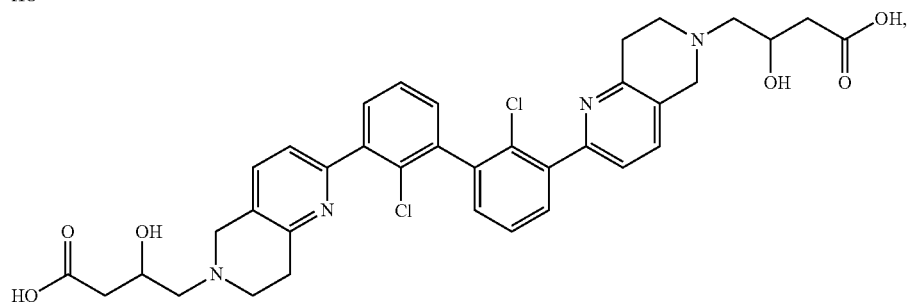

-continued
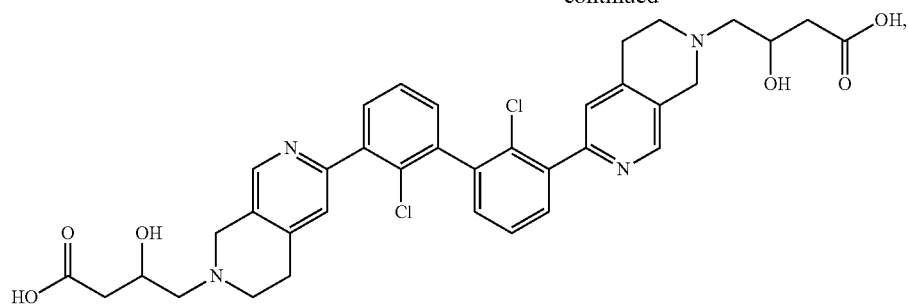
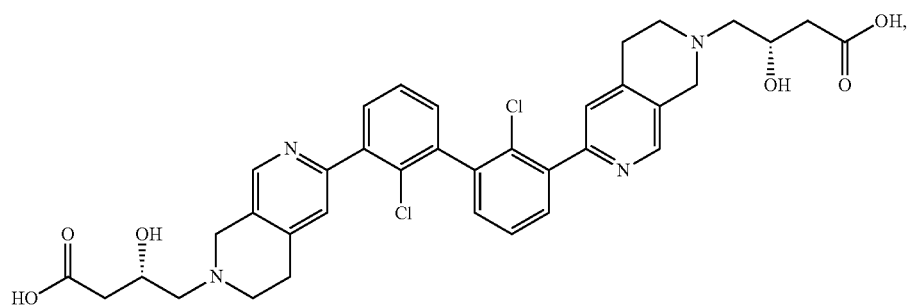
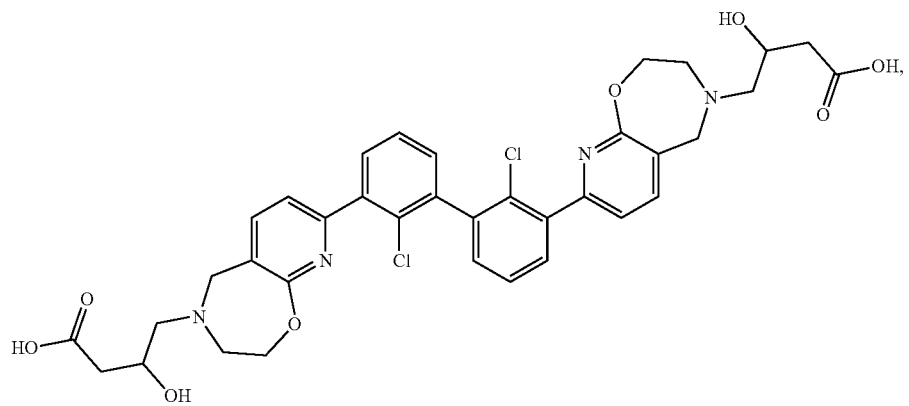
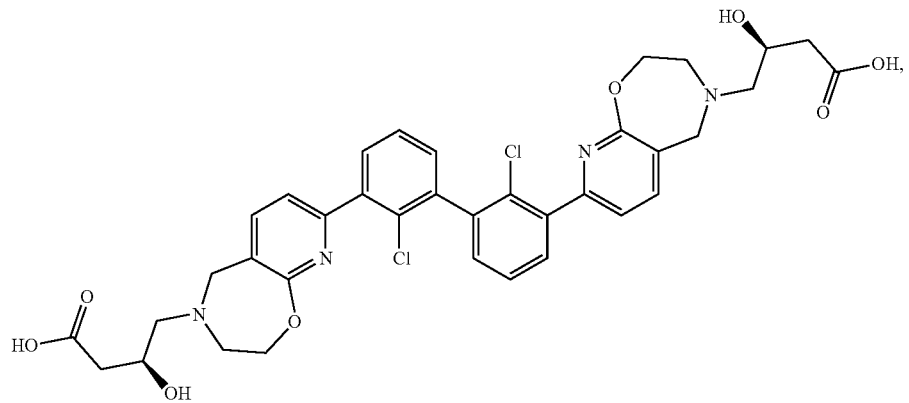

-continued
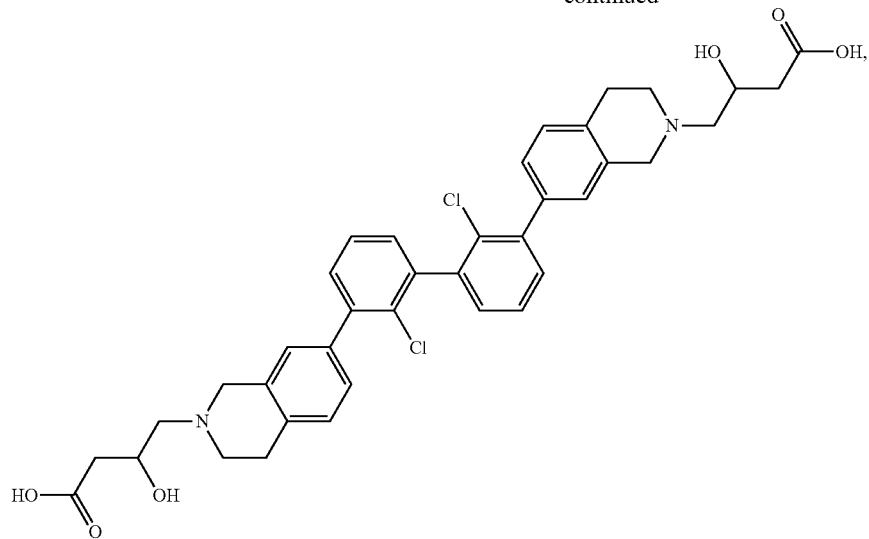
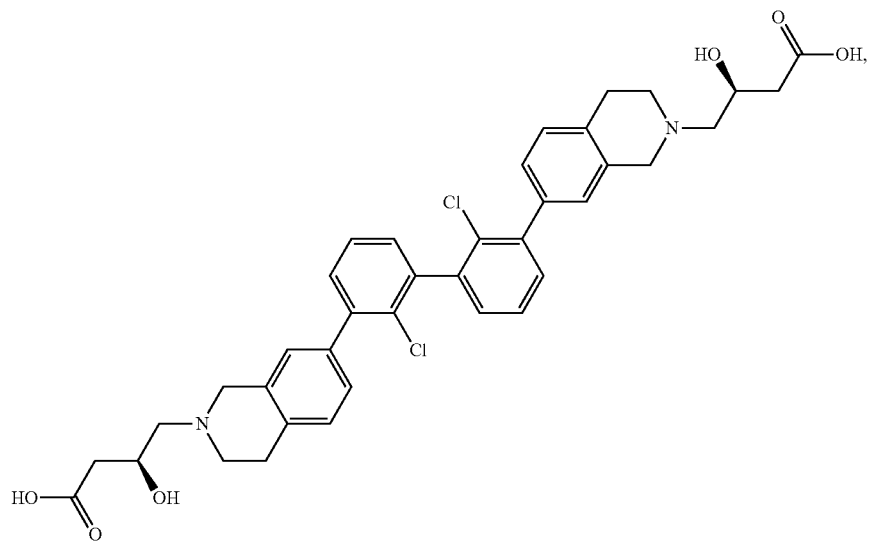
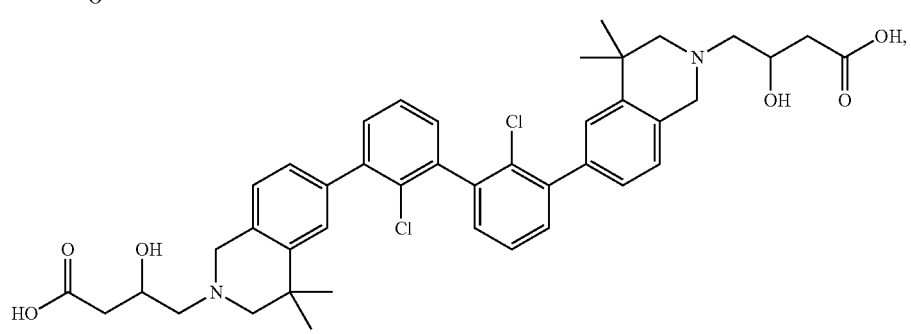
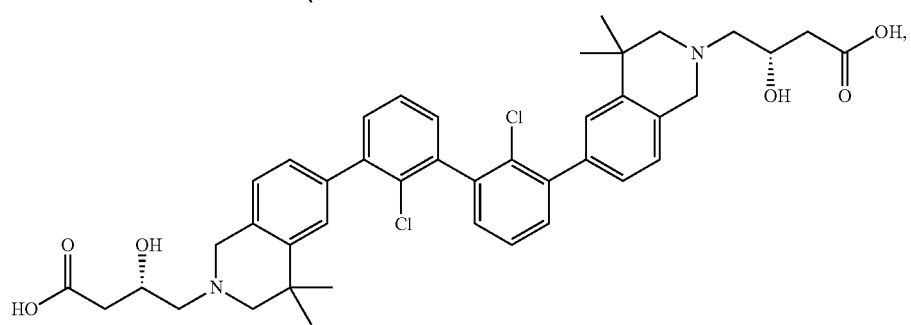

-continued
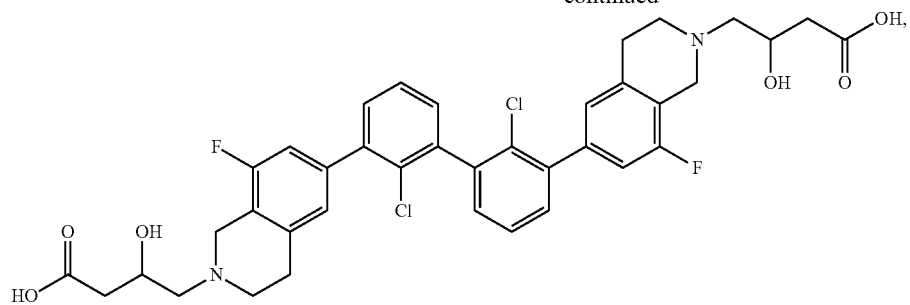
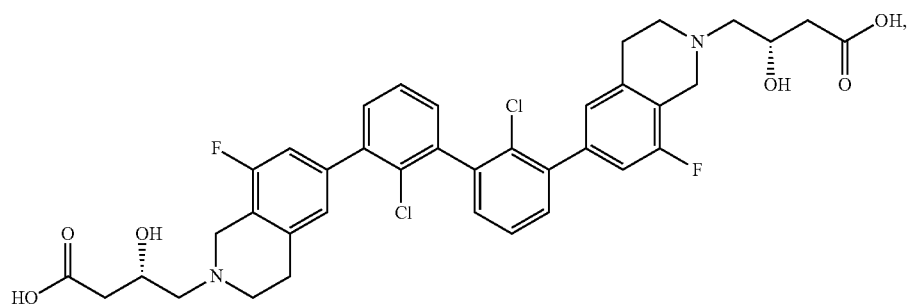
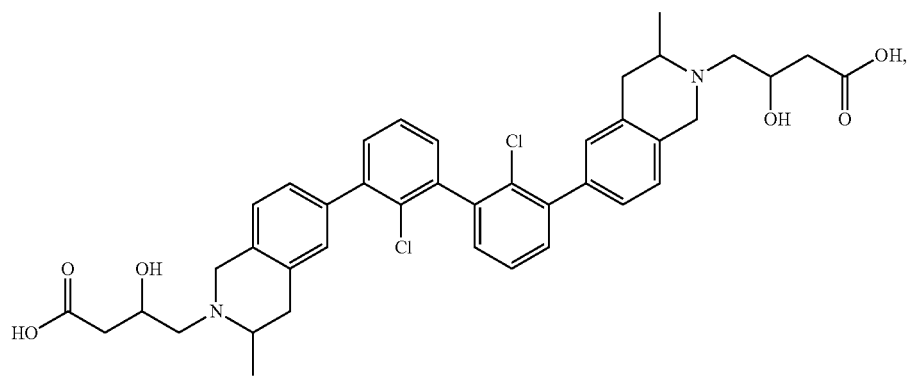
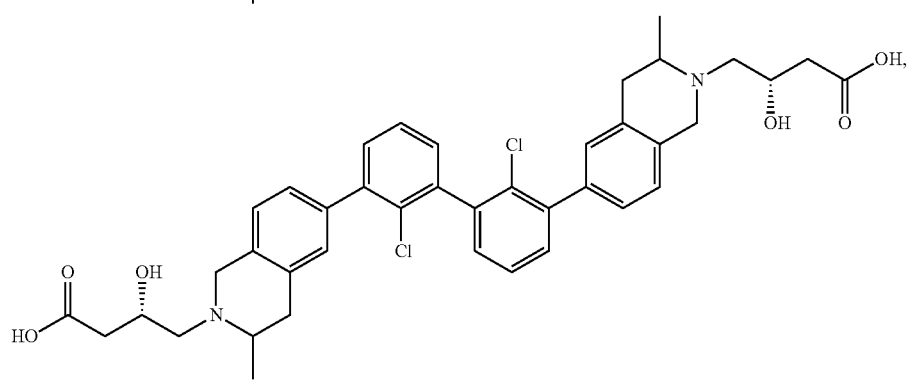
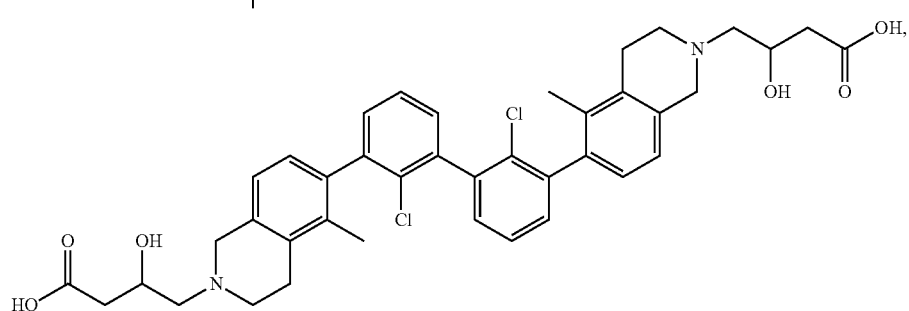

-continued
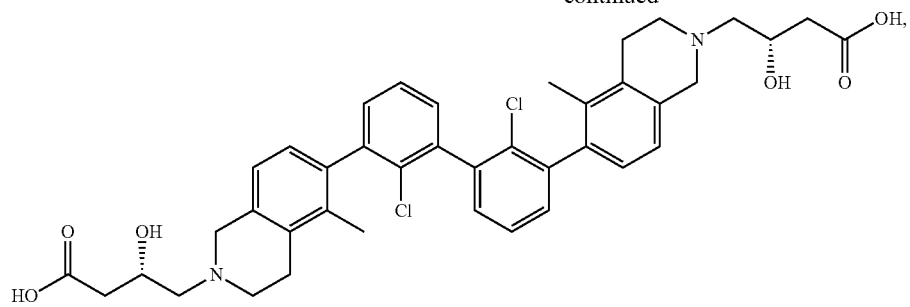
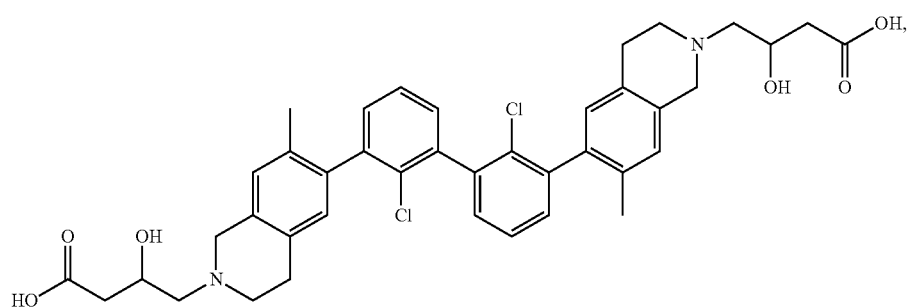
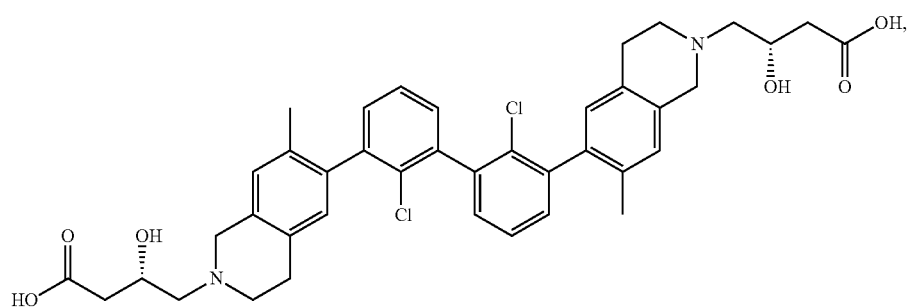
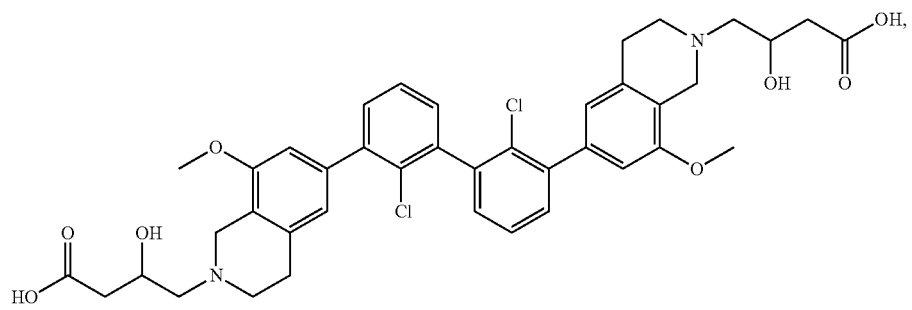
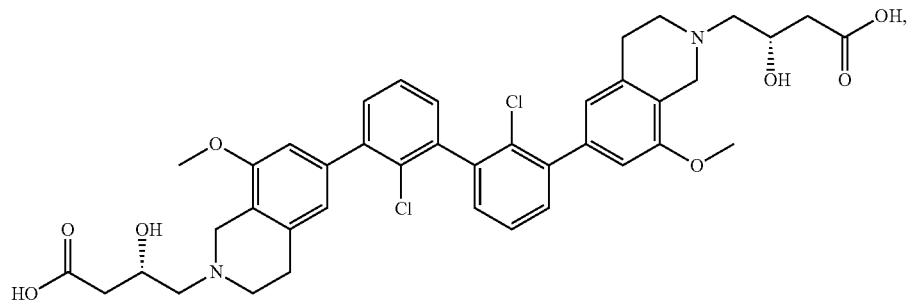

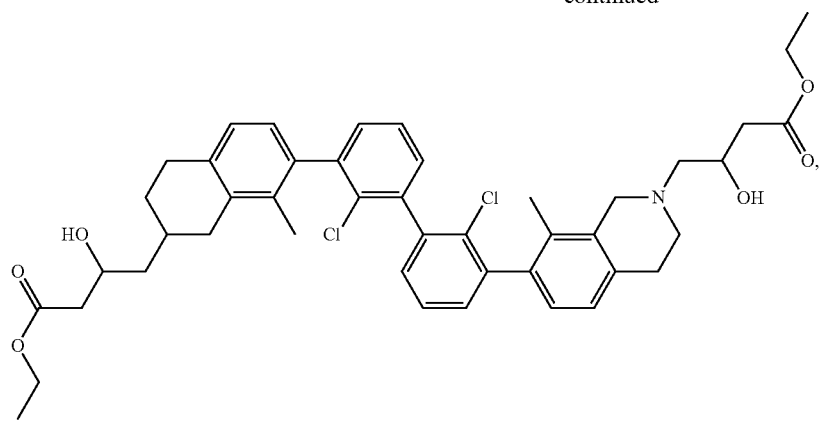
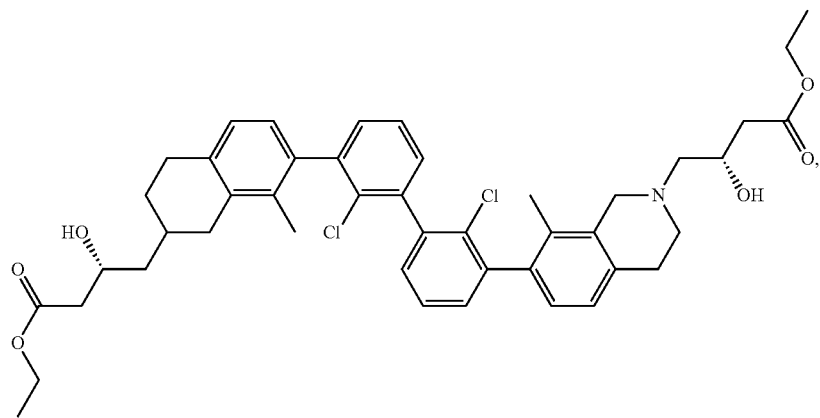
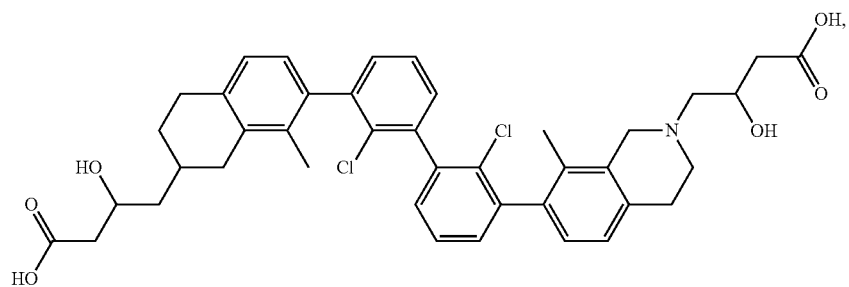
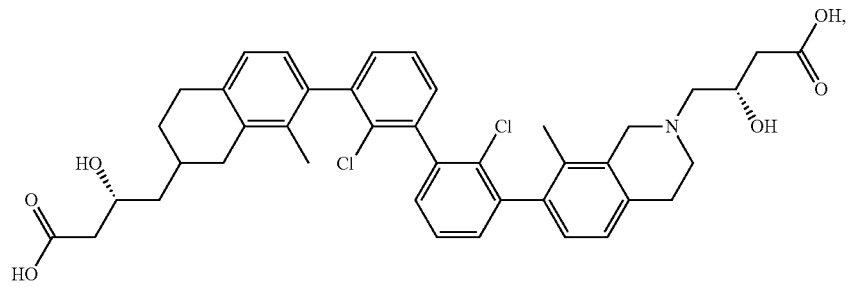

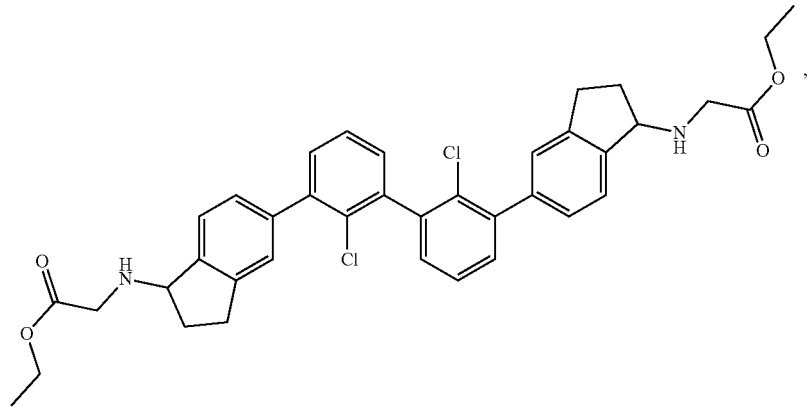
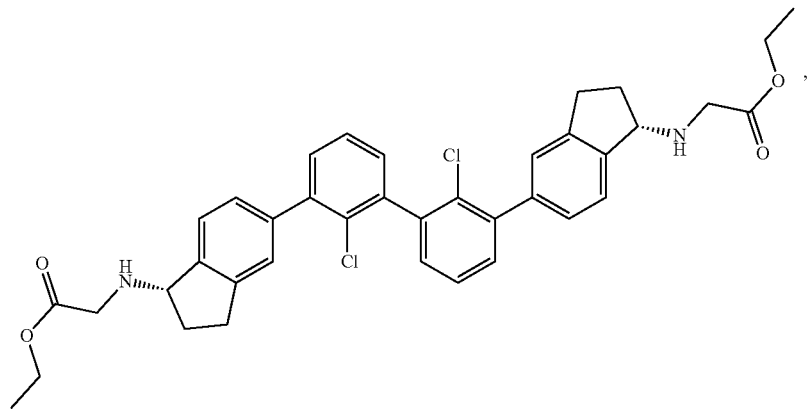
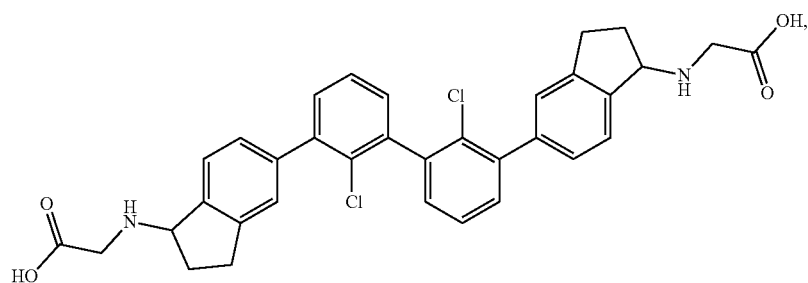
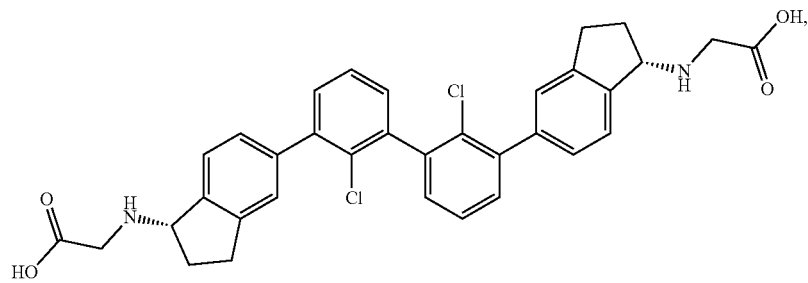
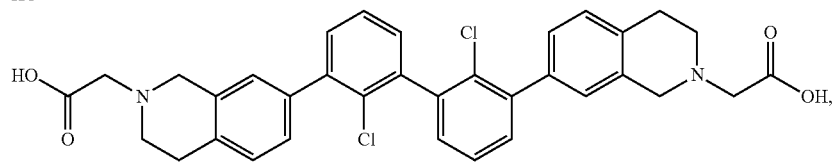

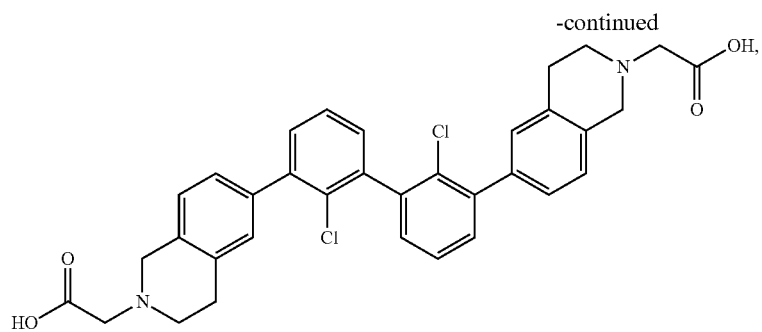
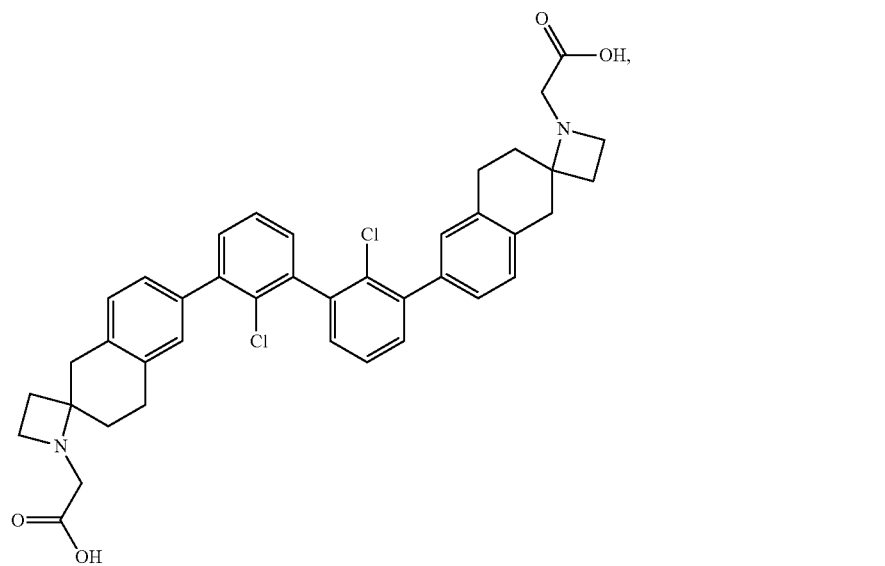
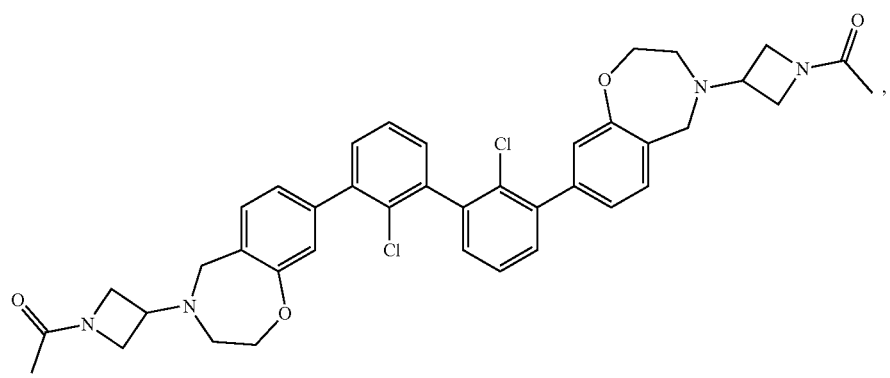

-continued
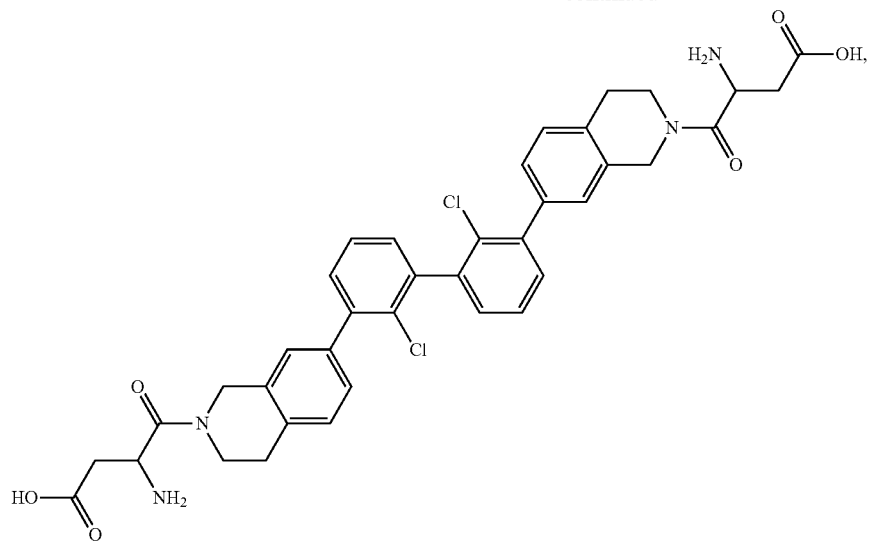
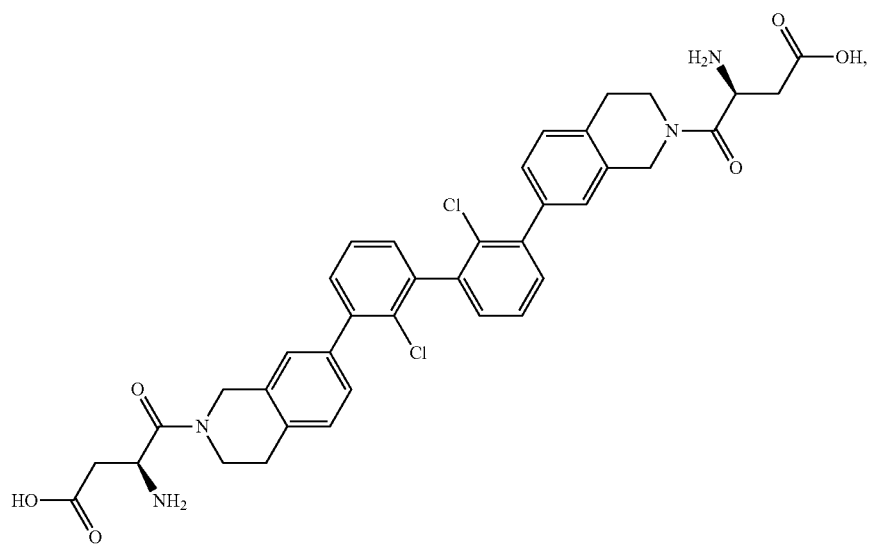
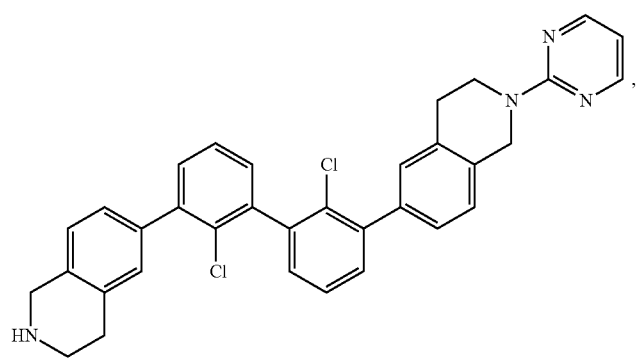

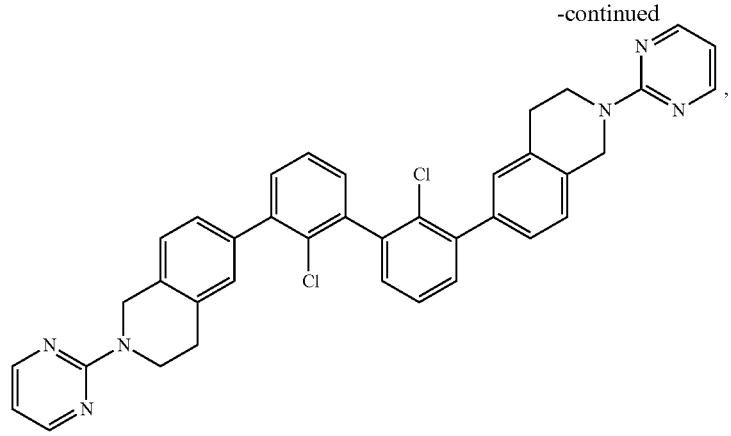
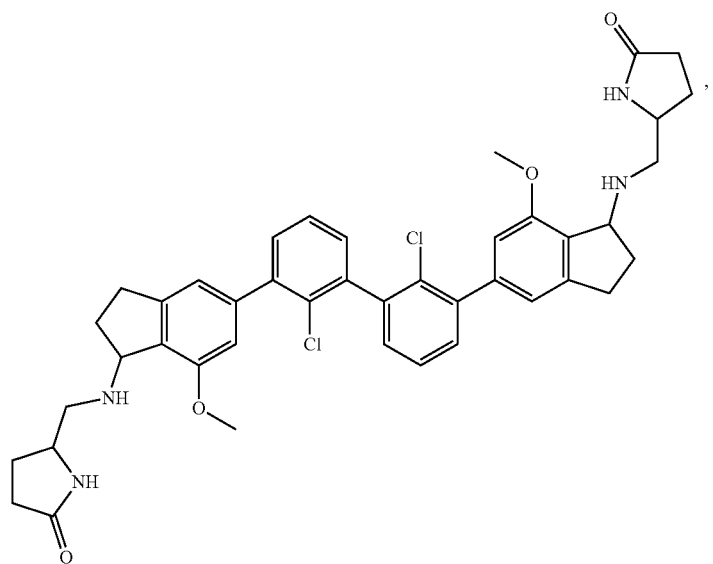
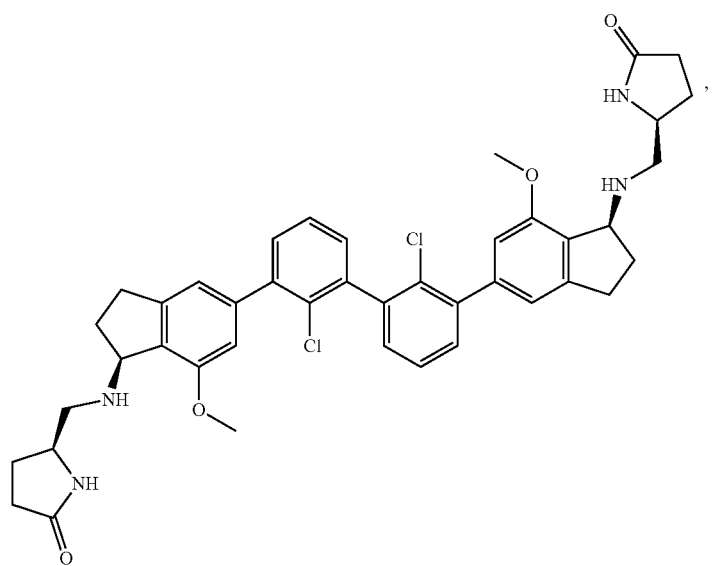

-continued
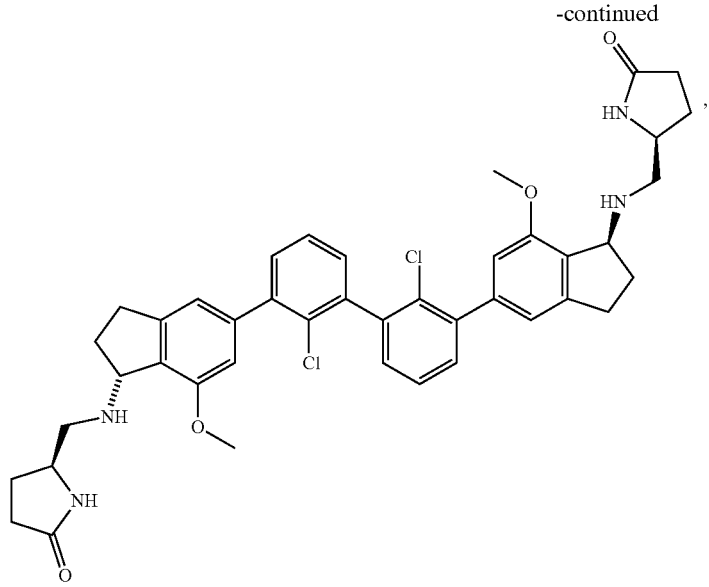
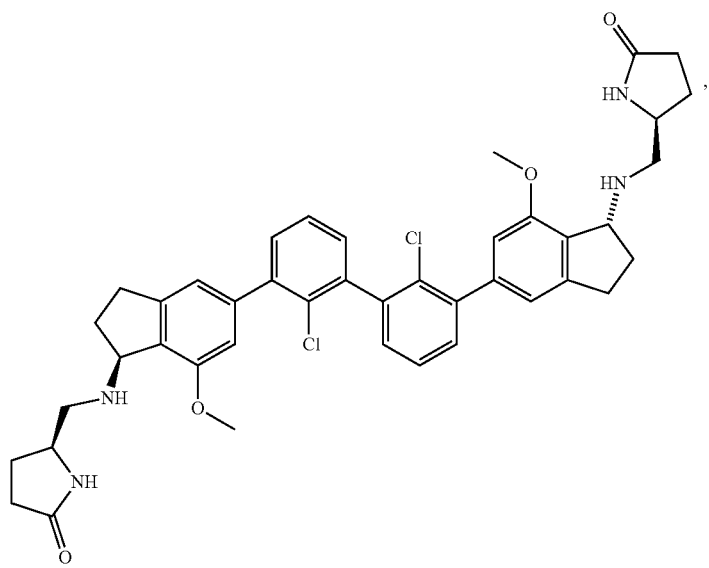
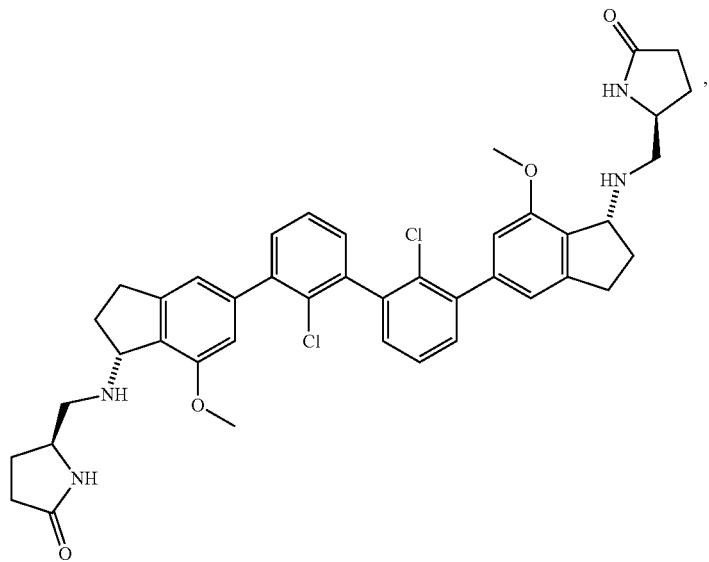

-continued
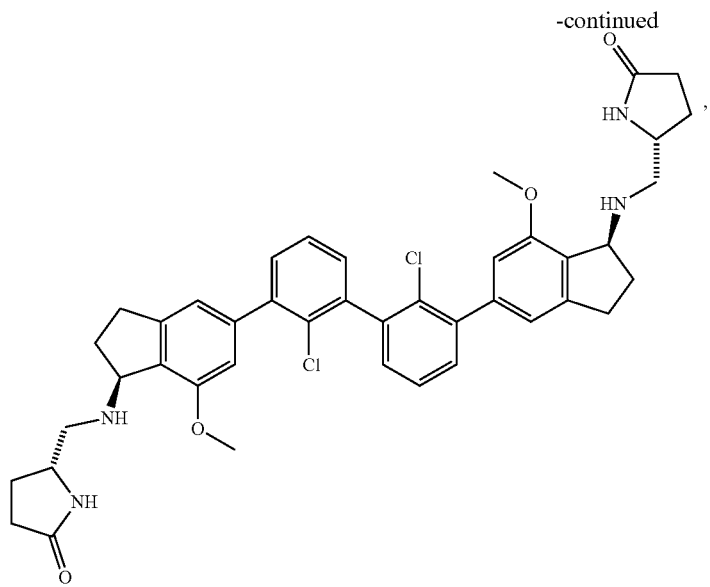
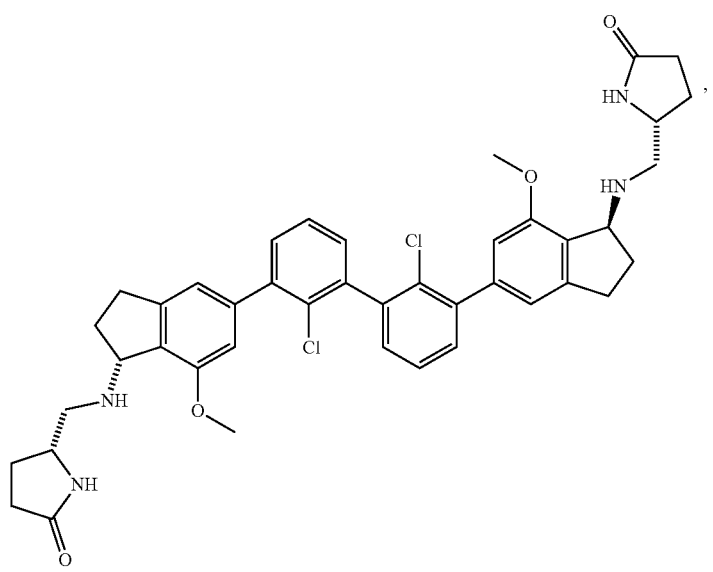
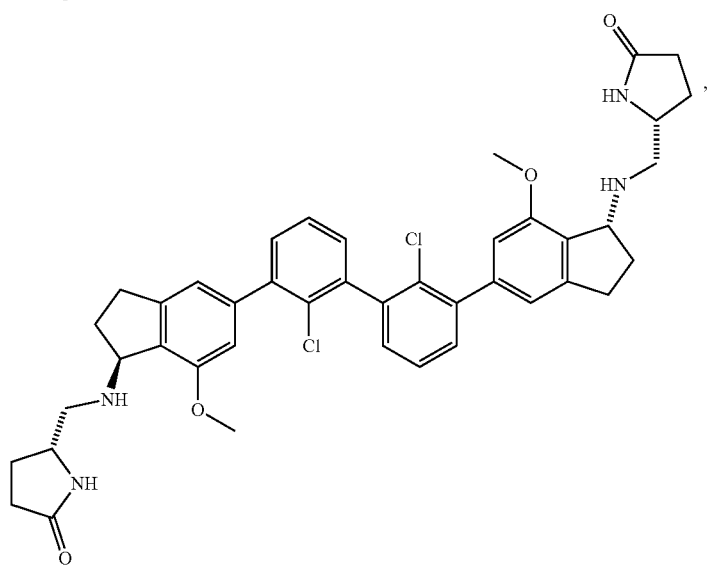

-continued
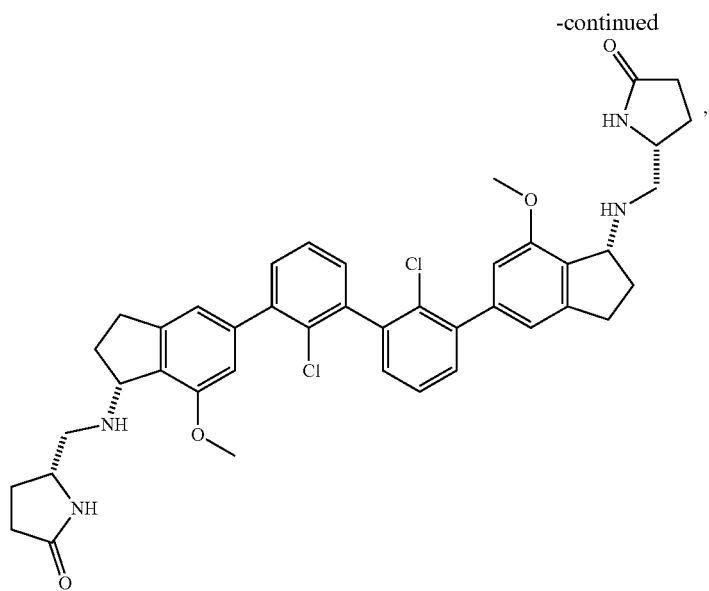
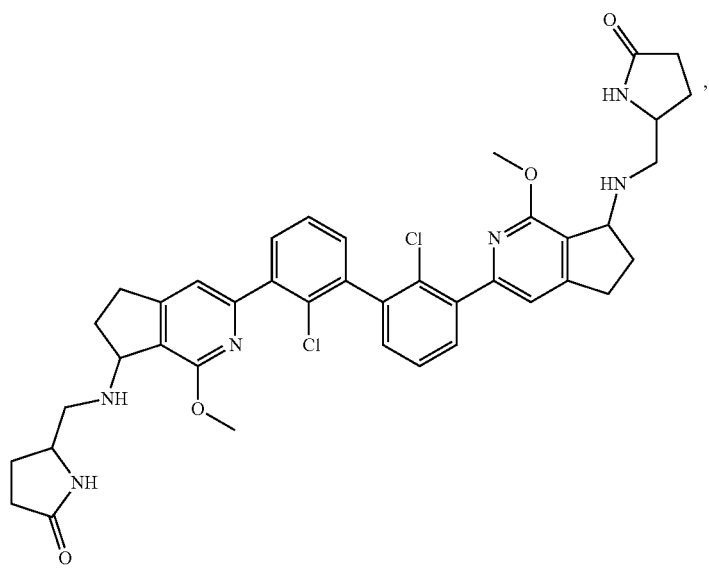
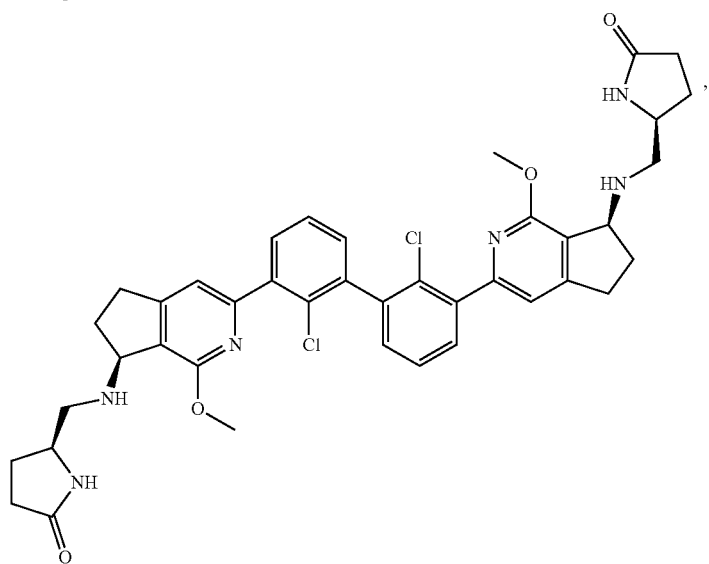

-continued
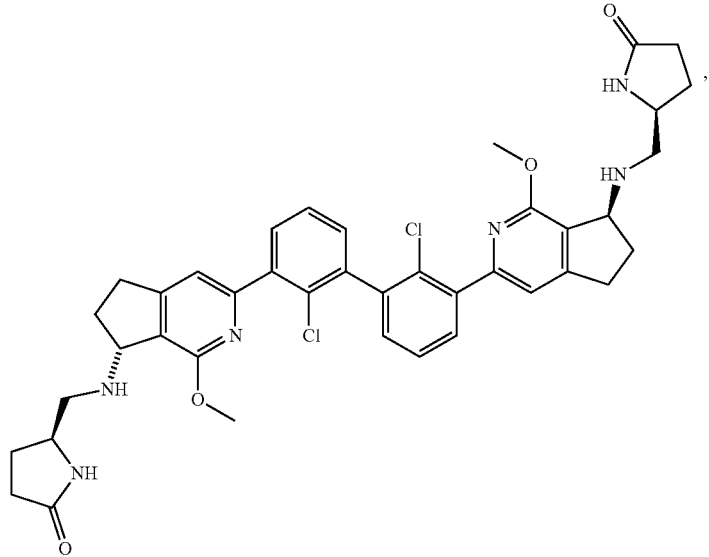
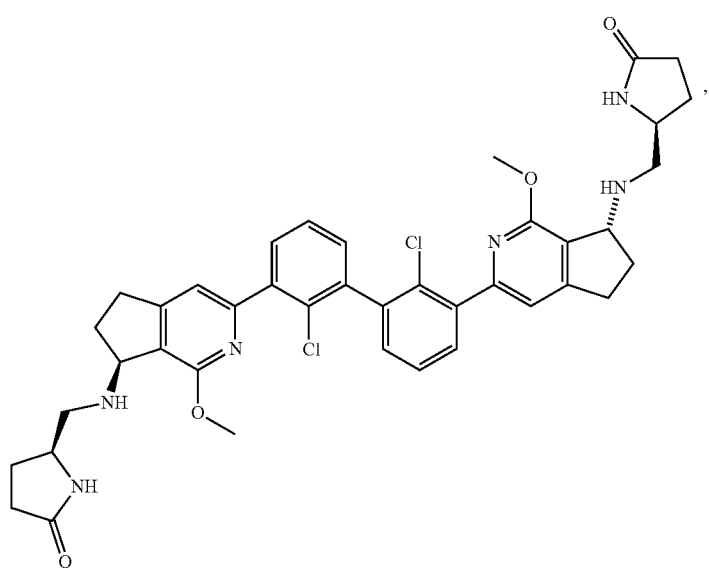
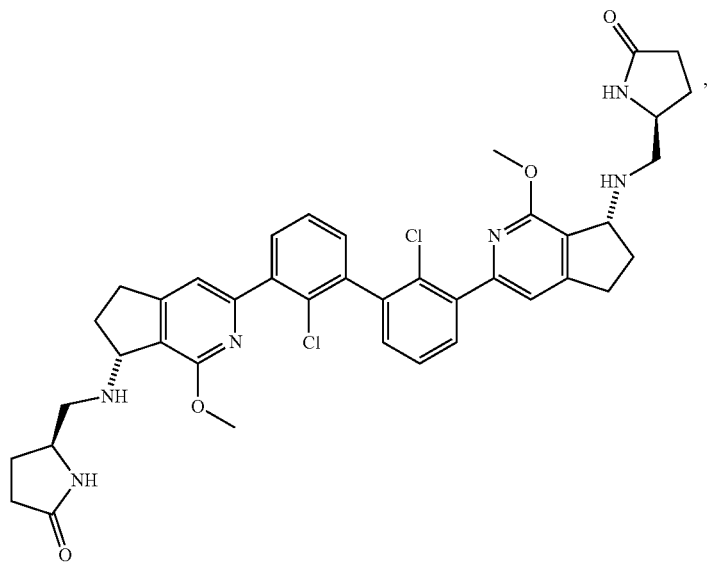

-continued
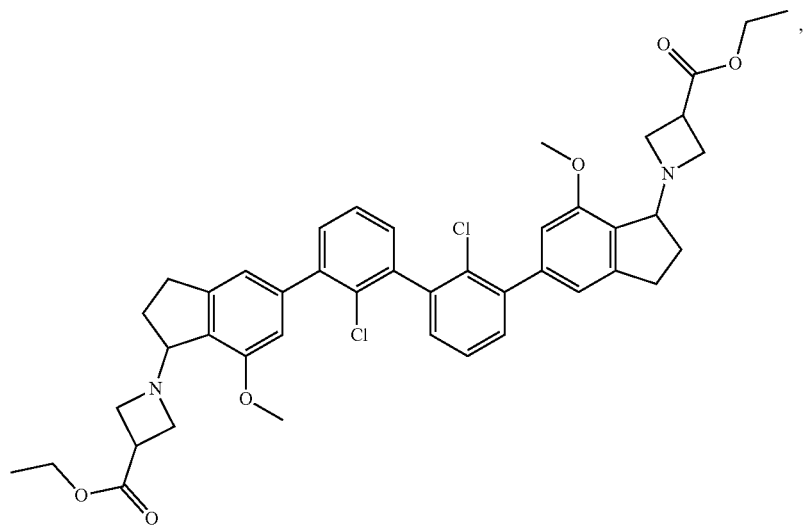
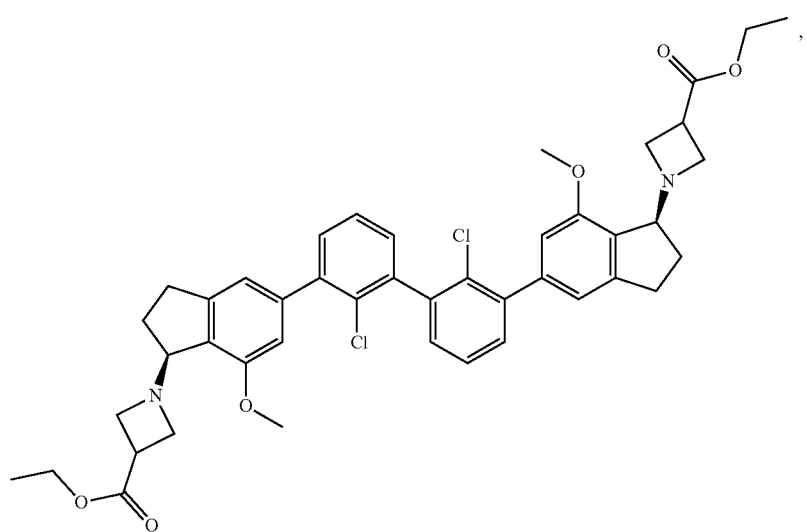
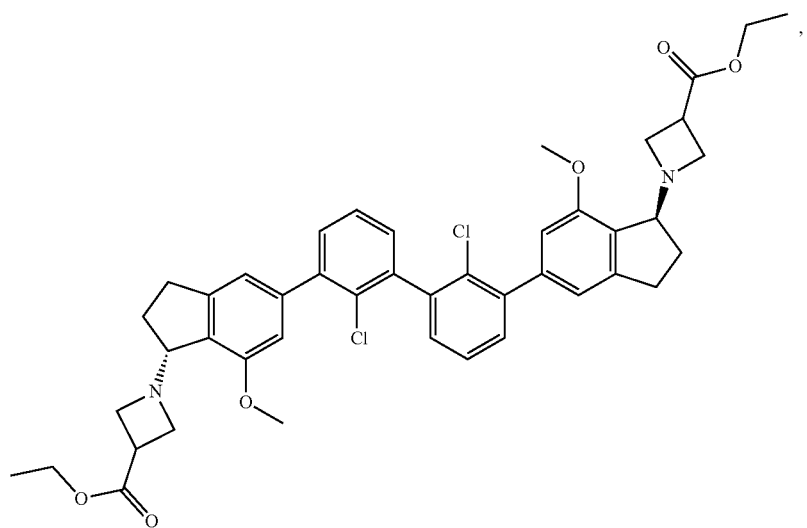

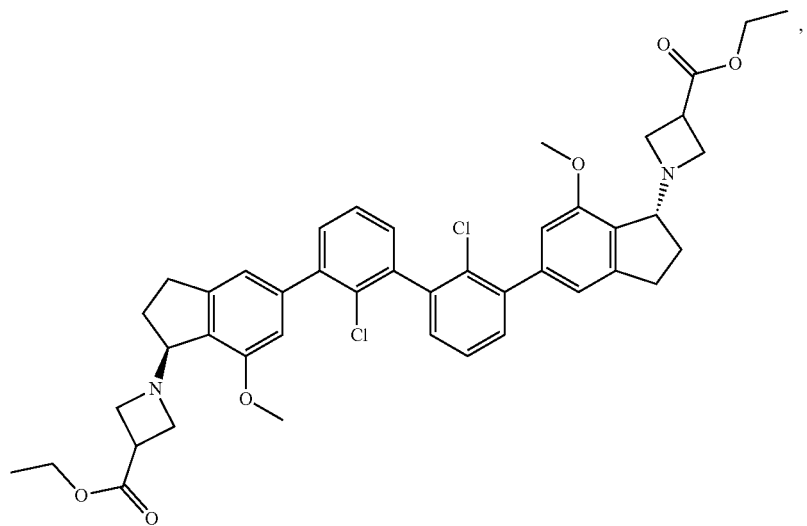
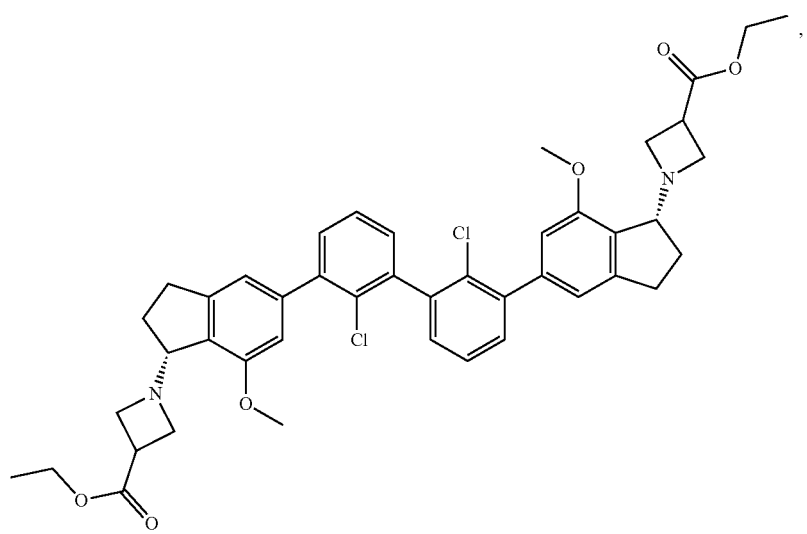
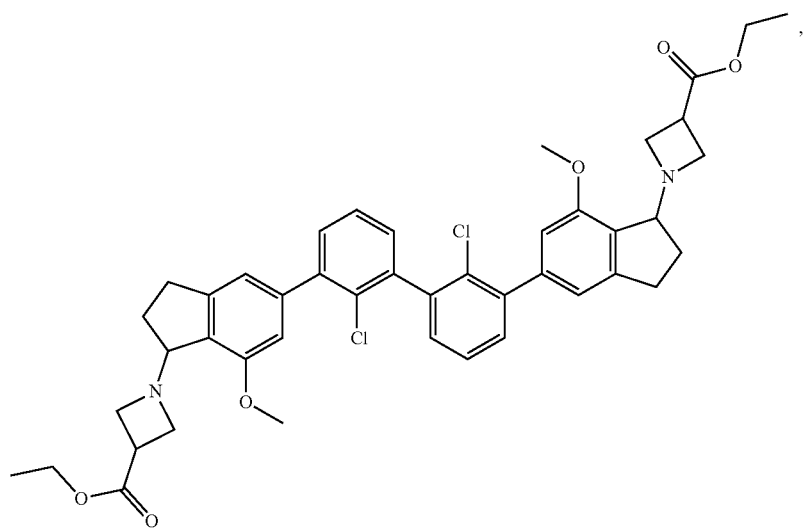

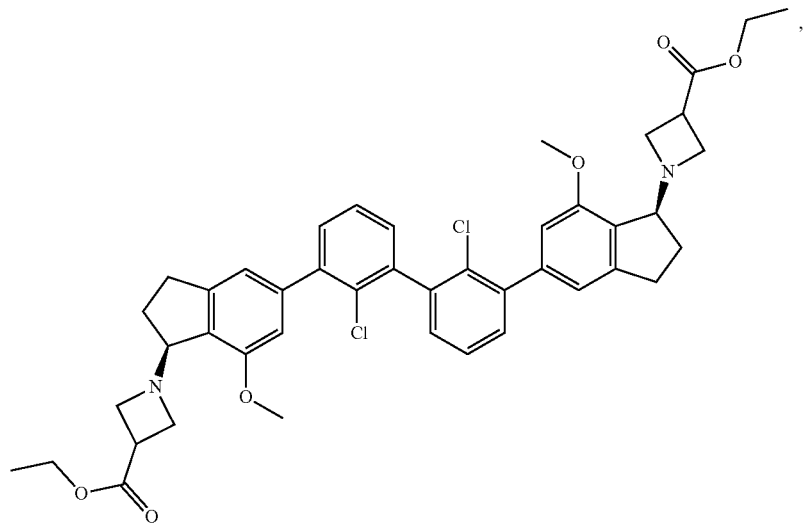
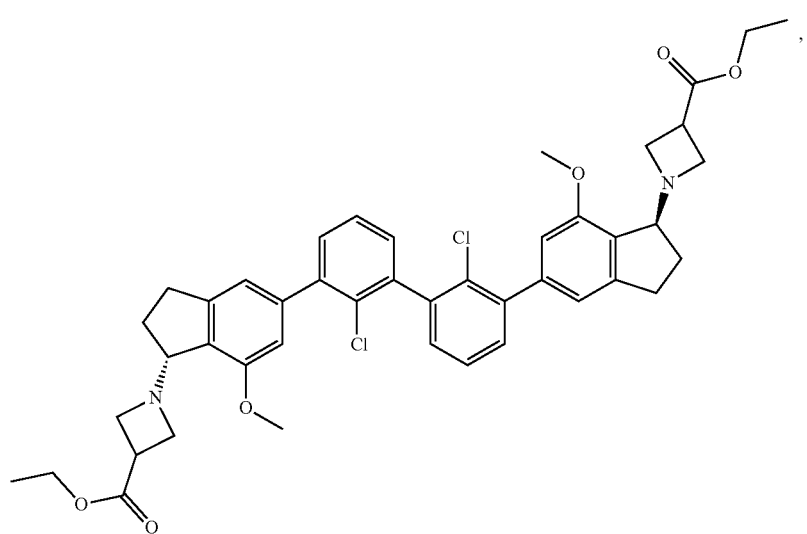
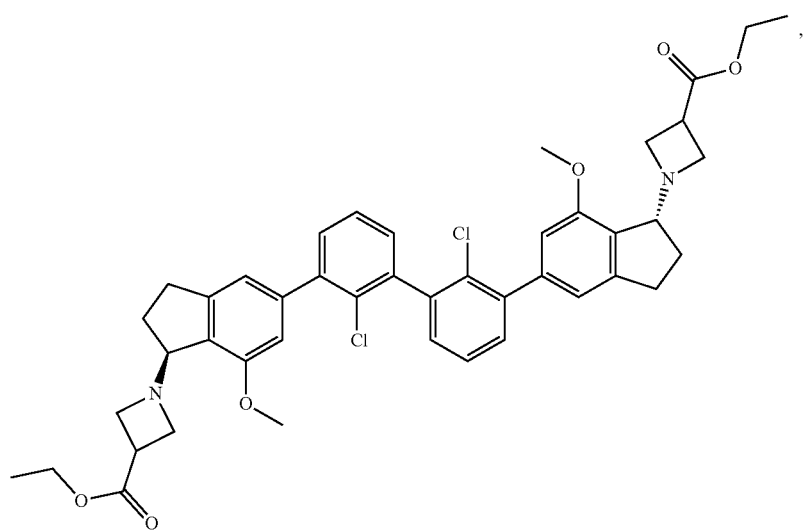

-continued
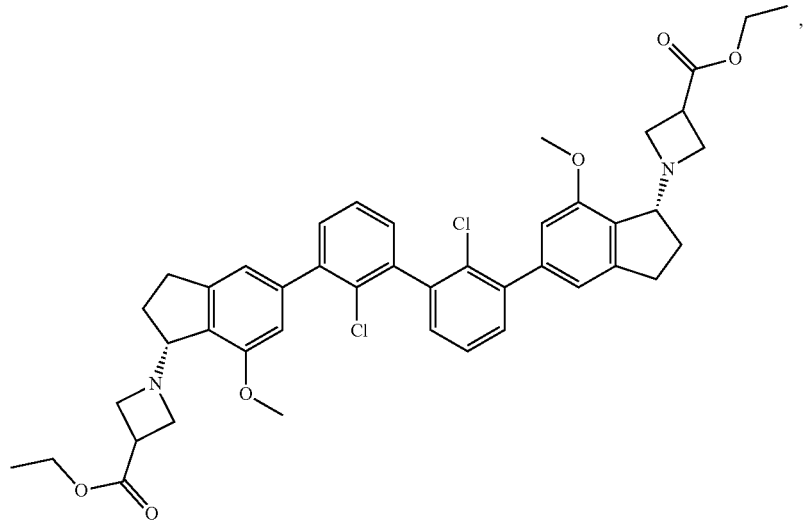
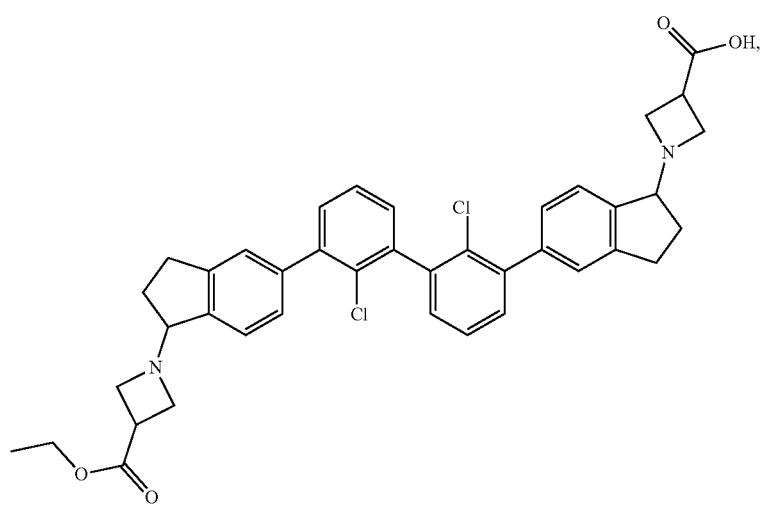
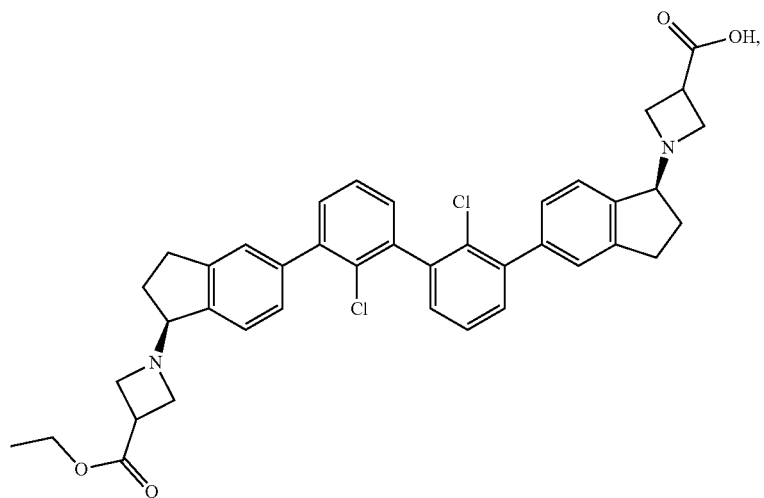

-continued
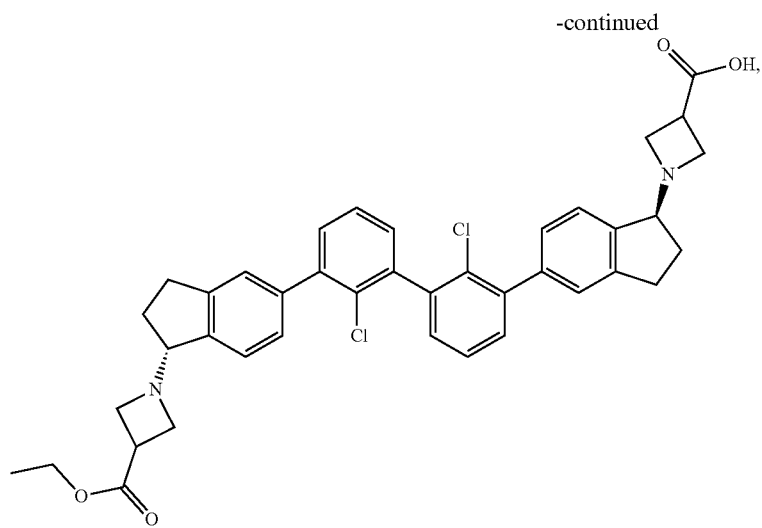
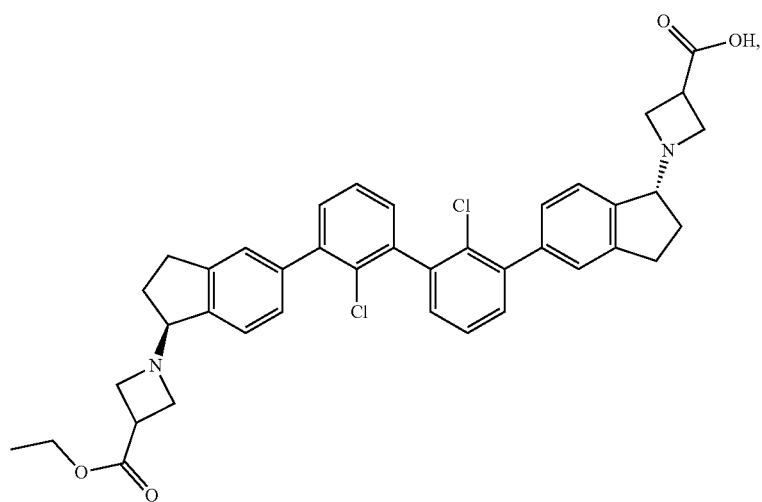
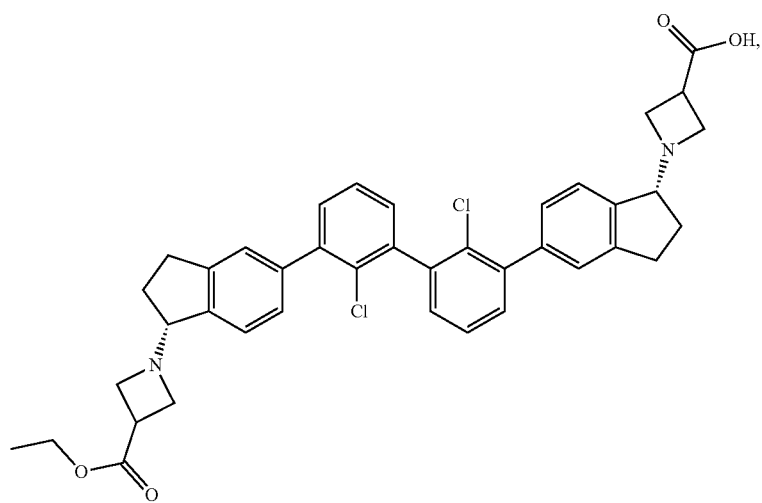

-continued
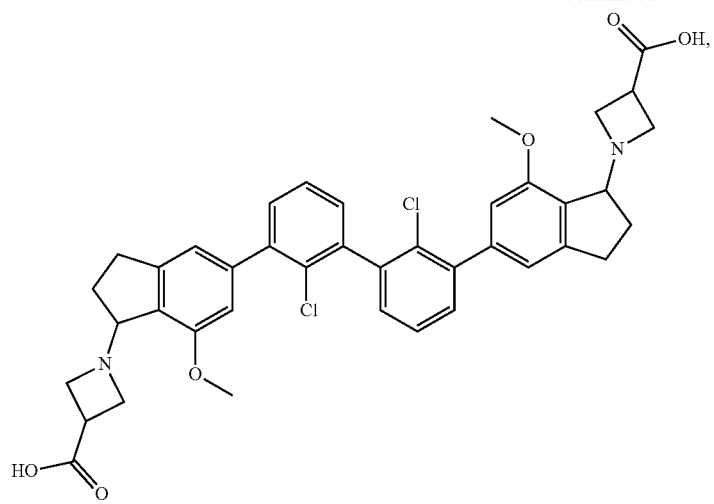
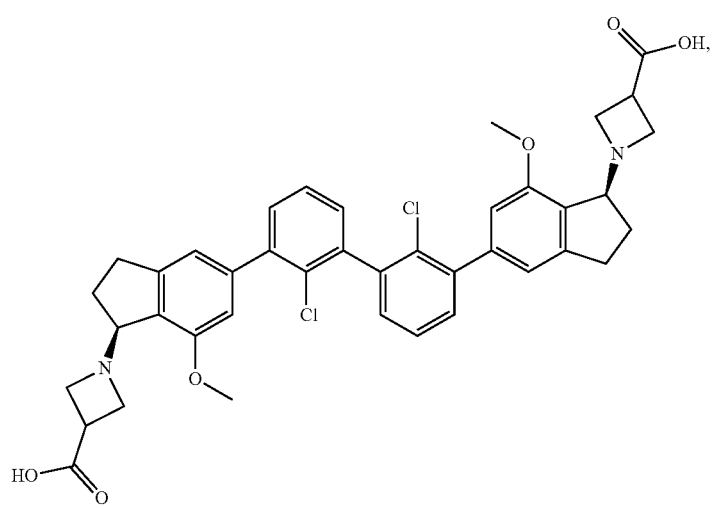
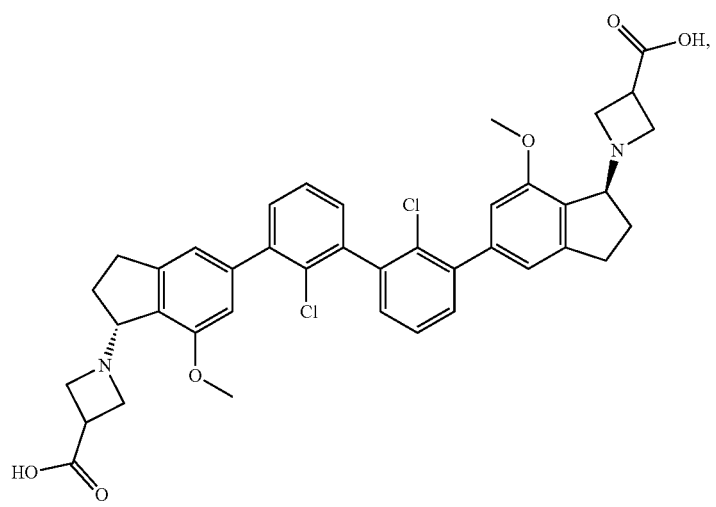

-continued
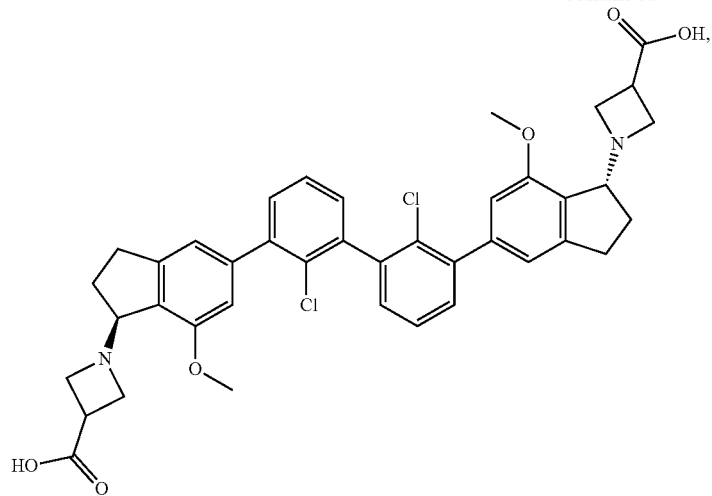
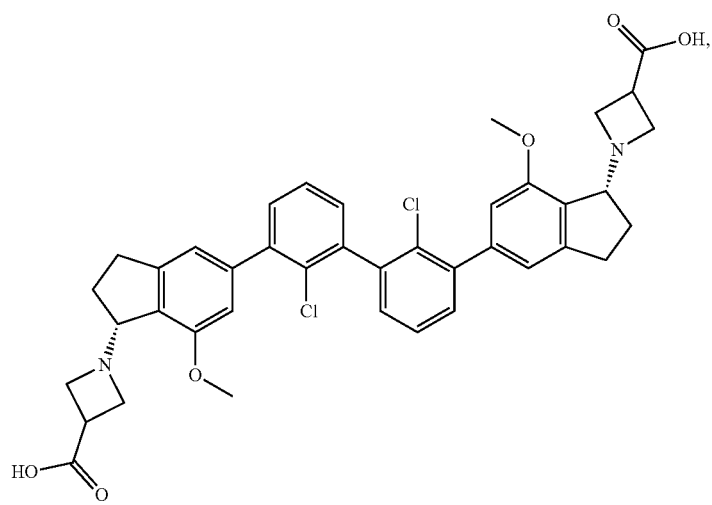
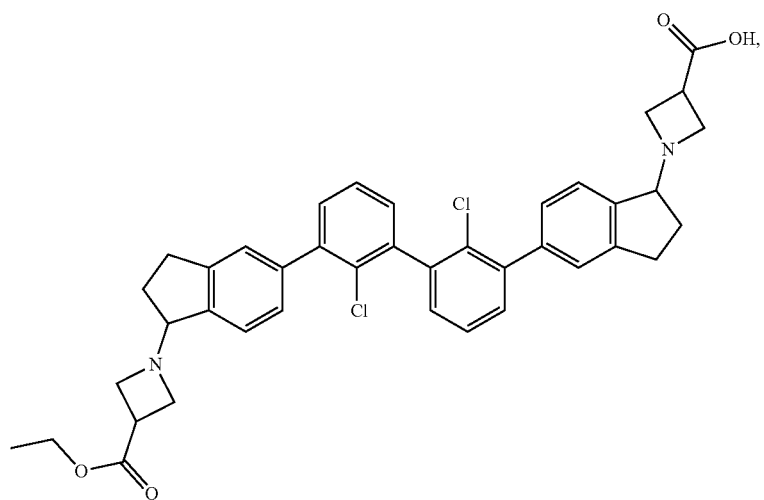

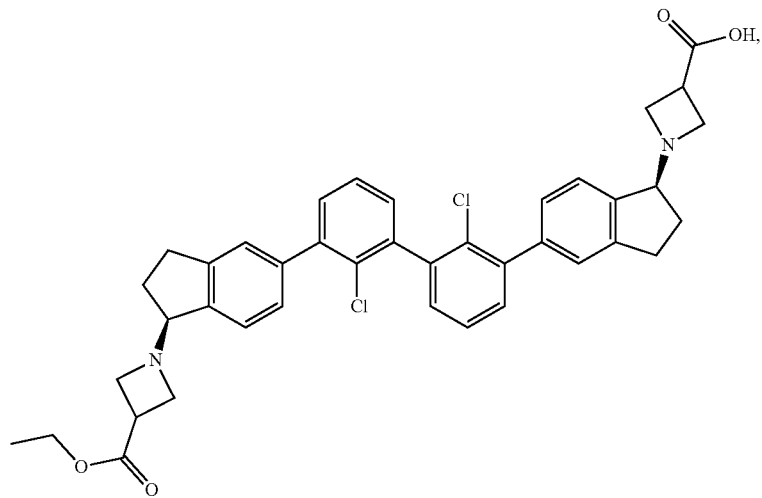
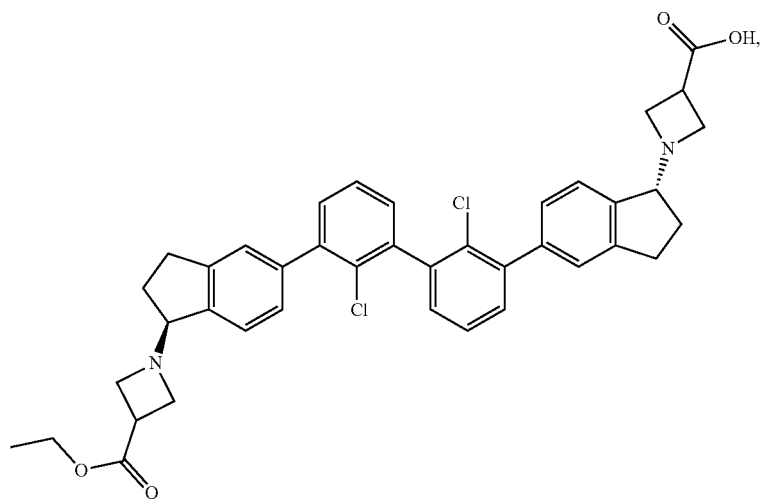

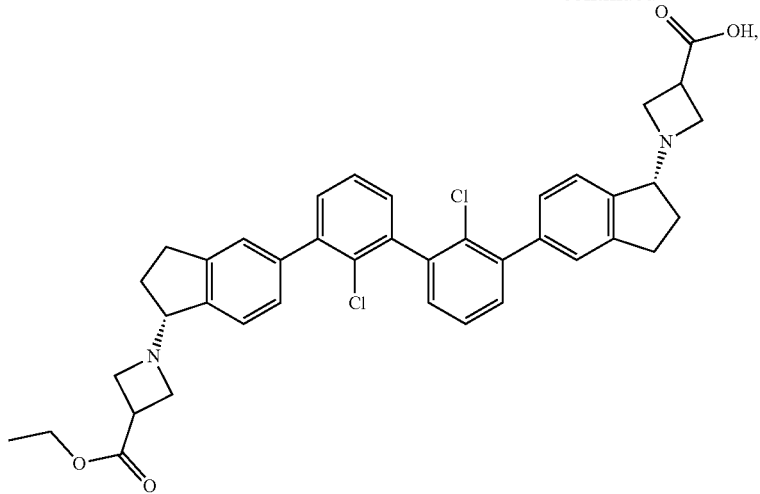
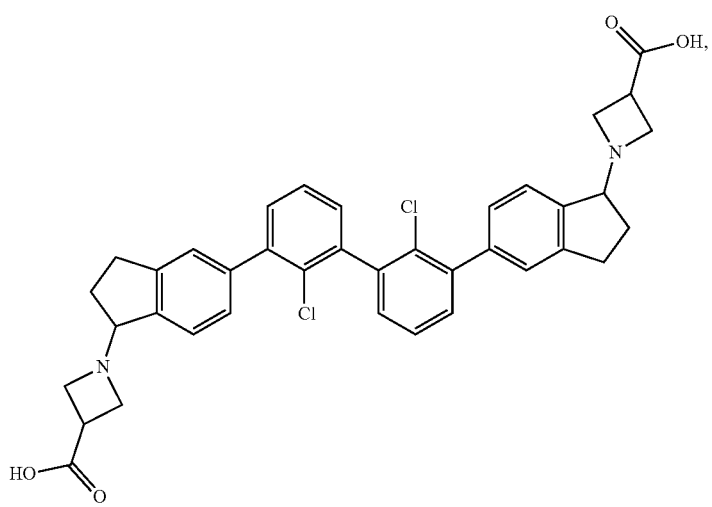
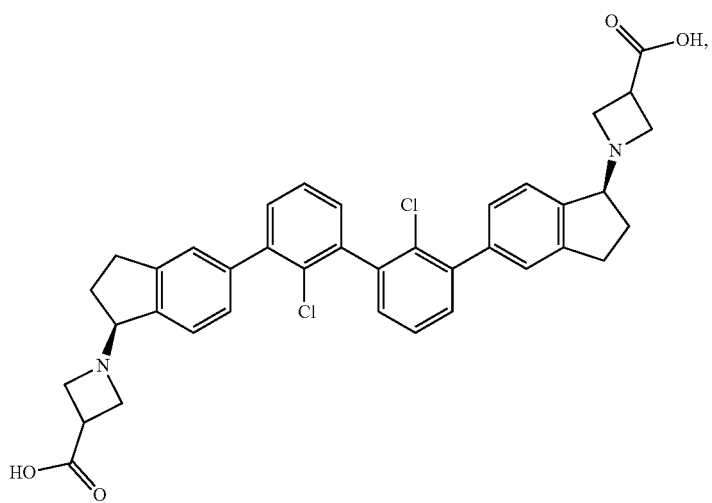

147
-continued
148
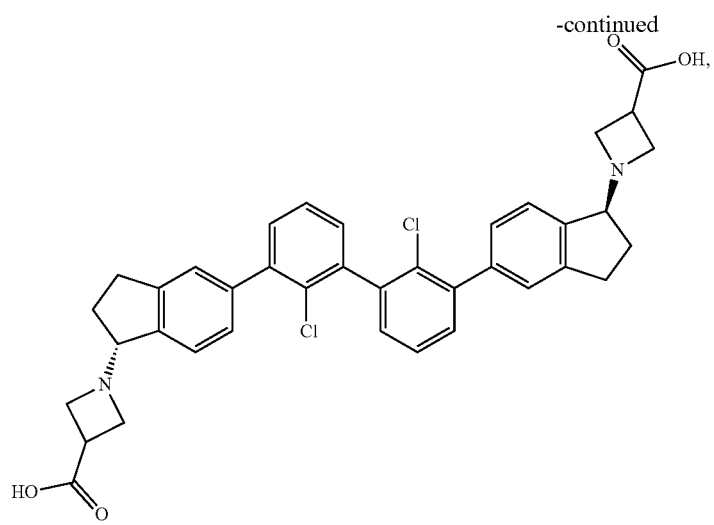
-continued
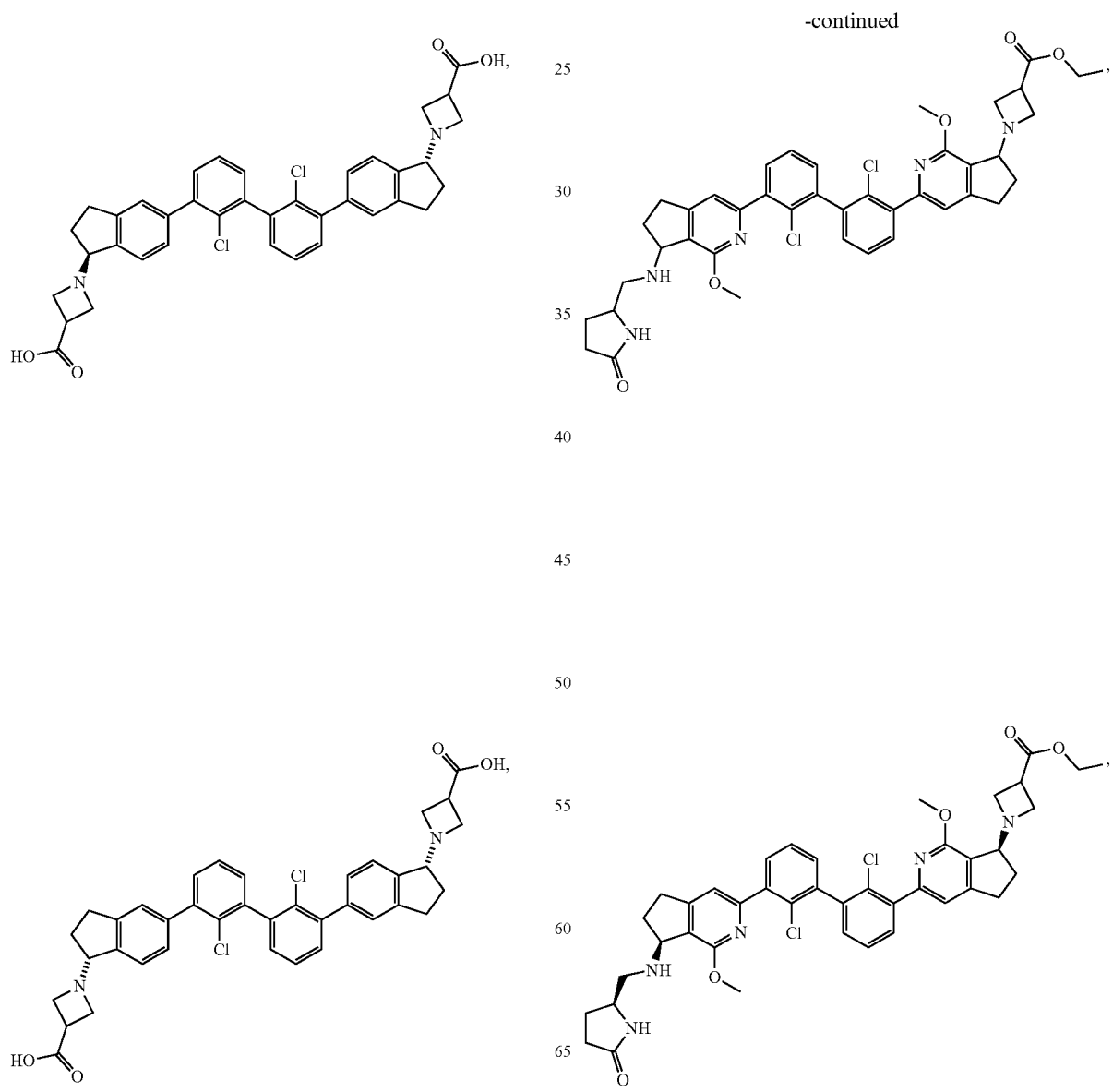

149
-continued
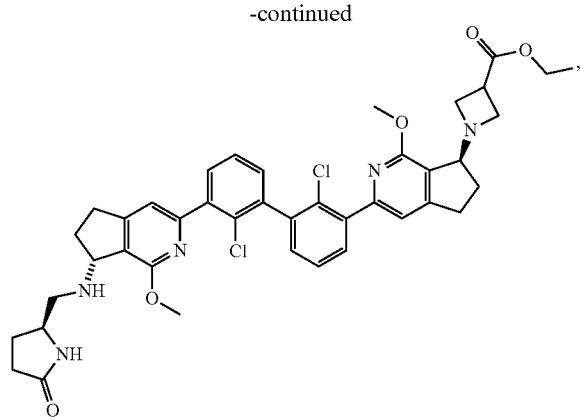
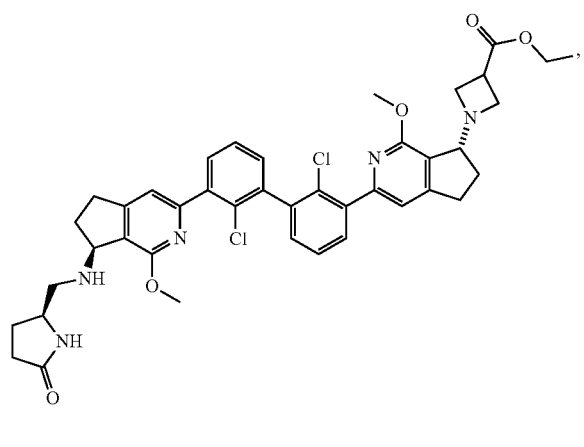
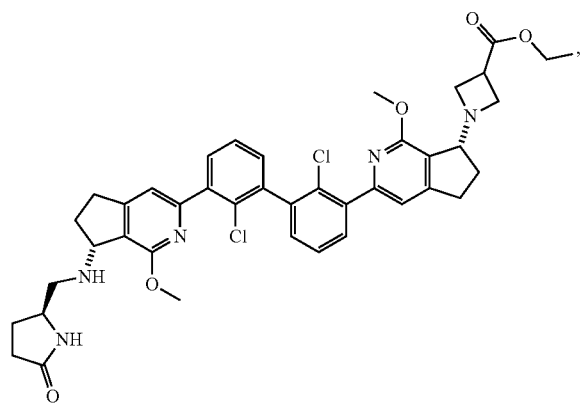
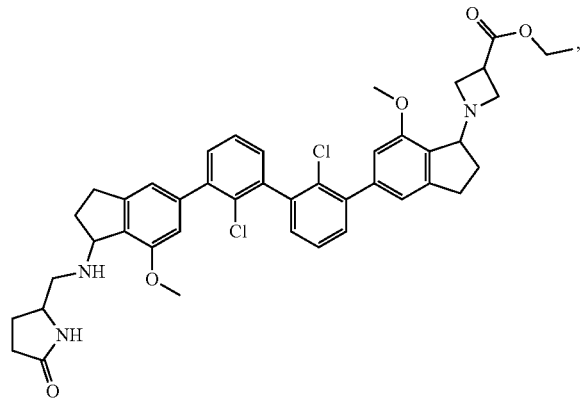
150
-continued
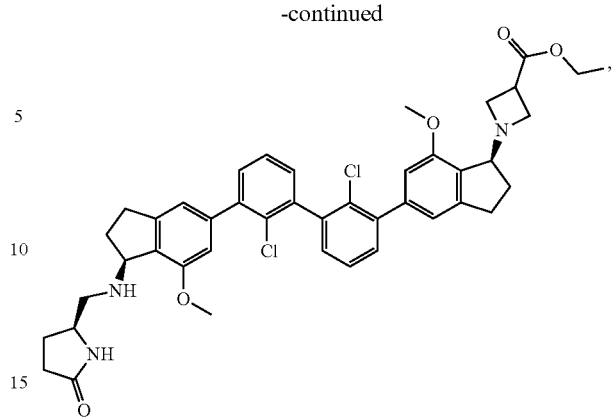
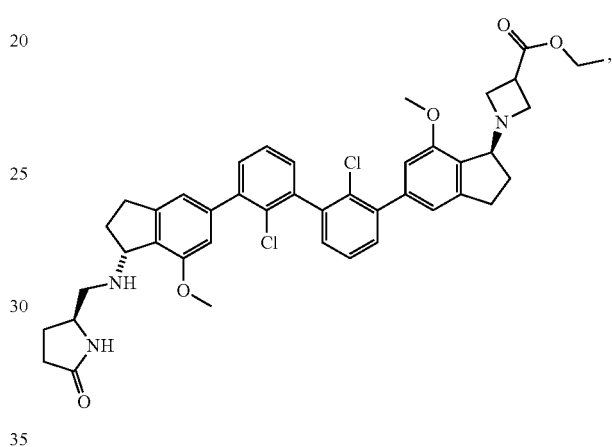
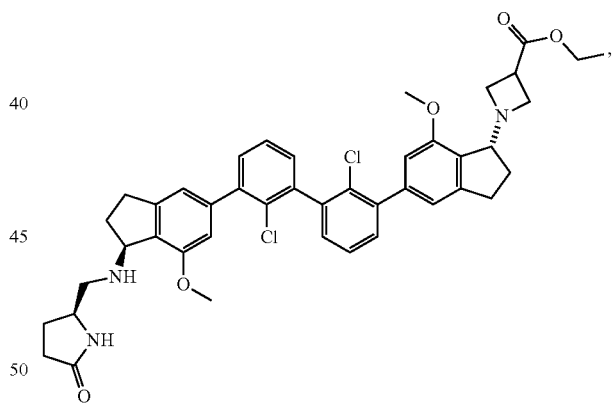
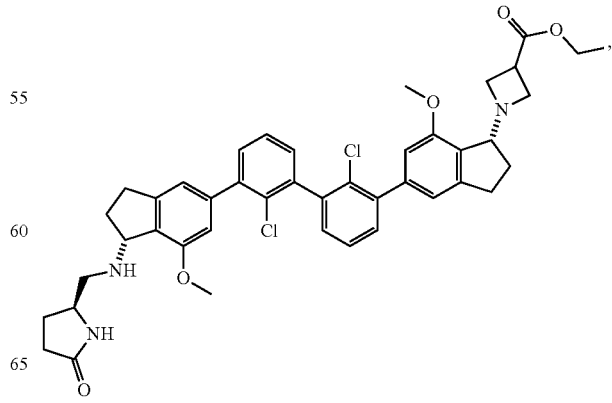

151
-continued
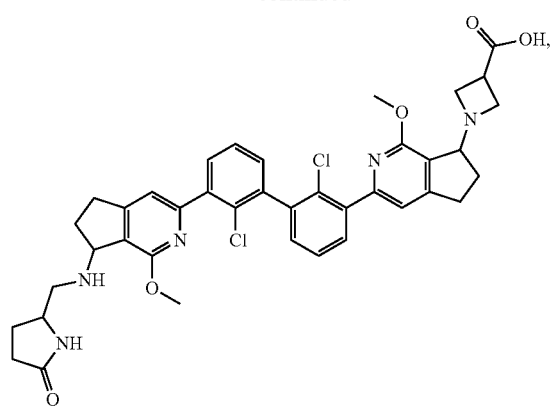
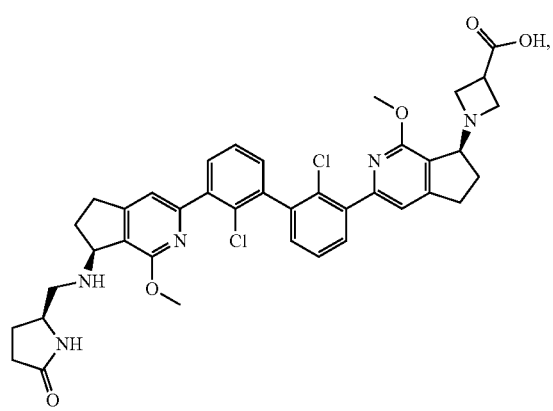
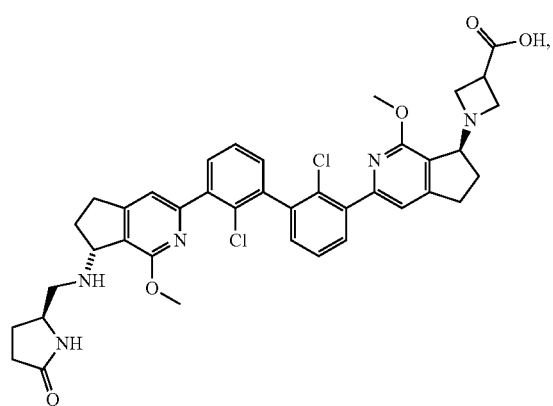
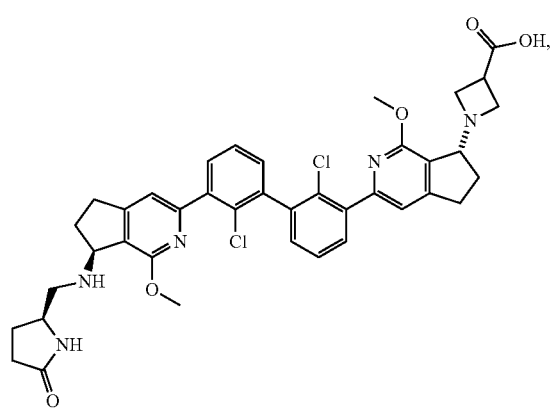
152
-continued
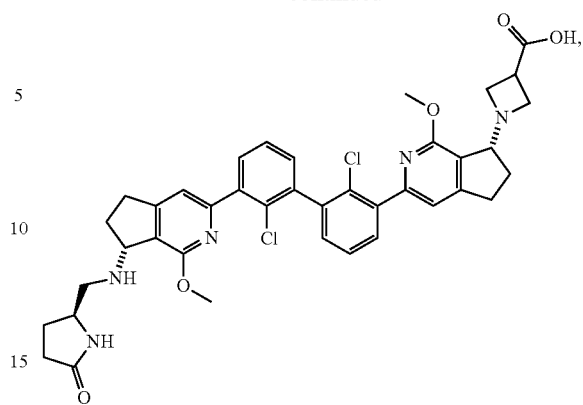
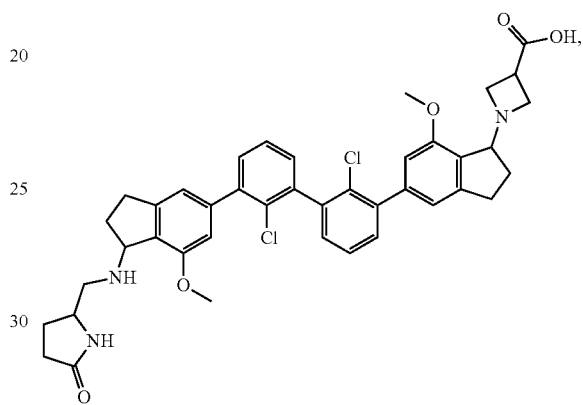
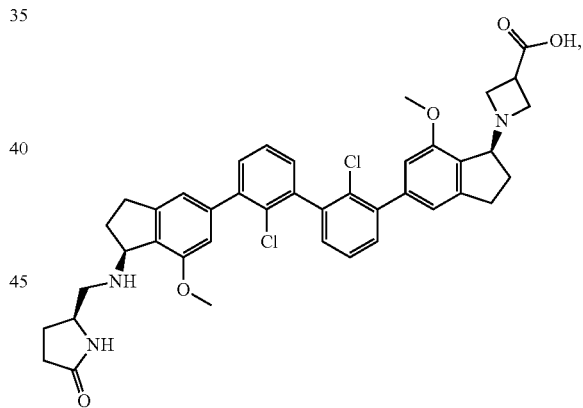

153
-continued
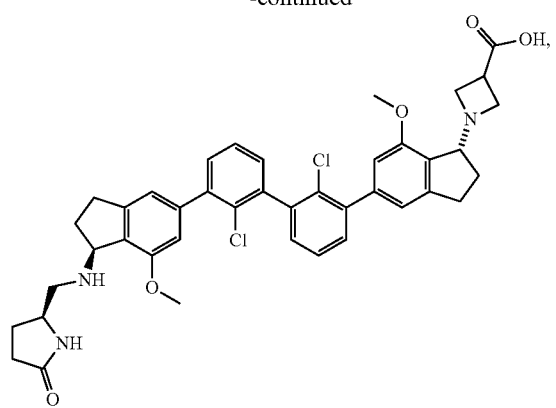
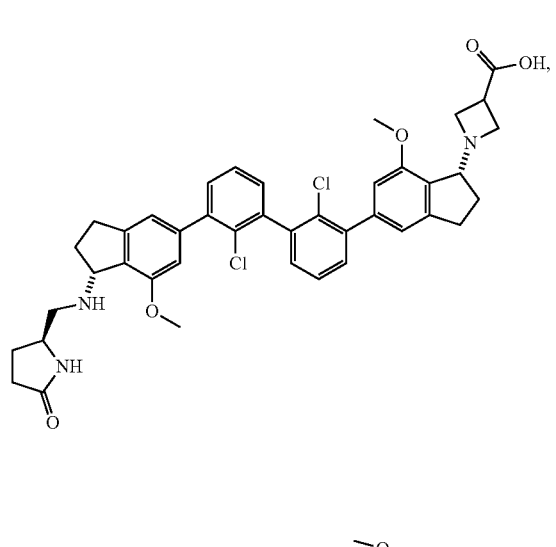
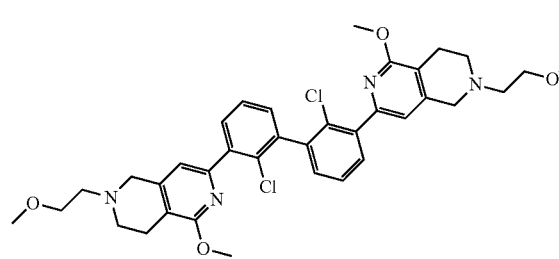
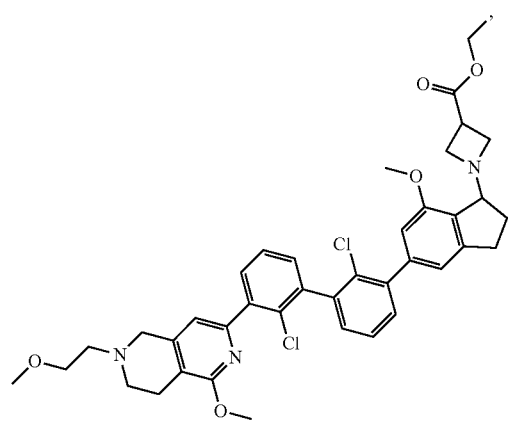
154
-continued
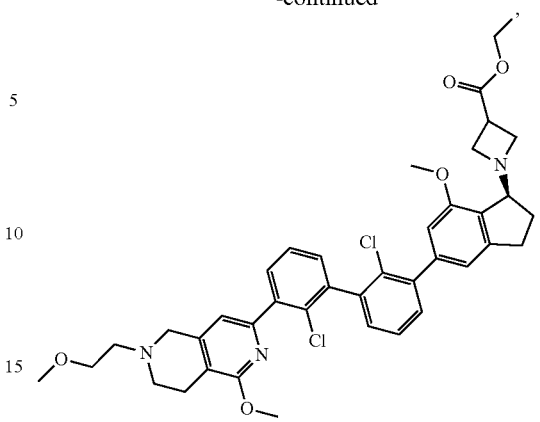
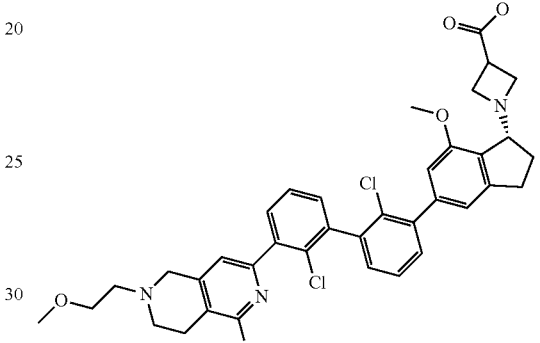
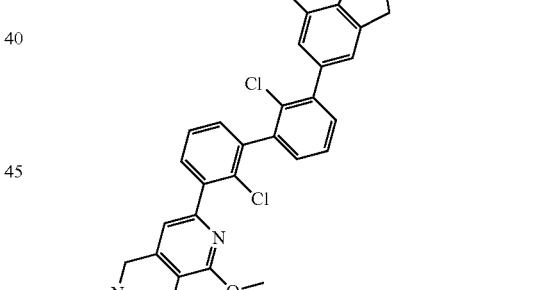
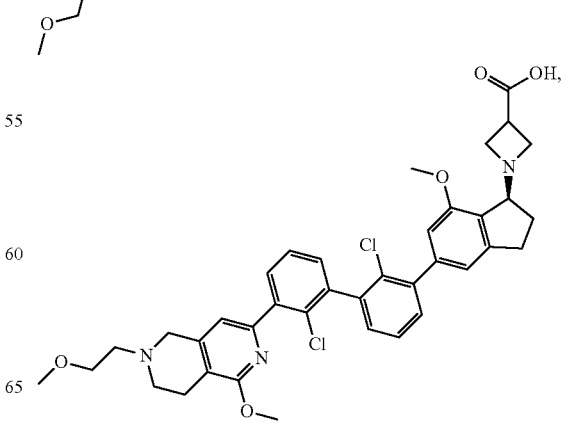

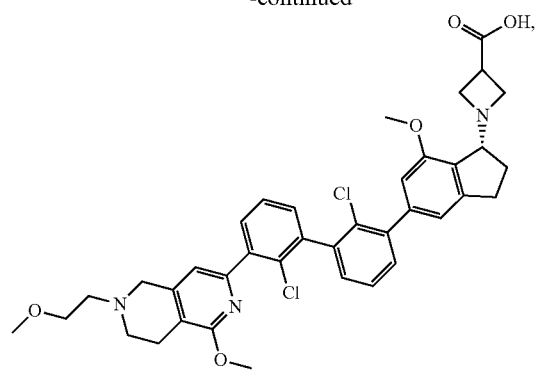
,
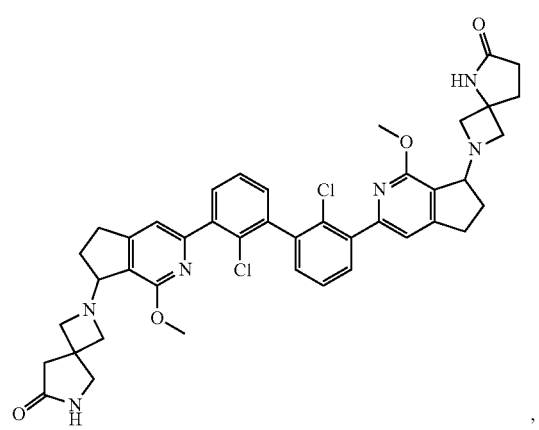
,
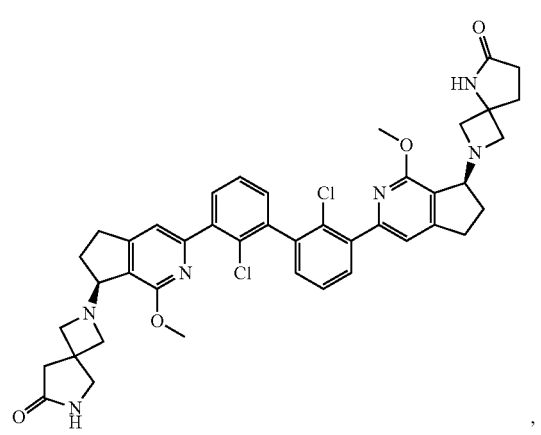
,
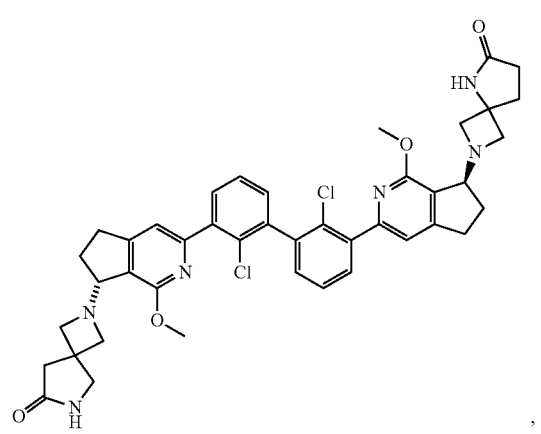
,
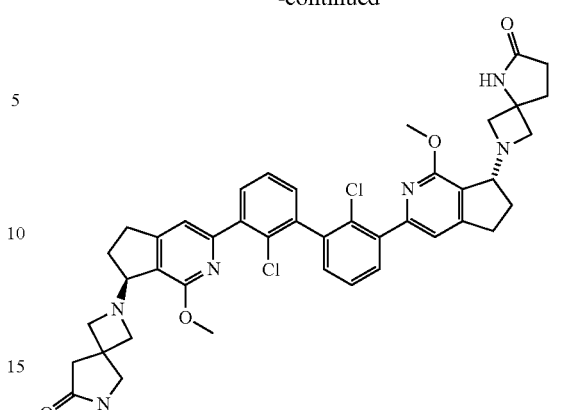
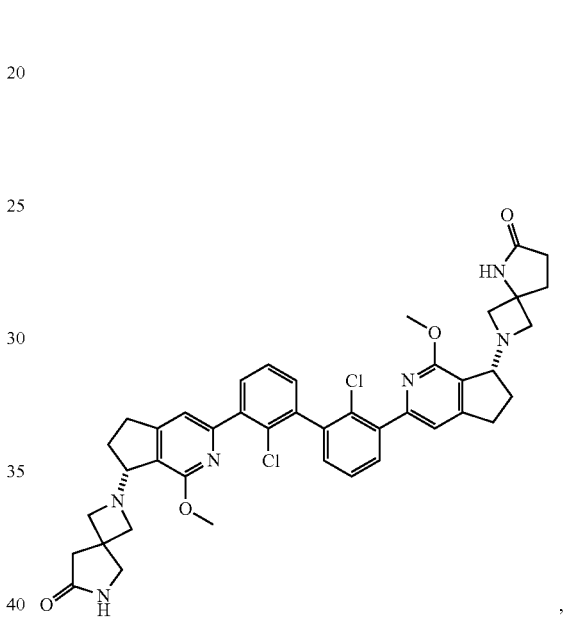
,
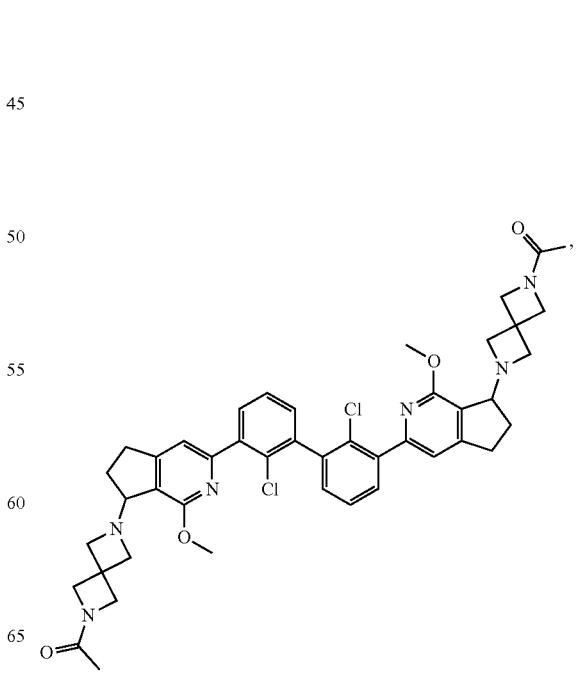
,

157
-continued
158
-continued
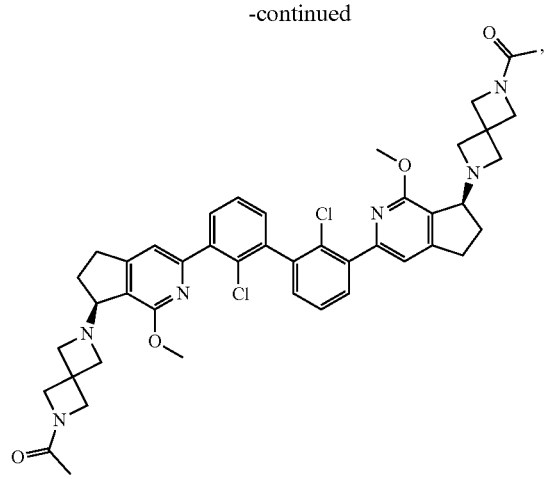
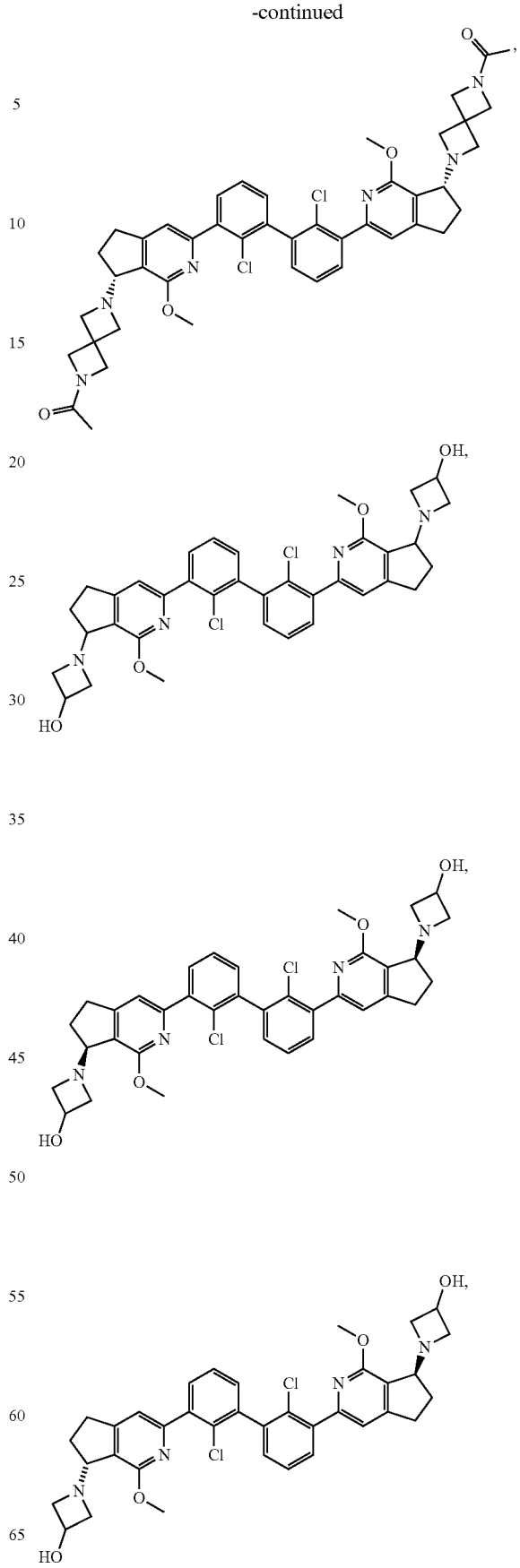

159
-continued
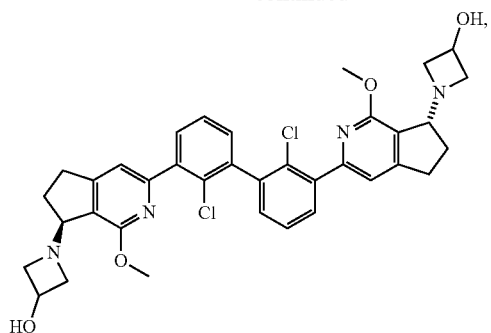
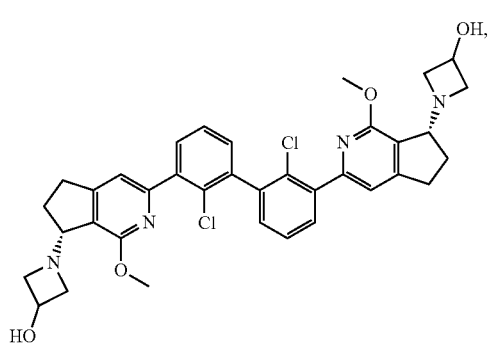
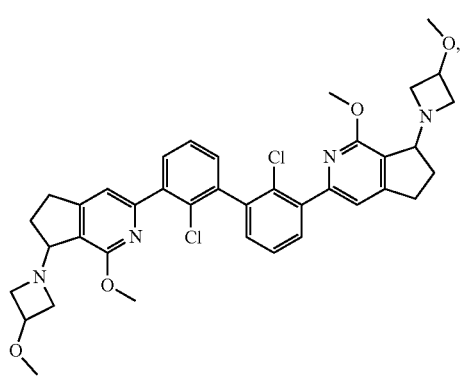
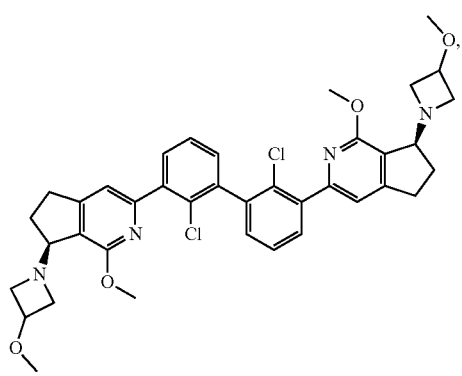
160
-continued
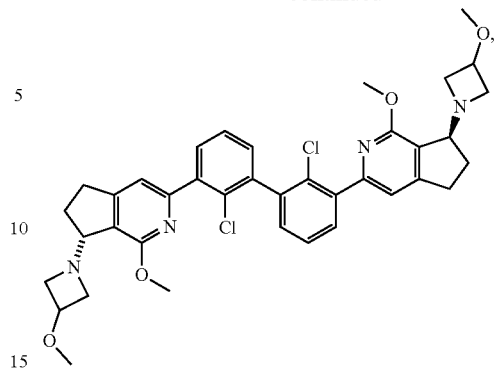
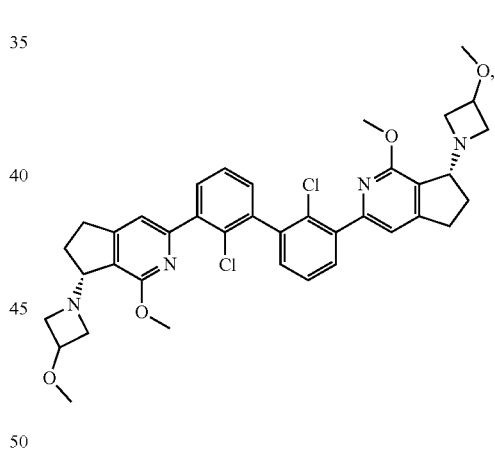
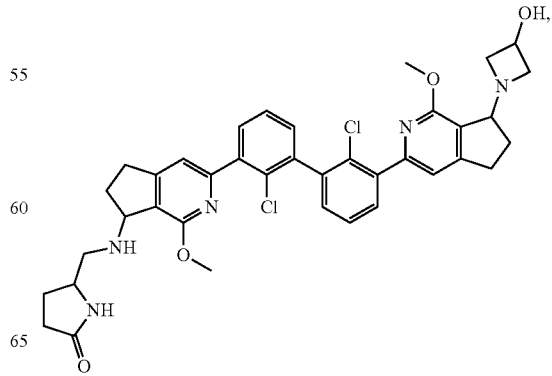

161
-continued
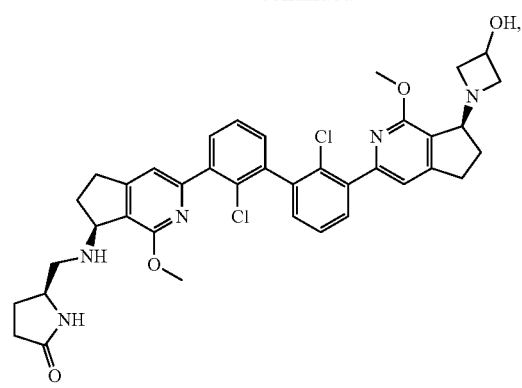
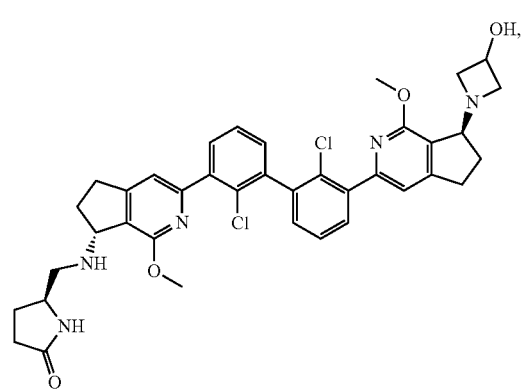
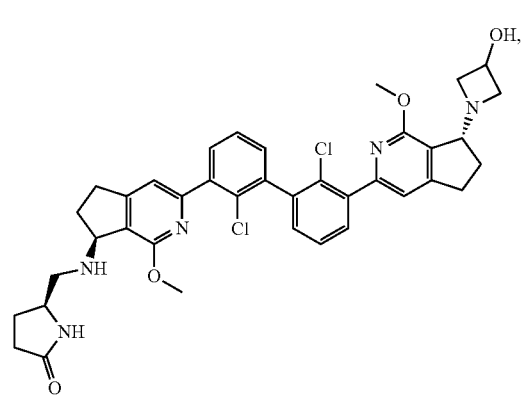
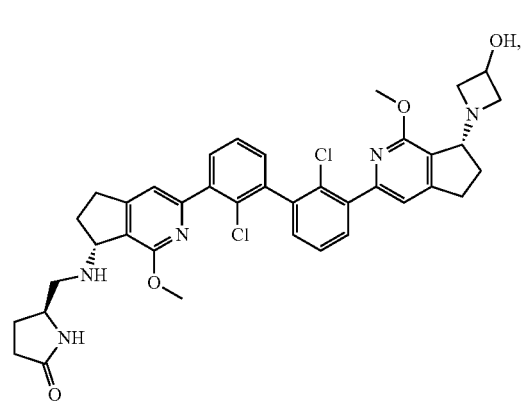
162
-continued
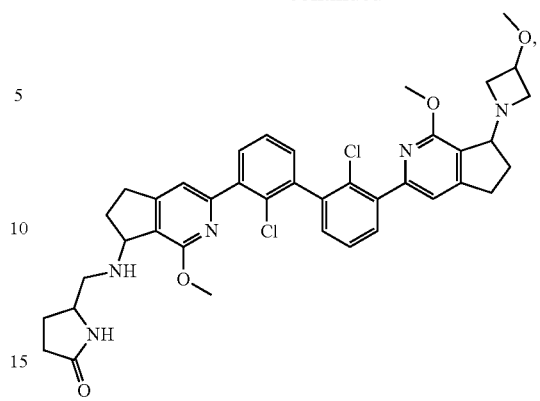
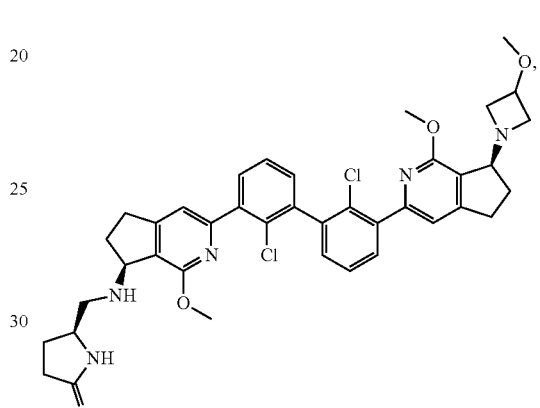
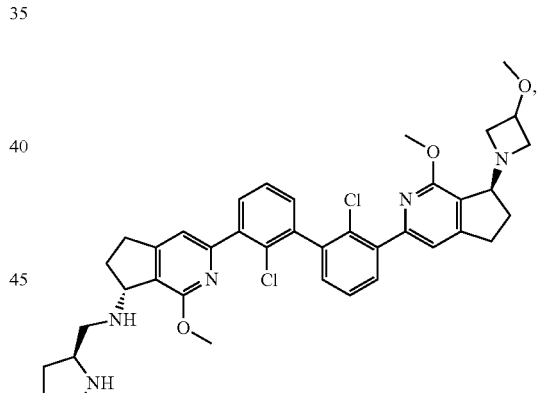
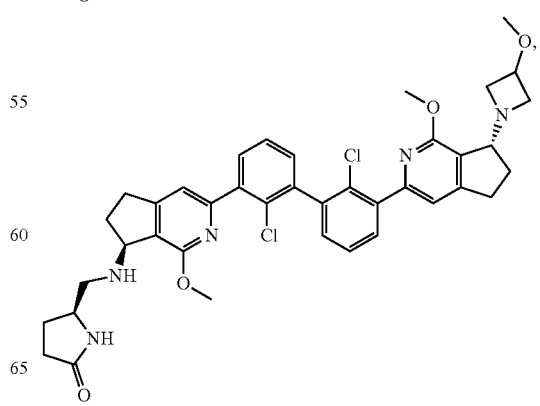

163
-continued
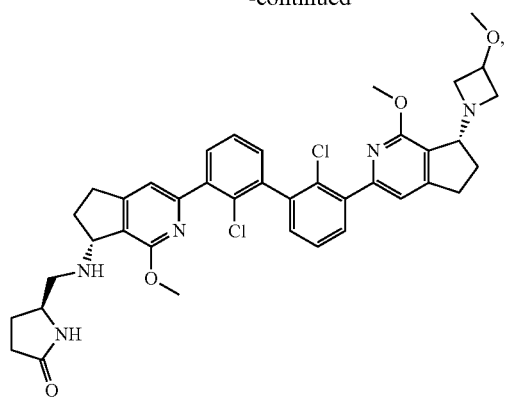
,
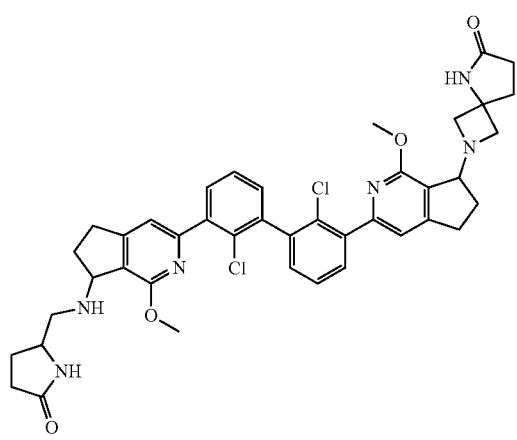
,
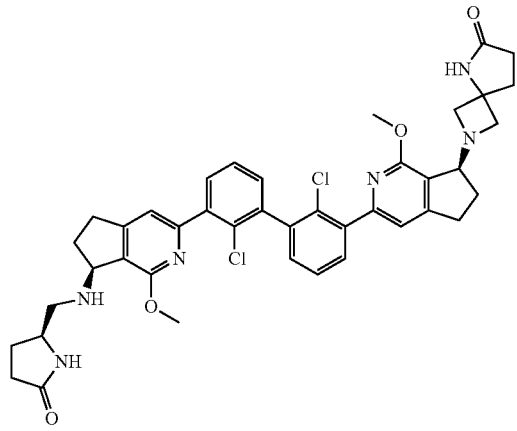
,
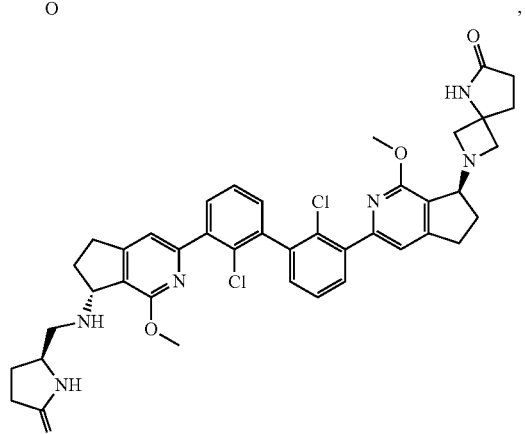
,
164
-continued
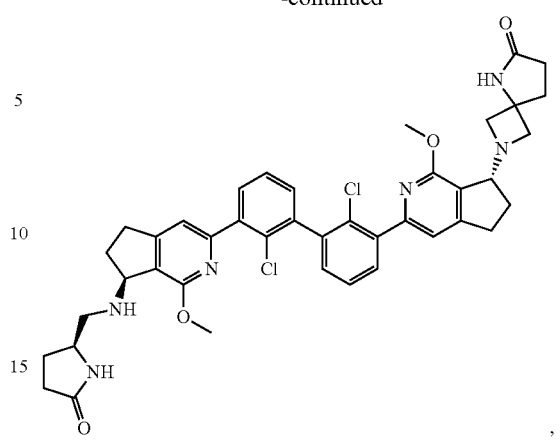
,
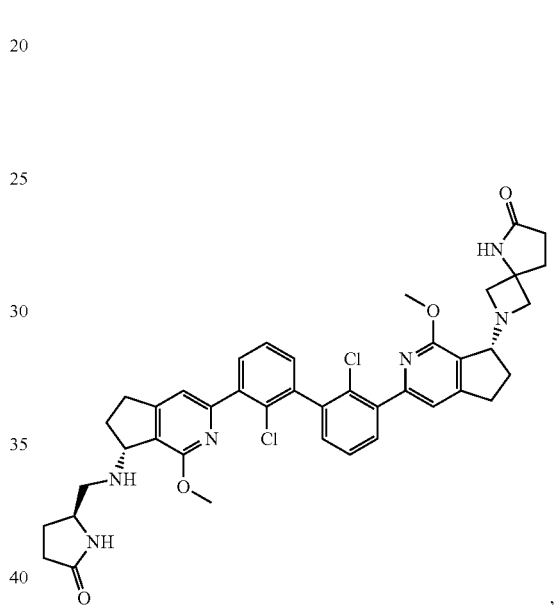
,
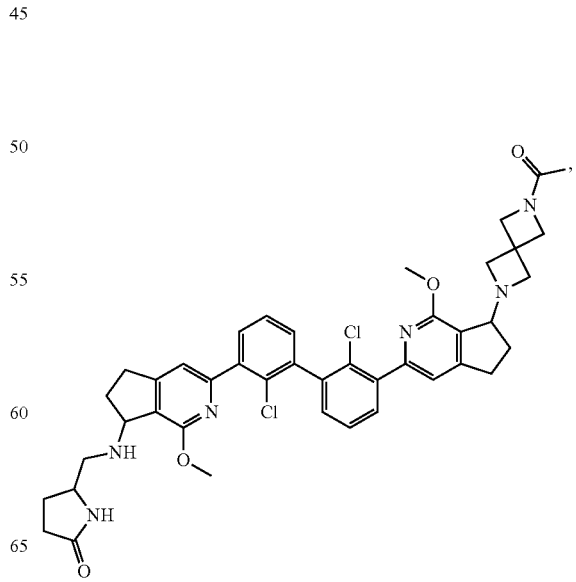
,

165
-continued
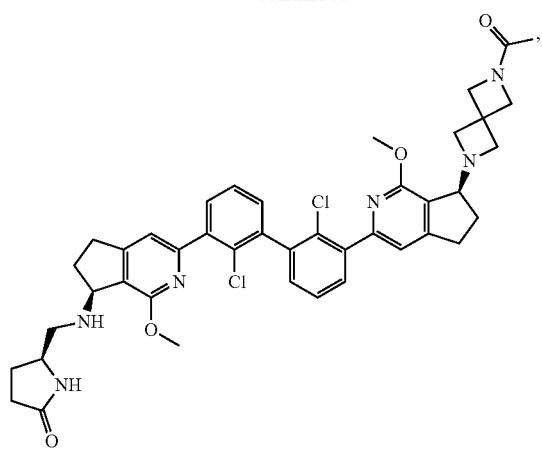
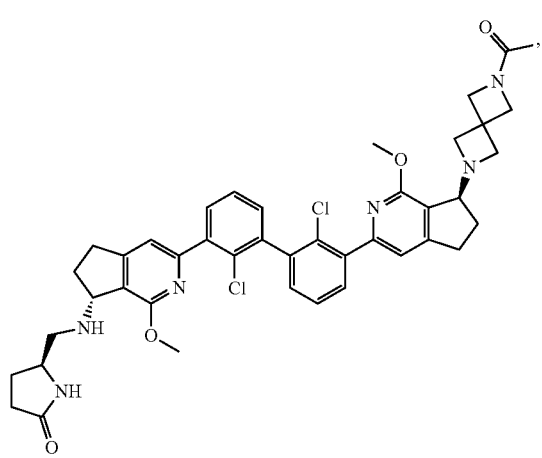
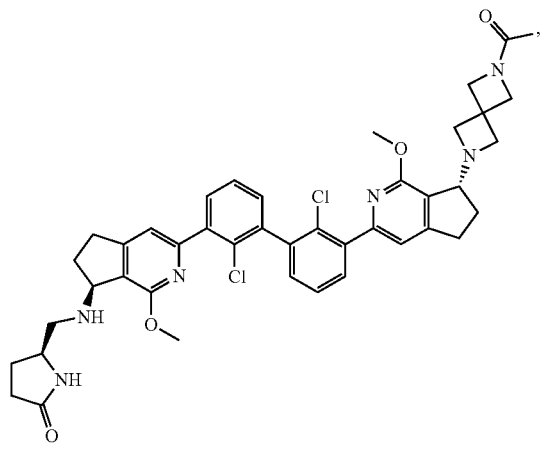
166
-continued
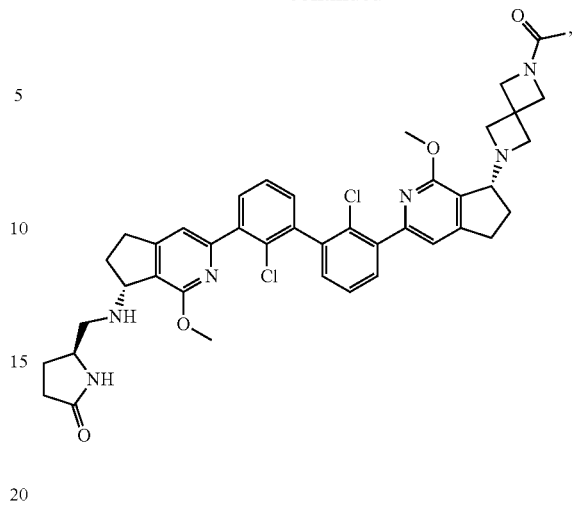
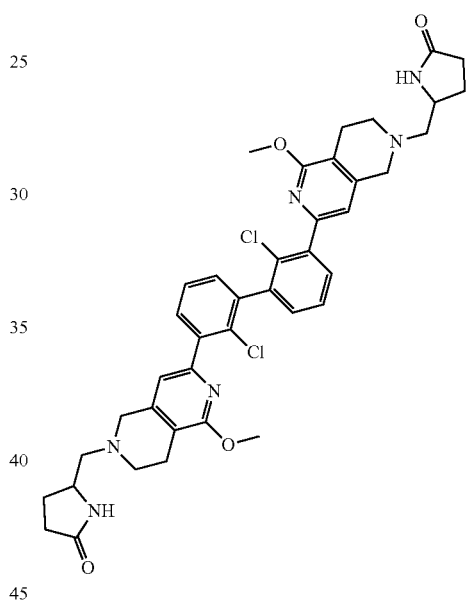
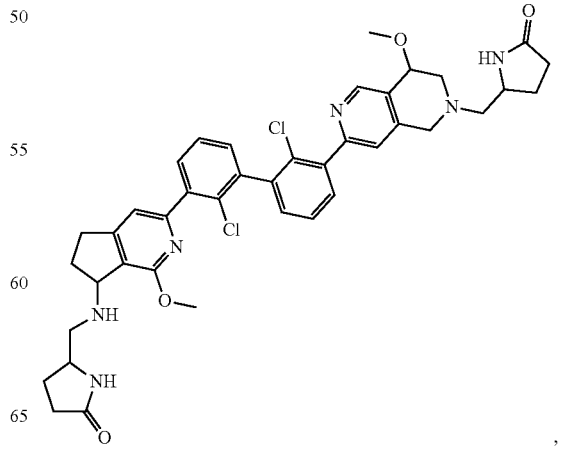

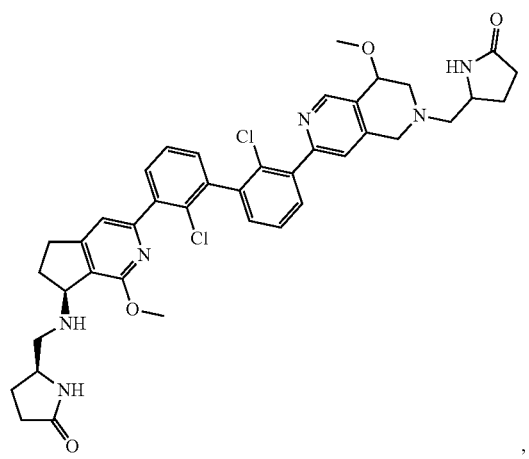
,
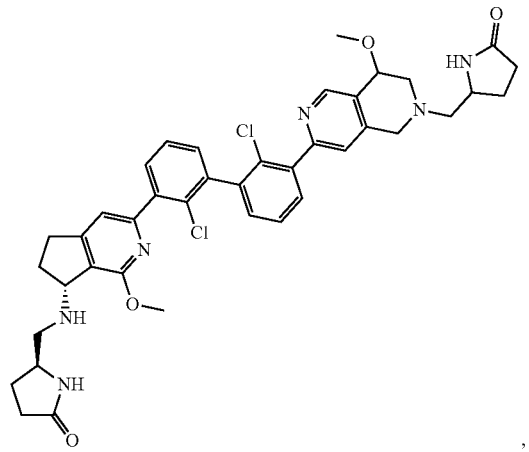
,
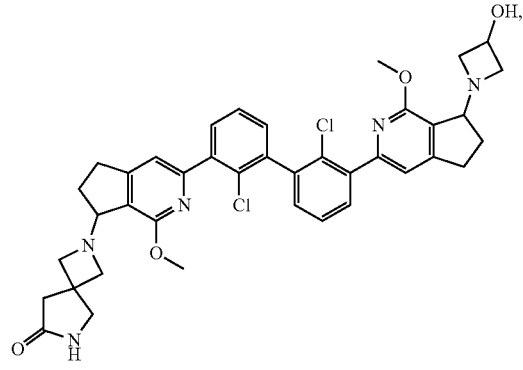
,
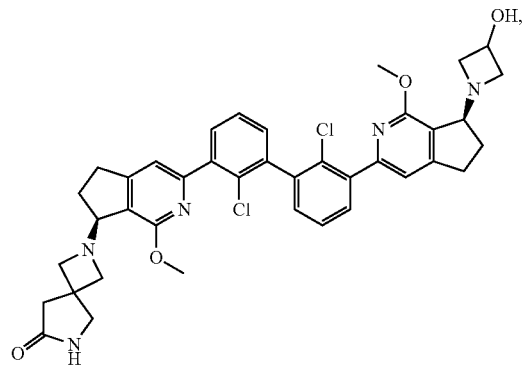
,
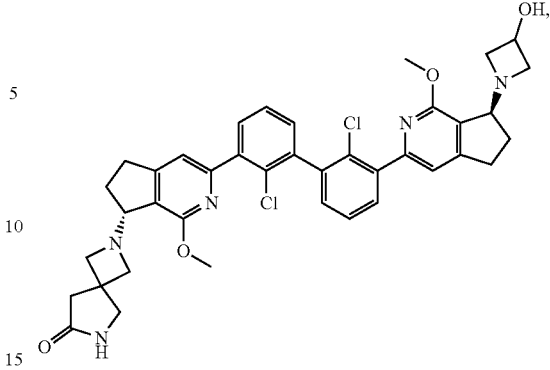
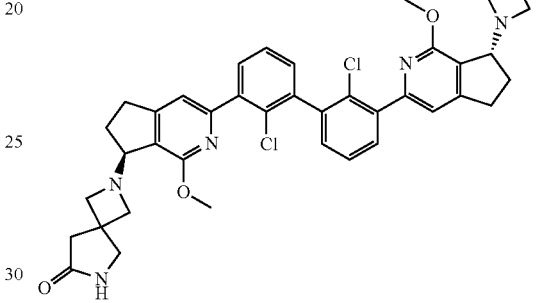
,
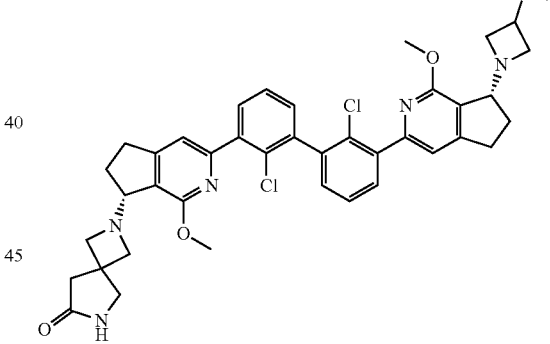
,
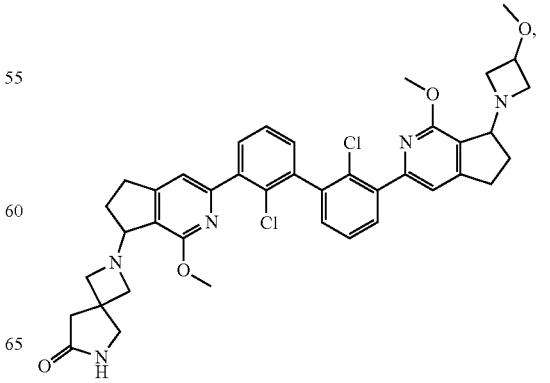
, 169
-continued
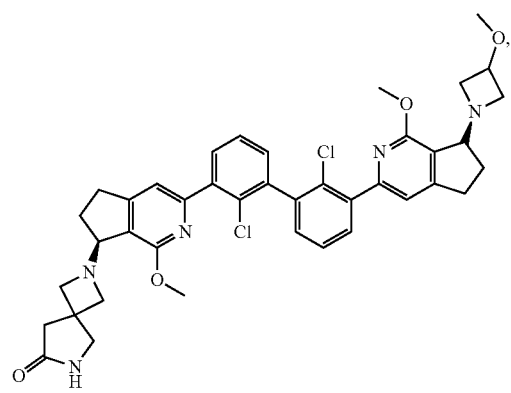
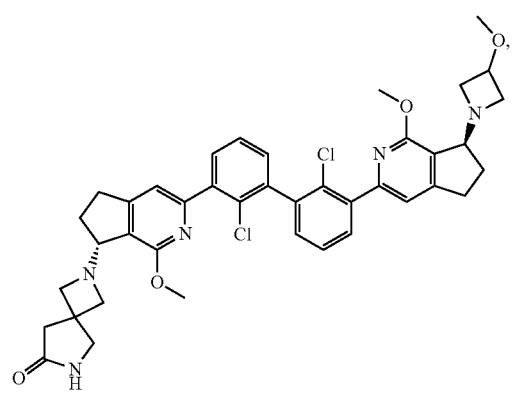
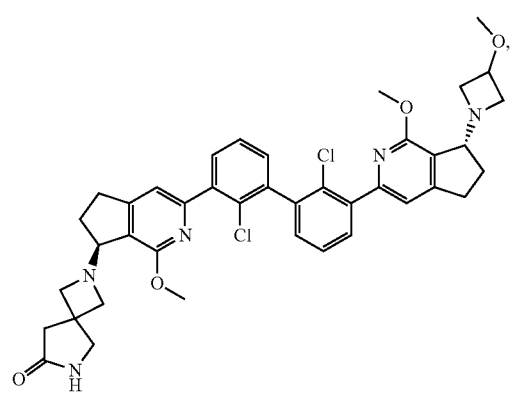
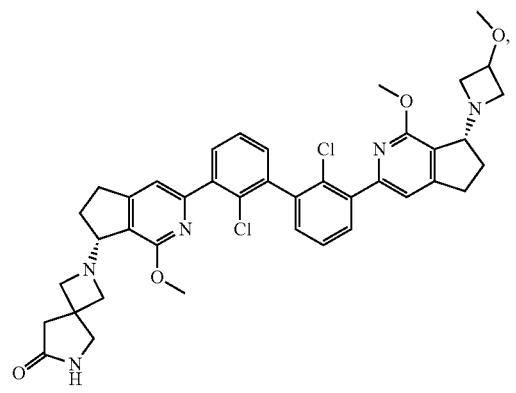
170
-continued
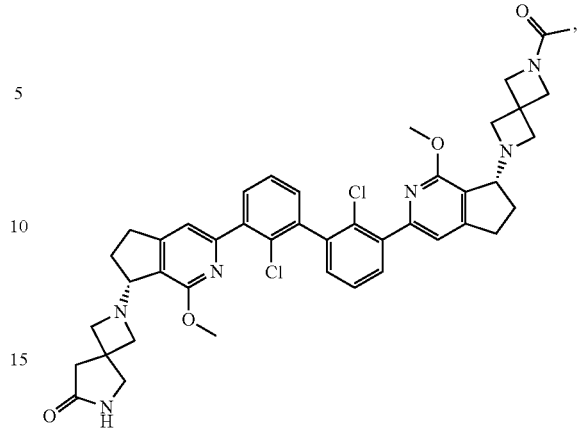
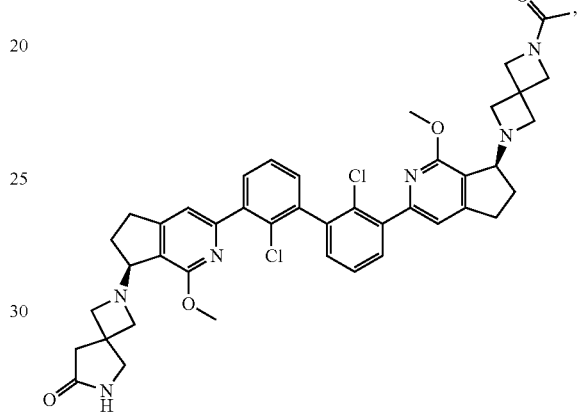
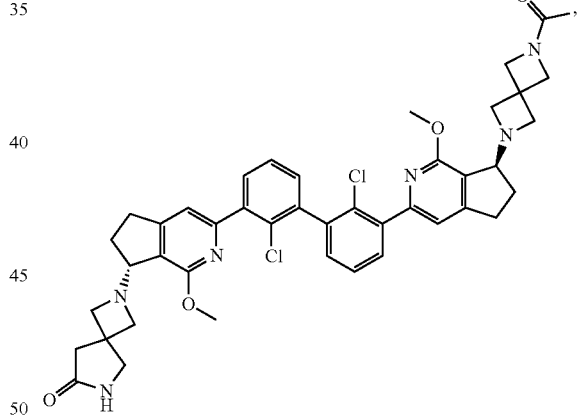
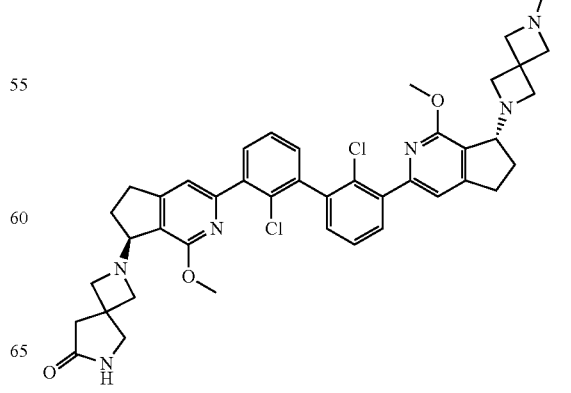

171
-continued
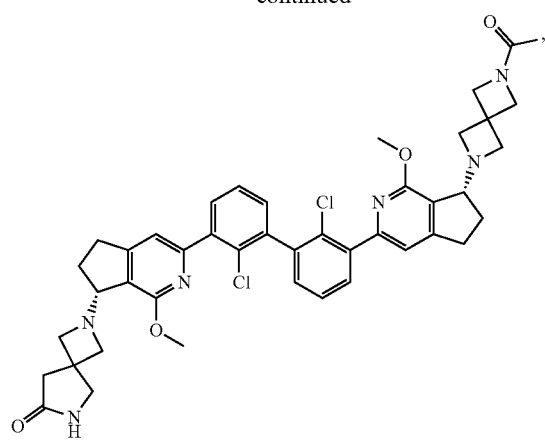
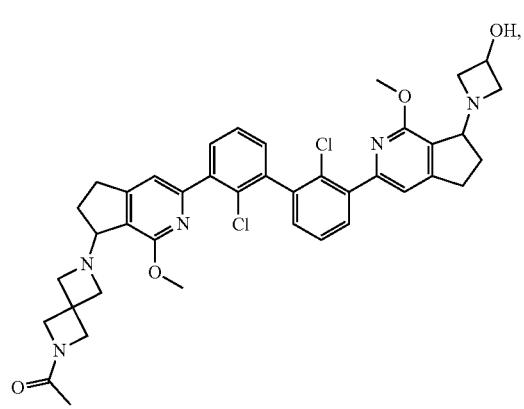
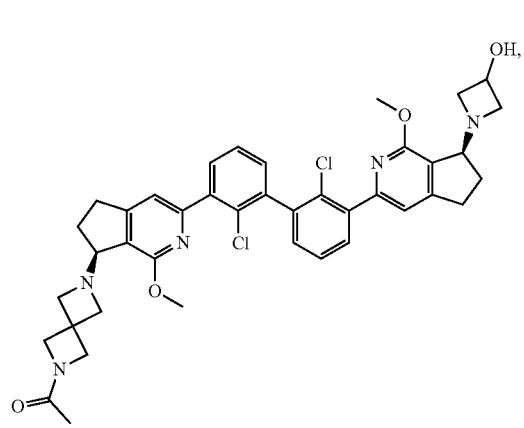
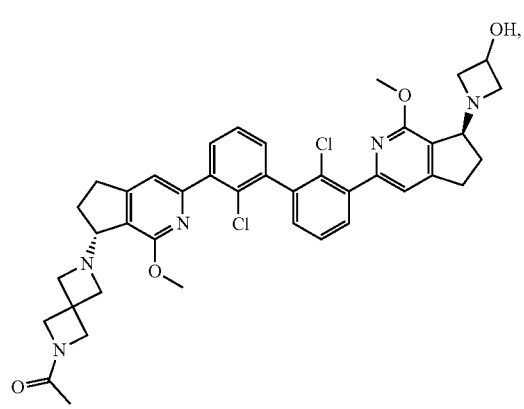
172
-continued
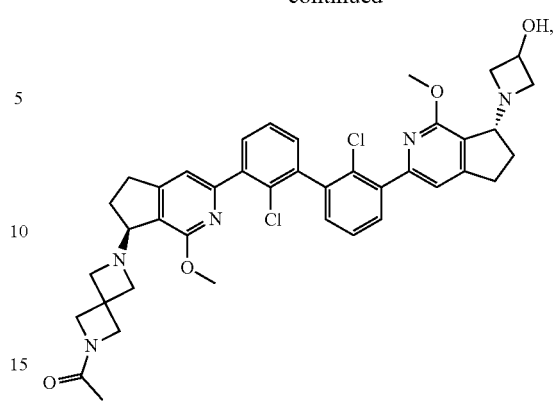
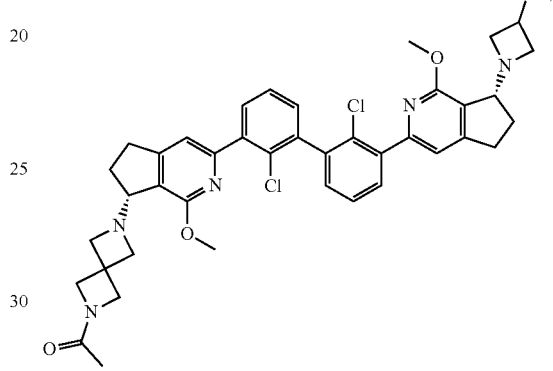
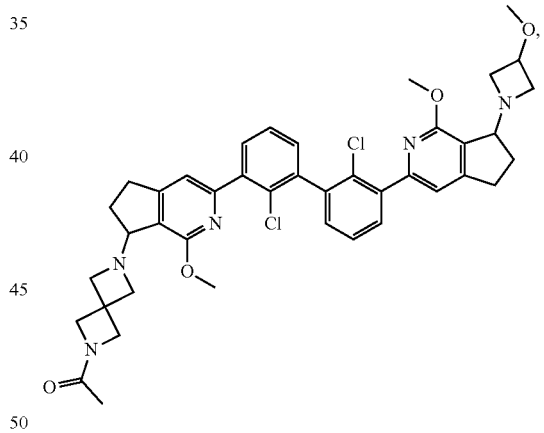
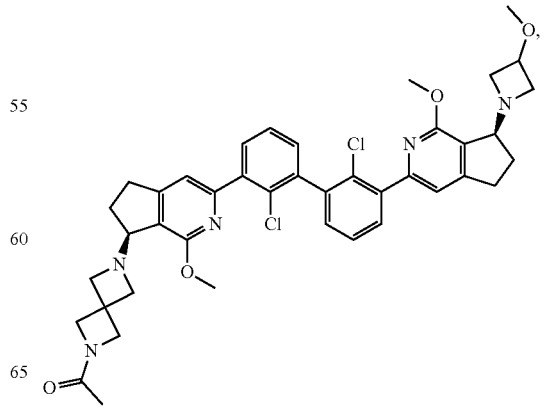

173
-continued
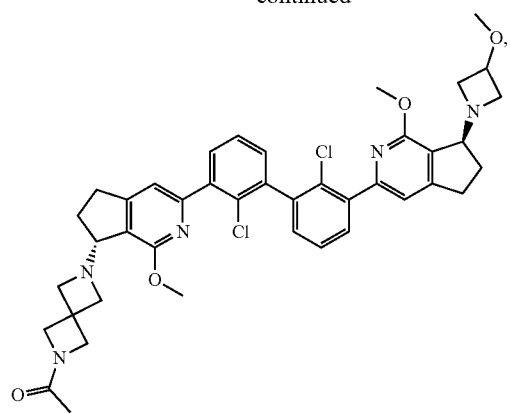
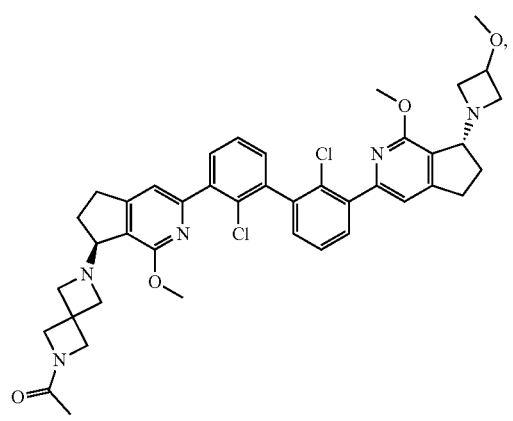
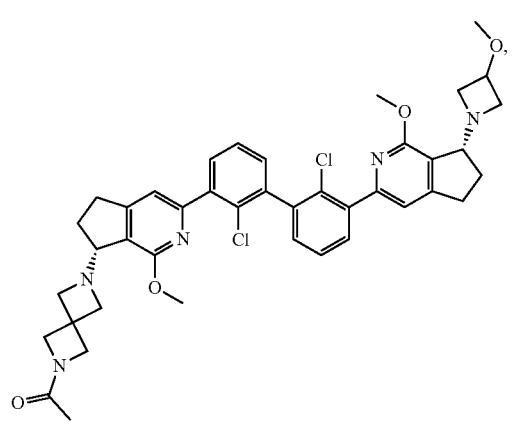
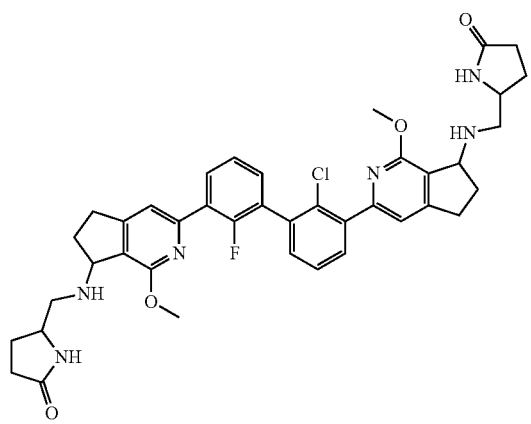
174
-continued
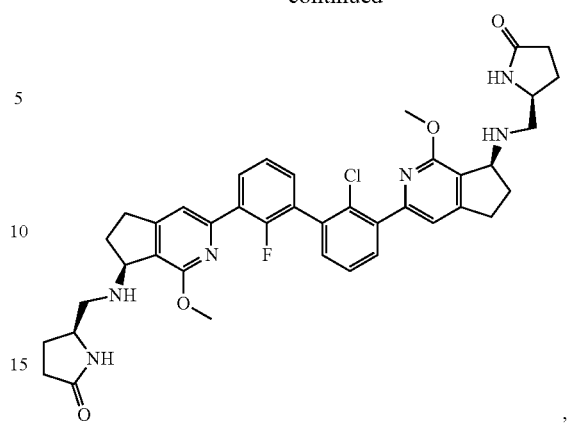
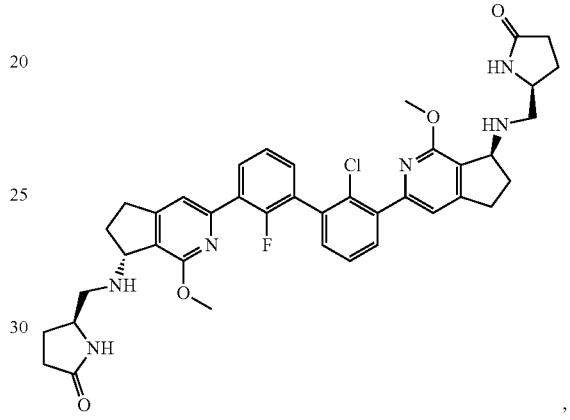
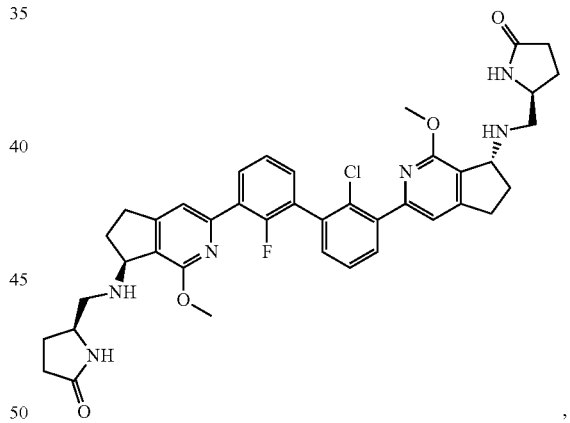
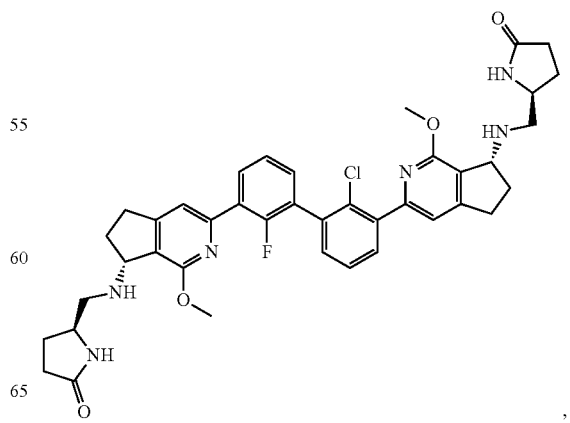

175
-continued
176
-continued
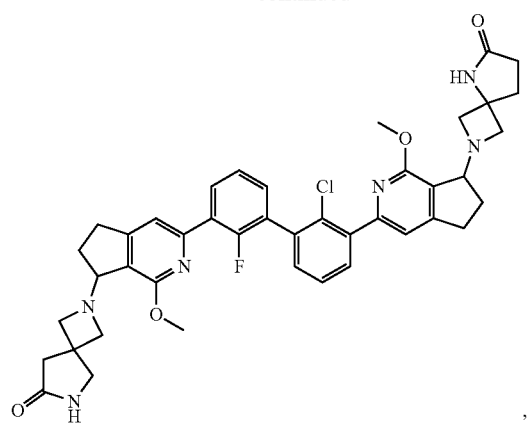
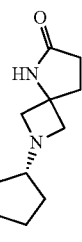
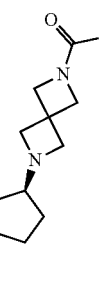

177
-continued
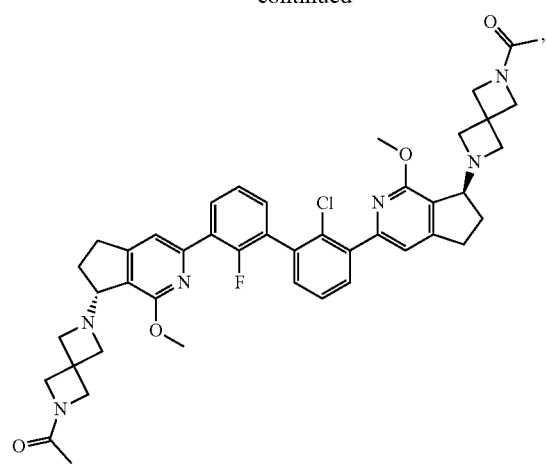
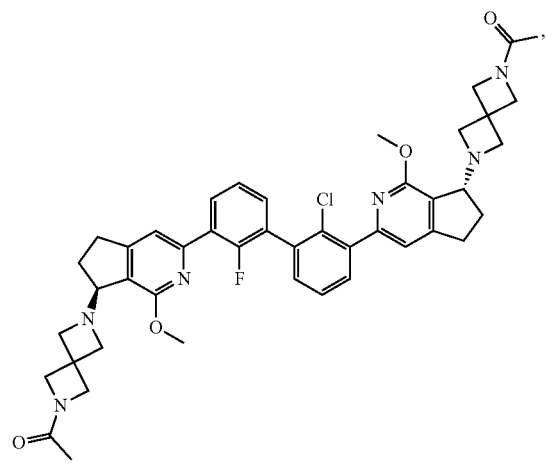
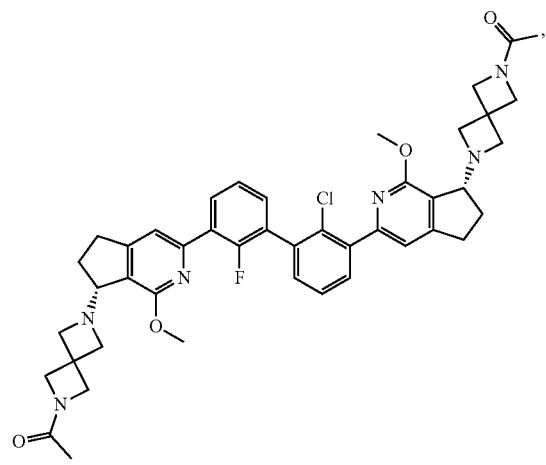
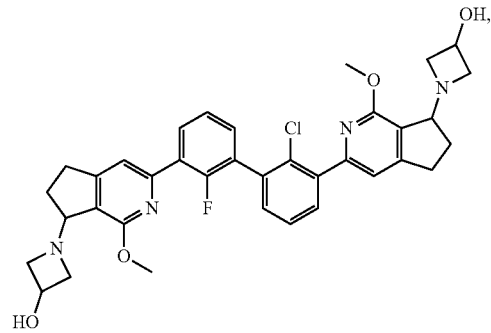
178
-continued
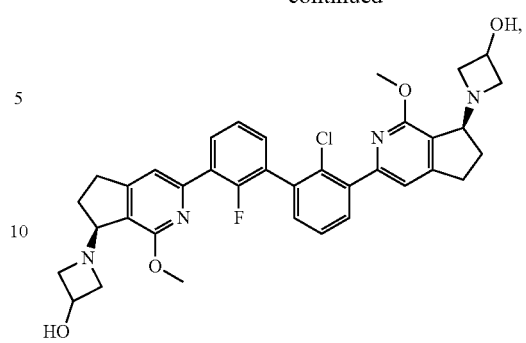
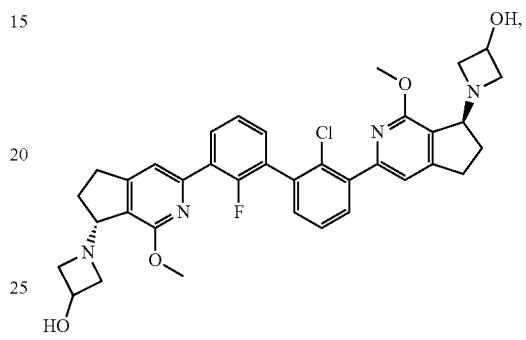
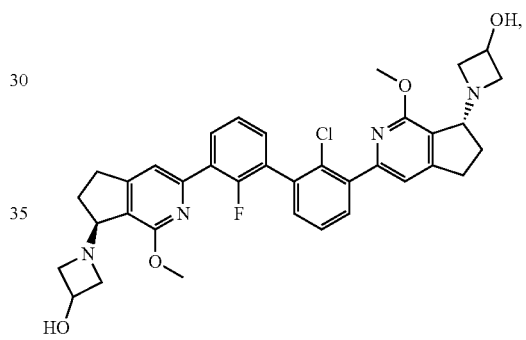
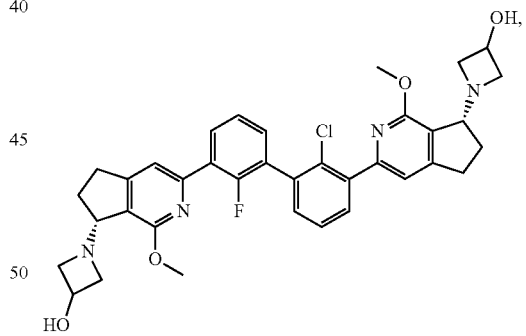
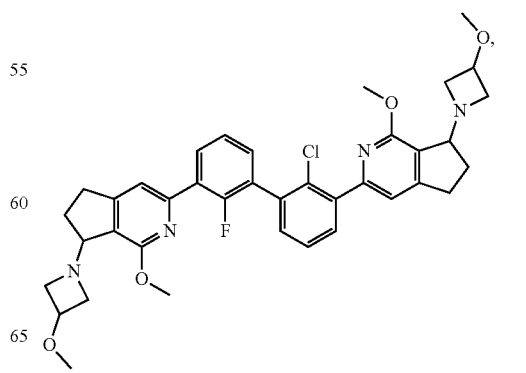

-continued
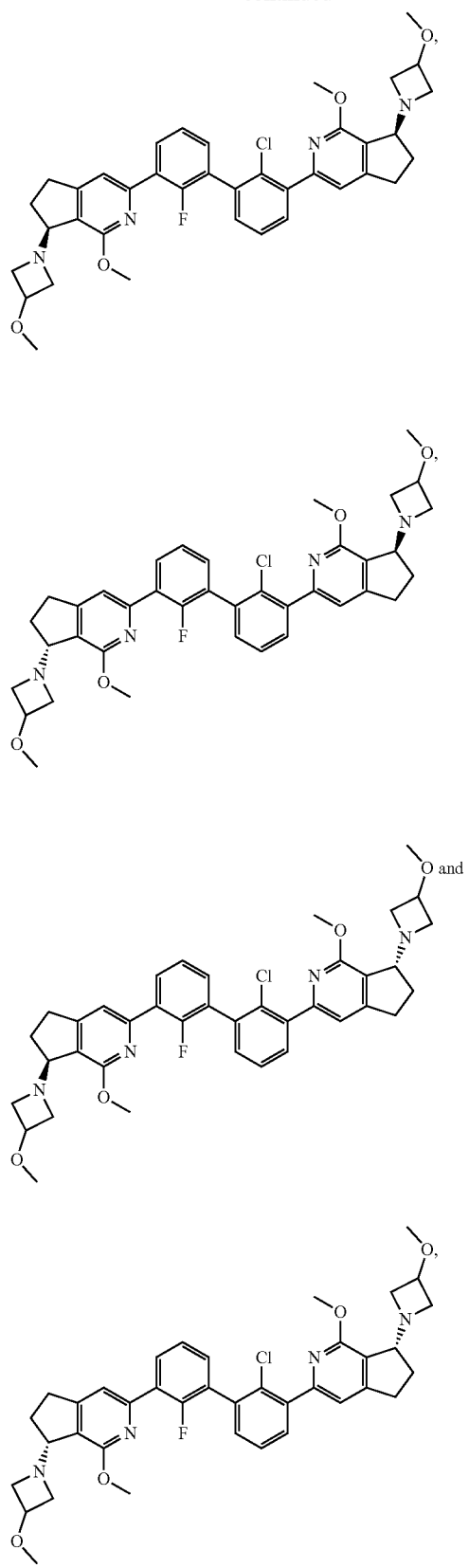
or a pharmaceutically acceptable salt of any of the foregoing.
In some embodiments, a compound of Formula (I) can be selected from:
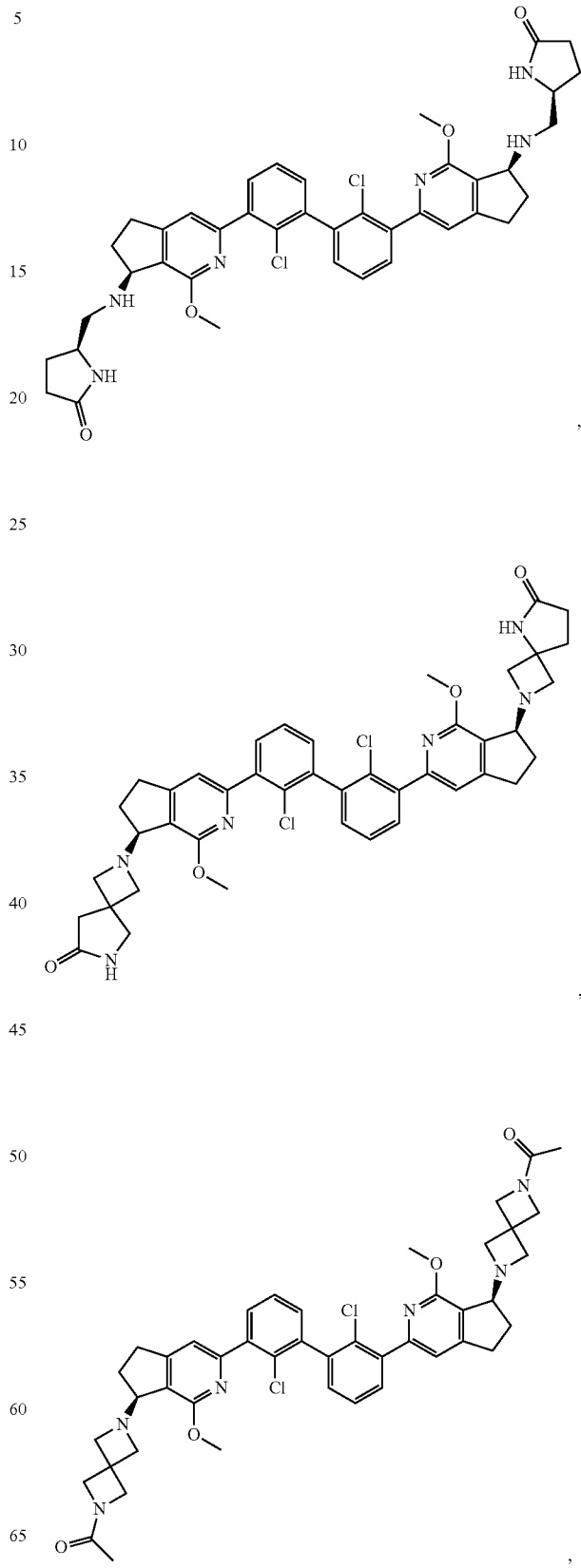

181
-continued
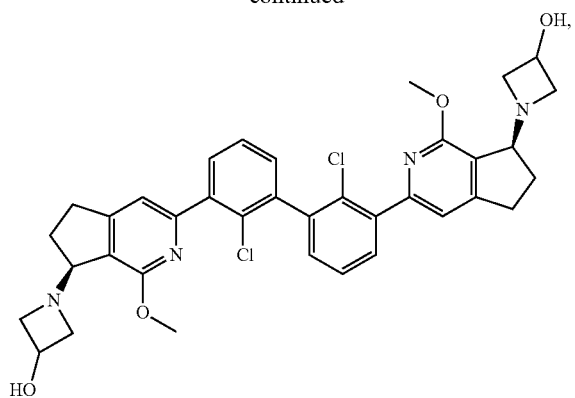
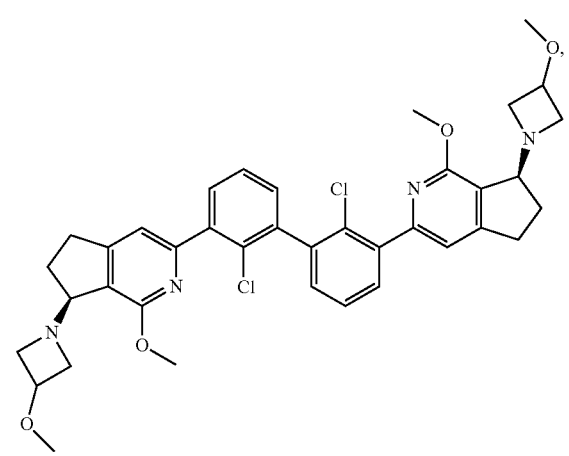
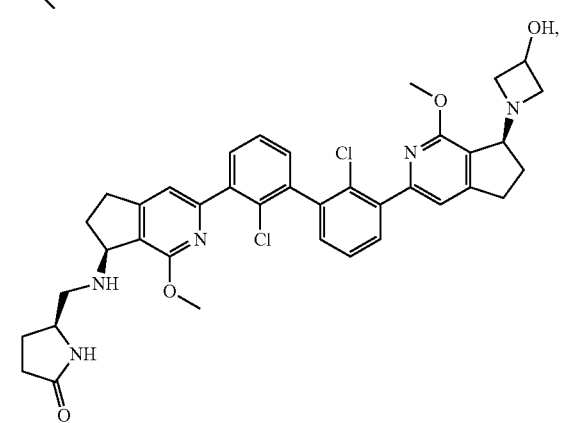
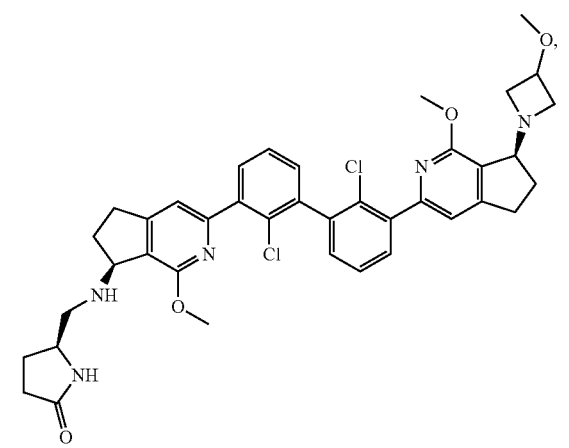
182
-continued
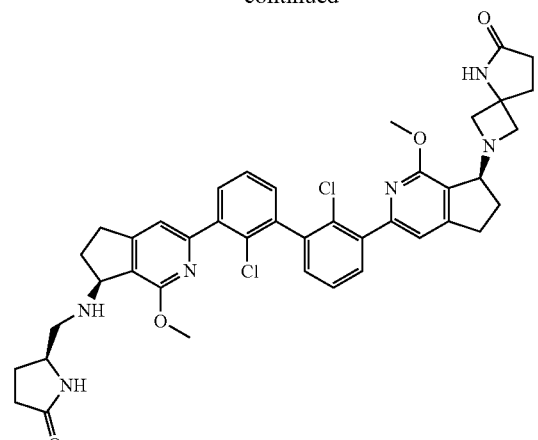
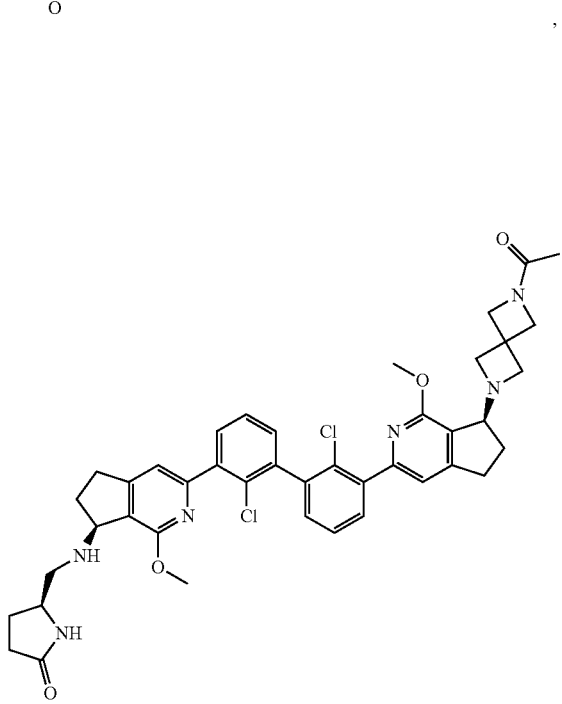
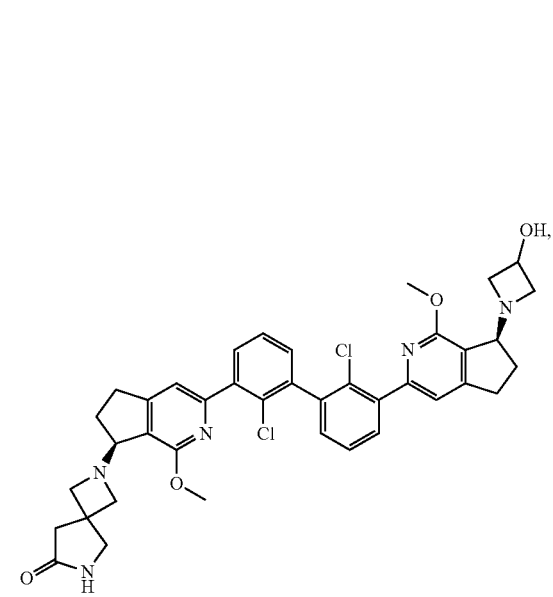

183
-continued
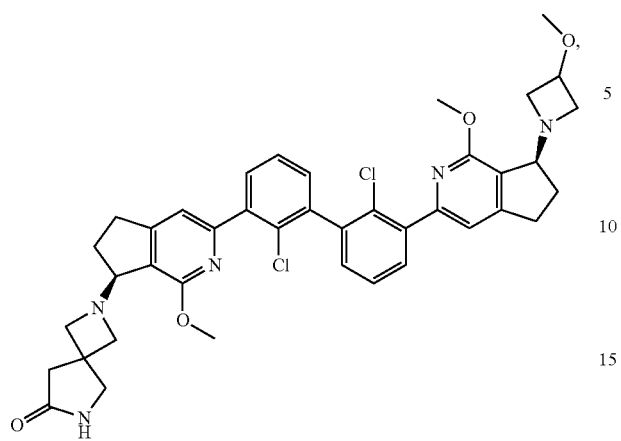
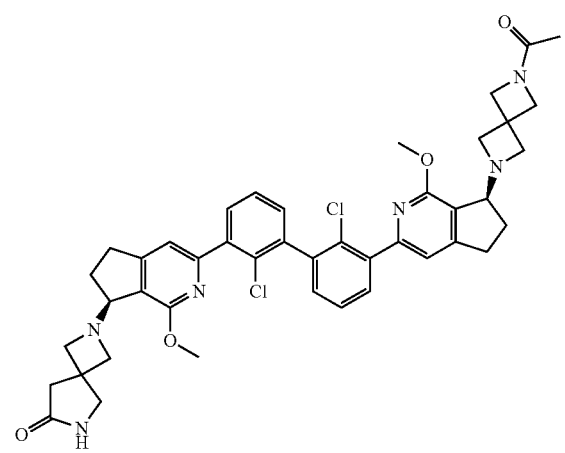
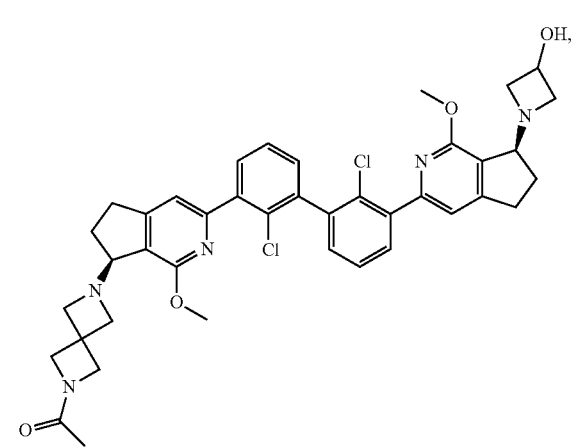
184
-continued
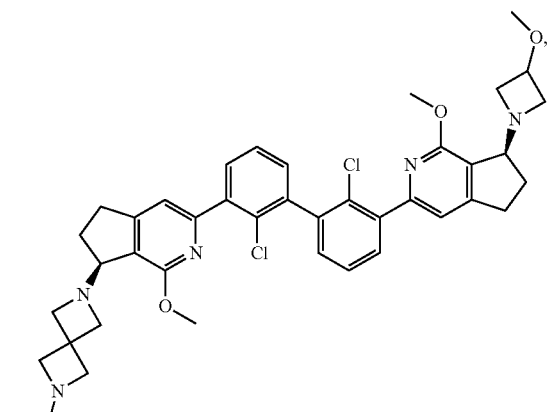
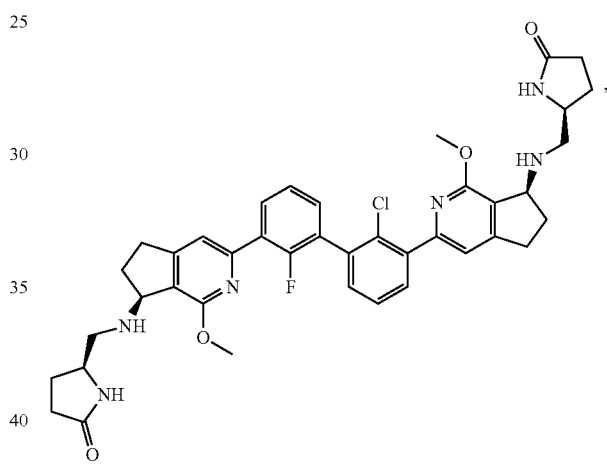
,
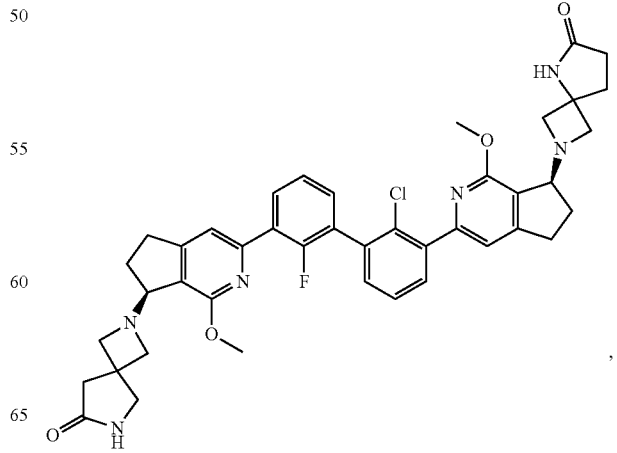
,

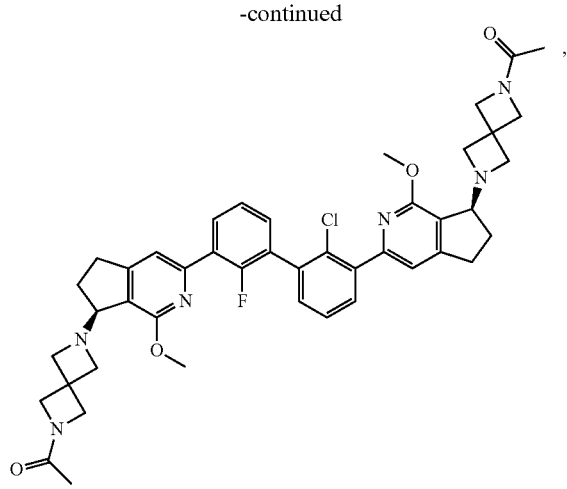

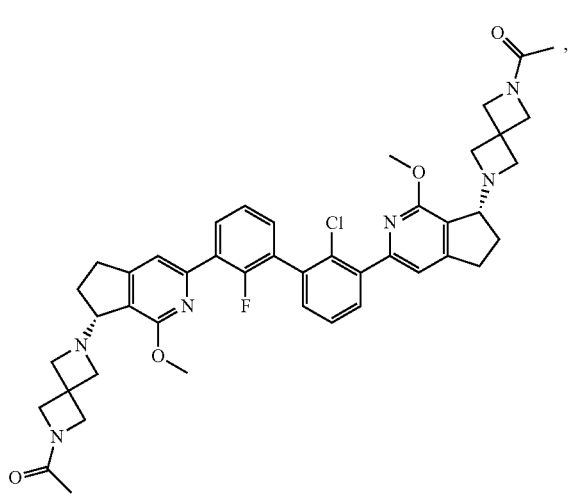

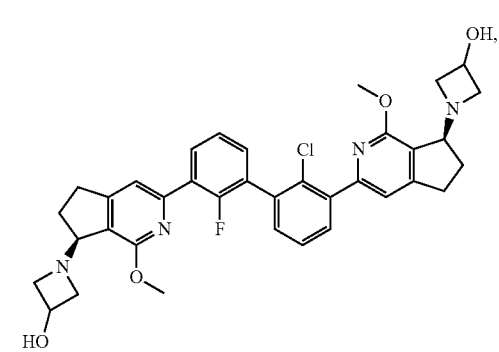

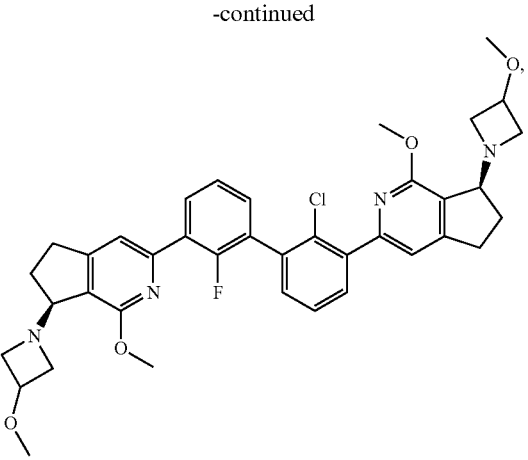

or a pharmaceutically acceptable salt of any of the foregoing.

Embodiment 511

The compound of any one of Embodiments 1-510, wherein a compound of Formula (I), or a pharmaceutically acceptable salt thereof, cannot be

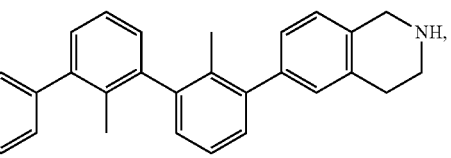

or a pharmaceutically acceptable salt thereof. The compound of any one of Embodiments 1-510, wherein a compound of Formula (I), or a pharmaceutically acceptable salt thereof, cannot be selected from

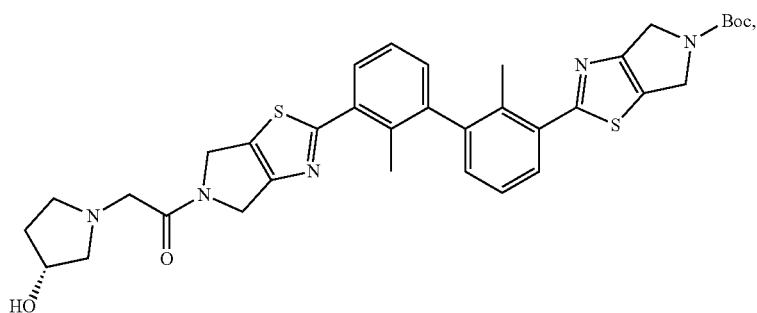

-continued

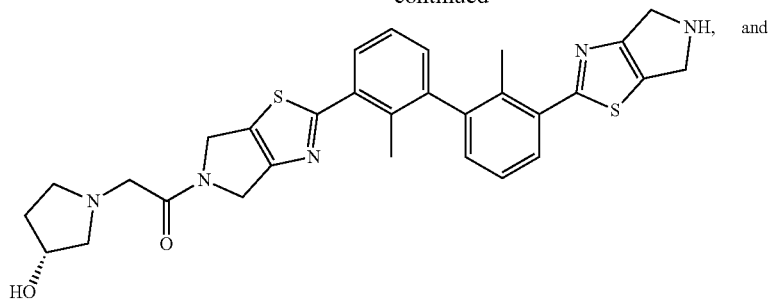

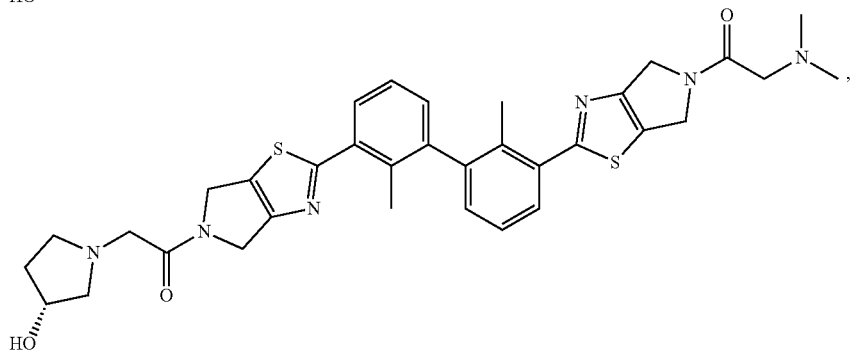

or a pharmaceutically acceptable salt thereof. In some embodiments, a compound of Formula (I), or a pharmaceutically acceptable salt thereof, cannot be a compound, or a pharmaceutically acceptable salt thereof, provide in WO 2020/257549. In some embodiments, a compound of Formula (I), or a pharmaceutically acceptable salt thereof, cannot be a compound, or a pharmaceutically acceptable salt thereof, provide in WO 2018/119263. In some embodiments, $R^{2d}$ cannot be fluoro. In some embodiments, including those of this paragraph, $R^{2f}$ cannot be fluoro. In some embodiments, $R^{2d}$ cannot be —$CH_3$. In some embodiments, including those of this paragraph, $R^{2f}$ cannot be —$CH_3$. In some embodiments, Ring $A^{1a}$, $A^{2a}$, $A^{3a}$ and/or $A^{4a}$ cannot be a 5-membered oxygen-containing monocyclic heterocyclyl, such as

and/or

wherein asterisks indicate the position of the fused bond. In some embodiments, Ring $A^{1b}$, $A^{2b}$, $A^{3b}$ and/or $A^{4b}$ cannot be a 5-membered oxygen-containing monocyclic heterocyclyl**, such as

and/or

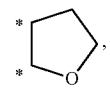

wherein asterisks indicate the position of the fused bond. In some embodiments, $R^{1a}$ cannot be

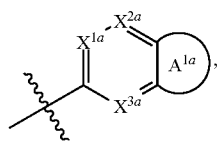

such as

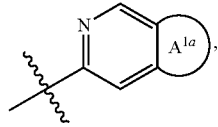 [SMILES: *c1ccccn1]

wherein Ring $A^{1a}$ is a 5-membered oxygen-containing monocyclic heterocyclyl (for example,

and/or

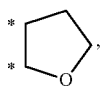

wherein asterisks indicate the position of the fused bond). In some embodiments, $R^{1b}$ cannot be

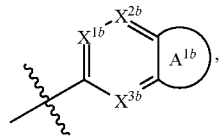

such as

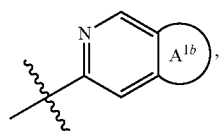 [SMILES: *c1ccccn1]

wherein Ring $A^{1b}$ is a 5-membered oxygen-containing monocyclic heterocyclyl (for example,

and/or

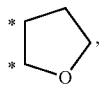

wherein asterisks indicate the position of the fused bond). In some embodiments, $R^{1a}$ cannot be

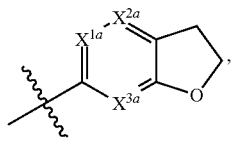

including

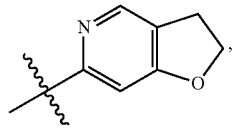

In some embodiments, $R^{1b}$ cannot be

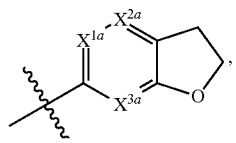

for example,

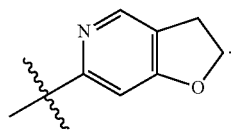 [SMILES: *c1cc2c(cn1)CCO2]

Methods for the Preparation

In this section, as in all other sections unless the context indicates otherwise, references to Formula (I), along with pharmaceutical acceptable salts thereof, include all other sub-groups and examples thereof as provided herein. The general preparations of some representative examples of compounds of Formula (I) are described herein, and are generally prepared from starting materials which are either commercially available or prepared by standard synthetic processes used by those skilled in the art.

The following schemes a represent example preparations compounds of Formula (I), along with pharmaceutically acceptable salts thereof. Compounds of Formula (I), along with pharmaceutically acceptable salts thereof may also be prepared by analogous reaction protocols as described in the general schemes below, combined with standard synthetic processes used by those skilled in the art.

All variables shown in the schemes are defined as mentioned herein, unless otherwise is indicated or is clear from the context. Compounds of Formula (I) where $R^{1a}$ and $R^{1b}$ are different can be prepared according to General Scheme 1.

General Scheme 1

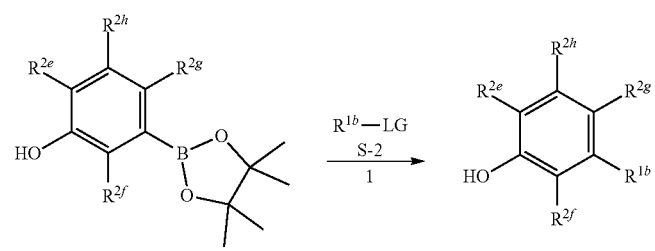

-continued
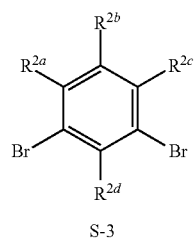 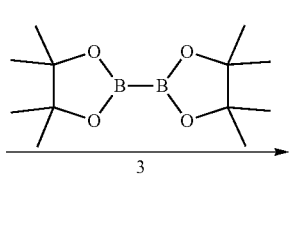 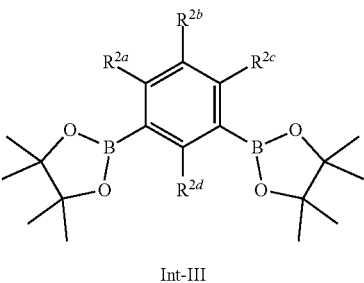
S-3 → Int-III
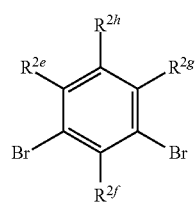 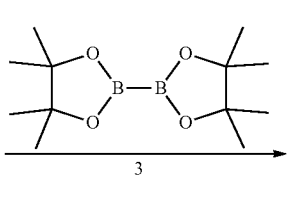 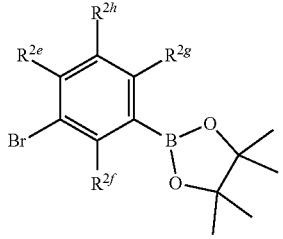
Int-V
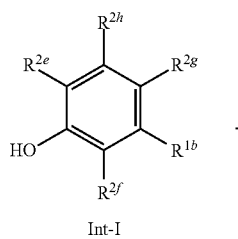  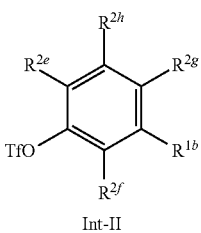
Int-I → Int-II
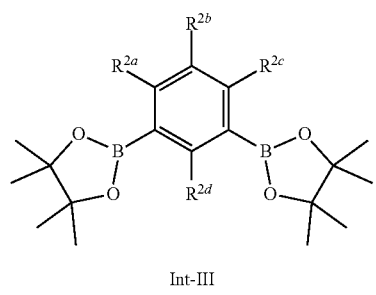 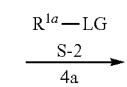 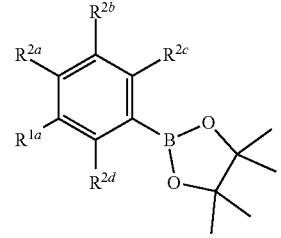 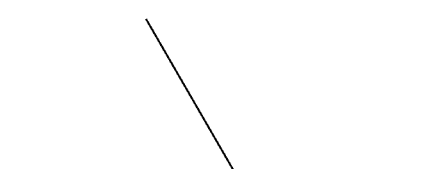
Int-III → Int-IV → (I)
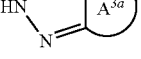
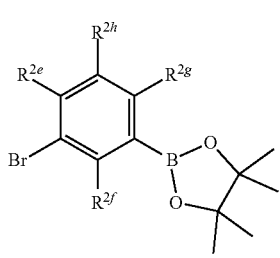 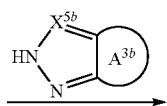 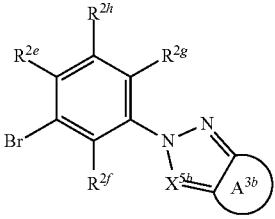
Int-V → Int-VI
R^{1a}—LG:
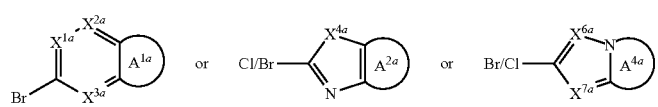

$R^{1b}$—LG:

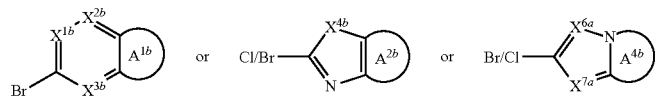

In General Scheme 1, $R^{1a}$-LG is defined as Br or Cl connected to the 5 or 6 aromatic rings of $R^{1a}$ shown in above scheme. All other variables shown in General Scheme 1 are as provided herein.

In General Scheme 1, the following reaction conditions can be used in each of the indicates reactions: (1) In the presence of suitable catalyst, such as bis(triphenylphosphine)palladium(II) dichloride, in a suitable solvent, such as 1,4-dioxane, with a suitable base (for example $K_3PO_4$) at a suitable temperature, such as approximately 90° C.; (2) In the presence of suitable base, such as DIPEA, in a suitable solvent, such as DCM, at a suitable temperature, for example, approximately 20° C.; (3) In the presence of suitable catalyst, such as for example, bis(triphenylphosphine)-palladium(II) dichloride, in a suitable solvent, such as 1,4-dioxane, with a suitable base (for example, $K_2CO_3$) at a suitable temperature (such as approximately 90° C.; (4a) In the presence of suitable catalyst (such as bis(triphenylphosphine)palladium(II) dichloride) in a suitable solvent, (for example, 1,4-dioxane) with a suitable base, such as $K_2CO_3$, at a suitable temperature (such as approximately 90° C.); (4b) In the presence of $O_2$, with suitable catalyst (for example, copper (II) acetate hydrate) in a suitable solvent, such DCM, with a suitable base (such as pyridine) at a suitable temperature, for example approximately 20° C.; and (5) In the presence of suitable catalyst, such as bis(triphenylphosphine)-palladium(II) dichloride, in a suitable solvent (for example, 1,4-dioxane) with a suitable base, such as $K_2CO_3$, at a suitable temperature (for example approximately 90° C.

Compounds of Formula (I) that can be obtained from General Scheme 1 are shown below:

I.I

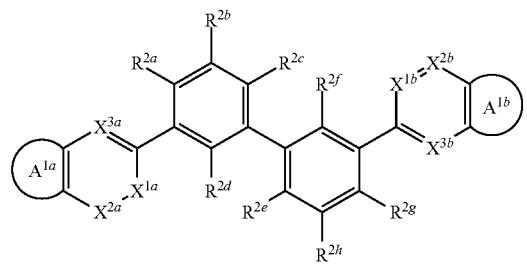

I.II

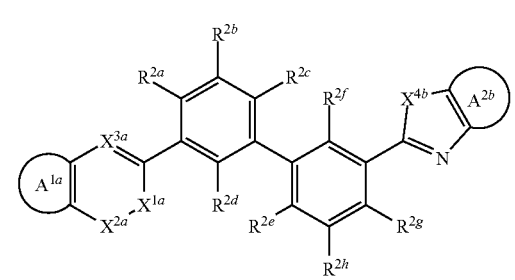

I.III

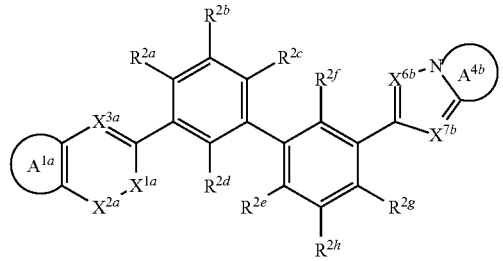

I.IV

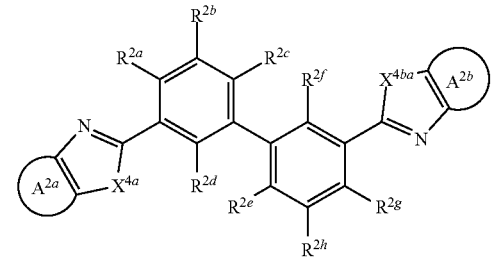

I.V

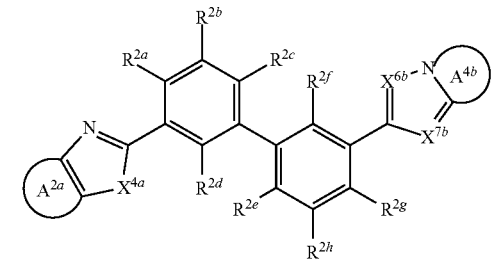

I.VI

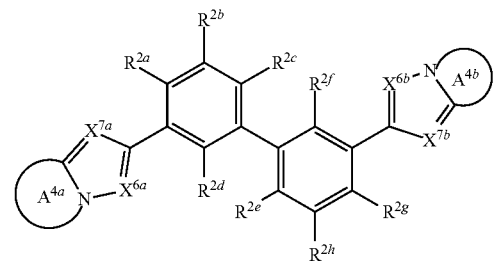

I.VII

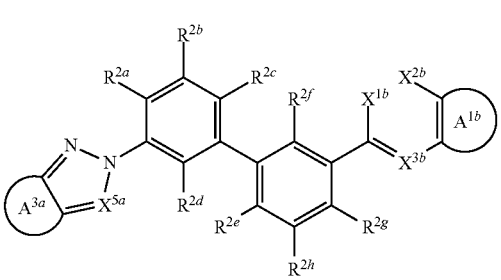

I.VIII
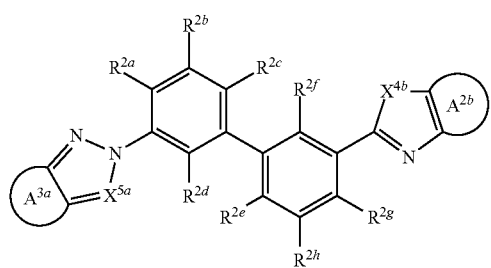
I.IX
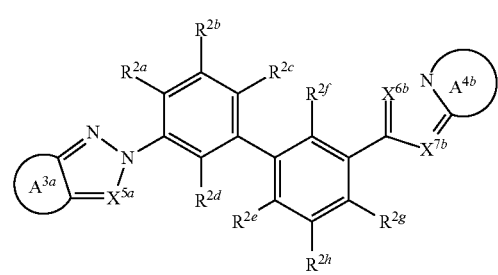
I.X
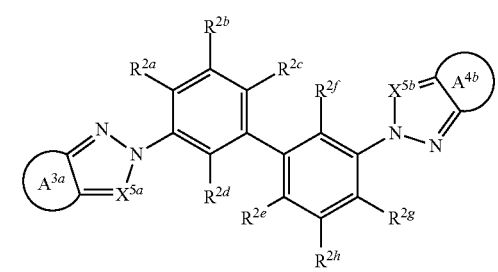
In general, compounds of Formula (I) where $R^{1a}$ and $R^{1b}$ are the same can be prepared according to General Scheme 2.
General Scheme 2
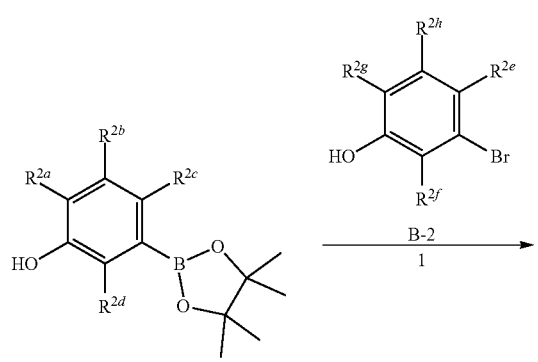
-continued
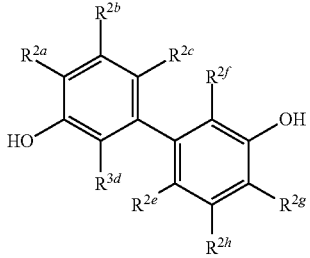
Int-1
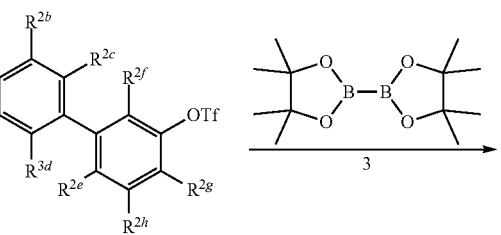
Int-2
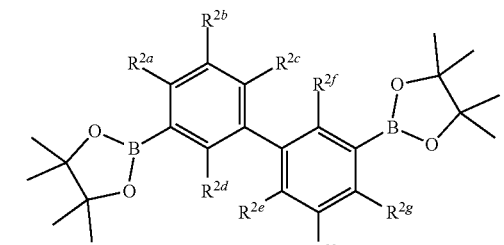
Int-3
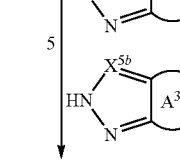
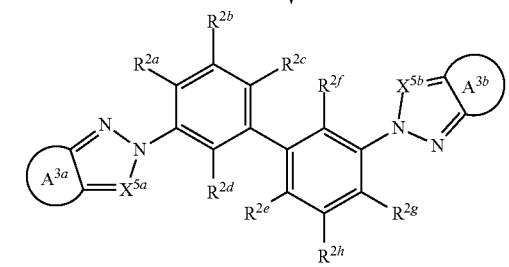
I.XI
$R^{1a}$—LG:
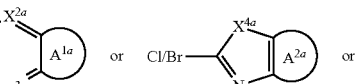

-continued $R^{1b}$—LG:

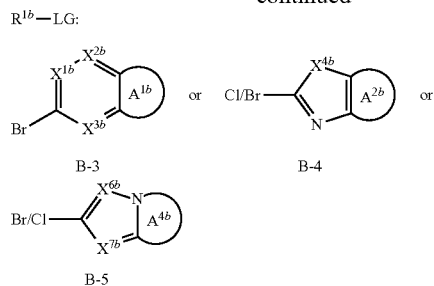

In General Scheme 2, $R^{1a}$-LG is defined as Br or Cl connected to the 5 or 6 aromatic rings of $R^{1a}$ shown in above scheme. All other variables shown in General Scheme 2 are as provided herein.

In General Scheme 2, the following reaction conditions can be used in each of the indicates reactions: (1) In the presence of suitable catalyst, such as bis(triphenylphosphine)palladium(II) dichloride, in a suitable solvent, such as 1,4-dioxane, with a suitable base (for example, $K_3PO_4$) at a suitable temperature (for example, approximately 90° C.); (2) In the presence of suitable base (for example, DIPEA) in a suitable solvent, such as DCM, at a suitable temperature, such as approximately 20° C.; (3) In the presence of suitable catalyst (for example, bis(triphenylphosphine)palladium(II) dichloride) in a suitable solvent, such as 1,4-dioxane, with a suitable base (for example KOAc) at a suitable temperature (for example, approximately 90° C.); (4) In the presence of suitable catalyst, such as bis(triphenylphosphine)palladium (II) dichloride, in a suitable solvent, such as 1,4-dioxane, with a suitable base (for example, $K_2CO_3$) at a suitable temperature (for example approximately 90° C.); and (5) In the presence of $O_2$, with suitable catalyst, such as for example copper (II) acetate hydrate, in a suitable solvent, such as for example DCM, with a suitable base, such as for example pyridine, at a suitable temperature, such as for example 20° C.

General Scheme 3

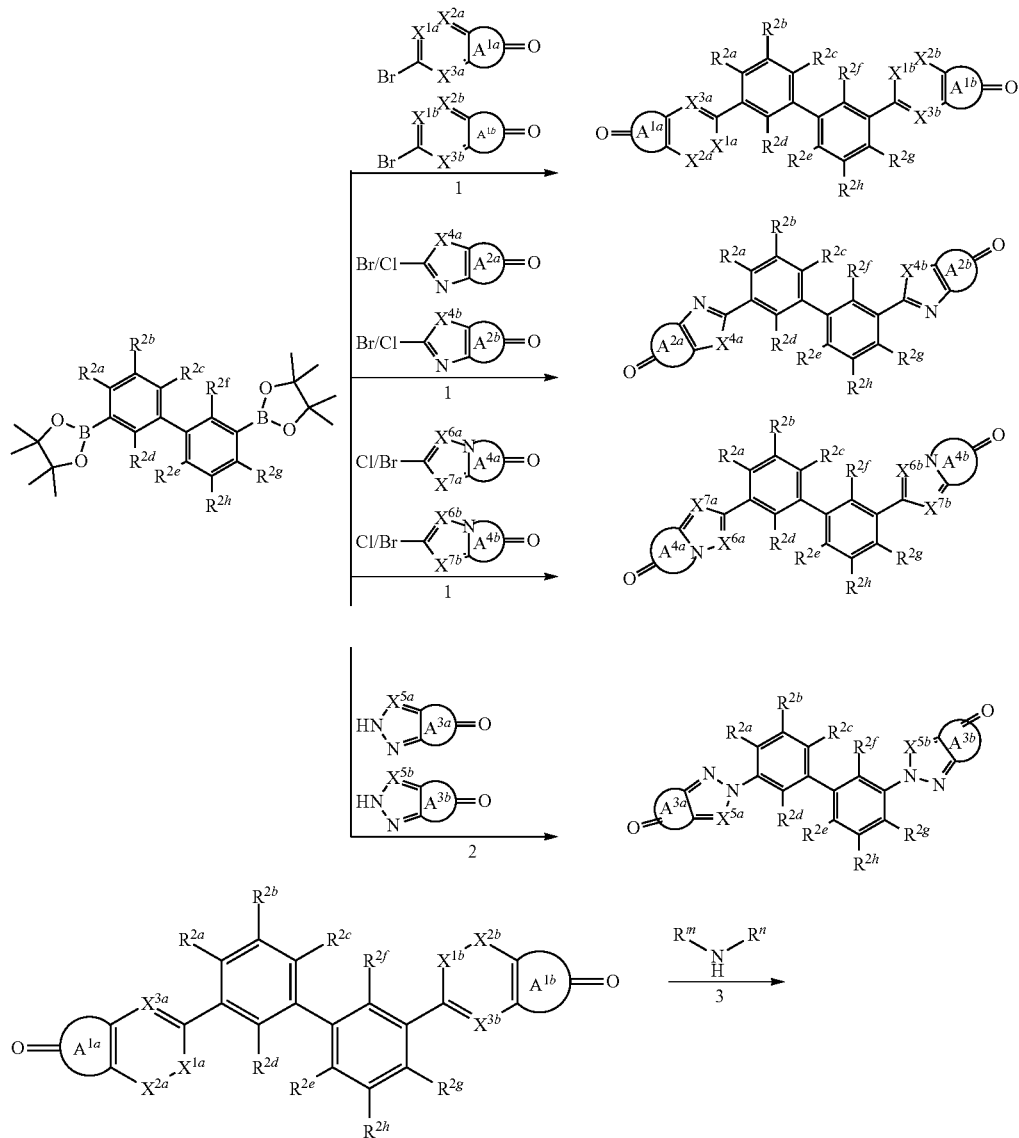

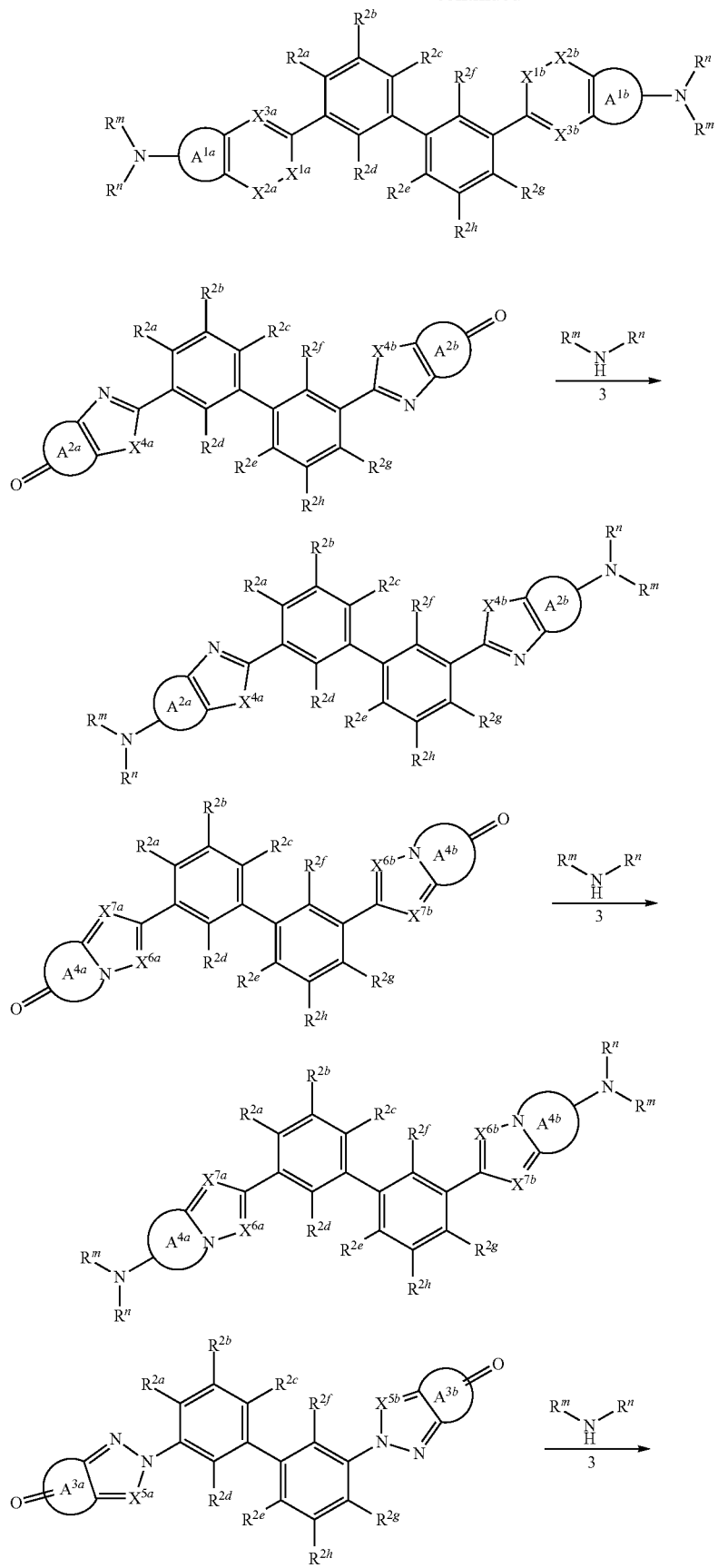

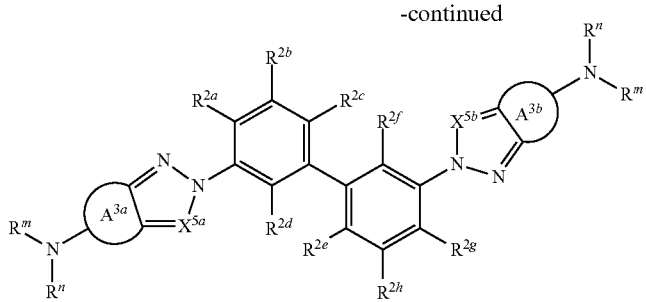

In General Scheme 3, the following reaction conditions can be used in each of the indicates reactions: (1) In the presence of suitable catalyst, such as bis(triphenylphosphine)palladium(II) dichloride, in a suitable solvent (for example, 1,4-dioxane) with a suitable base, such as $K_2CO_3$, at a suitable temperature (for example approximately 90° C.); (2) In the presence of $O_2$, with suitable catalyst (for example, copper (II) acetate hydrate) in a suitable solvent (for example, DCM0 with a suitable base, such as pyridine, at a suitable temperature, such as approximately 20° C.; and (3) In the presence of appropriate reductive reagent, such as sodium cyanoborohydride or sodium triacetoxyborohydride, in a suitable solvent (for example, DCM or MeOH) at a suitable temperature, such as approximately 20° C.

General Scheme 4

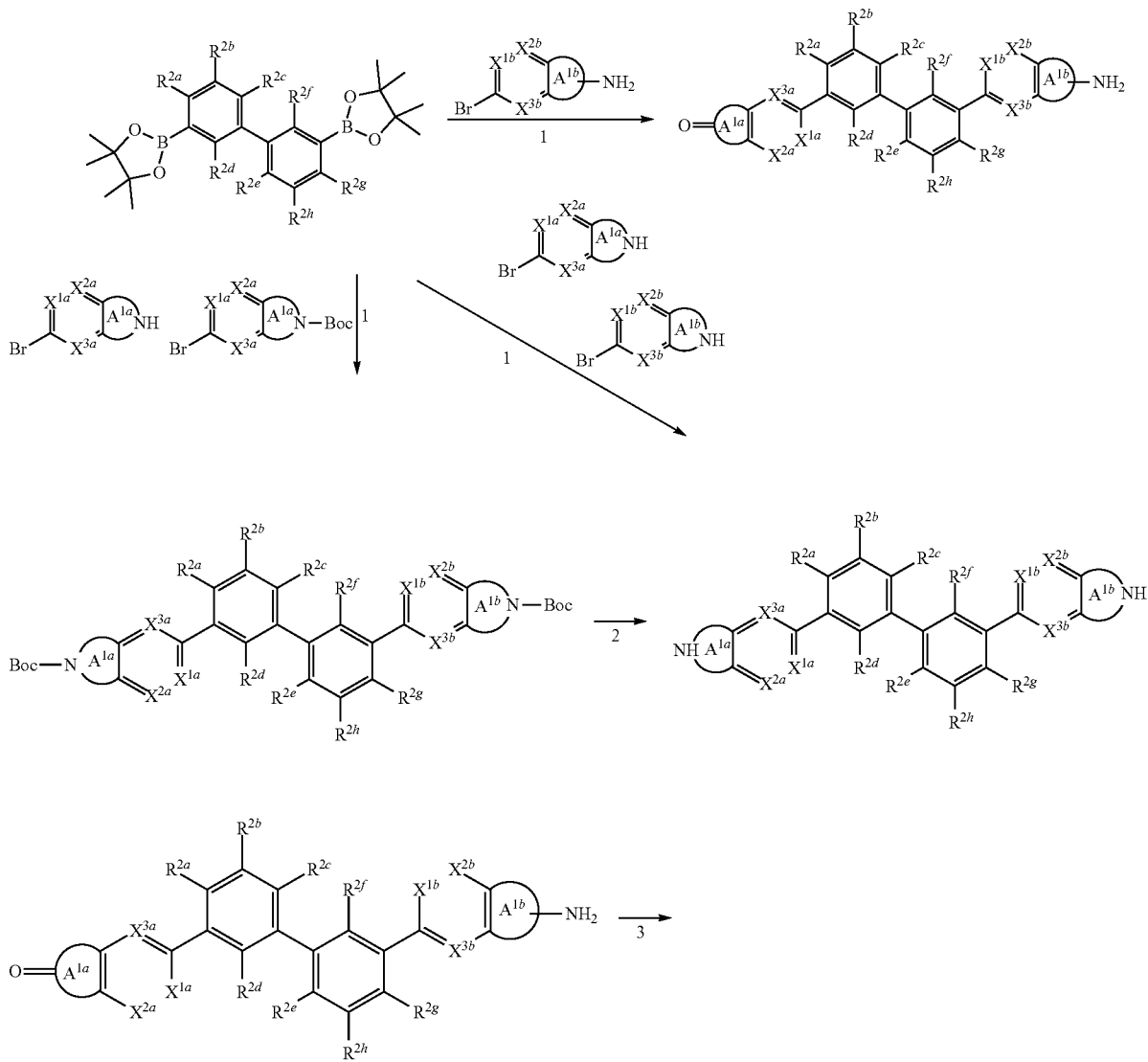

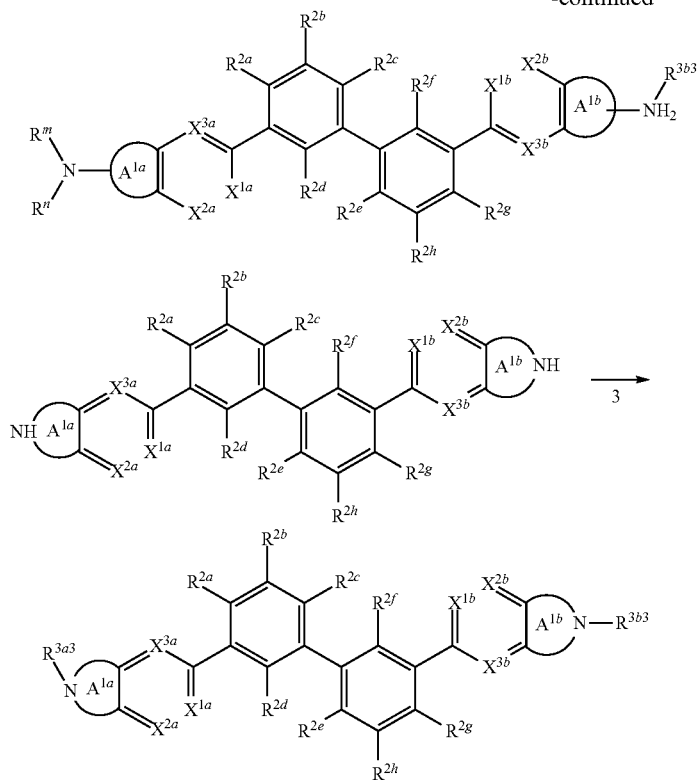

In General Scheme 4, the following reaction conditions can be used in each of the indicates reactions: (1) In the presence of suitable catalyst (for example, bis(triphenylphosphine)palladium(II) dichloride) in a suitable solvent (for example, 1,4-dioxane) with a suitable base, such as $K_2CO_3$, at a suitable temperature, such as approximately 90° C.; (2) In the presence of suitable acid, such as TFA or HCl, in a suitable solvent (for example, DCM or dioxane) at a suitable temperature, such as approximately 20° C.; (3) Different sets of reaction conditions may be used based on the coupling reagents for introducing $R^{3a3}$: (3a) When the coupling reagent contains an aldehyde or a ketone as reactive group—in the presence of appropriate reductive reagent, such as sodium cyanoborohydride or sodium triacetoxyborohydride, in a suitable solvent (for example DCM or MeOH) at a suitable temperature, such as approximately 20° C.; (3b) When the coupling reagent contains a halogen as leaving group connected to an non-aromatic carbon adjacent to a nitrogen—in the presence of appropriate base, such as TEA or DIEA, at suitable temperature (for example approximately 50° C.) with or without a suitable solvent, such as DCM; (3c) When the coupling reagent contains a halogen as leaving group connected to an aromatic carbon adjacent to nitrogen—in the presence of appropriate base such as TEA or DIEA, at suitable temperature, such as approximately 150° C., with or without a suitable solvent (for example, NMP); (3d) When the coupling reagent contains a halogen as leaving group connected to a non-aromatic carbon—in the presence of an appropriate a palladium catalyst, such as for example Ruphos-Pd-G3, with a suitable ligand (for example, Ruphos) with a suitable base, such as $Cs_2CO_3$ in in a suitable solvent, such as 1,4-dioxane, at suitable temperature (for example approximately 100° C.); (3e) When the coupling reagent contains an epoxide as reactive group—in the presence of suitable base, such as TEA, in a suitable solvent, such as EtOH, at a suitable temperature, such as approximately 80° C.; and (3f) When the coupling reagent contain a carboxylic acid as reactive group to form an amide bond—in the presence of suitable amide coupling reagent (for example, HATU) in a suitable base, such as DIEA, at a suitable temperature, such as approximately 20° C.

The skilled person will realize that typically after a column purification, the desired fractions were collected, and the solvent was evaporated to obtain the desired compound or intermediate. In addition, the skilled person will realize that in the reactions described in the following schemes, it may be necessary to protect reactive functional groups, for example, hydroxy, amino, or carboxy groups, where these are desired in the final product, to minimize any side reactions. Conventional protecting groups can be used in accordance with standard practice. The skilled person will realize that in the reactions described in schemes herein, it may be advisable or necessary to perform the reaction under an inert atmosphere, such as for example under $N_2$-gas atmosphere. It will be apparent for the skilled person that it may be preferable to cool the reaction mixture before reaction work-up (refers to the series of manipulations required to isolate and purify the product(s) of a chemical reaction such as for example quenching, column chromatography, extraction). The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the schemes herein, may also provide a compound of Formula (I), or a pharmaceutically acceptable salt thereof. The skilled person will realize that intermediates and final compounds shown in the schemes herein may be further functionalized according to methods well-known by the person skilled in the art. For example, a primary or secondary amine group may be reductively alkylated by reaction with an aldehyde or a ketone in the presence of a suitable reducing reagent (for example, sodium triacetoxyborohydride (NaBH(AcO)$_3$) together with a suitable solvent (such as, DCM) at a suitable temperature (for example, room temperature); or alternatively in the presence of NaBH$_3$CN together with a suitable solvent (for example, MeOH) at a suitable temperature, such as between room temperature and 50° C. In case one of the starting materials is available as a salt form, the skilled person will realize that it may be necessary to first treat the salt with abase, for example, N,N-diisopropylethylamine (DIPEA). The skilled person will realize that additional compounds of Formula (I), along with pharmaceutically acceptable salts thereof, can be prepared by using similar synthetic protocols as described in the schemes herein.

Pharmaceutical Compositions

Some embodiments described herein relate to pharmaceutical compositions that comprise, consist essentially of, or consist of an effective amount of a compound described herein (such as a compound of Formula (I), or a pharmaceutically acceptable salt thereof) and a pharmaceutically acceptable carrier, excipient, or combination thereof. A pharmaceutical composition described herein is suitable for human and/or veterinary applications.

The terms "function" and "functional" as used herein refer to a biological, enzymatic, or therapeutic function.

The terms "effective amount" or "effective dose" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "pharmaceutically acceptable salts" includes relatively non-toxic, inorganic and organic acid, or base addition salts of compositions, including without limitation, analgesic agents, therapeutic agents, other materials, and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc, and the like. Salts may also be formed with suitable organic bases, including those that are non-toxic and strong enough to form such salts. For example, the class of such organic bases may include but are not limited to mono-, di-, and trialkylamines, including methylamine, dimethylamine, and triethylamine; mono-, di-, or trihydroxyalkylamines including mono-, di-, and triethanolamine; amino acids, including glycine, arginine and lysine; guanidine; N-methylglucosamine; N-methylglucamine; L-glutamine; N-methylpiperazine; morpholine; ethylenediamine; N-benzylphenethylamine; trihydroxymethyl aminoethane.

"Formulation", "pharmaceutical composition", and "composition" as used interchangeably herein are equivalent terms referring to a composition of matter for administration to a subject.

The term "pharmaceutically acceptable" means compatible with the treatment of a subject, and in particular, a human.

The terms "agent" refers to an active agent that has biological activity and may be used in a therapy. Also, an "agent" can be synonymous with "at least one agent," "compound," or "at least one compound," and can refer to any form of the agent, such as a derivative, analog, salt or a prodrug thereof. The agent can be present in various forms, components of molecular complexes, and pharmaceutically acceptable salts (e.g., hydrochlorides, hydrobromides, sulfates, phosphates, nitrates, borates, acetates, maleates, tartrates, and salicylates). The term "agent" can also refer to any pharmaceutical molecules or compounds, therapeutic molecules or compounds, matrix forming molecules or compounds, polymers, synthetic molecules and compounds, natural molecules and compounds, and any combination thereof.

The term "subject" as used herein has its ordinary meaning as understood in light of the specification and refers to an animal that is the object of treatment, inhibition, amelioration, observation or experiment. "Animal" has its ordinary meaning as understood in light of the specification and includes cold- and warm-blooded vertebrates and/or invertebrates such as fish, shellfish, or reptiles and, in particular, mammals. "Mammal" has its ordinary meaning as understood in light of the specification, and includes but is not limited to mice, rats, rabbits, guinea pigs, dogs, cats, sheep, goats, cows, horses, primates, such as humans, monkeys, chimpanzees, or apes. In some embodiments, the subject is human.

Proper formulation is dependent upon the route of administration chosen. Techniques for formulation and administration of the compounds described herein are known to those skilled in the art. Multiple techniques of administering a compound exist in the art including, but not limited to, enteral, oral, rectal, topical, sublingual, buccal, intraaural, epidural, epicutaneous, aerosol, parenteral delivery, including intramuscular, subcutaneous, intra-arterial, intravenous, intraportal, intra-articular, intradermal, peritoneal, intramedullary injections, intrathecal, direct intraventricular, intraperitoneal, intranasal or intraocular injections. Pharmaceutical compositions will generally be tailored to the specific intended route of administration. Pharmaceutical compositions can also be administered to isolated cells from a patient or individual, such as T cells, Natural Killer cells, B cells, macrophages, lymphocytes, stem cells, bone marrow cells, or hematopoietic stem cells.

The pharmaceutical compound can also be administered in a local rather than systemic manner, for example, via injection of the compound directly into an organ, tissue, cancer, tumor or infected area, often in a depot or sustained release formulation. Furthermore, one may administer the compound in a targeted drug delivery system, for example, in a liposome coated with a tissue specific antibody. The liposomes may be targeted to and taken up selectively by the organ, tissue, cancer, tumor, or infected area.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

As used herein, a "carrier" refers to a compound, particle, solid, semi-solid, liquid, or diluent that facilitates the passage, delivery and/or incorporation of a compound to cells, tissues and/or bodily organs. For example, without limitation, a lipid nanoparticle (LNP) is a type of carrier that can encapsulate a compound, or a pharmaceutically acceptable salt thereof, as described herein to thereby protect the compound, or a pharmaceutically acceptable salt thereof, as described herein from degradation during passage through the bloodstream and/or to facilitate delivery to a desired organ, such as to the liver.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

The term "excipient" has its ordinary meaning as understood in light of the specification, and refers to inert substances, compounds, or materials added to a pharmaceutical composition to provide, without limitation, bulk, consistency, stability, binding ability, lubrication, disintegrating ability etc., to the composition. Excipients with desirable properties include but are not limited to preservatives, adjuvants, stabilizers, solvents, buffers, diluents, solubilizing agents, detergents, surfactants, chelating agents, antioxidants, alcohols, ketones, aldehydes, ethylenediaminetetraacetic acid (EDTA), citric acid, salts, sodium chloride, sodium bicarbonate, sodium phosphate, sodium borate, sodium citrate, potassium chloride, potassium phosphate, magnesium sulfate sugars, dextrose, fructose, mannose, lactose, galactose, sucrose, sorbitol, cellulose, serum, amino acids, polysorbate 20, polysorbate 80, sodium deoxycholate, sodium taurodeoxycholate, magnesium stearate, octylphenol ethoxylate, benzethonium chloride, thimerosal, gelatin, esters, ethers, 2-phenoxyethanol, urea, or vitamins, or any combination thereof. The amount of the excipient may be found in a pharmaceutical composition at a percentage of 0%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 20%, 30%, 40%, 50%, 60%, 70%, 80%, 90%, 95%, 100% w/w or any percentage by weight in a range defined by any two of the aforementioned numbers.

The term "adjuvant" as used herein refers to a substance, compound, or material that stimulates the immune response and increase the efficacy of protective immunity and is administered in conjunction with an immunogenic antigen, epitope, or composition. Adjuvants serve to improve immune responses by enabling a continual release of antigen, up-regulation of cytokines and chemokines, cellular recruitment at the site of administration, increased antigen uptake and presentation in antigen presenting cells, or activation of antigen presenting cells and inflammasomes. Commonly used adjuvants include but are not limited to alum, aluminum salts, aluminum sulfate, aluminum hydroxide, aluminum phosphate, calcium phosphate hydroxide, potassium aluminum sulfate, oils, mineral oil, paraffin oil, oil-in-water emulsions, detergents, MF59®, squalene, AS03, α-tocopherol, polysorbate 80, AS04, monophosphoryl lipid A, virosomes, nucleic acids, polyinosinic:polycytidylic acid, saponins, QS-21, proteins, flagellin, cytokines, chemokines, IL-1, IL-2, IL-12, IL-15, IL-21, imidazoquinolines, CpG oligonucleotides, lipids, phospholipids, dioleoyl phosphatidylcholine (DOPC), trehalose dimycolate, peptidoglycans, bacterial extracts, lipopolysaccharides, or Freund's Adjuvant, or any combination thereof.

The term "purity" of any given substance, compound, or material as used herein refers to the actual abundance of the substance, compound, or material relative to the expected abundance. For example, the substance, compound, or material may be at least 80, 85, 90, 91, 92, 93, 94, 95, 96, 97, 98, 99, or 100% pure, including all decimals in between. Purity may be affected by unwanted impurities, including but not limited to side products, isomers, enantiomers, degradation products, solvent, carrier, vehicle, or contaminants, or any combination thereof. Purity can be measured technologies including but not limited to chromatography, liquid chromatography, gas chromatography, spectroscopy, UV-visible spectrometry, infrared spectrometry, mass spectrometry, nuclear magnetic resonance, gravimetry, or titration, or any combination thereof.

Methods of Use

Some embodiments disclosed herein related to selecting a subject or patient in need. In some embodiments, a patient is selected who is in need of treatment, inhibition, amelioration, prevention or slowing of diseases or conditions associated with PD-L1 dysregulation. In some embodiments, such diseases or conditions associated with PD-L1 dysregulation may include, for example, cancer, HCC, viral infections, or HBV. In some embodiments, a subject can be selected who has previously been treated for the disease or disorder described herein. In some embodiments, a subject can be selected who has previously been treated for being at risk for the disease or disorder described herein. In some embodiments, a subject can be selected who has developed a recurrence of the disease or disorder described herein. In some embodiments, a subject can be selected who has developed resistance to therapies for the disease or disorder described herein. In some embodiments, a subject can be selected who may have any combination of the aforementioned selection criteria.

Compounds, and pharmaceutically acceptable salts thereof, disclosed herein can be evaluated for efficacy and toxicity using known methods. A non-limiting list of potential advantages of a compound, or a pharmaceutically acceptable salt thereof, described herein include improved stability, increased safety profile, increased efficacy, increased binding to the target, increased specificity for the target (for example, a cancer cell or virally infected cell).

The terms "treating," "treatment," "therapeutic," or "therapy" as used herein has its ordinary meaning as understood in light of the specification, and do not necessarily mean total cure or abolition of the disease or condition. The term "treating" or "treatment" as used herein (and as well understood in the art) also means an approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable. "Treating" and "treatment" as used herein also include prophylactic treatment. Treatment methods comprise administering to a subject a therapeutically effective amount of an active agent. The administering step may consist of a single administration or may comprise a series of administrations. The compositions are administered to the subject in an amount and for a duration sufficient to treat the subject. The length of the treatment period depends on a variety of factors, such as the severity of the condition, the age and genetic profile of the subject, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required.

Some embodiments described herein relate to a method of treating, inhibiting, ameliorating, preventing, or slowing the disease or disorder described herein. In some embodiments, the methods include administering to a subject identified as suffering from the disease or disorder described herein an effective amount of a compound, or a pharmaceutically acceptable salt thereof, described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating, inhibiting ameliorating, preventing, or slowing the disease or disorder described herein. Still other embodiments described herein relate to the use of a compound, or a pharmaceutically acceptable salt thereof, as described herein or a pharmaceutical composition that includes an effective amount of a compound, or a pharmaceutically acceptable salt thereof, as described herein for treating, inhibiting ameliorating, preventing, or slowing the disease or disorder described herein.

Some embodiments described herein relate to a method for inhibiting replication of a cancer cell or a virus that can include contacting the cell or virus or administering to a subject identified as suffering from a cancer or a viral infection with an effective amount of a compound, or a pharmaceutically acceptable salt thereof, described herein, or a pharmaceutical composition that includes an effective amount of a compound, or a pharmaceutically acceptable salt thereof, described herein. Other embodiments described herein relate to the use of an effective amount of a compound, or a pharmaceutically acceptable salt thereof, described herein, or a pharmaceutical composition that includes an effective amount of a compound, or a pharmaceutically acceptable salt thereof, described herein in the manufacture of a medicament for inhibiting replication of a cancer cell or virus. Still other embodiments described herein relate to an effective amount of a compound, or a pharmaceutically acceptable salt thereof, described herein, or a pharmaceutical composition that includes an effective amount of a compound, or a pharmaceutically acceptable salt thereof, described herein for inhibiting replication of a cancer cell or virus. In some embodiments, the cancer cell is an HCC cell. In some embodiments, the virus is hepatitis B.

Some embodiments described herein relate to a method for inhibiting cell proliferation, such as inhibiting cell proliferation of a cancer cell or cell infected with a virus, that can include administering to a subject identified as suffering from a disease wherein inhibiting cell proliferation is desirable with an effective amount of a compound, or a pharmaceutically acceptable salt thereof, described herein, or a pharmaceutical composition that includes effective amount of a compound, or a pharmaceutically acceptable salt thereof, described herein. Other embodiments described herein relate to the use of an effective amount of a compound, or a pharmaceutically acceptable salt thereof, described herein, or a pharmaceutical composition that includes an effective amount of a compound, or a pharmaceutically acceptable salt thereof, described herein in the manufacture of a medicament for inhibiting cell proliferation, such as inhibiting cell proliferation of a cancer cell or cell infected with a virus. Still other embodiments described herein relate to an effective amount of a compound, or a pharmaceutically acceptable salt thereof, described herein, or a pharmaceutical composition that includes an effective amount of a compound, or a pharmaceutically acceptable salt thereof, described herein for inhibiting cell proliferation, such as inhibiting cell proliferation of a cancer cell or cell infected with a virus. In some embodiments, the cancer cell is an HCC cell. In some embodiments, the cell infected with a virus is infected with hepatitis B virus.

Some embodiments described herein relate to a method of inducing apoptosis of a cell (for example, a cancer cell or cell infected with a virus) that can include contacting the cell with an effective amount of a compound, or a pharmaceutically acceptable salt thereof, described herein, or a pharmaceutical composition that includes an effective amount of a compound of Formula (I), or a pharmaceutically acceptable salt thereof, as described herein. Other embodiments described herein relate to using an effective amount of a compound, or a pharmaceutically acceptable salt thereof, as described herein or a pharmaceutical composition that includes an effective amount of a compound, or a pharmaceutically acceptable salt thereof, described herein in the manufacture of a medicament for inducing apoptosis of a cell, such as a cancer cell or cell infected with a virus. Still other embodiments described herein relate to the use of an effective amount of a compound, or a pharmaceutically acceptable salt thereof, as described herein or a pharmaceutical composition that includes an effective amount of a compound, or a pharmaceutically acceptable salt thereof, as described herein for inducing apoptosis of a cell, such as a cancer cell or cell infected with a virus. In some embodiments, the cancer cell is an HCC cell. In some embodiments, the cell infected with a virus is infected with hepatitis B virus.

Some embodiments described herein relate to a method of decreasing the viability of a cell (for example, a cancer cell or cell infected with a virus) that can include contacting the cell with an effective amount of a compound, or a pharmaceutically acceptable salt thereof, described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for decreasing the viability of a cell, such as a cancer cell or cell infected with a virus. Still other embodiments described herein relate to the use of an effective amount of a compound, or a pharmaceutically acceptable salt thereof, as described herein or a pharmaceutical composition that includes an effective amount of a compound, or a pharmaceutically acceptable salt thereof, as described herein for decreasing the viability of a cell, such as a cancer cell or cell infected with a virus. In some embodiments, the cancer cell is an HCC cell. In some embodiments, the cell infected with a virus is infected with hepatitis B virus.

Those of skill in the treatment of such diseases could determine the effective therapeutic daily amount from test results. An effective therapeutic daily amount would be from about 0.005 mg/kg to 50 mg/kg. in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight.

In some embodiments, the effective amount of a compound, or a pharmaceutically acceptable salt thereof, described herein is dosed more than one time. In some embodiments, the compound, or a pharmaceutically acceptable salt thereof, described herein can be administered every 1, 2, 3, 4, 5, 6, 7 days, or 1, 2, 3, 4 weeks, or 1, 2, 3, 4, 5, 6, 7, 8, 9, 10, 11, 12 months, or 1, 2, 3, 4, 5 years, or any period or combination thereof within the range defined by any two aforementioned times. In some embodiments, at least one loading dose and at least one maintenance dose is administered to the subject, where the at least one loading dose is a higher dose of a compound, or a pharmaceutically acceptable salt thereof, described herein than the at least one maintenance dose.

As used herein, the term "combination therapy" is intended to define therapies which comprise the use of a combination of two or more pharmaceutical compounds/agents or therapies. Thus, references to "combination therapy", "combinations" and the use of compounds/agents "in combination" in this application may refer to compounds/agents that are administered as part of the same overall treatment regimen. As such, the dosage or timing of each of the two or more compounds/agents may differ: each may be administered at the same time or at different times. Accordingly, the compounds/agents of the combination may be administered sequentially (e.g. before or after) or simultaneously, either in the same pharmaceutical formulation (i.e. together), or in different pharmaceutical formulations (i.e. separately). Each of the two or more compounds/agents in a combination therapy may also differ with respect to the route of administration.

The term "inhibitor", as used herein, refers to an enzyme inhibitor or receptor inhibitor which is a molecule that binds to an enzyme or receptor, and decreases and/or blocks its activity. The term may relate to a reversible or an irreversible inhibitor.

Cancer may be treated with surgery, radiation therapy, chemotherapy, targeted therapies, immunotherapy or hormonal therapies. Any of these mentioned therapies may be used in conjunction with another therapy as a combination therapy. Chemotherapeutic compounds include but are not limited to alemtuzumab, altretamine, azacitidine, bendamustine, bleomycin, bortezomib, busulfan, cabazitaxel, capecitabine, carboplatin, carmofur, carmustine, chlorambucil, chlormethine, cisplatin, cladribine, clofarabine, cyclophosphamide, cytarabine, dacarbazine, dactinomycin, daunorubicin, decitabine, denosumab, docetaxel, doxorubicin, epirubicin, estramustine, etoposide, everolimus, floxuridine, fludarabine, fluorouracil, fotemustine, gemcitabine, gemtuzumab, hydroxycarbamide, ibritumomab, idarubicin, ifosfamide, irinotecan, ixabepilone, lomustine, melphalan, mercaptopurine, methotrexate, mitomycin, mitoxantrone, nedaplatin, nelarabine, ofatumumab, oxaliplatin, paclitaxel, pemetrexed, pentostatin, pertuzumab, procarbazine, raltitrexed, streptozotocin, tegafur, temozolomide, temsirolimus, teniposide, tioguanine, topotecan, tositumomab, valrubicin, vinblastine, vincristine, vindesine, vinflunine, or vinorelbine, or any combination thereof.

As used herein, the term "protein kinase inhibitor" refers to inhibitors of protein kinases, serine/threonine kinases, tyrosine kinases, or dual-specificity kinases for the treatment of cancer or other illness. In some embodiments, the protein kinase inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the protein kinase inhibitor includes but is not limited to acalabrutinib, adavosertib, afatinib, alectinib, axitinib, binimetinib, bosutinib, brigatinib, cediranib, ceritinib, cetuximab, cobimetinib, crizotinib, cabozantinib, dacomitinib, dasatinib, entrectinib, erdafitinib, erlotinib, fostamatinib, gefitinib, ibrutinib, imatinib, lapatinib, lenvatinib, lestaurtinib, lortatinib, masitinib, momelotinib, mubritinib, neratinib, nilotinib, nintedanib, olmutinib, osimertinib, pacritinib, panitumumab, pazopanib, pegaptanib, ponatinib, radotinib, regorafenib, rociletinib, ruxolitinib, selumetinib, semaxanib, sorafenib, sunitinib, SU6656, tivozanib, toceranib, trametinib, trastuzumab, vandetanib, or vemurafenib, or any combination thereof.

As used herein, the term "checkpoint inhibitor" refers to an immunotherapy that targets immune checkpoints to stimulate immune function. In some embodiments, the checkpoint inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the immune checkpoint is the PD-1/PD-L1 checkpoint. In some embodiments, the PD-1 checkpoint includes but is not limited to nivolumab, pembrolizumab, spartalizumab, cemiplimab, camrelizumab, sintilimab, tislelizumab, toripalimab, AMP-224 or AMP-514, or any combination thereof. In some embodiments, the PD-L1 checkpoint inhibitor includes but is not limited to atezolizumab, avelumab, durvalumab, KN035, AUNP12, CA-170, or BMS-986189, or any combination thereof. In some embodiments, the immune checkpoint is the CTLA-4 checkpoint. In some embodiments, the CTLA-4 checkpoint inhibitor includes but is not limited to ipilimumab or tremilimumab, or any combination thereof.

As used herein, the term "VEGF inhibitor" refers to inhibitors of vascular endothelial growth factor (VEGF) or a VEGF receptor (VEGFR). In some embodiments, the VEGF inhibitor is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the VEGF inhibitor includes but is not limited to aflibercept, axitinib, bevacizumab, brivanib, cabozantinib, cediranib, lenvatinib, linifinib, nintedanib, pazopanib, ponatinib, ramucirumab, regorafenib, semaxanib, sorafenib, sunitinib, tivozanib, toceranib, or vandetanib, or any combination thereof.

As used herein, the term "antiviral medication" refers to a pharmaceutical composition administered to treat a viral infection. In some embodiments, the viral infection is caused by adenovirus, Ebola virus, coronavirus, Epstein-Barr virus (EBV), Friend virus, hantavirus, hepatitis B virus (HBV), hepatitis C virus (HCV), herpes simplex virus, human immunodeficiency virus (HIV), human metapneumovirus, human papillomavirus (HPV), influenza virus, Japanese encephalitis virus, Kaposi's sarcoma-associated herpesvirus, lymphocytic choriomeningitis virus, parainfluenza virus, rabies virus, respiratory syncytial virus, rhinovirus, varicella zoster virus. In some embodiments, the antiviral medication is a small molecule, compound, polysaccharide, lipid, peptide, polypeptide, protein, antibody, nucleoside, nucleoside analog, nucleotide, nucleotide analog, nucleic acid, or oligonucleotide. In some embodiments, the antiviral medication is an interferon, a capsid assembly modulator, a sequence specific oligonucleotide, an entry inhibitor, or a small molecule immunomodulatory. In some embodiments, the antiviral medication includes but is not limited to AB-423, AB-506, ABI-H2158, ABI-HO731, acyclovir, adapromine, adefovir, alafenamide, amantadine, asunaprevir, baloxavir marboxil, beclabuvir, boceprevir, brivudine, cidofovir, ciluprevir, clevudine, cytarabine, daclatasvir, danoprevir, dasabuvir, deleobuvir, dipivoxil, edoxudine, elbasvir, entecavir, faldaprevir, famciclovir, favipiravir, filibuvir, fomivirsen, foscarnet, galidesivir, ganciclovir, glecaprevir, GLS4, grazoprevir, idoxuridine, imiquimod, IFN-α, interferon alfa 2b, JNJ-440, JNJ-6379, lamivudine, laninamivir, ledipasvir, mericitabine, methisazone, MK-608, moroxydine, narlaprevir, NITD008, NZ-4, odalasvir, ombitasvir, oseltamivir, paritaprevir, peginterferon alfa-2a, penciclovir, peramivir, pibrentasvir, pimodivir, pleconaril, podophyllotoxin, presatovir, radalbuvir, ravidasvir, remdesivir, REP 2139, REP 2165, resiquimod, RG7907, ribavirin, rifampicin, rimantadine, ruzasvir, samatasvir, setrobuvir, simeprevir, sofosbuvir, sorivudine, sovaprevir, taribavirin, telaprevir, telbivudine, tenofovir, tenofovir disoproxil, triazavirin, trifluridine, tromantadine, umifenovir, uprifosbuvir, valaciclovir, valgancicovir, vaniprevir, vedroprevir, velpatasvir, vidarabine, voxilaprevir, or zanamivir, or any combination thereof.

The term "% w/w" or "% wt/wt" as used herein has its ordinary meaning as understood in light of the specification and refers to a percentage expressed in terms of the weight of the ingredient or agent over the total weight of the composition multiplied by 100. The term "% v/v" or "% vol/vol" as used herein has its ordinary meaning as understood in the light of the specification and refers to a percentage expressed in terms of the liquid volume of the compound, substance, ingredient, or agent over the total liquid volume of the composition multiplied by 100.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention, as it is described herein above and in the claims.

Hereinafter, the term "rt", "r.t." or "RT" means room temperature; "Me" means methyl; "MeOH" means methanol; "Et" means ethyl; "EtOH" means ethanol; "NaH" means sodium hydride; "NaBH(AcO)₃" or "NaBH(OAc)₃" means sodium triacetoxyborohydride; "EtOAc" means ethyl acetate; "TEA" or "Et₃N" means triethylamine; "DCM" means dichloromethane; "MeCN" or "ACN" means acetonitrile; "DMF" means -dimethyl formamide; "DMA" means dimethylacetamide; "Pd(dppf)Cl₂." means [1.1'-Bis(diphenylphosphino)ferrocene]-dichloropalladium(II); "THF" means tetrahydrofuran; "i-PrOH" or "iPrOH" means 2-propanol; "LC" means liquid chromatography; "LCMS" means Liquid Chromatography/Mass spectrometry; "HPLC" means high-performance liquid chromatography; "prep-HPLC" means preparative high-performance liquid chromatography; "TFA" means trifluoroacetic acid; "RP" means reversed phase; "min" means minute(s); "h" means hour(s); "PE" means petroleum ether; "v/v" means volume per volume; "Celite®" means diatomaceous earth; "DMSO" means dimethyl sulfoxide; "SFC" means Supercritical Fluid Chromatography; "DIPE" means diisopropyl ether; "DIPEA" or "DIEA" means N,N-diisopropylethylamine; "Pd₂(dba)₃" means Tris(dibenzylideneacetone)-dipalladium; "Pd(OAc)₂" means palladium(II) acetate; "AcOH" means acetic acid; "DMAP" means 4-(dimethylamino)pyridine; "t-BuOK", "BuO" or "KOtBu" means potassium tert-butoxide; "TLC" means thin layer chromatography; "prep-TLC" means preparative TLC; "KOAc" means potassium acetate.

For intermediates that were used in a next reaction step as a crude or as a partially purified intermediate, estimated mol amounts (in some cases indicated by ~) are indicated in the reaction protocols described below, or alternatively theoretical mol amounts are indicated.

The meanings of the abbreviations in the nuclear magnetic resonance spectra are provided as follows: s=singlet, d=doublet, dd=double doublet, dt=double triplet, ddd=double doublet, Sept=septet, t=triplet, m=multiplet, br=broad, brs=broad singlet, q=quartet.

Preparation of Intermediates

Example A1

Preparation of Intermediate 4

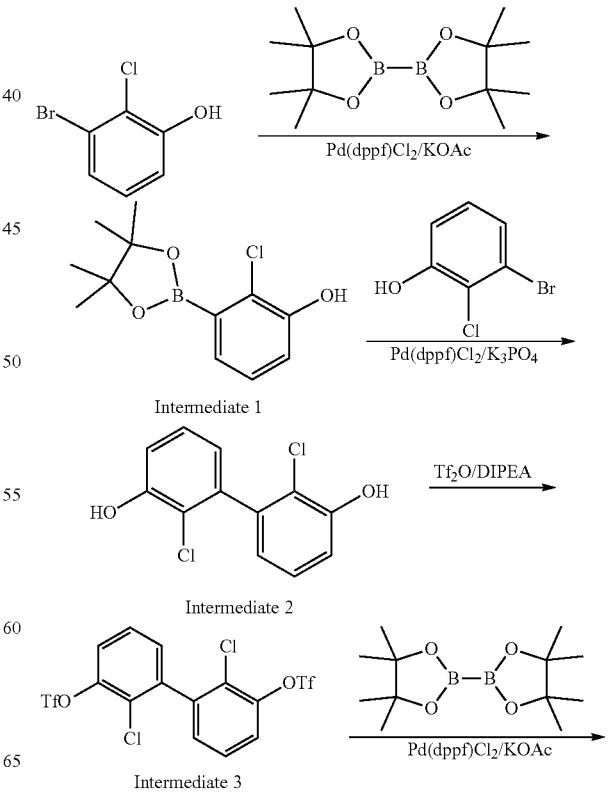

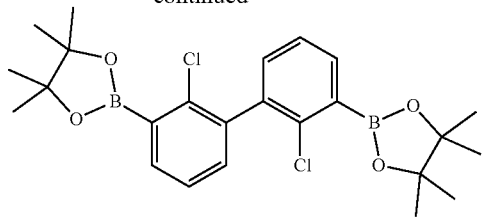

Intermediate 4

Step 1: A mixture of 3-Bromo-2-chlorophenol (110 g, 530 mmol), Pd(dppf)Cl$_2$ (38.8 g, 53.0 mmol), KOAc (146 g, 1.48 mol) and Bis(pinacolato)diboron (148 g, 583 mmol) in dioxane (1220 mL) was degassed and purged with N$_2$ (3×). The mixture was stirred at 90° C. for 16 hrs. The two batches of the same reaction were combined to work up. The reaction was cooled to 20° C. and then filtered. The filter cake was washed with DCM (2×1000 mL). The filtrate was concentrated to give the crude product, which was purified by column chromatography (100-200 mesh silica gel) eluted with petroleum ether:ethyl acetate (1:0~20:1) to give a residue (240 g), which was triturated with petroleum ether (500 mL) for 2 hrs and then filtered. The filter cake was dried in vacuum to give Intermediate 1 (172 g, 64% yield) as a white solid. $^1$H NMR: (400 MHz, DMSO-d$^6$) δ 10.02 (s, 1H), 7.17-7.08 (m, 1H), 7.08-6.98 (m, 2H), 1.30 (s, 12H).

Step 2: A mixture of Intermediate 1 (81.0 g, 318 mmol), 3-Bromo-2-chlorophenol (72.6 g, 350 mmol), K$_3$PO$_4$ (203 g, 955 mmol), Pd(dppf)Cl$_2$ (11.6 g, 15.9 mmol) in a solution of dioxane (1620 mL) and H$_2$O (540 mL) was degassed and purged with N$_2$ (3×). The mixture was stirred at 90° C. for 16 hrs. The reaction was cooled to 20° C. and concentrated to give a residue. The residue was dissolved in ethyl acetate (1000 mL) and H$_2$O (500 mL), and then the mixture was filtered. The filter cake was washed with ethyl acetate (2×100 mL) and then separated. The aqueous phase was adjusted to pH=3 with 6 N HCl and extracted with DCM (2×500 mL). The combined organic layer were concentrated to give Intermediate 2 (91.0 g, crude) as a brown solid. $^1$H NMR: (400 MHz, DMSO-d$^6$) δ 10.22 (br s, 2H), 7.21-7.15 (m, 2H), 7.02-6.97 (m, 2H), 6.69 (dd, J=1.4, 7.5 Hz, 2H).

Step 3: To a solution of Intermediate 2 (91.0 g, 357 mmol) and DIPEA (173 g, 1.34 mol, 234 mL) in DCM (2200 mL) was slowly added Tf$_2$O (237 g, 838 mmol, 138 mL) at 0° C.~5° C. The reaction was warmed up to 20° C. and stirred for 2 hrs. TLC (petroleum ether:ethyl acetate=5:1, R$_f$=0.64) showed the starting material was consumed completely. The reaction was washed with aqueous sat. NaHCO$_3$ (1000 mL), brine (500 mL), dried over MgSO$_4$ and concentrated to give crude product. The crude product was purified by column chromatography (100-200 mesh silica gel) eluted with THF:petroleum ether (0:1~1:9) to give Intermediate 3 (100.3 g, 60.6% yield over two steps) as a yellow solid. $^1$H NMR: (400 MHz, DMSO-d$^6$) δ 7.86 (dd, J=1.3, 8.3 Hz, 2H), 7.74 (t, J=8.0 Hz, 2H), 7.66 (dd, J=1.4, 7.7 Hz, 2H).

Step 4: A mixture of Intermediate 3 (95.3 g, 184 mmol), KOAc (90.1 g, 918 mmol), Pd(dppf)Cl$_2$ (20.2 g, 27.5 mmol) and Bis(pinacolato)diboron (117 g, 459 mmol) in dioxane (1300 mL) was degassed and purged with N$_2$ (3×). The mixture was stirred at 90° C. for 16 hrs. TLC (petroleum ether:ethyl acetate=5:1, Rf=0.60) showed the starting material was consumed completely. The mixture was cooled to 20° C., and then the mixture was filtered. The filter cake was washed with DCM (2×100 mL). The filtrate was concentrated to the crude product. The crude product was purified by column chromatography (100-200 mesh silica gel) eluted with THF:petroleum ether (0:1~1:20) to give a residue (110 g), which was triturated with petroleum ether (500 mL) for 16 hrs, and then filtered. The filter cake was dried in vacuum to give Intermediate 4 (55.0 g, 62.1% yield) as a white solid. $^1$H NMR: (400 MHz, DMSO-d$^6$) δ 7.65 (dd, J=1.8, 7.2 Hz, 2H), 7.51-7.27 (m, 4H), 1.32 (s, 24H).

Example A1-B

Preparation of Intermediate 4b

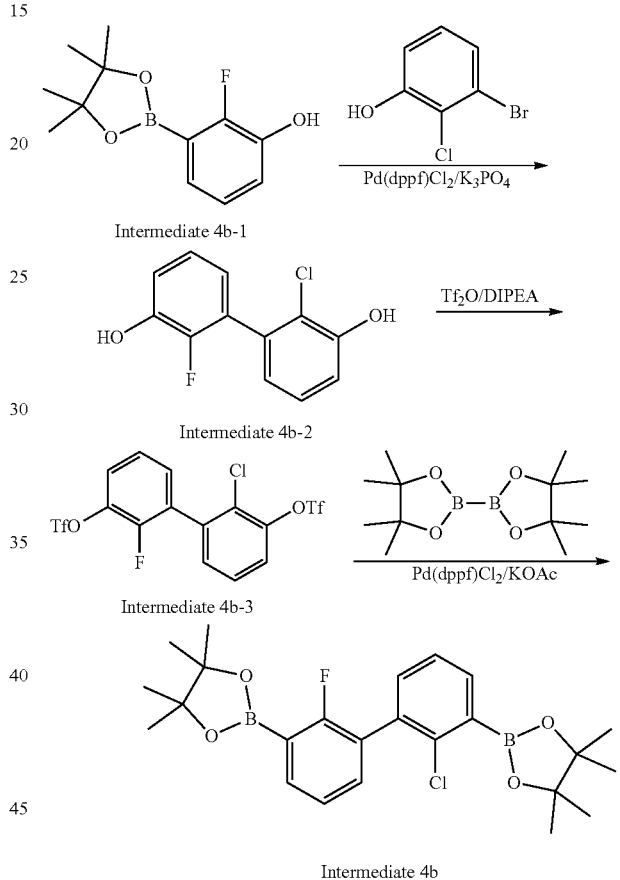

Step 1: A mixture of Intermediate 4b-1 (41.0 g, 161 mmol), 3-Bromo-2-chlorophenol (32.3 g, 169 mmol), K$_3$PO$_4$ (103 g, 483 mmol), Pd(dppf)Cl$_2$ (5.89 g, 8.05 mmol) in dioxane (800 mL) and H2O (160 mL) was degassed and purged with N$_2$ (3×) and then was stirred at 90° C. for 16 h. The mixture was cooled to 20° C. and then concentrated to provide a residue. The residue was dissolved in ethyl acetate (500 mL) and H$_2$O (250 mL), and then the mixture was filtered. The filter cake was washed with ethyl acetate (2×100 mL) and separated. The aqueous phase was adjusted to pH=3 with 6 N HCl and extracted with DCM (2×250 mL). The combined organic layers were concentrated to give Intermediate 4b-2 (51.0 g, crude) as a brown solid. $^1$H NMR: (400 MHz, DMSO-d$^6$) δ 10.26 (br s, 1H), 9.90 (br s, 1H), 7.25-7.11 (m, 1H), 7.11-6.88 (m, 3H), 6.77 (dd, J=1.3, 7.6 Hz, 1H), 6.70-6.53 (m, 1H).

Step 2: To a solution of Intermediate 4b-2 (44.0 g, 184 mmol) and DIPEA (90.6 g, 701 mmol, 122 mL) in DCM (1200 mL) was added slowly Tf$_2$O (122 g, 433 mmol, 71.5 mL) at 0~5° C. The mixture was warmed to 20° C. and stirred for 2 h. The mixture was washed with aq. sat. NaHCO$_3$ (1000 mL) and brine (500 mL), dried over Na$_2$SO$_4$ and concentrated to give a crude product. The crude product was purified by column chromatography (100-200 mesh silica gel) eluted with THF:PE (1:0~9:1) to give Intermediate 4b-3 (44.0 g, 54.3% yield over two steps) as a yellow solid. $^1$H NMR (400 MHz, DMSO-d$^6$) δ 7.94-7.78 (m, 2H), 7.77-7.60 (m, 3H), 7.56 (br d, J=4.6 Hz, 1H).

Step 3: A mixture of Intermediate 4b-3 (44.0 g, 87.5 mmol), KOAc (34.4 g, 350 mmol), Pd(dppf)Cl$_2$ (9.61 g, 13.1 mmol) and Bis(pinacolato)diboron (45.6 g, 179 mmol) in dioxane (600 mL) was degassed and purged with N$_2$ (3×), and then the mixture was stirred at 90° C. for 16 h. The mixture was cooled to 25° C. and filtered. The filter cake was washed with DCM (2×50 mL). The filtrate was concentrated to the crude product. The crude product was purified by column chromatography (100-200 mesh silica gel) eluted with THF:PE (1:0~20:1) to give a residue (40.0 g), which was triturated with petroleum ether (100 mL) for 2 h and then filtered. The filter cake was dried in vacuum to give Intermediate 4-b (21.4 g, 51.6% yield) as a white solid. $^1$H NMR: (400 MHz, DMSO-d$^6$) δ 7.86-7.55 (m, 2H), 7.54-7.37 (m, 2H), 7.36-7.26 (m, 1H), 1.32 (d, J=7.4 Hz, 20H).

Example A2

Preparation of Intermediate 5

A mixture of Intermediate 4 (500 mg, 1.05 mmol), 5-Brormo-1-indanone (500 mg, 2.37 mmol), Pd (dppf)Cl$_2$ (116 mg, 157.89 μmol,) and AcOK (310 mg, 3.16 mmol) in dioxane (5 mL) and H$_2$O (0.5 mL) was purged with N$_2$ for 3 times. Then the mixture was stirred at 110° C. for 2 hours under N$_2$ atmosphere. The reaction mixture was filtered, and the filtrate was concentrated to give a residue. The residue was diluted with H$_2$O (15 mL) and extracted with EtOAc (15 mL) for three times. The combined organic layers were washed with brine (5 mL×2), dried over anhydrous Na$_2$SO$_4$, filtered and concentrated to give a residue, which was purified by flash silica gel chromatography (ISCO®; 12 g SepaFlash® Silica Flash Column, Eluent of 0~30% Ethyl acetate/Petroleum ether) to give crude product (290 mg). 40 mg of the crude product was purified by prep-HPLC (column: Welch Xtimate C18 150×25 mm×5 um; mobile phase: water (0.225% FA)-ACN; B %: 65%-95%, 7.8 min; 100% B Hold Time (2 min); Flow Rate (25 mL/min) to give Intermediate 5 (3.47 mg) as a brown solid. LCMS (C$_{30}$H$_{21}$Cl$_2$O$_2$$^+$) (ES, m/z): 483.0 [M+H]$^+$.

The intermediates show in Table 1 were prepared by an analogous reaction protocol as was used for the preparation of Intermediate 5 using the appropriate starting materials.

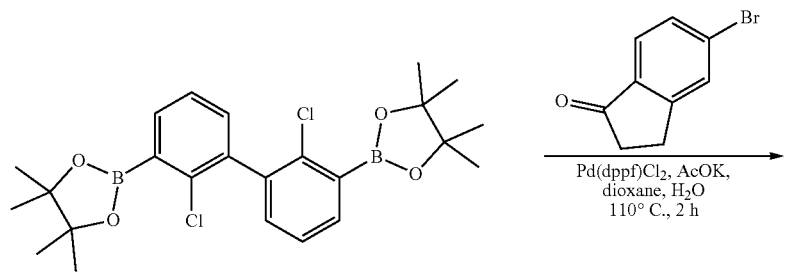

Intermediate 4

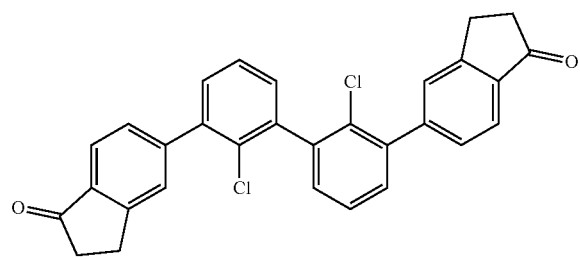

Intermediate 5

TABLE 1

| Intermediate No. | Structure | Starting materials |
| --- | --- | --- |
| 6 | 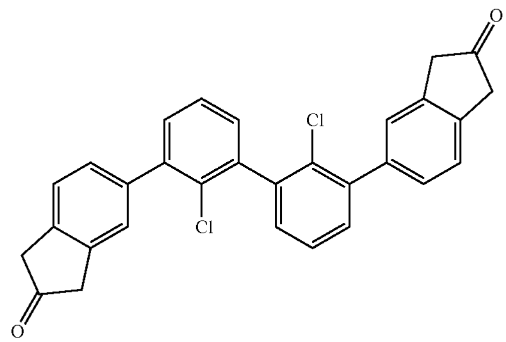 [SMILES: O=C1Cc2ccc(-c3cccc(-c4cccc(-c5ccc6c(c5)CC(=O)C6)c4Cl)c3Cl)cc2C1] | Intermediate 4<br>5-Bromo-1H-inden-2(3H)-One |
| 7 | 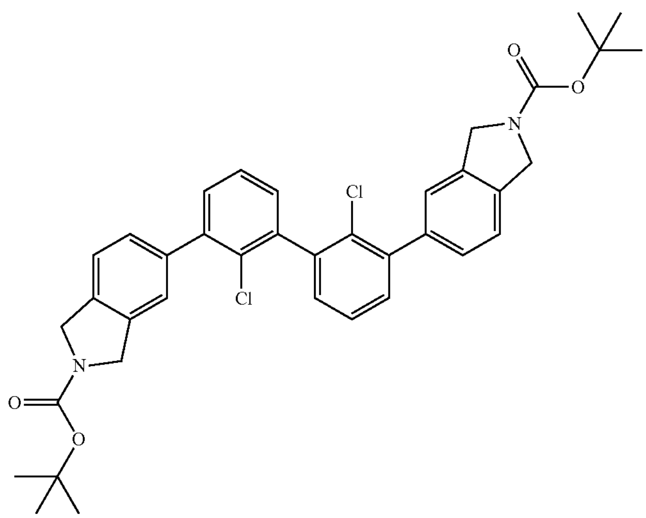 [SMILES: CC(C)(C)OC(=O)N1Cc2ccc(-c3cccc(-c4cccc(-c5ccc6c(c5)CN(C(=O)OC(C)(C)C)C6)c4Cl)c3Cl)cc2C1] | Intermediate 4<br>tert-Butyl 5-bromoisoindoline-2-carboxylate |
| 8 | 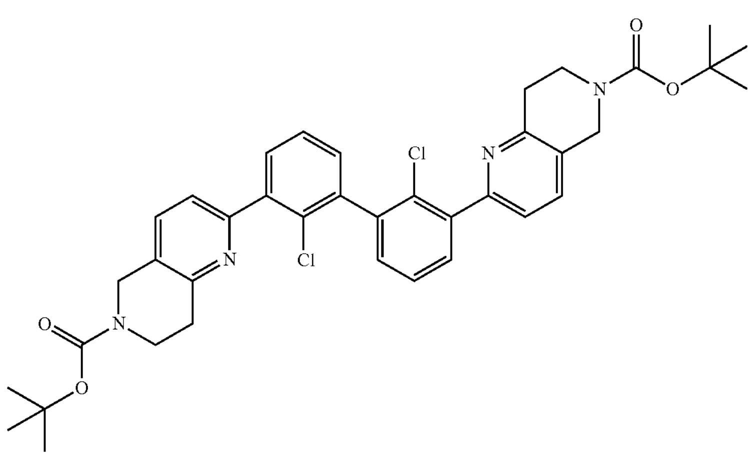 [SMILES: CC(C)(C)OC(=O)N1CCc2nc(-c3cccc(-c4cccc(-c5ccc6c(n5)CCN(C(=O)OC(C)(C)C)C6)c4Cl)c3Cl)ccc2C1] | Intermediate 4<br>tert-butyl 2-bromo-5,6,7,8-tetrahydro-1,6-naphthyridine-6-carboxylate |

TABLE 1-continued

| Intermediate No. | Structure | Starting materials |
|---|---|---|
| 9 | 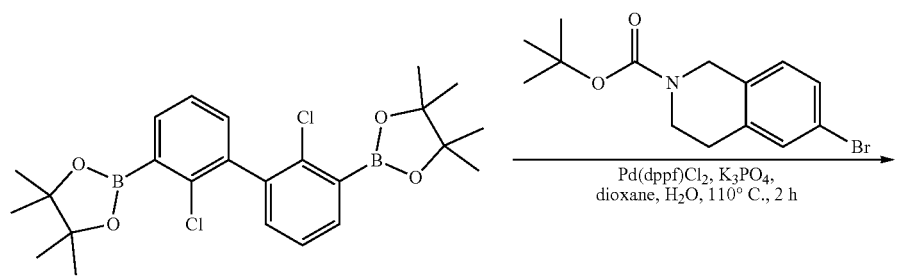 | Intermediate 4 tert-Butyl 8-chloro-2,3-dihydropyrido [3,2-f][1,4] oxazepine-4(5H)-carboxylate |

Example A3

Preparation of Intermediate 10

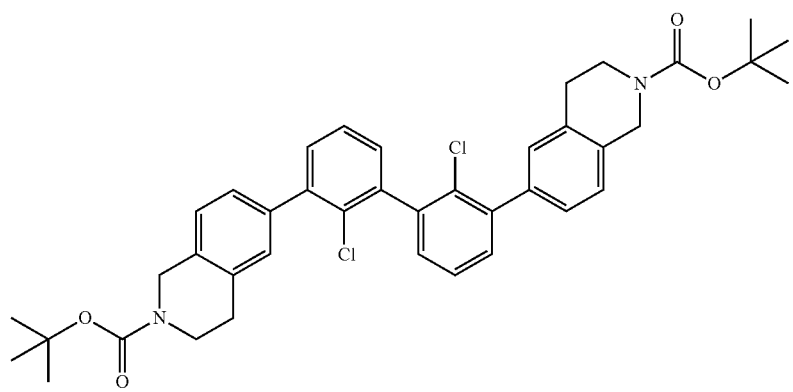

A mixture of Intermediate 4 (2.5 g, 5.26 mmol), tert-Butyl 6-bromo-3,4-dihydroisoquinoline-2(1H)-carboxylate (4.11 g, 13.2 mmol), $K_3PO_4$ (4.47 g, 21.1 mmol) and $Pd(dppf)Cl_2$ (385 mg, 526 µmol) in dioxane (150 mL) and $H_2O$ (5 mL) was purged with $N_2$ (3×), and then the mixture was stirred at 110° C. for 2 hrs under $N_2$ atmosphere. The reaction mixture was filtered. The filtrate was diluted with $H_2O$ (100 mL) and extracted with EtOAc (3×50 mL). The combined organic layers were washed with brine (2×15 mL), dried over anhydrous $Na_2SO_4$, filtered and concentrated to give a residue. The residue was purified by flash silica gel chromatography (ISCO®; 220 g SepaFlash® Silica Flash Column, Eluent of 0~18% Ethyl acetate/Petroleum ether) to give Intermediate 10 (2.06 g) as a white solid. LCMS $(C_{40}H_{42}Cl_2N_2O_4Na^+)$ (ES, m/z): 707.9 $[M+Na]^+$.

The intermediates shown in Table 2 were prepared by an analogous reaction protocol as was used for the preparation of Intermediate 10 using the appropriate starting materials.

TABLE 2

| Intermediate No. | Structure | Starting materials |
|---|---|---|
| 11 | 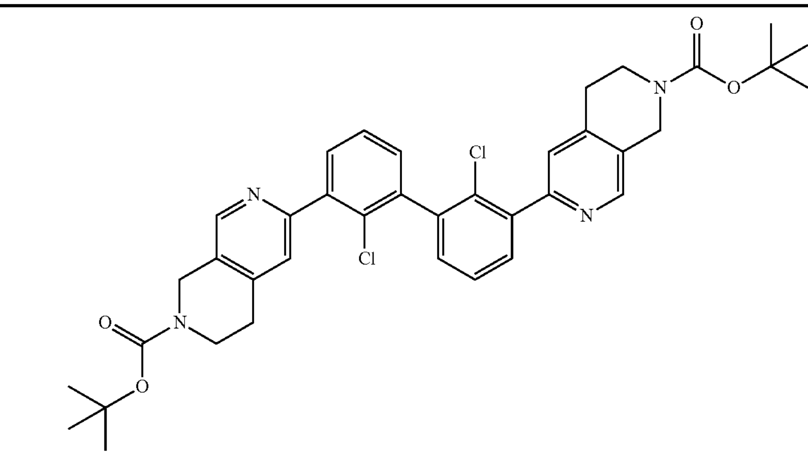 | Intermediate 4<br>t-Butyl 2-chloro-5,6-dihydro-1,7-naphthyridine-7(8H)-carboxylate |
| 12 | 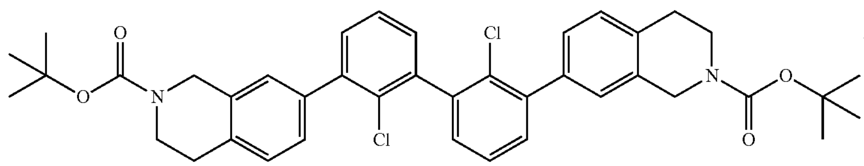 [SMILES: CC(C)(C)OC(=O)N1CCc2ccc(-c3cccc(-c4cccc(-c5ccc6c(c5)CN(C(=O)OC(C)(C)C)CC6)c4Cl)c3Cl)cc2C1] | Intermediate 4<br>tert-Butyl 7-bromo-3,4-dihydroisoquinoline-2(1H)-carboxylate |

Example 1

Preparation of Compound A-1

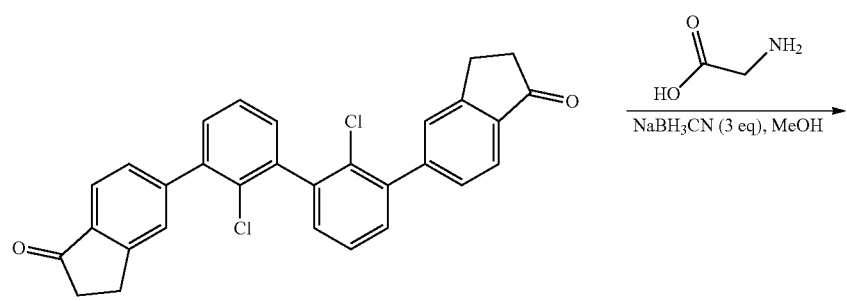

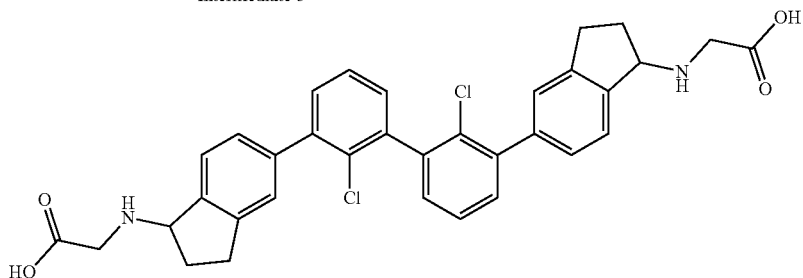

A solution of Intermediate 5 (30 mg, 62 μmol) and glycine (10.7 mg, 143 μmol) in MeOH (0.5 mL) and DCM (0.5 mL) was stirred at 20° C. for 0.5 hr. NaBH$_3$CN (12 mg, 186 μmol) was added into the mixture. The mixture was stirred at 60° C. for 12 hrs. The mixture was concentrated. The residue was diluted with H$_2$O (2 mL) and extracted with EtOAc (3×2 mL). The combined organic layers were washed with brine (2×2 mL), dried over anhydrous Na$_2$SO$_4$, filtered and concentrated to give a residue, which was purified by prep-HPLC (column: Phenomenex luna C18 80*40 mm*3 μm; mobile phase: water (0.05% ammonia hydroxide v/v)-ACN; B %: 10%-60%, 16 min; 100% B Hold Time (3 min); Flow Rate (25 mL/min)) to give Compound A-1 (1.89 mg) as white solid with 2 equivalents of ammonia.

The compounds shown in Table 3 were prepared by an analogous reaction protocol as was used for the preparation of Compound A-1 using the appropriate starting materials and suitable prep-HPLC conditions. For the compounds which were obtained as formate salt. The equivalent of the formate is determined by NMR. For the compounds which were obtained as HCl salt, the equivalent salt of the HCl is calculate basic on the number of basic nitrogen.

TABLE 3

| Cmpd No. | Structure | Salt | Starting materials |
|---|---|---|---|
| A-2 | 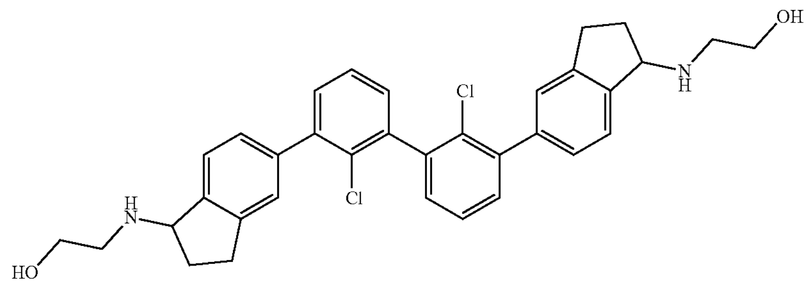 [SMILES: OCCNC1CCc2cc(-c3cccc(-c4cccc(-c5ccc6c(c5)CCC6NCCO)c4Cl)c3Cl)ccc21] | 0.14 eq of Formate | Intermediate 5 2-aminoethanol |
| A-3 | 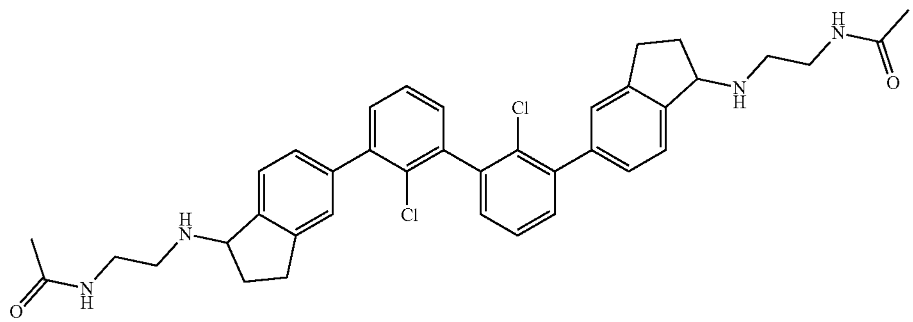 [SMILES: CC(=O)NCCNC1CCc2cc(-c3cccc(-c4cccc(-c5ccc6c(c5)CCC6NCCNC(C)=O)c4Cl)c3Cl)ccc21] | | Intermediate 5 N-Acetyl-ethylene-diamine |
| A-4 | 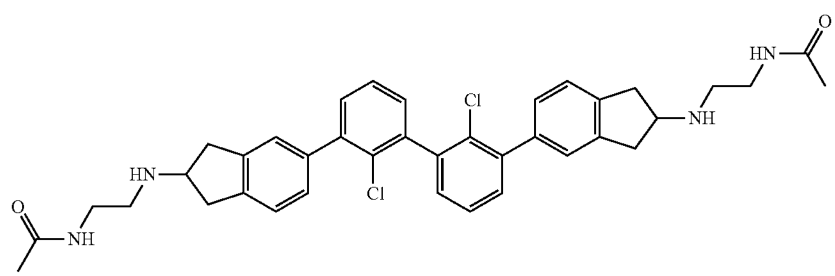 [SMILES: CC(=O)NCCNC1Cc2ccc(-c3cccc(-c4cccc(-c5ccc6c(c5)CC(NCCNC(C)=O)C6)c4Cl)c3Cl)cc2C1] | | Intermediate 6 N-Acetyl-ethylene-diamine |
| A-5 | 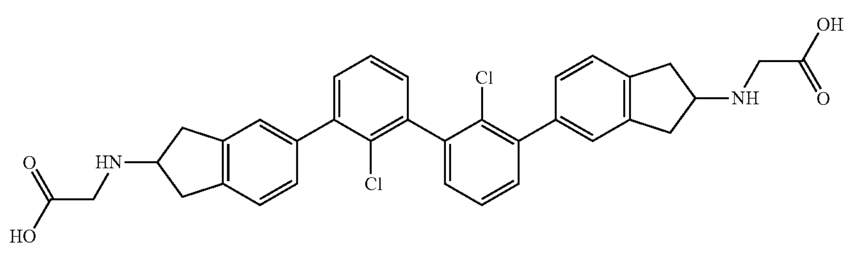 [SMILES: O=C(O)CNC1Cc2ccc(-c3cccc(-c4cccc(-c5ccc6c(c5)CC(NCC(=O)O)C6)c4Cl)c3Cl)cc2C1] | 2 eq of HCl salt | Intermediate 6 Glycine |
| A-6 | 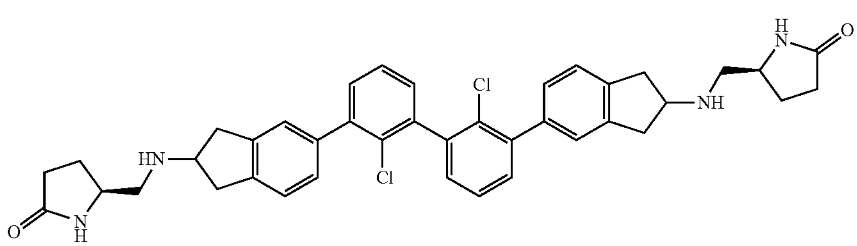 [SMILES: O=C1CC[C@@H](CNC2Cc3ccc(-c4cccc(-c5cccc(-c6ccc7c(c6)CC(NC[C@@H]6CCC(=O)N6)C7)c5Cl)c4Cl)cc3C2)N1] | 1 eq of Formate | Intermediate 6 (S)-5-Amino-methyl-pyrrolidin-2-one |

TABLE 3-continued

| Cmpd No. | Structure | Salt | Starting materials |
|---|---|---|---|
| A-7 | 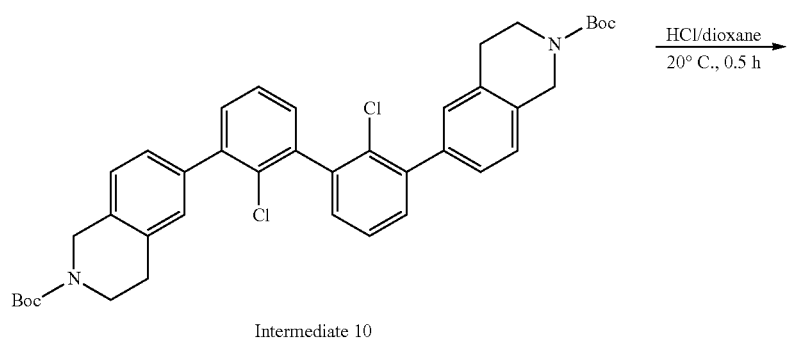 | 1 eq of Formate | Intermediate 6 (S)-5-Amino-methyl-pyrrolidin-2-one |
| A-8 | 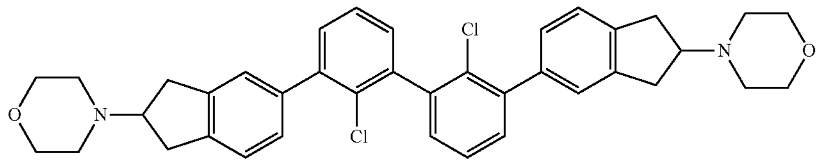 [SMILES: Clc1c(-c2ccc3c(c2)CC(N2CCOCC2)C3)cccc1-c1cccc(-c2ccc3c(c2)CC(N2CCOCC2)C3)c1Cl] | | Intermediate 6 Morpholine |

Example 2

Preparation of Compound B-1

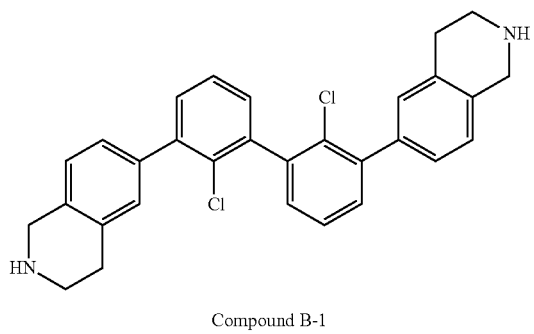

Intermediate 10

Compound B-1

The solution of Intermediate 10 (60 mg, 87.5 μmol) in HCl/dioxane (4 M, 1 mL) was stirred at 20° C. for 0.5 h. The mixture was concentrated to give a residue, which was purified by prep-HPLC (prep-HPLC (column: Phenomenex luna C18 80*40 mm*3 um.; mobile phase: water (0.05% HCl)-ACN; B %: 8%-48%, 11 min; 100% B Hold Time (3 min); Flow Rate (25 mL/min); Injections: 3) to give Compound B-1 (4.33 mg) as a white solid with two equivalent of HCl.

The compounds in Table 4 were prepared by an analogous reaction protocol as was used for the preparation of Compound B-1 using the appropriate starting materials and Prep-HPLC. For the compounds which were obtained as formate salt. The equivalent of the formate is determined by NMR. For the compounds which were obtained as HCl salt, the equivalent salt of the HCl is calculate basic on the number of basic nitrogen.

TABLE 4

| Cmpd No. | Structure | Salt | Starting materials |
|---|---|---|---|
| B-2 | 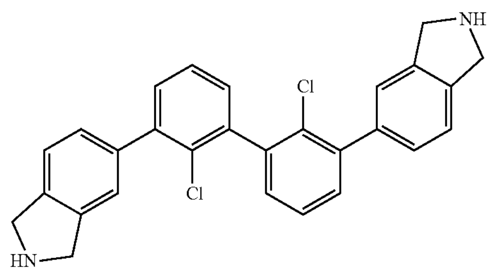 [SMILES: Clc1c(-c2ccc3c(c2)CNC3)cccc1-c1cccc(-c2ccc3c(c2)CNC3)c1Cl] | 2 eq of HCl | Intermediate 7 |
| B-3 | 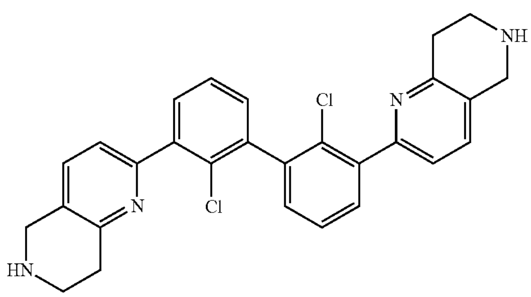 [SMILES: Clc1c(-c2ccc3c(n2)CCNC3)cccc1-c1cccc(-c2ccc3c(n2)CCNC3)c1Cl] | 2 eq of HCl | Intermediate 8 |
| B-4 | 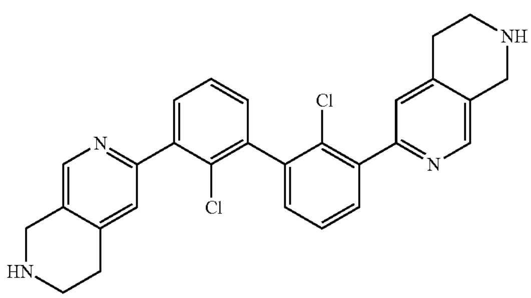 [SMILES: Clc1c(-c2cc3c(cn2)CNCC3)cccc1-c1cccc(-c2cc3c(cn2)CNCC3)c1Cl] | 2 eq of HCl | Intermediate 11 |
| B-5 | 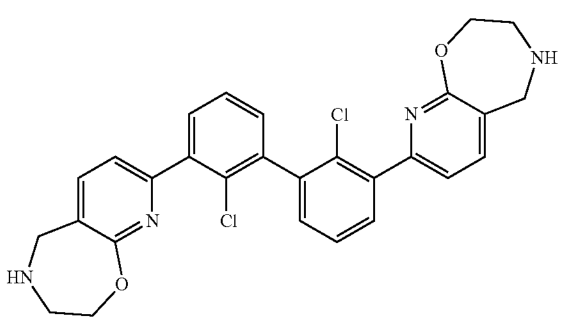 [SMILES: Clc1c(-c2ccc3c(n2)OCCNC3)cccc1-c1cccc(-c2ccc3c(n2)OCCNC3)c1Cl] | 2 eq of HCl | Intermediate 9 |
| B-6 | 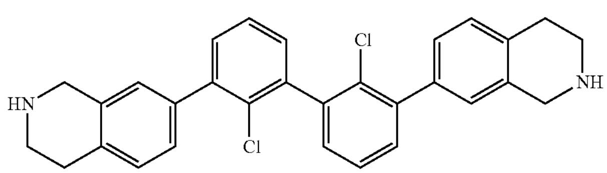 [SMILES: Clc1c(-c2ccc3c(c2)CNCC3)cccc1-c1cccc(-c2ccc3c(c2)CNCC3)c1Cl] | 2 eq of HCl | Intermediate 12 |

Example 3

Preparation of Compound B-7

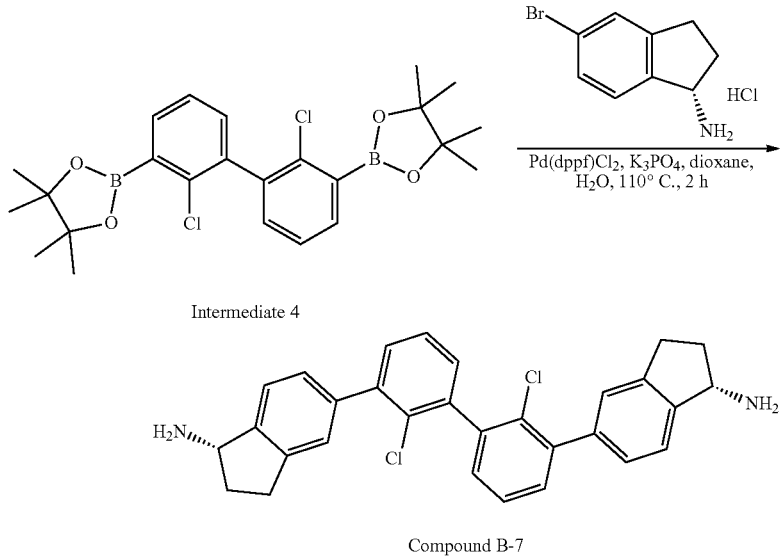

Intermediate 4

Compound B-7

A mixture of Intermediate 4 (43 mg, 91 μmol), (S)-5-Bromo-2,3-dihydro-1H-inden-1-amine hydrochloride (50 mg, 201 μmol), $K_3PO_4$ (78 mg, 365 μmol) and Pd(dppf)$Cl_2$ (6.7 mg, 9.1 μmol) in dioxane (1 mL) and $H_2O$ (0.1 mL) was degassed and purged with $N_2$ (3×). The mixture was stirred at 110° C. for 2 hrs under $N_2$ atmosphere. The mixture was filtered and concentrated to give a residue, which was purified prep-HPLC (acid condition; Column: Phenomenex luna C18 100*40 mm*3 um; Condition: water (0.225% FA)-ACN; Begin B:0; End B:40; Gradient Time (min): 10; 100% B Hold Time (min): 2; Flow Rate (mL/min): 25) to give Compound B-7 (15 mg) as a light pink solid of formate salt.

The compounds shown in Table 5 were prepared by an analogous reaction protocol as was used for the preparation of Compound B-7 using the appropriate starting materials and Prep-HPLC. For the compounds which were obtained as formate salt. The equivalent of the formate is determined by NMR. For the compounds which were obtained as HCl salt, the equivalent salt of the HCl is calculated based on the number of basic nitrogen.

TABLE 5

| Cmpd No. | Structure | Salt | Starting materials |
|---|---|---|---|
| B-8 | 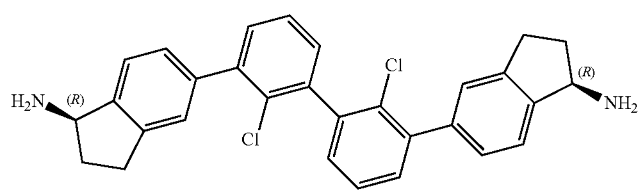 | 2 eq of Formate | Intermediate 6 (R)-5-Bromo-2,3-dihydro-1H-inden-1-amine |
| B-9 | 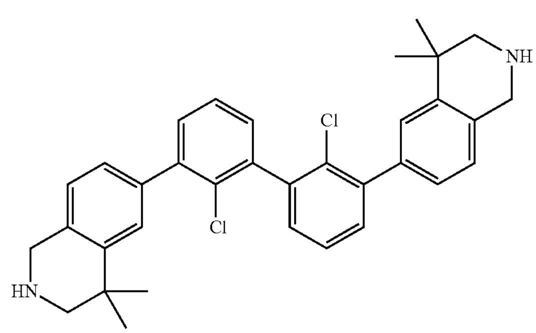 [SMILES: CC1(C)CNCc2ccc(-c3cccc(-c4cccc(-c5ccc6c(c5)C(C)(C)CNC6)c4Cl)c3Cl)cc21] | 1 eq of Formate | Intermediate 6 6-Bromo-4,4-dimethyl-1,2,3,4-tetrahydroisoquinoline hydrochloride |

TABLE 5-continued

| Cmpd No. | Structure | Salt | Starting materials |
|---|---|---|---|
| B-10 | 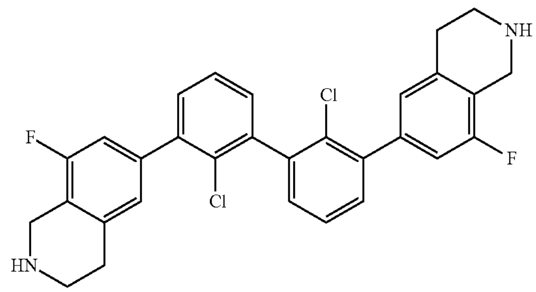 [SMILES: Fc1cc(-c2cccc(-c3cccc(-c4cc(F)c5c(c4)CCNC5)c3Cl)c2Cl)cc2c1CNCC2] | 2 eq of Formate | Intermediate 6 6-bromo-8-fluoro-1,2,3,4-tetrahydro-isoquinoline |
| B-11 | 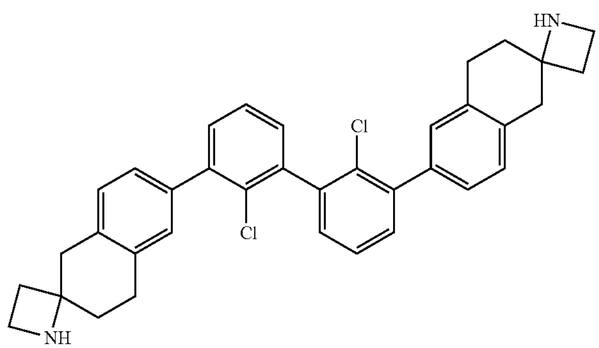 [SMILES: Clc1c(-c2ccc3c(c2)CCC2(CCN2)C3)cccc1-c1cccc(-c2ccc3c(c2)CCC2(CCN2)C3)c1Cl] | | Intermediate 6 6'-Bromo-3',4'-dihydro-1'H-spiro[azetidine-2,2'-naphthalene] |
| B-12 | 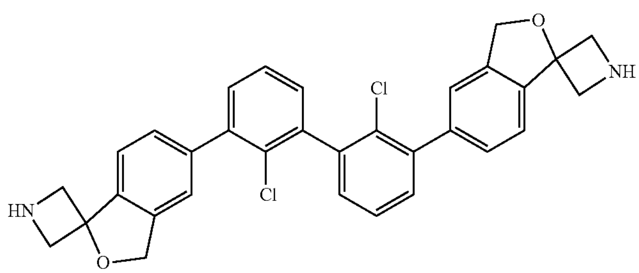 [SMILES: Clc1c(-c2ccc3c(c2)COC32CNC2)cccc1-c1cccc(-c2ccc3c(c2)COC32CNC2)c1Cl] | | Intermediate 6 5'-bromo-3'H-spiro[azetidine-3,1'-[2]benzofuran] |
| B-13 | 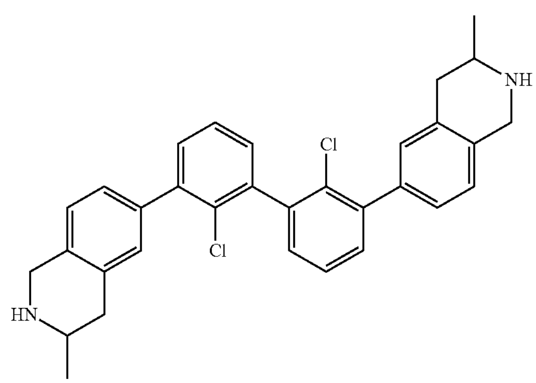 [SMILES: CC1Cc2cc(-c3cccc(-c4cccc(-c5ccc6c(c5)CC(C)NC6)c4Cl)c3Cl)ccc2CN1] | 2 eq of Formate | Intermediate 6 6-Bromo-3-methyl-1,2,3,4-tetrahydro-isoquinoline |
| B-14 | 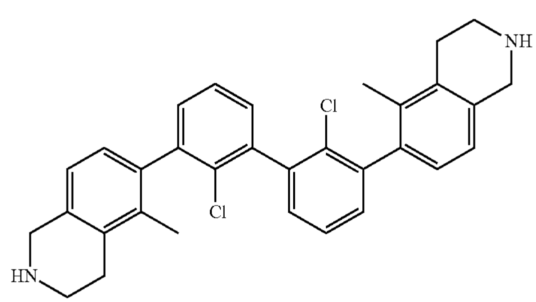 [SMILES: Cc1c(-c2cccc(-c3cccc(-c4ccc5c(c4C)CCNC5)c3Cl)c2Cl)ccc2c1CCNC2] | 2 eq of Formate | Intermediate 6 6-Bromo-5-methyl-1,2,3,4-tetrahydro-isoquinoline hydrochloride |

TABLE 5-continued
| Cmpd No. | Structure | Salt | Starting materials |
|---|---|---|---|
| B-15 | 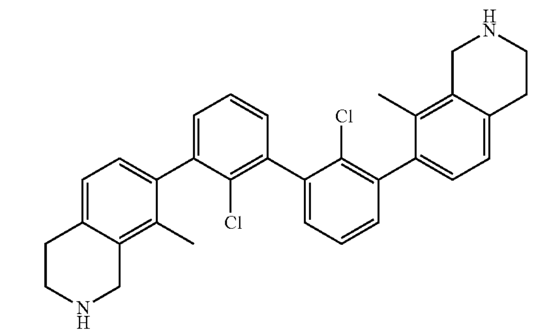 [SMILES: Cc1c(-c2cccc(-c3cccc(-c4ccc5c(c4C)CNCC5)c3Cl)c2Cl)ccc2c1CNCC2] | 2 eq of Formate | Intermediate 6 7-bromo-8-methyl-1,2,3,4-tetrahydroisoquinoline |
| B-16 | 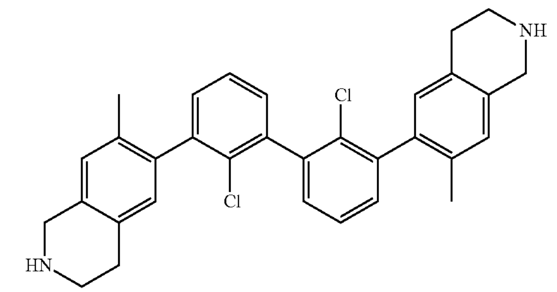 [SMILES: Cc1cc2c(cc1-c1cccc(-c3cccc(-c4cc5c(cc4C)CNCC5)c3Cl)c1Cl)CCNC2] | 2 eq of Formate | Intermediate 6 6-bromo-7-methyl-1,2,3,4-tetrahydroisoquinoline |
| B-17 | 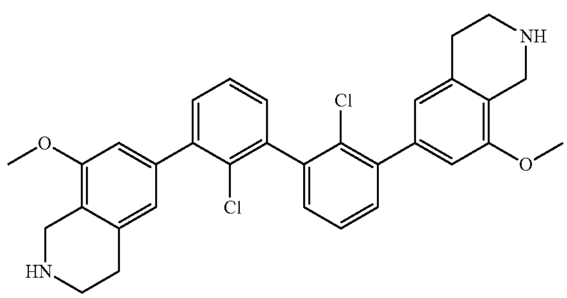 | 1 eq of Formate | Intermediate 6 6-bromo-8-methoxy-1,2,3,4-tetrahydroisoquinoline |
Example 4
Preparation of Compound C-1
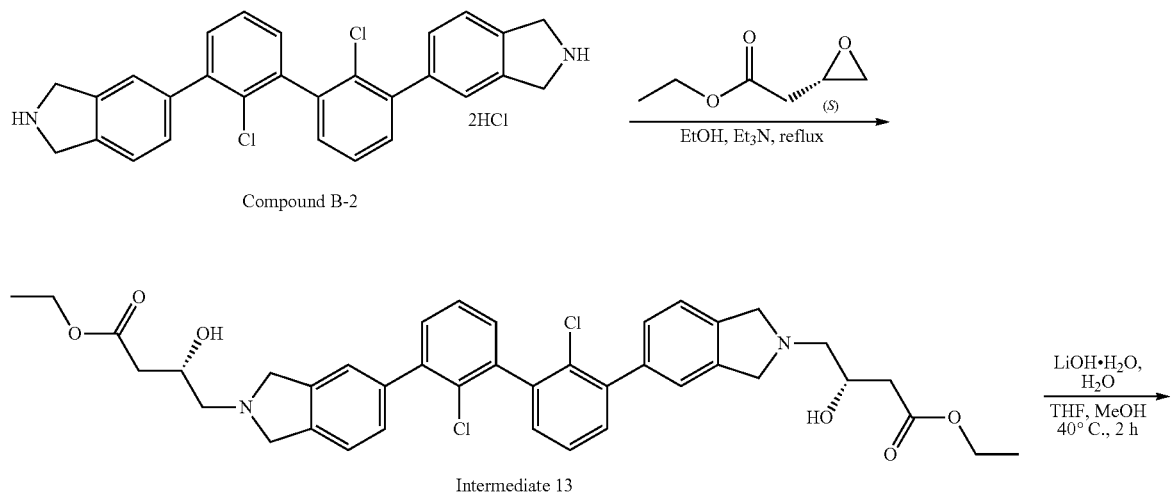

-continued

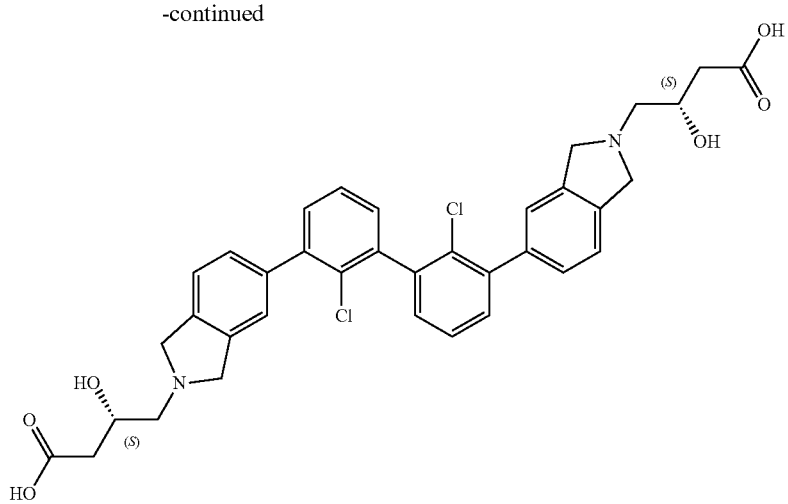

Compound C-1

A mixture of Compound B-2 (40 mg, 81 µmol), ethyl (2S)-2-oxiranylacetate (42 mg, 324 µmol) and TEA (56.37 uL, 405 µmol) in EtOH (0.8 mL) was stirred at 80° C. for 3 hrs under $N_2$ atmosphere. The mixture was concentrated to give Intermediate 13 (120 mg, crude) as a brown gum. The crude produce was used for next step reaction without further purification. LCMS ($C_{40}H_{43}Cl_2N_2O_6^+$) (ES, m/z): 718.0 [M+H]$^+$.

A mixture of crude Intermediate 13 (88 mg) and LiOH·H$_2$O (10 mg, 245 µmol) in mixture of H$_2$O (0.5 mL), THF (1 mL) and MeOH (1.5 mL) was stirred at 40° C. for 2 hours. The mixture was concentrated under reduced pressure to remove THF. The residue was adjusted to pH~3 with 1N aq. HCl, and then was purified by prep-HPLC (column: Waters X bridge BEH C18 100*25 mm*5 um; mobile phase: water (0.04% HCl)-ACN; B %: 5%-35%, 10 min; 100% B Hold Time (1 min); Flow Rate (25 mL/min) to give Compound C-1 (21.25 mg) as a white solid.

The compounds shown below in Table 6 were prepared by an analogous reaction protocol as was used for the preparation of Compound C-1 using the appropriate starting materials.

TABLE 6

| Cmpd No. | Structure | Salt | Starting materials |
|---|---|---|---|
| C-2 | 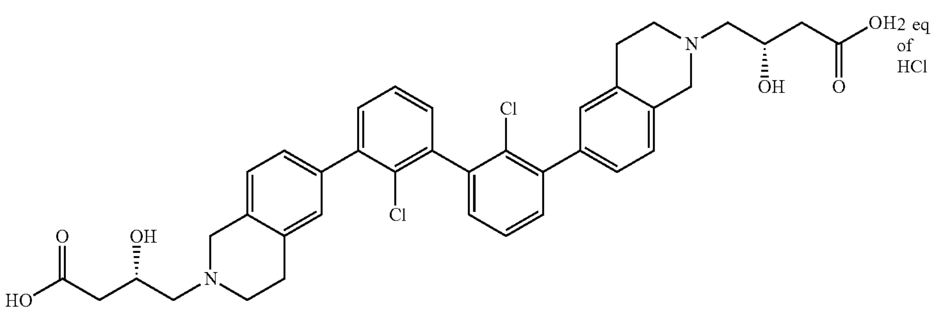 | 2 eq of HCl | Compound B-1 ethyl (2S)-2-oxiranylacetate |
| C-3 | 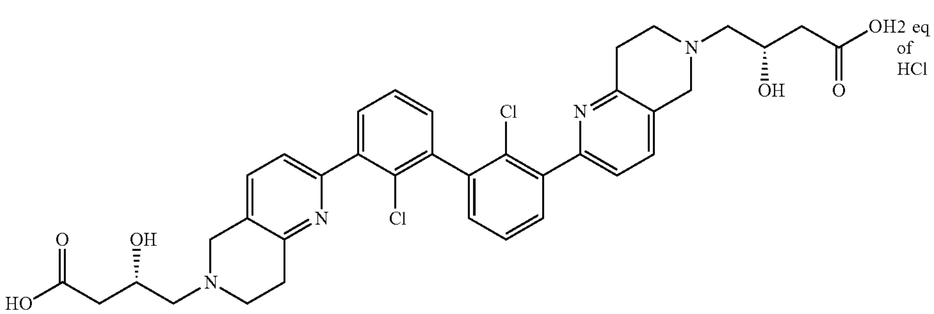 | 2 eq of HCl | Compound B-3 ethyl (2S)-2-oxiranylacetate |

TABLE 6-continued

| Cmpd No. | Structure | Salt | Starting materials |
|---|---|---|---|
| C-4 | 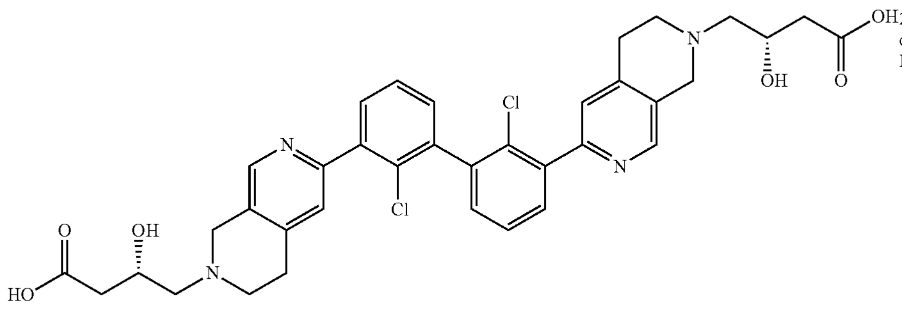 | 2 eq of HCl | Compound B-4 ethyl (2S)-2-oxiranylacetate |
| C-5 | 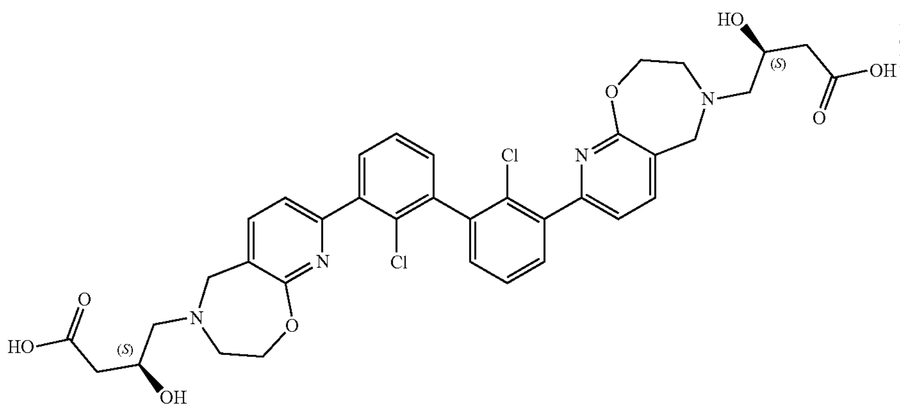 | 2 eq of HCl | Compound B-5 ethyl (2S)-2-oxiranylacetate |
| C-6 | 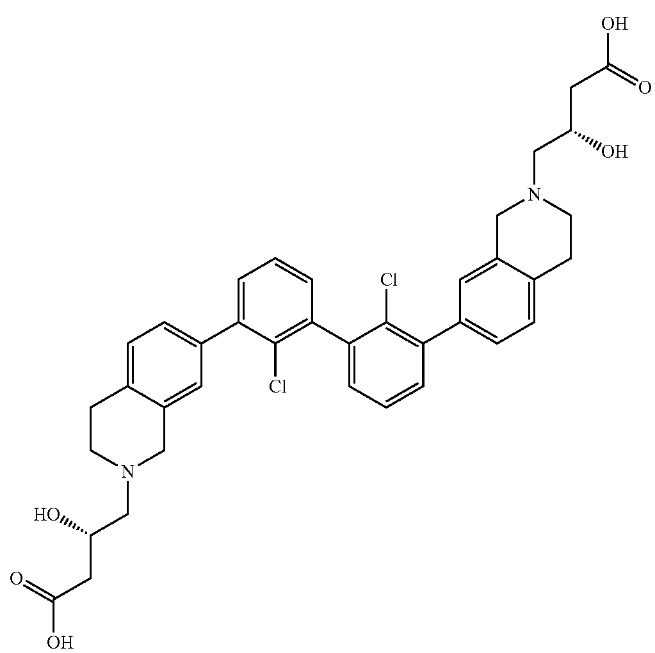 [SMILES: O=C(O)C[C@H](O)CN1CCc2ccc(-c3cccc(-c4cccc(-c5ccc6c(c5)CN(C[C@@H](O)CC(=O)O)CC6)c4Cl)c3Cl)cc2C1] | 2 eq of HCl | Compound B-6 ethyl (2S)-2-oxiranylacetate |

TABLE 6-continued

| Cmpd No. | Structure | Salt | Starting materials |
|---|---|---|---|
| C-7 | 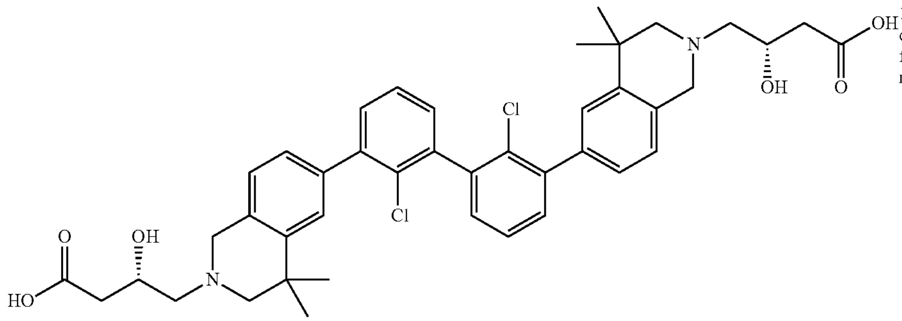 [SMILES: CC1(C)CN(C[C@@H](O)CC(=O)O)Cc2ccc(-c3cccc(-c4cccc(-c5ccc6c(c5)C(C)(C)CN(C[C@@H](O)CC(=O)O)C6)c4Cl)c3Cl)cc21] | 1 eq of formate | Compound B-9 ethyl (2S)-2-oxiranylacetate |
| C-8 | 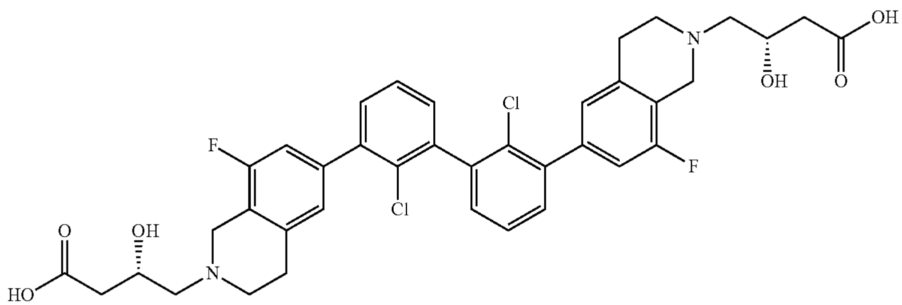 [SMILES: O=C(O)C[C@H](O)CN1CCc2cc(-c3cccc(-c4cccc(-c5cc(F)c6c(c5)CCN(C[C@@H](O)CC(=O)O)C6)c4Cl)c3Cl)cc(F)c2C1] | | Compound B-10 ethyl (2S)-2-oxiranylacetate |
| C-9 | 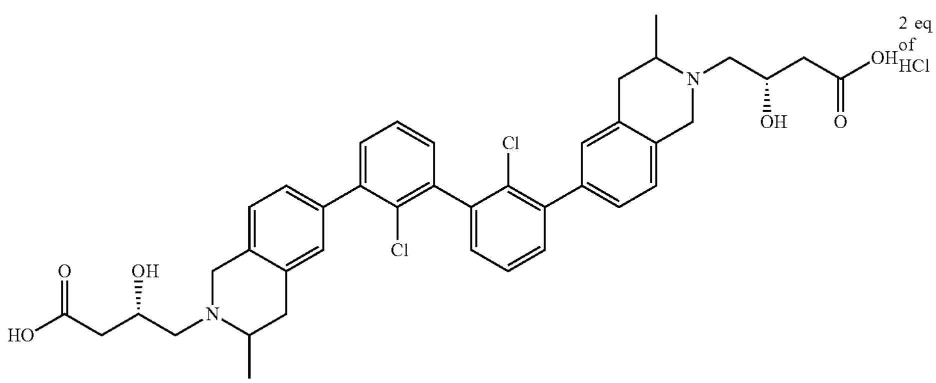 | 2 eq of HCl | Compound B-13 ethyl (2S)-2-oxiranylacetate |
| C-11 | 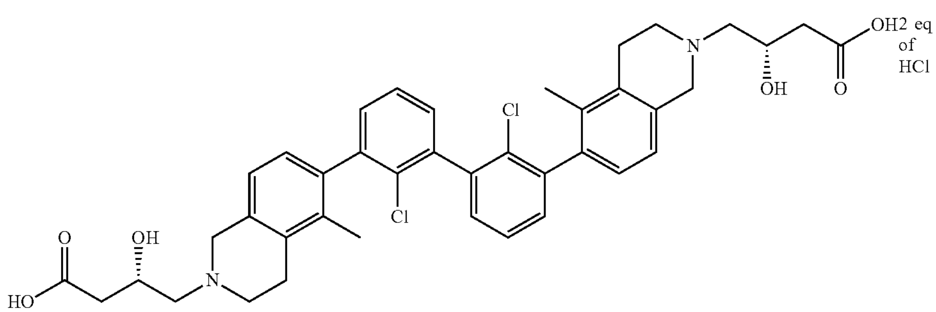 | 2 eq of HCl | Compound B-14 ethyl (2S)-2-oxiranylacetate |

TABLE 6-continued
| Cmpd No. | Structure | Salt | Starting materials |
|---|---|---|---|
| C-12 | 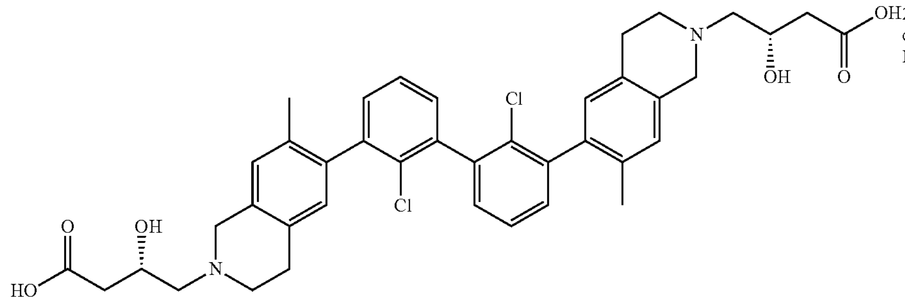 | 2 eq of HCl | Compound B-16 ethyl (2S)-2-oxiranylacetate |
| C-13 | 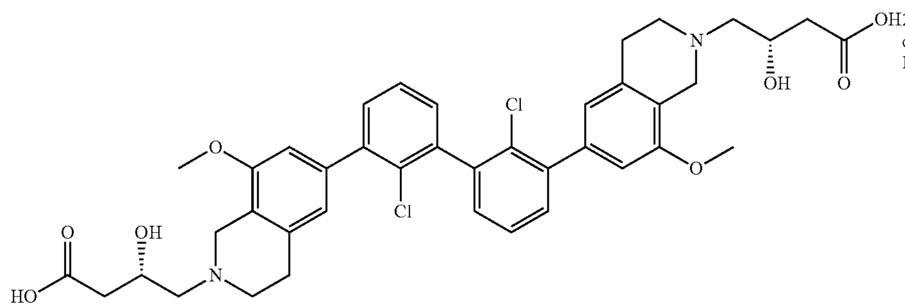 | 2 eq of HCl | Compound B-17 ethyl (2S)-2-oxiranylacetate |
Example 5
Preparation of Compound D-1
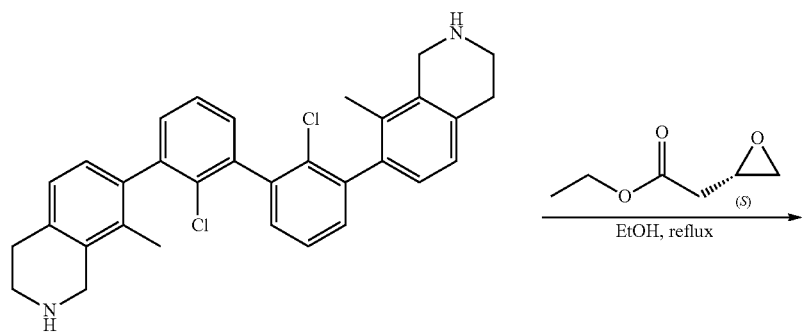
Compound B-15

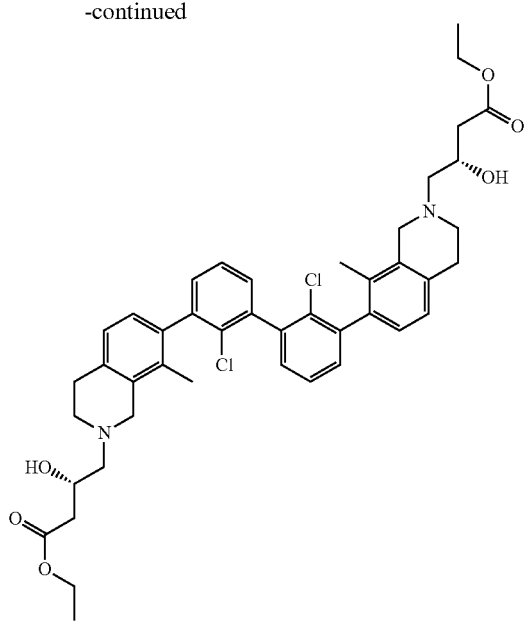

Compound D-1

A mixture of Compound B-15 (30 mg, 58 μmol) and ethyl (2S)-2-oxiranylacetate (32 mg, 234 μmol) in EtOH (1 mL) was stirred at 80° C. for 3 hrs. The mixture was concentrated to give a residue (40 mg). The crude reside (20 mg) was purified by prep-HPLC (acid condition; Column: Phenomenex luna C18 100*40 mm*3 um; Condition: water (0.225% FA)-ACN; Begin B:0; End B:60; Gradient Time (min):10; 100% B Hold Time (min):2; Flow Rate (mL/min): 25; Injections:1) to give Compound D-1 (5.49 mg) as a white solid of formate salt.

Example 6

Preparation of Compound E-1

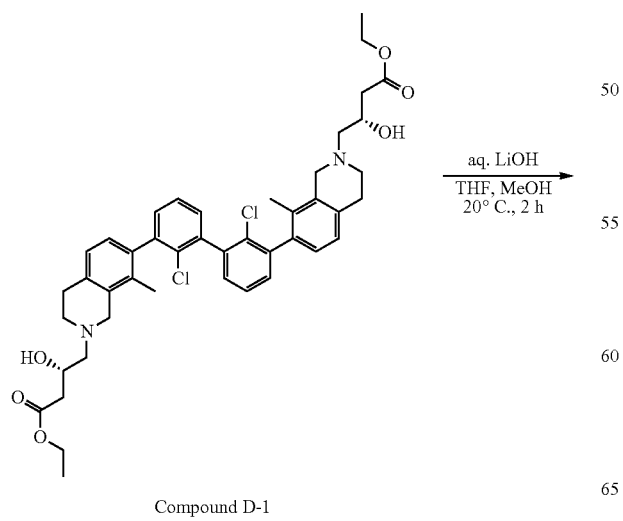

Compound D-1 aq. LiOH
THF, MeOH
20° C., 2 h

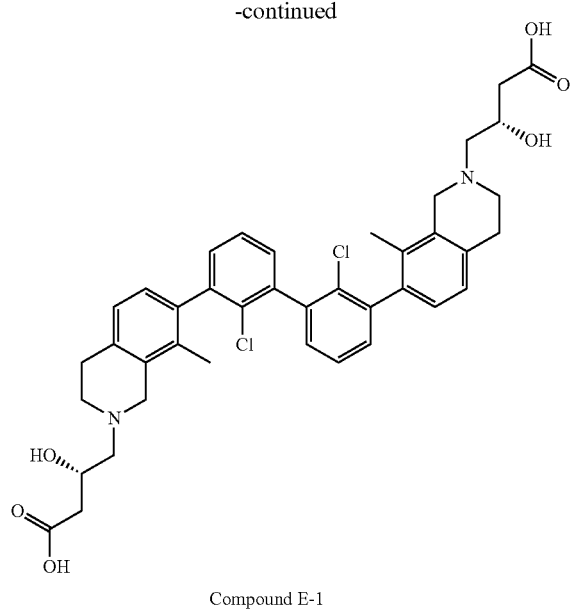

Compound E-1

A mixture of crude Compound D-1 (15 mg) and LiOH·H$_2$O (10 mg, 245 μmol) in mixture of H$_2$O (0.5 mL), THF (1 mL) and MeOH (1.5 mL) was stirred at 40° C. for 2 hrs. The mixture was concentrated under reduced pressure to remove THF. The residue was adjusted to pH~3 with 1N aq. HCl, and then was purified by prep-HPLC, to provide Compound E-1 (3.9 mg) as a white solid of HCl salt.

Example 7

Preparation of Compound F-1

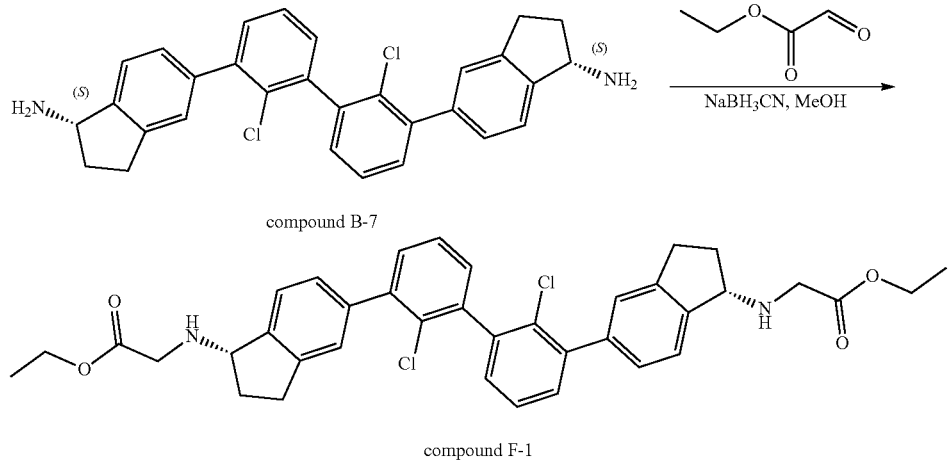

A mixture of Compound B-7 (20 mg, 41.20 μmol), ethyl glyoxalate (17 mg, 82 μmol, 50% purity) in MeOH (1 mL) was stirred at 20° C. for 14 hrs. NaBH$_3$CN (13 mg, 206 μmol, 5 eq) was added, and the mixture was stirred at 20° C. for 1 hour. The mixture was filtered and concentrated under reduced pressure to give a residue, which was purified prep-HPLC (Column: 1 Welch Xtimate 75*40 mm*3 μm; Condition: water (0.225% FA)-ACN; Begin B:15; End B:45; Gradient Time (min):12; 100% B Hold Time (min):2; Flow Rate (mL/min): 25) to give Compound F-1 (2.51 mg) as a white solid.

Example 8

Preparation of Compound G-1

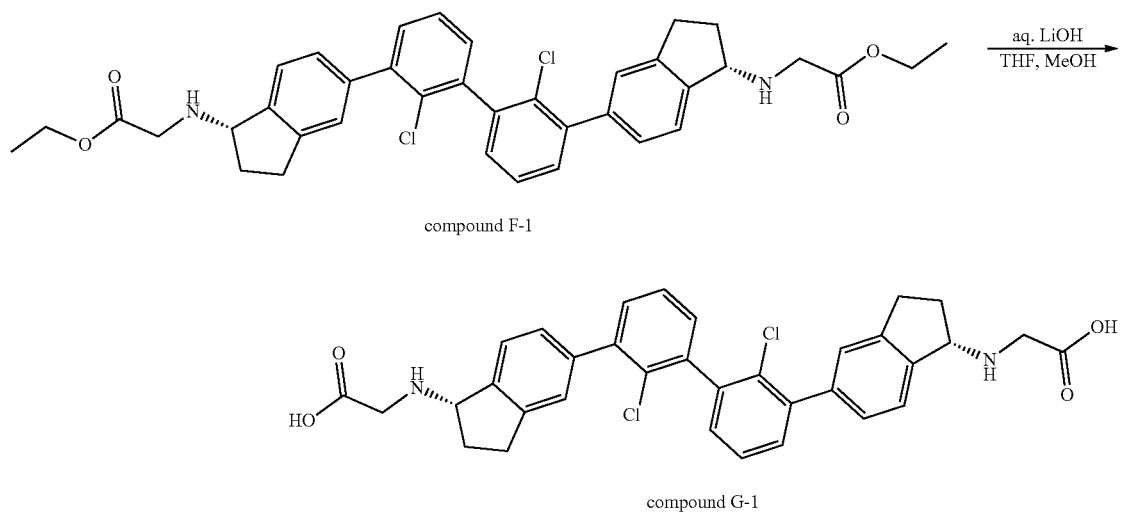

A mixture of Compound F-1 (15 mg, 23 μmol) and LiOH·H$_2$O (2 mg, 46 μmol) in mixture of H$_2$O (0.2 mL), THF (0.4 mL) and MeOH (0.6 mL) was stirred at 20° C. for 2 hrs. The mixture was adjusted to pH 5~6 with 1N HCl. The mixture was filtered and concentrated to give a residue, which was purified prep-HPLC (Phenomenex luna C18 80*40 mm*3 μm; Condition: water (0.05% HCl)-ACN; Begin B: 0; End B:40; Gradient Time (min):10; 100% B Hold Time (min):1; Flow Rate (mL/min): 25; Injections:1) to give Compound G-1 (3.64 mg) as a white solid.

Example 9

Preparation of Compound H-1

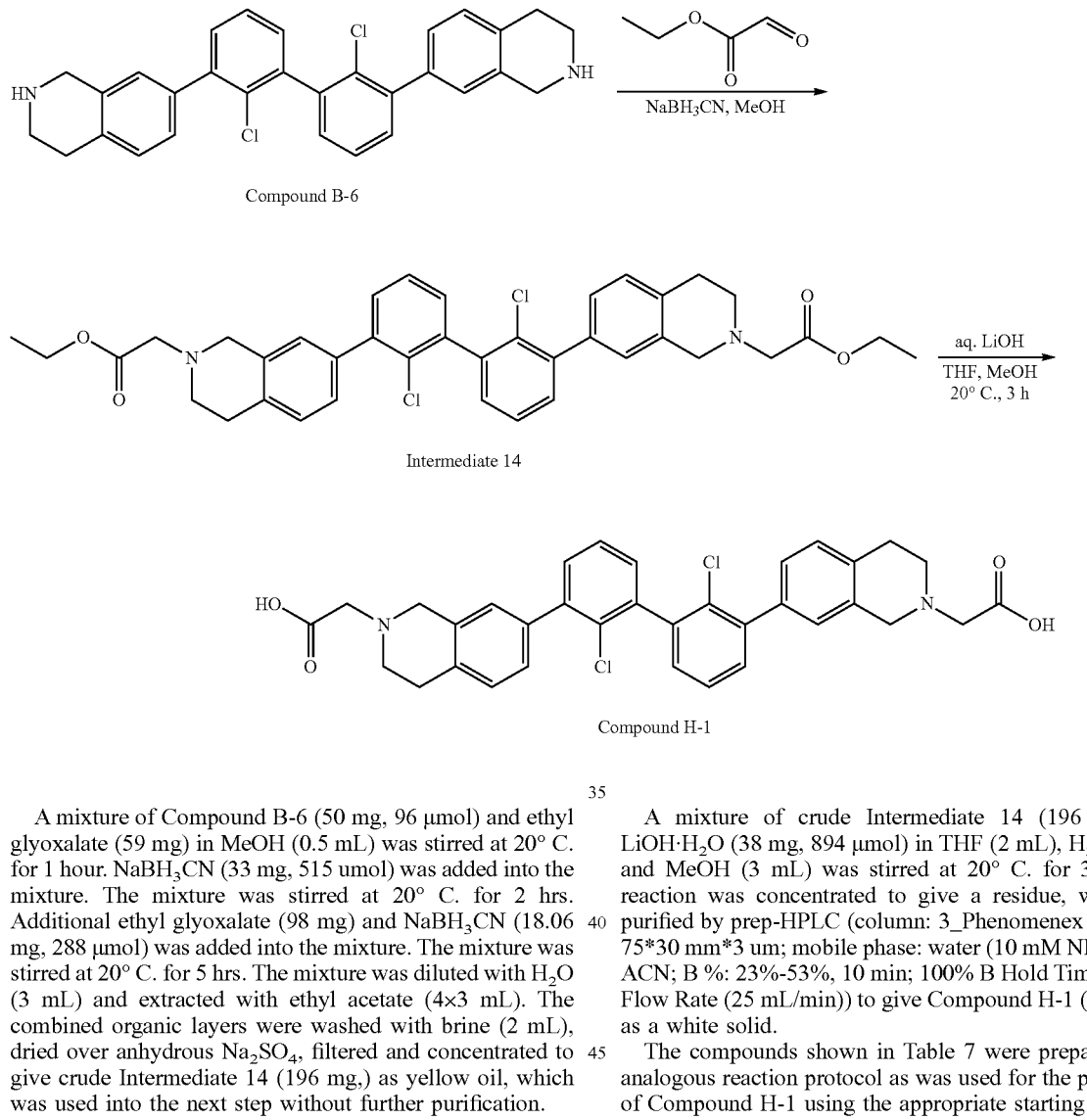

A mixture of Compound B-6 (50 mg, 96 μmol) and ethyl glyoxalate (59 mg) in MeOH (0.5 mL) was stirred at 20° C. for 1 hour. NaBH$_3$CN (33 mg, 515 umol) was added into the mixture. The mixture was stirred at 20° C. for 2 hrs. Additional ethyl glyoxalate (98 mg) and NaBH$_3$CN (18.06 mg, 288 μmol) was added into the mixture. The mixture was stirred at 20° C. for 5 hrs. The mixture was diluted with H$_2$O (3 mL) and extracted with ethyl acetate (4×3 mL). The combined organic layers were washed with brine (2 mL), dried over anhydrous Na$_2$SO$_4$, filtered and concentrated to give crude Intermediate 14 (196 mg,) as yellow oil, which was used into the next step without further purification.

A mixture of crude Intermediate 14 (196 mg) and LiOH·H$_2$O (38 mg, 894 μmol) in THF (2 mL), H$_2$O (1 mL) and MeOH (3 mL) was stirred at 20° C. for 3 hrs. The reaction was concentrated to give a residue, which was purified by prep-HPLC (column: 3_Phenomenex Luna C18 75*30 mm*3 um; mobile phase: water (10 mM NH$_4$HCO$_3$)-ACN; B %: 23%-53%, 10 min; 100% B Hold Time (2 min); Flow Rate (25 mL/min)) to give Compound H-1 (12.58 mg) as a white solid.

The compounds shown in Table 7 were prepared by an analogous reaction protocol as was used for the preparation of Compound H-1 using the appropriate starting materials.

TABLE 7

| Cmpd No. | Structure | Salt | Starting materials |
|---|---|---|---|
| H-2 | ![structure] | | Compound B-1<br>Ethyl glyoxalate |

TABLE 7-continued
| Cmpd No. | Structure | Salt | Starting materials |
|---|---|---|---|
| H-3 | 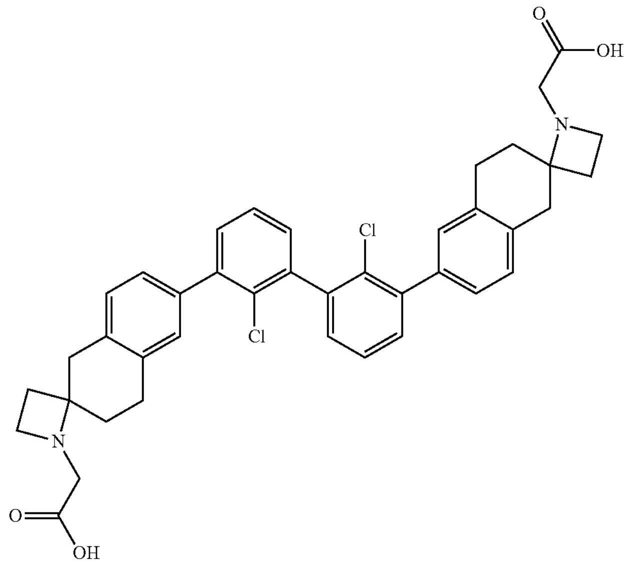 [SMILES: O=C(O)CN1CCC12CCc1cc(-c3cccc(-c4cccc(-c5ccc6c(c5)CCC5(CCN5CC(=O)O)C6)c4Cl)c3Cl)ccc1C2] | 2 eq of HCl | Compound B-11 Ethyl glyoxalate |
| H-4 | 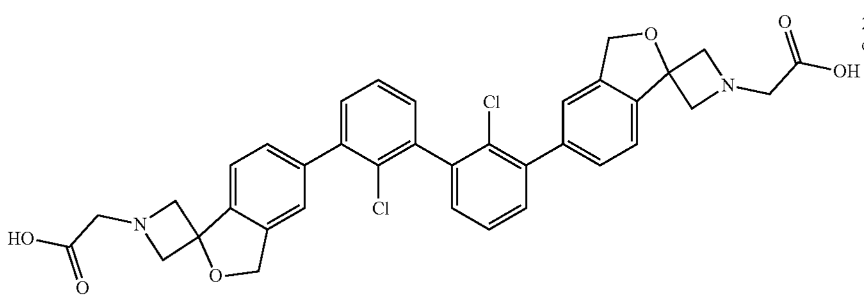 [SMILES: O=C(O)CN1CC2(C1)OCc1cc(-c3cccc(-c4cccc(-c5ccc6c(c5)COC65CN(CC(=O)O)C5)c4Cl)c3Cl)ccc12] | 2 eq of HCl | Compound B-12 Ethyl glyoxalate |
Example 10
Preparation of Compound I-1
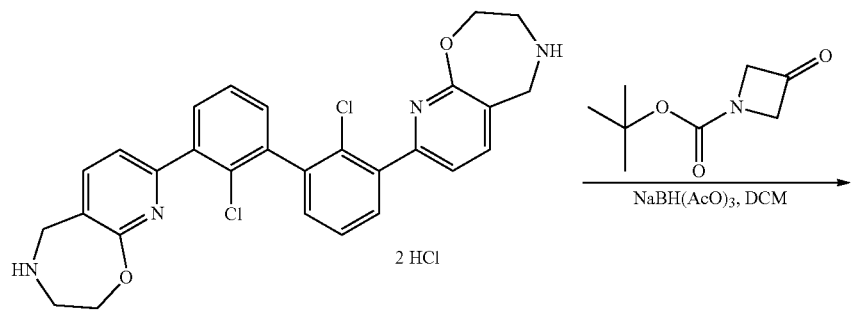
Compound B-5

-continued

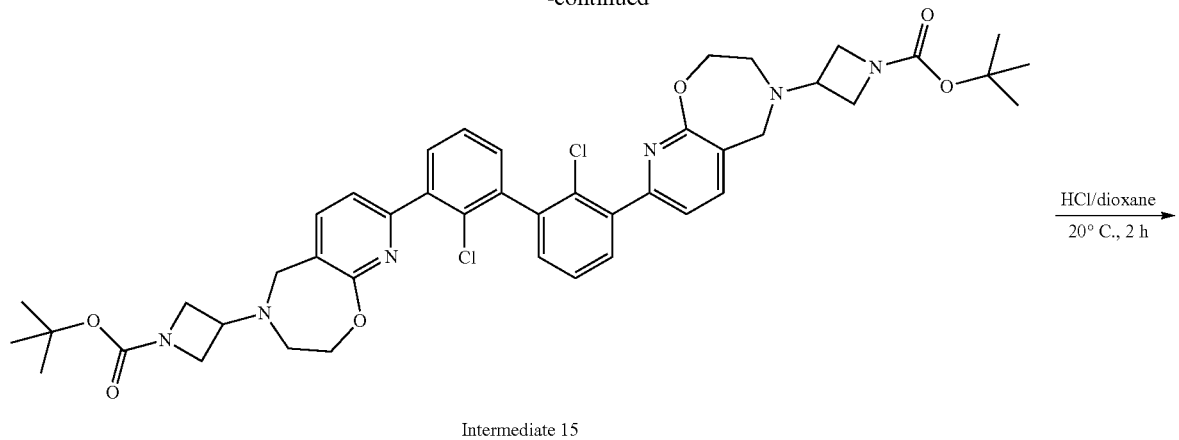

Intermediate 15

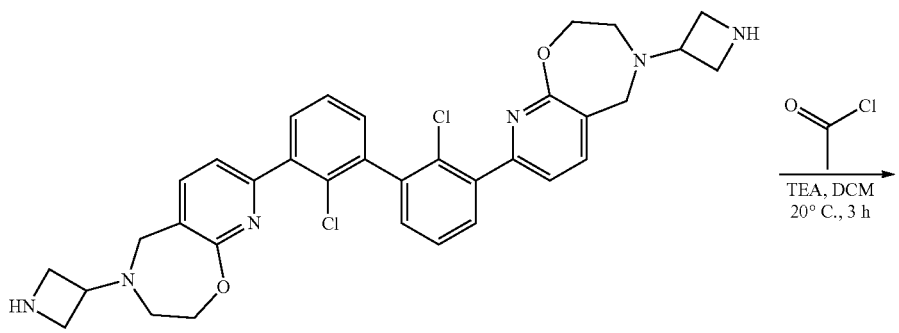

Intermediate 16

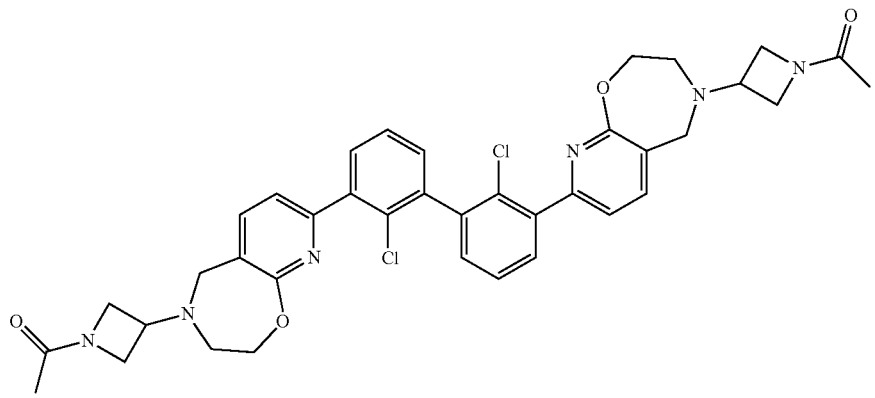

Compound I-1

A mixture of Compound B-5 (80 mg, 144 μmol,) and t-Butyl 3-oxoazetidine-1-carboxylate (54 mg, 317 μmol) in DCM (0.8 mL) was stirred at 20° C. for 0.5 hour. NaBH(OAc)$_3$ (91.50 mg, 431.75 μmol) was added into the mixture. The mixture was stirred at 20° C. for 14 hrs. The mixture was concentrated, and the residue was purified by prep-TLC (SiO$_2$, DCM:MeOH=10:1) to give compound Intermediate 15 (86 mg) as a yellow solid. LCMS ($C_{44}H_{51}Cl_2N_6O_6^+$) (ES, m/z): 829.9 [M+H]$^+$.

A mixture of Intermediate 15 (86 mg, 103.64 μmol) in HCl/dioxane (2 mL) was stirred at 20° C. for 2 hrs. The mixture was concentrated to give Intermediate 16 (90 mg) as yellow HCl salt, which was used into the next step without further purification. LCMS ($C_{34}H_{35}Cl_2N_6O_2^+$) (ES, m/z): 629.9 [M+H]$^+$.

To solution of Intermediate 16 (70 mg, 105 μmol) and TEA (117.03 uL, 841 μmol) was added acetyl chloride (17 μL, 231.22 μmol) at 20° C. The mixture was stirred at 20° C. for 2 hrs. The mixture was concentrated, and the residue was purified by prep-HPLC (column: Phenomenex Gemini NX-C18 (75*30 mm*3 um); mobile phase: water (0.04% NH$_3$H$_2$O+10 mM NH$_4$HCO$_3$)-ACN; B %: 0%-60%, 11 min; 100% B Hold Time (3 min); Flow Rate (25 mL/min); Injections: 5) to give Compound I-1 (17 mg) as off-white solid.

Example 11

Preparation of Compound J-1

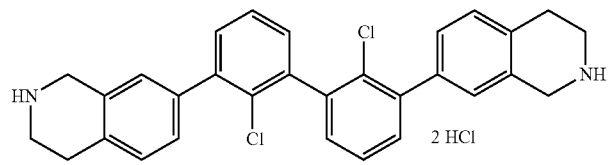

Compound B-6

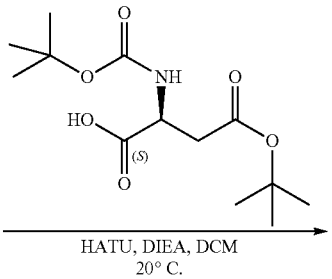

HATU, DIEA, DCM
20° C.

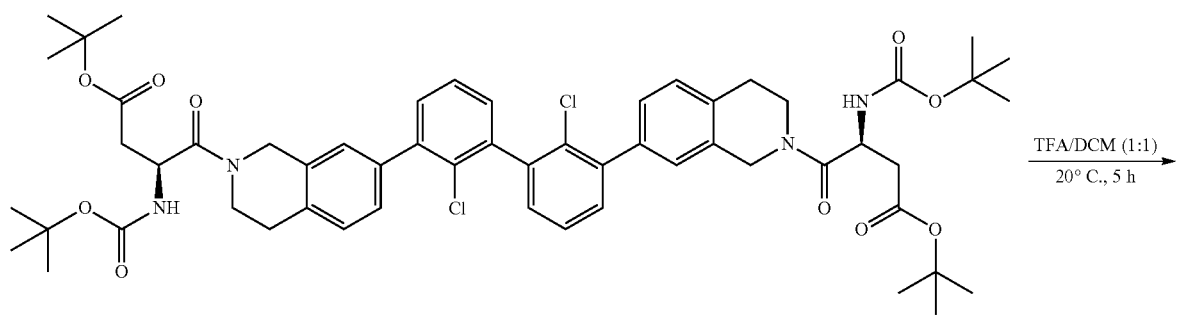

Intermediate 17

TFA/DCM (1:1)
20° C., 5 h

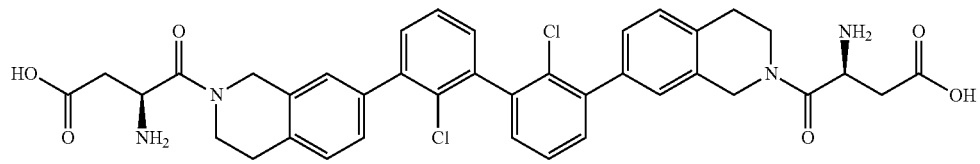

Compound J-1

A mixture of Compound B-6 (50 mg, 95.80 μmol), Boc-L-aspartic acid 4-tert-butyl ester (69 mg, 240 μmol) and DIEA (66.75 μL, 383 μmol,) in DCM (2 mL) was stirred at 20° C. for 1 hour. To the mixture was added HATU (102 mg, 268.25 μmol), and the mixture was stirred at 20° C. for 2 hrs. The mixture was diluted with H₂O (5 mL) and extracted with DCM (3×5 mL). The combined organic layers were washed with brine (5 mL), dried over anhydrous Na₂SO₄, filtered and concentrated to give crude Intermediate 17 (233 mg) as yellow solid, which was used into the next step without further purification.

A mixture of crude Intermediate 17 (233 mg, 227 μmol) and TFA (1 mL, 13.51 mmol) in DCM (1 mL) was stirred at 20° C. for 5 hrs. The mixture was concentrated to give a residue. The residue were purified by prep-HPLC (column: Phenomenex luna C18 100*40 mm*3 um; mobile phase: water (0.225% FA)-ACN; B %: 10%-50%, 10 min; 100% B Hold Time (2 min); Flow Rate (25 mL/min) to give Compound J-1 (21.80 mg) as a white solid of formate salt.

Example 12

Preparation of Compound K-1

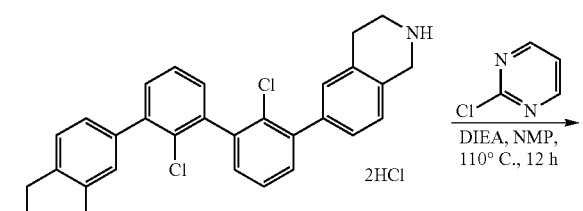

Compound B-1

DIEA, NMP,
110° C., 12 h

257
-continued

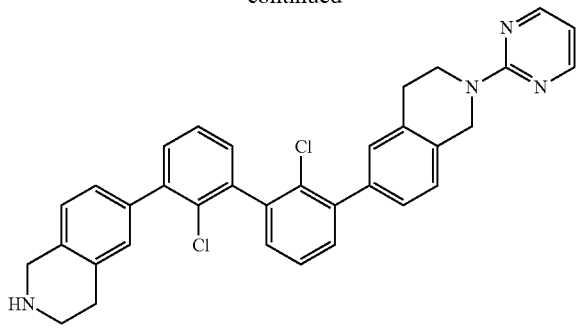

Compound K-1

A mixture of Compound B-1 (100 mg, 192 μmol), 2-Cl-pyrimidine (4.79 uL, 192 μmol,) and DIEA (200 μL, 1.15 mmol) in NMP (1 mL) was stirred at 110° C. for 12 hrs. The mixture was concentrated to give a residue, which was purified by prep-HPLC (column: 1_Welch Xtimate 75*40 mm*3 um; mobile phase: water (0.225% FA)-ACN; B %: 30%-60%, 10 min; 100% B Hold Time (2 min); Flow Rate (25 mL/min) to give Compound K-1 (3.52 mg) as a white solid of formate salt.

Example 13

Preparation of Compound K-2

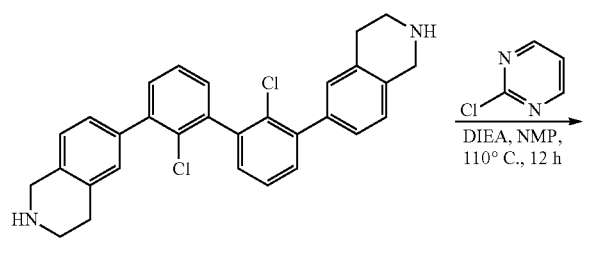

258
-continued

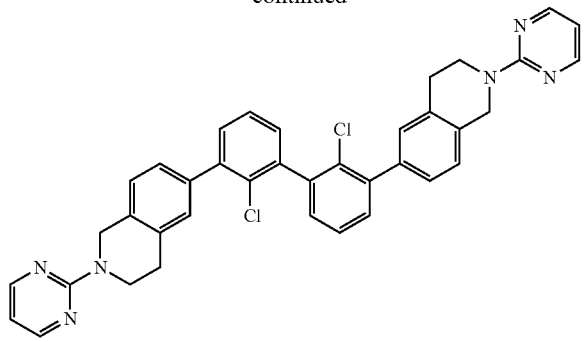

Compound K-2

A mixture of Compound B-1 (50 mg, 96 μmol), 2-Cl-pyrimidine (14.26 mg, 4.79 μL, 125 μmol) and DIEA (16.69 uL, 95.80 μmol) in NMP (0.5 mL) was stirred at 110° C. for 12 hours. The mixture was diluted with H₂O (3 mL) and extracted with EtOAc (3×2 mL). The combined organic layers were washed with brine (2 mL), dried over anhydrous Na₂SO₄, filtered and concentrated under reduced pressure to give a residue, which was purified by prep-TLC (SiO₂, EA:PE=3:1) and prep-HPLC (column: Phenomenex luna C18 100*40 mm*3 um; mobile phase: water (0.225% FA)-ACN; B %: 60%-100%, 10 min; 100% B Hold Time (2 min); Flow Rate: 25 mL/min) to give Compound K-2 (1.83 mg) as a white solid.

Example 14

Preparation of Intermediate i-3

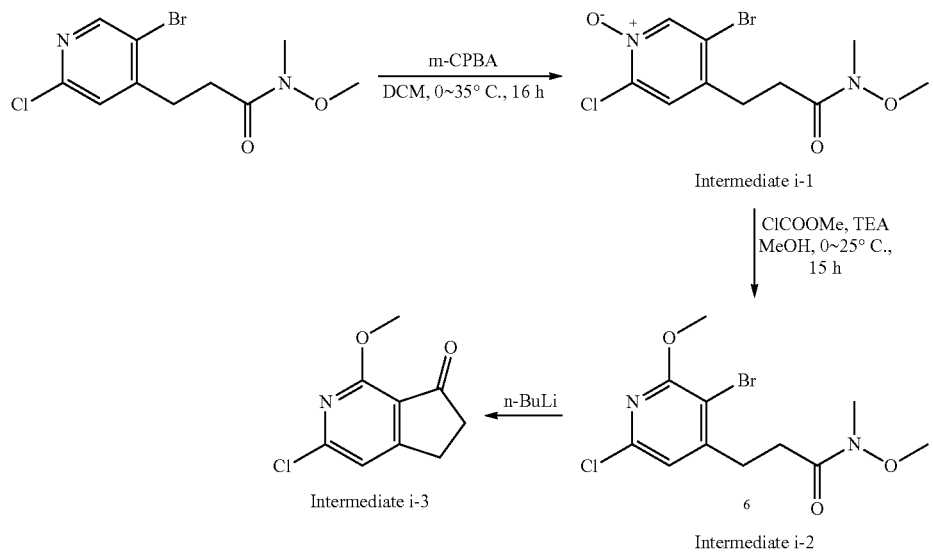

To a solution of 3-(5-bromo-2-chloro-4-pyridyl)-N-methoxy-N-methyl-propanamide (27.5 g, 89.4 mmol) in DCM (400 mL) was added m-CPBA (46.3 g, 268.23 mmol) at 0° C. The mixture was stirred at 55° C. for 16 h. The mixture was poured into sat. aq. Na₂S₂O₄ (300 mL) and extracted with DCM (2×100 mL). The combined organic phases were concentrated in vacuo. The residue was purified by flash silica gel chromatography, offering Intermediate i-1 as a yellow solid. ¹H NMR (400 MHz, CDCl₃) δ 8.50 (s, 1H), 7.48 (s, 1H), 3.67 (s, 3H), 3.18 (s, 3H), 3.06-2.99 (m, 2H), 2.81-2.75 (m, 2H)

To a solution of Intermediate i-1 (26.8 g, 82.8 mmol) and methyl carbonochloridate (26.9 g, 285 mmol) in MeOH (150 mL) was added dropwise TEA (41.91 g, 414 mmol) at 0° C., and the mixture was stirred at 0° C. for 1.5 h. Methyl carbonochloridate (39.13 g, 414 mmol) was added, followed by TEA (41.91 g, 414 mmol) added dropwise at 0° C. The mixture was stirred at 0° C. for 1.5 h. Further methyl carbonochloridate (26.9 g, 285 mmol) was added, followed by TEA (41.91 g, 414.13 mmol) added dropwise at 0° C. The mixture was stirred at 30° C. for 15 h and then concentrated under reduced pressure. The mixture was diluted with 1N aq. NaOH (300 mL) and extracted with EtOAc (2×200 mL). The combined organic layers were wished with brine (100 mL×2), dried over anhydrous Na₂SO₄, filtered and concentrated under reduced pressure to give a residue. The residue was purified by flash silica gel chromatography to provide Intermediate i-2 as a white solid (17 g, 61% yield). ¹H NMR (400 MHz, CDCl₃) δ 6.87 (s, 1H), 4.00 (s, 3H), 3.66 (s, 3H), 3.19 (s, 3H), 3.06-3.01 (m, 2H), 2.74 (br t, 2H).

To a solution of Intermediate i-2 (3.4 g, 10.07 mmol) in THF (40 mL) was added n-BuLi (2.5 M, 6.04 mL) at −70° C. The mixture was stirred at −70° C. for 0.5 h. The mixture was poured into sat.aq. NH₄Cl (80 mL) and extracted with EtOAc (2×100 mL). The combined organic layers were washed with brine (2×80 mL), dried over anhydrous Na₂SO₄, filtered and concentrated under reduced pressure to give a residue. The residue was purified by flash silica gel chromatography to provide Intermediate i-3 as a white solid (1.45 g, 73% yield). ¹H NMR (400 MHz, CDCl₃) δ 7.03 (s, 1H), 4.11 (s, 3H), 3.20-2.97 (m, 2H), 2.79-2.52 (m, 2H).

Example 15

Preparation of Intermediates i-4a and i-4b

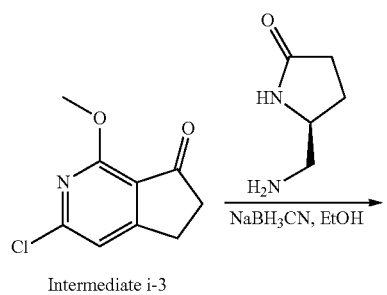

Intermediate i-3

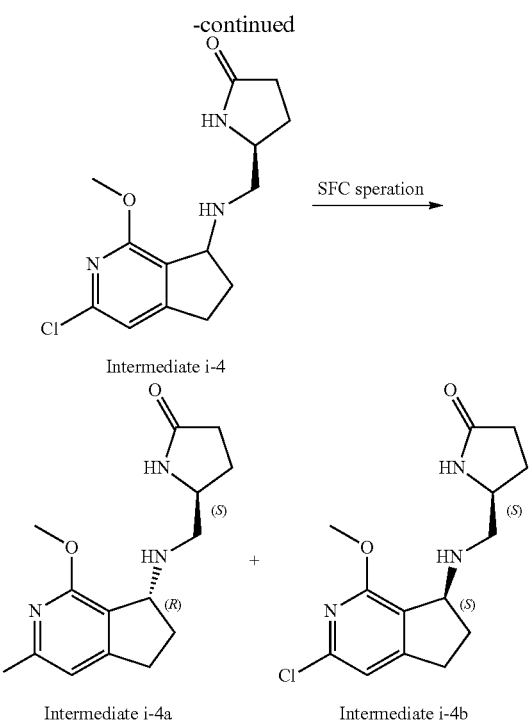

The mixture of Intermediate i-3 (1.45 g, 7.34 mmol) and (5S)-5-(aminomethyl)pyrrolidin-2-one HCl salt (2.21 g, 14.7 mmol) in EtOH (20 mL) was stirred at 20-45° C. for 1 h. NaBH₃CN (1.38 g, 22 mmol) was added at 20° C. The mixture was stirred at 20-45° C. for 15 g. The mixture was filtered and concentrated under reduced pressure to give a residue. The residue was diluted with H₂O (80 mL) and extracted with EtOAc (2×100 mL). The combined organic layers were washed with brine (2×80 mL), dried over anhydrous Na₂SO₄, filtered and concentrated under reduced pressure to give a residue. The residue was purified by flash silica gel chromatography. Intermediate i-4 (2.2 g, 92% purity) was obtained as a yellow oil.

Intermediate i-4 was further separated by SFC (Column: DAICEL CHIRALPAK IC (250 mm*50 mm, 10 um), Mobile phase: A: CO2; B: IPA (0.1% NH₃H₂O); Gradient: 55% B; Flow Rate (ml/min): 140; Injections: 300 min (3 ml per injection, Cycle time: ~6.8 min); Column temperature: 40° C.) to give pure enantiomers Intermediate i-4a and Intermediate i-4b. The absolute chiral centers of the intermediates are assigned based on a single crystal structure of Intermediate 1-4b.

Intermediate i-4a (800 mg) was obtained as a yellow oil with SFC. Rt=3.44 minutes (SFC analytical Instrument: CAS-QD-ANA-SFC-SD (Agilent 1260 with DAD detector); Method: Column: Chrialpak IC-3 100×4.6 mm I.D., 3 μm; Mobile phase: 40% of IPA (0.05%) in CO₂; Flow rate: 2.8 mL/min Column temperature: 40° C.). ¹H NMR (400 MHz, CD₃OD) δ 6.96 (s, 1H), 4.51 (dd, J=3.9, 7.7 Hz, 1H), 3.98 (s, 3H), 3.91-3.80 (m, 1H), 3.61 (q, J=7.1 Hz, 1H), 3.18-3.02 (m, 1H), 2.95-2.74 (m, 3H), 2.52-2.40 (m, 1H), 2.39-2.25 (m, 3H), 2.08 (tdd, J=4.4, 8.9, 13.4 Hz, 1H), 1.92-1.76 (m, 1H).

Figure 1B:
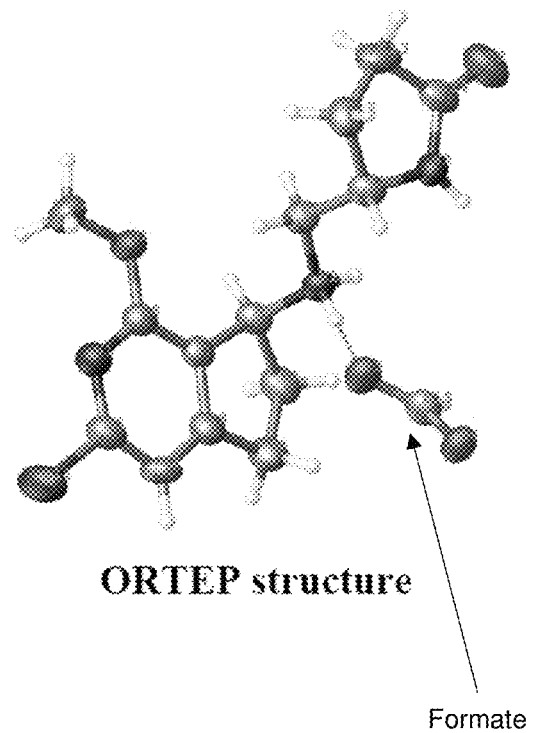
FIG. 1B shows the ORTEP crystal structure of the formate salt of intermediate 1-4b.

Intermediate i-4b (1.14 g) was obtained as a yellow solid with SFC. Rt=4.74 minutes (SFC analytical Instrument: CAS-QD-ANA-SFC-SD (Agilent 1260 with DAD detector) Method: Column: Chrialpak IC-3 100×4.6 mm I.D., 3 μm Mobile phase: 40% of IPA (0.05%) in CO₂; Flow rate: 2.8 mL/min Column temperature:40° C.). ¹H NMR (400 MHz, CD₃OD) δ 6.91 (s, 1H), 4.37 (dd, J=4.8, 7.5 Hz, 1H), 3.96 (s, 3H), 3.86-3.74 (m, 1H), 3.05 (ddd, J=5.9, 8.8, 17.1 Hz, 1H), 2.89-2.68 (m, 2H), 2.59 (dd, J=7.1, 11.9 Hz, 1H), 2.46-2.19 (m, 4H), 1.97 (tdd, J=5.3, 8.4, 13.5 Hz, 1H), 1.89-1.72 (m, 1H). The single crystal of intermediate 1-4b's formate salt was obtained. The crystal was a colorless needle with the following dimensions: 0.30×0.04×0.04 mm³. The symmetry of the crystal structure was assigned the monoclinic space group $P2_1$ with the following parameters: a=20.8793(7) Å, b=5.8084(2) Å, c=28.1836(9) Å, α=90°, β=102.238(3°), γ=90°, V=3340.3(2) Å3, Z=8, Dc=1.359 g/cm3, F(000)=1440.0, μ(CuKα)=2.236 mm-1, and T=149.99(10) K. FIGS. 1A and 1B shows the absolute configuration structure and ORTEP crystal structure of the formate salt of intermediate 1-4b.

The intermediates shown in Table S1-1 were prepared by an analogous reaction protocol as was used for the preparation of Intermediates i-4a and i-4b using the appropriate starting materials.

TABLE S1-1

| Intermediate No. | Structure | SFC Method | Retention time (minute) | Starting materials |
|---|---|---|---|---|
| i-5a | 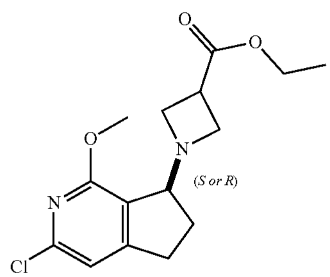 [SMILES: CCOC(=O)C1CN([C@H]2CCc3cc(Cl)nc(OC)c32)C1] | H | 1.63 | Intermediate i-3 Ethyl azetidine-3-carboxylate hydrochloride |
| i-5b | 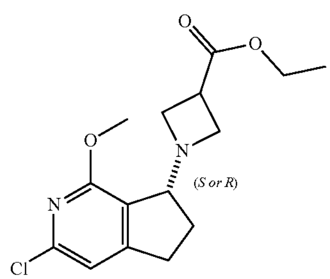 [SMILES: CCOC(=O)C1CN([C@@H]2CCc3cc(Cl)nc(OC)c32)C1] | H | 1.92 | Intermediate i-3 Ethyl azetidine-3-carboxylate hydrochloride |
| i-6a | 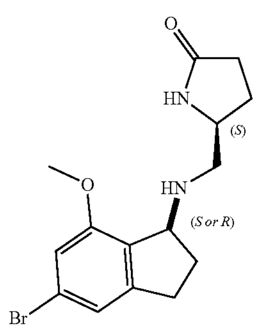 | F | 2.08 | 5-Bromo-7-methoxy-indan-1-one (5S)-5-(aminomethyl)pyrrolidin-2-one 2HCl |
| i-6b | 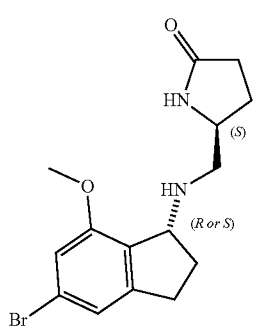 | F | 2.25 | 5-Bromo-7-methoxy-indan-1-one (5S)-5-(aminomethyl)pyrrolidin-2-one 2HCl |

TABLE S1-1-continued

| Intermediate No. | Structure | SFC Method | Retention time (minute) | Starting materials |
|---|---|---|---|---|
| i-7a | 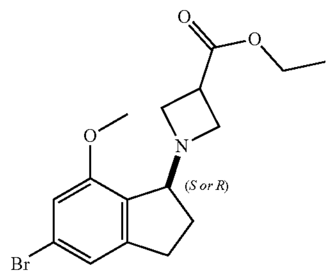 [SMILES: CCOC(=O)C1CN([C@H]2CCc3cc(Br)cc(OC)c32)C1] | G | 1.88 | 5-Bromo-7-methoxy-indan-1-one<br>Ethyl azetidine-3-carboxylate hydrochloride |
| i-7b | 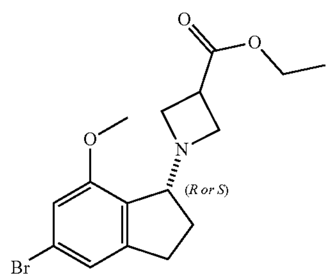 [SMILES: CCOC(=O)C1CN([C@@H]2CCc3cc(Br)cc(OC)c32)C1] | G | 2.23 | 5-Bromo-7-methoxy-indan-1-one<br>Ethyl azetidine-3-carboxylate hydrochloride |
| i-8a | 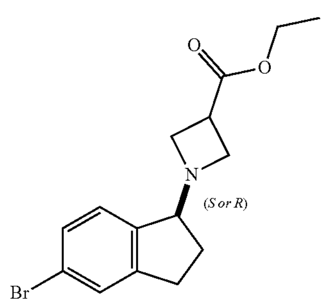 [SMILES: CCOC(=O)C1CN([C@H]2CCc3cc(Br)ccc32)C1] | D | 1.92 | 5-Bromo-1-indanone<br>Ethyl azetidine-3-carboxylate hydrochloride |
| i-8b | 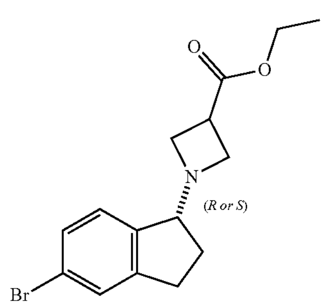 [SMILES: CCOC(=O)C1CN([C@@H]2CCc3cc(Br)ccc32)C1] | D | 2.04 | 5-Bromo-1-indanone<br>Ethyl azetidine-3-carboxylate hydrochloride |
| i-9a | 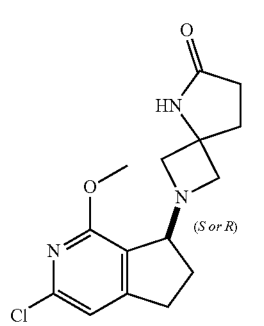 [SMILES: COc1nc(Cl)cc2c1[C@@H](N1CC3(CCC(=O)N3)C1)CC2] | I | 3.33 | Intermediate i-3<br>2,5-Diazaspiro[3.4]octan-6-one hydrochloride |

TABLE S1-1-continued

| Intermediate No. | Structure | SFC Method | Retention time (minute) | Starting materials |
|---|---|---|---|---|
| i-9b | (structure, R or S) | I | 4.00 | Intermediate i-3 2,5-Diazaspiro[3.4]octan-6-one hydrochloride |
| i-10a | (structure, S or R) | C | 1.19 | Intermediate i-3 1-(2,6-diazaspiro[3.3]heptan-2-yl)ethan-1-one |
| i-10b | (structure, R or S) | C | 1.34 | Intermediate i-3 1-(2,6-diazaspiro[3.3]heptan-2-yl)ethan-1-one |

SFC Method A: Column: Chiral NY 100×4.6 mm I.D., 3 μm; Mobile phase: A: $CO_2$; B: Ethanol (0.05% DEA); Gradient: from 5% to 40% of B in 4.5 min and hold 40% for 2.5 min, then 5% of B for 1 min; Flow rate: 2.8 mL/min; Column temperature:40° C.

SFC Method B: Column: Chiralpak ND-3 100×4.6 mm I.D., 3 μm; Mobile phase: A: $CO_2$; B: Ethanol (0.05% DEA); Gradient: from 5% to 40% of B in 4 min and hold 40% for 2.5 min, then 5% of B for 1.5 min; Flow rate: 2.8 mL/min; Column temp.: 35° C.; ABPR: 1500 psi.

SFC Method C: Column: Chiralpak AD-3 100×4.6 mm I.D., 3 μm; Mobile phase: A: $CO_2$, B: Ethanol (0.05% DEA); Gradient: from 5% to 40% of B in 4.5 min and hold 40% for 2.5 min, then 5% of B for 1 min; Flow rate: 2.8 mL/min Column temperature: 40° C.

SFC Method D: Column: UniChiral AD 100×4.6 mm I.D., 3 μm; Mobile phase: A: $CO_2$; B: iso-propanol (0.05% DEA); Gradient: from 5% to 40% of B in 4.5 min and hold 40% for 0.5 min, then 5% of B for 1 min; Flow rate: 2.8 mL/min Column temperature: 40° C.

SFC Method E: Column: Chrialpak IC-3 100×4.6 mm I.D., 3 μm; Mobile phase: A: $CO_2$; B: 40% of IPA (0.05% DEA); Gradient: from 5% to 40% of B in 4.5 min and hold 40% for 0.5 min, then 5% of B for 1 min; Flow rate: 2.8 mL/min Column temperature: 40° C.

SFC Method F: Column: Chrialpak IG 50×4.6 mm I.D., 3 μm; Mobile phase: A: $CO_2$; B: 40% of Methanol (0.05% DEA); Gradient: from 5% to 40% of B in 2.5 min and hold 40% for 0.5 min, then 5% of B for 1.5 min; Flow rate: 4 mL/min Column temperature: 35° C.

SFC Method G: Column: Chiral NY-3 100×4.6 mm I.D., 3 μm; Mobile phase: A: $CO_2$; B: 40% of Ethanol (0.05% DEA); Gradient: from 5% to 40% of B in 4.5 min and hold 40% for 2.5 min, then 5% of B for 1 min; Flow rate: 2.8 mL/min Column temperature: 35° C.

SFC Method H: Column: UniChiral ND 100×4.6 mm I.D., 5 μm; Mobile phase: A: $CO_2$; B: iso-propanol (0.05% DEA); Gradient: from 5% to 40% of B in 4.5 min and hold 40% for 0.5 min, then 5% of B for 1 min; Flow rate: 2.8 mL/min Column temperature: 40° C.

SFC Method I: Column: Chiral NS-3 100×4.6 mm I.D., 3 μm; Mobile phase: A: $CO_2$; B: Ethanol (0.05% DEA); Gradient: from 5% to 40% of B in 4.5 min and hold 40% for 0.5 min, then 5% of B for 1 min; Flow rate: 2.8 mL/min Column temperature: 35° C.

Example 16

Preparation of Intermediate 21

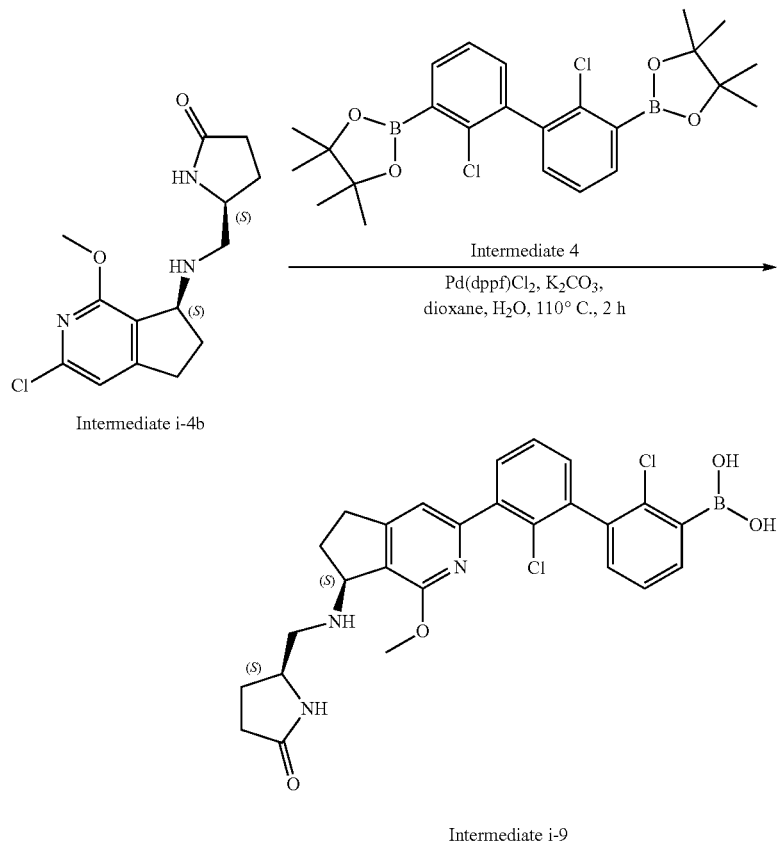

A mixture of Intermediate i-4b (130 mg, 440 μmol), Intermediate 4 (146 mg, 308 μmol), Pd(dppf)Cl$_2$ (32 mg, 44 μmol) and K$_2$CO$_3$ (182 mg, 1.32 mmol) in dioxane (2 mL) and H$_2$O (0.2 mL) was degassed and purged with N$_2$ (3×). The mixture was stirred at 110° C. for 2 h under N$_2$ atmosphere. The mixture was filtered and concentrated under reduced pressure to give a residue. The residue was purified by prep-HPLC. After lyophilization, Intermediate i-9 (40 mg, 98% purity) was obtained as a white solid. LCMS (C$_{26}$H$_{27}$BCl$_2$N$_3$O$_4{}^+$) (ES, m/z): 526.3 [M+H]$^+$.

The intermediates shown in Table S1-2 were prepared by an analogous reaction protocol as was used for the preparation of Intermediate i-9 using the appropriate starting materials.

TABLE S1-2

| Intermediate No. | Structure | Starting materials |
|---|---|---|
| i-10 | (structure shown) | Intermediate 4, Intermediate i-6a |

TABLE S1-2-continued

| Intermediate No. | Structure | Starting materials |
|---|---|---|
| i-11 | 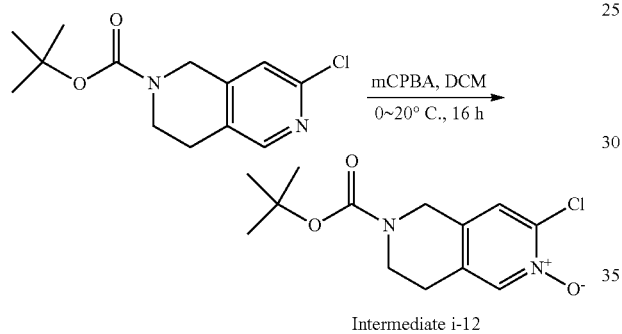 | Intermediate 4 Intermediate i-6b |

Example 17

Preparation of Intermediate i-12

To a solution of tert-butyl 7-chloro-3,4-dihydro-1H-2,6-naphthyridine-2-carboxylate (5 g, 18.6 mmol) in DCM (50 mL) was added MCPBA (4.91 g, 24.19 mmol, 85% purity) at 0° C. The mixture was stirred at 25° C. for 16 h. The reaction was quenched with sat. aq. NaHCO$_3$ (50 mL) and extracted with DCM (2×50 mL). The combined organic layers were washed with brine (80 mL), dried over anhydrous Na$_2$SO$_4$, filtered and concentrated under reduced pressure to give a residue. The residue was purified by flash silica gel chromatography to provide Intermediate i-12 (6.05 g) as a white solid. $^1$H NMR (400 MHz, CDCl$_3$) δ 8.20 (s, 1H), 7.27 (d, J=3.3 Hz, 1H), 4.54 (s, 2H), 3.67 (br t, J=5.7 Hz, 2H), 2.77 (br t, J=5.6 Hz, 2H), 1.50 (s, 9H).

Example 18

Preparation of Intermediate i-14

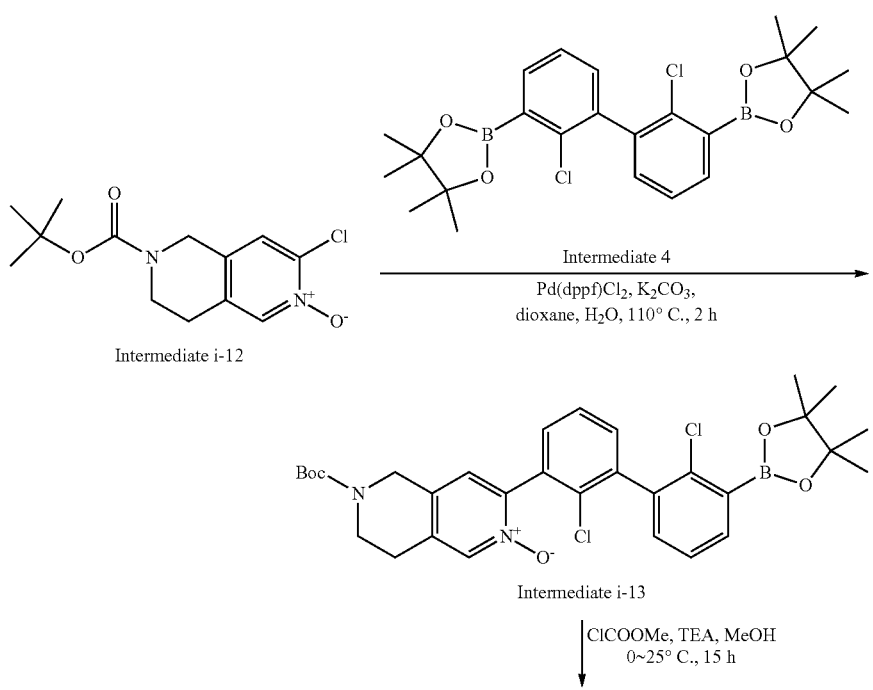

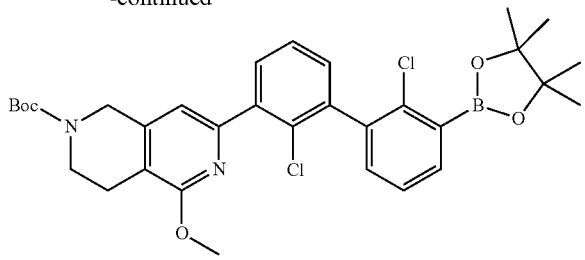

Intermediate i-14

A mixture of Intermediate i-12 (2.5 g, 8.78 mmol), Intermediate 4 (8.34 g, 17.56 mmol), Pd(dppf)Cl₂ (642.44 mg, 0.88 mmol) and K₂CO₃ (3.64 g, 26.34 mmol) in dioxane (70 mL) and H₂O (7 mL) was degassed and purged with N₂ (3×). The mixture was stirred at 110° C. for 2 h under a N₂ atmosphere. The mixture was filtered, concentrated in vacuo, diluted with H₂O (150 mL) and extracted with EtOAc (3×150 mL). The combined organic layers were washed with brine (2×100 mL×2), dried over anhydrous Na₂SO₄, filtered and concentrated under reduced pressure to give a residue. The residue was purified by flash silica gel chromatography to provide Intermediate i-13 (3.52 g, 67% yield) as a brown solid.

To a solution of Intermediate i-13 (3.52 g, 5.89 mmol) in MeOH (40 mL) was added methyl carbono-chloridate (1.94 mL, 25 mmol) and TEA (3.89 mL, 28 mmol) at 0° C. The mixture was stirred at 20° C. for 3 h. To the mixture was added methyl carbono-chloridate (1.94 mL, 25 mmol) and TEA (3.89 mL, 28 mmol,) at 0° C. The mixture was stirred at 20° C. for 15 h. The mixture was concentrated under reduced pressure. The residue was diluted with sat. aq. NaOH (100 mL) and extracted with DCM (3×150 mL). The combined organic layers were washed with brine (2×150 mL), dried over Na₂SO₄, filtered, and concentrated under reduced pressure to give a crude Intermediate i-14.

Example 19

Preparation of Compound L-1

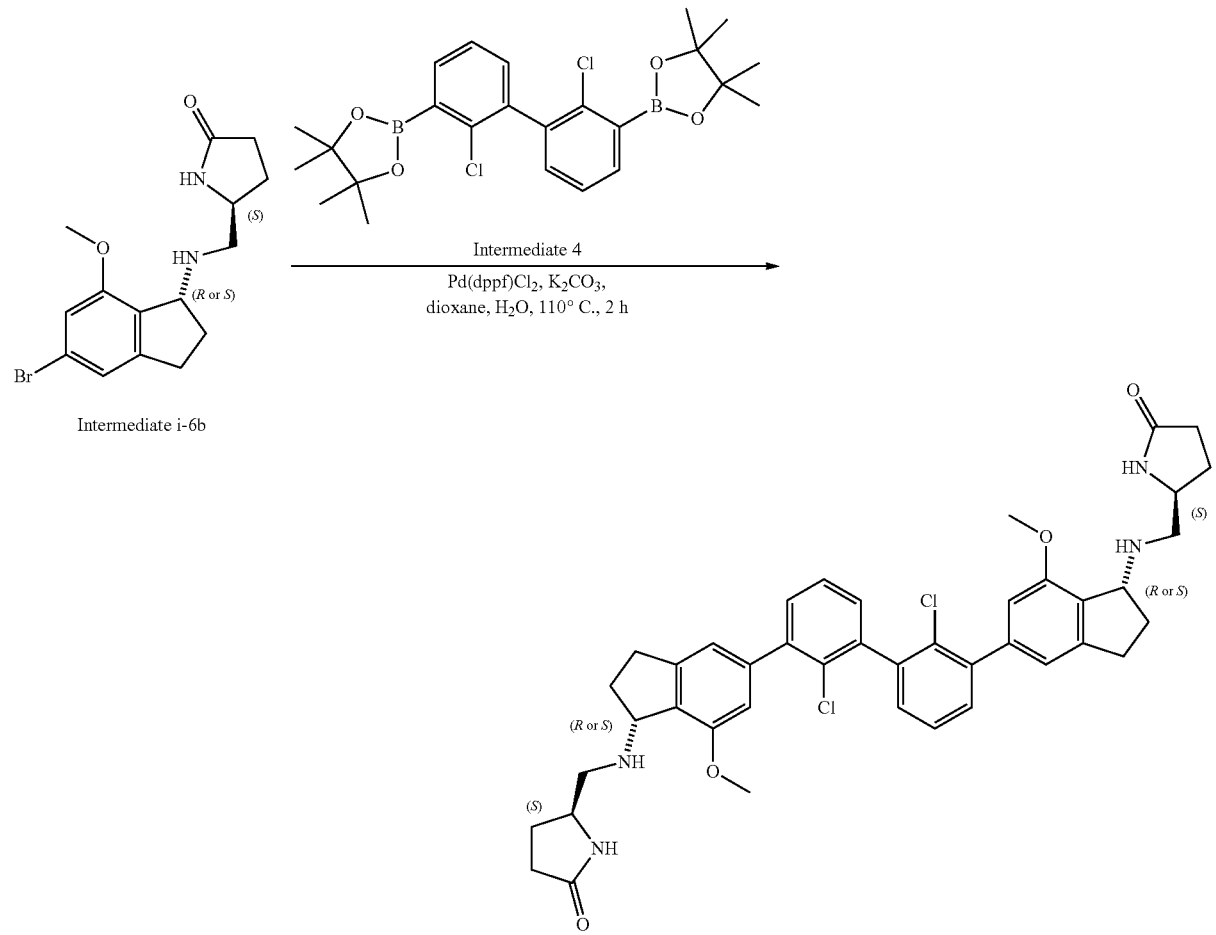

Compound L-1

A mixture of Intermediate i-6b (89 mg, 263 μmol), Intermediate 4 (50 mg, 105 μmol), K₂CO₃ (44 mg, 316 μmol) and Pd(dppf)Cl₂ (7.7 mg, 11 μmol) in dioxane (2 mL) and H₂O (0.2 mL) was stirred at 110° C. for 2 h under N₂ atmosphere. The mixture was filtered and concentrated under reduced pressure to give a residue. The residue was further purified by prep-HPLC to provide Compound L-1 (4.78 mg) as an off-white solid with 1 eq of formate.

The compounds shown in Table S1-3 were prepared by an analogous reaction protocol as was used for the preparation of Compound L-1 using the appropriate starting materials.

TABLE S1-3

| Cmpd No. | Structure | Salt | Starting materials |
|---|---|---|---|
| L-2 | 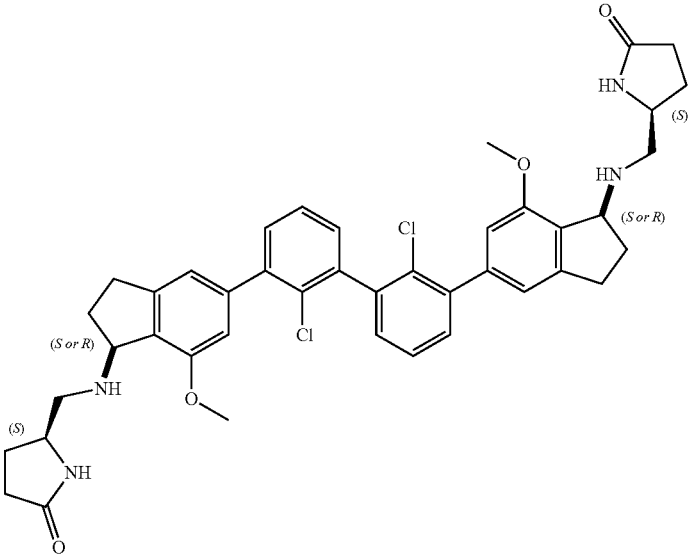 | 1 eq. of formate | Intermediate i-6a Intermediate 4 |
| L-3 | 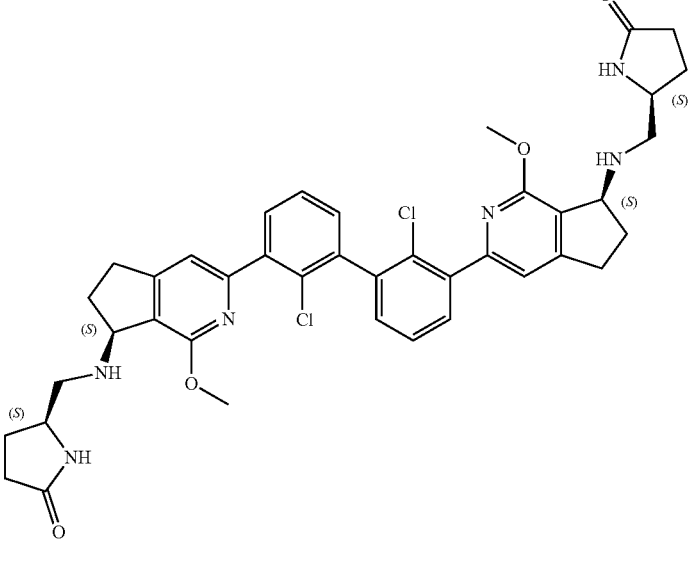 | 1 eq. of formate | Intermediate i-4b Intermediate 4 |

TABLE S1-3-continued

| Cmpd No. | Structure | Salt | Starting materials |
|---|---|---|---|
| L-4 | 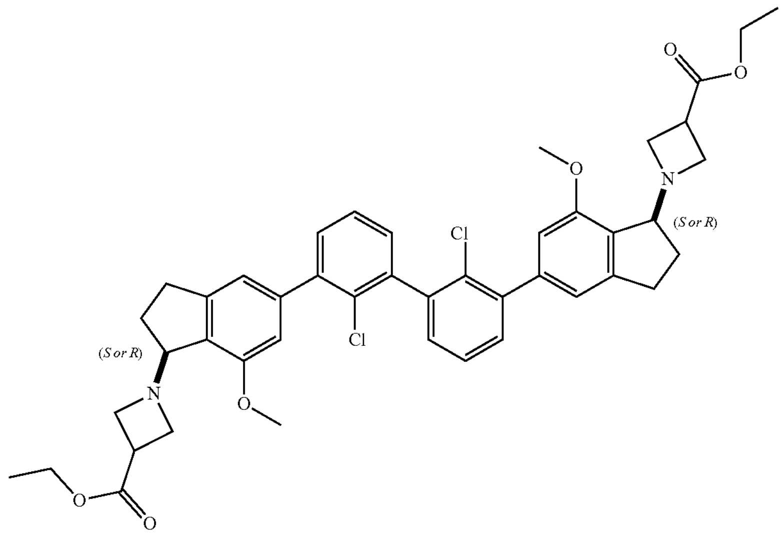 [SMILES: CCOC(=O)C1CN([C@H]2CCc3cc(-c4cccc(-c5cccc(-c6cc7c(c(OC)c6)[C@@H](N6CC(C(=O)OCC)C6)CC7)c5Cl)c4Cl)cc(OC)c32)C1] | 1 eq. of formate | Intermediate i-7a Intermediate 4 |
| L-5 | 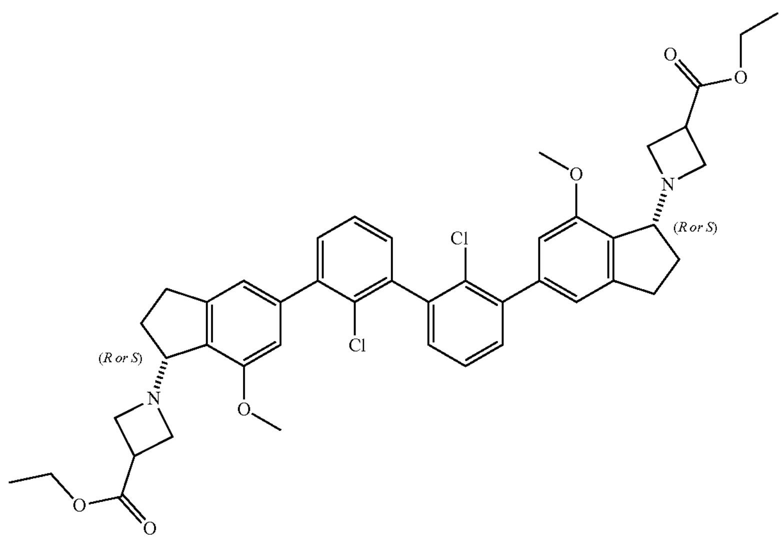 [SMILES: CCOC(=O)C1CN([C@@H]2CCc3cc(-c4cccc(-c5cccc(-c6cc7c(c(OC)c6)[C@H](N6CC(C(=O)OCC)C6)CC7)c5Cl)c4Cl)cc(OC)c32)C1] | 1 eq. of formate | Intermediate i-7b Intermediate 4 |
| L-6 | 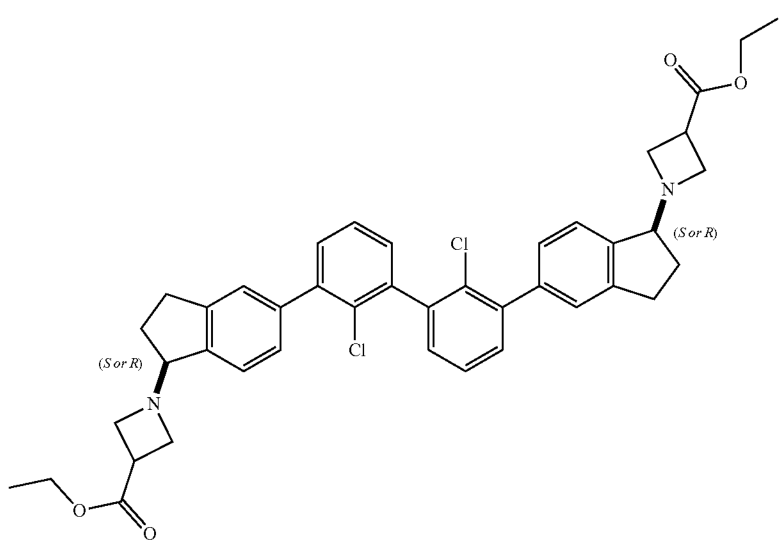 [SMILES: CCOC(=O)C1CN([C@H]2CCc3cc(-c4cccc(-c5cccc(-c6ccc7c(c6)CC[C@@H]7N6CC(C(=O)OCC)C6)c5Cl)c4Cl)ccc32)C1] | 1 eq. of formate | Intermediate i-8a Intermediate 4 |

TABLE S1-3-continued

| Cmpd No. | Structure | Salt | Starting materials |
|---|---|---|---|
| L-7 | 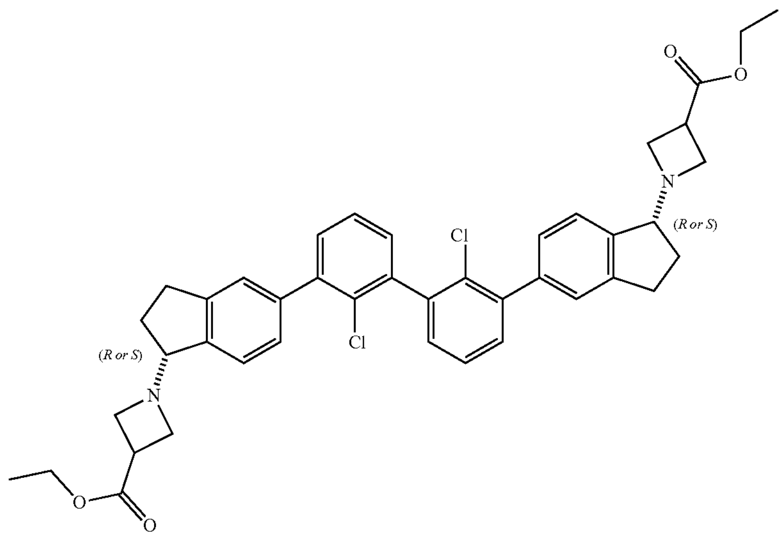 [SMILES: CCOC(=O)C1CN([C@@H]2CCc3cc(-c4cccc(-c5cccc(-c6ccc7c(c6)CC[C@H]7N6CC(C(=O)OCC)C6)c5Cl)c4Cl)ccc32)C1] | 1 eq. of formate | Intermediate i-8b Intermediate 4 |
| L-8 | 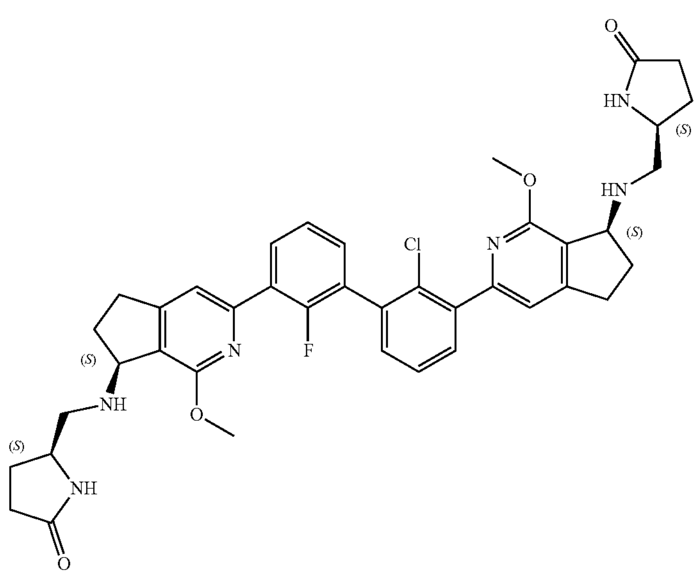 | | Intermediate i-4b Intermediate 4b |

| Cmpd No. | Structure | Salt | Starting materials |
|---|---|---|---|
| L-9 | 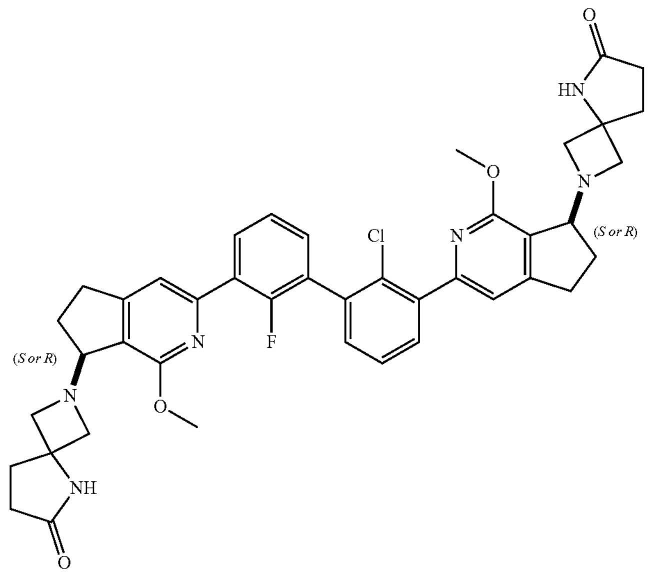 [SMILES: COc1nc(-c2cccc(-c3cccc(-c4cc5c(c(OC)n4)[C@@H](N4CC6(CCC(=O)N6)C4)CC5)c3Cl)c2F)cc2c1[C@@H](N1CC3(CCC(=O)N3)C1)CC2] | 1 eq. of formate | Intermediate i-9a<br>Intermediate 4b |
| L-10 | 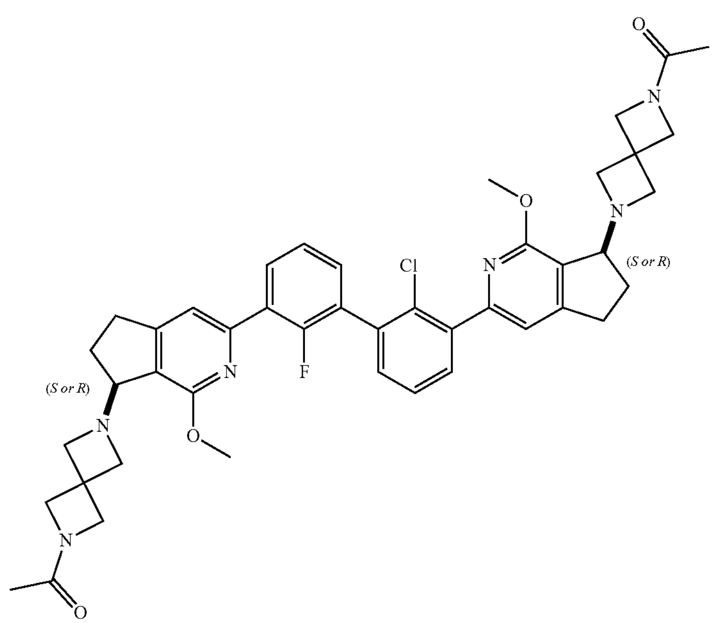 [SMILES: COc1nc(-c2cccc(-c3cccc(-c4cc5c(c(OC)n4)[C@@H](N4CC6(CN(C(C)=O)C6)C4)CC5)c3Cl)c2F)cc2c1[C@@H](N1CC3(CN(C(C)=O)C3)C1)CC2] | 1 eq. of formate | Intermediate i-10a<br>Intermediate 4b |

TABLE S1-3-continued
| Cmpd No. | Structure | Salt | Starting materials |
|---|---|---|---|
| L-11 | 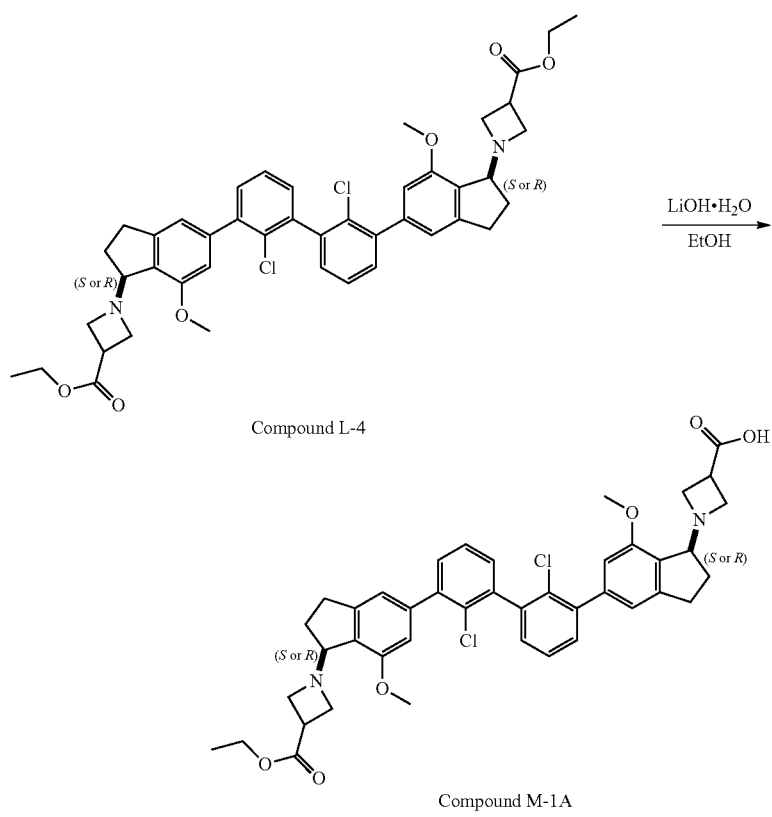 | 1 eq. of formate | Intermediate i-10b<br>Intermediate 4b |
Example 20
Preparation of Compound M-1A and M-1B

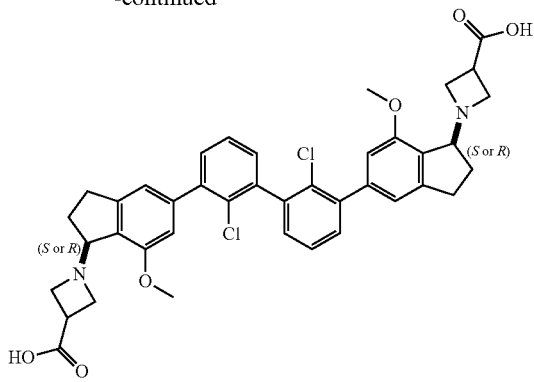

Compound M-1B

To a solution of Compound L-4 (40 mg, 51.96 μmol) in EtOH (6 mL) was added LiOH·H₂O (0.01 M, 5.20 mL). The mixture was stirred at 40° C. for 18 h. The mixture was concentrated under reduced pressure to remove EtOH. The residue was extracted with EtOAC (3×15 mL). The combined organic layers were washed with brine (20 mL), dried over Na₂SO₄, filtered and concentrated under reduced pressure to give a residue. The residue was adjusted to pH~3 with 1N aqueous HCl. The combined aqueous mixture was purified by prep-HPLC. Compound M-1A (12.97 mg, 98% purity) and Compound M-1B (1.23 mg, 99%) purity) were each obtained as a white solid.

The compounds shown in Table S1-4 were prepared by an analogous reaction protocol as was used for the preparation of Compound M-1A and Compound M-1B using the appropriate starting materials.

TABLE S1-4

| Cmpd No. | Structure | Salt | Starting materials |
|---|---|---|---|
| M-2A | (structure shown) | | L-6 |

TABLE S1-4-continued
| Cmpd No. | Structure | Salt | Starting materials |
|---|---|---|---|
| M-2B | 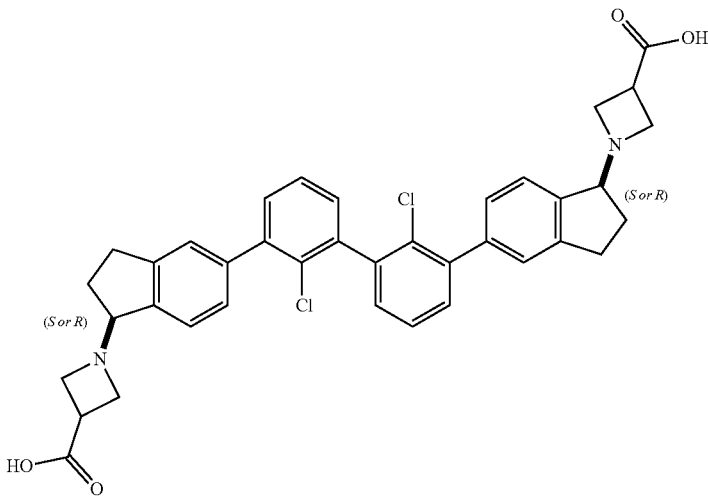 [SMILES: O=C(O)C1CN([C@H]2CCc3cc(-c4cccc(-c5cccc(-c6ccc7c(c6)CC[C@@H]7N6CC(C(=O)O)C6)c5Cl)c4Cl)ccc32)C1] | | L-6 |
| M-3A | 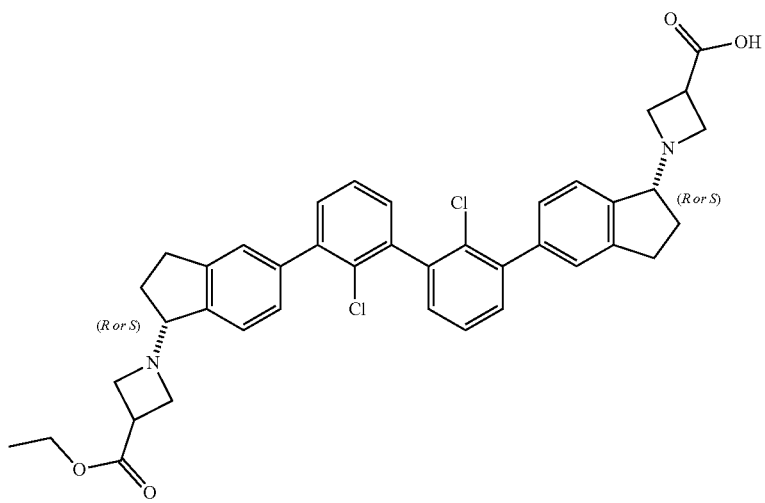 [SMILES: CCOC(=O)C1CN([C@@H]2CCc3cc(-c4cccc(-c5cccc(-c6ccc7c(c6)CC[C@H]7N6CC(C(=O)O)C6)c5Cl)c4Cl)ccc32)C1] | | L-7 |

TABLE S1-4-continued

| Cmpd No. | Structure | Salt | Starting materials |
|---|---|---|---|
| M-3B | 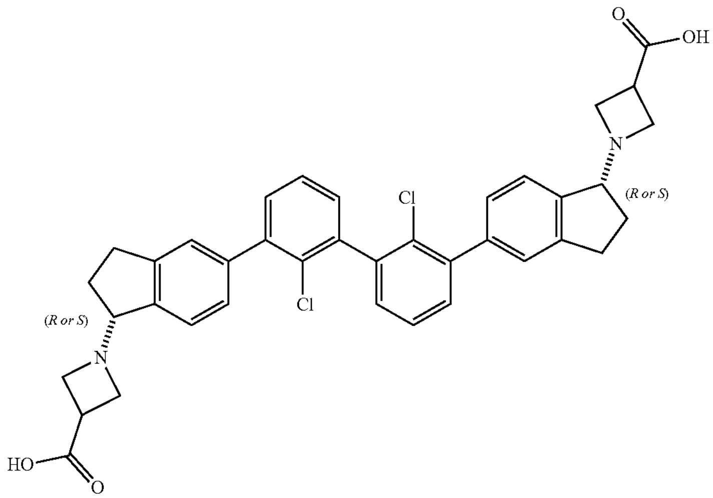 [SMILES: O=C(O)C1CN([C@@H]2CCc3cc(-c4cccc(-c5cccc(-c6ccc7c(c6)CC[C@H]7N6CC(C(=O)O)C6)c5Cl)c4Cl)ccc32)C1] | | L-7 |
| M-4B | 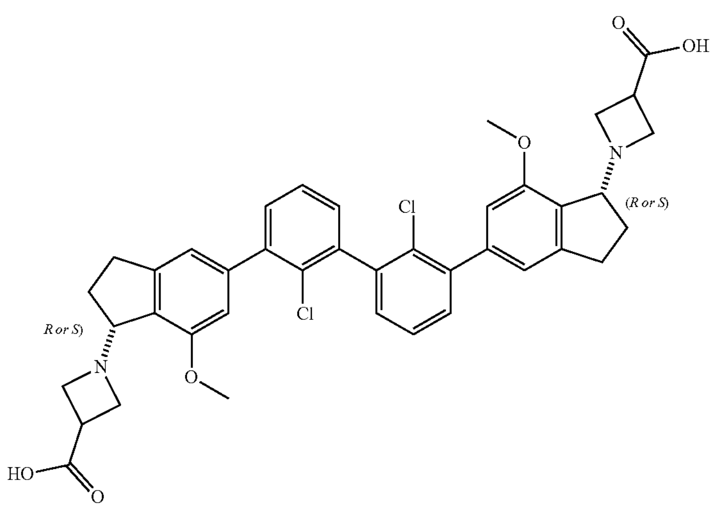 [SMILES: COc1cc(-c2cccc(-c3cccc(-c4cc5c(c(OC)c4)[C@H](N4CC(C(=O)O)C4)CC5)c3Cl)c2Cl)cc2c1[C@H](N1CC(C(=O)O)C1)CC2] | 1 eq. of formate | L-5 |

Example 21

Preparation of Compound N-1A

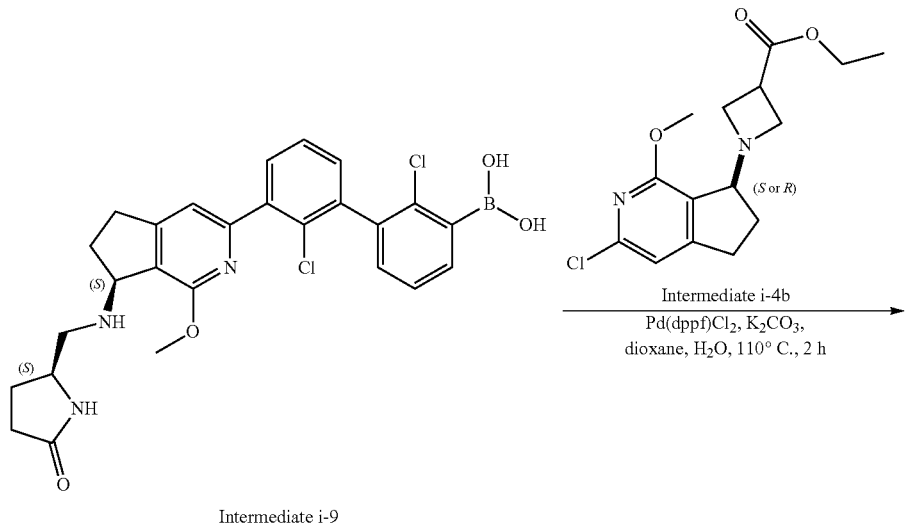

Intermediate i-9

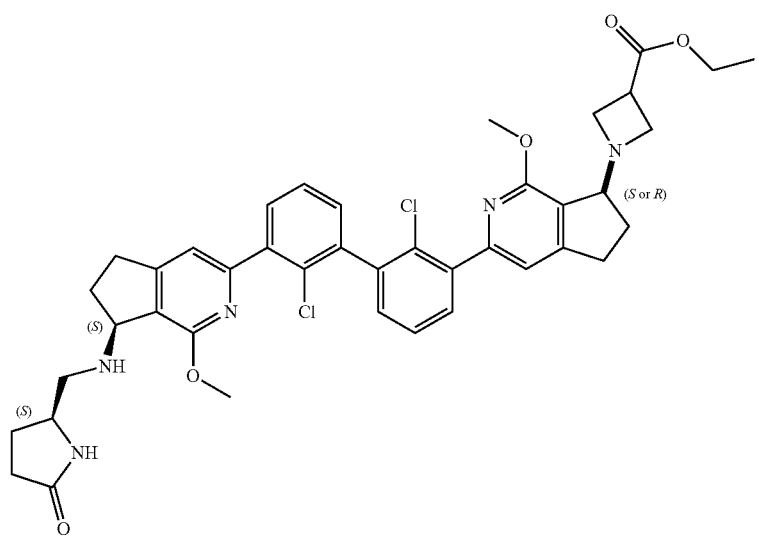

Compound N-1A

A mixture of Intermediate i-9 (40 mg, 76 μmol), Intermediate i-4b (28 mg, 91 μmol), Pd(dppf)Cl$_2$ (5.56 mg, 7.60 μmol) and K$_2$CO$_3$ (32 mg, 228 μmol) in dioxane (1.5 mL) was degassed and purged with N$_2$ (3×). The mixture was stirred at 110° C. for 2 h under a N$_2$ atmosphere. The residue was purified by prep-HPLC. After lyophilization, Compound N-1A (14 mg, 99% purity) was obtained as a white solid with 1 eq. of formate.

The compounds shown in Table S1-5 were prepared by an analogous reaction protocol as was used for the preparation of Compound N-1A using the appropriate starting materials.

TABLE S1-5

| Cmpd No. | Structure | Salt | Starting materials |
|---|---|---|---|
| N-2A | 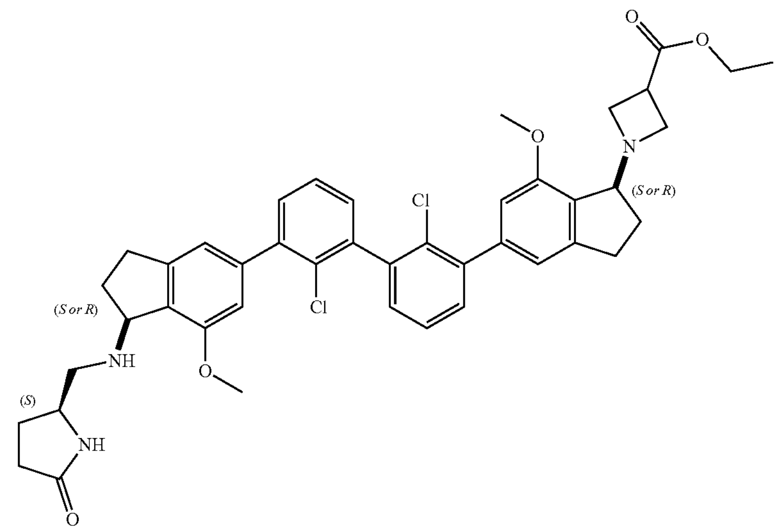 | | Intermediate i-10<br>Intermediate i-7a |
| N-3A | 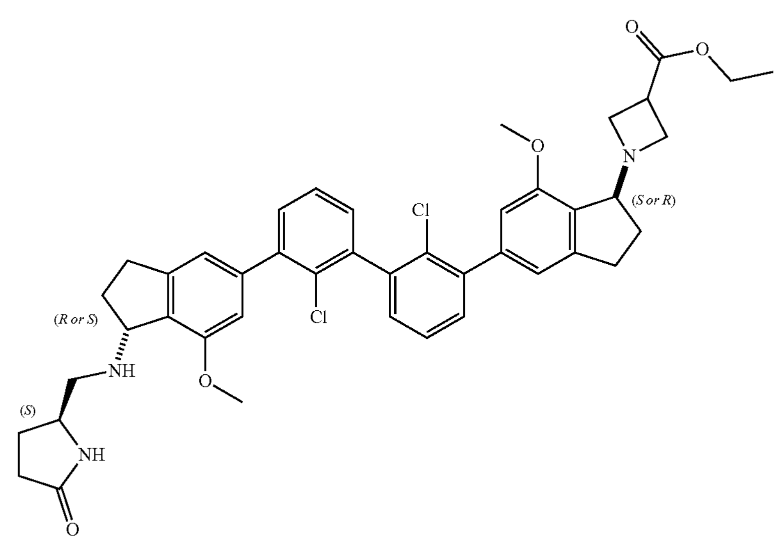 | | Intermediate i-11<br>Intermediate i-7a |

Example 22

Preparation of Compound N-1B

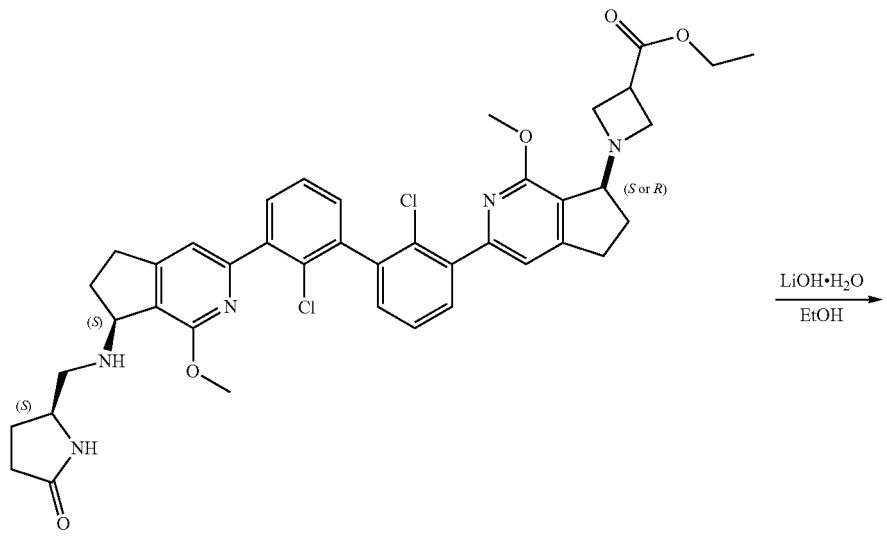

Compound N-1A

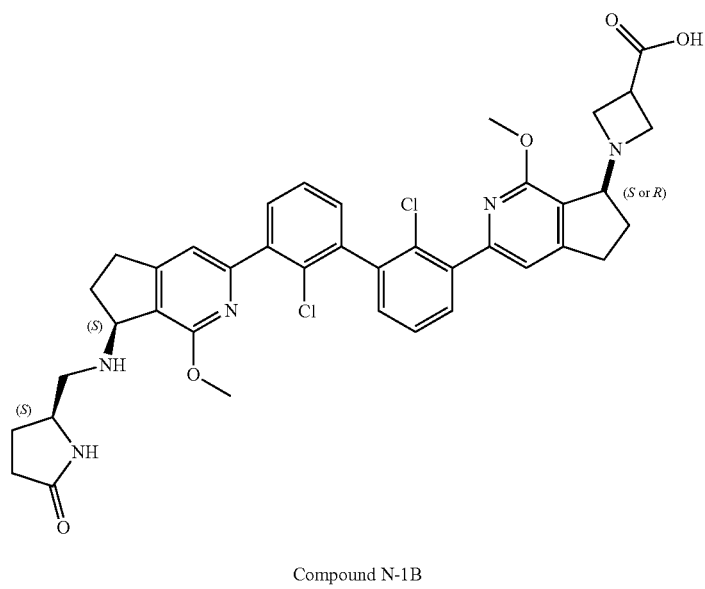

Compound N-1B

To a solution of Compound N-1A (10 mg, 13.22 umol) in the solvent mixture of EtOH (0.3 mL), THF (0.2 mL) and $H_2O$ (0.1 mL) was added $LiOH \cdot H_2O$ (5.55 mg, 132.15 μmol). The mixture was stirred at 40° C. for 2 h, and then concentrated. The aqueous residue was diluted with $H_2O$ (1 mL), and then the pH was adjusted to ~6 with 4 M aqueous HCl. The aqueous residue was filtered and purified by prep-HPLC. After lyophilization, Compound N-1B (4.76 mg, 99% purity) was obtained as a white solid with 1 eq. of formate.

The compounds shown in Table S1-6 were prepared by an analogous reaction protocol as was used for the preparation of Compound N-1B using the appropriate starting materials.

TABLE S1-6
| Cmpd No. | Structure | Salt | Starting materials |
|---|---|---|---|
| N-2B | (structure shown) | | N-2A |
| N-3B | (structure shown) | | N-3A |
Example 23
Preparation of Compound O-1
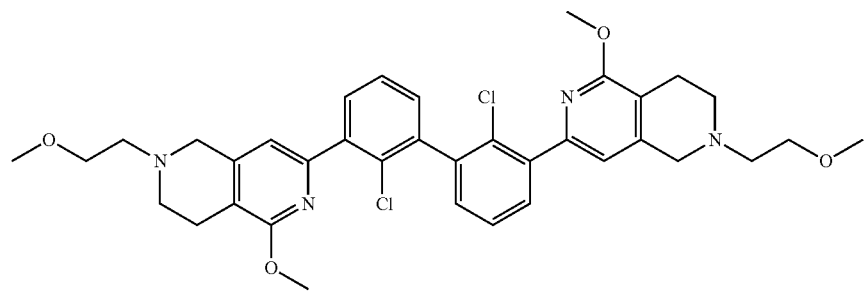
Compound O-1

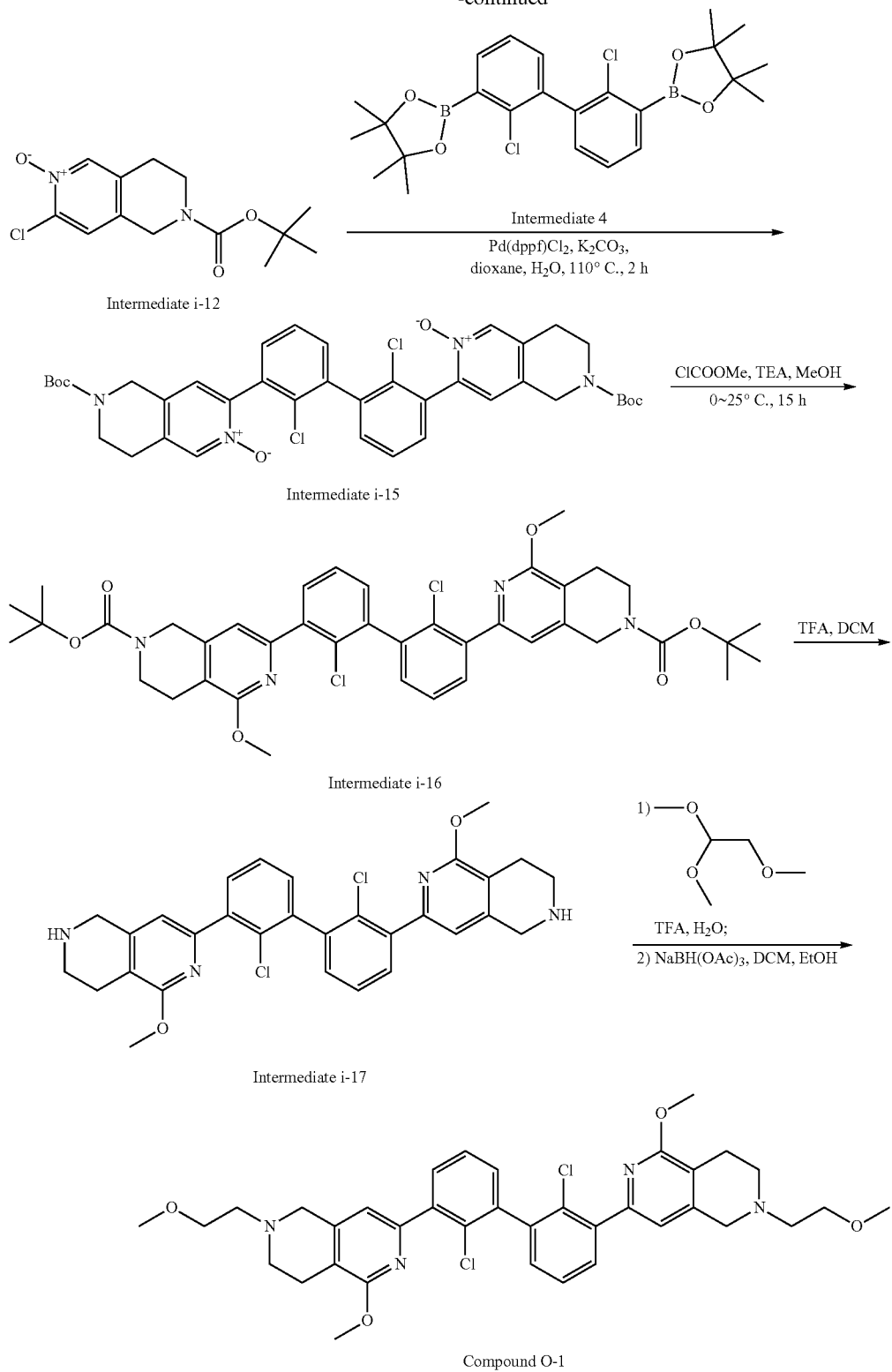

A mixture of Intermediate i-12 (5.45 g, 19.1 mmol), Intermediate 4 (4.55 g, 9.57 mmol), Pd(dppf)Cl₂ (700 mg, 957 μmol) and K₂CO₃ (3.97 g, 28.71 mmol) in dioxane (60 mL) and H₂O (3 mL) was degassed and purged with N₂ (3×). The mixture was stirred at 110° C. for 2 h under N₂ atmosphere. The mixture was filtered and concentrated in vacuo, diluted with H₂O (150 mL) and extracted with EtOAc (3×200 mL). The combined organic layers were washed with brine (2×200 mL), dried over anhydrous Na₂SO₄, filtered and concentrated under reduced pressure to give a residue. The residue was purified by flash silica gel chromatography. Intermediate i-15 (3.37 g, 90% purity) was obtained as a brown solid.

To a solution of Intermediate i-15 (500 mg, 695 μmol) in MeOH (7 mL) was added was added methyl carbonochloridate (250 μL, 3.23 mmol) and TEA (500 μL, 3.60 mmol) at 0° C. The mixture was stirred at 20° C. for 15 h. The mixture was concentrated under reduced pressure. The residue was diluted with sat. aq. NaOH (80 mL) and extracted with DCM (2×100 mL). The combined organic layers were washed with brine (150 mL), dried over anhydrous $Na_2SO_4$, filtered and concentrated under reduced pressure to give a residue. The residue was purified by flash silica gel chromatography. Intermediate i-16 (80 mg, 83% purity) was obtained as a yellow oil.

To a solution of Intermediate i-16 (80 mg) in DCM (1 mL) was added TFA (1 mL) at 20° C. The mixture was stirred at 20° C. for 1 h. The mixture was concentrated under reduced pressure to give Intermediate i-17 (60 mg, crude) was obtained as a yellow oil, which was used directly for next step without purification.

A mixture of 1,1,2-trimethoxyethane (57 μL, 438 μmol,), TFA (32 μL, 438 μmol) in $H_2O$ (33 μL 1.80 mmol) was stirred at 50° C. for 15 mins. The mixture was removed from the heating bath. TEA (61 μL, 438 μmol) was added, followed a solution of Intermediate i-17 (60 mg, 110 μmol) in DCM (0.5 mL) and EtOH (0.5 mL). To the resulting mixture was added $NaBH(OAc)_3$ (93 mg, 438 μmol), and the mixture was stirred at 25° C. for 3 h. The mixture was filtered and concentrated under reduced pressure to give a residue. The residue was purified by prep-HPLC. After lyophilization, Compound O-1 (16 mg, 97% purity) was obtained as an off-white solid.

Example 24

Preparation of Compound O-2A

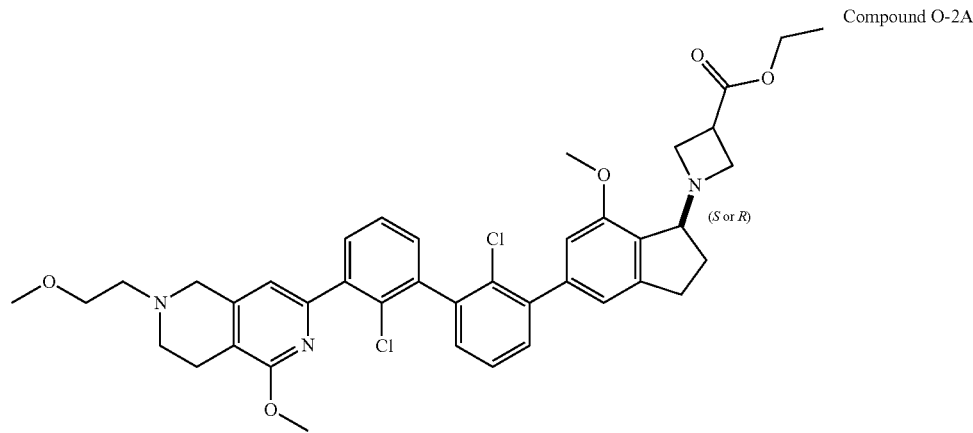 [SMILES: CCOC(=O)C1CN([C@H]2CCc3cc(-c4cccc(-c5cccc(-c6cc7c(c(OC)n6)CCN(CCOC)C7)c5Cl)c4Cl)cc(OC)c32)C1]

Compound O-2A

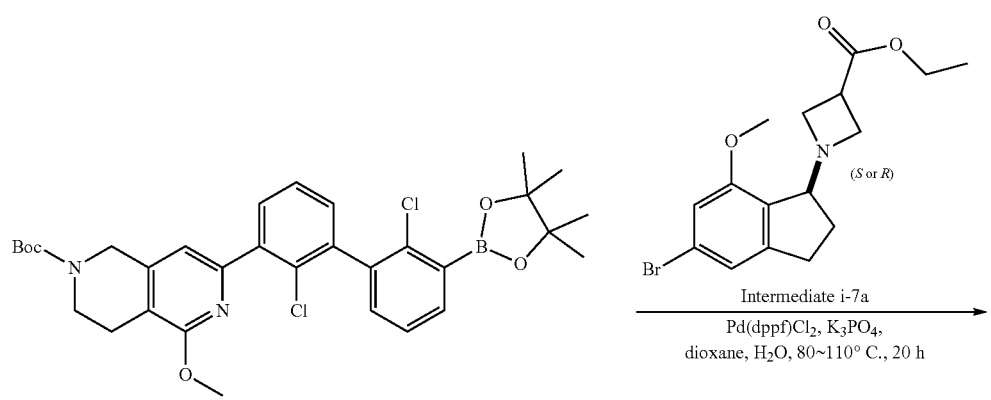

Intermediate i-14

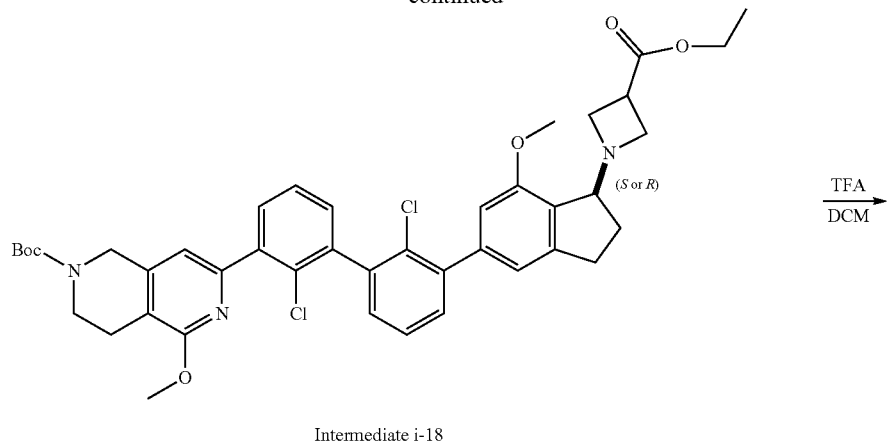

Intermediate i-18

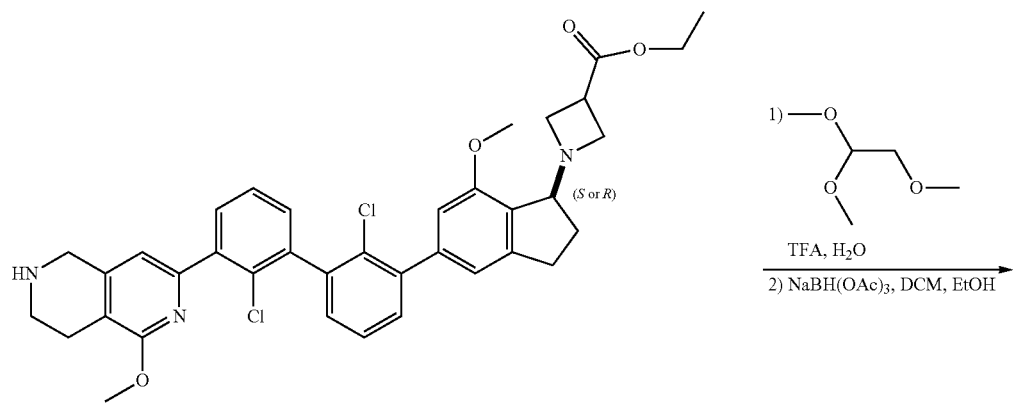

Intermediate i-19

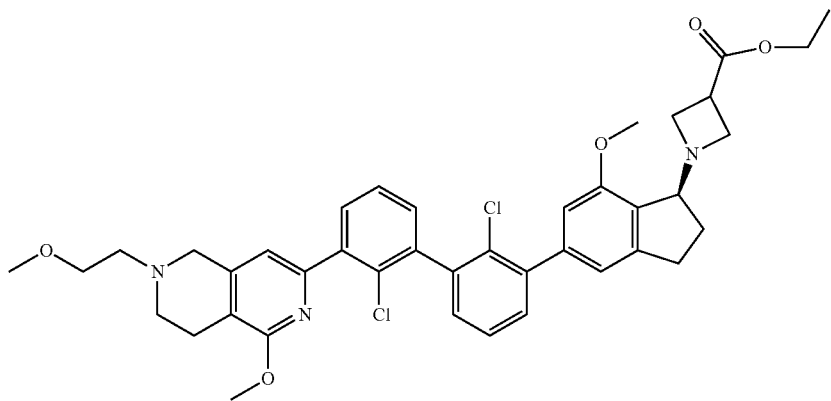

Compound O-2A

A mixture of Intermediate i-14 (370 mg), Intermediate i-7a (375 mg, 1.06 mmol), Pd(dppf)Cl$_2$ (31 mg, 42 µmol) and K$_2$CO$_3$ (176 mg, 1.27 mmol) in dioxane (8 mL) and H$_2$O (0.8 mL) was degassed and purged with N$_2$ (3×). The mixture was stirred at 110° C. for 16 h under a N$_2$ atmosphere. The mixture was filtered and concentrated in vacuo. The residues were diluted with H$_2$O (80 mL) and extracted with EtOAc (3×80 mL). The combined organic layers were washed with brine (100 mL), dried over anhydrous Na$_2$SO$_4$, filtered and concentrated under reduced pressure to give a residue. The residue was purified by flash silica gel chromatography to provide Intermediate i-18 as a yellow solid.

To a solution of Intermediate i-18 (450 mg, 70% purity) in DCM (9 mL) was added TFA (4.50 mL) at 0° C. The mixture was stirred at 20° C. for 5 h, and then concentrated under reduced pressure. The residue was poured into sat. aq. NaHCO₃ (100 mL) and extracted with DCM (2×100 mL). The combined organic layers were washed with brine (2×80 mL), dried over anhydrous Na₂SO₄, filtered and concentrated under reduced pressure to give Intermediate i-19 (crude) as a yellow solid, which was used directly for the next step without purification.

A mixture of 1,1,2-trimethoxyethane (58.72 µL, 455.50 µmol) and TFA (45 µL, 607 µmol) in H₂O (45 µL) was stirred at 50° C. for 15 mins. The mixture was removed from the heating bath. TEA (85 µL, 607.34 µmol) was added, followed by a solution of Intermediate i-19 (200 mg, crude) in DCM (2 mL) and EtOH (2 mL). To the mixture was added NaBH(OAc)₃ (257 mg, 1.21 mmol), and then stirred at 25° C. for 3 h. The mixture was concentrated under reduced pressure. The residue was purified by prep-HPLC. After lyophilization, Compound O-2A (85 mg, 98% purity) was obtained as a yellow solid with 2 eq of HCl.

Example 25

Preparation of Compound O-2B

To a solution of Compound O-2A (330 mg, 460 µmol) in EtOH (3 mL), THF (2 mL) and H₂O (1 mL) was added LiOH·H₂O (193 mg, 4.60 mmol). The mixture was stirred at 40° C. for 2 h. The mixture was concentrated to remove EtOH and THF. The aqueous residue was diluted with H₂O (1 mL), and the pH was adjusted to ~6 with 4 M aqueous HCl. The residue was purified by prep-HPLC. Compound O-2B (144 mg, 99% purity) was obtained as an off-white solid 1 eq of formate.

Example 26

Additional Compounds

Other compounds that can be prepared applying similar procedures as those described herein include the following:

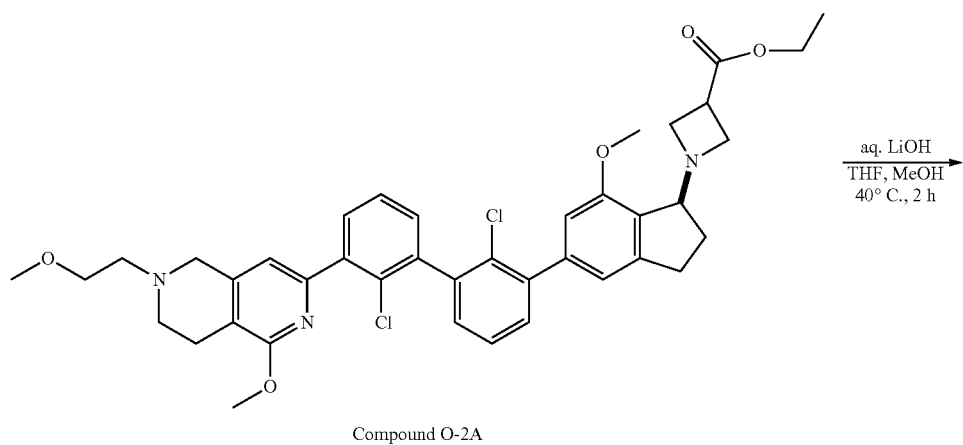

Compound O-2A

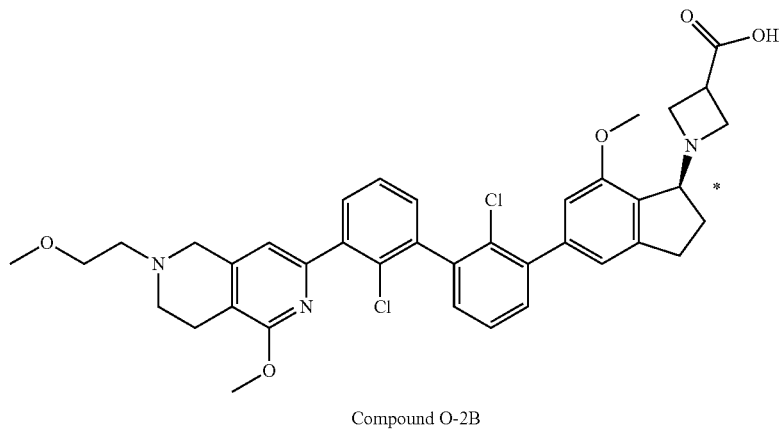

Compound O-2B

305
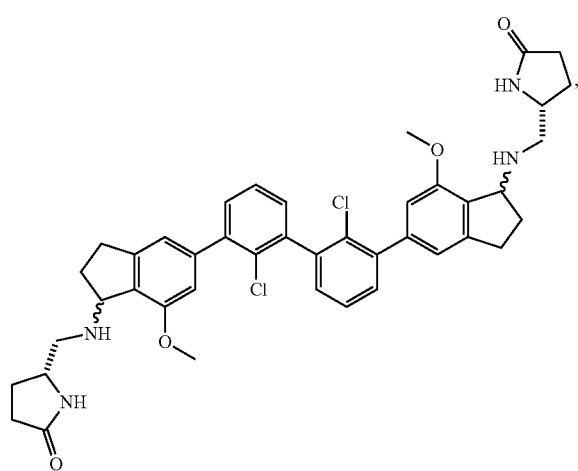
306
-continued
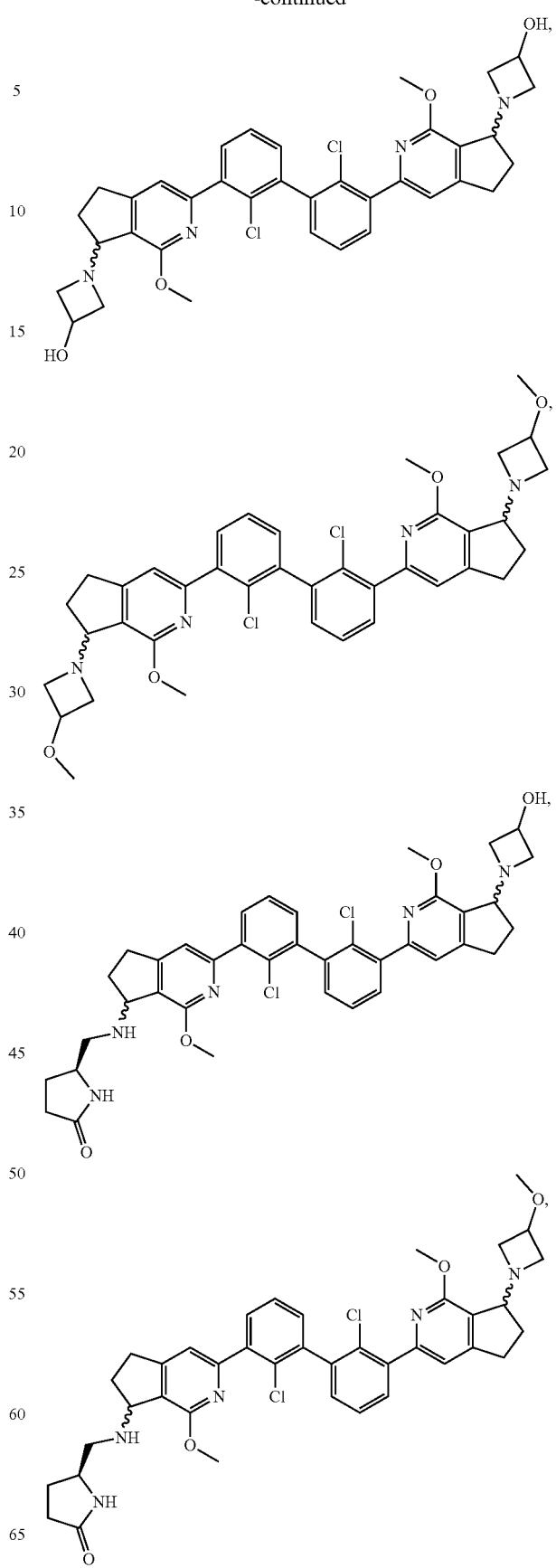

307
-continued
308
-continued
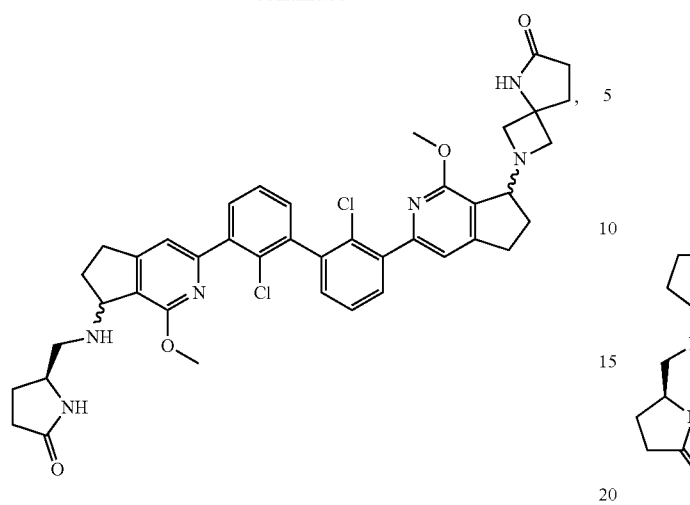
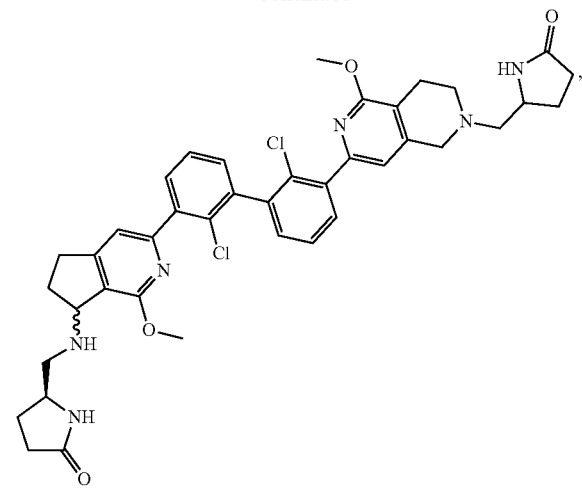
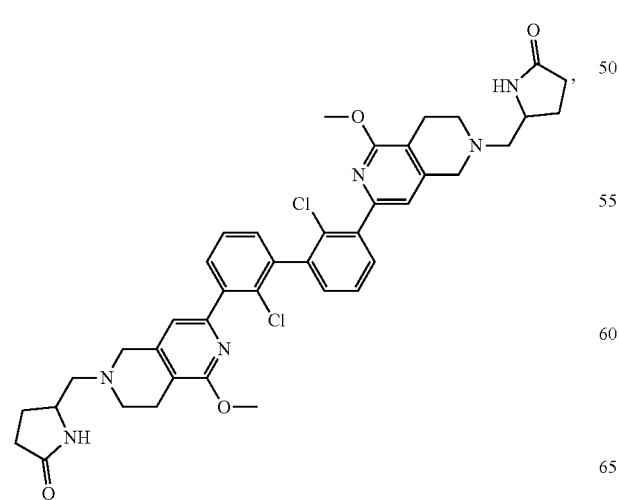

-continued

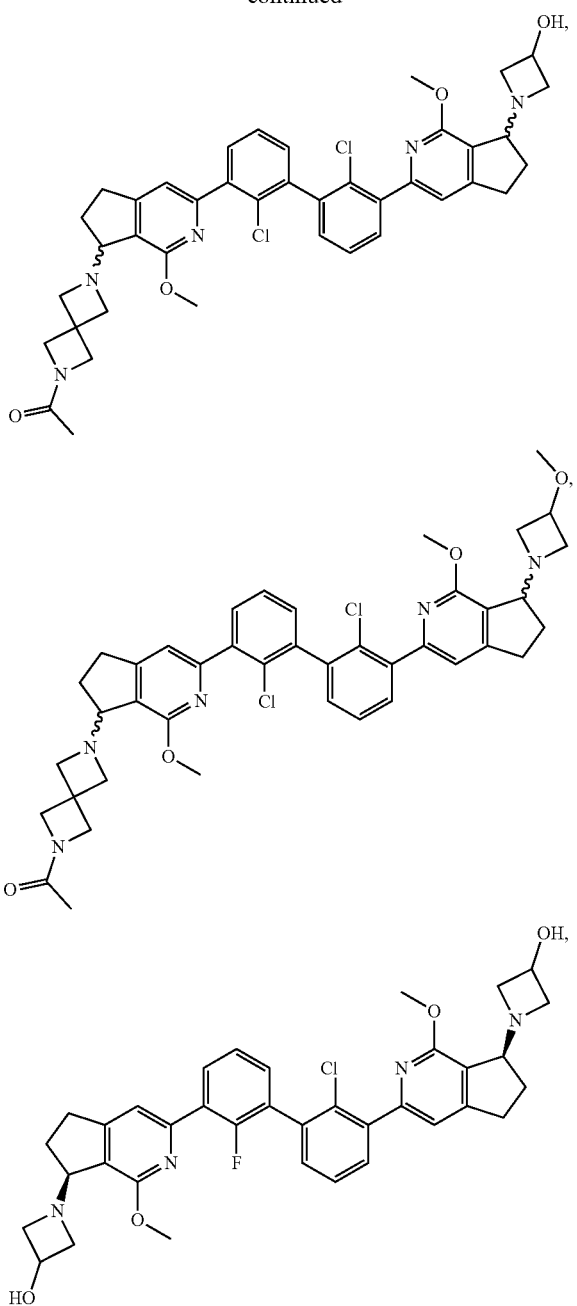

-continued

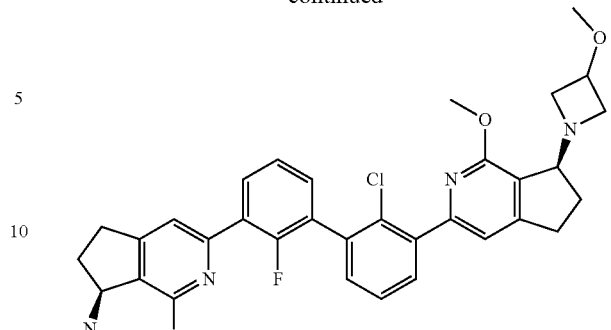

(including pharmaceutically acceptable salts of any of the foregoing).

Example A

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below). Flow from the column was brought to the Mass Spectrometer (MS) which was configured with an atmospheric pressure ion source. It is within the knowledge of the skilled person to set the tune parameters (e.g. scanning range, dwell time) in order to obtain ions allowing the identification of the compound's nominal monoisotopic molecular weight (MW). Data acquisition was performed with appropriate software. Compounds are described by their experimental retention times (Rt) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+Na]$^+$, [M+HCOO]$^-$, etc.). For molecules with multiple isotopic patterns (Br, Cl), the reported value is the one obtained for the lowest isotope mass. All results were obtained with experimental uncertainties that are commonly associated with the method used. Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof Quadrupole Time-off light mass spectrometers, "CLND", ChemiLuminescent Nitrogen Detector, "ELSD" Evaporative Light Scanning Detector.

TABLE A

LCMS Method Codes

| Method code | Instrument | Column | Mobile phase | Gradient | Flow T | Run Time |
|---|---|---|---|---|---|---|
| 1 | Shimadzu LCMS2020 | Chromolith ® Flash RP-18e 25-3 mm | A: water(4 L) + TFA(1.5 mL) B: acetonitrile (4 L) + TFA (0.75 mL) | from 95% A to 5% A in 0.7 minutes and holding at 5% for 0.4 minutes, to 95% A in 0.01 min held for 0.49 min | 1.50 | 1.5 |

TABLE A-continued

LCMS Method Codes

| Method code | Instrument | Column | Mobile phase | Gradient | Flow T | Run Time |
|---|---|---|---|---|---|---|
| 2 | Shimadzu LC20-MS2020 | Agilent Pursit 5 C18 20*2.0 mm | A: water(4 L) + TFA(1.5 mL) B: acetonitrile (4 L) + TFA (0.75 mL) | from 95% A to 5% A in 0.7 minutes and holding at 5% for 0.4 minutes, to 95% A in 0.01 min held for 0.39 min | 1.5 50 | 1.5 |
| 3 | Shimadzu LCMS2020 | Xbrige Shield RP-18.5 um, 2.1 *50 mm | A: water(4 L) + $NH_3H_2O$ (0.8 mL) B: acetonitrile (4 L) | from 90% A to 20% A in 3 minutes and holding at 20% for 0.5 minutes, to 90% A in 0.01 min held for 0.49 min | 1.0 50 | 4.0 |
| 4 | Shimadzu LCMS2020 | Xtimate ® C18 2.1*30 mm, 3 um | A: water(4 L) + TFA(1.5 mL) B: acetonitrile (4 L) + TFA (0.75 mL) | from 95% A to 5% A in 3 minutes and holding at 5% for 0.5 minutes, to 95% A in 0.01 min held for 0.49 min | 1.0 50 | 4.0 |
| 5 | Shimadzu LCMS2020 | Xtimate ® C18 2.1*30 mm, 3 um | A: water(4 L) + TFA(1.5 mL) B: acetonitrile (4 L) + TFA (0.75 mL) | from 95% A to 5% A in 3 minutes and holding at 5% for 0.5 minutes, to 95% A in 0.01 min held for 0.49 min | 1.2 50 | 4.0 |
| 6 | Shimadzu LCMS2020 | Xtimate C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.0 50 | 4.0 |
| 7 | Shimadzu LCMS2020 | Xtimate ® C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.2 50 | 4.0 |
| 8 | Shimadzu LCMS2020 | Xtimate C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.0 50 | 4.0 |
| 9 | Shimadzu LCMS2020 | Xtimate ® C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.2 50 | 4.0 |
| 10 | Shimadzu LCMS2020 | Xtimate C18 2.1*30 mm, 3 um | A: water(4 L) + TFA(1.5 mL) B: acetonitrile (4 L) + TFA (0.75 mL) | From 90% A to 20% A in 3 minutes and holding at 20% for 0.5 minutes, to 90% A in 0.01 min held for 0.49 min | 1.0 50 | 4.0 |

Flow expressed in mL/min; column temperature (T) in ° C.; Run time in minutes

TABLE B

LCMS

| Cmpd No. | Rt | LC/MS | LCMS Method |
|---|---|---|---|
| A-1 | 0.95 | 601 | 3 |
| A-2 | 0.76 | 573 | 1 |
| A-3 | 0.69 | 655 | 2 |
| A-4 | 1.34 | 655 | 10 |
| A-5 | 1.39 | 601 | 10 |
| A-6 | 1.31 | 701 | 10 |
| A-7 | 1.73 | 583 | 10 |
| A-8 | 1.34 | 625 | 10 |
| B-1 | 0.76 | 485 | 1 |
| B-2 | 0.73 | 457 | 1 |
| B-3 | 0.68 | 487 | 1 |
| B-4 | 0.75 | 487 | 4 |
| B-5 | 1.26 | 519 | 5 |
| B-6 | 1.52 | 485 | 9 |
| B-7 | 1.31 | 468 $[M-NH_3 + H]^+$ | 8 |
| B-8 | 1.49 | 468 $[M-NH_3 + H]^+$ | 9 |
| B-9 | 1.04 | 541 | 9 |
| B-10 | 1.53 | 521 | 9 |

TABLE B-continued

| Cmpd No. | Rt | LC/MS | LCMS Method |
|---|---|---|---|
| B-11 | 1.70 | 565 | 9 |
| B-12 | 1.57 | 541 | 9 |
| B-13 | 1.76 | 513 | 8 |
| B-14 | 1.39 | 513 | 8 |
| B-15 | 1.43 & 1.52 | 513 | 8 |
| B-16 | 1.35 | 513 | 10 |
| B-17 | 1.33 | 545 | 10 |
| C-1 | 1.46 | 661 | 5 |
| C-2 | 1.52 | 689 | 5 |
| C-3 | 1.23 | 691 | 5 |
| C-4 | 1.15 | 691 | 5 |
| C-5 | 1.28 | 723 | 8 |
| C-6 | 1.50 | 689 | 8 |
| C-7 | 1.61 | 745 | 9 |
| C-8 | 1.53 | 725 | 9 |
| C-9 | 1.59 | 717 | 9 |
| C-11 | 1.386 | 717 | 9 |
| C-12 | 1.601 | 717 | 5 |
| C-13 | 1.552 | 749 | 9 |
| D-1 | 1.70 & 1.75 | 773 | 9 |
| E-1 | 1.40 & 1.49 | 717 | 9 |
| F-1 | 2.21 | 657 | 8 |
| G-1 | 1.32 | 451 | 8 |
| | | $[M-C_4H_{10}N_2O_4 + H]^{4+}$ | |
| H-1 | 1.58 | 601 | 9 |
| H-2 | 0.95 | 601 | 9 |
| H-3 | 1.72 | 681 | 9 |
| H-4 | 1.62 | 657 | 9 |
| I-1 | 1.41 | 713 | 5 |
| J-1 | 1.64 | 715 | 9 |
| K-1 | 2.05 | 563 | 9 |
| K-2 | 2.72 | 671 | 9 |
| L-1 | 1.31 | 741.6 | 6 |
| L-2 | 1.33 | 741.5 | 6 |
| L-3 | 1.14 | 741.5 | 6 |
| L-4 | 1.71 | 769.5 | 6 |
| L-5 | 1.70 | 769.5 | 6 |
| L6 | 1.58 | 709.5 | 6 |
| L-7 | 1.56 | 709.4 | 6 |
| L-8 | 1.36 | 725.6 | 6 |
| L-9 | 1.36 | 749.6 | 6 |
| L-10 | 1.40 | 777.7 | 6 |
| L-11 | 1.40 | 777.6 | 6 |
| M-1A | 1.58 | 741.4 | 6 |
| M-1B | 1.44 | 715.3 | 6 |
| M-2A | 1.46 | 681.4 | 6 |
| M-2B | 1.36 | 653.4 | 6 |
| M-3A | 1.45 | 681.4 | 6 |
| M-3B | 1.36 | 653.5 | 6 |
| M-4B | 1.48 | 713.4 | 6 |
| N-1A | 1.31 | 756.5 | 6 |
| N-2A | 1.50 | 754.5 | 7 |
| N-3A | 1.46 | 754.6 | 6 |
| N-1B | 1.18 | 728.5 | 6 |
| N-2B | 1.34 | 726.5 | 6 |
| N-3B | 1.37 | 726.5 | 6 |
| O-1 | 3.17 | 663.3 | 3 |
| O-2A | 1.37 | 716.5 | 6 |
| O-2B | 1.28 | 688.5 | 6 |

Retention time ($R_t$) in min; LC/MS: without indication the mass is corresponding to $[M + H]^+$ Example B PDL1/PD1 Binding Assay Compounds to be tested were serially diluted in DMSO, and further diluted in assay buffer (25 mM Hepes pH 7.4, 150 mM NaCl, 0.005% Tween 20, BSA 0.01%). Diluted compounds were added to the wells with final concentration of DMSO at 1%. PDL1-6×His protein was added to the wells, mixed well with compound. The plates were incubated for 30 min at room temperature. PD1-Fc-Avi-Biotin protein was added to the wells. Final concentration of PDL1 and PD1 protein is 0.3 nM and 2.5 nM, respectively. After a binding time of 30 min at room temperature, Anti-6×His Acceptor beads (final concentration 20 ug/ml) were added to the wells, and the incubation continued for 1 h. Streptavidin Donor beads (final concentration 20 ug/mL) were added at reduced light. The plates were sealed with foil and incubated in the dark for additional 1 h or overnight before reading on an Envision reader. The $IC_{50}$s were determined by fitting the curves using a four-parameter equation in Graphpad Prism 8.

Example C

PDL1 Dimerization Assay

Serially diluted compounds were added to plate wells with the final concentration of DMASO at 1%. PDL1-6×His and PDL1-strep proteins were diluted in assay buffer (25 mM Hepes pH 7.4, 150 mM NaCl, 0.005% Tween 20, BSA 0.01%), added to the wells, and mixed well with the compounds. The plates were incubated for 2 h at room temperature. Anti-6×His Acceptor beads were added to the wells and the plates were further incubated for 1 h at room temperature. Strep-tactin Donor beads were added to the wells at reduced light. After additional 1 h incubation in the dark, the plates were read on a Envision reader. The final concentrations were 0.5 nM PDL1-6×His, 0.5 nM PDL1-strep, 20 ug/mL Anti-6×His Acceptor beads, 20 ug/mL Strep-tactin Donor beads. The $EC_{50}$ values were determined by fitting the curves using a four-parameter equation in Graphpad Prism 8.

Example D

PD-1/PD-L1 NFAT Reporter Assay

Cellular activity of the compounds was assessed using a co-culture reporter assay in which TCR-mediated NF-AT activity of Jurkat T cells is constitutively inhibited by the engagement of PD-1 by PD-L1 expressing CHO cells. Blocking the PD-1/PD-L1 interaction will release the inhibitory signal and results in TCR signaling and NFAT-mediated luciferase activity.

CHO cells expressing surface-bound anti-CD3 antibodies and PD-L1 were first seeded overnight and treated with the compounds. Jurkat cells overexpressing PD-1 and a luciferase construct under NF-AT promoter were then immediately seeded on the monolayer of CHO cells. The co-culture was then incubated for 6 hrs at 37° C. Luciferase activity was assessed by adding the ONE-Glo reagent and measuring luminescence with a plate reader. EC50s values were determined from the fit of the dose-response curves Compounds described herein, as exemplified in the Examples, showed $IC_{50}$ values in the following ranges: A=≤10 nM; B=>10 nM≤ to ≤100 nM; C=>100 nM to ≤1000 nM; D=>1000 nM $IC_{50}$ to ≤10000 nM; E=>10000 nM; n.d.=not determined.

TABLE C

| Cmpd No. | PD-1/PD-L1 PPI $IC_{50}$ |
|---|---|
| A-1 | A |
| A-2 | B |

TABLE C-continued

| Cmpd No. | PD-1/PD-L1 PPI IC$_{50}$ |
|---|---|
| A-3 | B |
| A-4 | B |
| A-5 | A |
| A-6 | A |
| A-7 | C |
| A-8 | C |
| B-1 | A |
| B-2 | B |
| B-3 | B |
| B-4 | B |
| B-5 | C |
| B-6 | n.d. |
| B-7 | C |
| B-8 | C |
| B-9 | D |
| B-10 | B |
| B-11 | C |
| B-12 | D |
| B-13 | B |
| B-14 | C |
| B-15 | D |
| B-16 | C |
| B-17 | B |
| C-1 | A |
| C-2 | A |
| C-3 | C |
| C-4 | B |
| C-5 | D |
| C-6 | A |
| C-7 | C |
| C-8 | A |
| C-9 | A |
| C-11 | n.d. |
| C-12 | n.d. |
| C-13 | n.d. |
| D-1 | n.d. |
| E-1 | n.d. |
| F-1 | C |
| G-1 | n.d. |
| H-1 | A |
| H-2 | A |
| H-3 | C |
| H-4 | B |
| I-1 | E |
| J-1 | B |
| K-1 | D |
| K-2 | E |
| L-8 | A |
| L-9 | A |
| L-10 | A |
| L-11 | A |

Compounds described herein, as exemplified in the Examples, showed EC$_{50}$ or IC$_{50}$ values in the following ranges: A: IC$_{50}$ or EC$_{50}$≤10 nM; B: 10 nM<IC$_{50}$ or EC$_{50}$≤100 nM; C: 100 nM<IC$_{50}$ or EC$_{50}$≤1000 nM; D: 1000 nM<IC$_{50}$ or EC$_{50}$≤10000 nM; E: IC$_{50}$ or EC$_{50}$>10000 nM; n.d.=not determined; n.r.=EC$_{50}$ not reached in the range of tested concentrations starting from 1 nM to 10000 nM.

TABLE C-1:

| Cmpd No. | Biological Data Biochem PD-1/PD-L1 | PD-1/PD-L1 NFAT Reporter Assay |
|---|---|---|
| L-1 |  | B |
| L-2 |  | n.r. |
| L-3 |  | A |
| L-4 | A | C |
| L-5 | C | n.r |
| L-6 | A | D |
| L-7 | A | C |
| L-8 | A | A |
| L-9 | A | A |
| L-10 | A | n.r. |
| L-11 | A | A |
| M-1A | A | C |
| M-1B | A | C |
| M-2A | A | C |
| M-2B | A | C |
| M-3A | A | C |
| M-3B | A | C |
| M-4B | B | n.r |
| N-1A |  | B |
| N-2A |  | n.r |
| N-3A |  | B |
| N-1B |  | A |
| N-2B |  | C |
| N-3B |  | B |
| O-1 | A | D |
| O-2A |  | C |
| O-2B |  | B |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the present disclosure.

What is claimed is:

1. A compound of Formula (I), or a pharmaceutically acceptable salt thereof, having the structure:

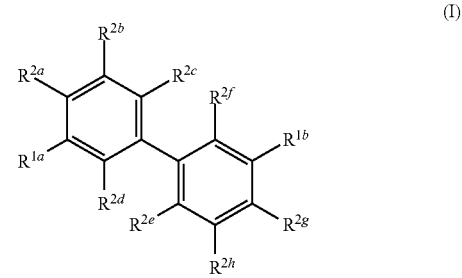

wherein:

R$^{1a}$ is selected from the group consisting of:

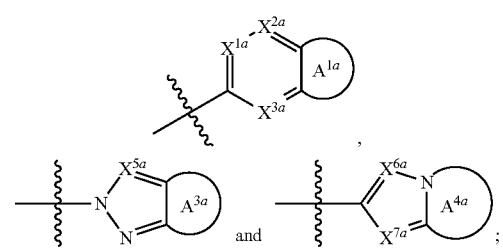

Ring $A^{1a}$, Ring $A^{3a}$ and Ring $A^{4a}$ are independently selected from the group consisting of:
- a monocyclic $C_{5-7}$ cycloalkyl substituted with $R^{3a1}$;
- a bicyclic $C_{6-12}$ cycloalkyl substituted with $R^{3a2}$;
- a 5-7 membered nitrogen-containing monocyclic heterocyclyl, wherein a nitrogen of the 5-7 membered nitrogen-containing monocyclic heterocyclyl is optionally substituted with $R^{3a3}$, wherein a carbon of the 5-7 membered nitrogen-containing monocyclic heterocyclyl is optionally substituted with $R^{3a4}$ or $R^{3a5}$, and wherein when $R^{3a5}$ is present, $R^{3a5}$ is attached at a carbon atom adjacent to a nitrogen of the 5-7 membered nitrogen-containing monocyclic heterocyclyl;
- a 6-12 membered nitrogen-containing bicyclic heterocyclyl, wherein a nitrogen of the 6-12 membered nitrogen-containing bicyclic heterocyclyl is optionally substituted with $R^{3a6}$; wherein a carbon of the 6-12 membered nitrogen-containing bicyclic heterocyclyl is optionally substituted with $R^{3a7}$ or $R^{3a8}$, and wherein $R^{3a8}$ is present, $R^{3a8}$ is attached at the carbon atom adjacent to a nitrogen of the 6-12 membered nitrogen-containing bicyclic heterocyclyl; and
- a 5-7 membered oxygen-containing monocyclic heterocyclyl substituted with $R^{3a9}$ or $R^{3a10}$; wherein $R^{3a10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens;

wherein Ring $A^{1a}$, Ring $A^{2a}$, Ring $A^{3a}$ and Ring $A^{4a}$ is optionally further substituted;
wherein when $R^{1a}$ is

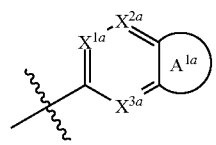

and Ring $A^{1a}$ is a 5-7 membered nitrogen-containing monocyclic heterocyclyl, then $R^{3a3}$ is present;
wherein when $R^{1a}$ is

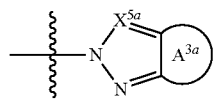

and Ring $A^{3a}$ is a 5-7 membered nitrogen-containing monocyclic heterocyclyl, then $R^{3a3}$ is present;
wherein when $R^{1a}$ is

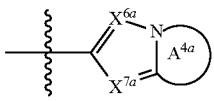

then Ring $A^{4a}$ cannot be a monocyclic $C_{5-7}$ cycloalkyl substituted with $R^{3a1}$ or a bicyclic $C_{6-12}$ cycloalkyl substituted with $R^{3a2}$; and wherein when $R^{1a}$ is

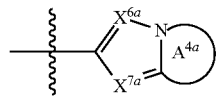

and Ring $A^{4a}$ is a 5-7 membered nitrogen-containing monocyclic heterocyclyl, then $R^{3a3}$ is present;
$X^{1a}$, $X^{2a}$ and $X^{3a}$ are independently N or $CR^{4a1}$;
$X^{5a}$, $X^{6a}$ and $X^{7a}$ are independently N or $CR^{4a3}$;
$R^{1b}$ is selected from the group consisting of:

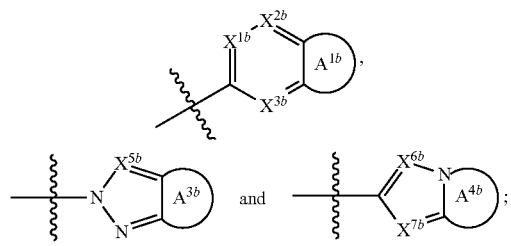

Ring $A^{1b}$, Ring $A^{3b}$ and Ring $A^{4b}$ are independently selected from the group consisting of:
- a monocyclic $C_{5-7}$ cycloalkyl substituted with $R^{3b1}$;
- a bicyclic $C_{6-12}$ cycloalkyl substituted with $R^{3b2}$;
- a 5-7 membered nitrogen-containing monocyclic heterocyclyl, wherein a nitrogen of the 5-7 membered nitrogen-containing monocyclic heterocyclyl is optionally substituted with $R^{3b3}$, wherein a carbon of the 5-7 membered nitrogen-containing monocyclic heterocyclyl is optionally substituted with $R^{3b4}$ or $R^{3b5}$, and wherein when $R^{3b5}$ is present, $R^{3b5}$ is attached at a carbon atom adjacent to a nitrogen of the 5-7 membered nitrogen-containing monocyclic heterocyclyl;
- a 6-12 membered nitrogen-containing bicyclic heterocyclyl, wherein a nitrogen of the 6-12 membered nitrogen-containing bicyclic heterocyclyl is optionally substituted with $R^{3b6}$; wherein a carbon of the 6-12 membered nitrogen-containing bicyclic heterocyclyl is optionally substituted with $R^{3b7}$ or $R^{3b8}$, and wherein $R^{3b8}$ is present, $R^{3b8}$ is attached at the carbon atom adjacent to a nitrogen of the 6-12 membered nitrogen-containing bicyclic heterocyclyl; and
- a 5-7 membered oxygen-containing monocyclic heterocyclyl substituted with $R^{3b9}$ or $R^{3b10}$; wherein $R^{3b10}$ is attached at a carbon atom adjacent to an oxygen of the 5-7 membered oxygen-containing monocyclic heterocyclyl, and the 5-7 membered oxygen-containing monocyclic heterocyclyl does not include any ring nitrogens;

wherein Ring $A^{1b}$, Ring $A^{2b}$, Ring $A^{3b}$ and Ring $A^{4b}$ is optionally further substituted;
wherein when $R^{1b}$ is

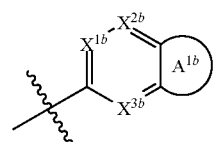

and Ring $A^{1b}$ is a 5-7 membered nitrogen-containing monocyclic heterocyclyl, then $R^{3b3}$ is present;

wherein when $R^{1b}$ is

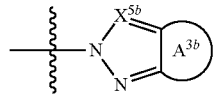

and Ring $A^{3b}$ is a 5-7 membered nitrogen-containing monocyclic heterocyclyl, then $R^{3b3}$ is present;

wherein when $R^{1b}$ is

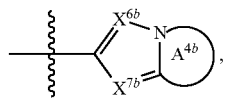

then Ring $A^{4b}$ cannot be a monocyclic $C_{5-7}$ cycloalkyl substituted with $R^{3b1}$ or a bicyclic $C_{6-12}$ cycloalkyl substituted with $R^{3b2}$; and wherein when $R^{1b}$ is

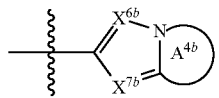

and Ring $A^{4b}$ is a 5-7 membered nitrogen-containing monocyclic heterocyclyl, then $R^{3b3}$ is optional;

$X^{1b}$, $X^{2b}$ and $X^{3b}$ are independently N or $CR^{4b1}$;

$X^{5b}$, $X^{6b}$ and $X^{7b}$ are independently N or $CR^{4b3}$;

$R^{3a1}$, $R^{3a2}$, $R^{3a9}$, $R^{3b1}$, $R^{3b2}$ and $R^{3b9}$ are independently selected from the group consisting of —OH, —N($R^m$)$R^n$, —$C_{1-4}$ alkyl-N($R^m$)$R^n$, —$OC_{2-4}$ alkyl-N($R^m$)$R^n$,

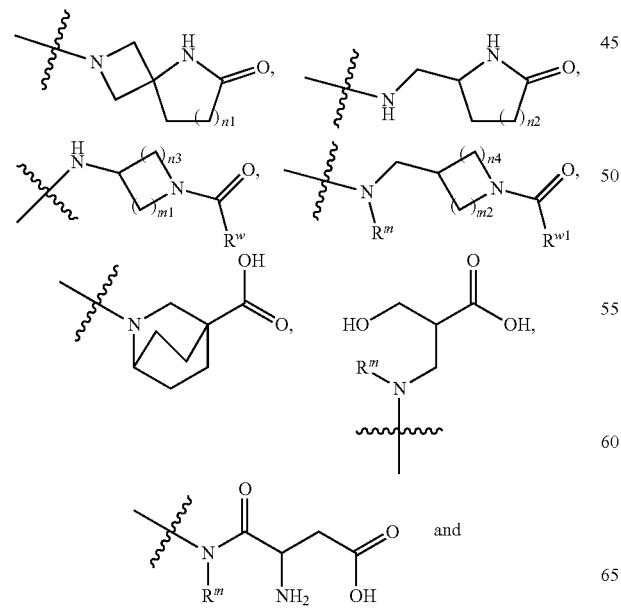

and

-continued

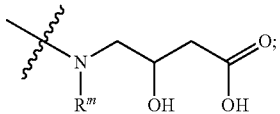

$R^{3a3}$, $R^{3b3}$, $R^{3a6}$ and $R^{3b6}$ are independently selected from the group consisting of —$R^{x1}$, $C_{1-4}$ alkyl, $C_{3-7}$ cycloalkyl, —C(=O)$C_{1-4}$ alkyl and -$Het^{a1}$, wherein the —$C_{3-7}$ cycloalkyl, the —C(=O)$C_{1-4}$ alkyl and the -$Het^{a1}$ is optionally substituted with one or two or three substituents selected from the group consisting of -halogen, —$C_{1-4}$ alkyl, —OH, —N($R^m$)$R^n$, —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N($R^m$)$R^n$, wherein the —$C_{1-4}$ alkyl is optionally substituted with one or two or three substituents selected from the group consisting of -halogen, —OH, —N($R^m$)$R^n$, $C_{1-4}$ alkoxy, —C(=O)OH, —C(=O)O$C_{1-4}$ alkyl, —C(=O)NHS(=O)$_2C_{1-4}$ alkyl, —NHC(=O)C alkyl and —C(=O)N($R^m$)$R^n$;

$R^{3a4}$, $R^{3a7}$, $R^{3b4}$ and $R^{3b7}$ are independently selected from the group consisting of -halogen, —$C_{1-4}$ alkyl, —$C_{3-7}$ cycloalkyl, —OH, —$OC_{1-4}$ alkyl, —N($R^m$)$R^n$, —$C_{1-4}$ alkyl($R^m$)$R^n$, —C(=O)OH, —$C_{1-4}$ alkyl-C(=O)OH, —C(=O)O$C_{1-4}$ alkyl and —$C_{1-4}$ alkyl-C(=O)O$C_{1-4}$ alkyl; wherein the —$C_{1-4}$ alkyl, is optionally substituted with one or two substituents selected from the group consisting of -halogen, —OH, —$C_{1-4}$ alkoxy, —C(=O)OH, —C(=O)O$C_{1-4}$ alkyl, —C(=O)NHS(=O)$_2C_{1-4}$ alkyl, —NHC(=O)$C_{1-4}$ alkyl and C(=O)N($R^m$)$R^n$, and wherein the —$C_{3-7}$ cycloalkyl and the —$OC_{1-4}$ alkyl is optionally substituted with one or two substituents selected from the group consisting of -halogen, —OH, —$C_{1-4}$ alkyl, —$C_{1-4}$ alkoxy, C(=O)OH, —C(=O)O$C_{1-4}$ alkyl, —C(=O)NHS(=O)$_2C_{1-4}$ alkyl, —NHC(=O)$C_{1-4}$ alkyl and —C(=O)N($R^m$)$R^n$, $R^{3a5}$, $R^{3a8}$, $R^{3b5}$ and $R^{3b8}$ are independently selected from the group consisting of —C(=O)OH, —$C_{1-4}$ alkyl and —$C_{3-7}$ cycloalkyl; wherein the —$C_{1-4}$ alkyl is optionally substituted with one or two or three substituents selected from the group consisting of -halogen, —OH, $C_{1-4}$ alkoxy, —C(=O)OH, —C(=O)O$C_{1-4}$ alkyl, —C(=O)NHS(=O)$_2C_{1-4}$ alkyl, —N($R^m$)C(=O)$C_{1-4}$ alkyl, —C(=O) N($R^m$)$R^n$ and —N($R^m$)$R^n$, and wherein the —$C_{3-7}$ cycloalkyl is optionally substituted with one or two or three substituents selected from the group consisting of -halogen, —OH, —$C_{1-4}$ alkyl, —$C_{1-4}$ alkoxy, —C(=O)OH, —C(=O)O$C_{1-4}$ alkyl, —C(=O)NHS(=O)$_2C_{1-4}$ alkyl, —N($R^m$)C(=O)$C_{1-4}$ alkyl, —C(=O) N($R^m$)$R^n$ and —N($R^m$)$R^n$;

$R^{3a10}$ and $R^{3b10}$ are independently selected from the group consisting of —$C_{1-4}$ alkyl, —$C_{3-7}$ cycloalkyl and —($C_{1-4}$ alkyl)N($R^m$)$R^n$, wherein the —$C_{1-4}$ alkyl is optionally substituted with one or two or three substituents selected from the group consisting of -halogen, OH, —$C_{1-4}$ alkoxy, —C(=O)OH, —(C=O)NHS(=O)$_2$($C_{1-4}$ alkyl) and —NHC(=O)$C_{1-4}$ alkyl, and wherein the —$C_{3-7}$ cycloalkyl and the —($C_{1-4}$ alkyl)N($R^m$)$R^n$ is optionally substituted with one or two or three substituents selected from the group consisting of -halogen, —OH, —$C_{1-4}$ alkyl, —$C_{1-4}$ alkoxy, —C(=O)OH, —C(=O)O$C_{1-4}$ alkyl, —(C=O)NHS(=O)$^2$($C_{1-4}$ alkyl) and —NHC(=O)$C_{1-4}$ alkyl;

each $R^m$ and each $R^n$ are independently selected from the group consisting of hydrogen, —$R^{x2}$, —$C_{1-4}$ alkyl, $C_{3-7}$ cycloalkyl, —C(=O)C$_{1-4}$ alkyl and -Het$^{a1}$, wherein the —C$_{1-4}$ alkyl, the —C$_{3-7}$ cycloalkyl and the —C(=O)C$_{1-4}$ alkyl is optionally substituted with one or two or three substituents selected from the group consisting of -halogen, —OH, -NH$_2$—C$_{1-4}$ alkyl, —OC$_{1-4}$ alkyl, C(=O)OH, —C(=O)OC$_{1-4}$ alkyl, —C(=O)NHS(=O)$_2$C$_{1-4}$ alkyl and —NHC(=O)C$_{1-4}$ alkyl; or R$^m$ and R$^n$ are taken together along with the atom to which R$^m$ and R$^n$ are attached to form an optionally substituted 4-7 monocyclic heterocyclic ring or an optionally substituted 7-10 bicyclic heterocyclic ring;

R$^{x1}$ and R$^{x2}$ are independently selected from the group consisting of:

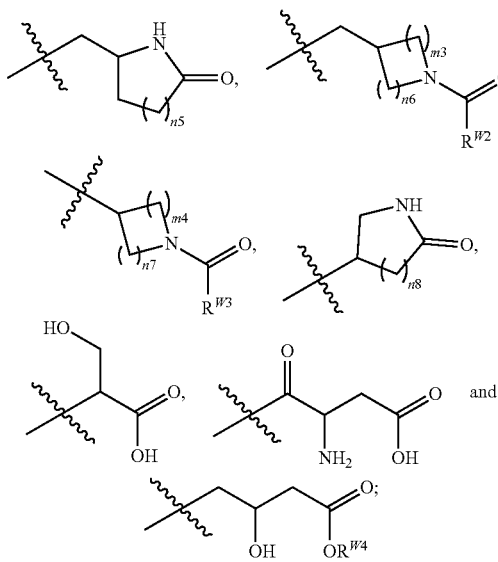

R$^W$, R$^{W1}$, R$^{W2}$, R$^{W3}$ and R$^{W4}$ are independently selected from the group consisting of an unsubstituted —C$_{1-4}$ alkyl and a substituted —C$_{1-4}$ alkyl substituted with one or two or three substituents selected from the group consisting of -halogen, —OH, —OC$_{1-4}$ alkyl, —C(=O)OH and —C(=O)OC$_{1-4}$ alkyl;

Het$^{a1}$ is an optionally substituted 5-, 6- or 7-membered monocyclic heteroaryl, an optionally substituted 4-, 5-, 6- or 7-membered monocyclic heterocyclyl, an optionally substituted fused 8-, 9-, 10- or 11-membered bicyclic heteroaryl or an optionally substituted fused 8-, 9-, 10- or 11-membered heterocyclyl, wherein each heteroaryl and each heterocyclyl contains at least one heteroatom independently selected from the group consisting of O, S, S(=O), S(=O)$_2$ and N;

n1, n2, n3, n4, n5, n6, n7 and n8 are independently 1 or 2;

m1, m2, m3 and m4 are independently 1 or 2;

R$^{2d}$ and R$^{2f}$ are independently selected from the group consisting of hydrogen, halogen, cyano, —CH$_3$, —CH$_2$CH$_3$, —CH$_2$OH, —OCH$_3$ and —SCH$_3$;

R$^{2a}$, R$^{2b}$, R$^{2c}$, R$^{2e}$, R$^{2g}$, R$^{2h}$ are independently selected from the group consisting of hydrogen and halogen;

R$^{4a1}$, R$^{4a3}$, R$^{4b1}$ and R$^{4b3}$ are selected from the group consisting of hydrogen, halogen, cyano, an unsubstituted C$_{1-4}$ alkyl, an unsubstituted C$_{1-4}$ haloalkyl, an unsubstituted C$_{1-4}$ alkoxy and an unsubstituted C$_{1-4}$ haloalkoxy.

2. The compound of claim 1, wherein R$^{1a}$ is

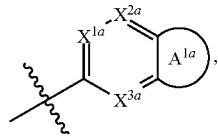

wherein X$^{1a}$ is N; X$^{2a}$ is CR$^{4a1}$, wherein R$^{4a1}$ is an unsubstituted C$_{1-4}$ alkoxy, X$^{3a}$ is CR$^{4a1}$, wherein R$^{4a1}$ is hydrogen; and R$^{1b}$ is

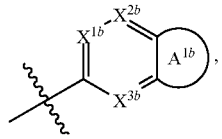

wherein X$^{1b}$ is N; X$^{2b}$ is CR$^{4b1}$, wherein R$^{4b1}$ is an unsubstituted C$_{1-4}$ alkoxy, and X$^{3b}$ is CR$^{4b1}$, wherein R$^{4b1}$ is hydrogen.

3. The compound of claim 2, wherein Ring A$^{1a}$ is a monocyclic C$_{5-7}$ cycloalkyl substituted with R$^{3a1}$; and Ring A$^{1b}$ is a monocyclic C$_{5-7}$ cycloalkyl substituted with R$^{3b1}$.

4. The compound of claim 2, wherein Ring A$^{1a}$ is a 5-7 membered nitrogen-containing monocyclic heterocyclyl, wherein a nitrogen of the 5-7 membered nitrogen-containing monocyclic heterocyclyl is substituted with R$^{3a3}$, wherein a carbon of the 5-7 membered nitrogen-containing monocyclic heterocyclyl is optionally substituted with R$^{3a4}$ or R$^{3a5}$, and wherein when R$^{3a5}$ is present, R$^{3a5}$ is attached at a carbon atom adjacent to a nitrogen of the 5-7 membered nitrogen-containing monocyclic heterocyclyl; and Ring A$^{1b}$ is a 5-7 membered nitrogen-containing monocyclic heterocyclyl, wherein a nitrogen of the 5-7 membered nitrogen-containing monocyclic heterocyclyl is substituted with R$^{3b3}$, wherein a carbon of the 5-7 membered nitrogen-containing monocyclic heterocyclyl is optionally substituted with R$^{3b4}$ or R$^{3b5}$, and wherein when R$^{3b5}$ is present, R$^{3b5}$ is attached at a carbon atom adjacent to a nitrogen of the 5-7 membered nitrogen-containing monocyclic heterocyclyl.

5. The compound of claim 3, wherein R$^{3a1}$ is —N(R$^m$)R$^n$; and R$^{3b1}$ is —N(R$^m$)R$^n$.

6. The compound of claim 3, wherein R$^{3a1}$ is

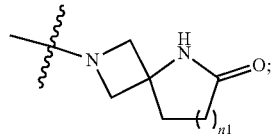

and R$^{3b1}$ is

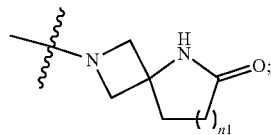

or wherein $R^{3a1}$ is

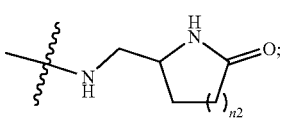

and $R^{3b1}$ is

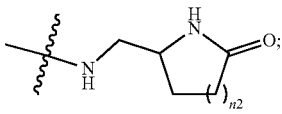

or wherein $R^{3a1}$ is

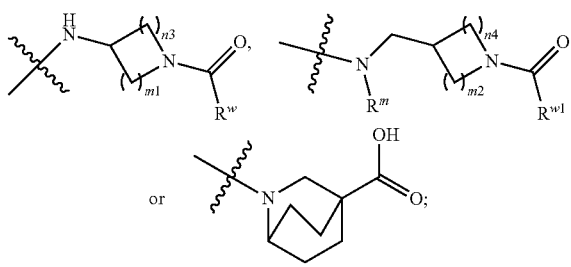

and $R^{3b1}$ is

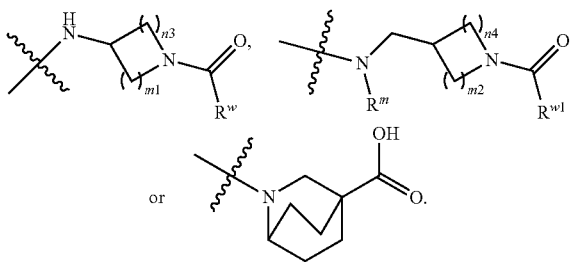

7. The compound of claim 4, wherein $R^{3a3}$ is hydrogen; and $R^{3b3}$ is hydrogen; or wherein $R^{3a3}$ is —$R^{x1}$; and $R^{3b3}$ is —$R^{x1}$.

8. The compound of claim 7, wherein each —$R^{x1}$ is

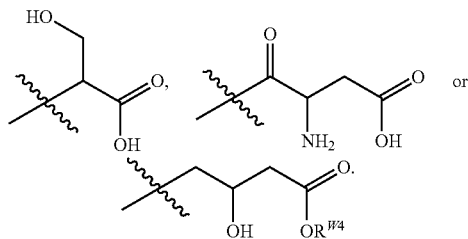

9. The compound of claim 3, wherein the monocyclic $C_{5-7}$ cycloalkyl substituted with $R^{3a1}$ is selected from the group consisting of:

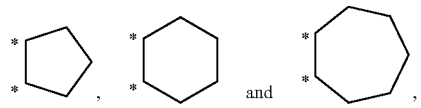

wherein asterisks indicate the position of the fused bond; and the monocyclic $C_{5-7}$ cycloalkyl substituted with $R^{3b1}$ is selected from the group consisting of:

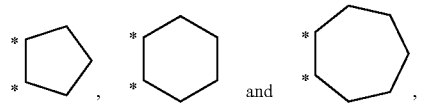

wherein asterisks indicate the position of the fused bond.

10. The compound of claim 4, wherein the 5-7 membered nitrogen-containing monocyclic heterocyclyl, wherein a nitrogen of the 5-7 membered nitrogen-containing monocyclic heterocyclyl is optionally substituted with $R^{3a3}$, wherein a carbon of the 5-7 membered nitrogen-containing monocyclic heterocyclyl is optionally substituted with $R^{3a4}$ or $R^{3a5}$, and wherein when $R^{3a5}$ is present, $R^{3a5}$ is attached at a carbon atom adjacent to a nitrogen of the 5-7 membered nitrogen-containing monocyclic heterocyclyl is selected from the group consisting of:

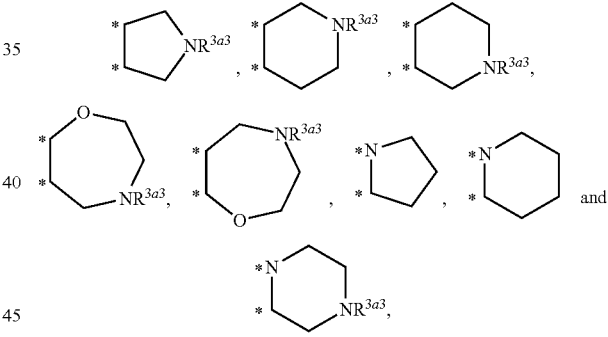

wherein asterisks indicate the position of the fused bond, and $R^{3a4}$ and $R^{3a5}$ are each optionally present; and the 5-7 membered nitrogen-containing monocyclic heterocyclyl, wherein a nitrogen of the 5-7 membered nitrogen-containing monocyclic heterocyclyl is optionally substituted with $R^{3b3}$, wherein a carbon of the 5-7 membered nitrogen-containing monocyclic heterocyclyl is optionally substituted with $R^{3b4}$ or $R^{3b5}$, and wherein when $R^{3b5}$ is present, $R^{3b5}$ is attached at a carbon atom adjacent to a nitrogen of the 5-7 membered nitrogen-containing monocyclic heterocyclyl is selected from the group consisting of:

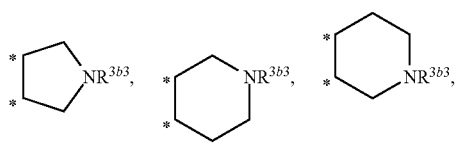

325
-continued

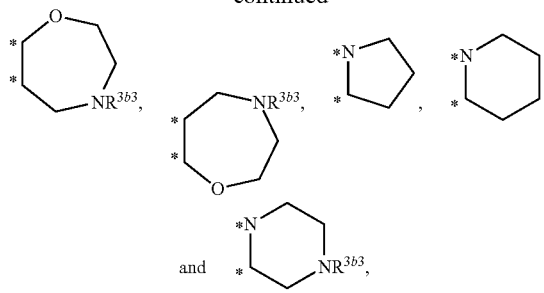

and

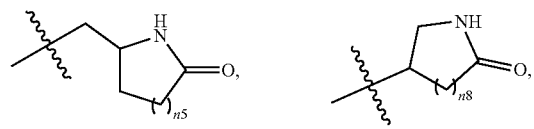

wherein asterisks indicate the position of the fused bond, and $R^{3b4}$ and $R^{3b5}$ are each optionally present.

11. The compound of claim 5, wherein each $R'''$ is —$R^{x2}$; and each $R''$ is hydrogen.

12. The compound of claim 11, wherein each —$R^{x2}$ is

326
-continued

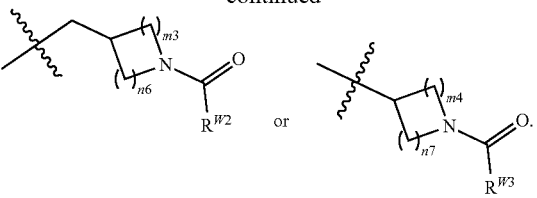

13. The compound of claim 5, wherein each $R'''$ and $R''$ are taken together along with the atom to which $R'''$ and $R''$ are attached to form an optionally substituted 4-7 monocyclic heterocyclic ring or an optionally substituted 7-10 bicyclic heterocyclic ring.

14. The compound of claim 1, wherein $R^{2a}$ is hydrogen; $R^{2b}$ is hydrogen; $R^{2c}$ is hydrogen; $R^{2d}$ is halogen; $R^{2e}$ is hydrogen; $R^{2f}$ is halogen; $R^{2g}$ is hydrogen; and $R^{2h}$ is hydrogen.

15. The compound of claim 1, wherein the compound is selected from the group consisting of:

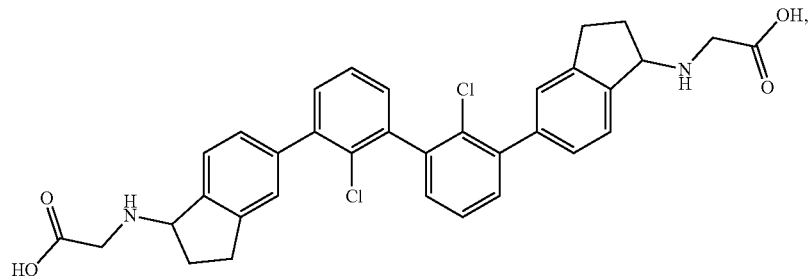

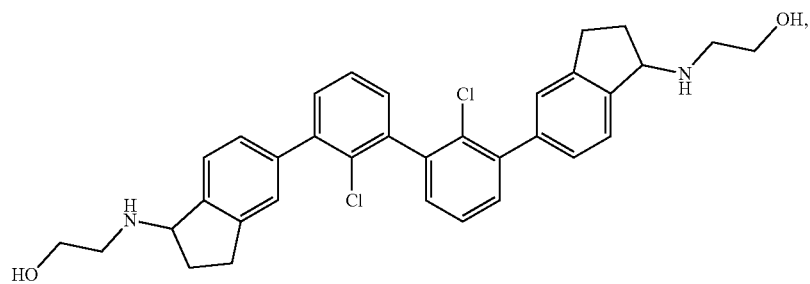

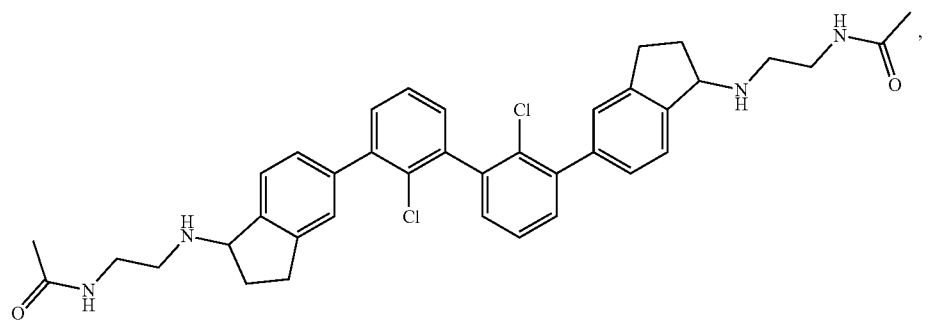

-continued
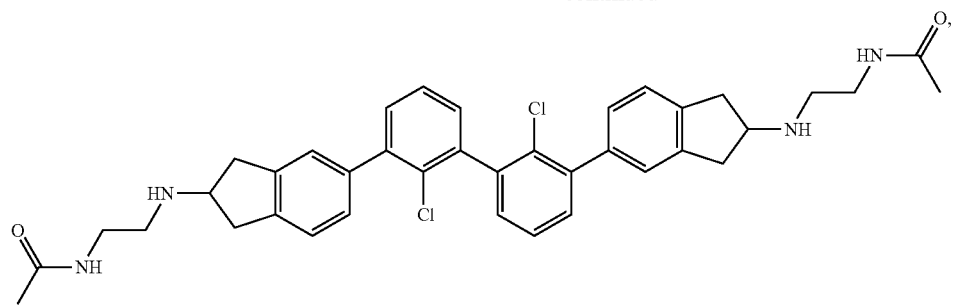
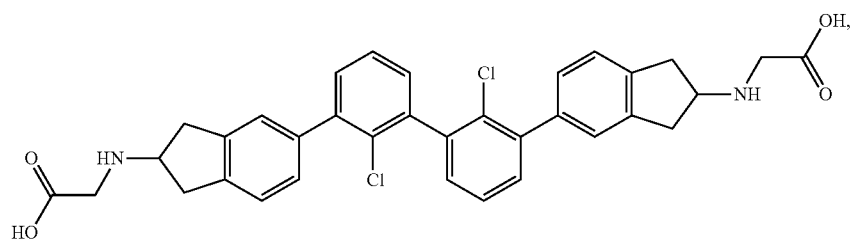
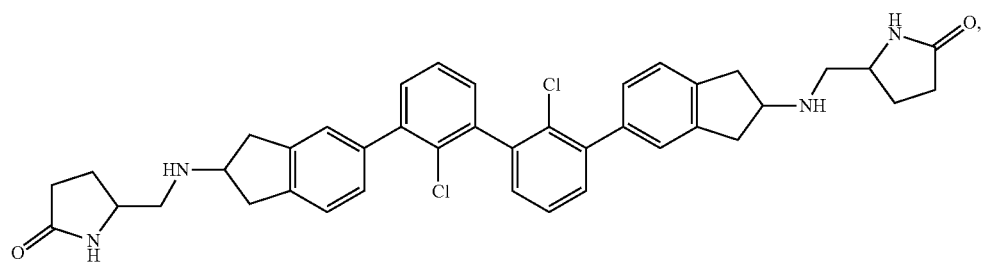
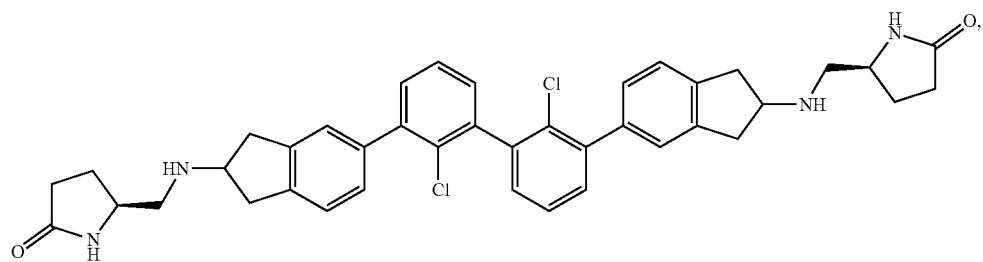
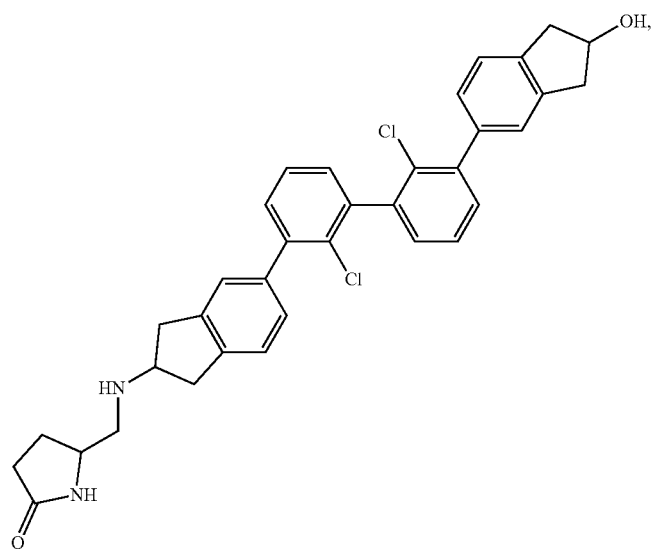

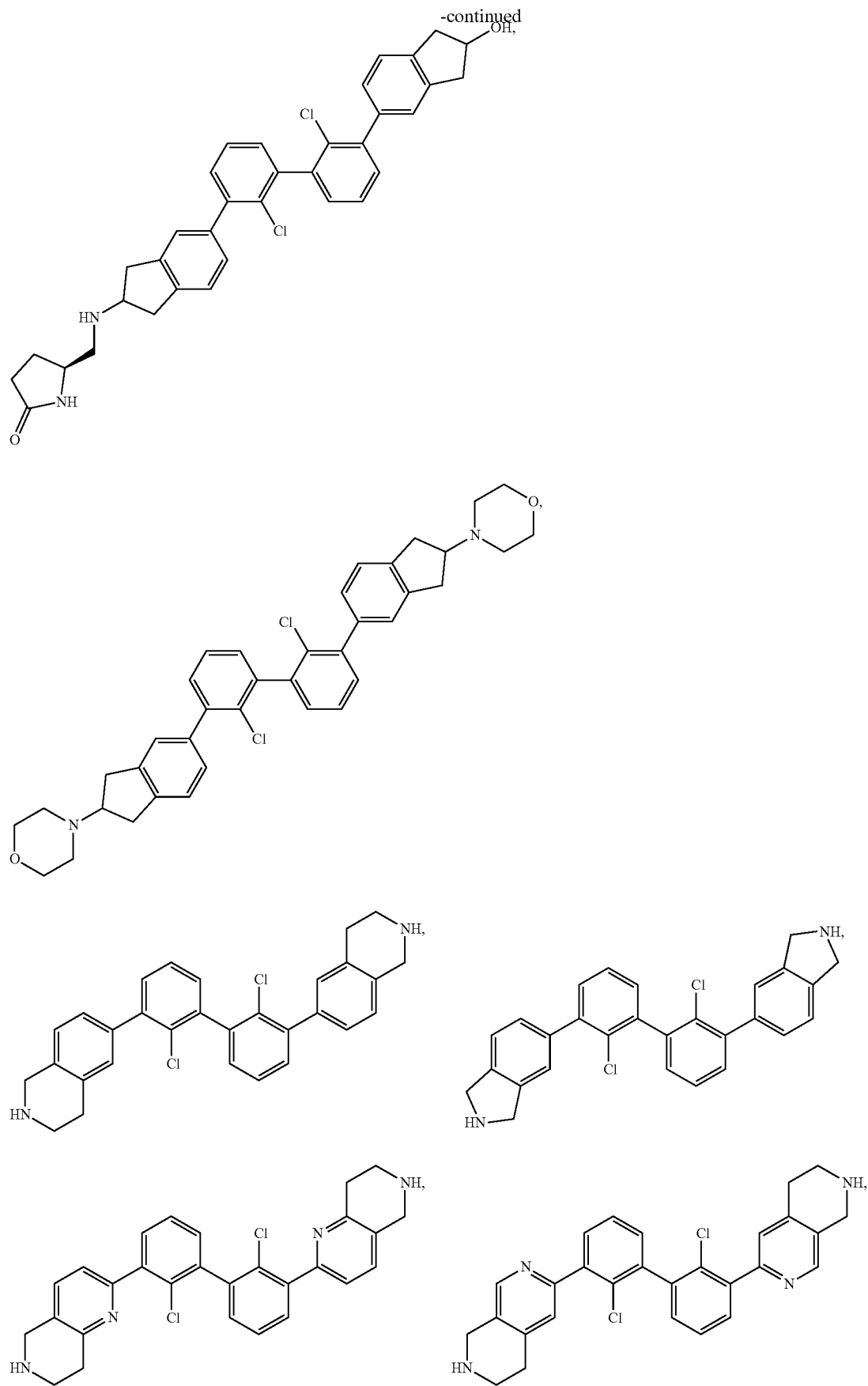

-continued
331 332
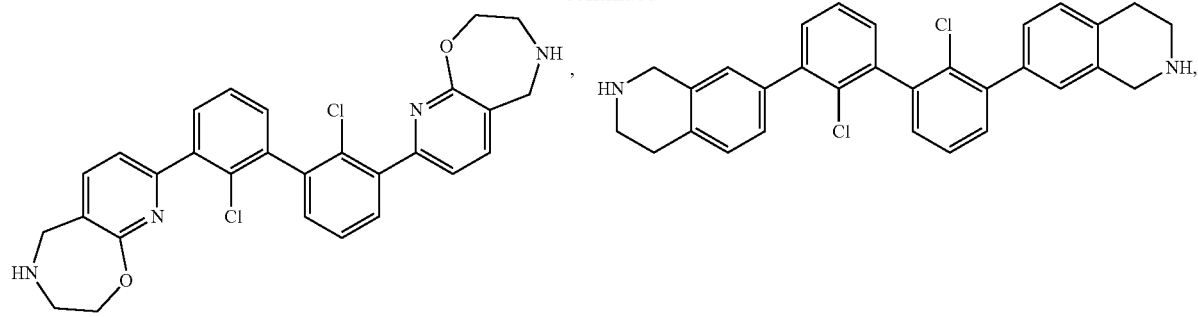
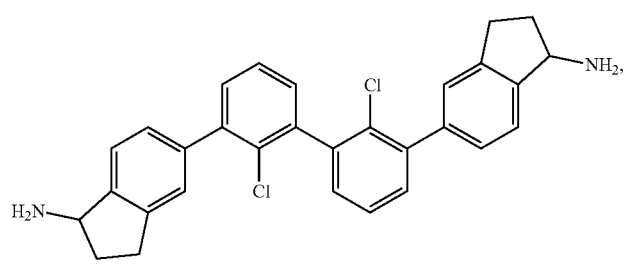
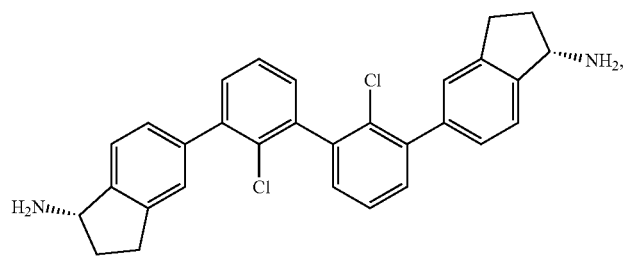
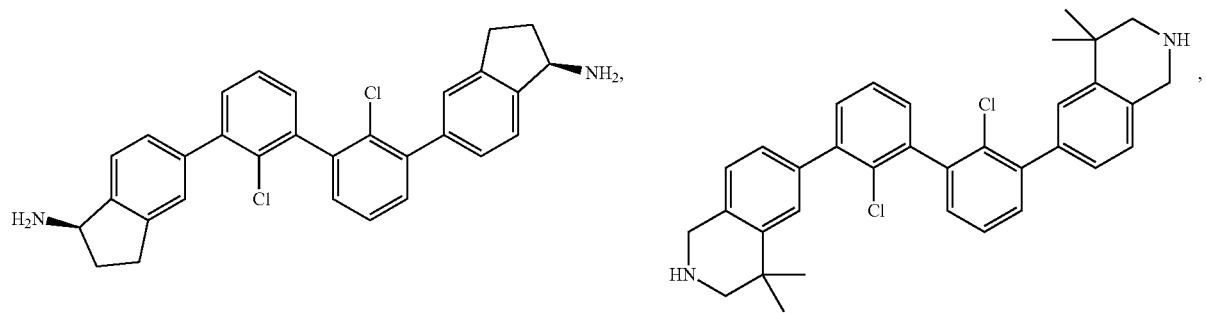
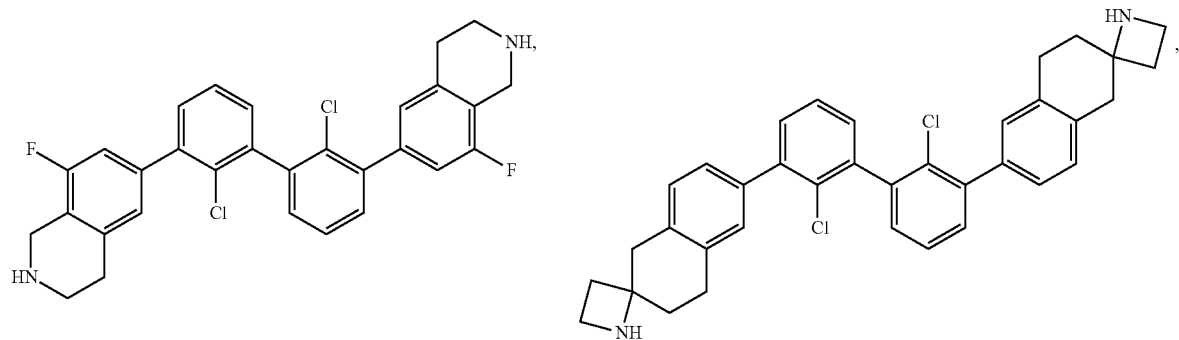

-continued
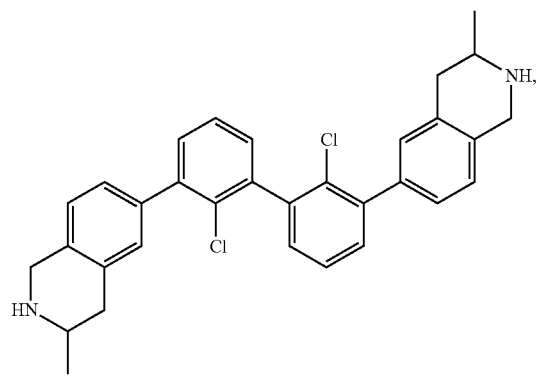
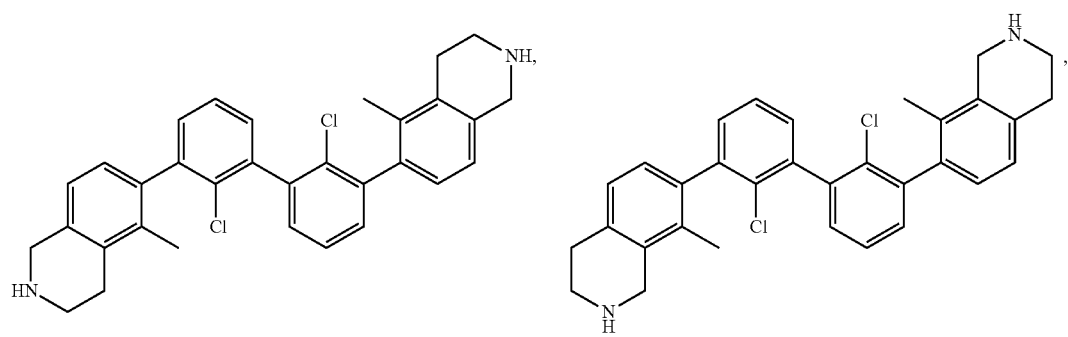
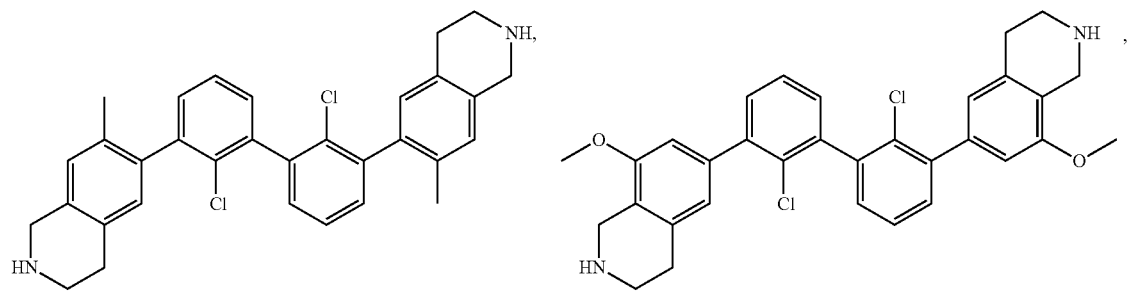
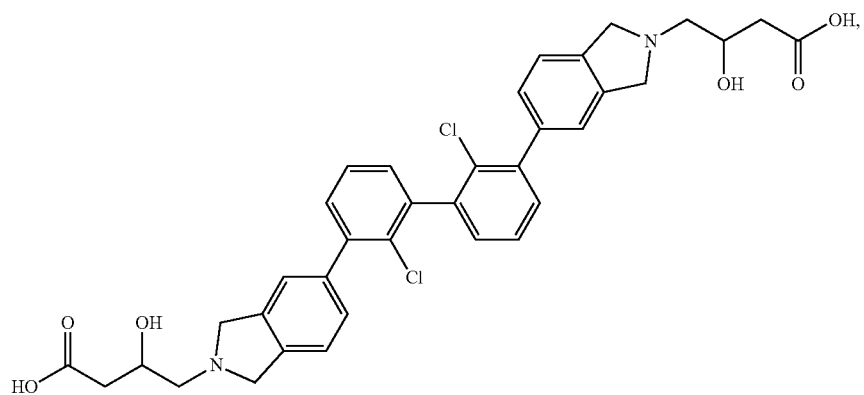

-continued
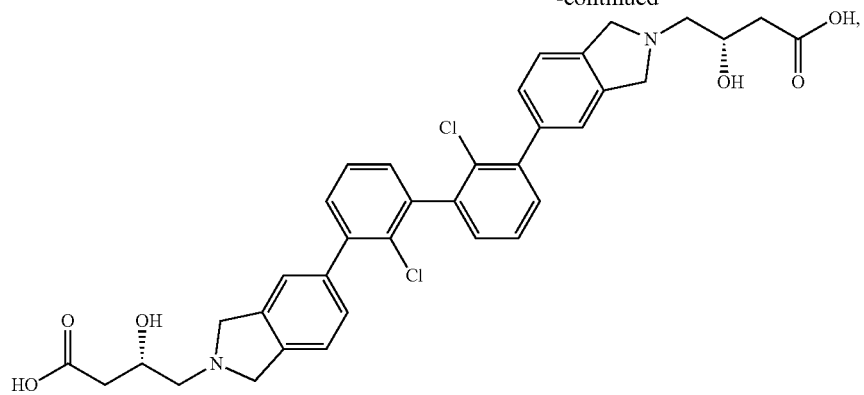
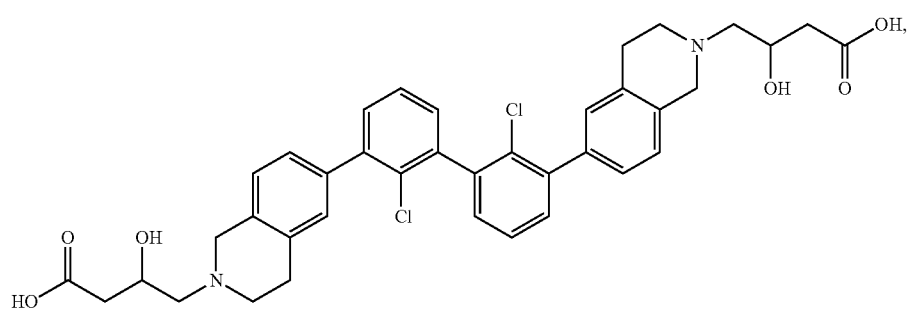
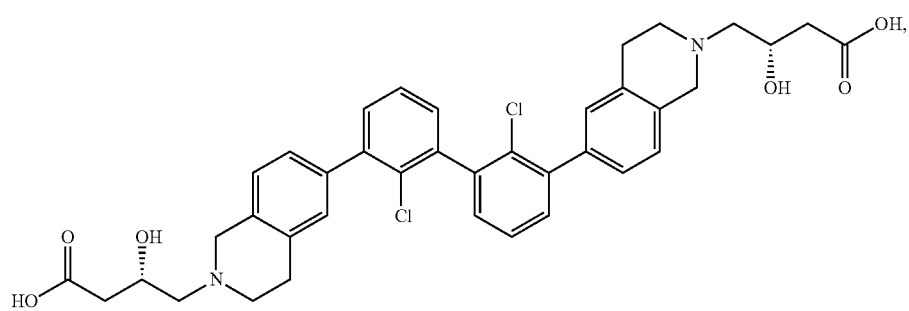
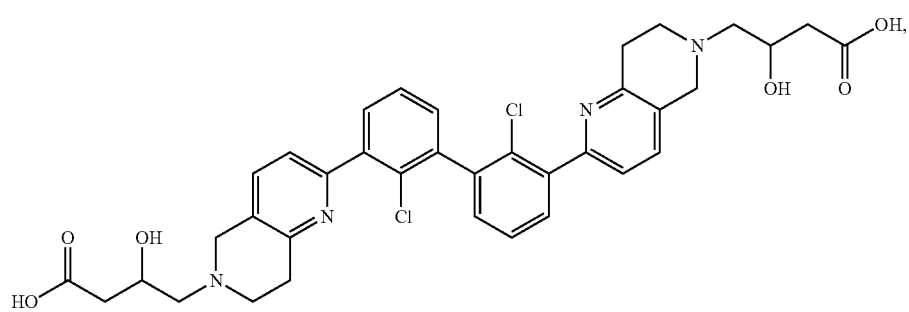
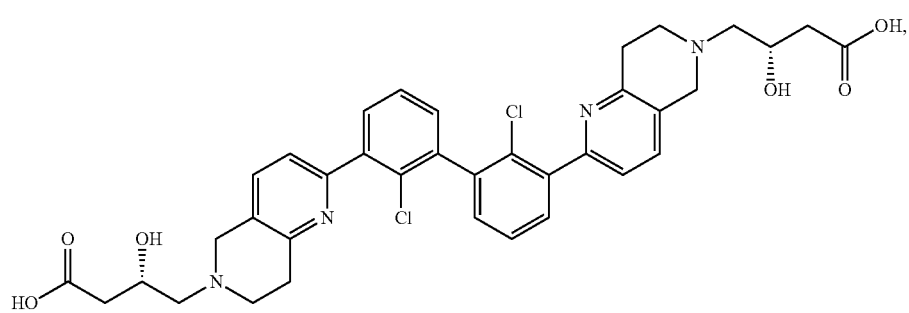

-continued
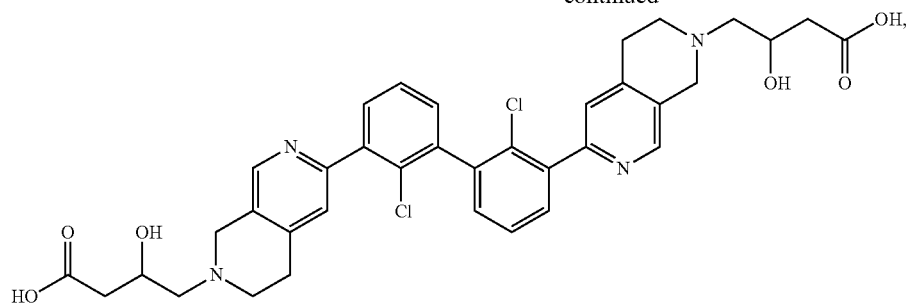
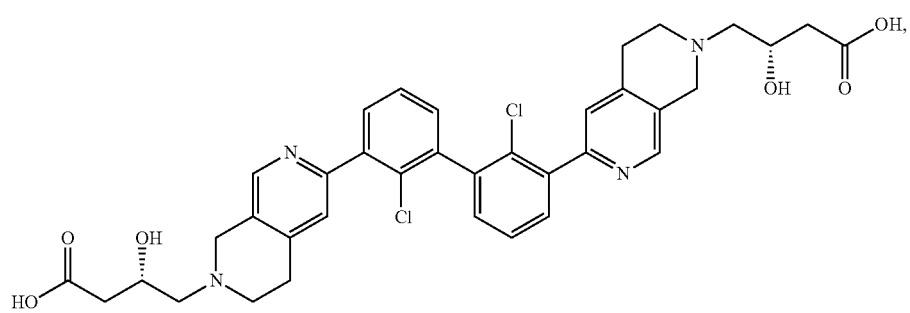
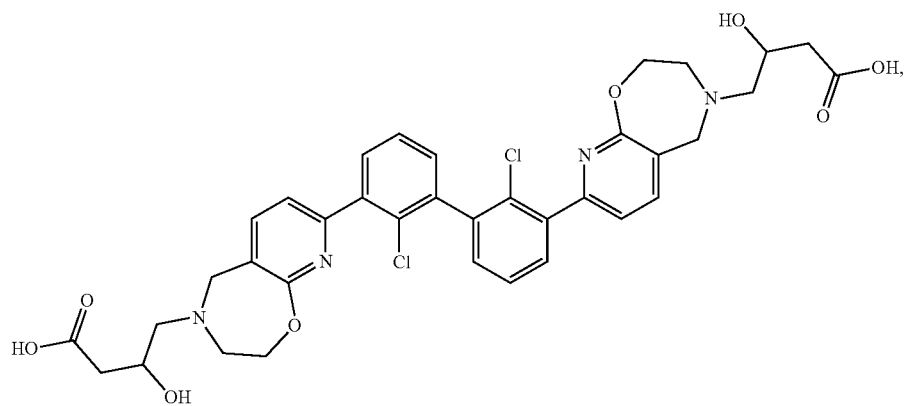
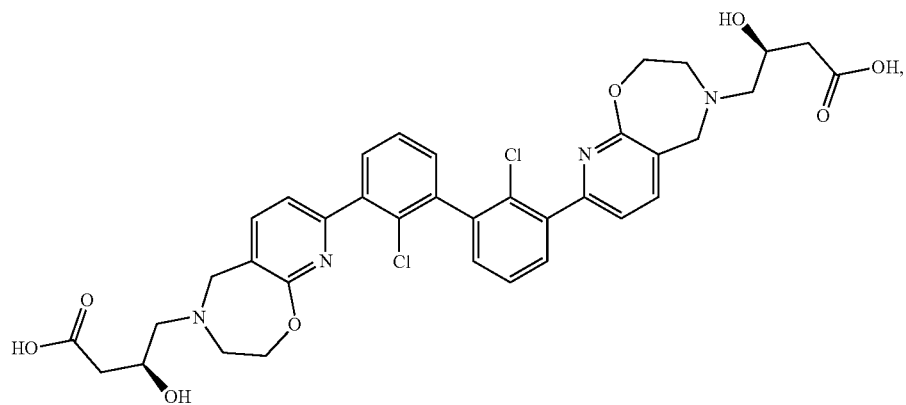

-continued
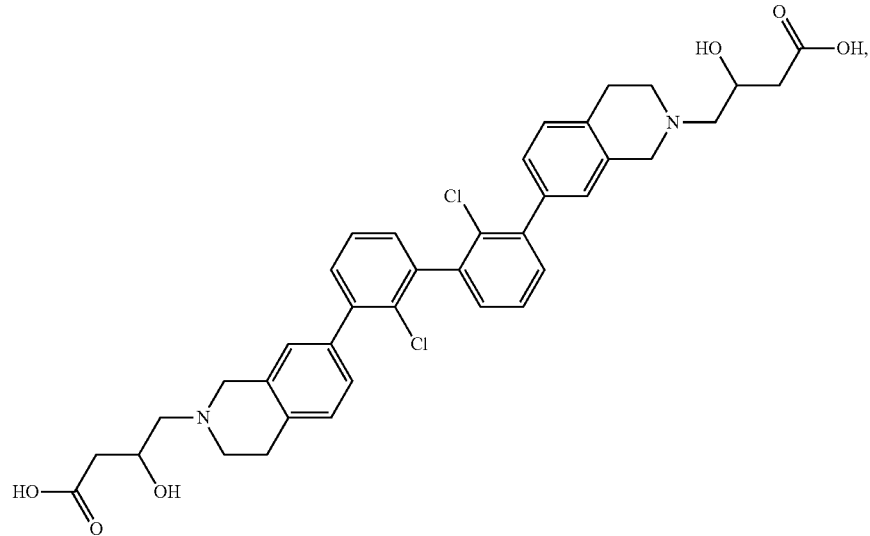
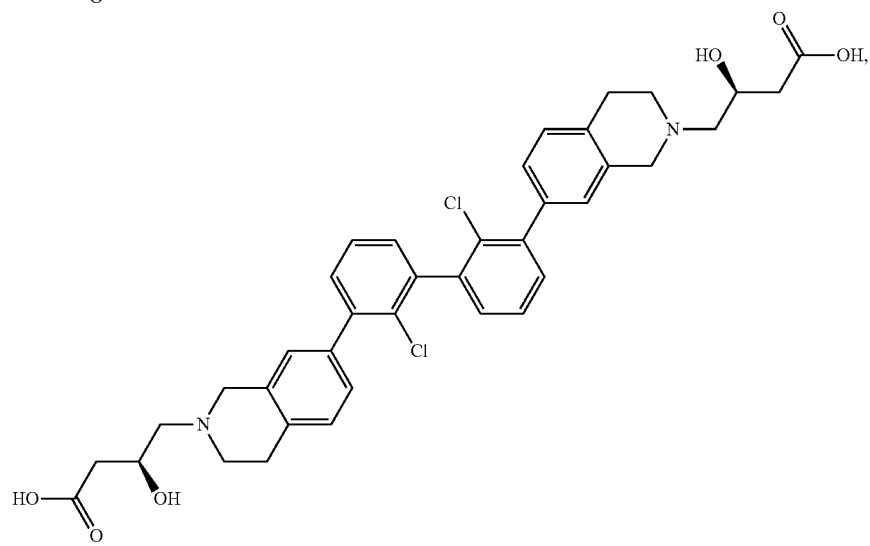
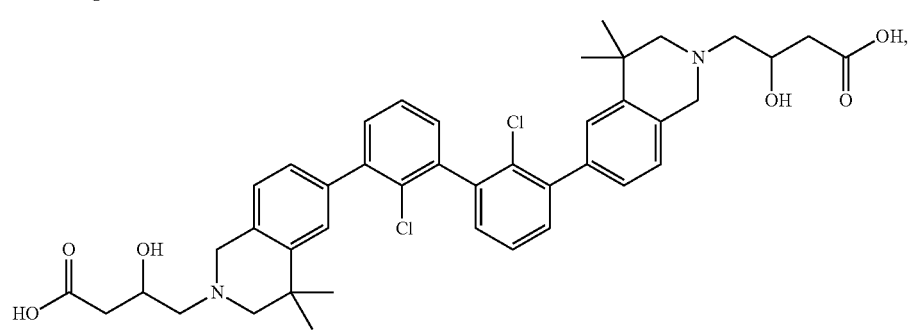
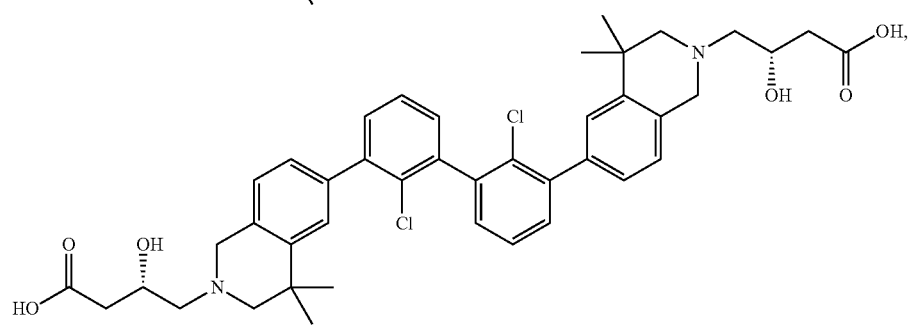

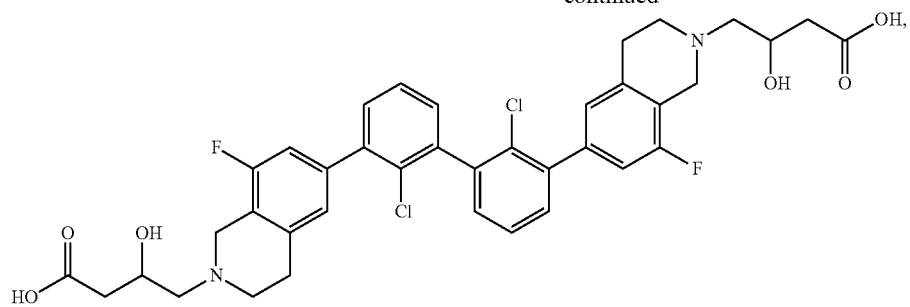
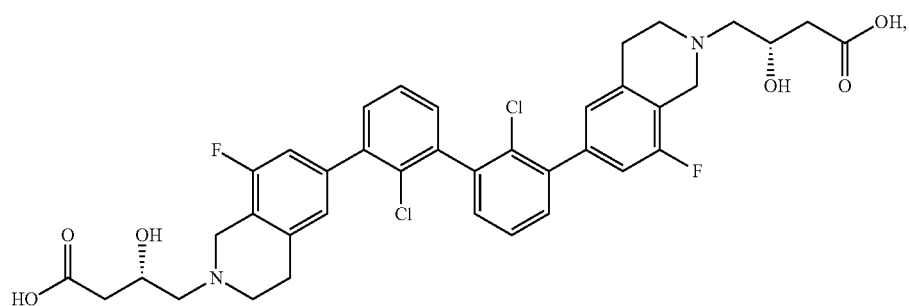
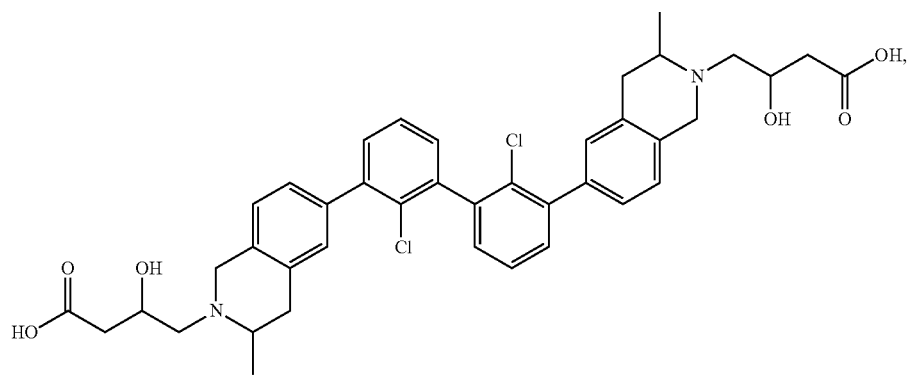
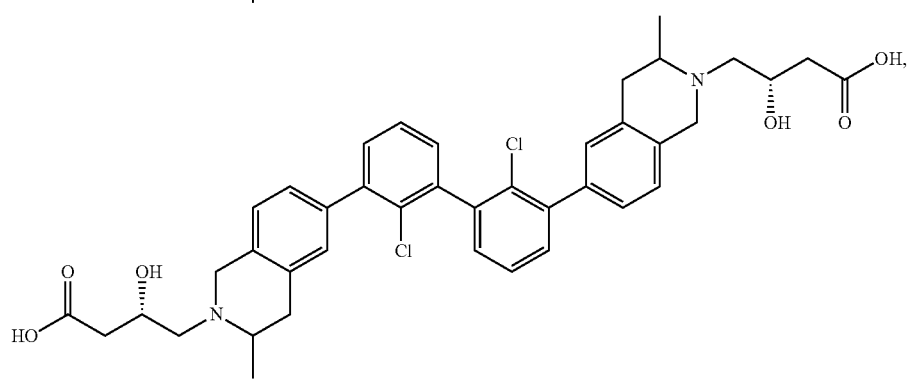
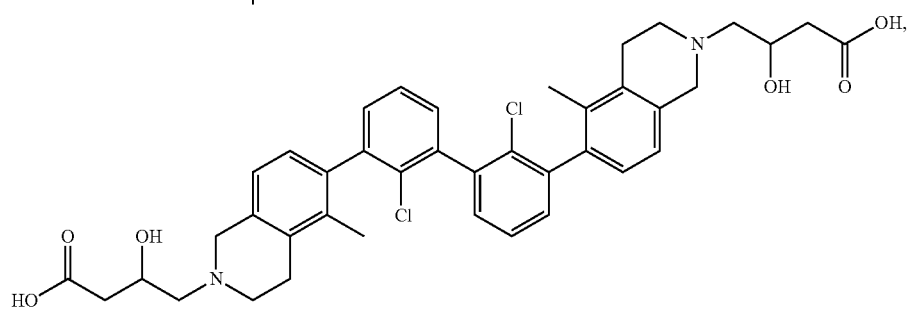

-continued
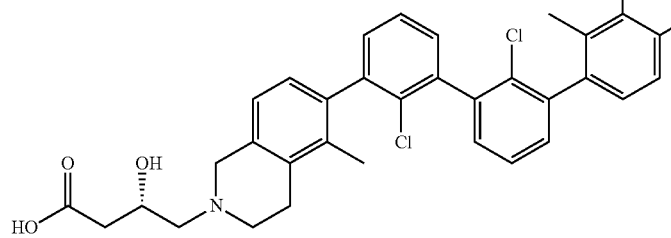
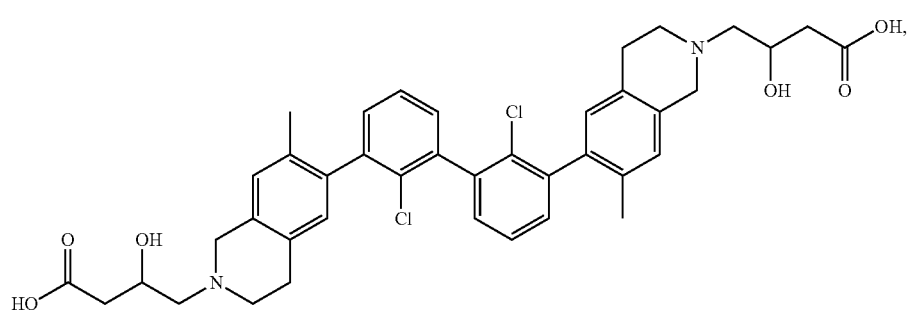
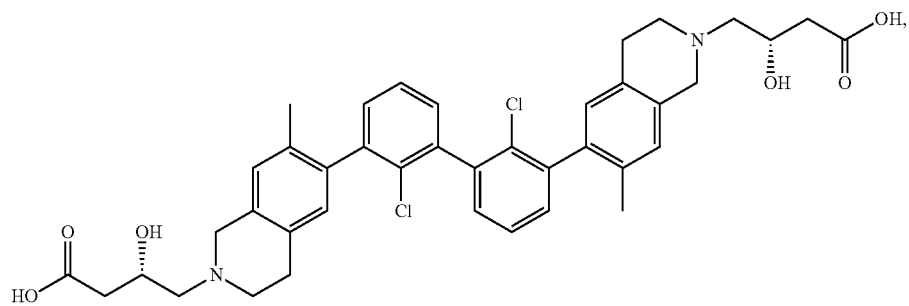
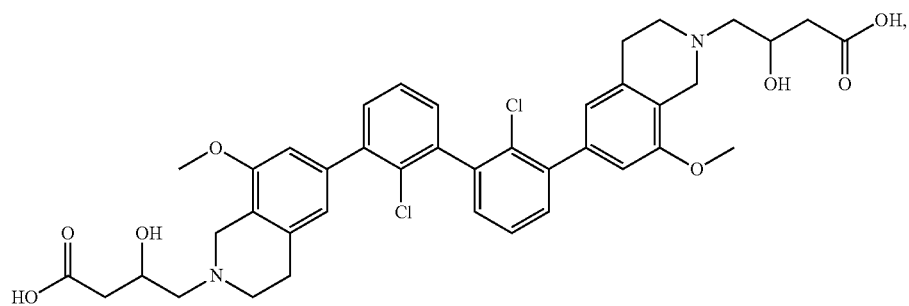
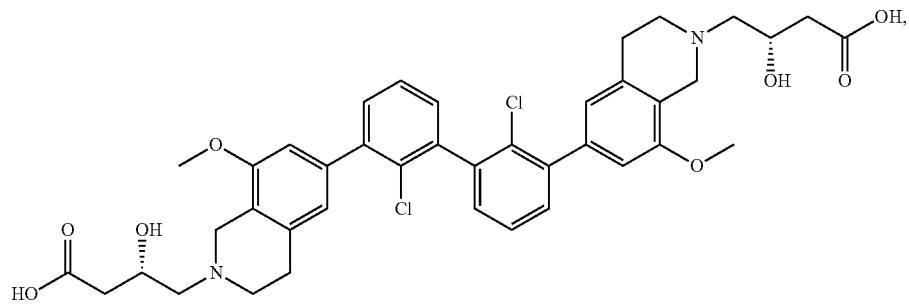

-continued
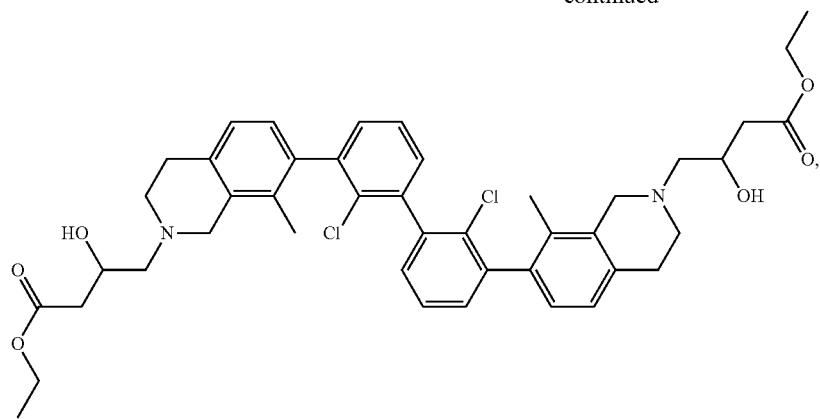
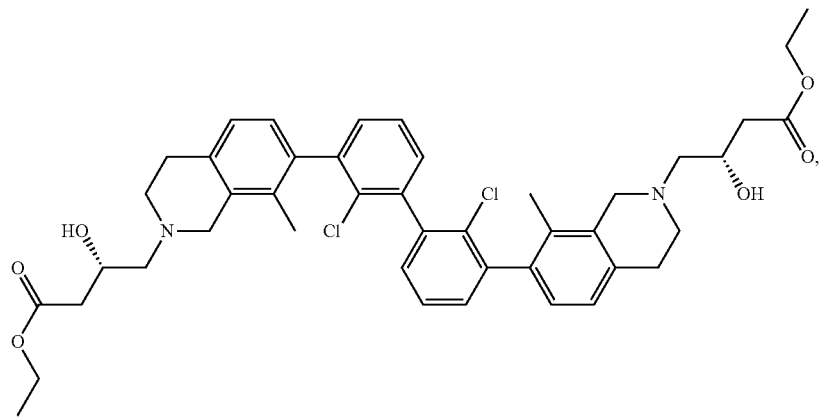
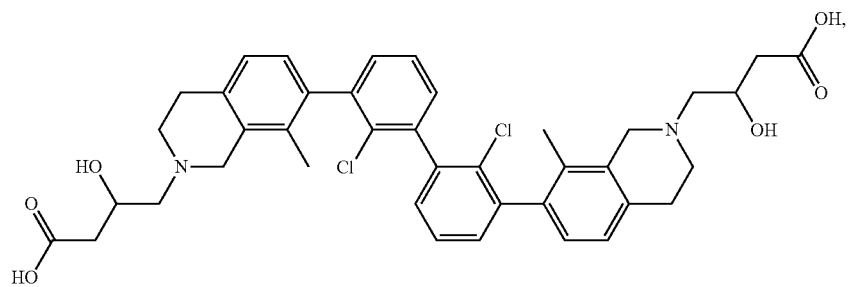
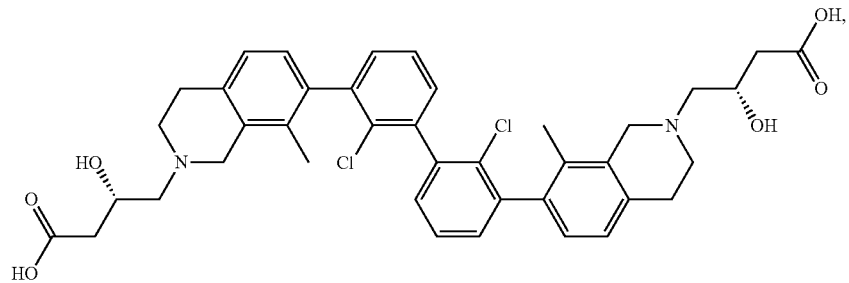

-continued
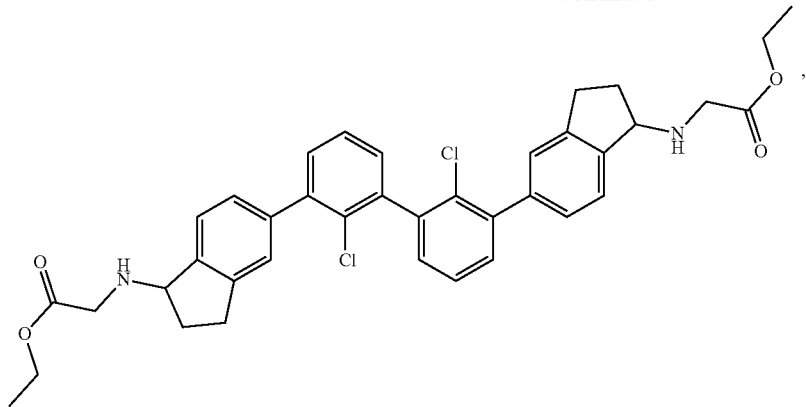
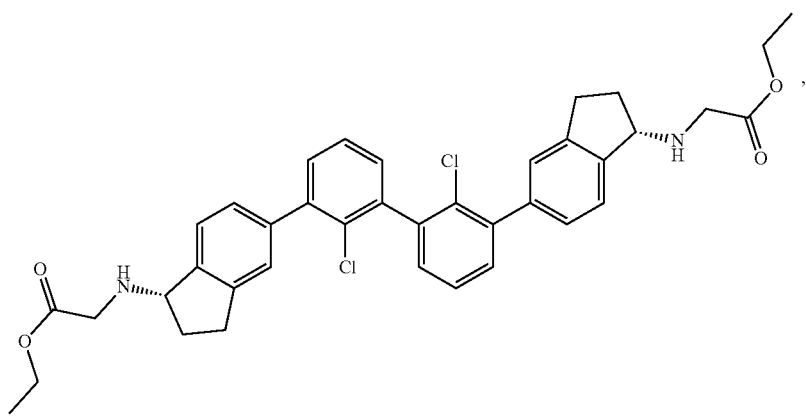
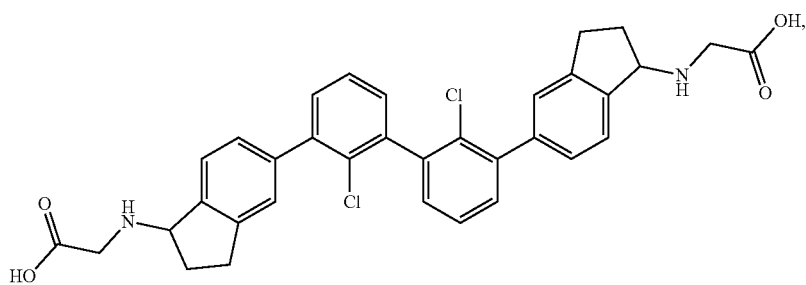
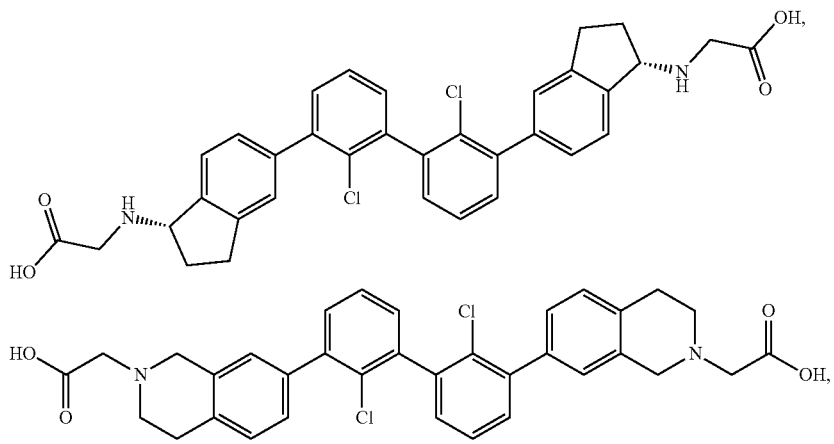

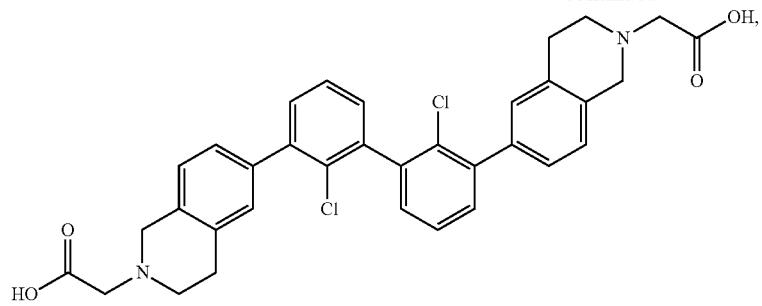
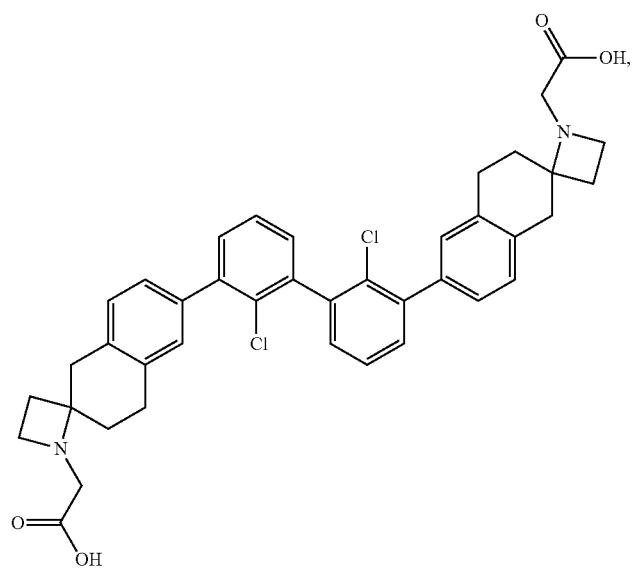
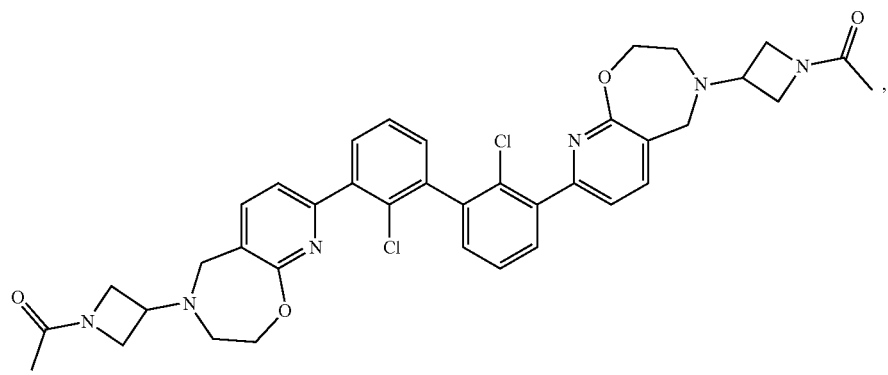

-continued
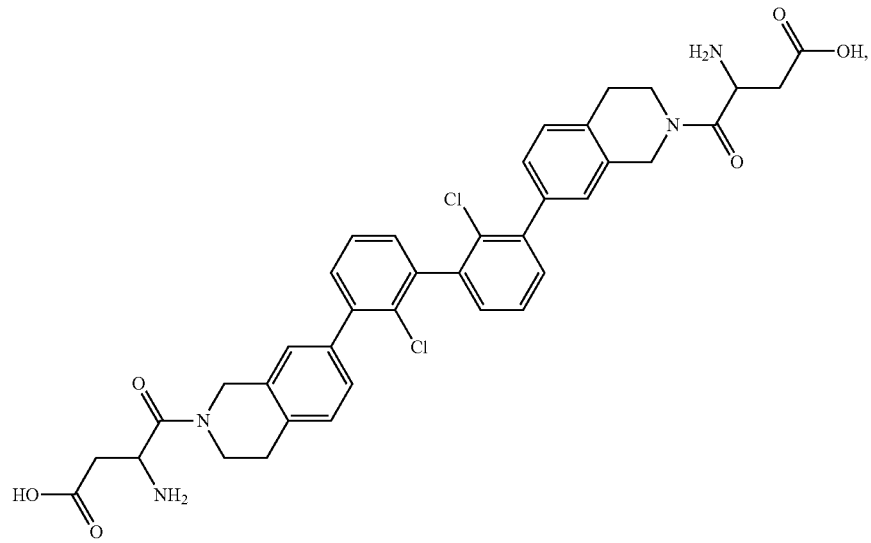
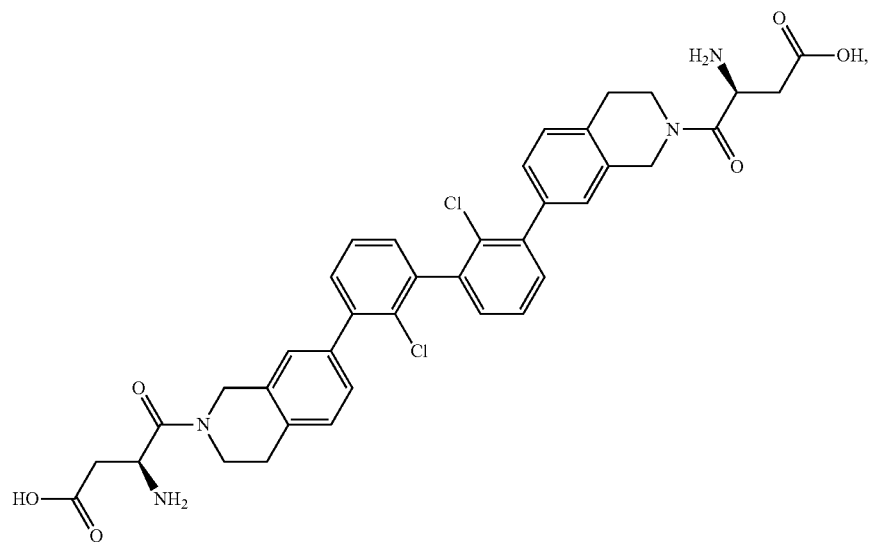
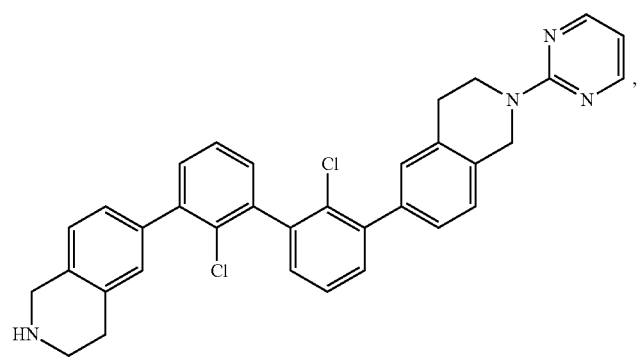

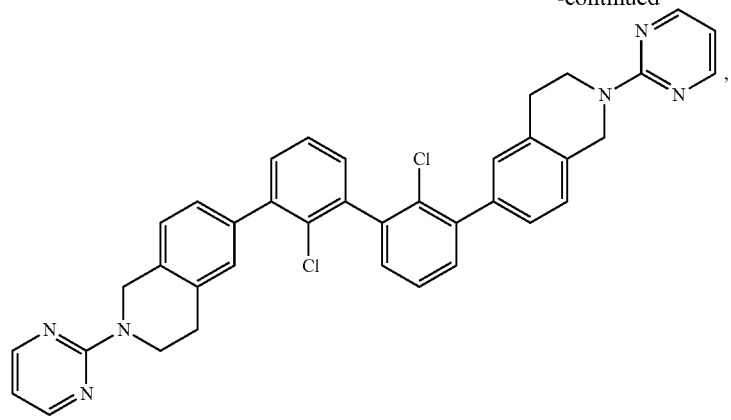
-continued
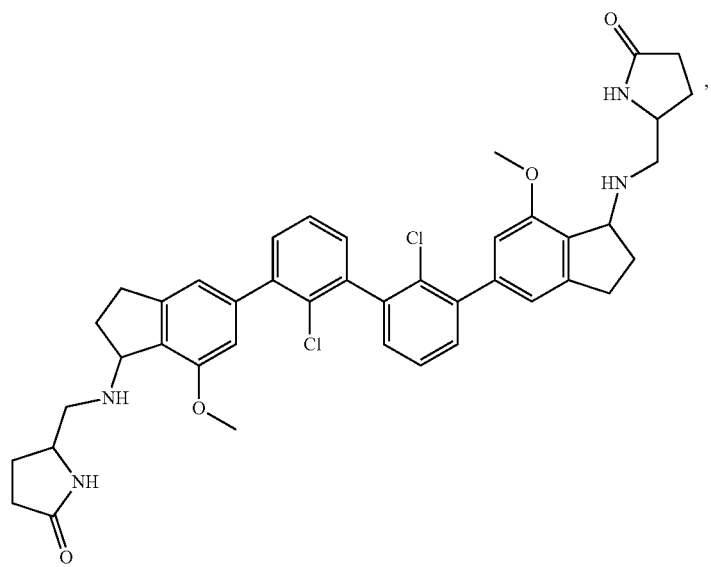
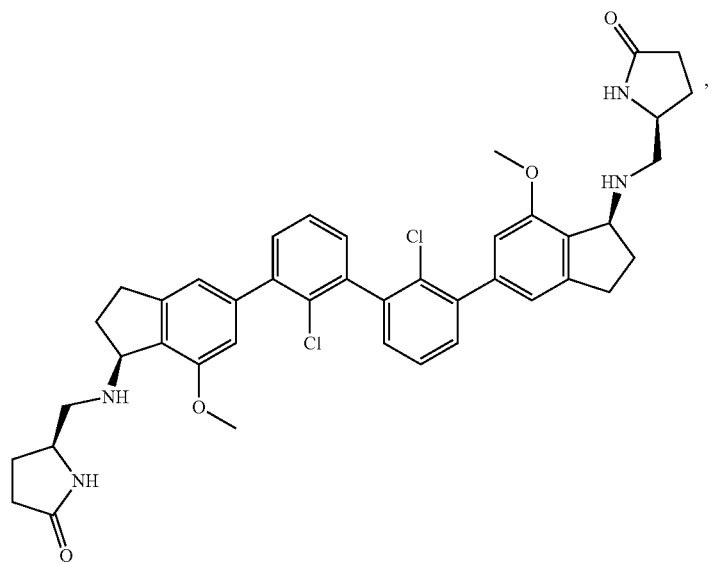

-continued
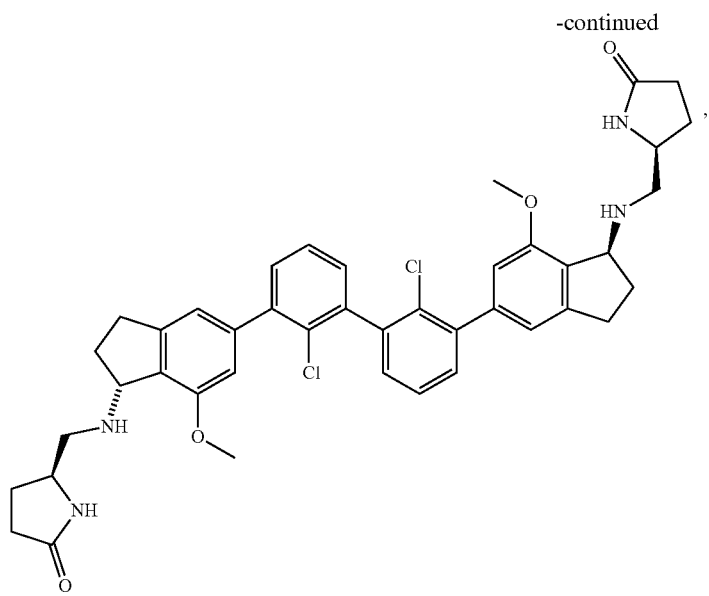
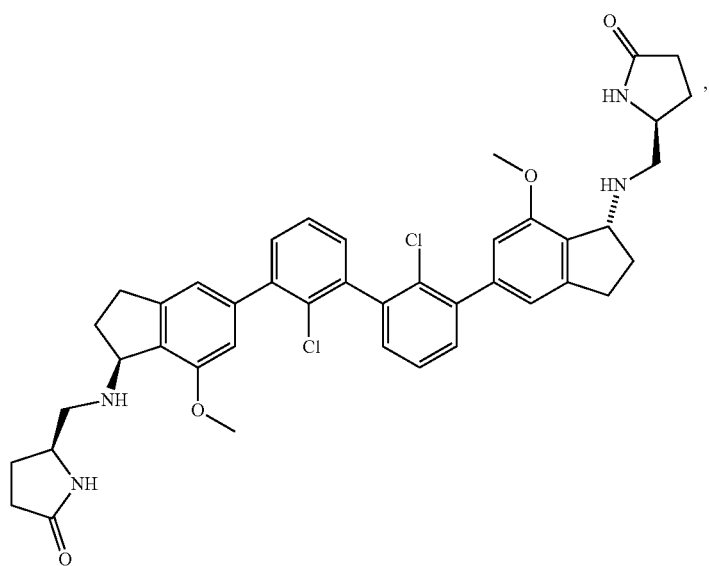
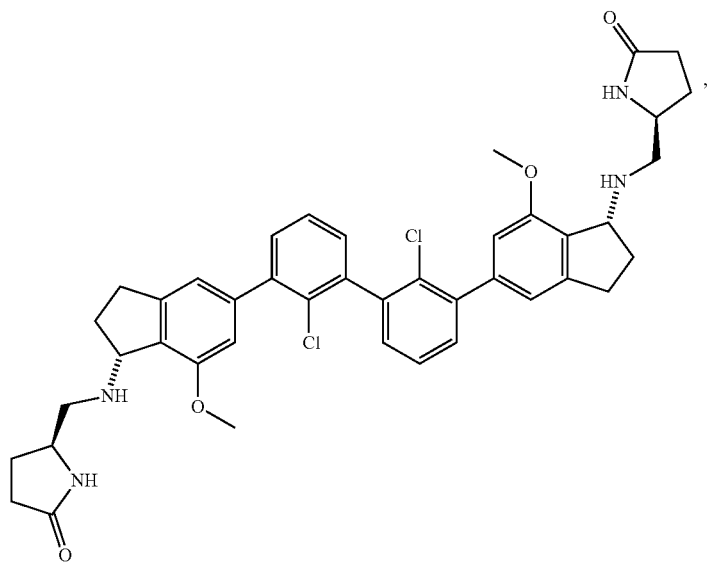

-continued
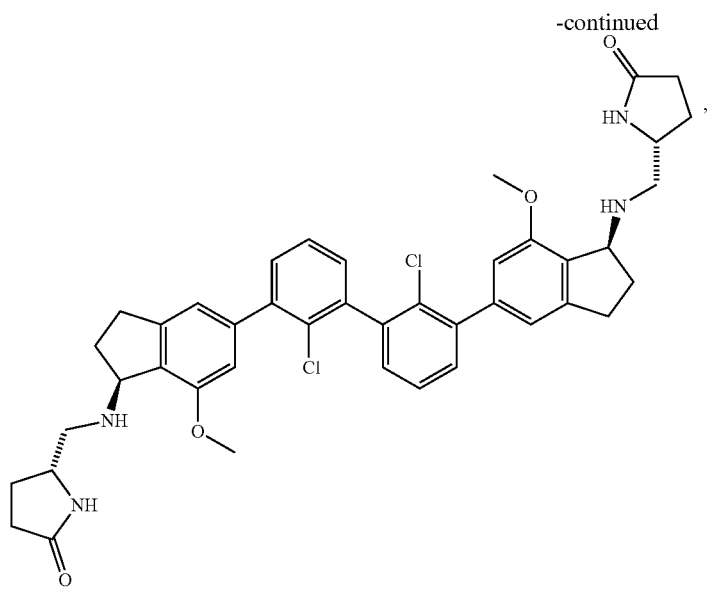
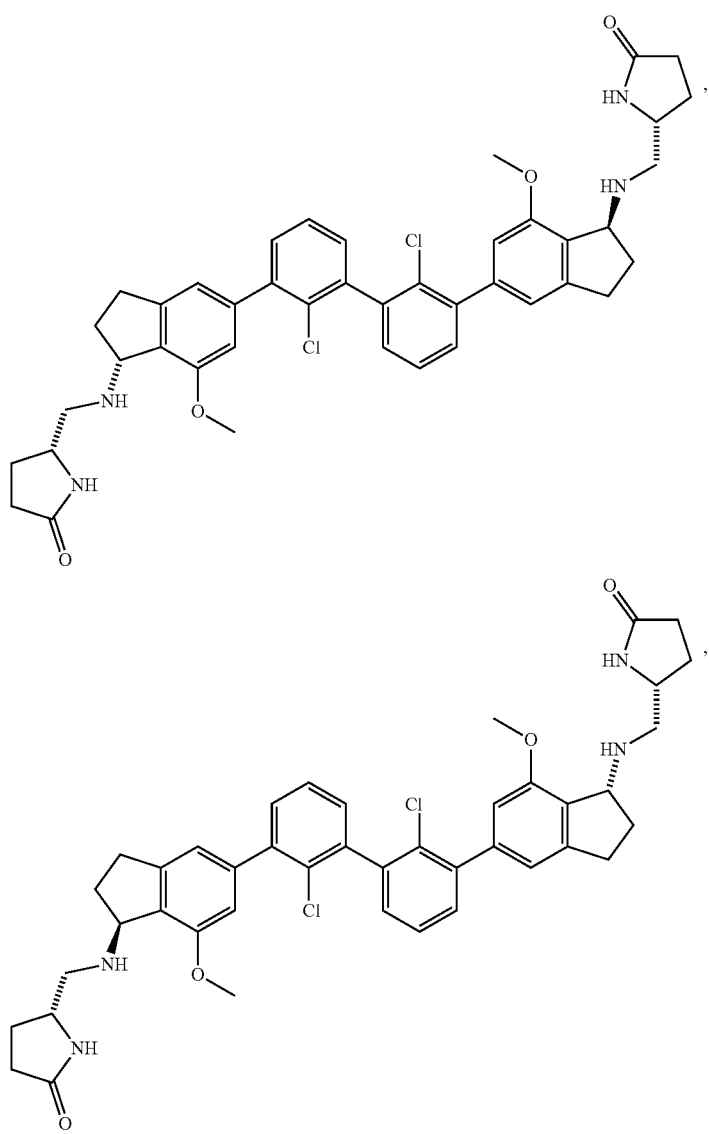

-continued
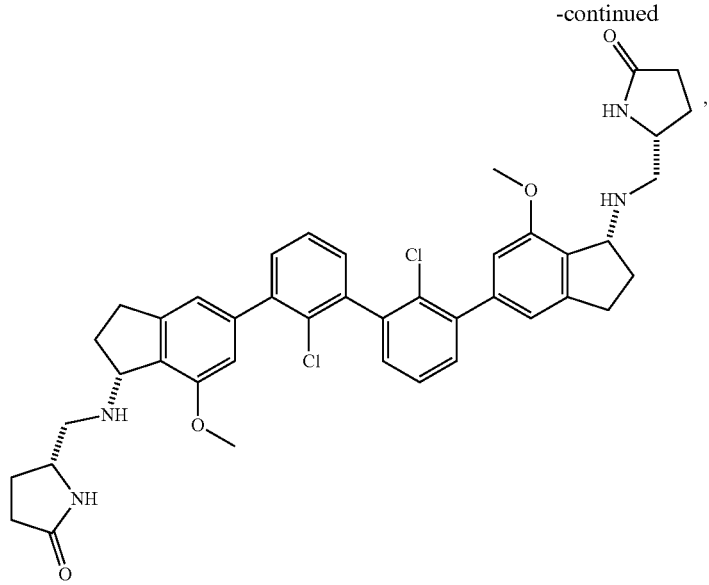
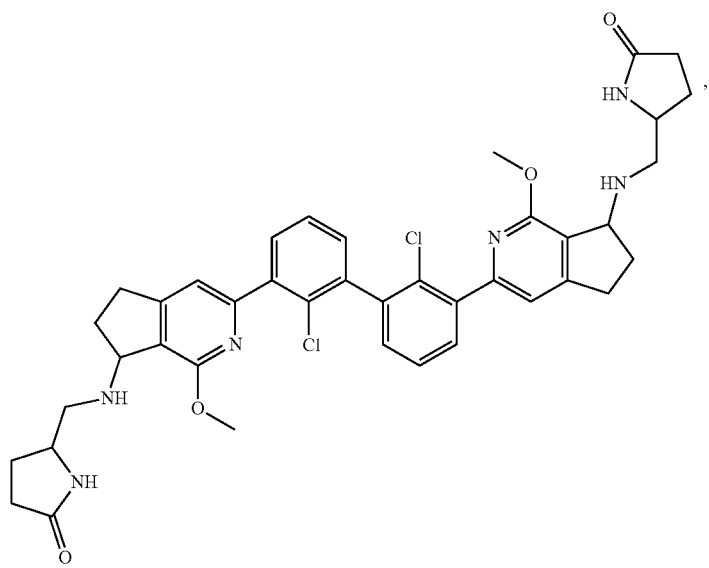
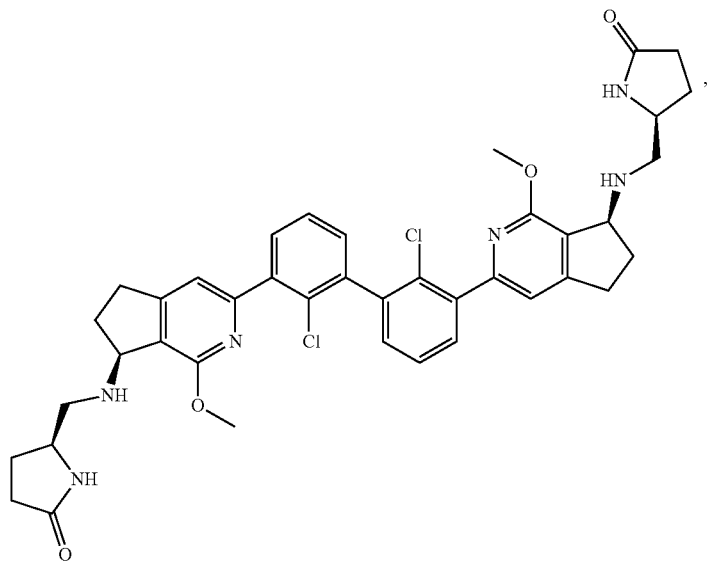

-continued
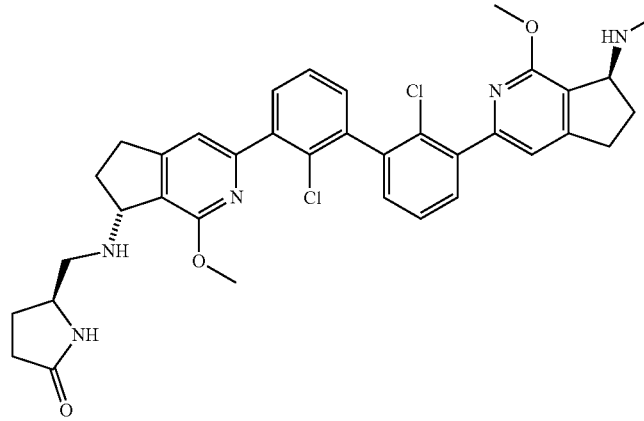
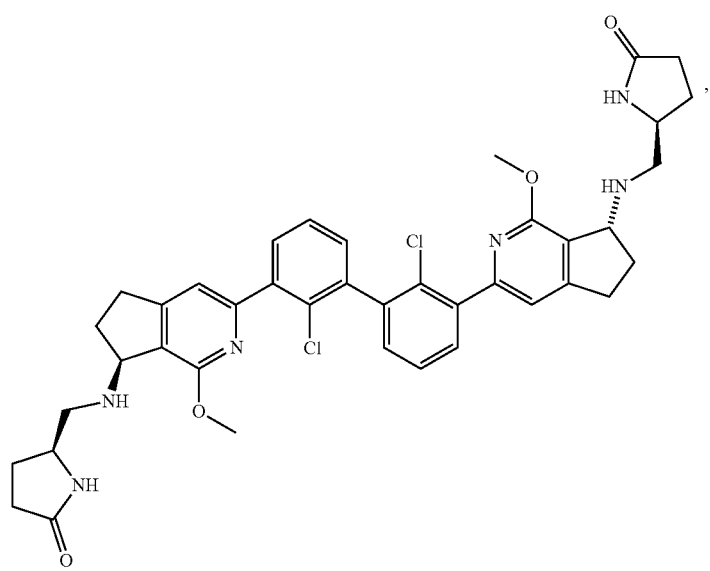
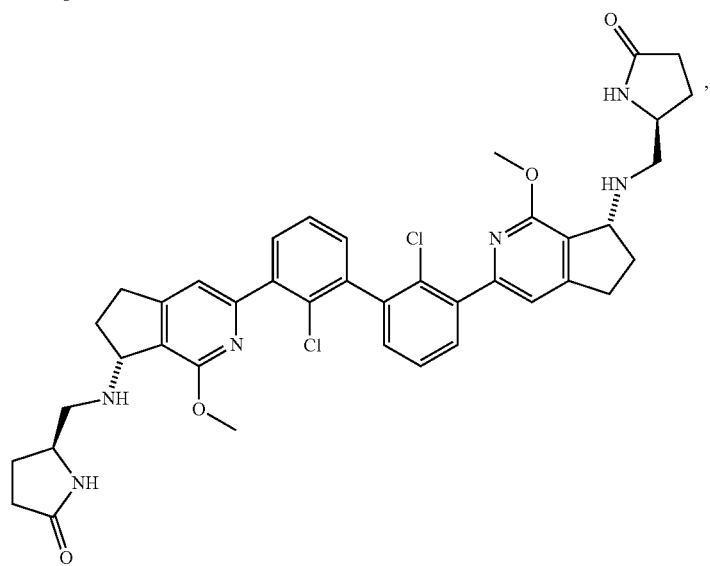

-continued
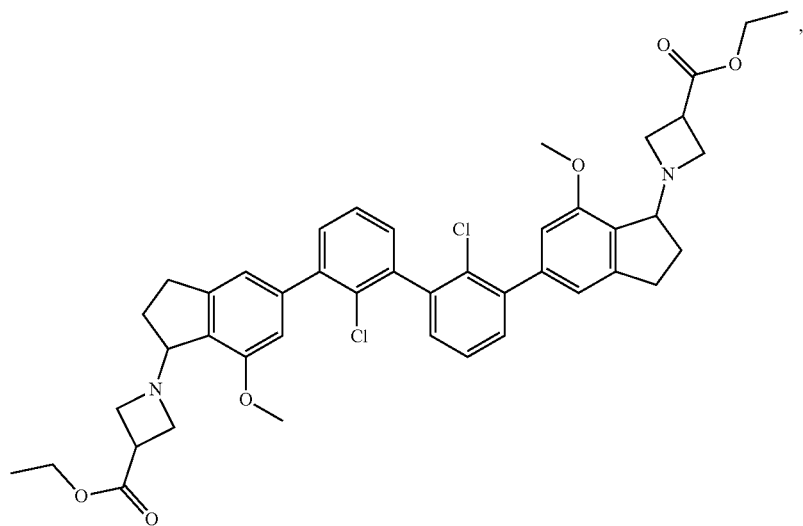
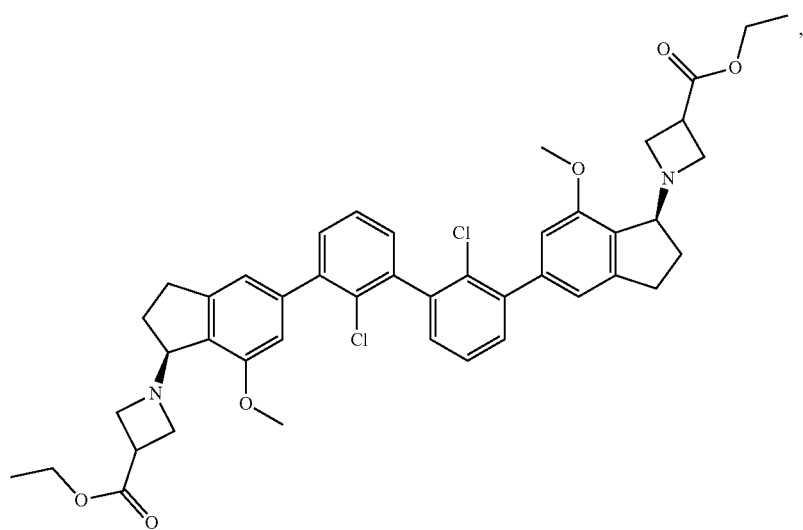
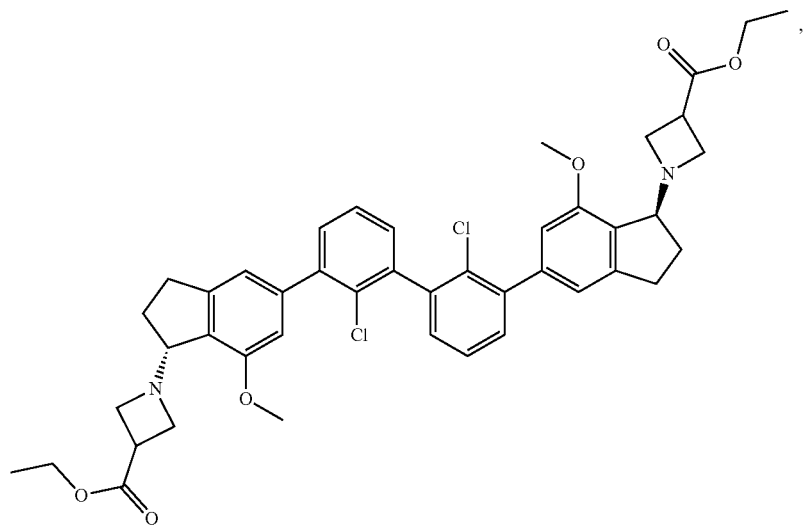

-continued
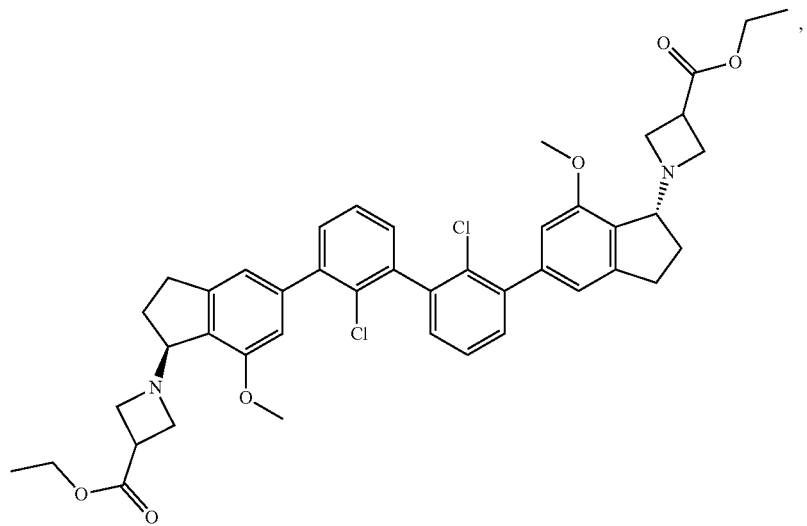
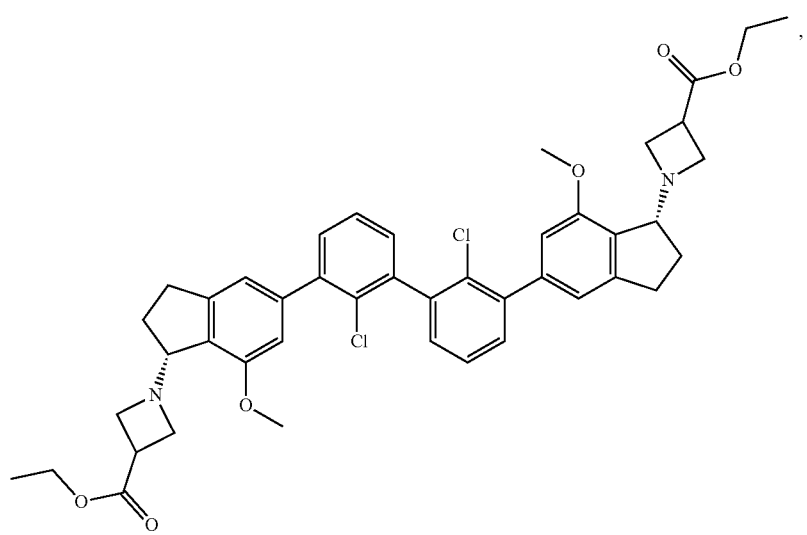
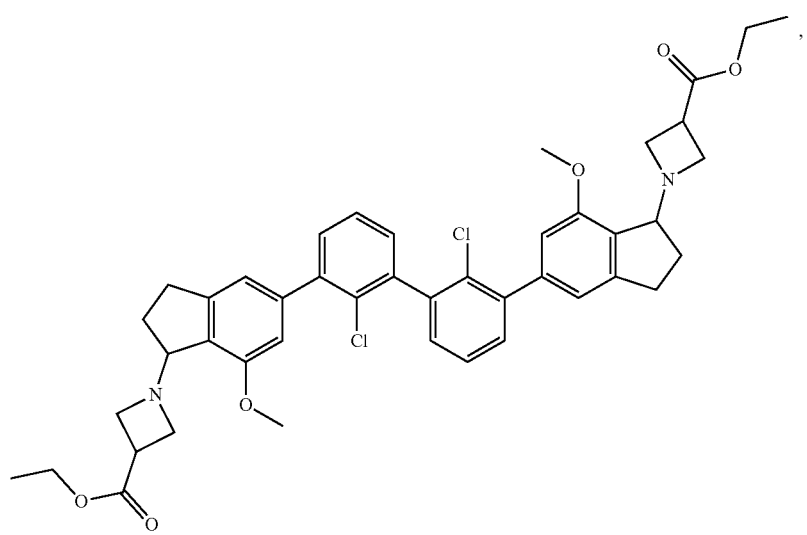

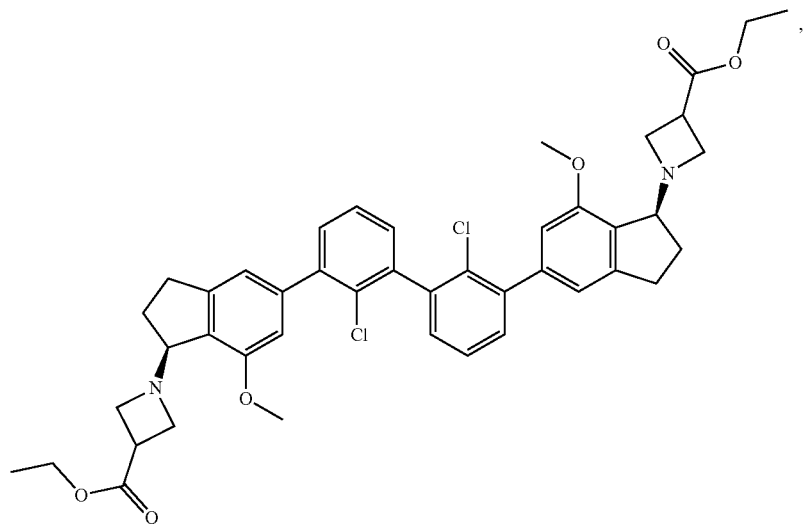
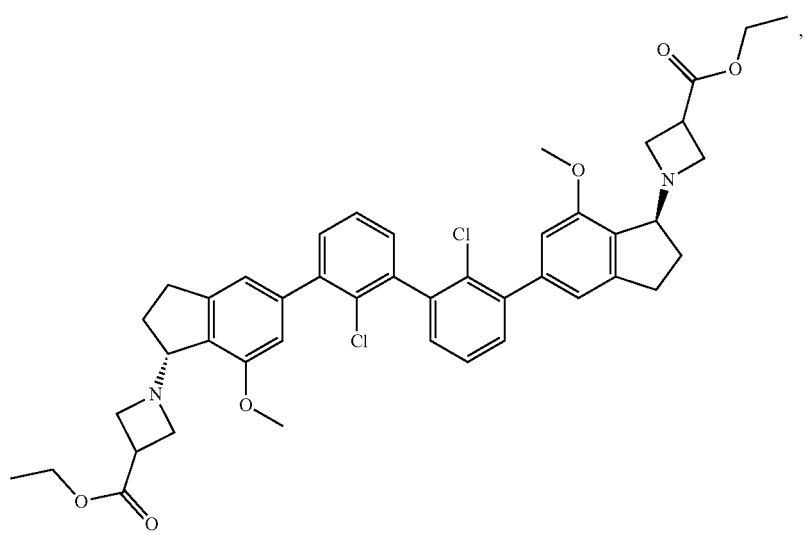
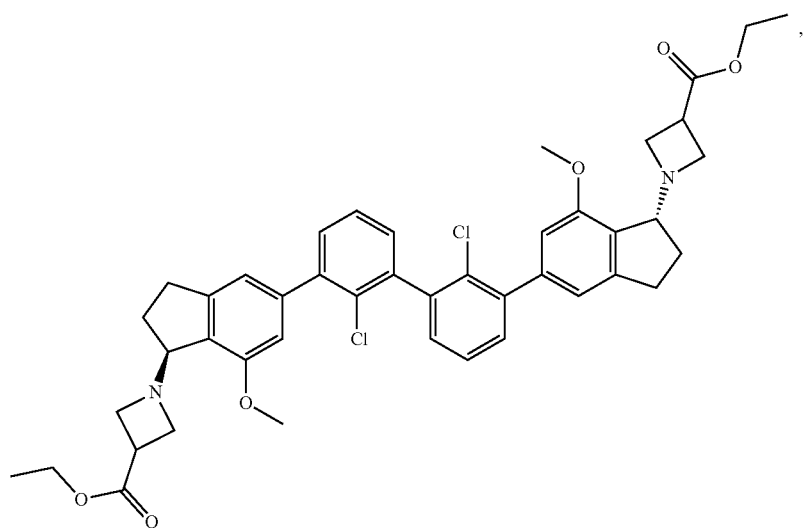

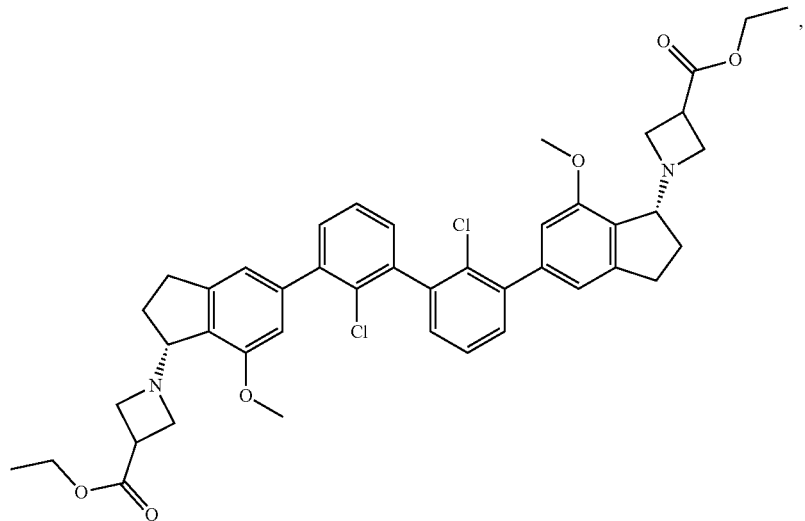
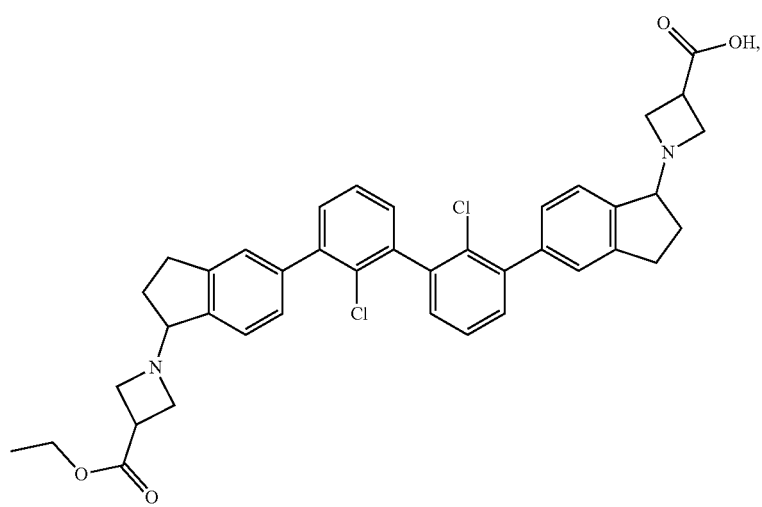
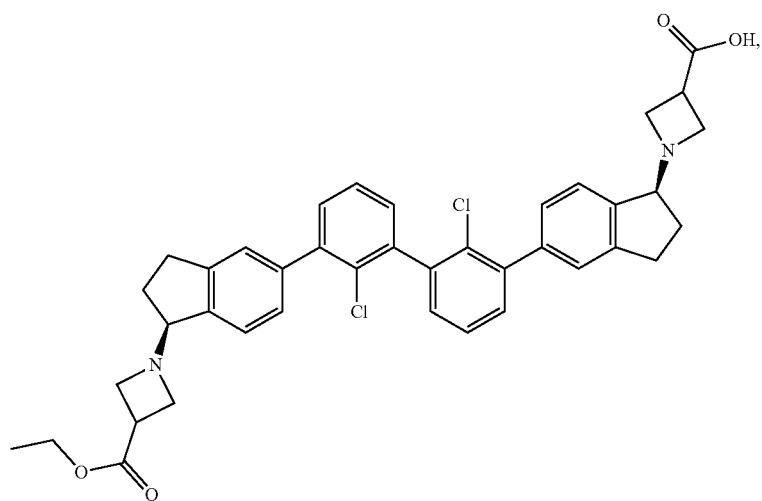

-continued
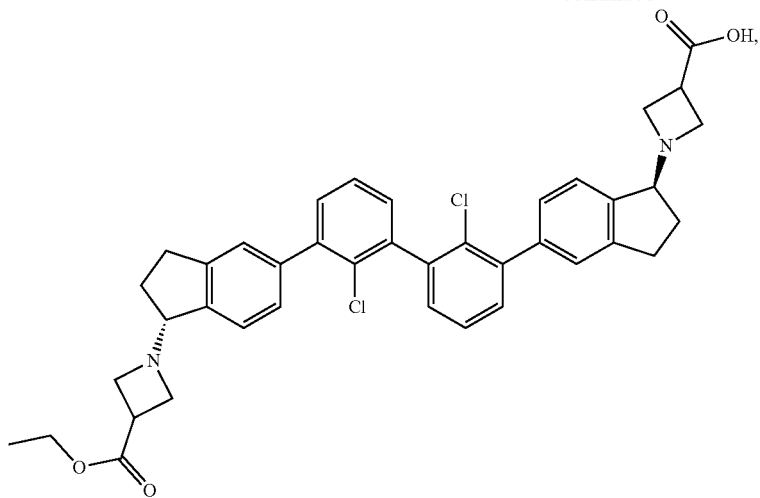
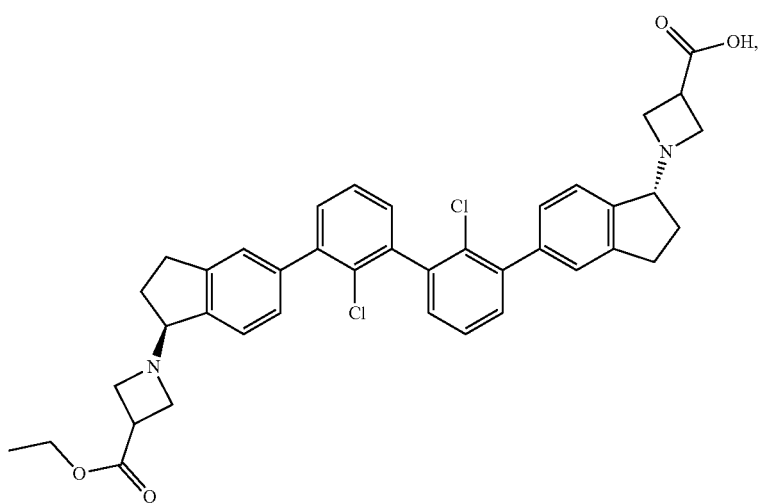
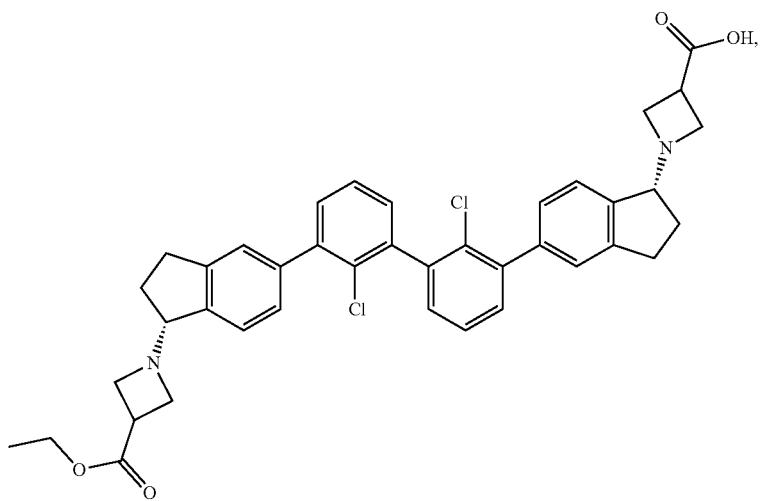

-continued
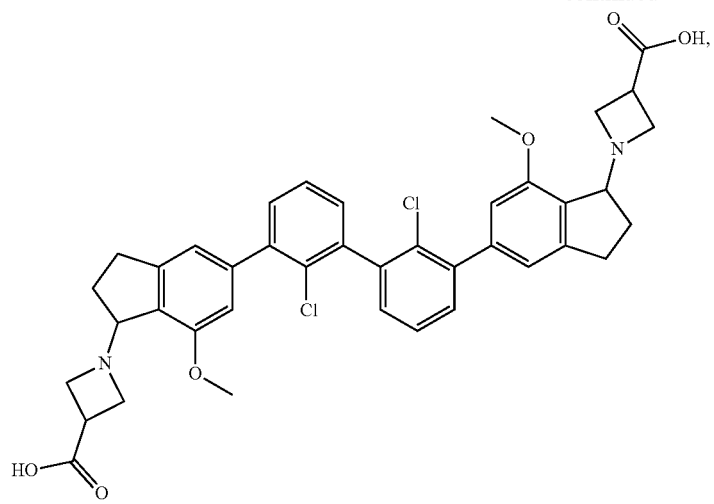
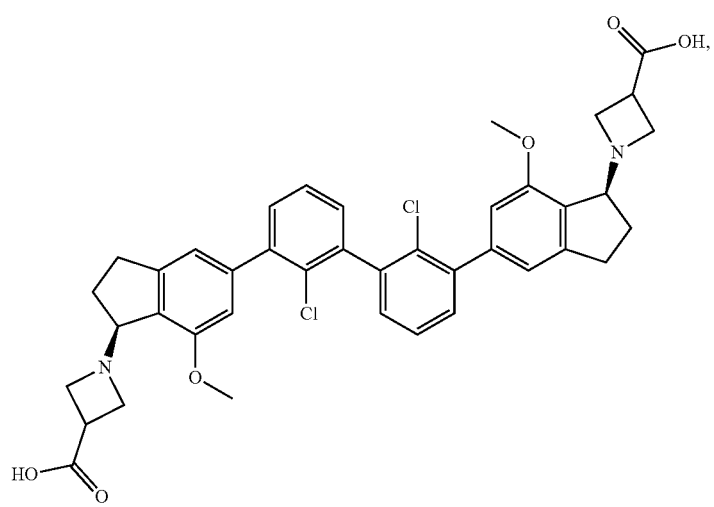
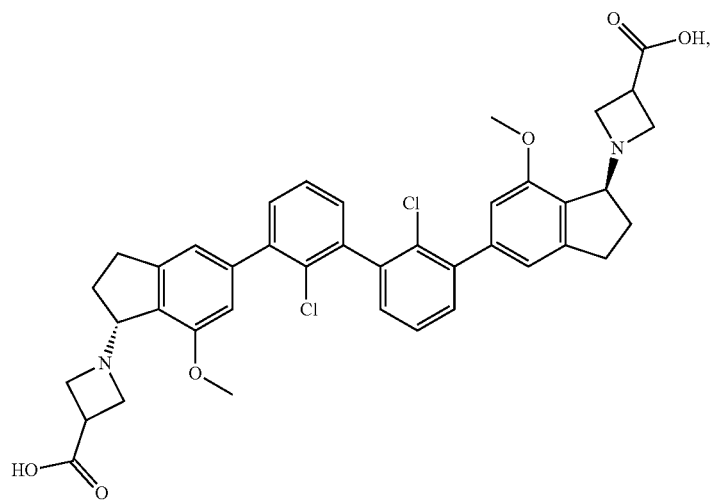

-continued
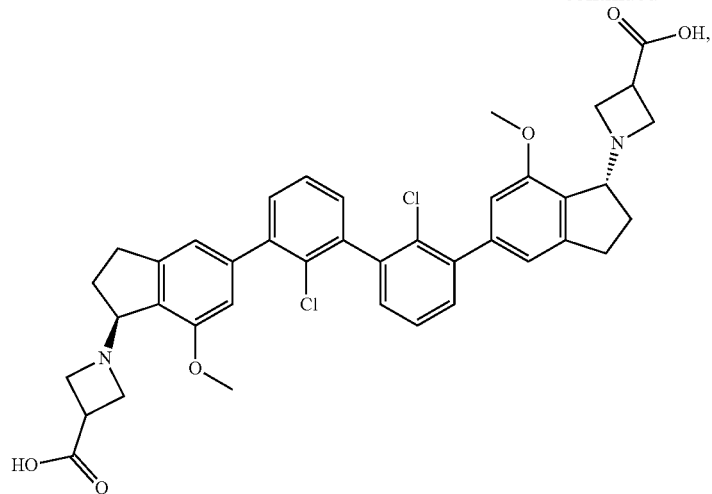
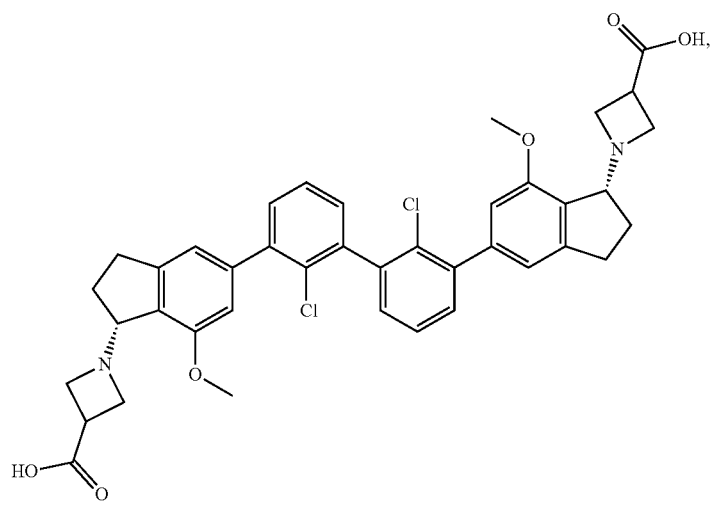
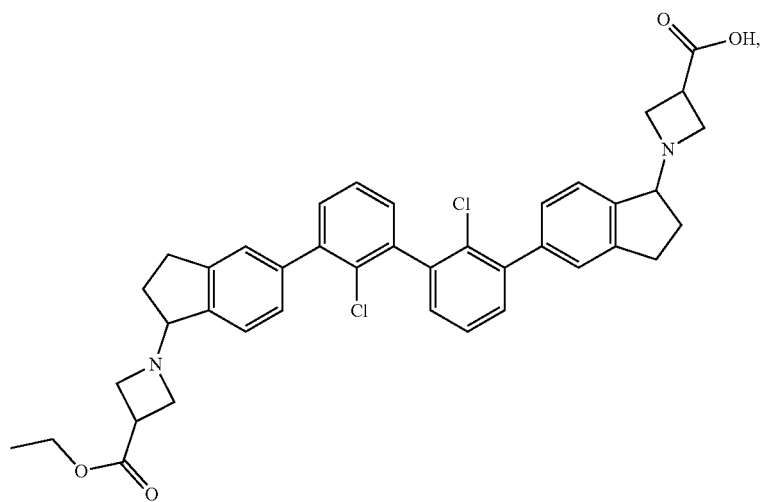

-continued
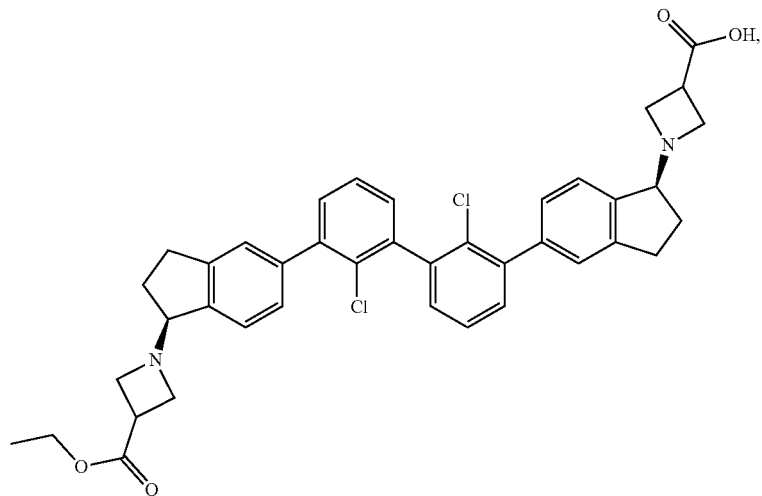
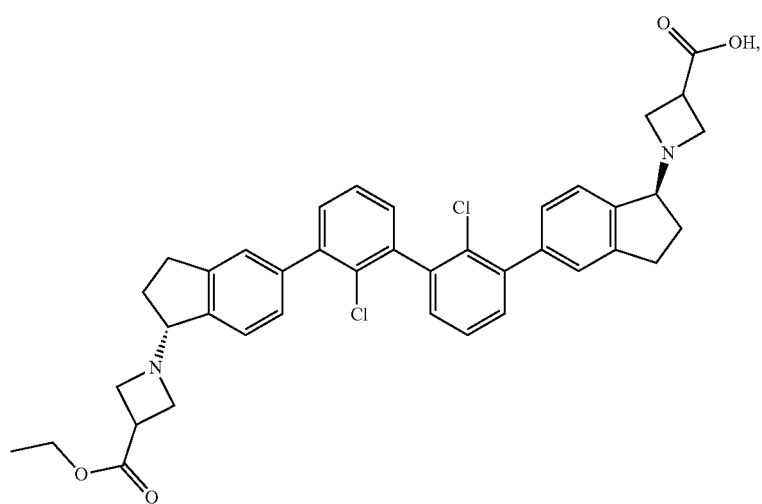
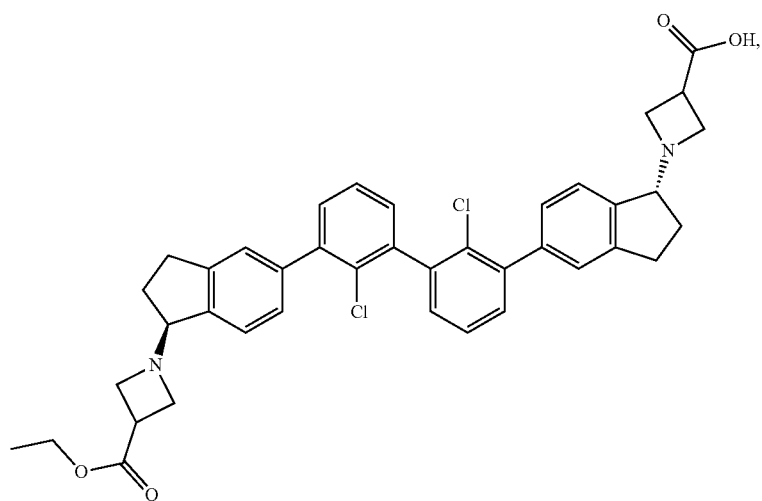

-continued
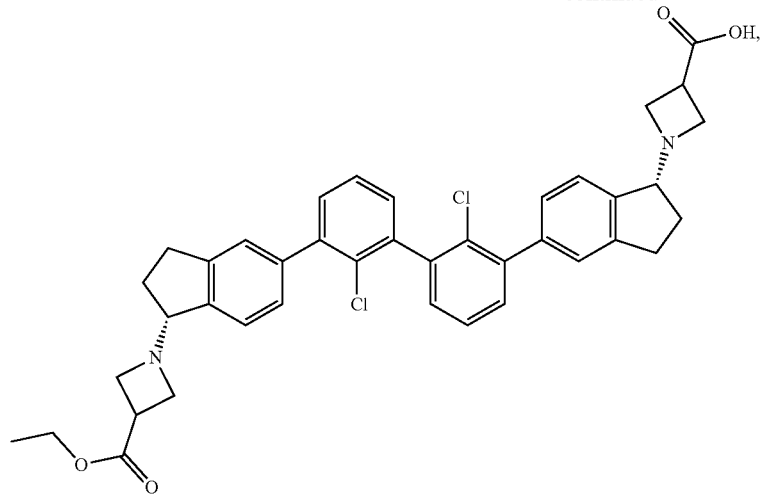
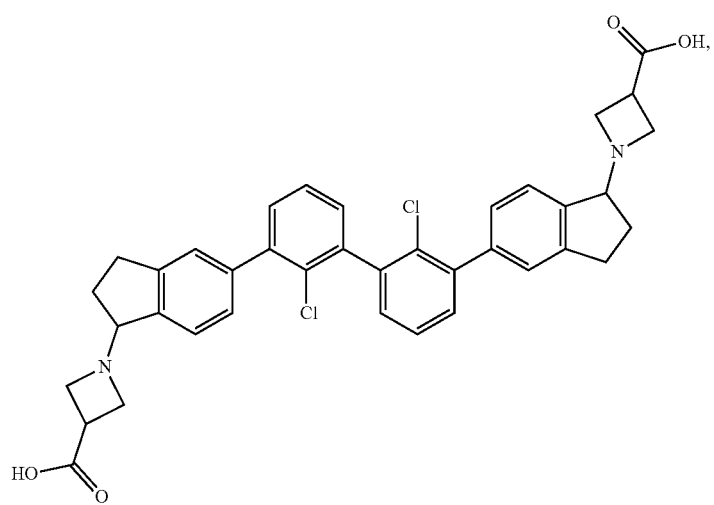
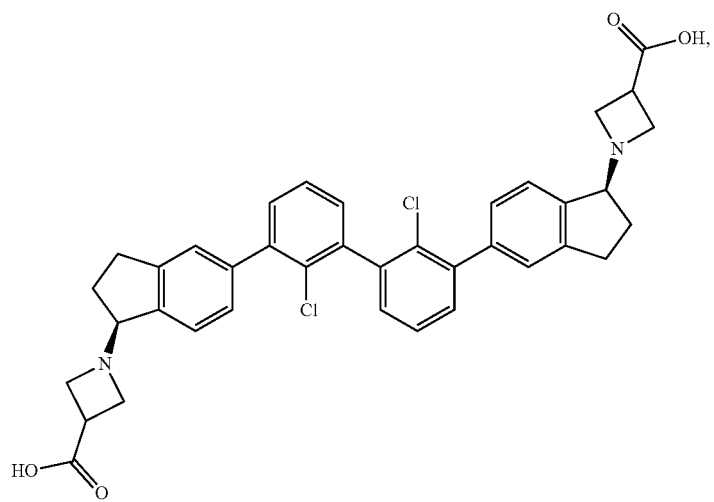

-continued
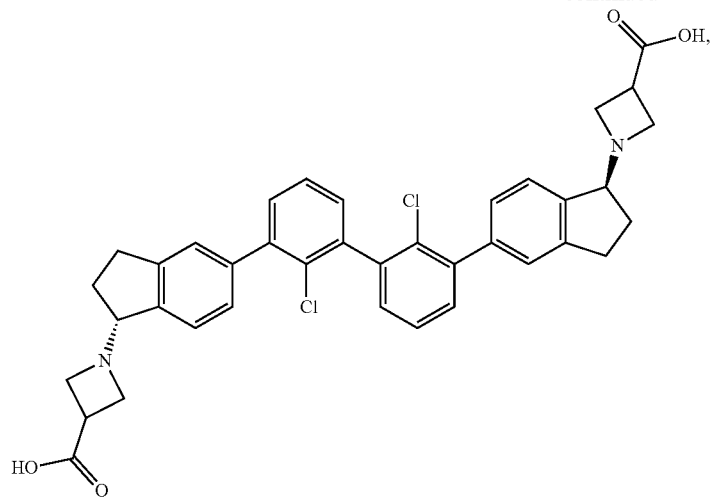
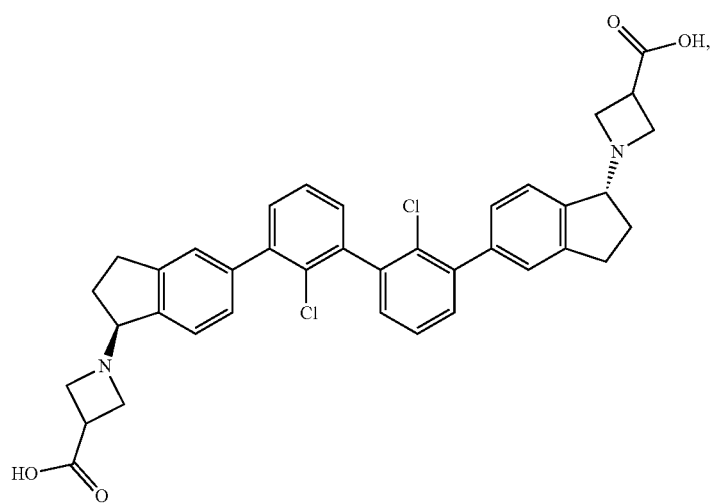
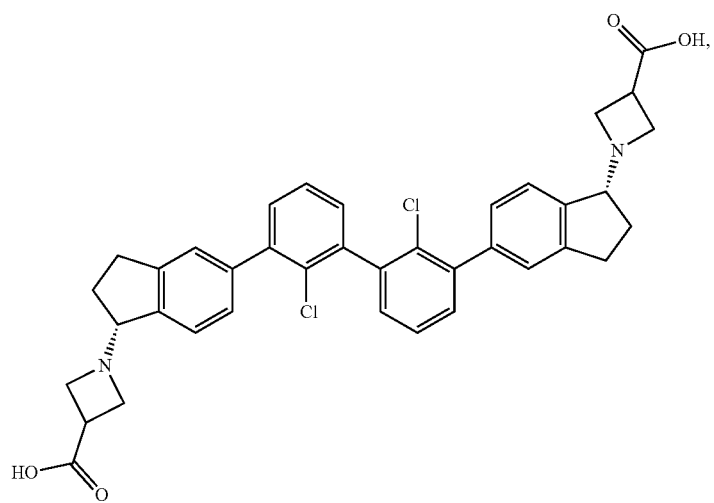

-continued
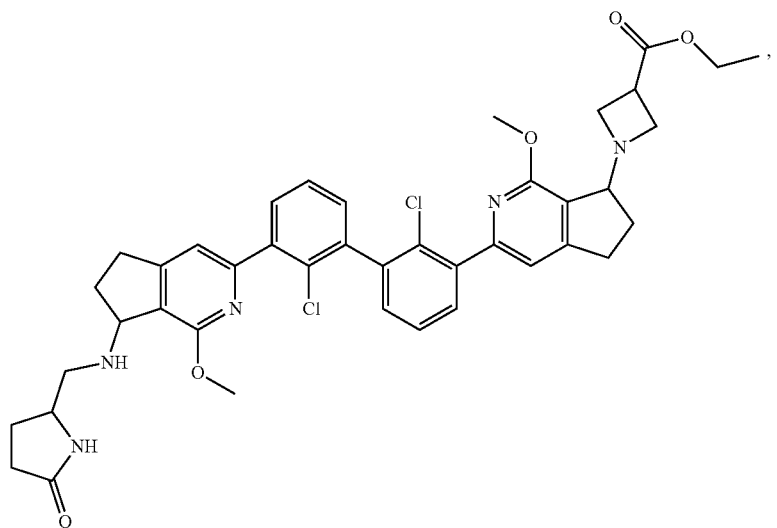
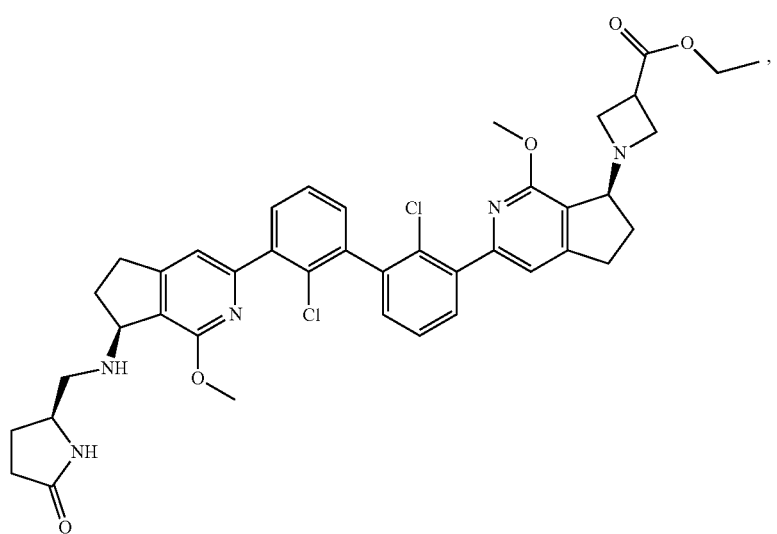
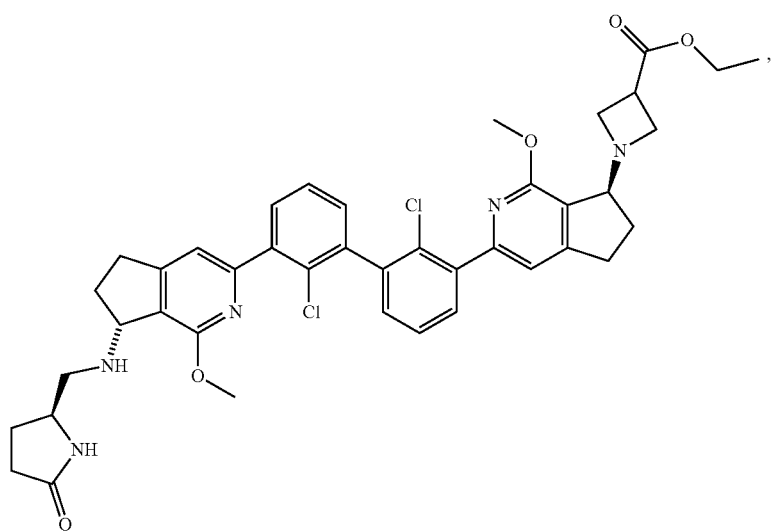

-continued
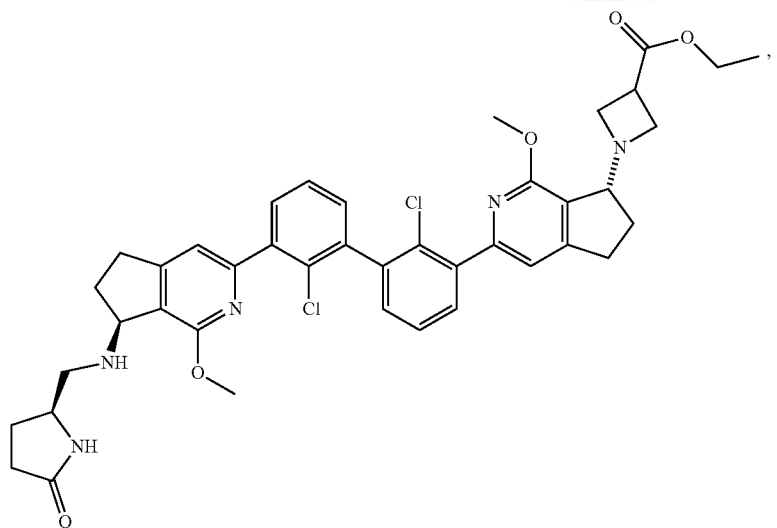
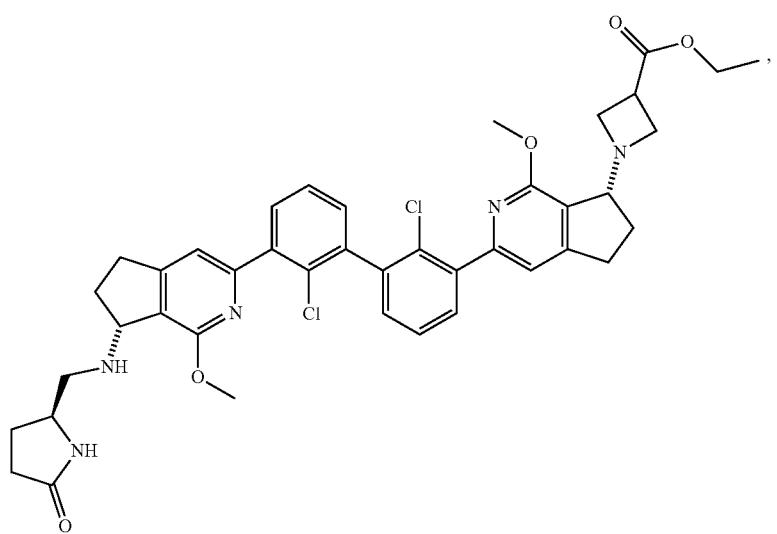
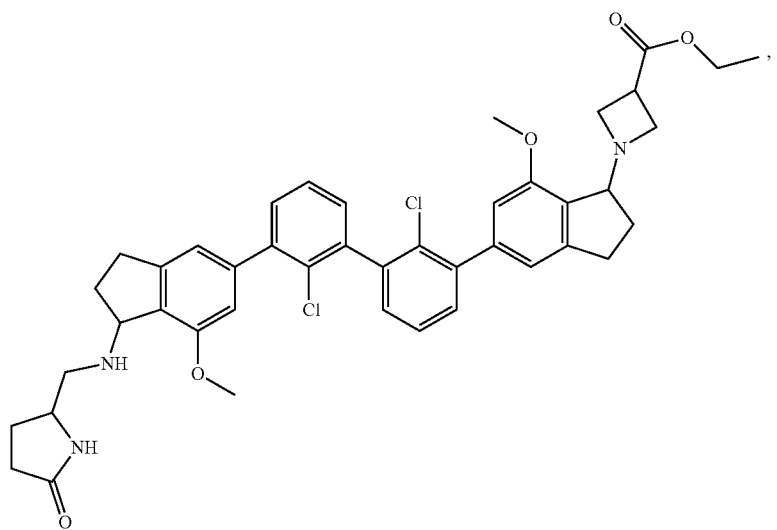

-continued
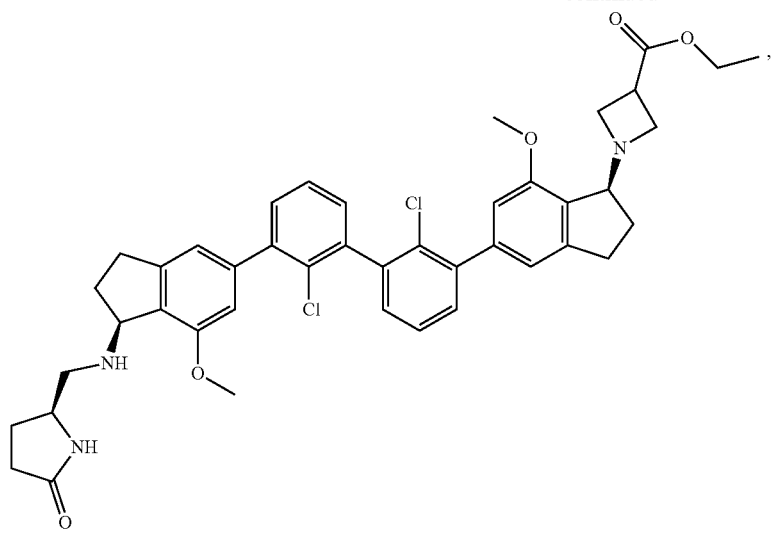
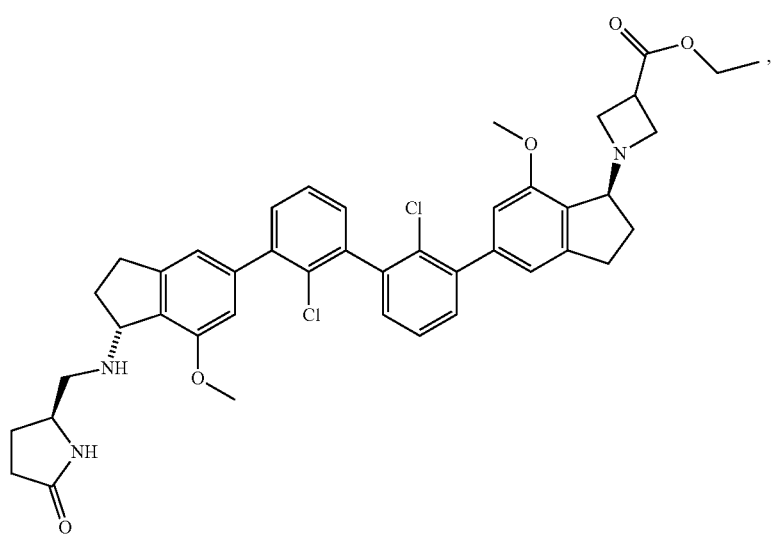
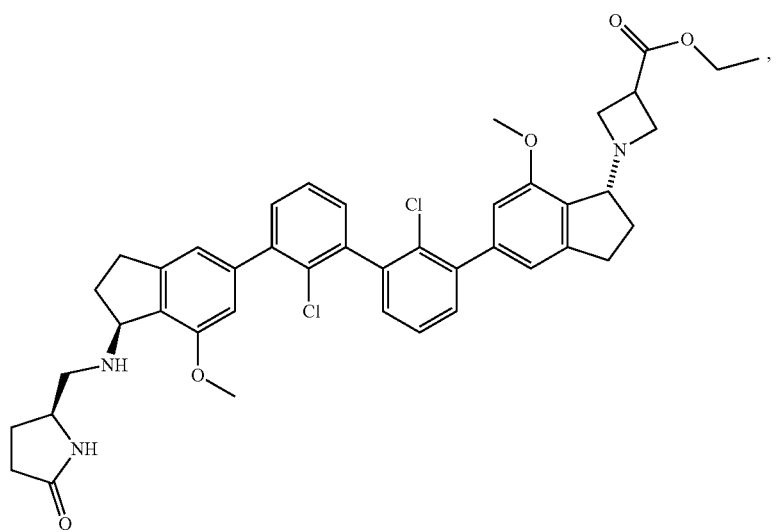

-continued
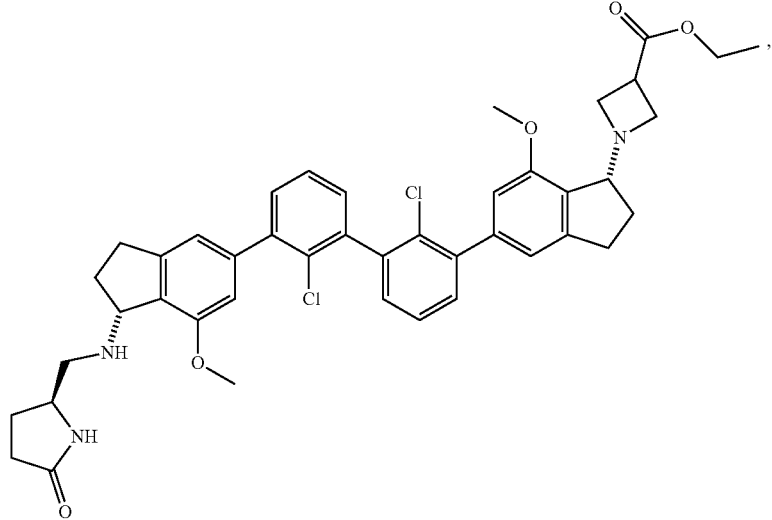
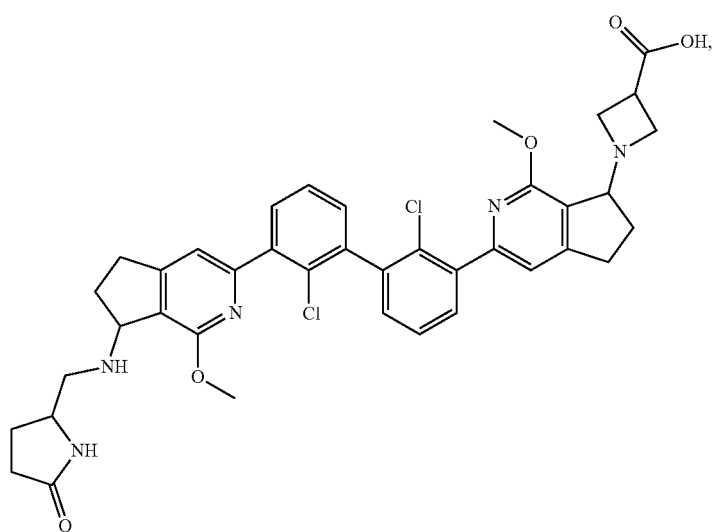
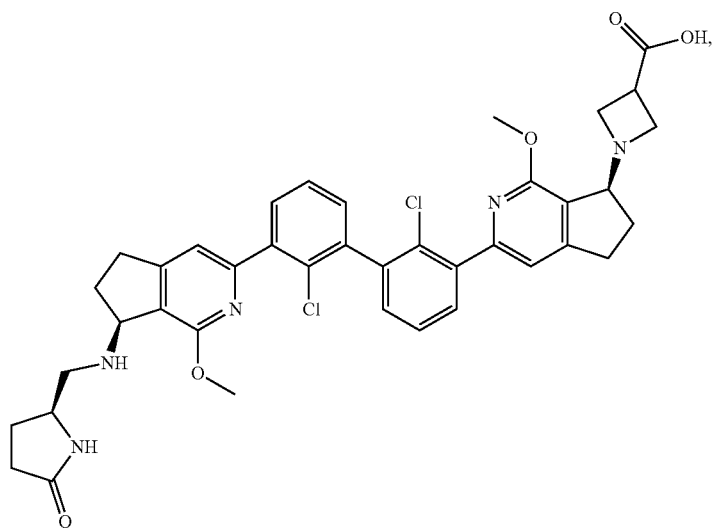

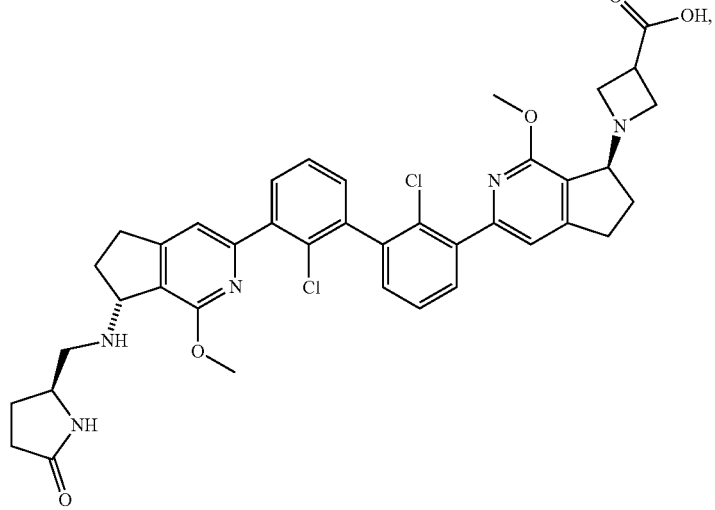
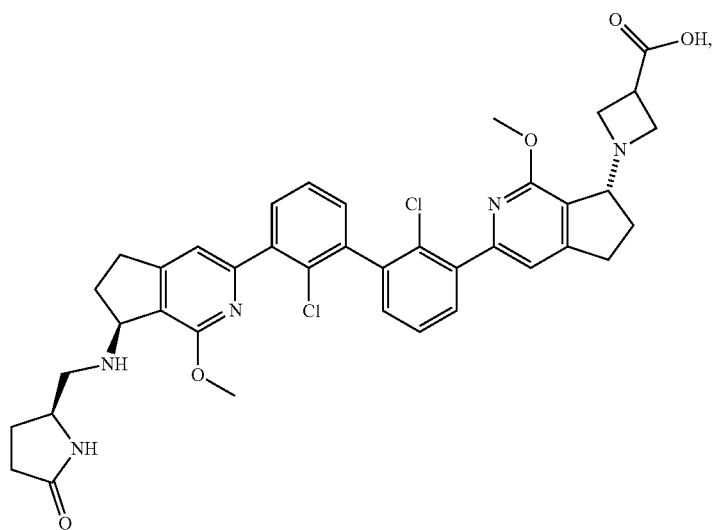
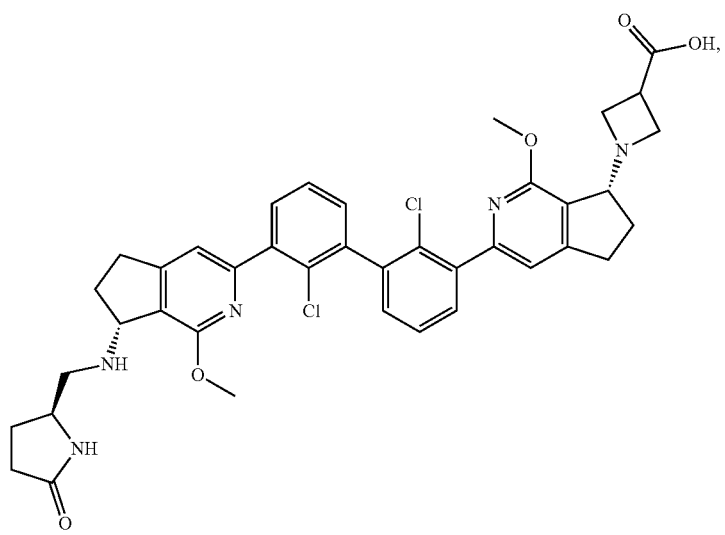

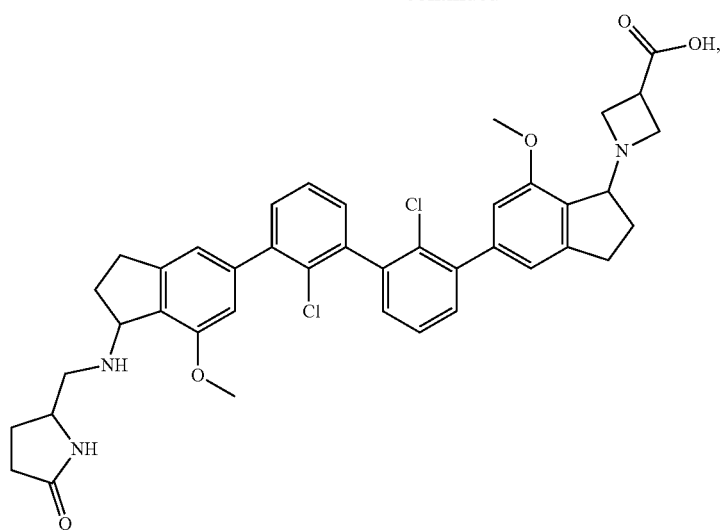
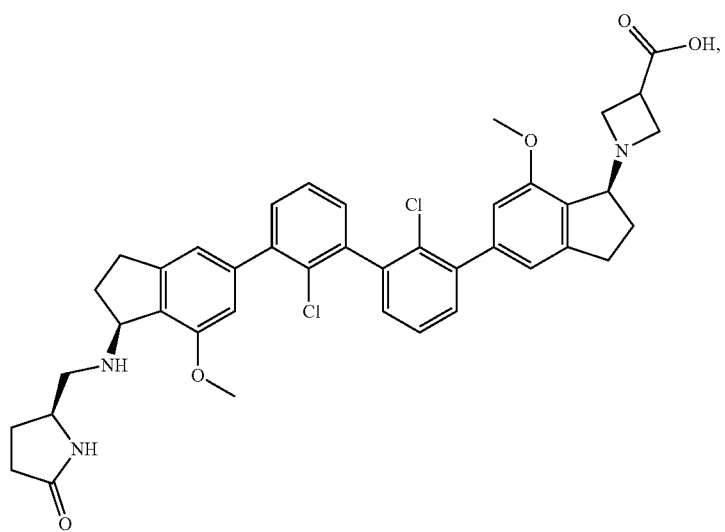
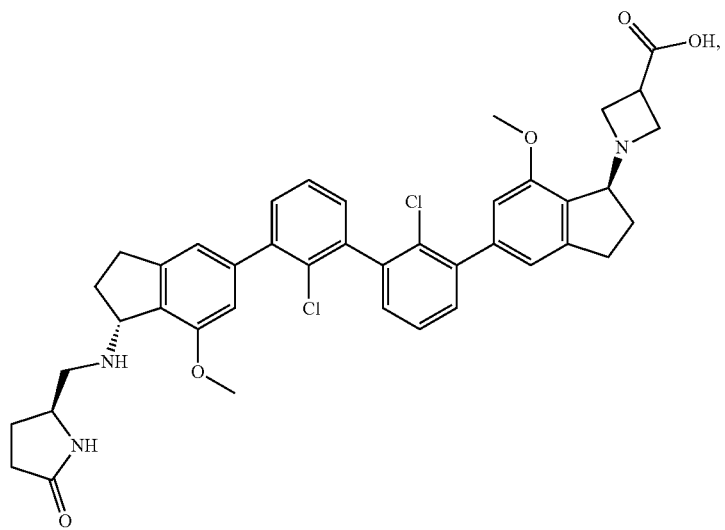

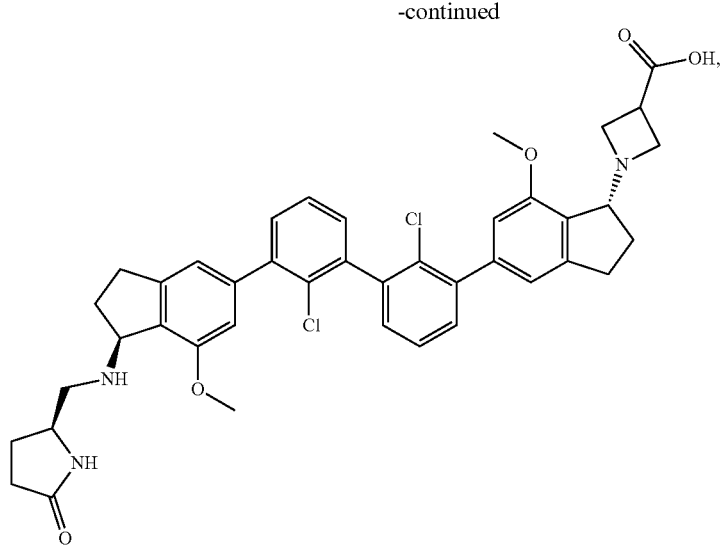
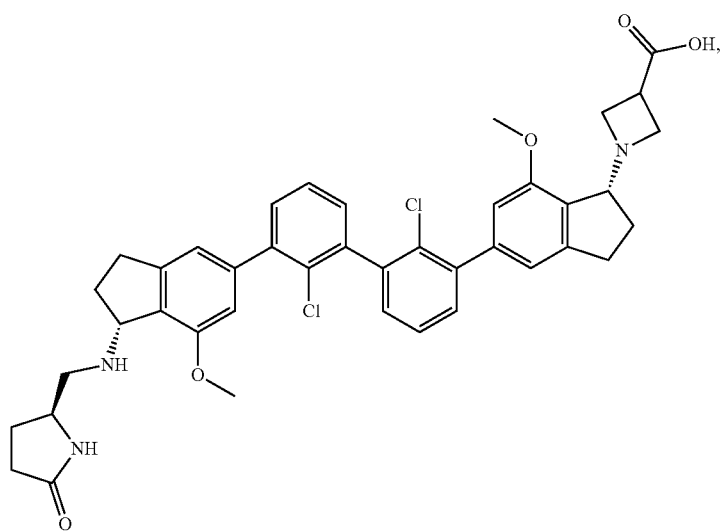
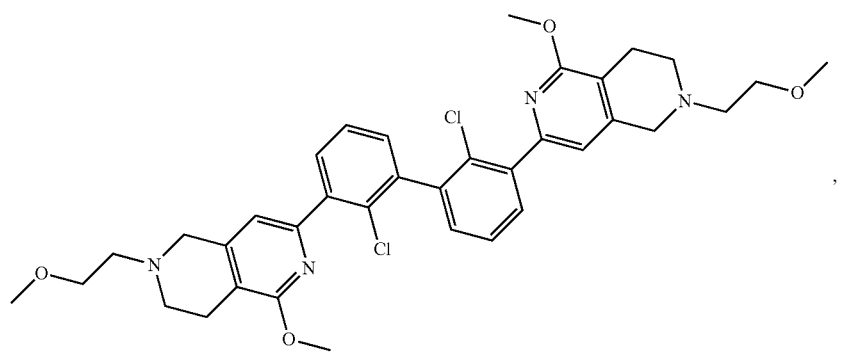

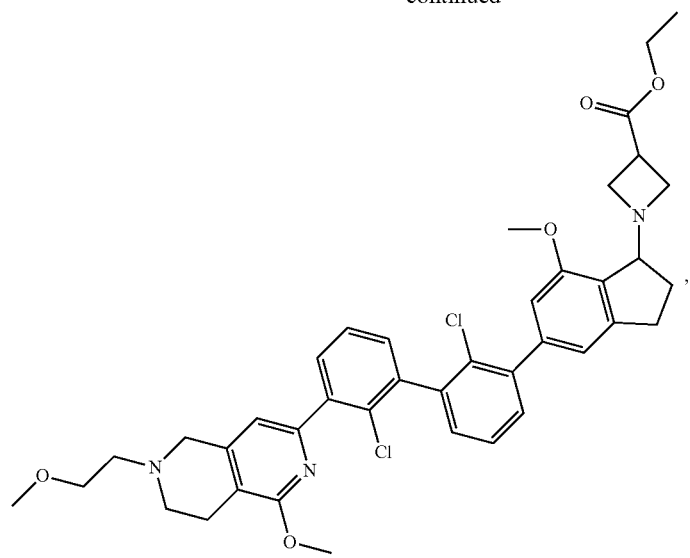
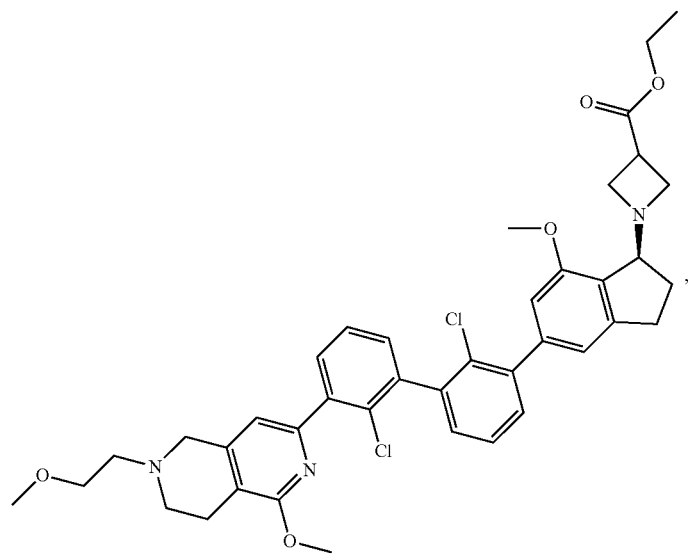
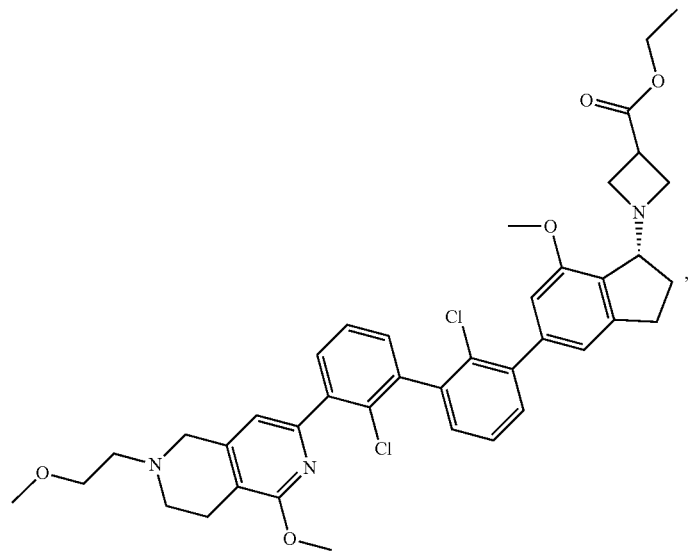

-continued
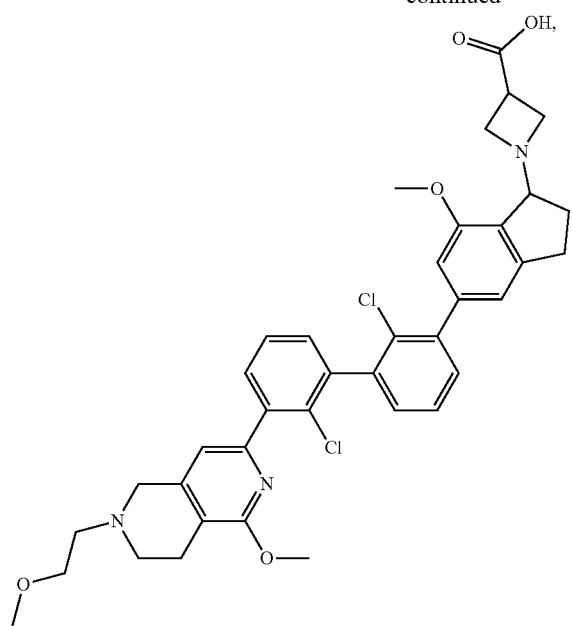
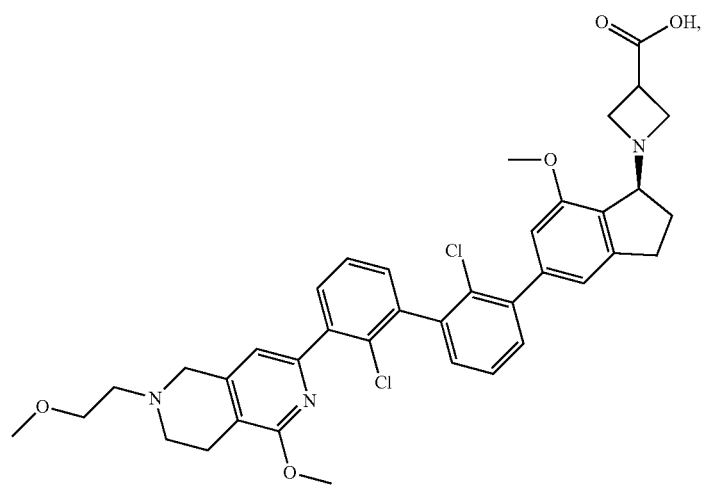
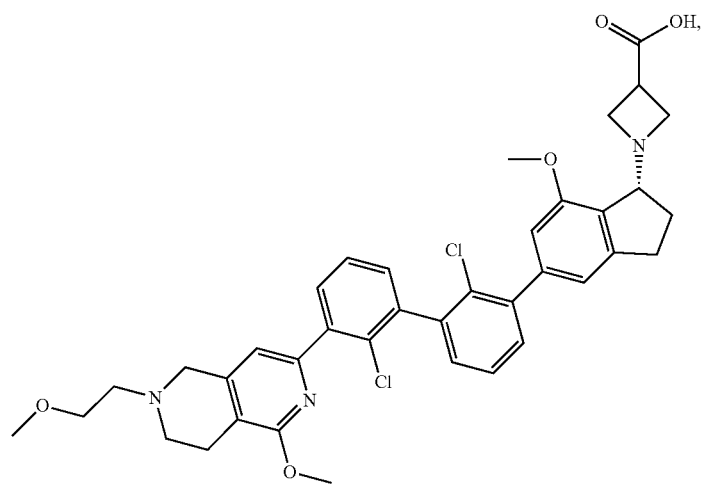

-continued
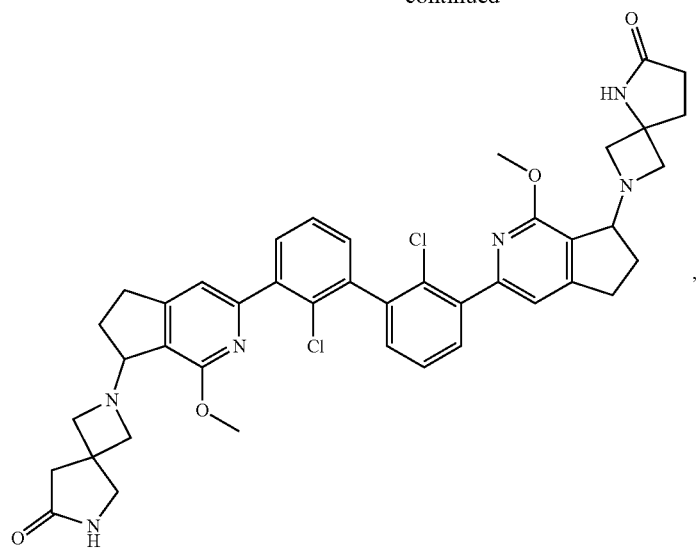
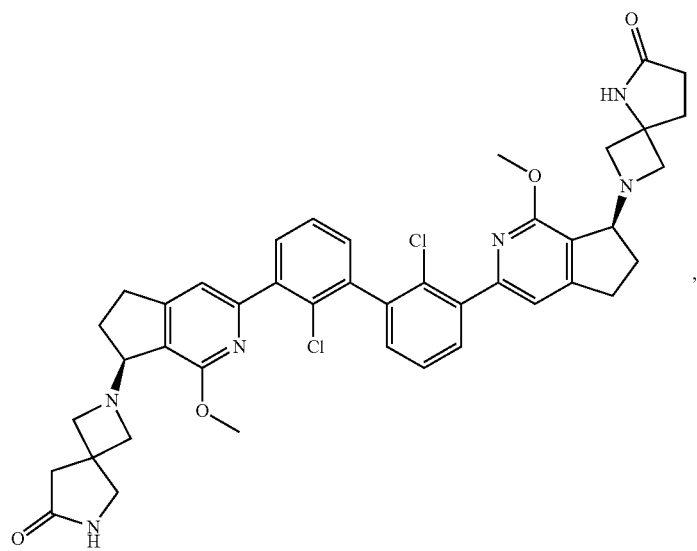
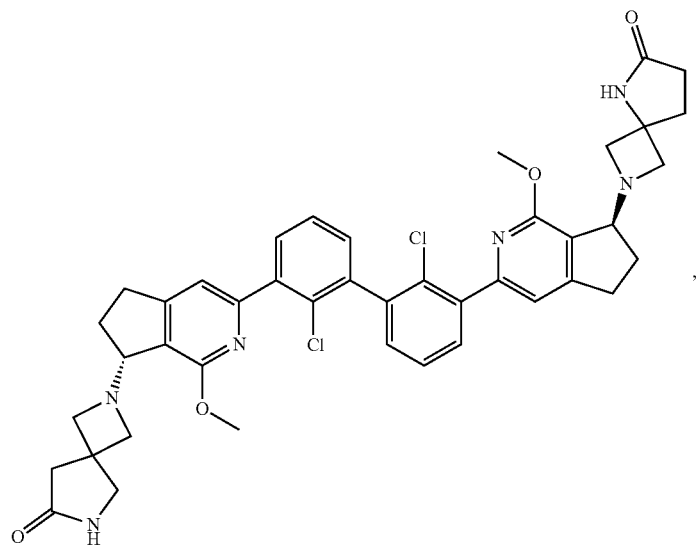

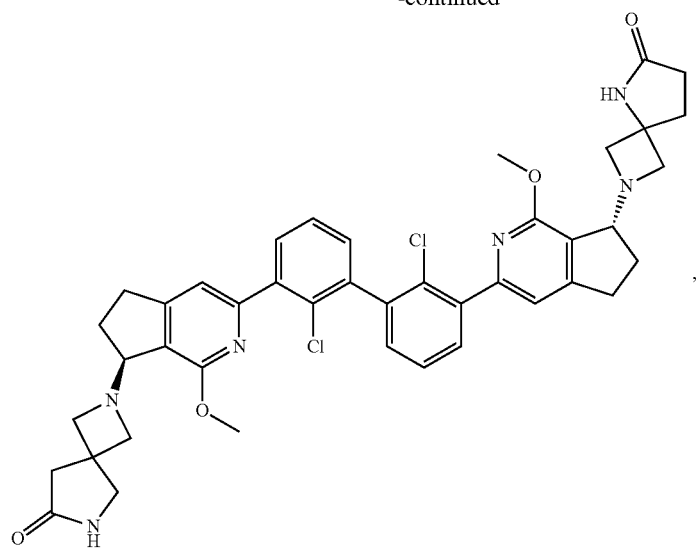
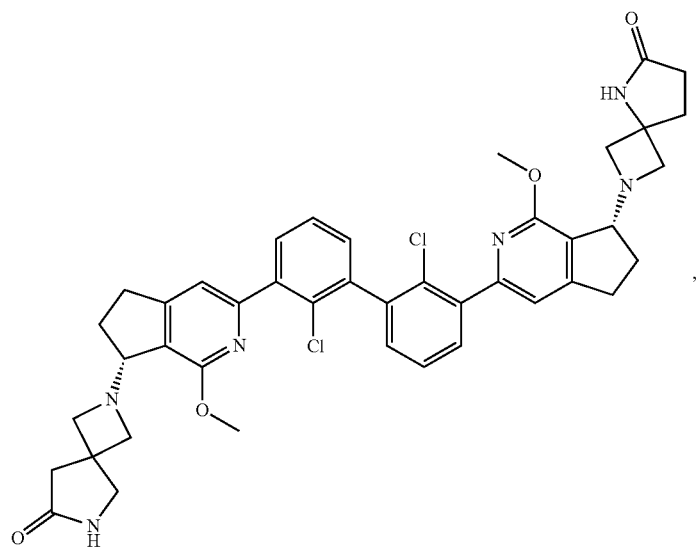
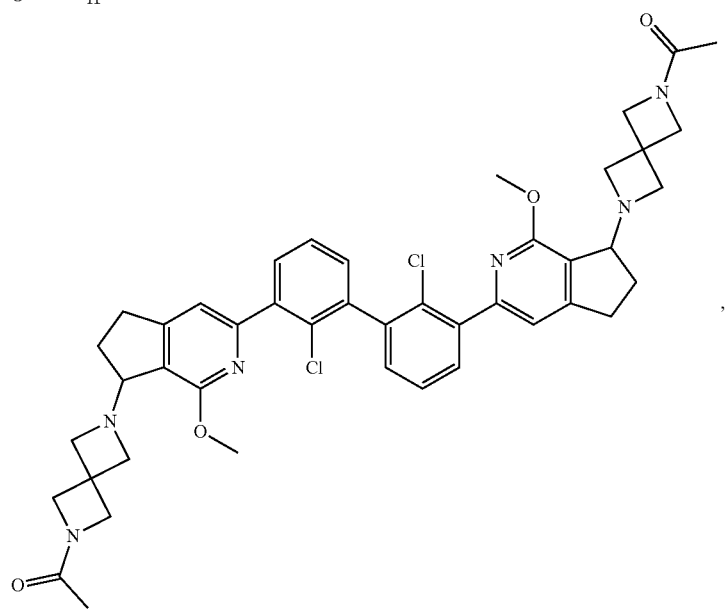

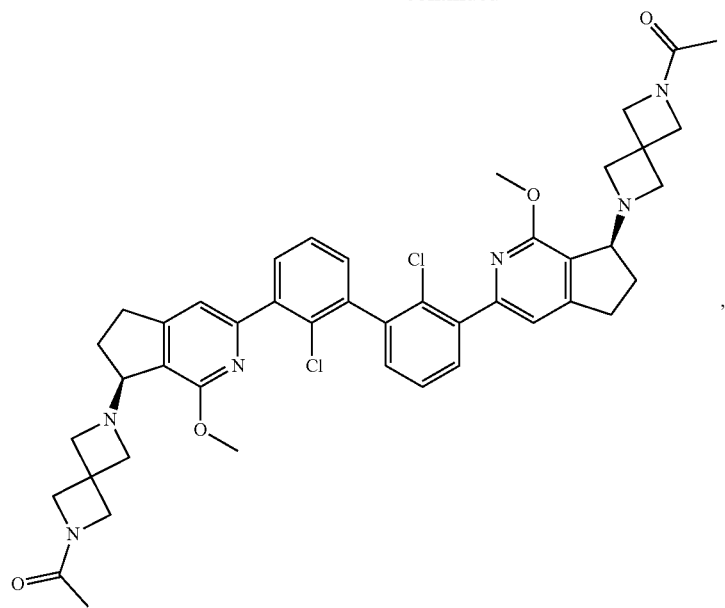
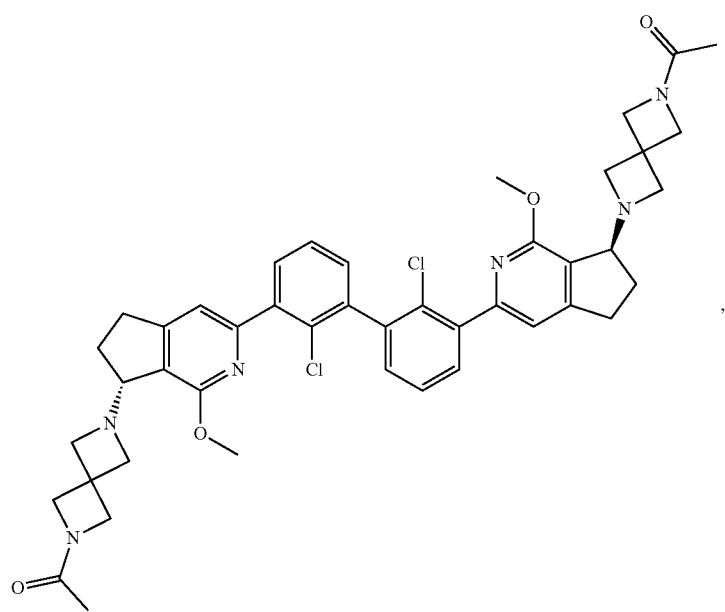

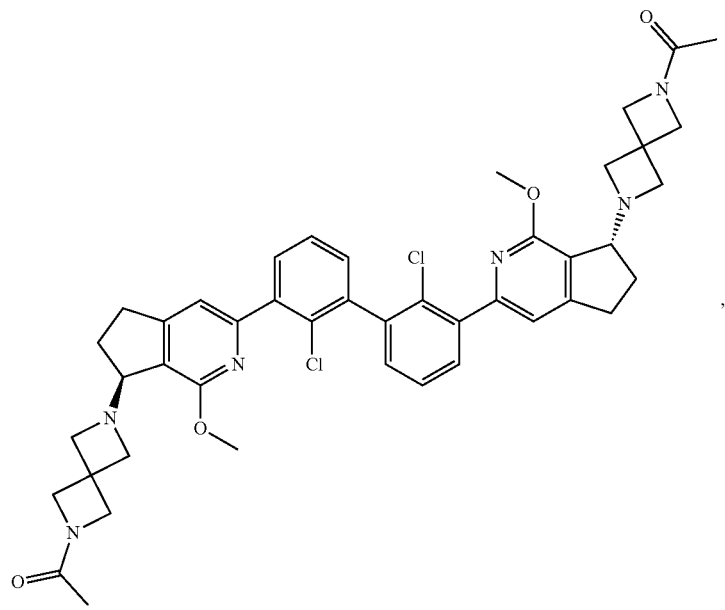
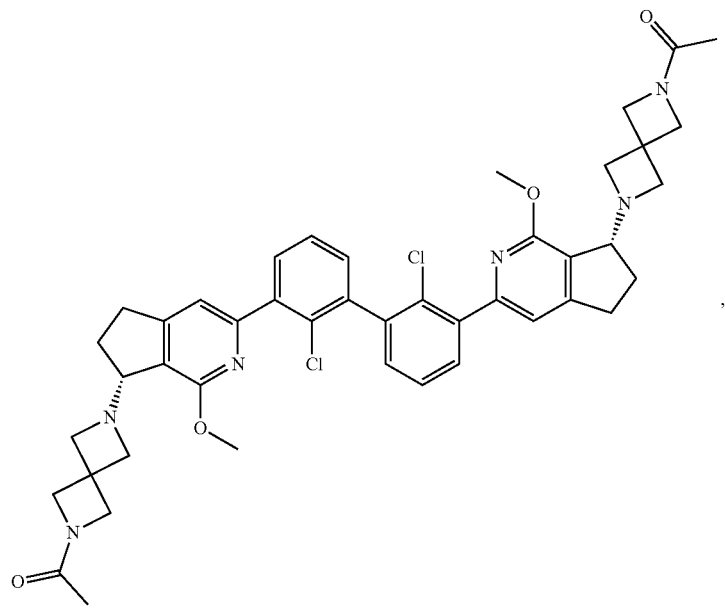
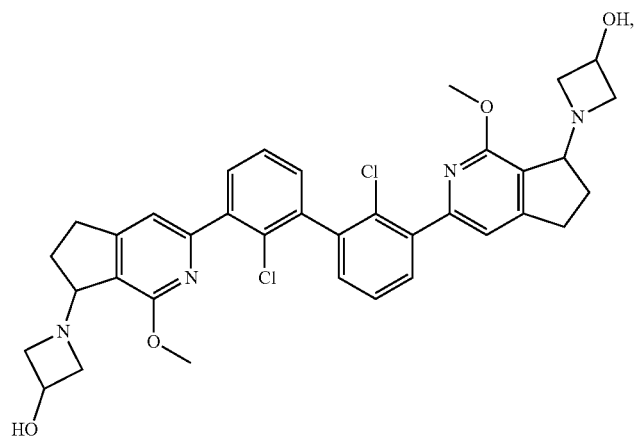

-continued
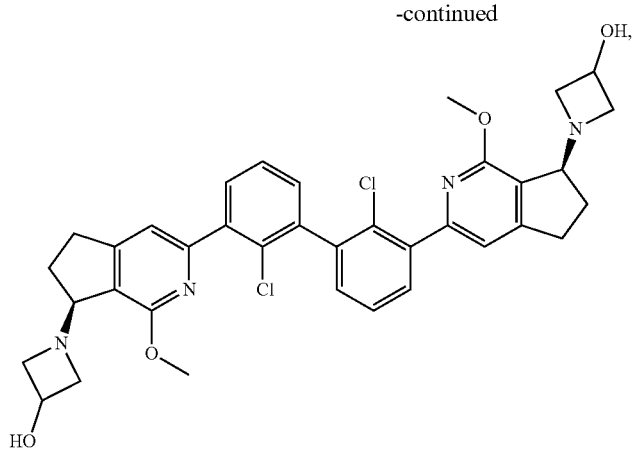
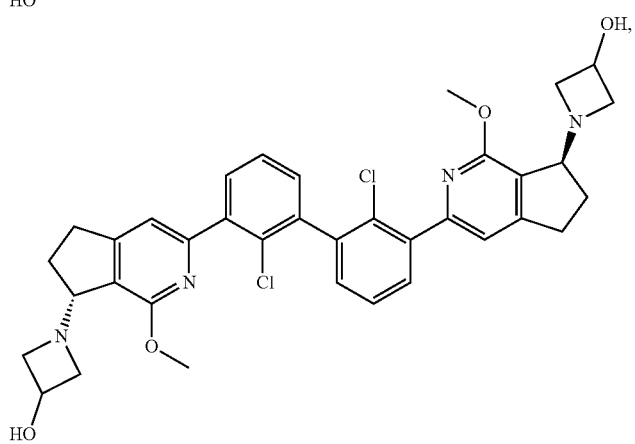
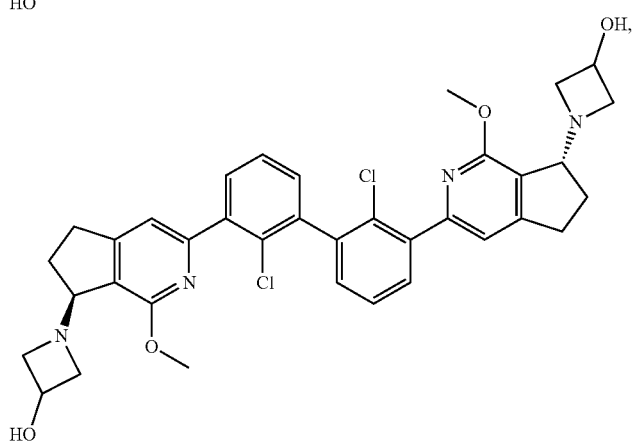
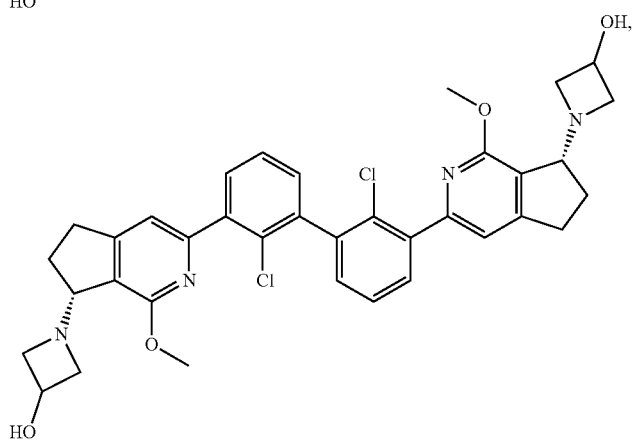

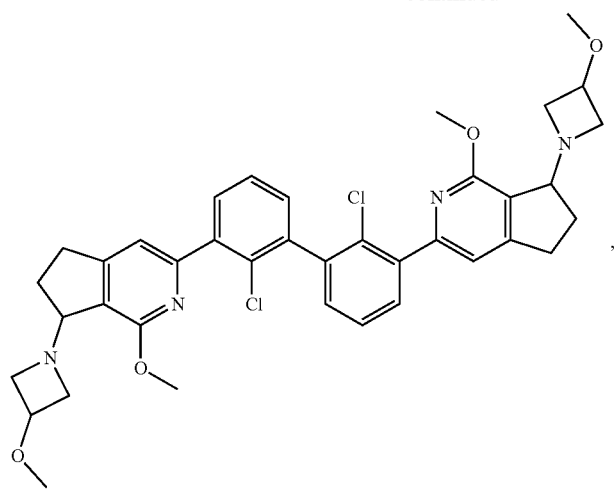
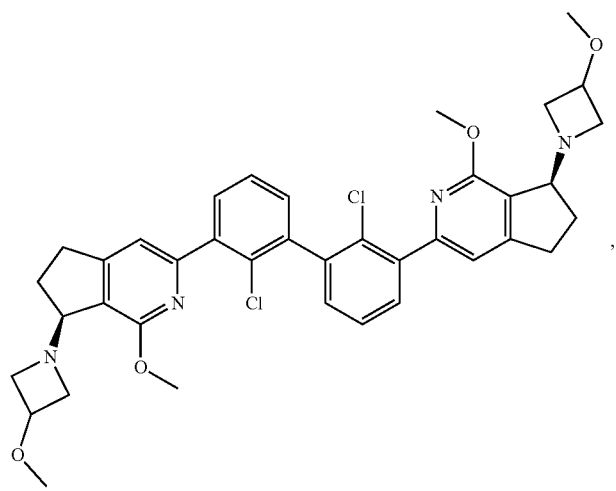
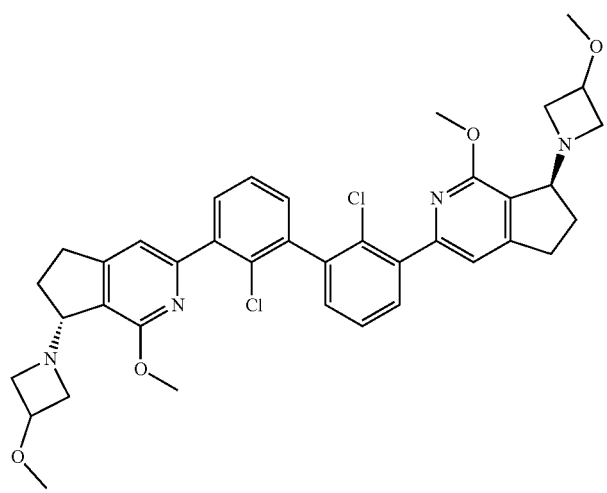

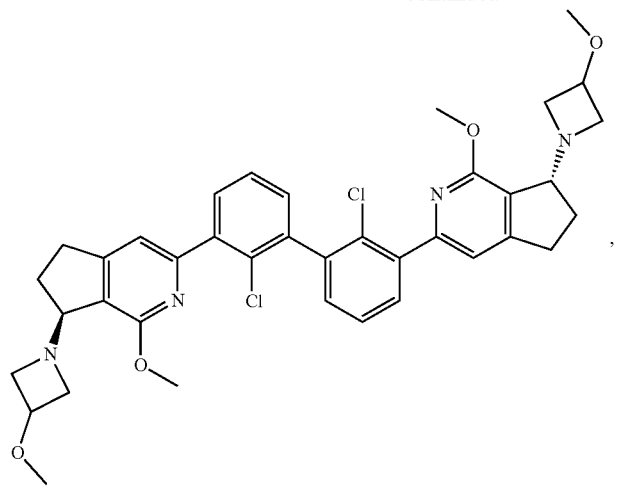
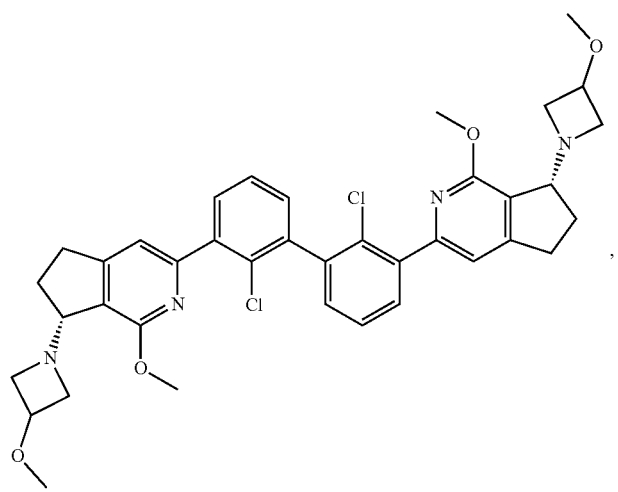
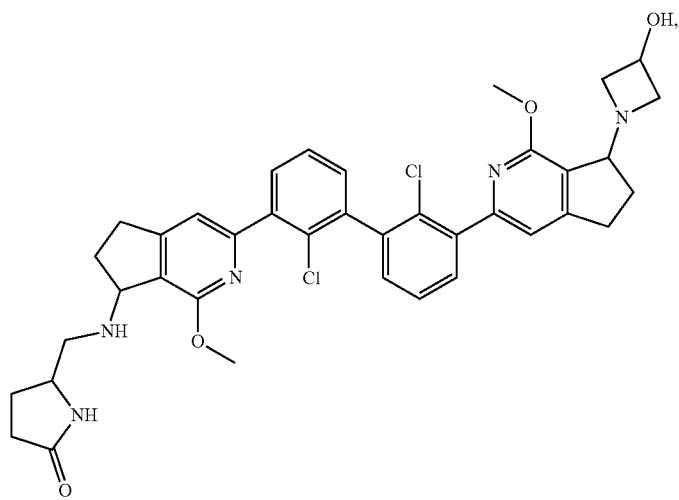

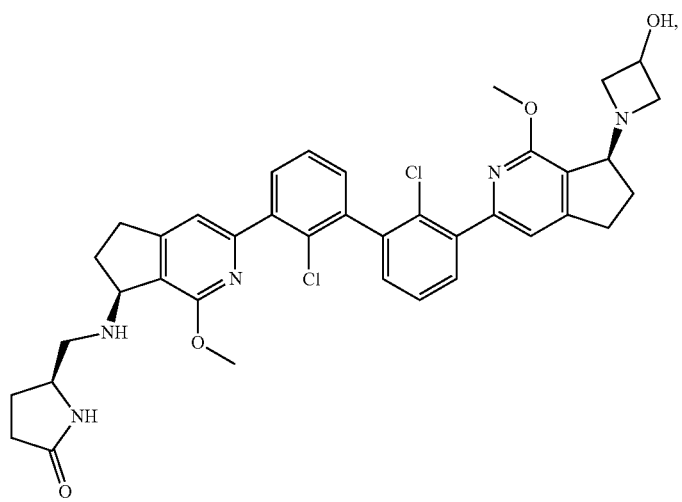
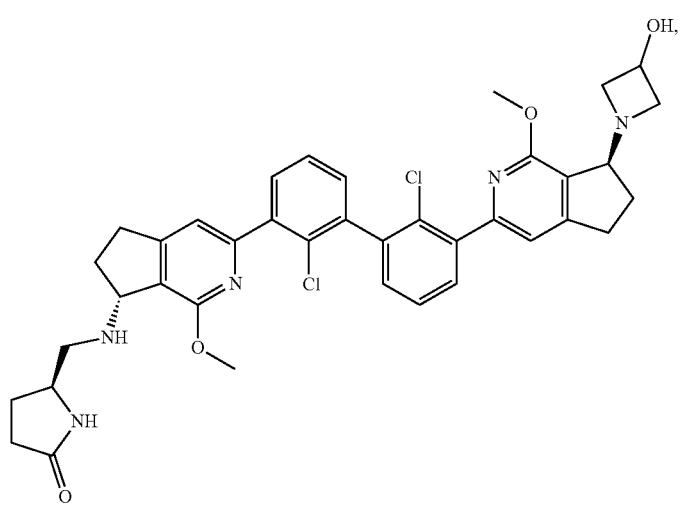
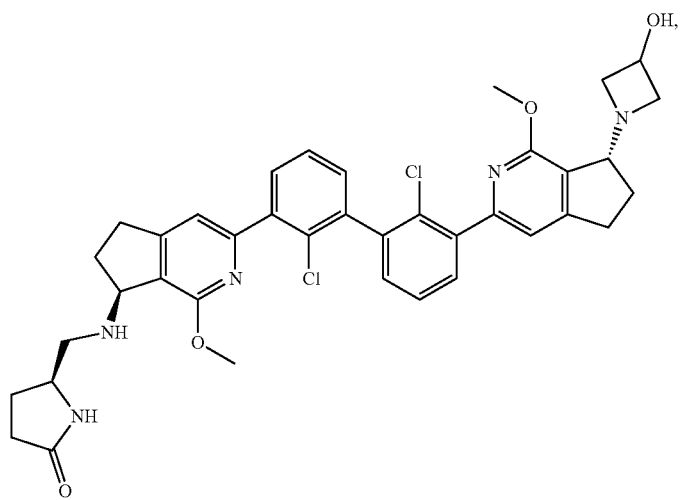

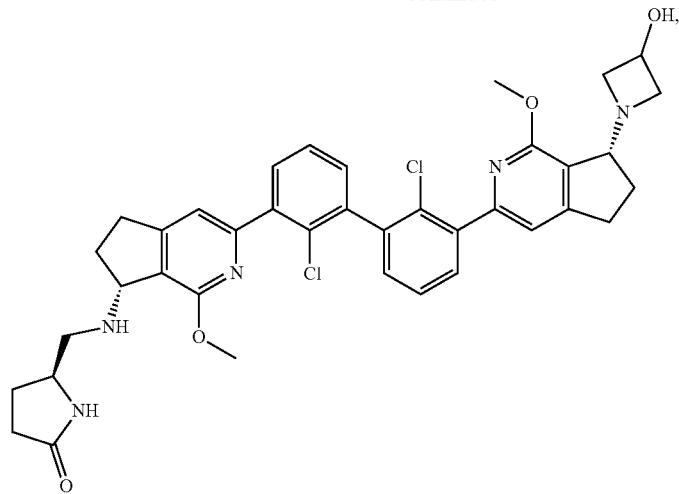
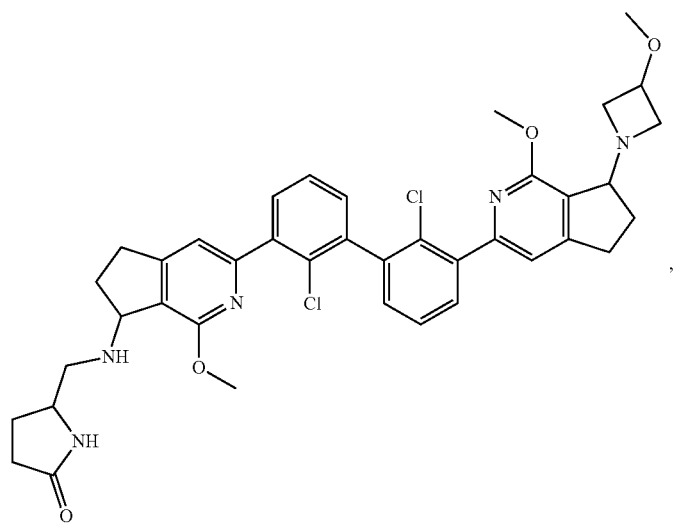
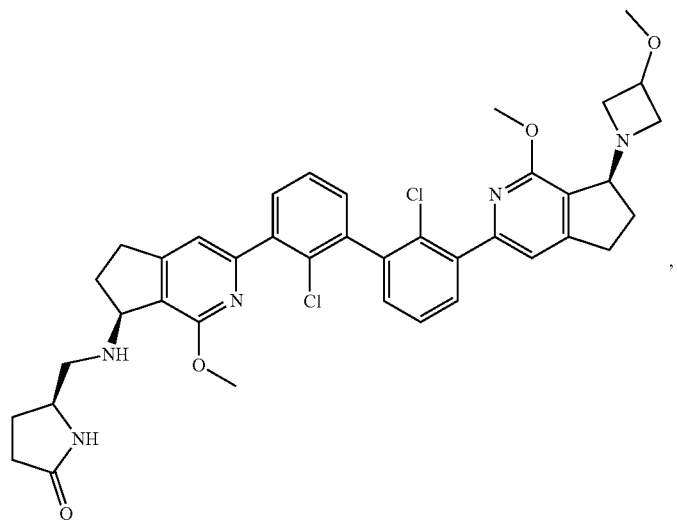

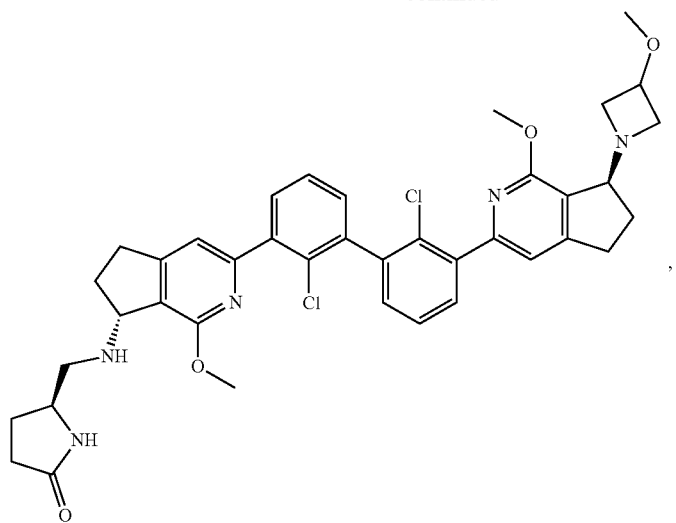
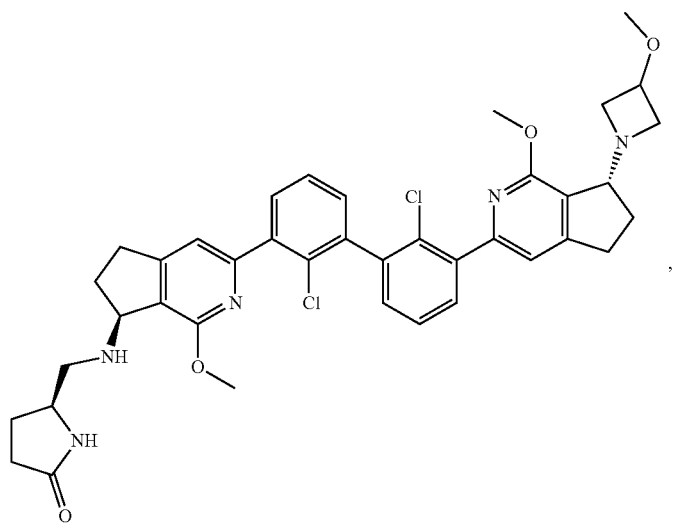
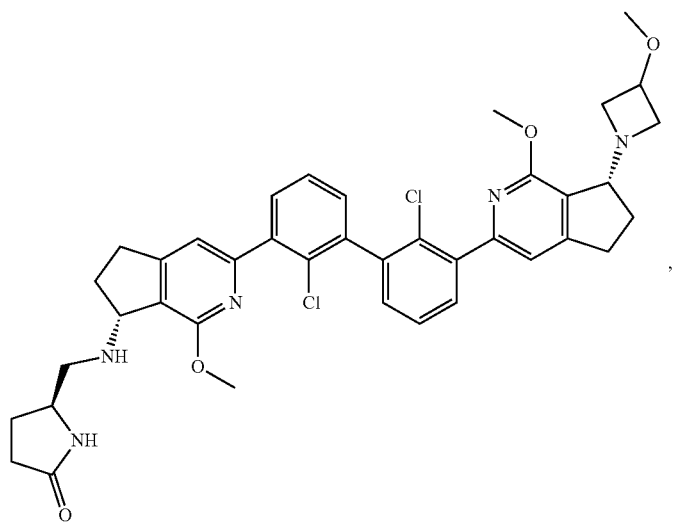

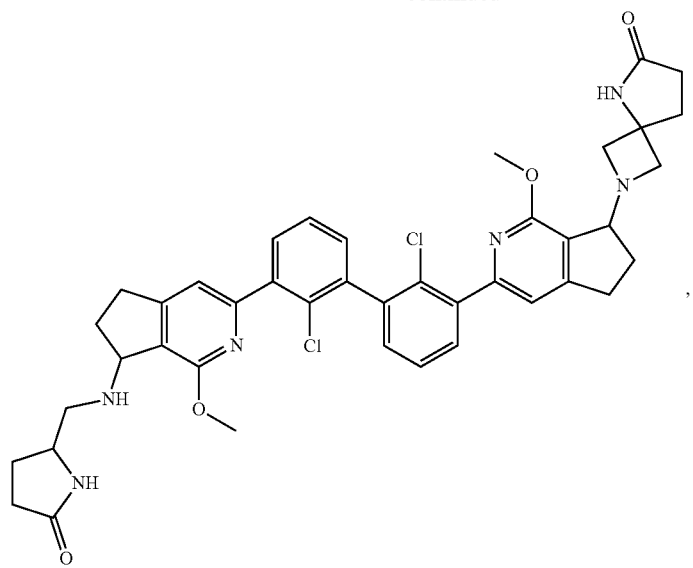
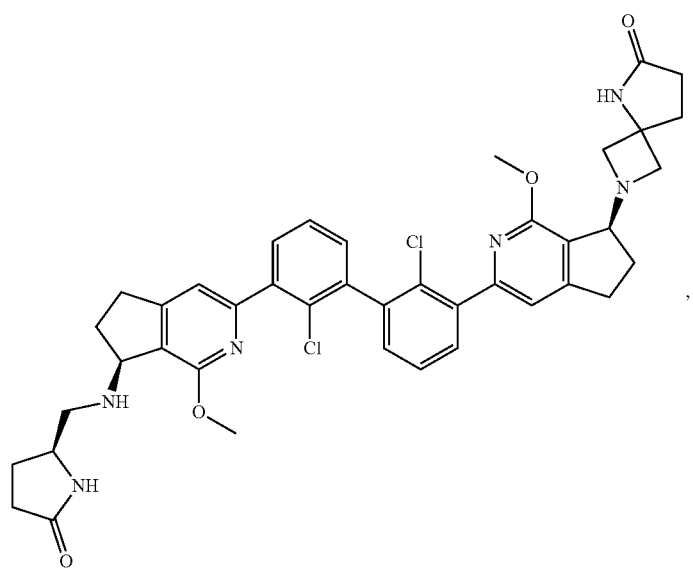
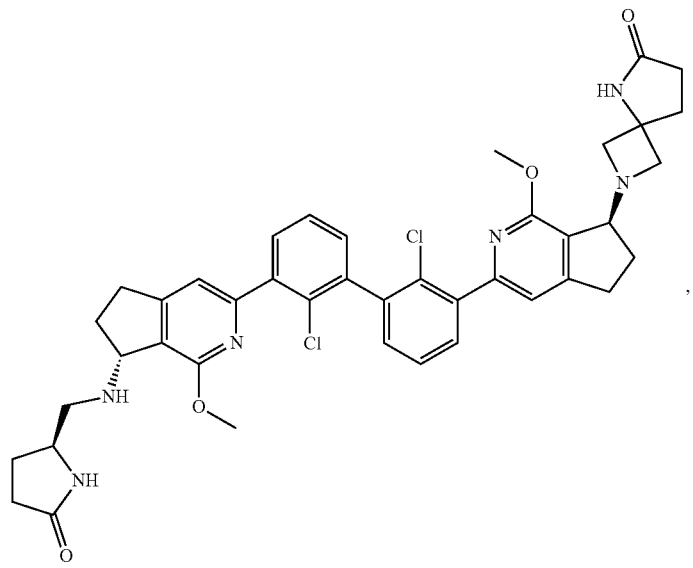

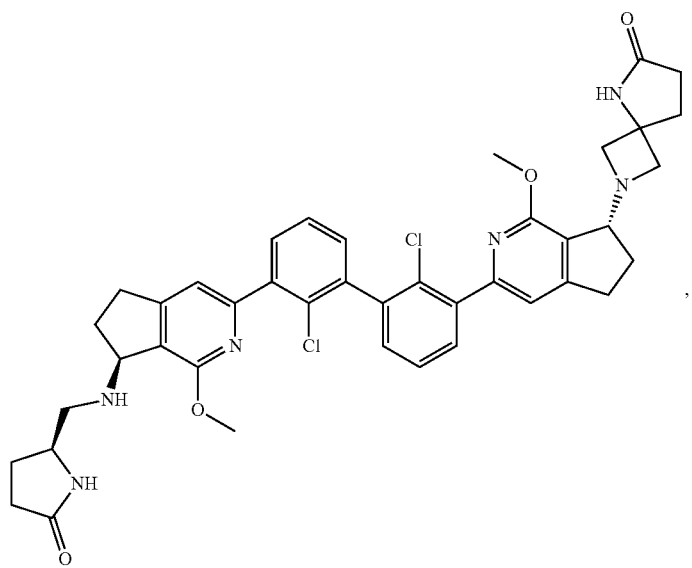
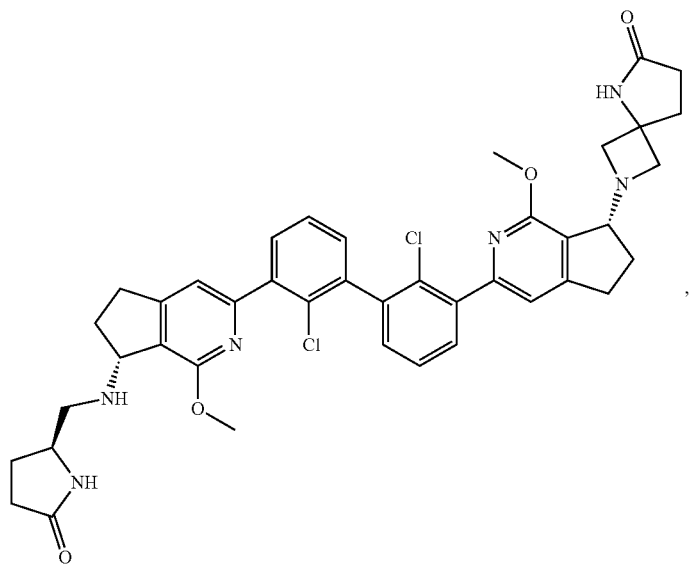
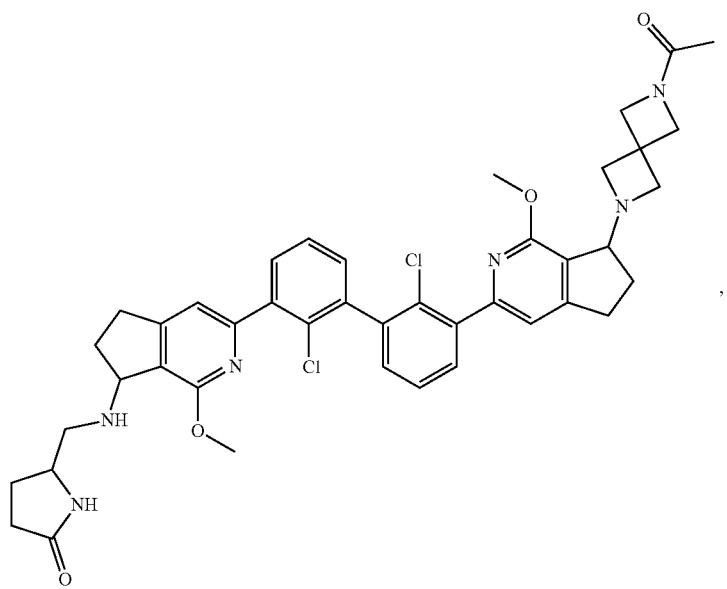

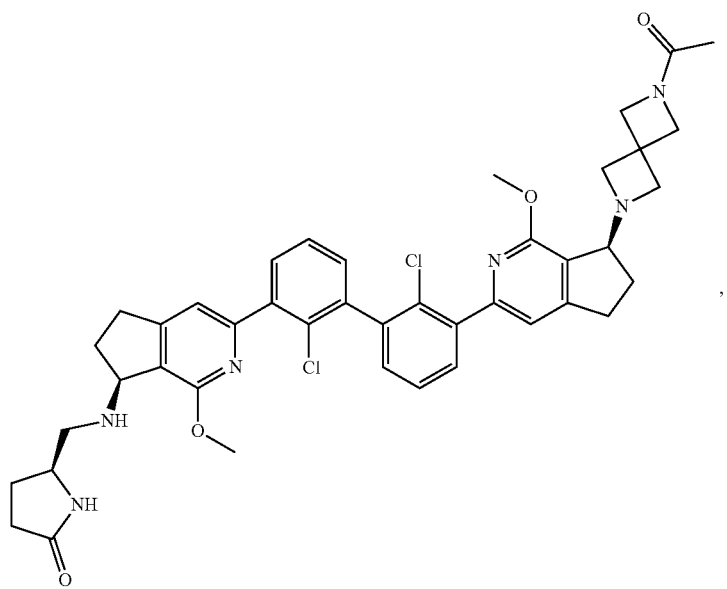
,
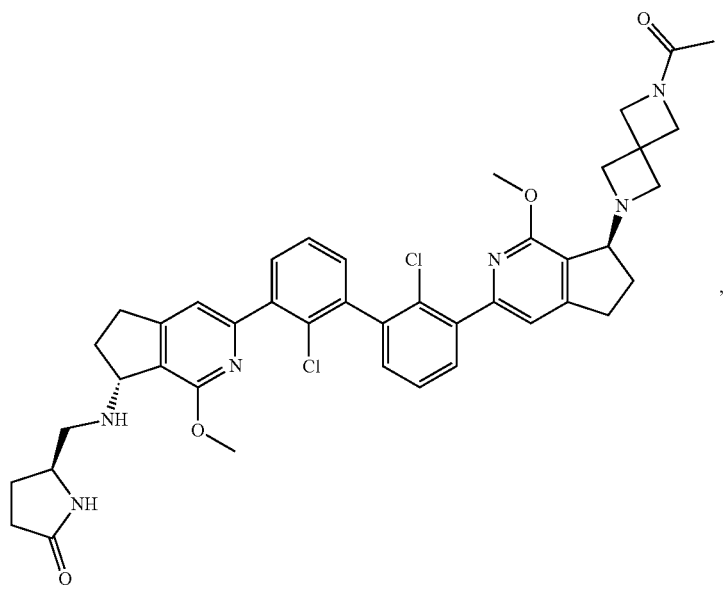
,

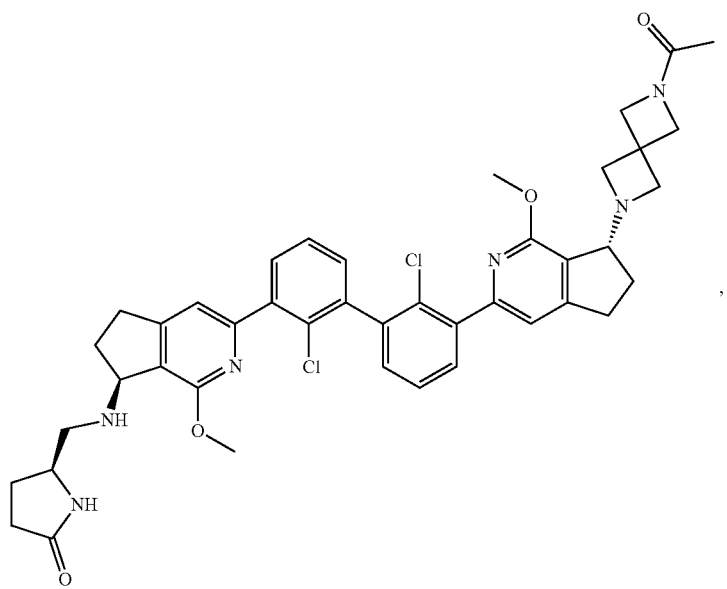
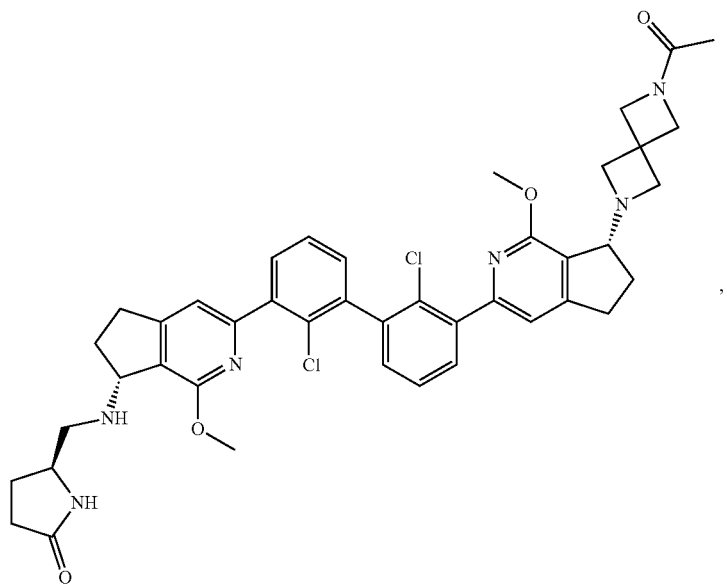

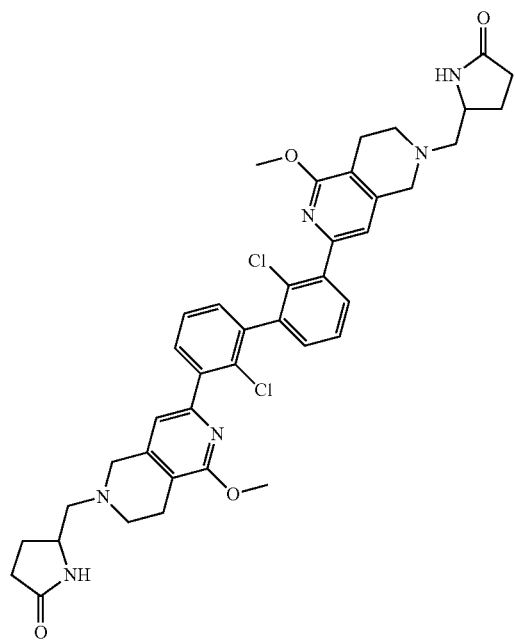
,
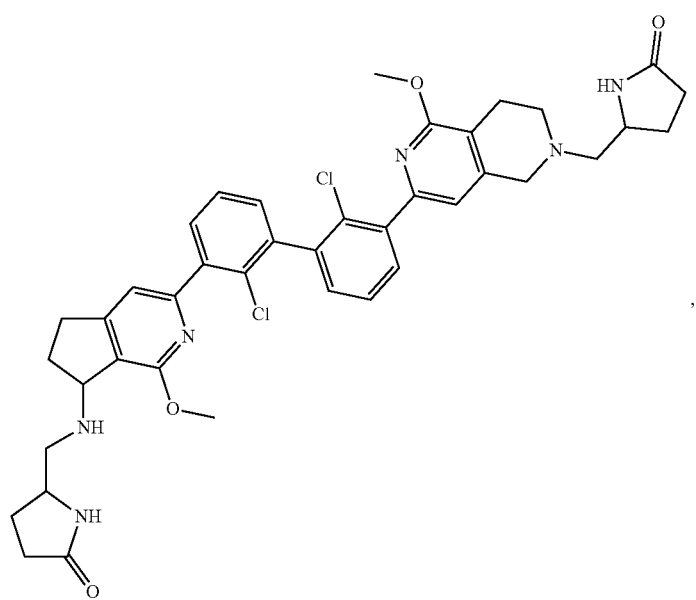
,

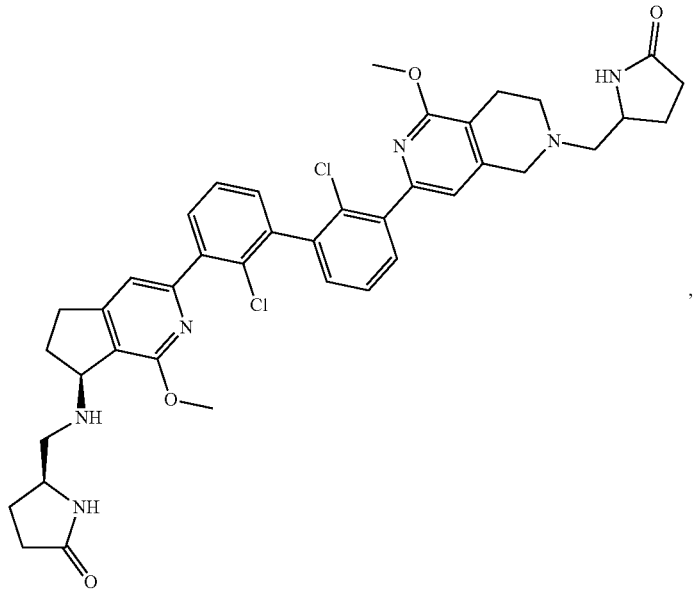
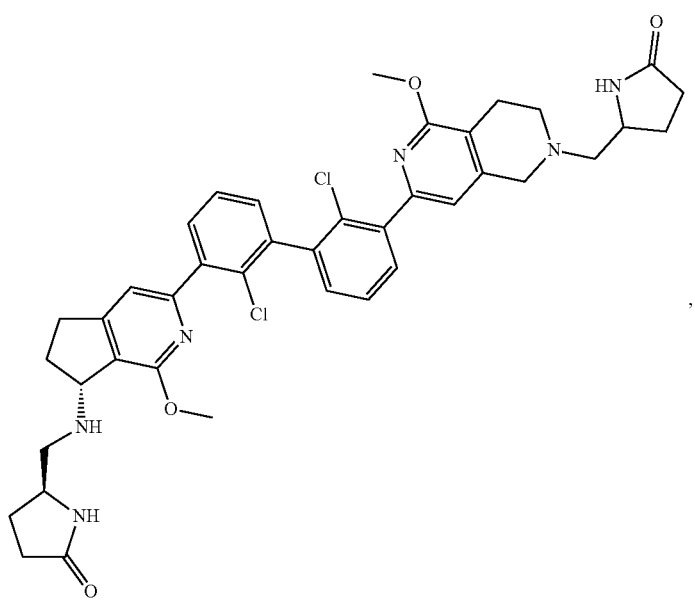
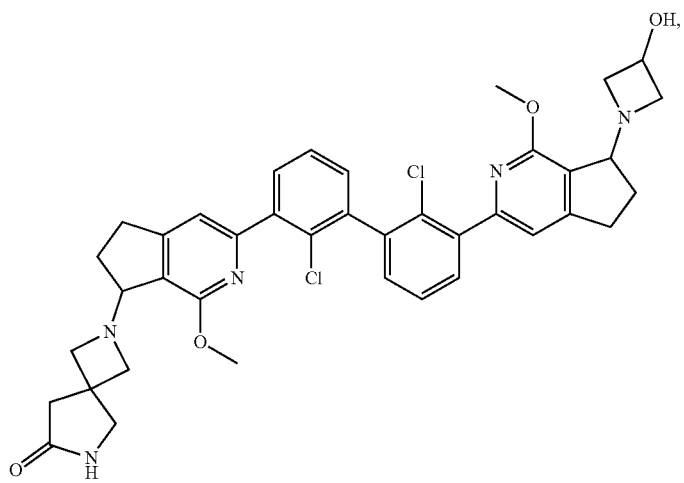

-continued
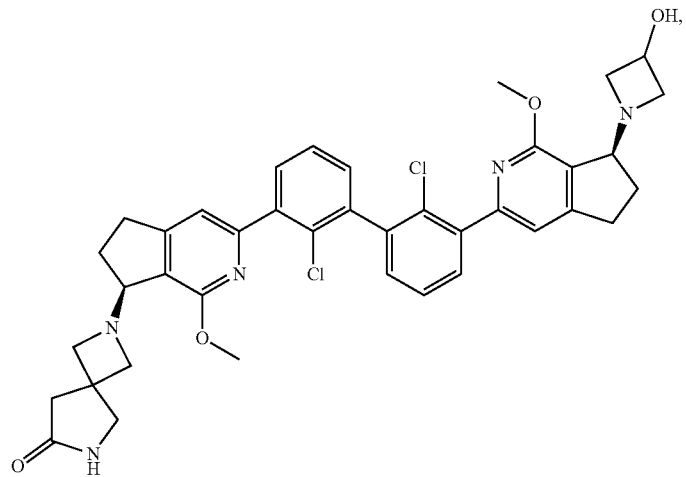
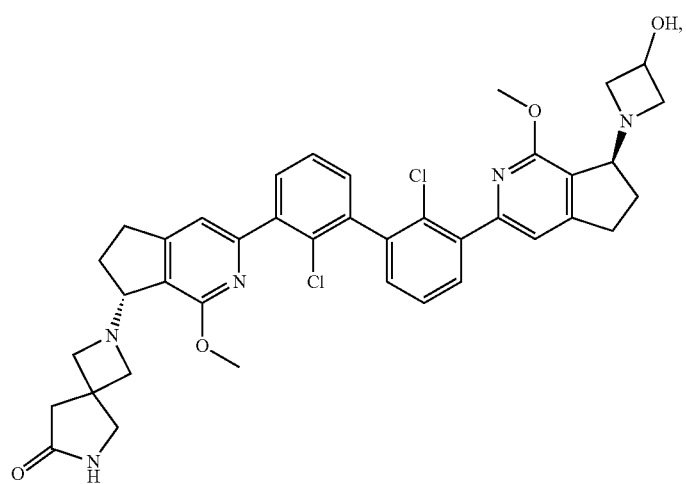
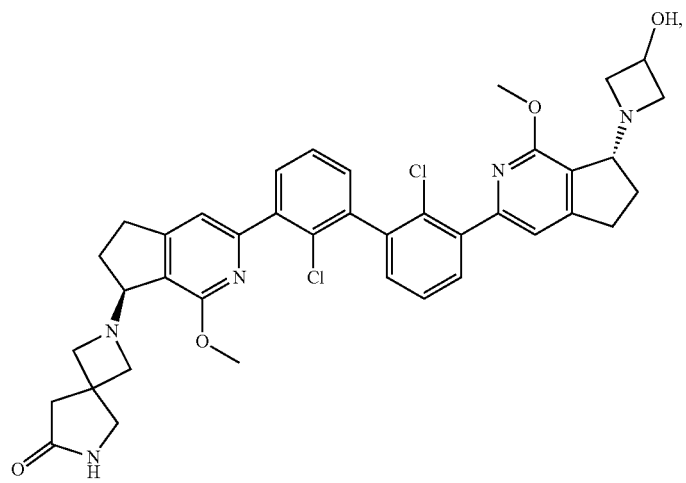

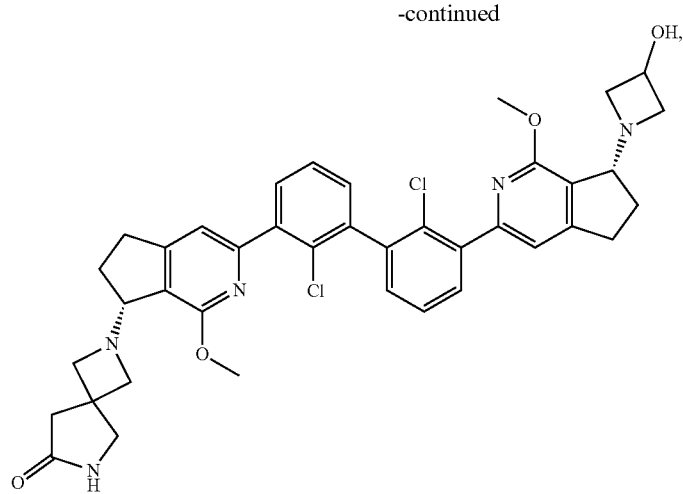
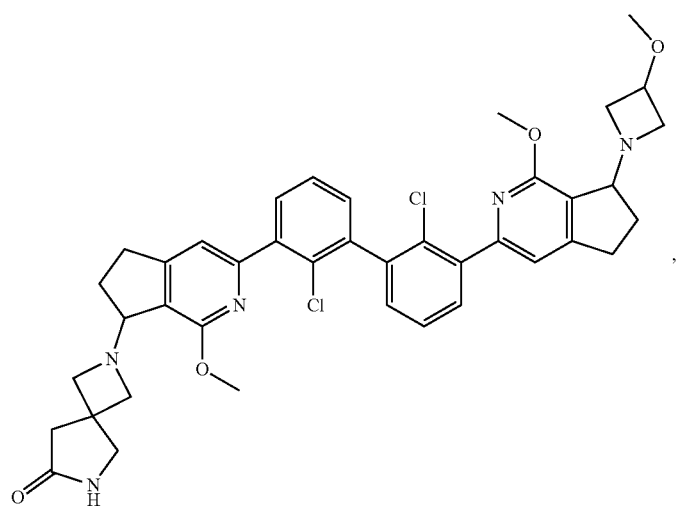
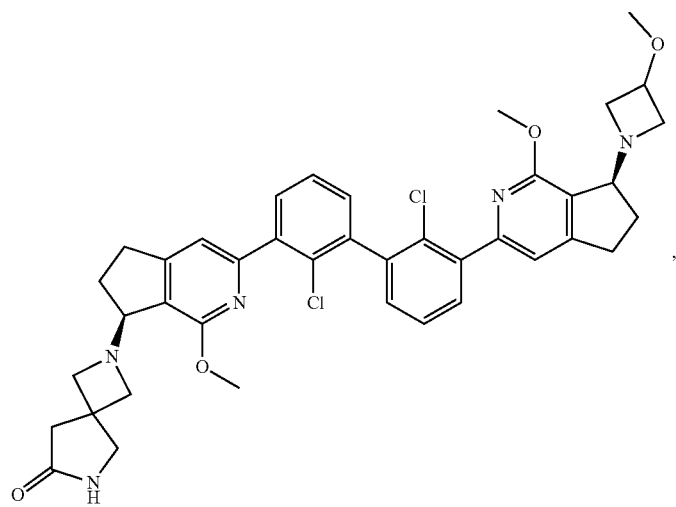

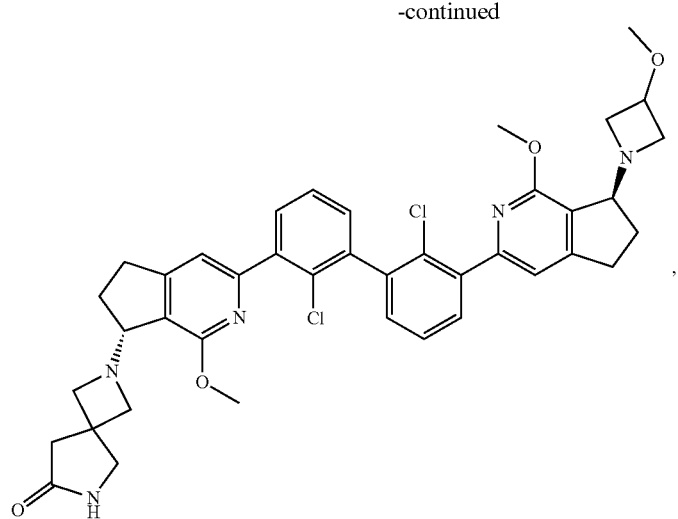,
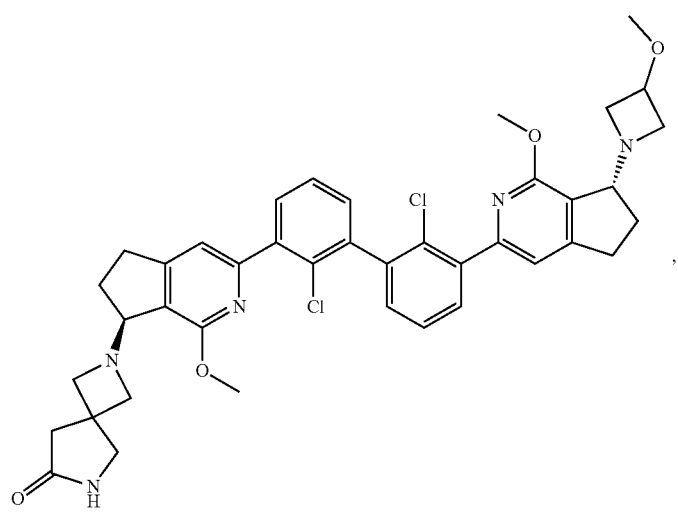,
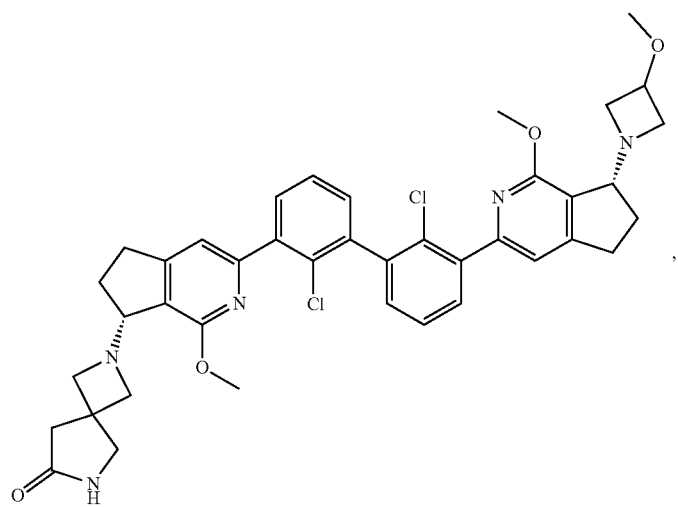,

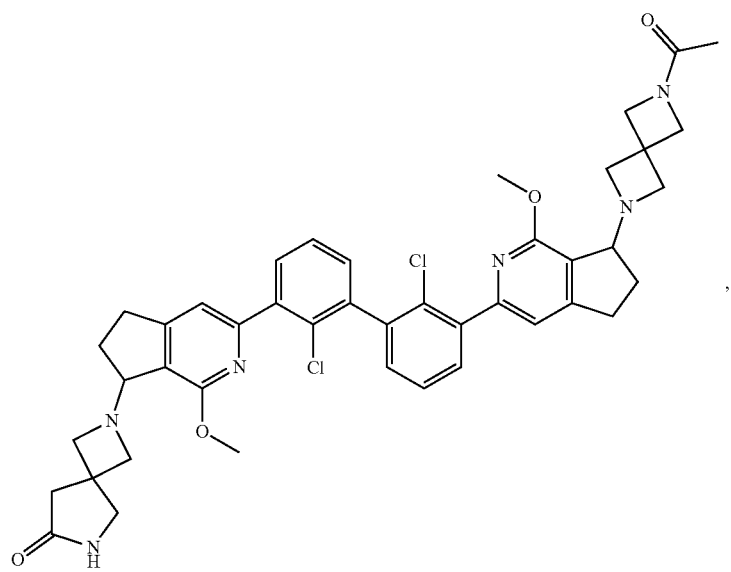
,
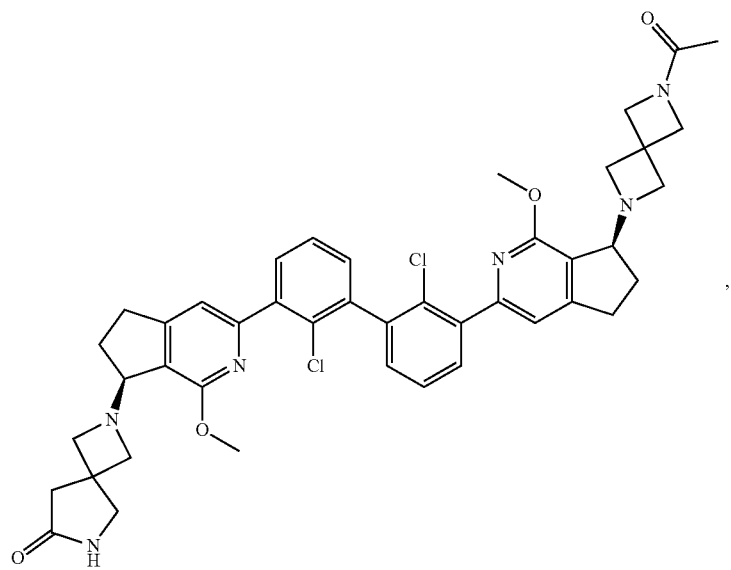
,
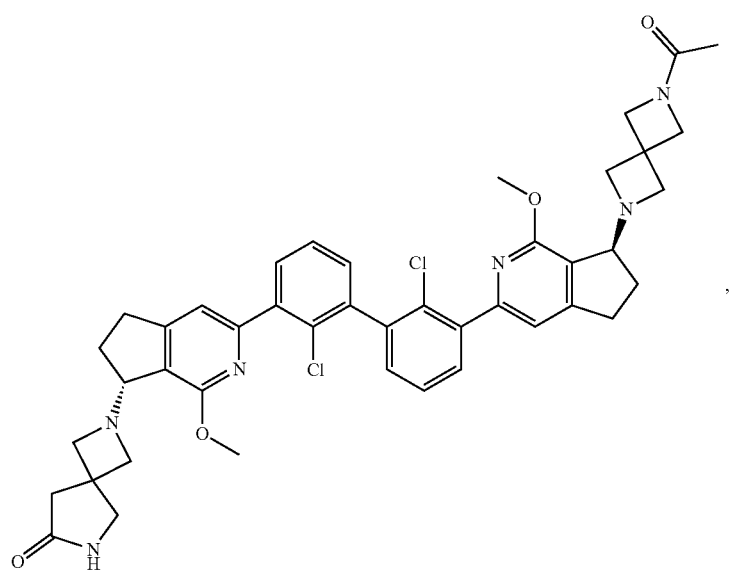
,

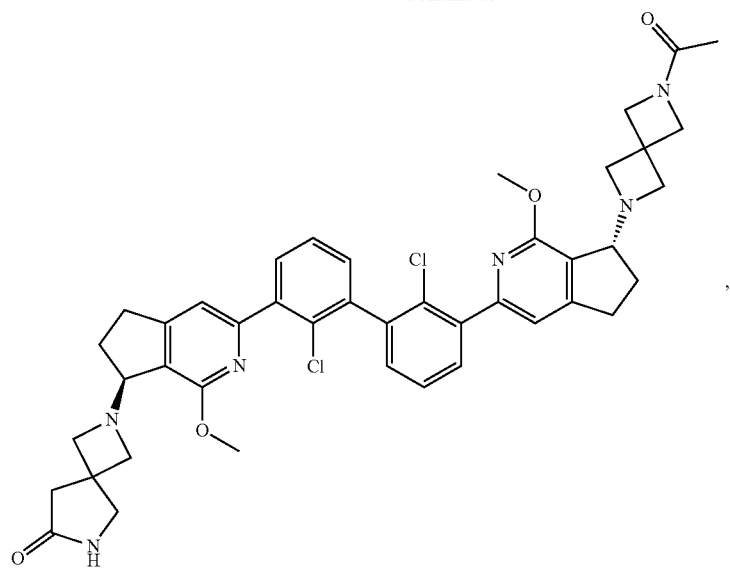
,
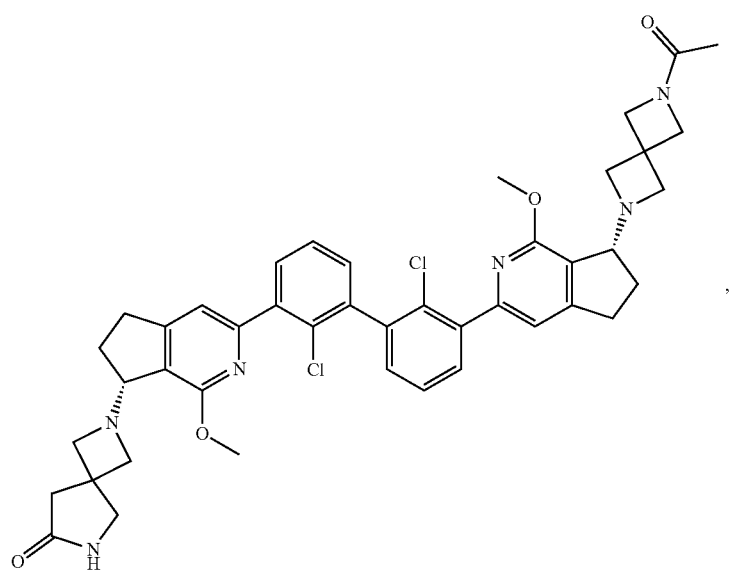
,
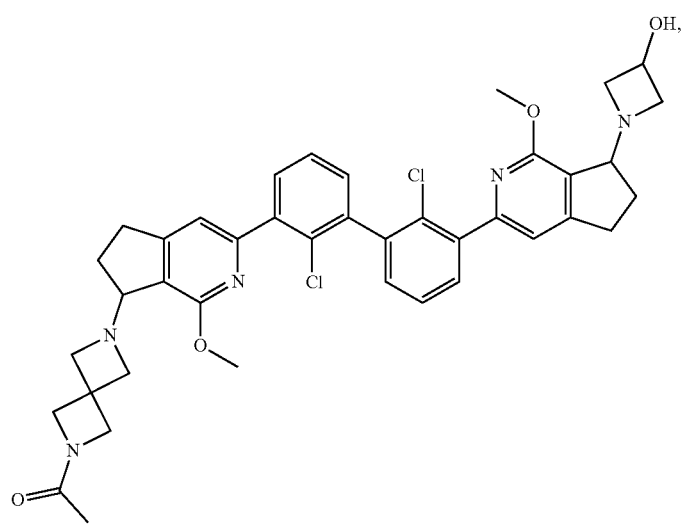

-continued
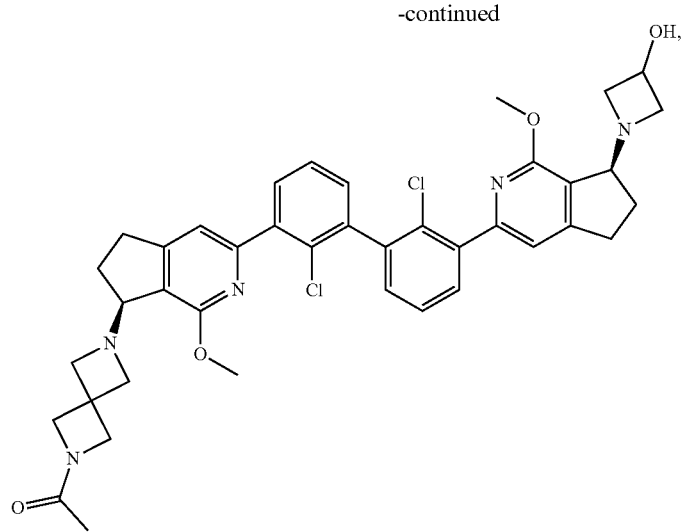
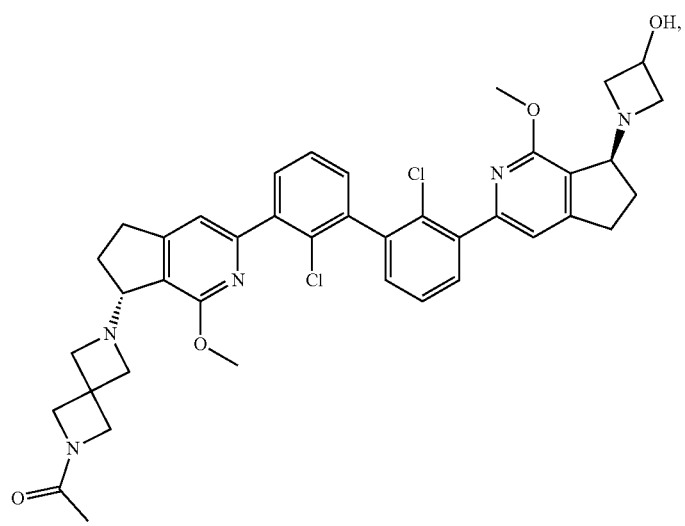
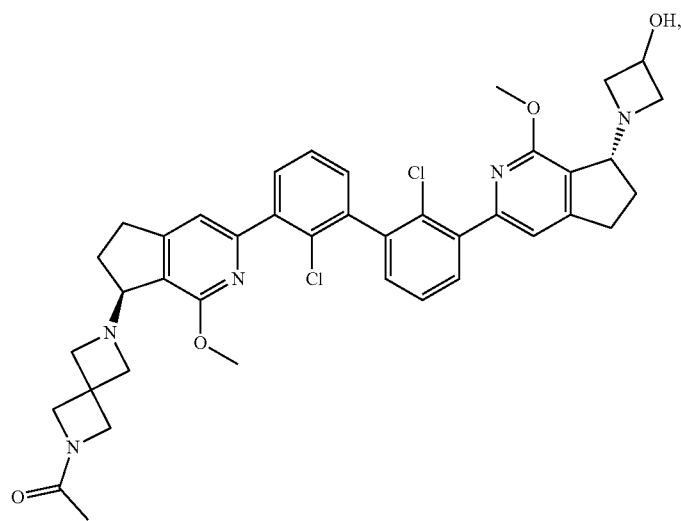

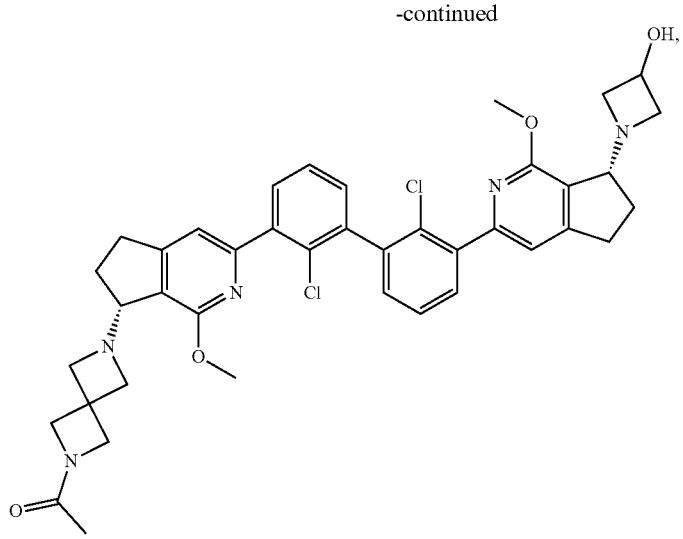
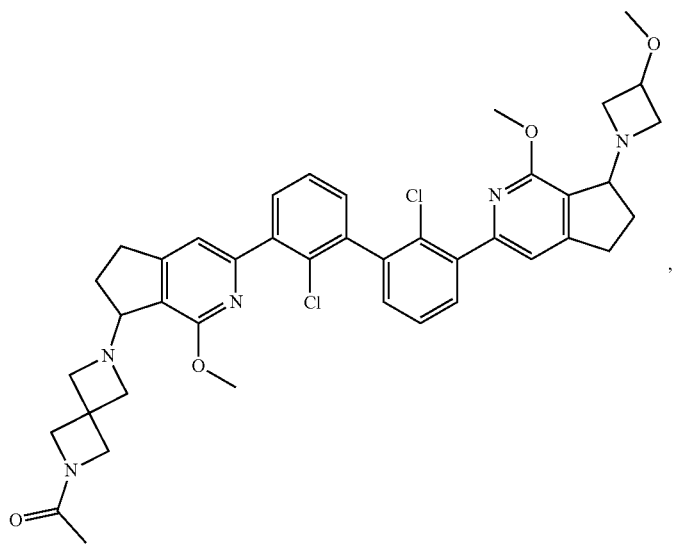
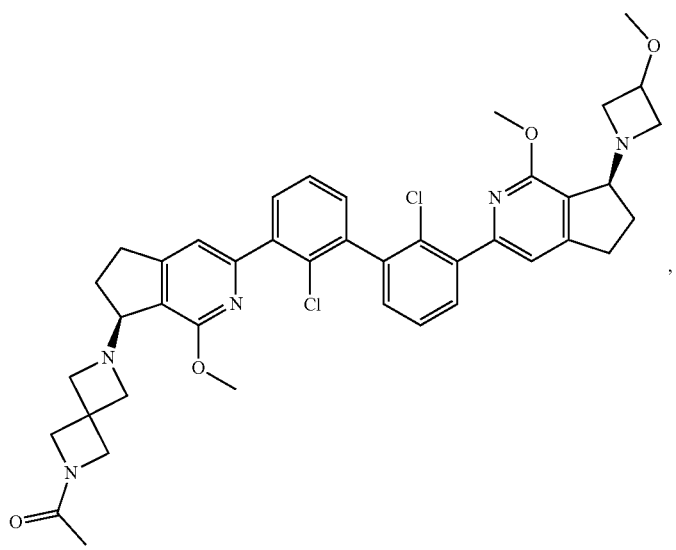

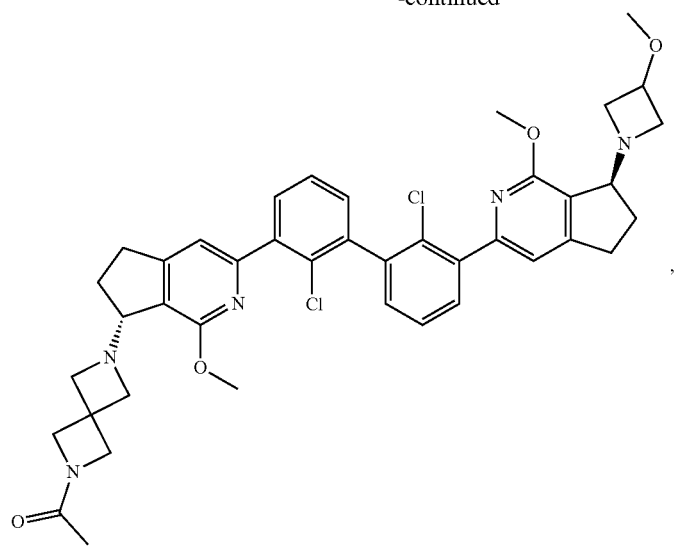,
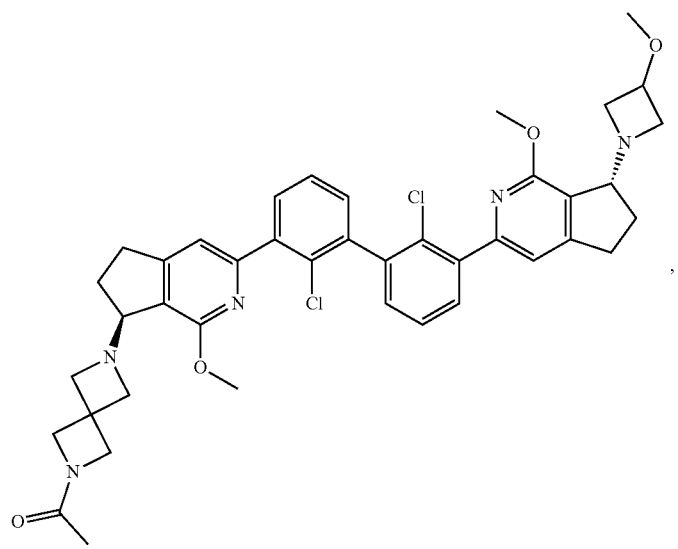,
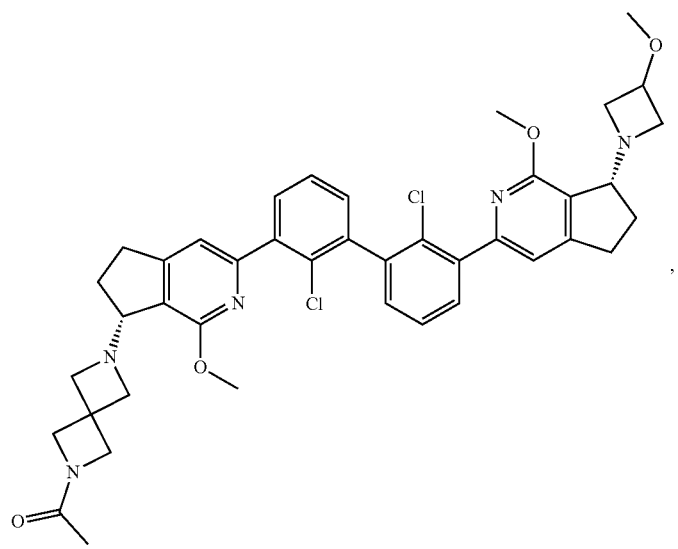,

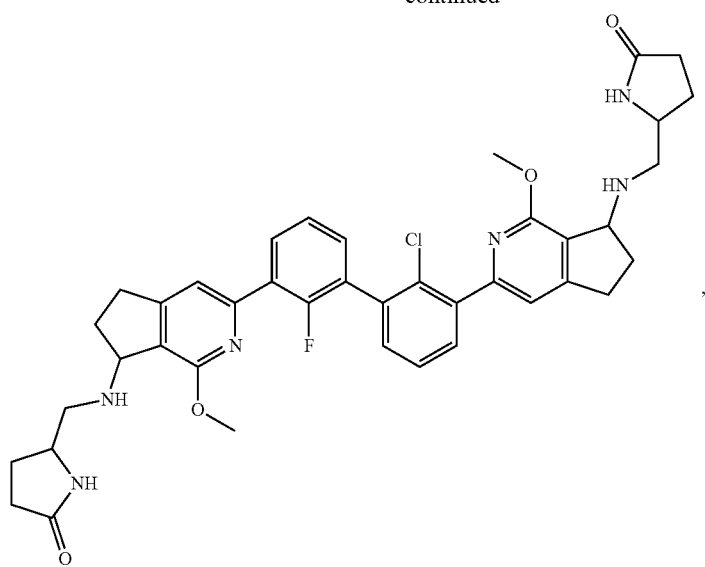,
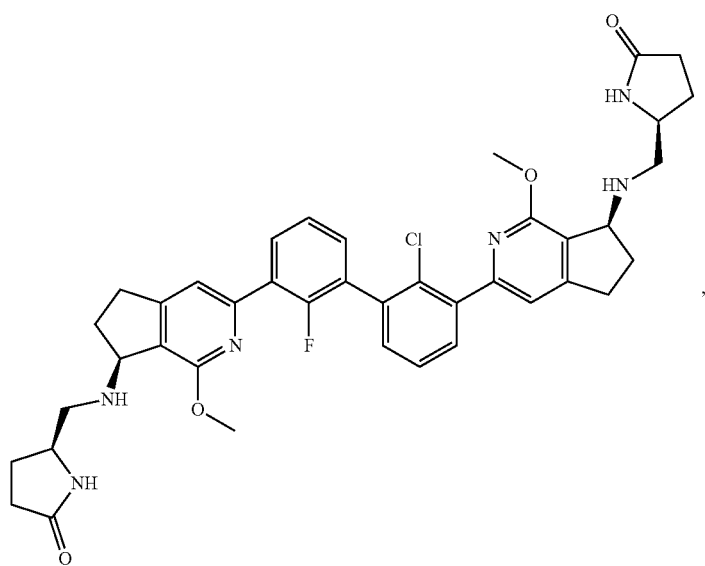,
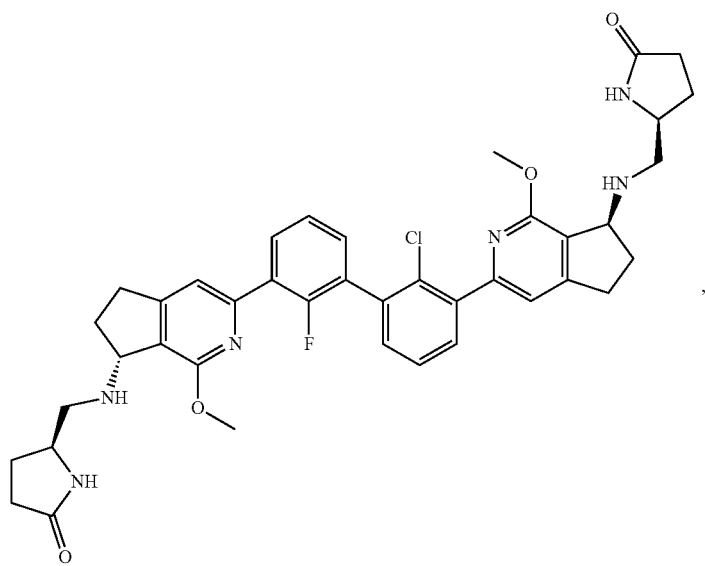,

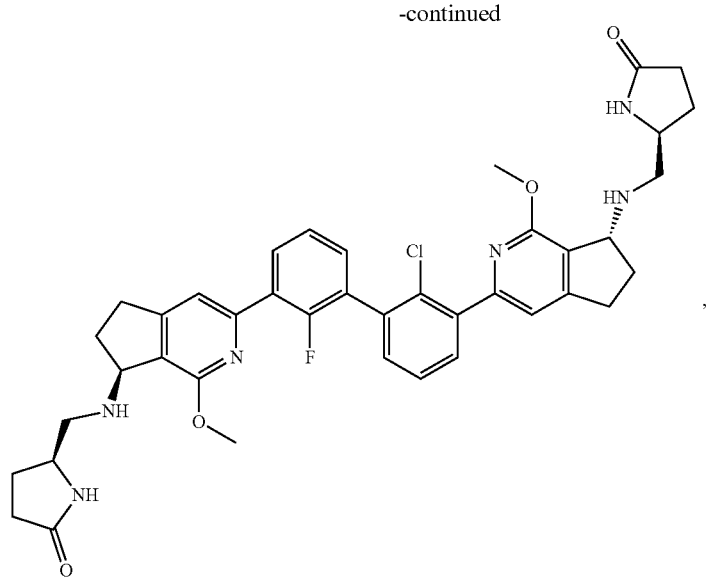,
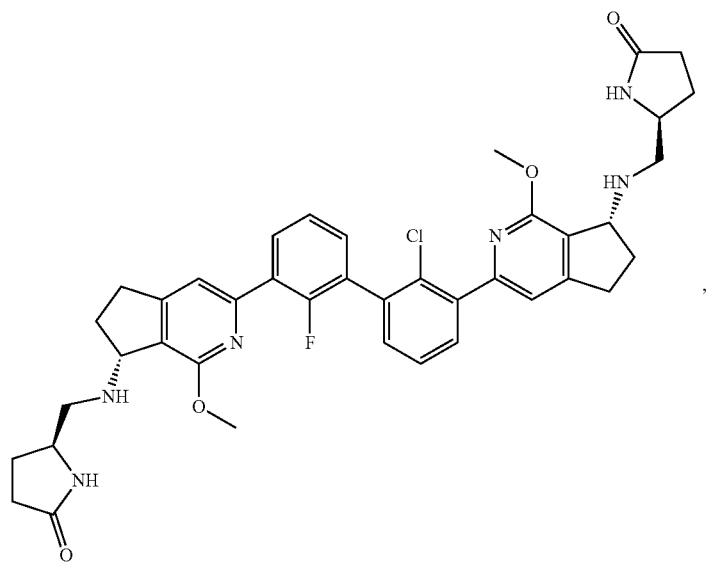,
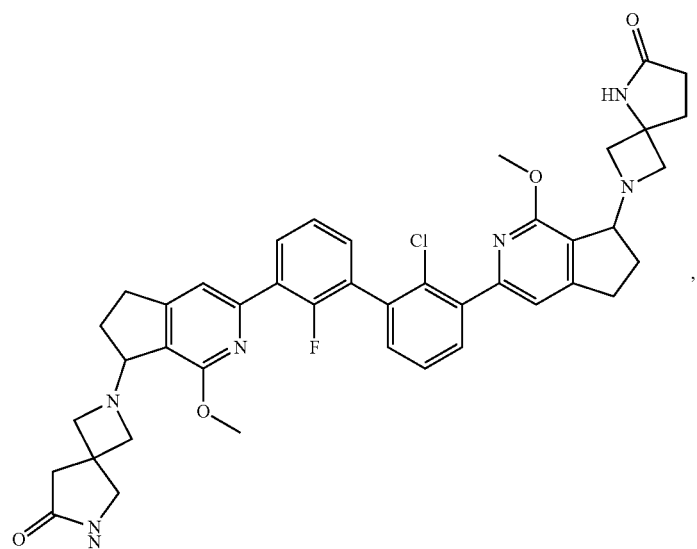,

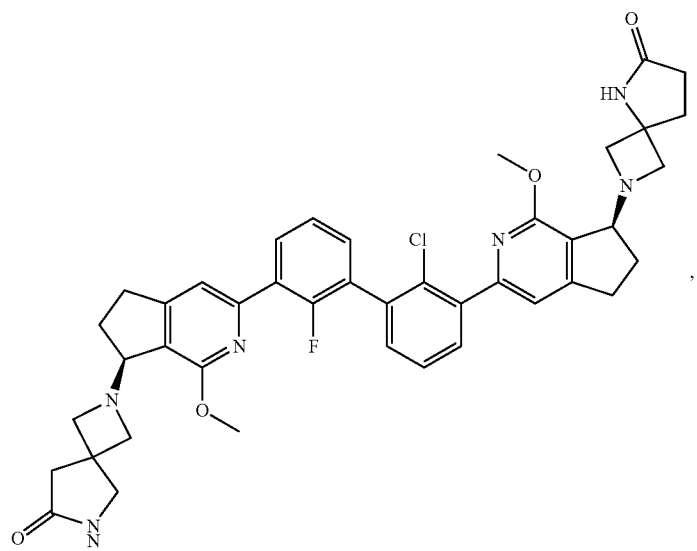
,
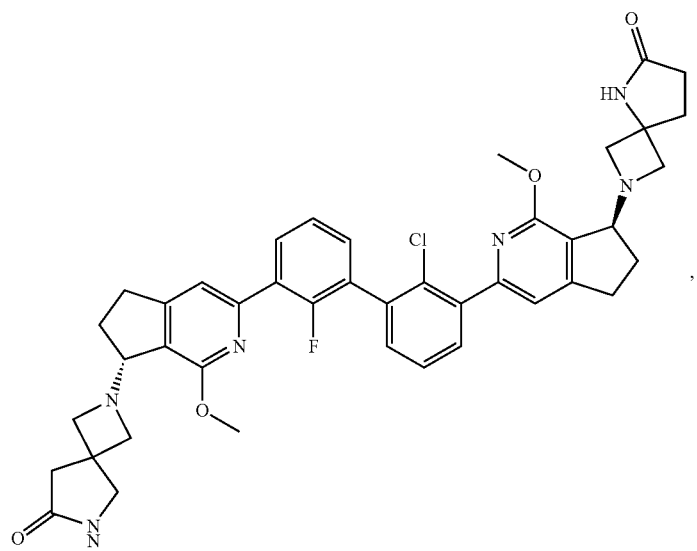
,
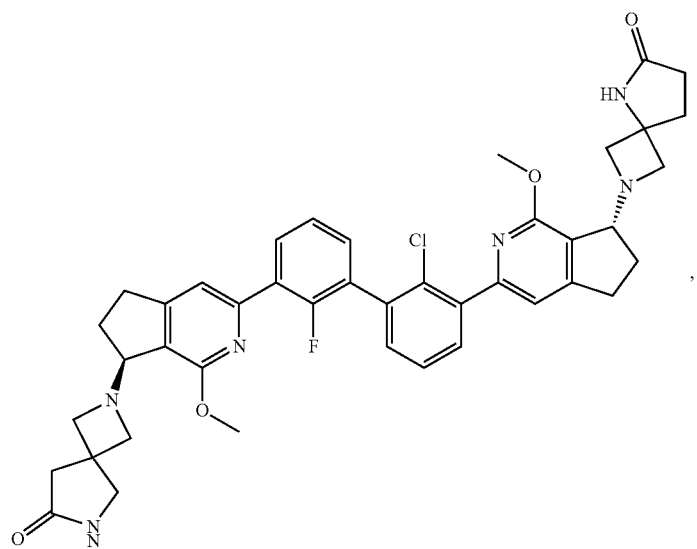
,

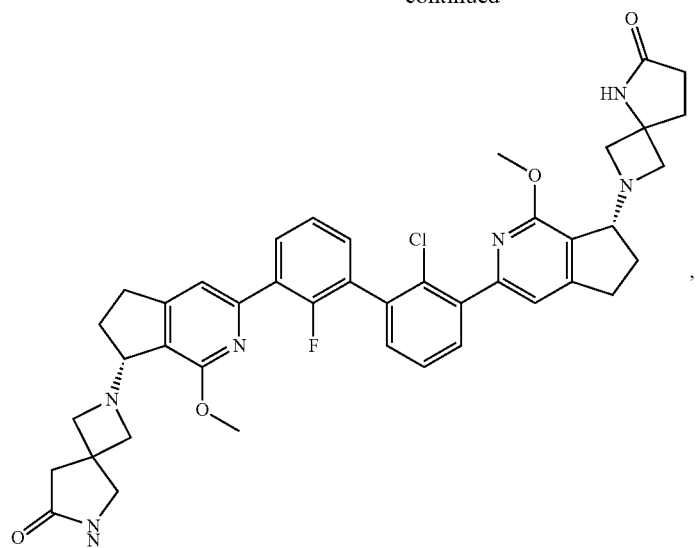
,
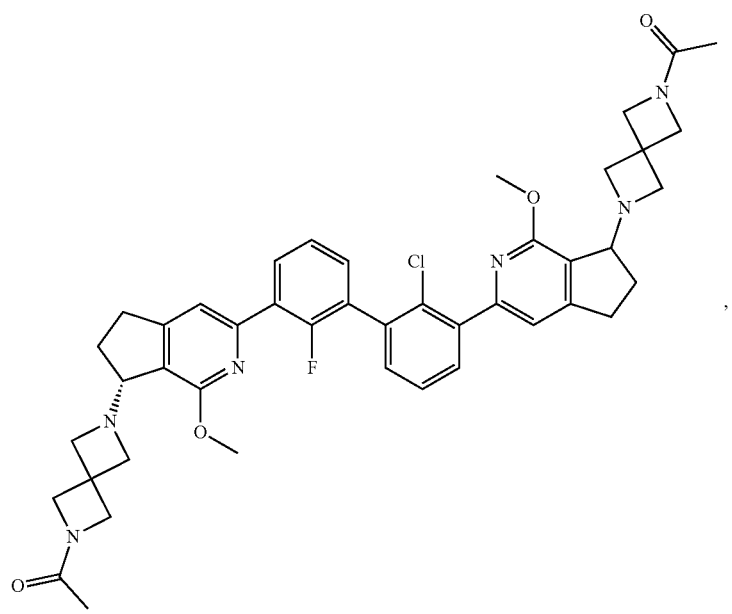
,

-continued
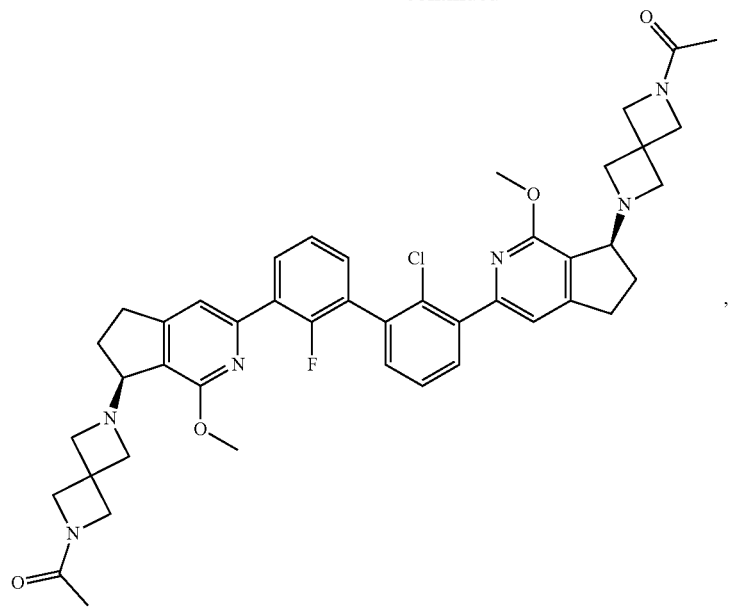
,
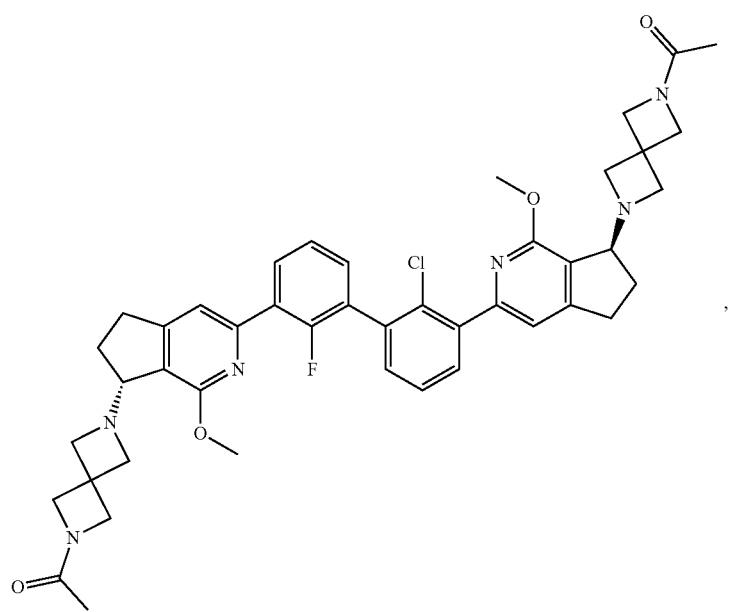
,

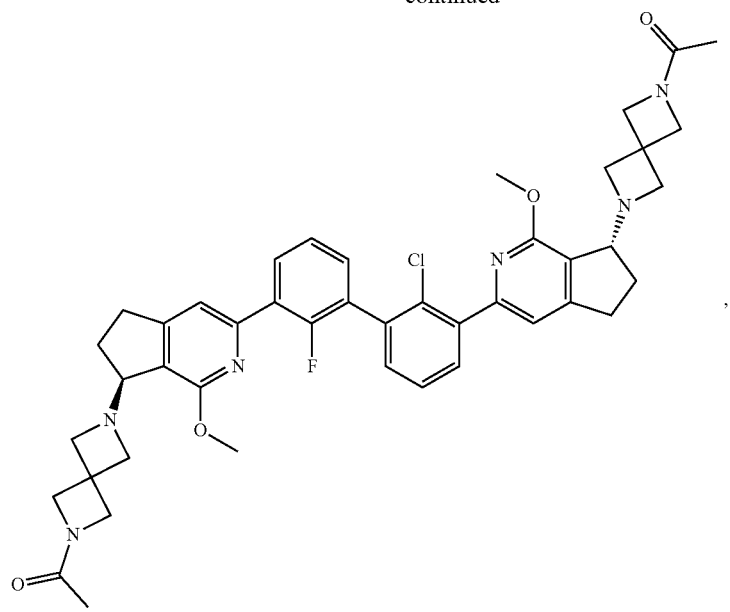
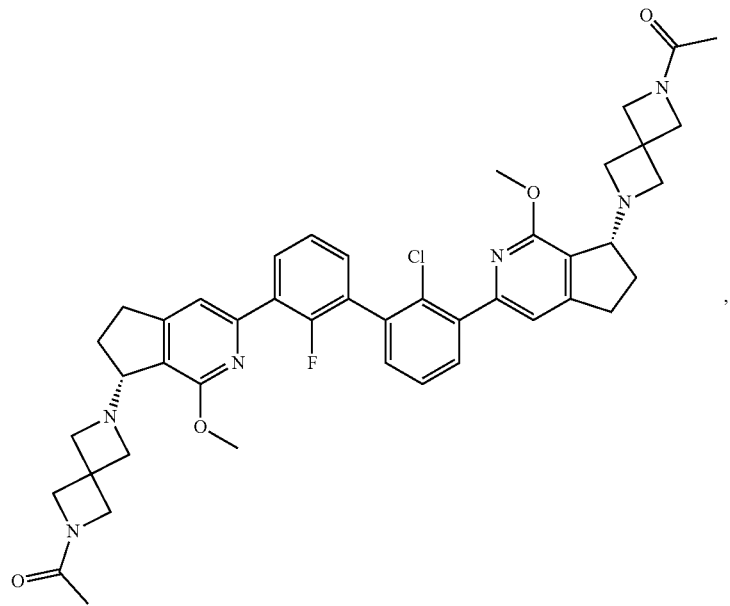
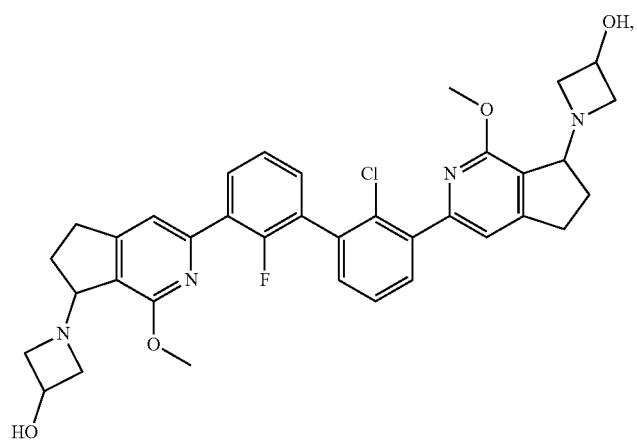

-continued
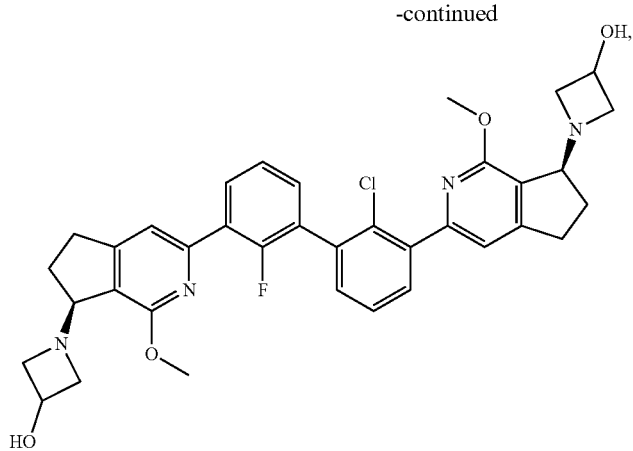
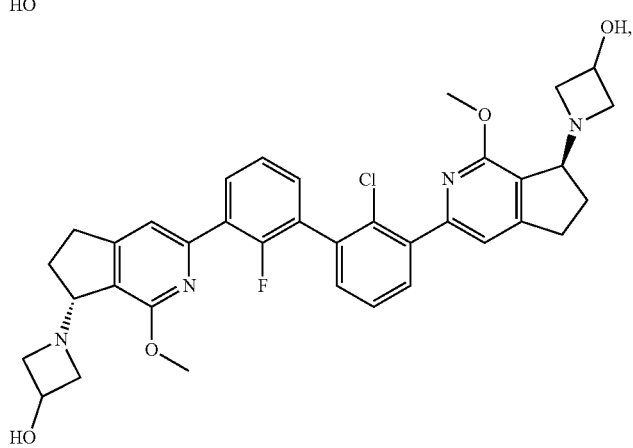
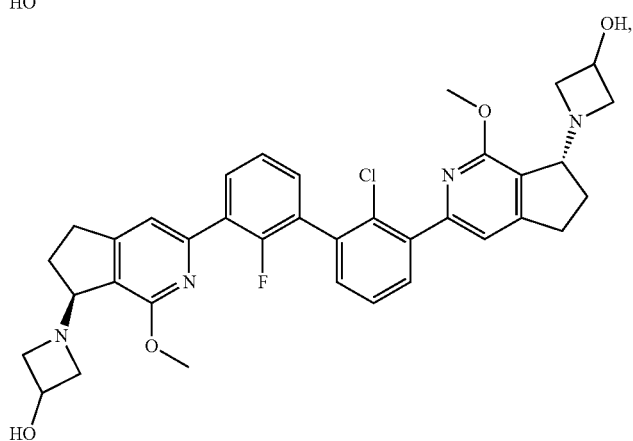
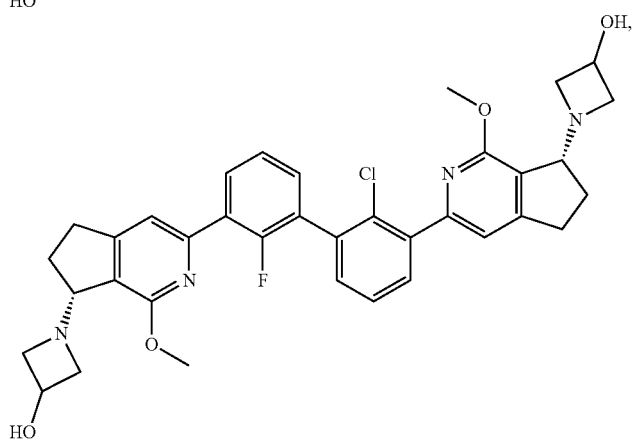

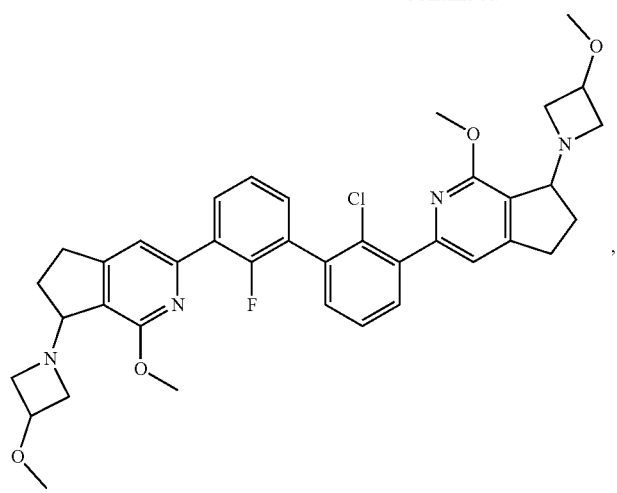,
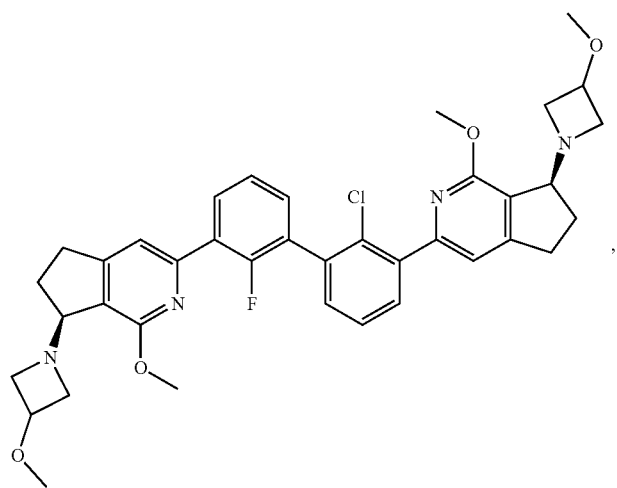,
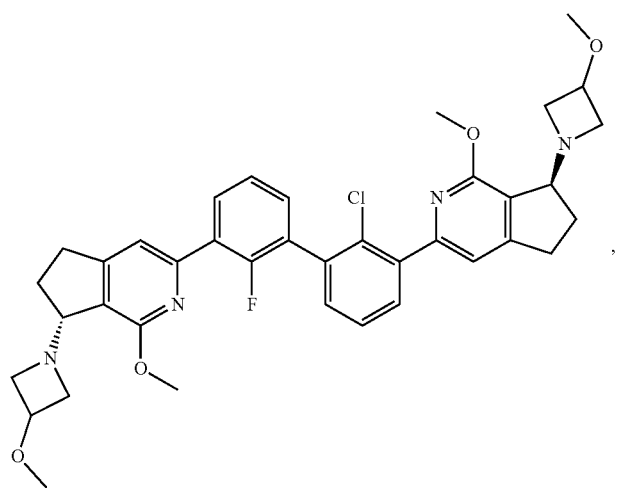,

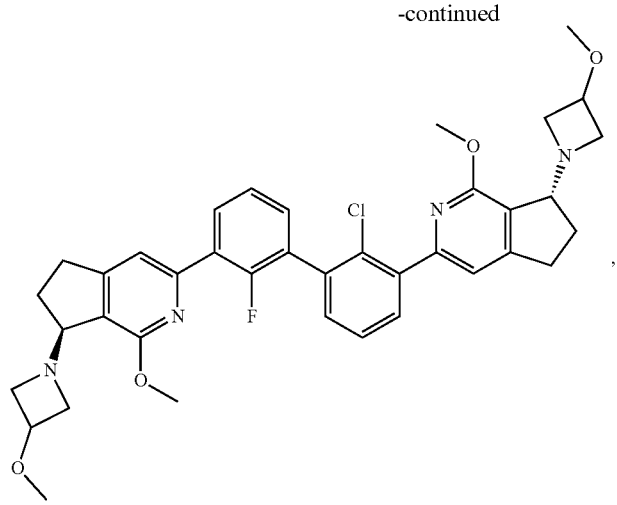
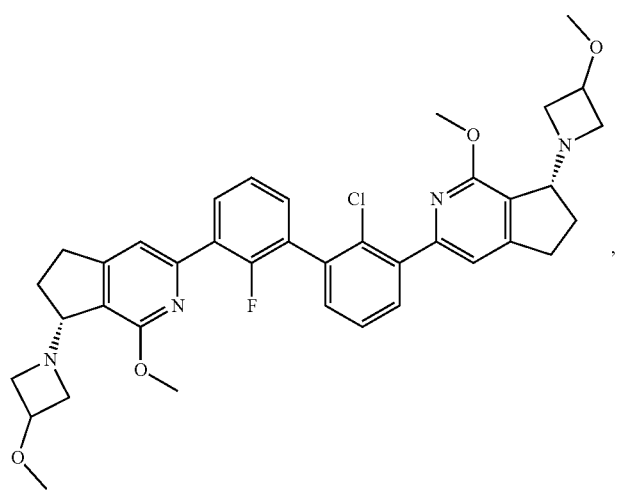
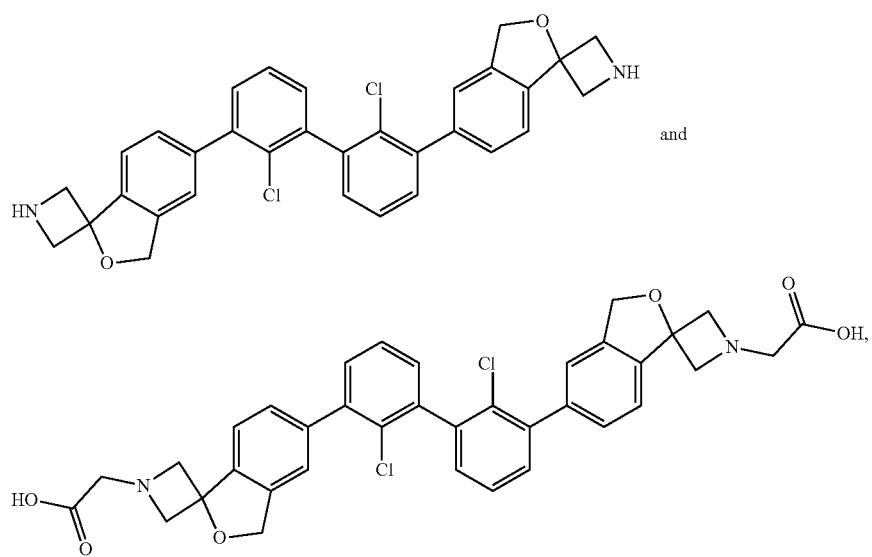
or a pharmaceutically acceptable salt of any of the foregoing.

16. The compound of claim 1, wherein the compound is selected from the group consisting of:
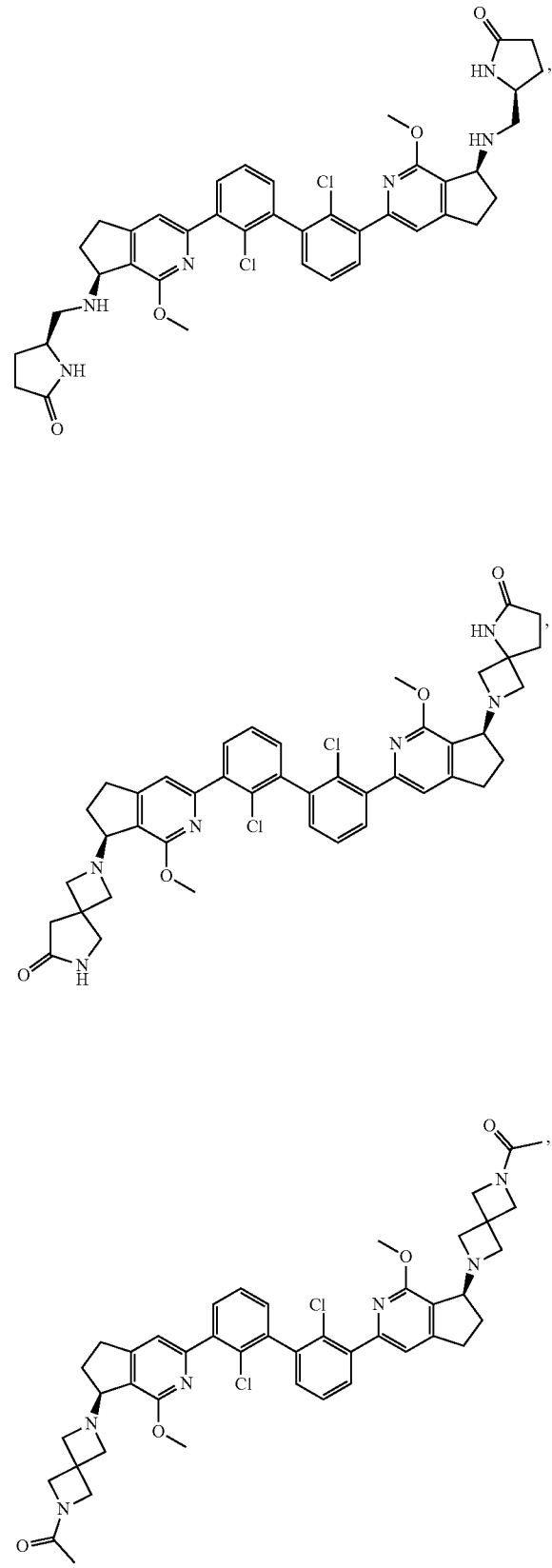
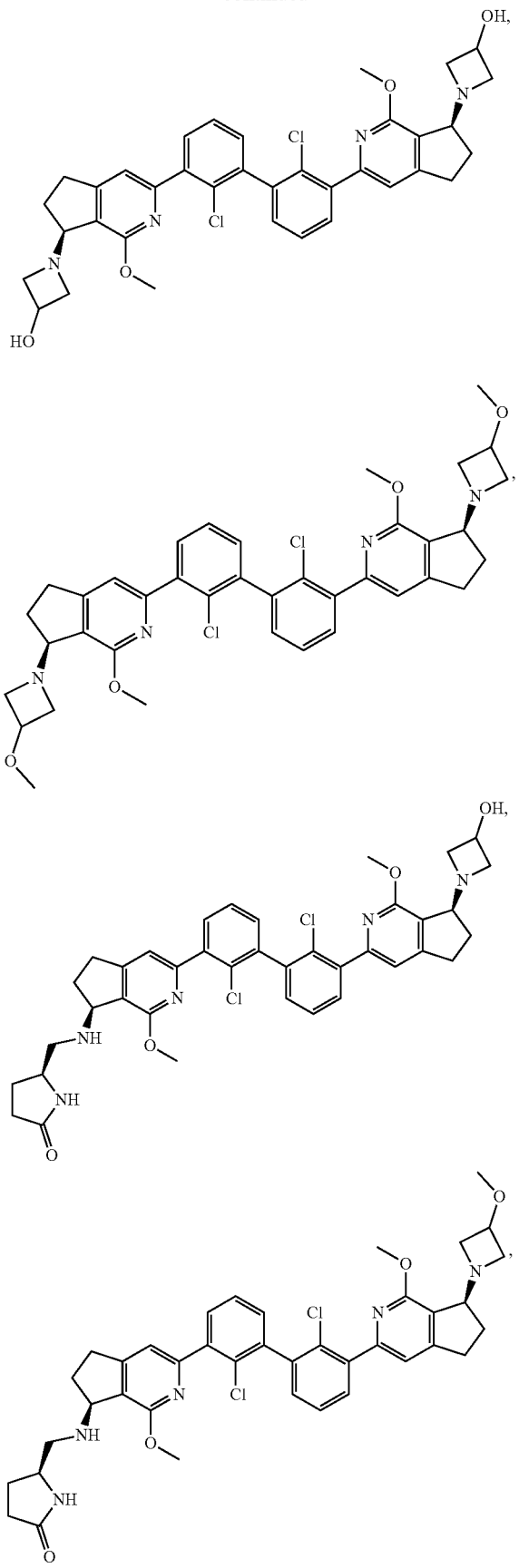

469
-continued
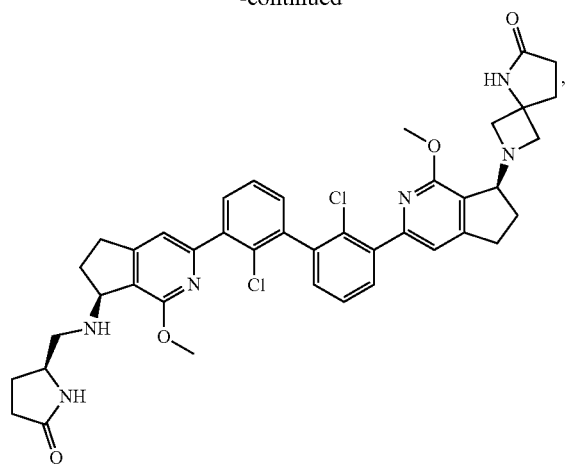
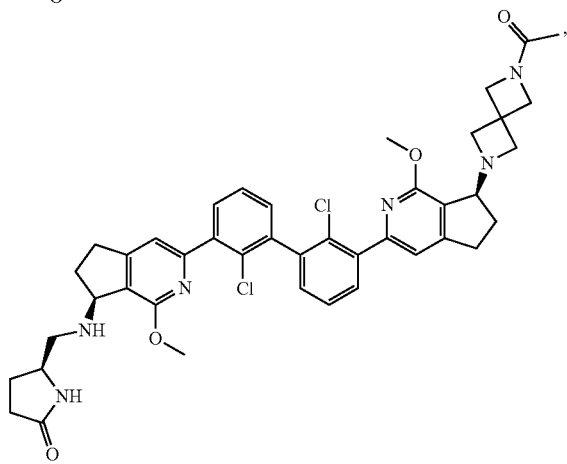
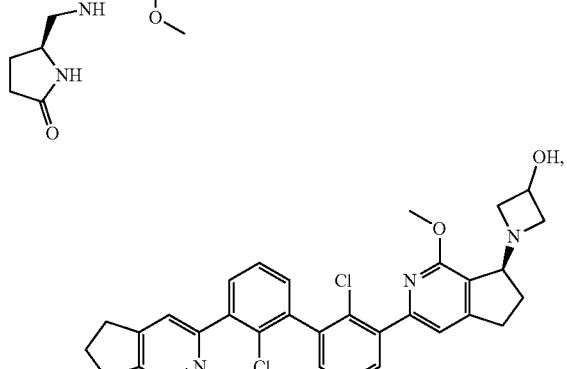
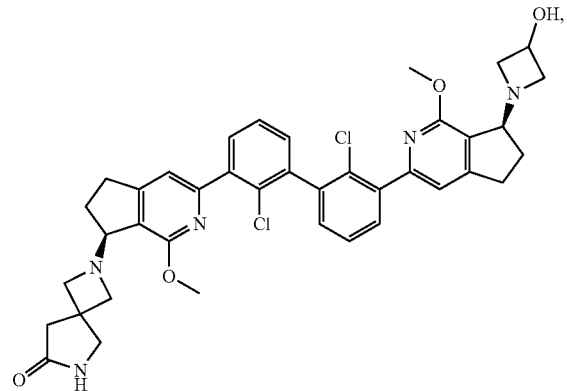
470
-continued
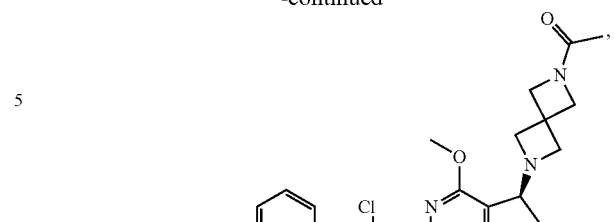
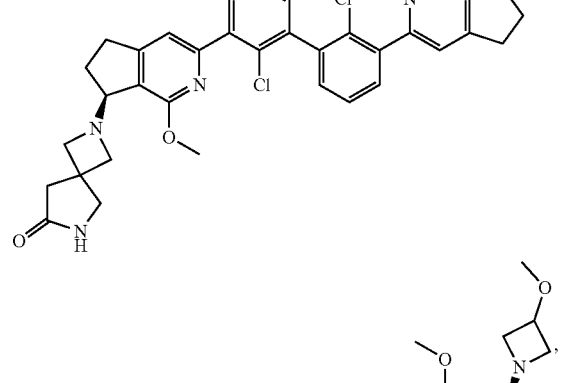
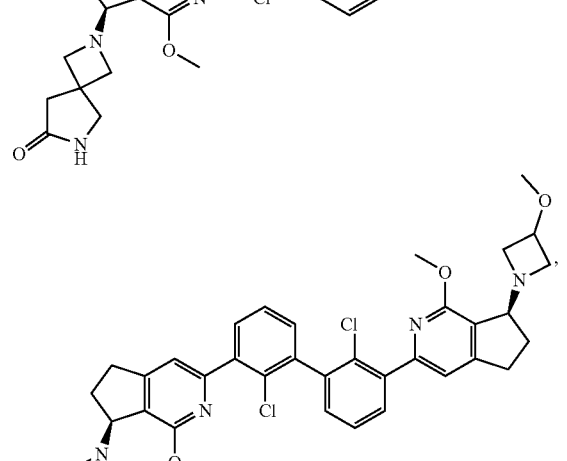
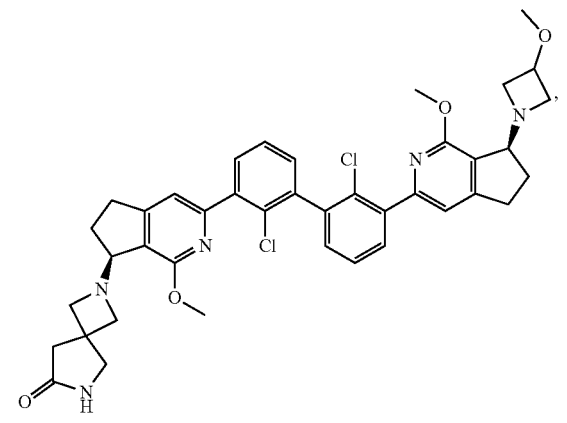

471
-continued

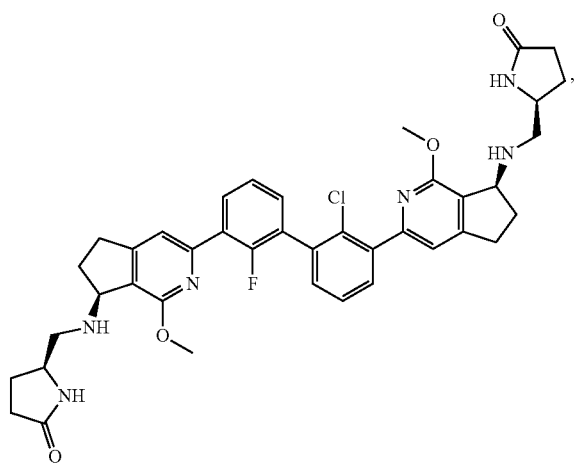

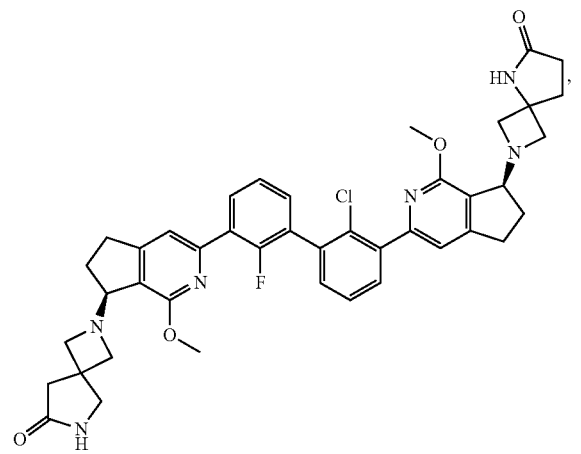

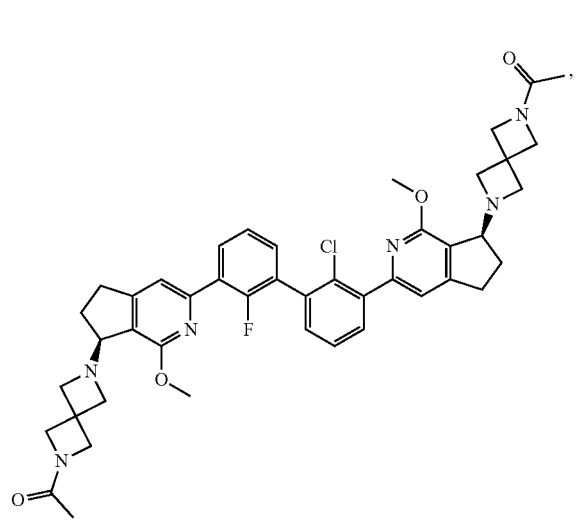

472
-continued

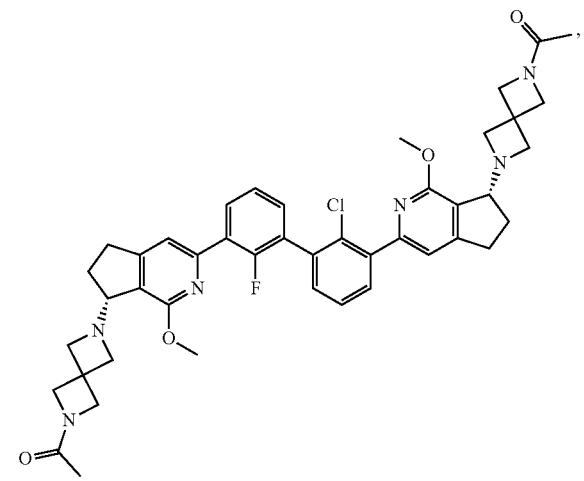

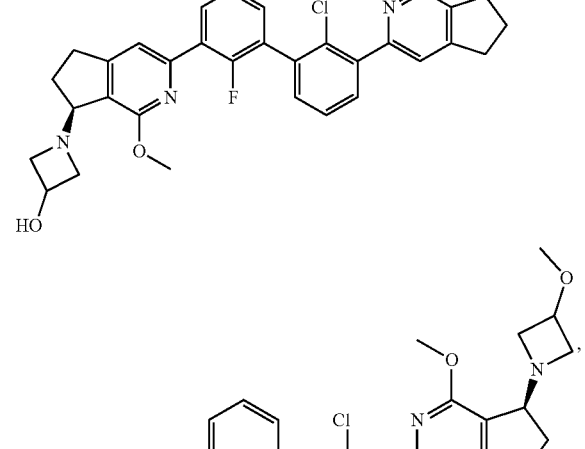

OH and or a pharmaceutically acceptable salt of any of the foregoing.

17. A pharmaceutical composition comprising an effective amount of a compound of claim 1, or a pharmaceutically acceptable salt thereof, and excipient.

18. A method for treating hepatitis B in a subject comprising administering to the subject in need thereof an effective amount of a compound of claim 1, or a pharmaceutically acceptable salt thereof.

19. A method for treating hepatocellular carcinoma (HCC) in a subject comprising administering to the subject in need thereof an effective amount of a compound of claim 1, or a pharmaceutically acceptable salt thereof.

20. The compound of claim 3, wherein $R^{3a1}$ is

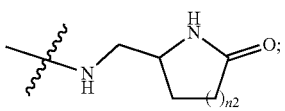 [SMILES: *NCC1CCC(=O)N1]

and $R^{3b1}$ is

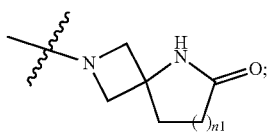 [SMILES: *N1CC2(CCC(=O)N2)C1]

or wherein $R^{3a1}$ is

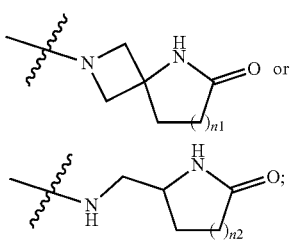

and $R^{3b1}$ is —N(R$^m$)R$^n$, wherein R$^m$ and R$^n$ are taken together along with the atom to which R$^m$ and R$^n$ are attached to form an optionally substituted 4-7 monocyclic heterocyclic ring or an optionally substituted 7-10 bicyclic heterocyclic ring.

21. The compound of claim 20, wherein the heterocyclic ring is selected from the group consisting of:

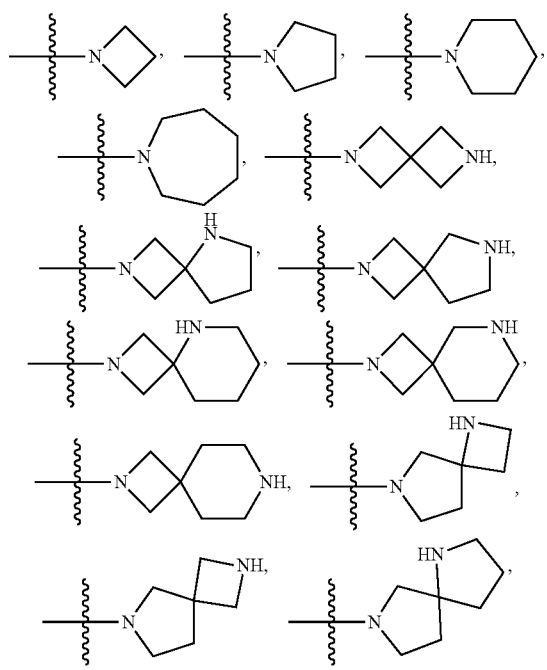

-continued

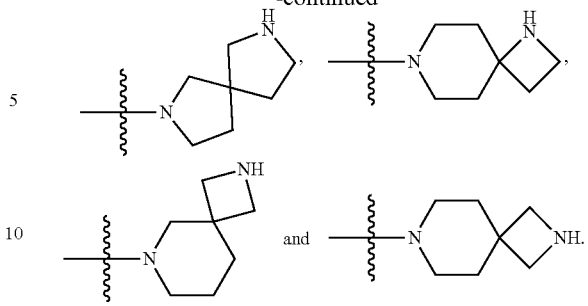

22. The compound of claim 21, wherein the 4-7 monocyclic heterocyclic ring is substituted with —C$_{1-4}$ alkyl, C$_{3-7}$ cycloalkyl, —OH, —C$_{1-4}$ alkoxy, —C(=O)C$_{1-4}$ alkyl, —C(=O)OH or —C(=O)OC$_{1-4}$ alkyl.

23. The compound of claim 13, wherein the heterocyclic ring is selected from the group consisting of:

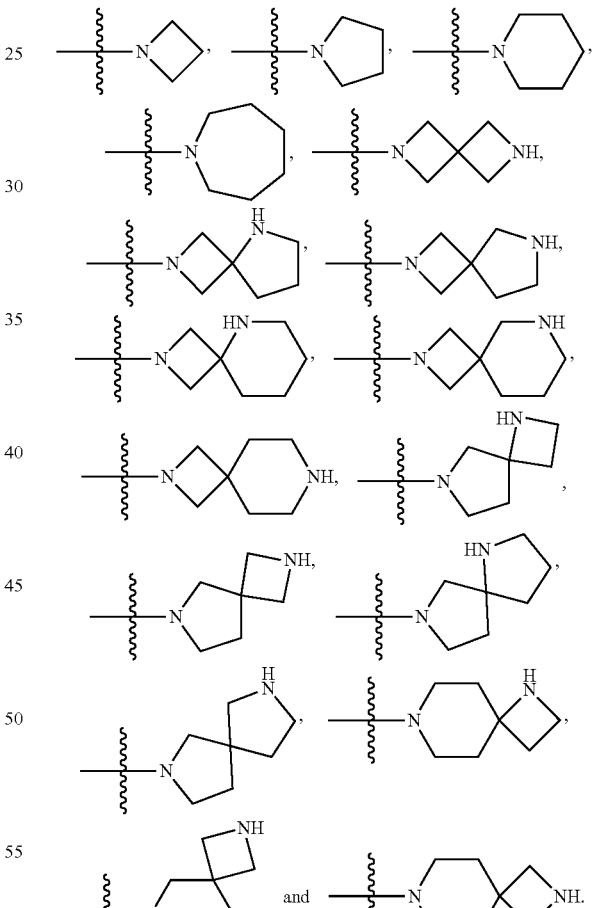

24. The compound of claim 23, wherein the 4-7 monocyclic heterocyclic ring is substituted with —C$_{1-4}$ alkyl, —C$_{3-7}$ cycloalkyl, —OH, —C$_{1-4}$ alkoxy, —C(=O)C$_{1-4}$ alkyl, —C(=O)OH or —C(=O)OC$_{1-4}$ alkyl.

* * * * *